United States Patent
Cha et al.

(10) Patent No.: US 11,261,176 B2
(45) Date of Patent: Mar. 1, 2022

(54) AMINE-BASED COMPOUND AND ORGANIC LIGHT EMITTING DEVICE USING THE SAME

(71) Applicant: LG CHEM, LTD., Seoul (KR)

(72) Inventors: Yong Bum Cha, Daejeon (KR); Sang Young Jeon, Daejeon (KR); Yeon Ho Cho, Daejeon (KR); Yeon Hwan Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 379 days.

(21) Appl. No.: 16/320,826

(22) PCT Filed: Dec. 21, 2017

(86) PCT No.: PCT/KR2017/015256
§ 371 (c)(1),
(2) Date: Jan. 25, 2019

(87) PCT Pub. No.: WO2018/139767
PCT Pub. Date: Aug. 2, 2018

(65) Prior Publication Data
US 2019/0169176 A1  Jun. 6, 2019

(30) Foreign Application Priority Data

Jan. 26, 2017 (KR) .................. 10-2017-0012952
Nov. 10, 2017 (KR) .................. 10-2017-0149677

(51) Int. Cl.
*H01L 51/00* (2006.01)
*C07D 409/12* (2006.01)
(Continued)

(52) U.S. Cl.
CPC ......... *C07D 409/12* (2013.01); *C07D 307/91* (2013.01); *C07D 333/76* (2013.01);
(Continued)

(58) Field of Classification Search
None
See application file for complete search history.

(56) References Cited

U.S. PATENT DOCUMENTS

2004/0251816 A1  12/2004 Leo et al.
2012/0146014 A1   6/2012 Kato
(Continued)

FOREIGN PATENT DOCUMENTS

CN          105503622    *  4/2016  ........... C07C 211/61
JP          2016092302 A    5/2016
(Continued)

OTHER PUBLICATIONS

Machine translation of CN-105503622, translation generated Apr. 2021, 12 pages. (Year: 2021).*
(Continued)

*Primary Examiner* — Robert S Loewe
(74) *Attorney, Agent, or Firm* — Dentons US LLP

(57) ABSTRACT

The present invention relates to a novel amine-based compound represented by Chemical Formula 1 and an organic light emitting device including the same. The compound provides improved efficiency, low driving voltage, and improved lifetime characteristic of the organic light emitting device.

[Chemical Formula 1]

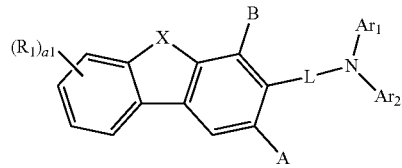

12 Claims, 1 Drawing Sheet

(51) Int. Cl.
  *C07D 307/91* (2006.01)
  *C07D 333/76* (2006.01)
  *C07D 409/04* (2006.01)
  *H01L 51/50* (2006.01)

(52) U.S. Cl.
  CPC .......... C07D 409/04 (2013.01); H01L 51/006 (2013.01); H01L 51/0054 (2013.01); H01L 51/0058 (2013.01); H01L 51/0061 (2013.01); *H01L 51/0073* (2013.01); *H01L 51/0074* (2013.01); *H01L 51/5056* (2013.01); *H01L 51/5096* (2013.01); *H01L 2251/308* (2013.01)

(56) References Cited

U.S. PATENT DOCUMENTS

| | | | |
|---|---|---|---|
| 2014/0027747 | A1 | 1/2014 | Mun et al. |
| 2014/0131681 | A1 | 5/2014 | To et al. |
| 2014/0155592 | A1 | 6/2014 | Takada |
| 2015/0179951 | A1* | 6/2015 | Fuchiwaki ............. C09K 11/06 257/40 |
| 2015/0333281 | A1 | 11/2015 | Kim et al. |
| 2015/0336937 | A1* | 11/2015 | Lee ...................... C07D 405/14 257/40 |
| 2016/0043316 | A1 | 2/2016 | Takada et al. |
| 2016/0133849 | A1 | 5/2016 | Miyake et al. |
| 2016/0141509 | A1 | 5/2016 | Fuchiwaki et al. |
| 2016/0141510 | A1 | 5/2016 | Sasaki et al. |
| 2018/0083197 | A1* | 3/2018 | Park ........................ H01L 51/50 |
| 2018/0226585 | A1 | 8/2018 | Park et al. |

FOREIGN PATENT DOCUMENTS

| | | |
|---|---|---|
| KR | 2000-0051826 A | 8/2000 |
| KR | 10-2011-0117548 A | 10/2011 |
| KR | 10-2012-0009761 A | 2/2012 |
| KR | 10-2015-0065944 A | 6/2015 |
| KR | 10-1535606 B1 | 7/2015 |
| KR | 10-2016-0019839 A | 2/2016 |
| KR | 10-2016-0027940 A | 3/2016 |
| KR | 10-2016-0059938 A | 5/2016 |
| KR | 10-2016-0060536 A | 5/2016 |
| KR | 10-2016-0132344 A | 11/2016 |
| WO | 03/012890 A2 | 2/2003 |
| WO | 2006/128800 A1 | 12/2006 |
| WO | 2011/133007 A2 | 10/2011 |
| WO | 2012/011756 A1 | 1/2012 |
| WO | 2012/134203 A2 | 10/2012 |
| WO | 2013/168534 A1 | 11/2013 |
| WO | 2014/069602 A1 | 5/2014 |
| WO | 2015/041492 A1 | 3/2015 |
| WO | 2016/208862 A1 | 12/2016 |
| WO | 2017/126818 A1 | 7/2017 |

OTHER PUBLICATIONS

Machine Translation of CN-106565433, translation generated Sep. 2021, 24 pages. (Year: 2021).*

* cited by examiner

[FIG. 1]
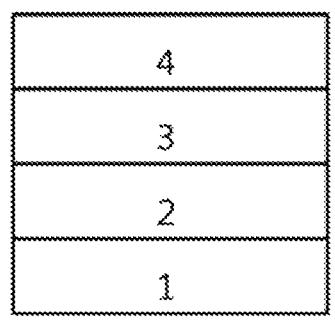
[FIG. 2]
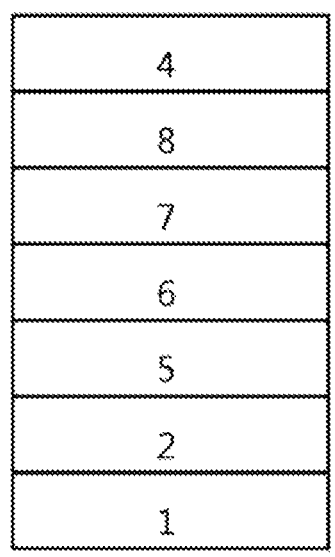

AMINE-BASED COMPOUND AND ORGANIC LIGHT EMITTING DEVICE USING THE SAME

TECHNICAL FIELD

This application is a National Stage Application of International Application No. PCT/KR2017/015256 filed on Dec. 21, 2017, and claims priority to and the benefits of Korean Patent Application No. 10-2017-0012952, filed on Jan. 26, 2017, and Korean Patent Application No. 10-2017-0149677, filed on Nov. 10, 2017, the disclosures of which are incorporated herein by reference in their entirety.

The present invention relates to a novel amine-based compound and an organic light emitting device including the same.

BACKGROUND ART

In general, an organic light emitting phenomenon is one where electrical energy is converted into light energy by using an organic material. The organic light emitting device using the organic light emitting phenomenon has characteristics such as a wide viewing angle, a fast response time, and excellent contrast, luminance, driving voltage, and response speed, and thus many studies have proceeded.

The organic light emitting device generally has a structure which includes an anode, a cathode, and an organic material layer interposed between the anode and the cathode. The organic material layer frequently has a multilayered structure that includes different materials in order to enhance efficiency and stability of the organic light emitting device, and for example, the organic material layer may be formed of a hole injection layer, a hole transport layer, a light emitting layer, an electron transport layer, an electron injection layer, and the like. In the structure of the organic light emitting device, if a voltage is applied between two electrodes, the holes are injected from an anode into the organic material layer and the electrons are injected from the cathode into the organic material layer, and when the injected holes and the electrons meet, an exciton is formed, and light is emitted when the exciton falls to a ground state.

There is a continuing need for developing new materials with respect to the organic materials used in the aforementioned organic light emitting device.

PRIOR ART LITERATURE

Patent Literature (Patent Literature 0001) Korean Patent Laid-open Publication No. 10-2000-0051826

DETAILED DESCRIPTION OF THE INVENTION

Technical Problem

The present invention relates to a novel amine-based compound and an organic light emitting device including the same.

Technical Solution

The present invention provides a compound represented by the following Chemical Formula 1:

[Chemical Formula 1]

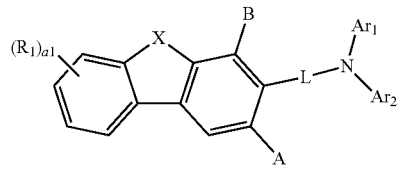

wherein, in Chemical Formula 1,

X is O or S,

A and B are each independently hydrogen; a substituted or unsubstituted $C_{6-60}$ aryl; or a substituted or unsubstituted $C_{2-60}$ heteroaryl containing 1 to 3 heteroatoms selected from the group consisting of N, O, and S, at least one of A and B is not hydrogen.

L is a single bond; a substituted or unsubstituted $C_{6-60}$ arylene; or a substituted or unsubstituted $C_{2-60}$ heteroarylene containing one or more heteroatoms selected from the group consisting of O, N, Si, and S, $Ar_1$ and $Ar_2$ are each independently a substituted or unsubstituted $C_{6-60}$ aryl; or a substituted or unsubstituted $C_{2-60}$ heteroaryl containing 1 to 3 heteroatoms selected from the group consisting of N, O, and S, $R_1$ is hydrogen; deuterium; a halogen; a cyano; a nitro; an amino; a substituted or unsubstituted $C_{1-60}$ alkyl; a substituted or unsubstituted $C_{1-60}$ haloalkyl; a substituted or unsubstituted $C_{1-60}$ alkoxy; a substituted or unsubstituted $C_{1-60}$ haloalkoxy; a substituted or unsubstituted $C_{3-60}$ cycloalkyl; a substituted or unsubstituted $C_{2-60}$ alkenyl; a substituted or unsubstituted $C_{6-60}$ aryl; a substituted or unsubstituted $C_{6-60}$ aryloxy; or a substituted or unsubstituted $C_{2-60}$ heterocyclic group containing one or more heteroatoms selected from the group consisting of N, O, and S; and a1 is an integer of 0 to 4.

The present invention also provides an organic light emitting device including a first electrode; a second electrode provided to face the first electrode; and at least one layer of the organic material layers provided between the first electrode and the second electrode, wherein the at least one layer of the organic material layers includes the compound represented by Chemical Formula 1.

Advantageous Effects

The compound represented by Chemical Formula 1 as described above can be used as a material of the organic material layer of the light emitting device, and enables improvement of the efficiency, low driving voltage, and/or improvement of the lifetime characteristic when applied to the organic light emitting device.

BRIEF DESCRIPTION OF DRAWINGS

FIG. 1 shows an example of an organic light emitting device including a substrate 1, an anode 2, a light emitting layer 3, and a cathode 4.

FIG. 2 shows an example of an organic light emitting device including a substrate 1, an anode 2, a hole injection layer 5, a hole transport layer 6, a light emitting layer 7, an electron transport layer 8, and a cathode 4.

DETAILED DESCRIPTION OF THE EMBODIMENTS

Hereinafter, the present invention will be described in more detail to help understanding of the present invention.

In the present specification, the notation ⫶ means a bond connected to another substituent, and a single bond means the case in which no separate atom is present at a part represented by L.

As used herein, the term "substituted or unsubstituted" means being unsubstituted or substituted by one or more substituents selected from the group consisting of deuterium; a halogen group; a nitrile group; a nitro group; a hydroxyl group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; or a heterocyclic group containing at least one of N, O, and S atoms, or being unsubstituted or substituted by a substituent to which two or more substituents are linked among the exemplified substituents. For example, "the substituent to which two or more substituents are linked" may be a biphenyl group. That is, the biphenyl group may be an aryl group, or may be interpreted as a substituent to which two phenyl groups are linked.

In the present specification, the number of carbon atoms in a carbonyl group is not particularly limited, but is preferably 1 to 40. Specifically, the carbonyl group may be compounds having the following structures, but is not limited thereto.

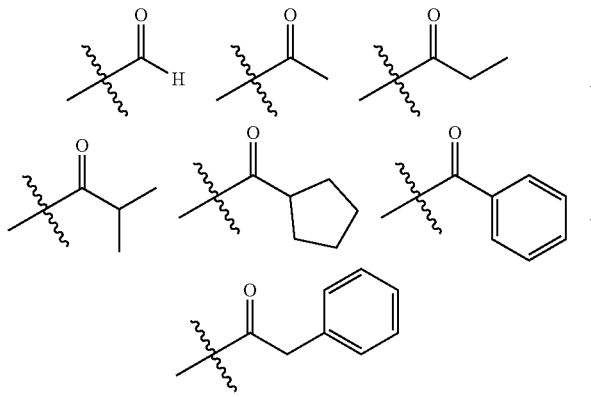

In the present specification, the ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be compounds having the following structures, but is not limited thereto.

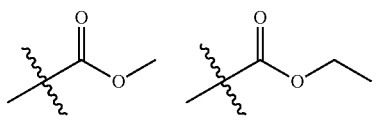

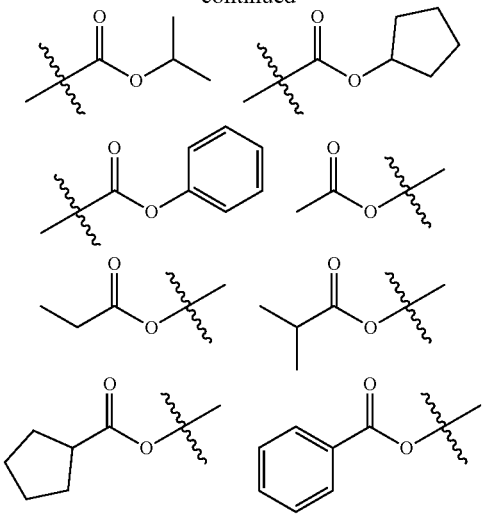

In the present specification, the number of carbon atoms in an imide group is not particularly limited, but is preferably 1 to 25. Specifically, the imide group may be compounds having the following structures, but is not limited thereto.

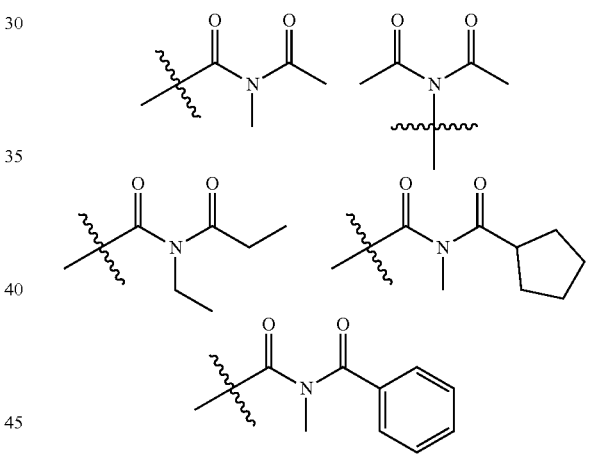

In the present specification, the silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, the boron group specifically includes a trimethylboron group, a triethylboron group, a t-butyldimethylboron group, a triphenylboron group, a phenylboron group, and the like, but is not limited thereto.

In the present specification, examples of a halogen group include fluorine, chlorine, bromine, and iodine.

In the present specification, the alkyl group may be a straight-chain or a branched-chain, and the number of carbon atoms thereof is not particularly limited, but is preferably 1 to 40. According to one embodiment, the alkyl group has 1 to 20 carbon atoms. According to another embodiment, the alkyl group has 1 to 10 carbon atoms. According to still another embodiment, the alkyl group has 1 to 6 carbon atoms. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group may be a straight-chain or a branched-chain, and the number of carbon atoms thereof is not particularly limited, but is preferably 2 to 40. According to one embodiment, the alkenyl group has 2 to 20 carbon atoms. According to another embodiment, the alkenyl group has 2 to 10 carbon atoms. According to still another embodiment, the alkenyl group has 2 to 6 carbon atoms. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, the cycloalkyl group is not particularly limited, but the number of carbon atoms thereof is preferably 3 to 60. According to one embodiment, the cycloalkyl group has 3 to 30 carbon atoms. According to another embodiment, the cycloalkyl group has 3 to 20 carbon atoms. According to another embodiment, the cycloalkyl group has 3 to 6 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the aryl group is not particularly limited, but preferably has 6 to 60 carbon atoms, and may be a monocyclic aryl group or a polycyclic aryl group. According to one embodiment, the aryl group has 6 to 30 carbon atoms. According to one embodiment, the aryl group has 6 to 20 carbon atoms. The aryl group may be a phenyl group, a biphenyl group, a terphenyl group, or the like as the monocyclic aryl group, but is not limited thereto. Examples of the polycyclic aryl group include a naphthyl group, an anthracenyl group, a phenanthryl group, a pyrenyl group, a perylenyl group, a chrycenyl group, a fluorenyl group, and the like, but are not limited thereto.

In the present specification, a fluorenyl group may be substituted, and two substituents may be linked with each other to form a spiro structure. In the case where the fluorenyl group is substituted,

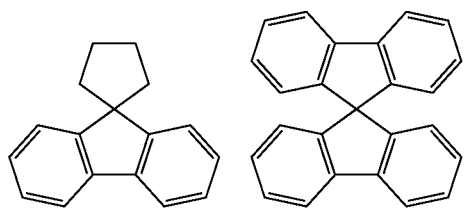

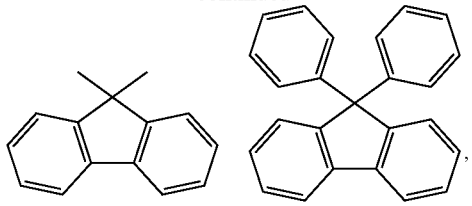

and the like can be formed. However, the structure is not limited thereto.

In the present specification, the heterocyclic group is a heterocyclic group containing at least one of O, N, Si, and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group, and the alkylamine group is the same as the aforementioned examples of the alkyl group. In the present specification, the heteroaryl in the heteroarylamine can be applied to the aforementioned description of the heterocyclic group. In the present specification, the alkenyl group in the aralkenyl group is the same as the aforementioned examples of the alkenyl group. In the present specification, the aforementioned description of the aryl group may be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but is formed by combining two substituents. In the present specification, the aforementioned description of the heterocyclic group can be applied, except that the heterocycle is not a monovalent group but is formed by combining two substituents.

Meanwhile, the present invention provides a compound represented by Chemical Formula 1.

In Chemical Formula 1, A and B may each independently be hydrogen, or any one selected from the group consisting of the following. That is, in Chemical Formula 1, one of A and B is hydrogen and the other is selected from the group consisting of the following, or both A and B may be selected from the group consisting of the following:

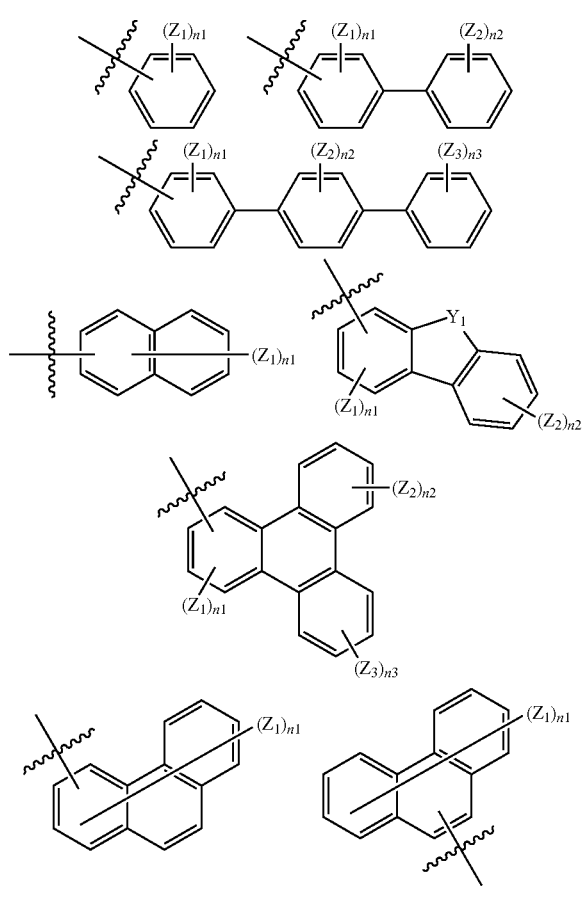

wherein

Y1 is O, S, or $CZ_4Z_5$, $Z_1$ to $Z_5$ are each independently hydrogen; deuterium; a halogen; a cyano; a nitro; an amino; a $C_{1-20}$ alkyl; a $C_{1-20}$ haloalkyl; a $C_{6-20}$ aryl; or a $C_{2-20}$ heteroaryl containing one or more heteroatoms of O or S, and n1 to n3 are each independently an integer of 0 to 3.

For example, A and B are each independently hydrogen, or any one selected from the group consisting of the following:

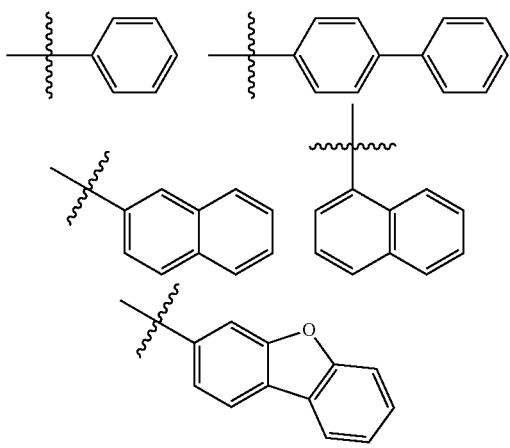

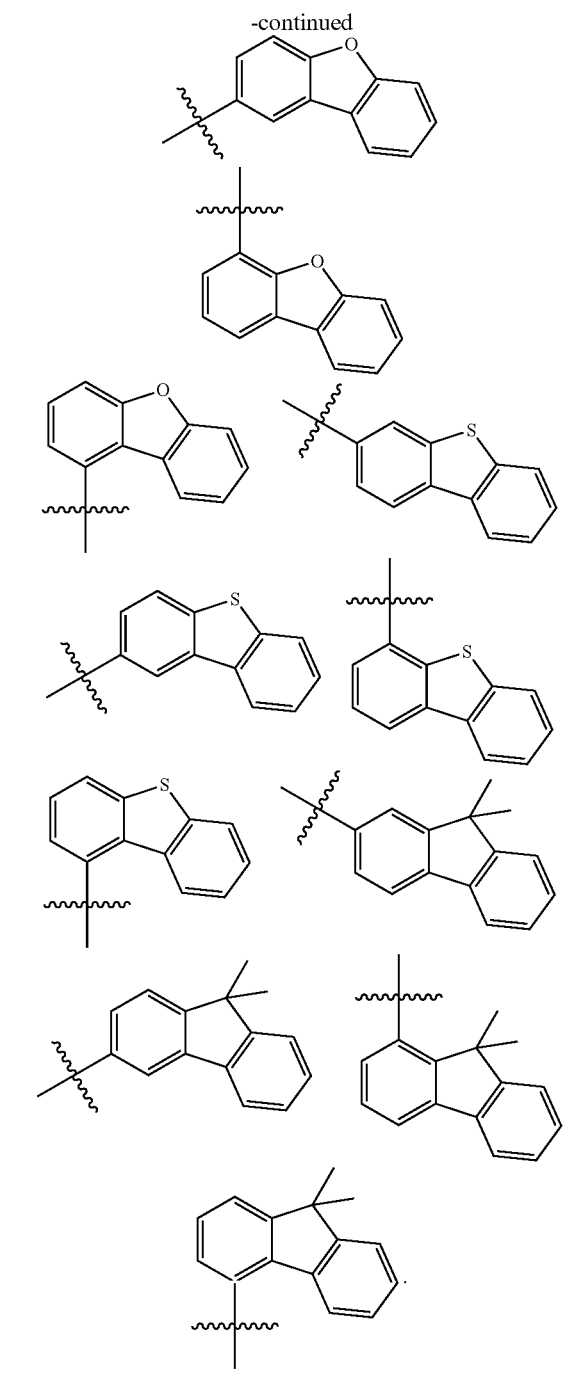

Specifically, in Chemical Formula 1, in the case of an organic light emitting device manufactured using a compound in which both A and B are hydrogen as an electron blocking layer or a hole transport layer, there is a limit in that the efficiency decreases by 10% or more and the lifetime decreases by 30% or more. Thereby, in Chemical Formula 1, when A and B each independently satisfy hydrogen, or any one selected from the group consisting of the foregoing, the efficiency of the device can be increased and at the same time the stability can be greatly increased.

In addition, L is a single bond, a substituted or unsubstituted phenylene, a substituted or unsubstituted biphenylene, a substituted or unsubstituted naphthylene, a substituted or unsubstituted phenanthrenylene, a substituted or unsubstituted anthracenylene, a substituted or unsubstituted fluoranthenylene, a substituted or unsubstituted triphenylenylene, a substituted or unsubstituted pyrenylene, a substituted or unsubstituted carbazolylene, a substituted or unsubstituted fluorenylene, or a substituted or unsubstituted spiro-fluorenylene.

For example, L may be a single bond, or any one selected from the group consisting of the following:

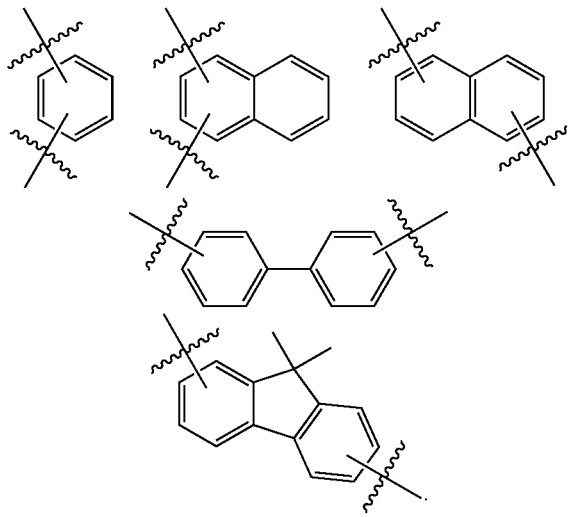

Specifically, for example, L may be a single bond, or any one selected from the group consisting of the following:

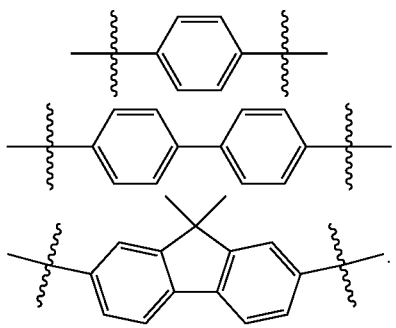

When the L has a long chain as described below, as the distance between the core and the arylamine group in Chemical Formula 1 becomes too far, characteristics of the organic light emitting device may be greatly deteriorated:

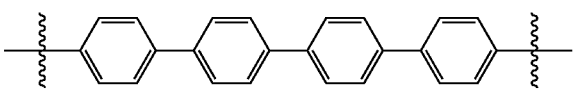

Further, $Ar_1$ and $Ar_2$ may each independently be a substituted or unsubstituted $C_{6-20}$ aryl; or a substituted or unsubstituted $C_{2-20}$ heteroaryl containing 1 to 3 heteroatoms of O or S.

For example, $Ar_1$ and $Ar_2$ may each independently be any one selected from the group consisting of the following:

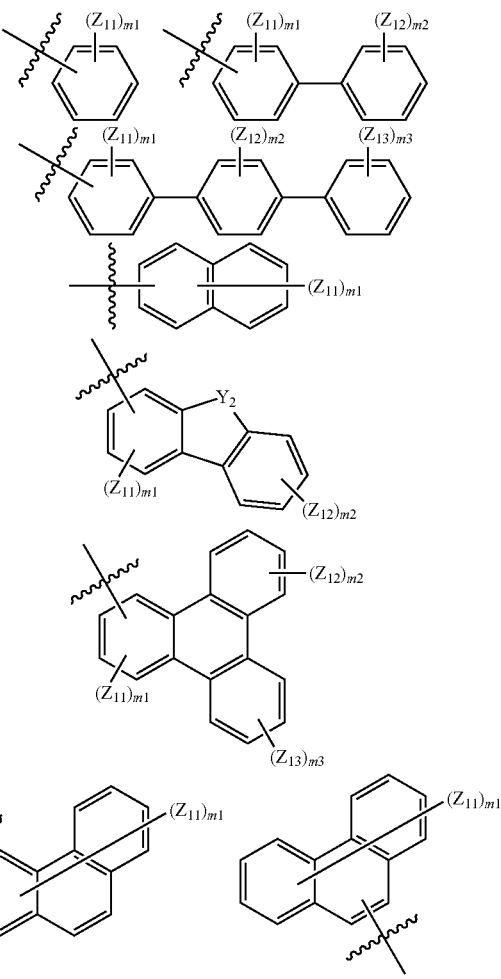

wherein $Y_2$ is O, S, or $CZ_{14}Z_{15}$, $Z_{11}$ to $Z_{15}$ are each independently hydrogen; deuterium; a halogen; a cyano; a nitro; a amino; a silyl; a $C_{1-20}$ alkyl; a $C_{1-20}$ haloalkyl; a $C_{6-20}$ aryl; or a $C_{2-20}$ heteroaryl containing one or more heteroatoms of O or S, provided that $Z_{14}$ and $Z_{15}$ may be linked to each other to form a monocyclic or polycyclic ring, and m1 to m3 are each independently an integer of 0 to 3.

Herein, $Z_{11}$ to $Z_{13}$ are each independently hydrogen, deuterium, a halogen, a cyano, a trimethylsilyl, a methyl, a tert-butyl, a phenyl, a naphthyl, a triphenylenyl, a dibenzofuranyl, or a dibenzothiophenyl, $Z_{14}$ and $Z_{15}$ are each independently methyl, or are linked to each other to form a monocyclic or polycyclic ring, and m1 to m3 are each independently 0 or 1.

Specifically, for example, $Ar_1$ and $Ar_2$ may each independently be any one selected from the group consisting of the following:

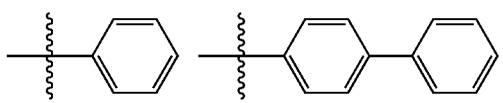

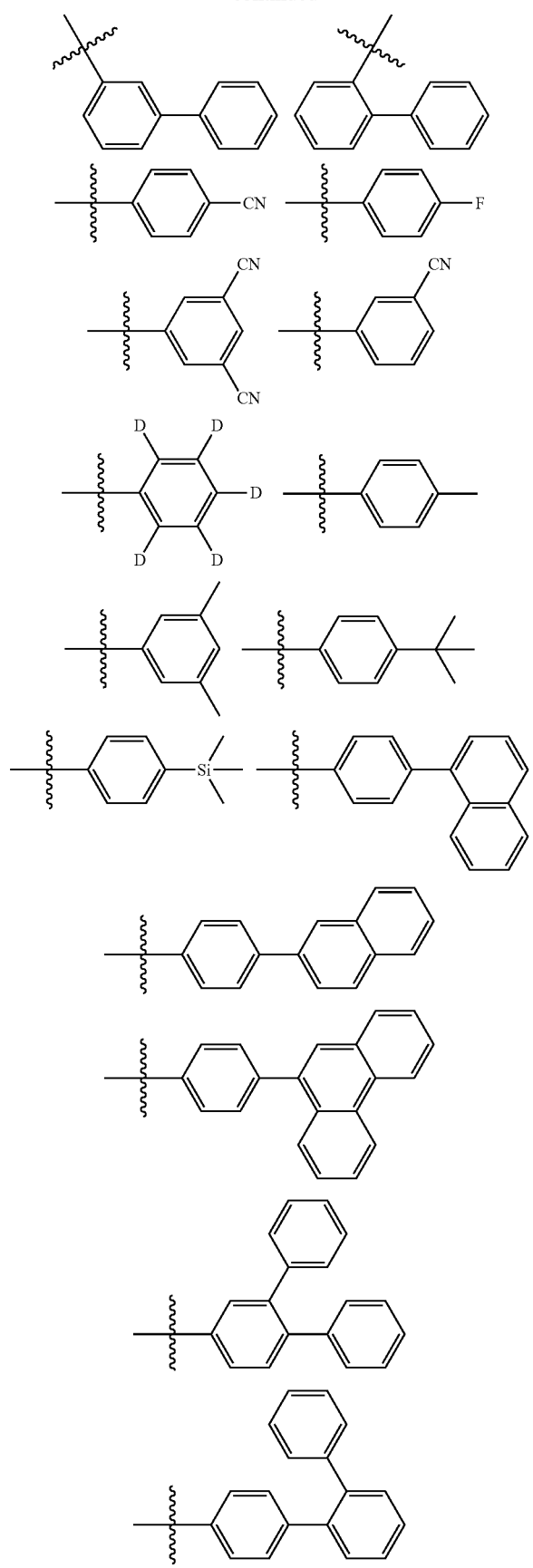
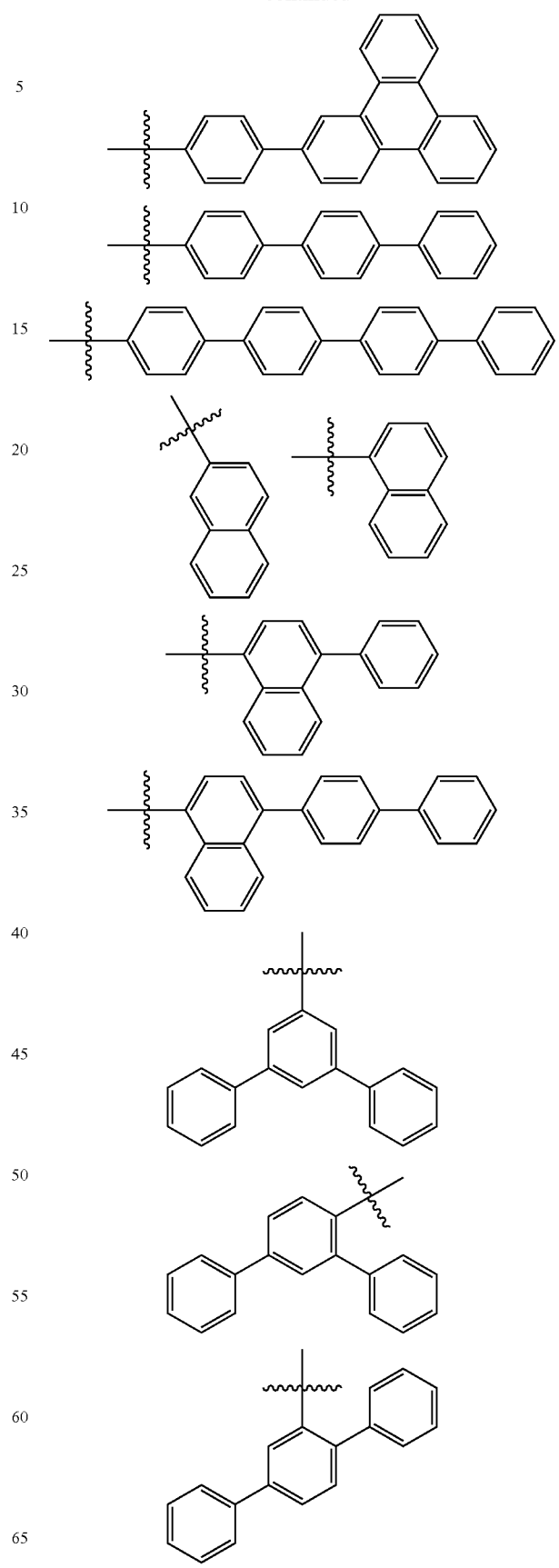

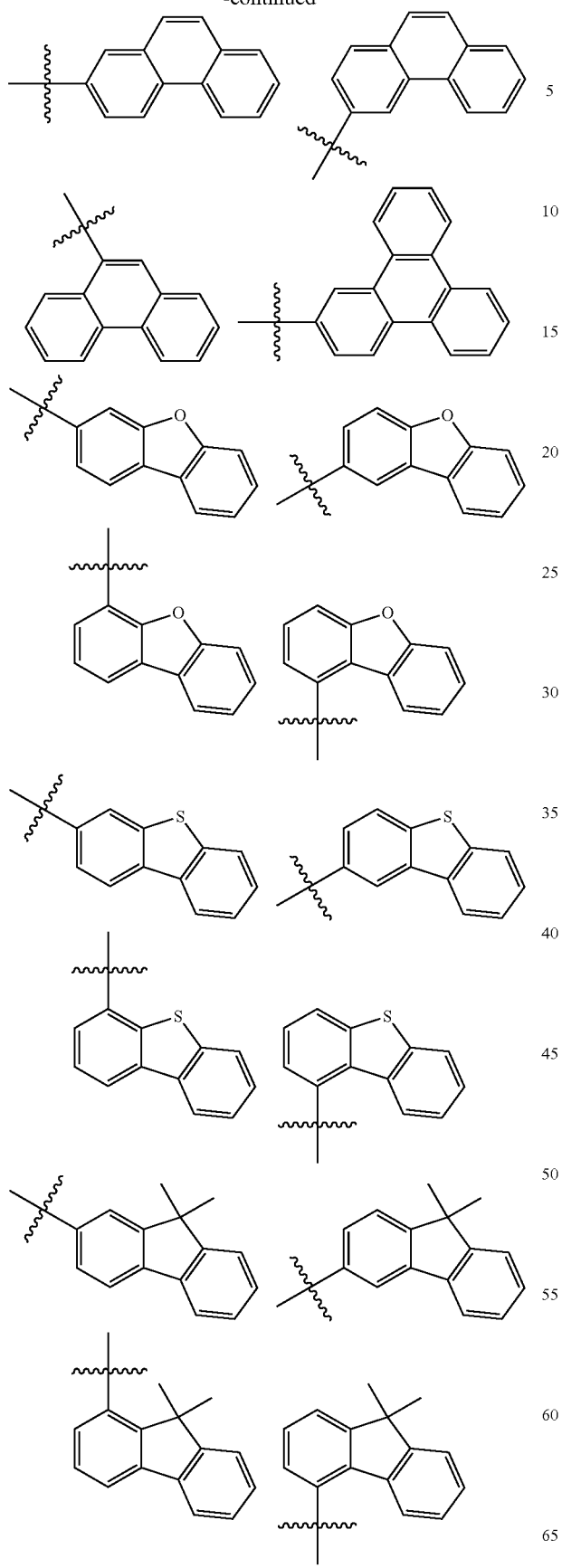
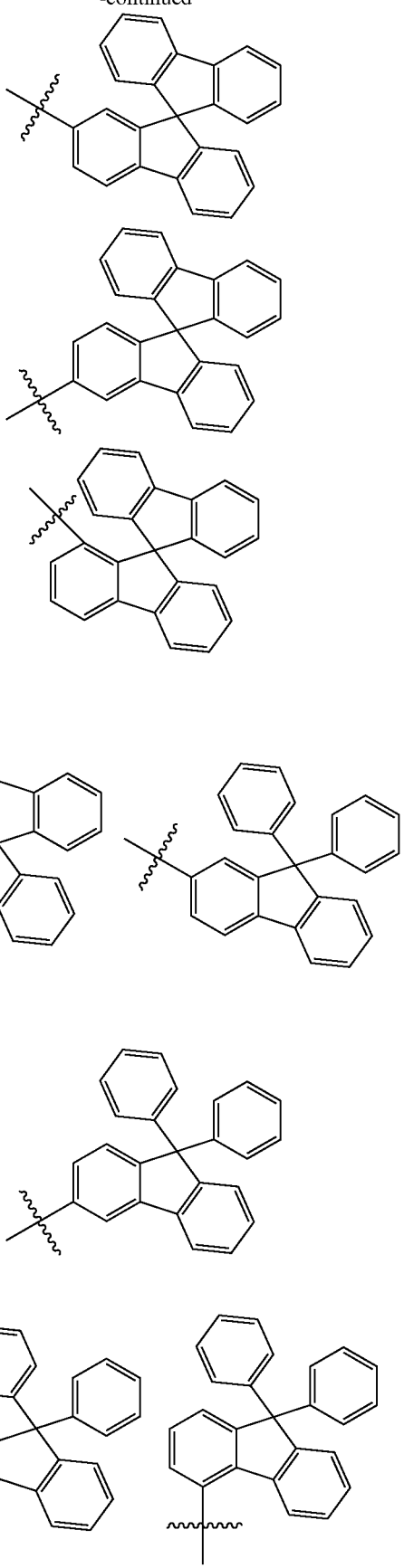

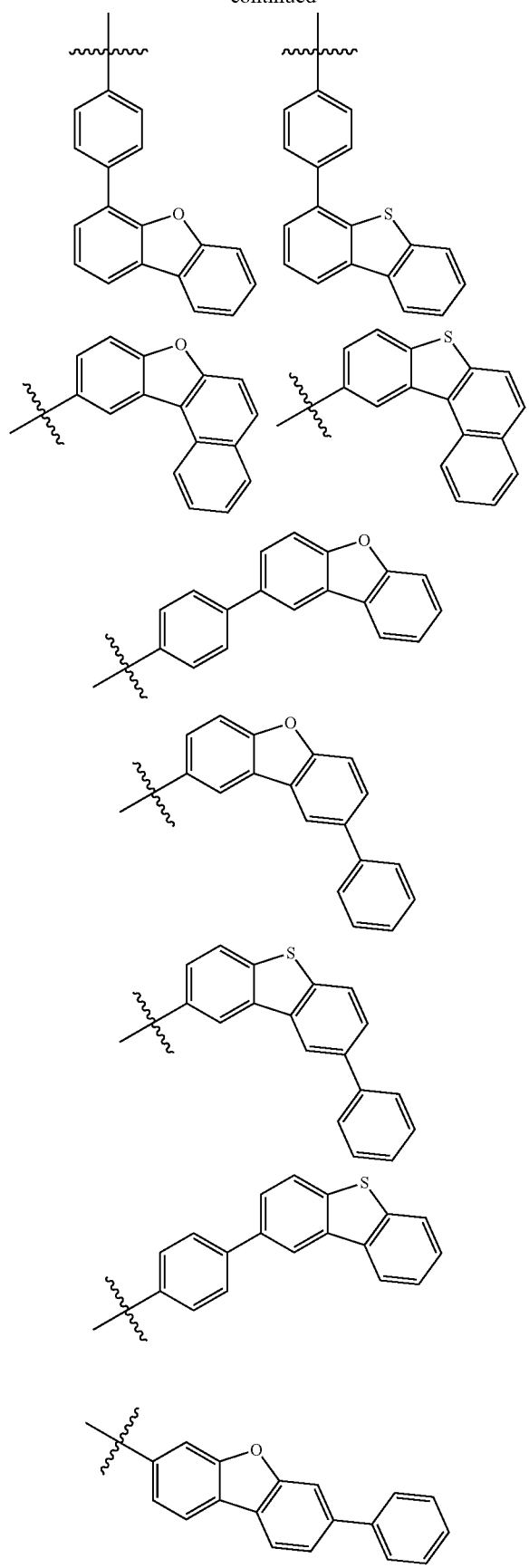
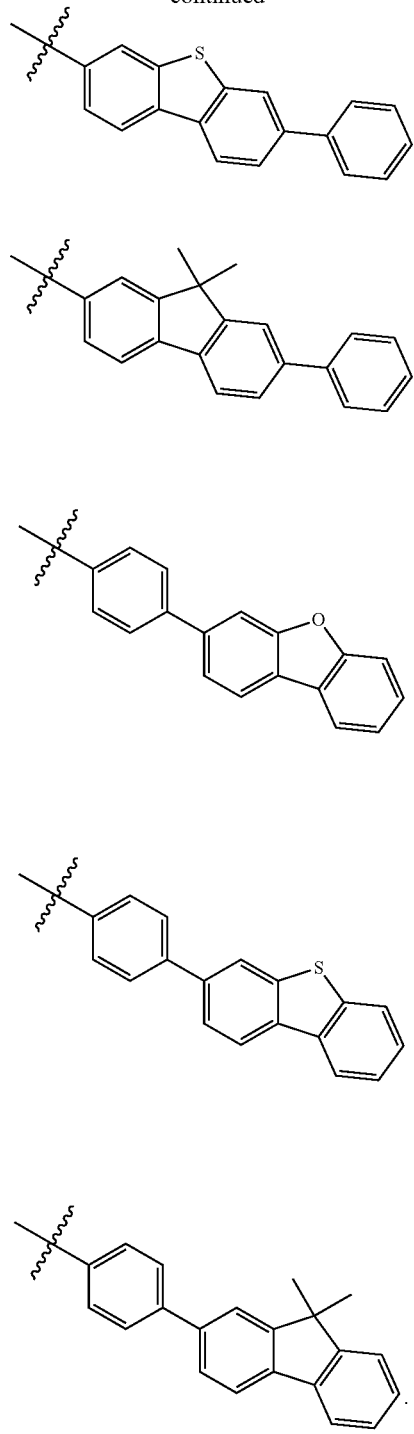

Further, $R_1$ may be hydrogen; deuterium; a halogen; a cyano; a nitro; a $C_{1-20}$ alkyl; or a $C_{6-20}$ aryl.

For example, $R_1$ may be hydrogen, deuterium, a halogen, a cyano, a nitro, a methyl, or a phenyl, and a1 may be 0 or 1.

Herein, a1 represents the number of $R_1$, and when a1 is 2 or more, two or more of R1 may be the same as or different from each other. The description of n1 to n3 and m1 to m3 can be understood with reference to the description of a1 and the structure of Chemical Formula 1.

Meanwhile, the compound can be represented by the following Chemical Formula 1A or 1B:
[Chemical Formula 1A]
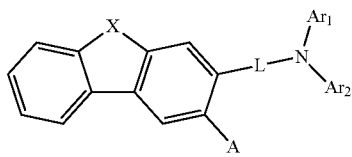
[Chemical Formula 1B]
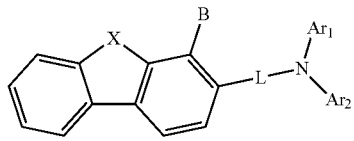
wherein, in Chemical Formula 1A and 1B,
X, A, B, L, $Ar_1$, and $Ar_2$ are the same as defined in Chemical Formula 1 above.
For example, the compound may be any one selected from the group consisting of the following:
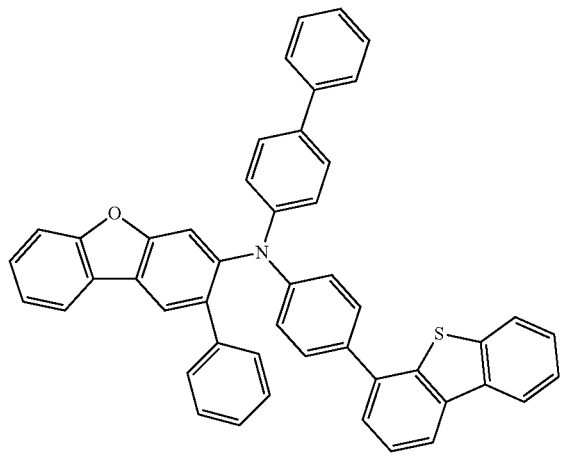
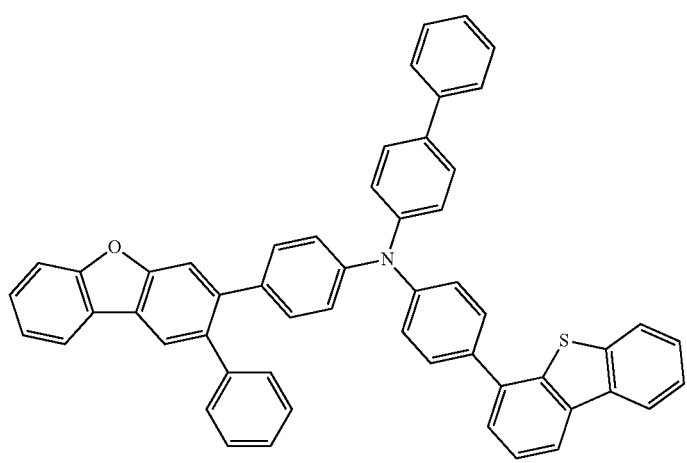

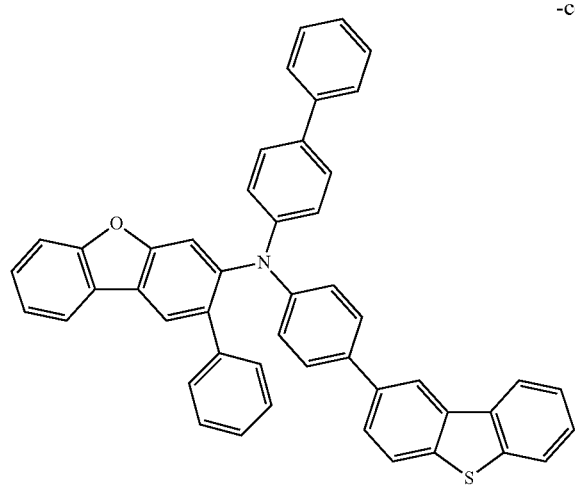
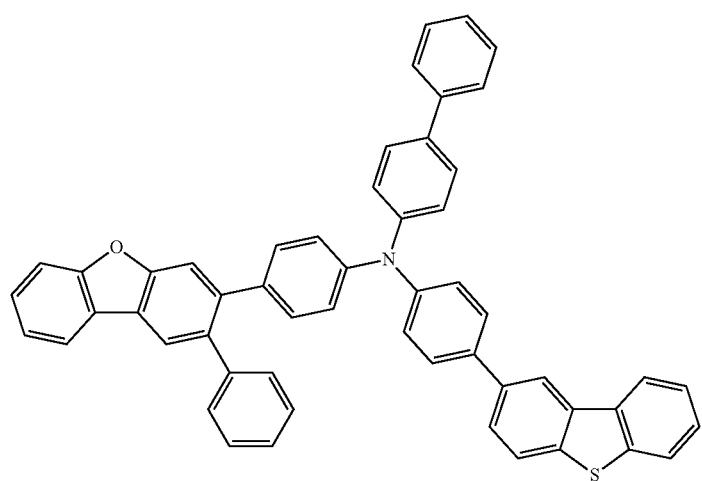
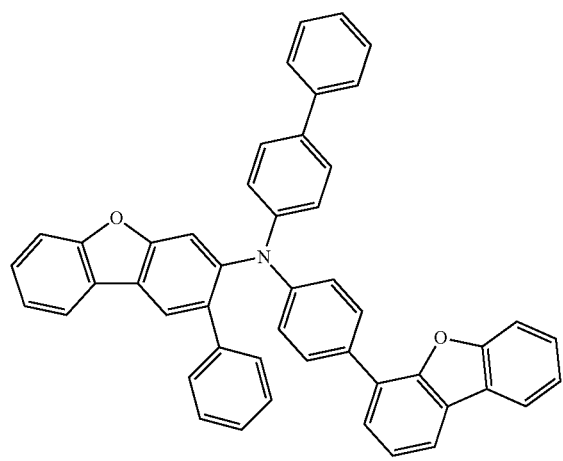

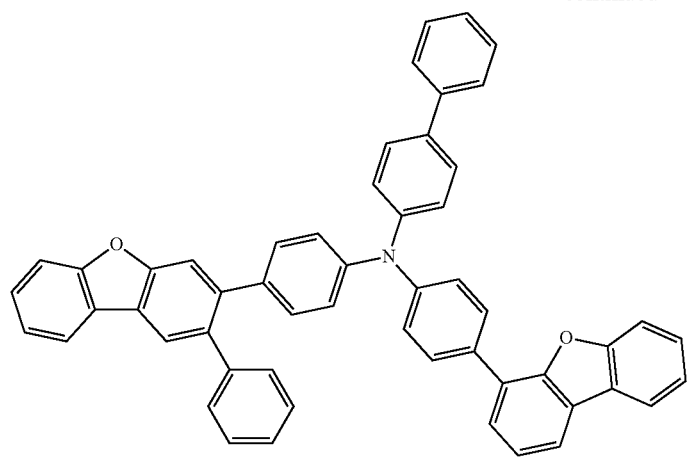
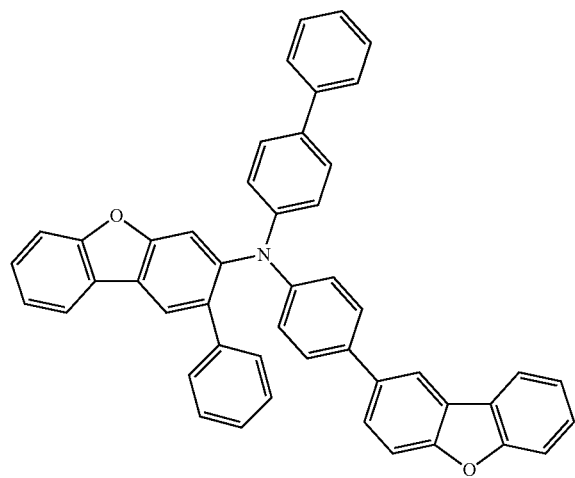
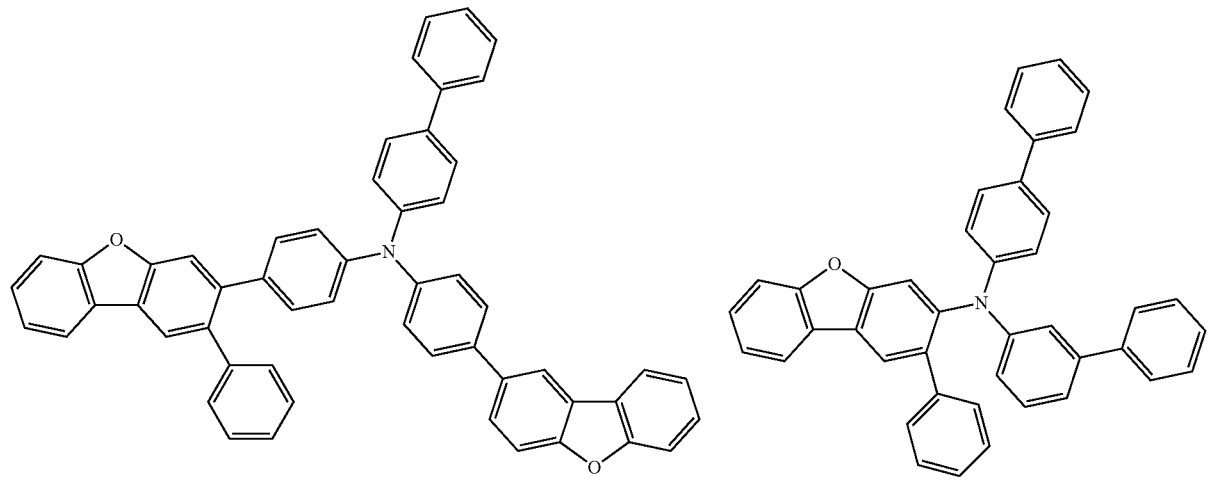

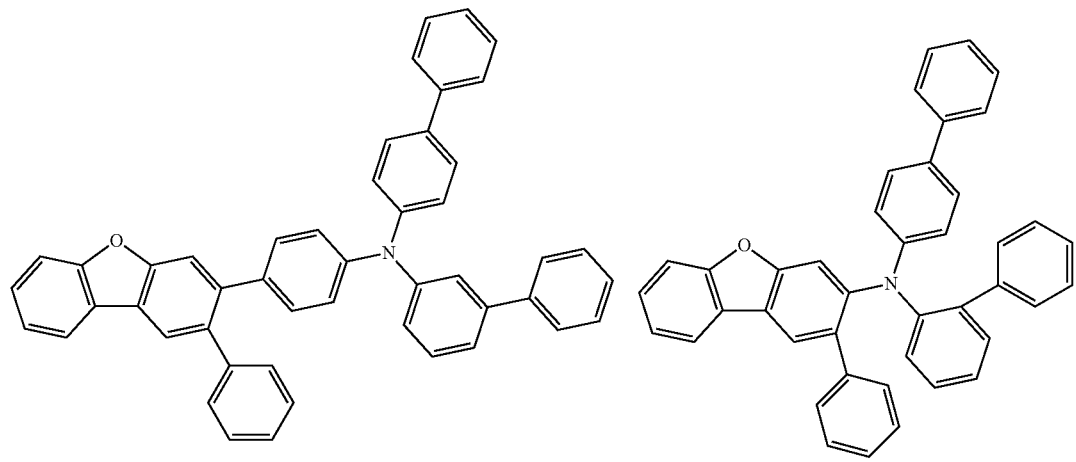
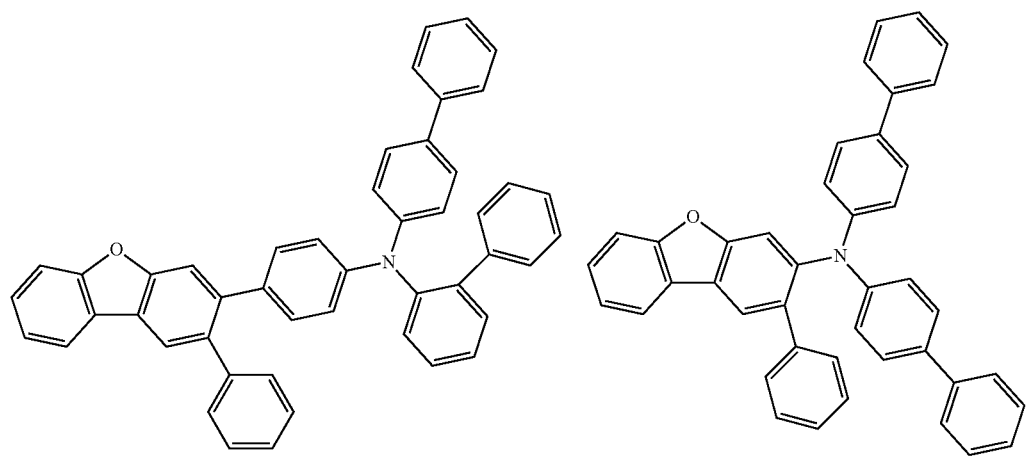
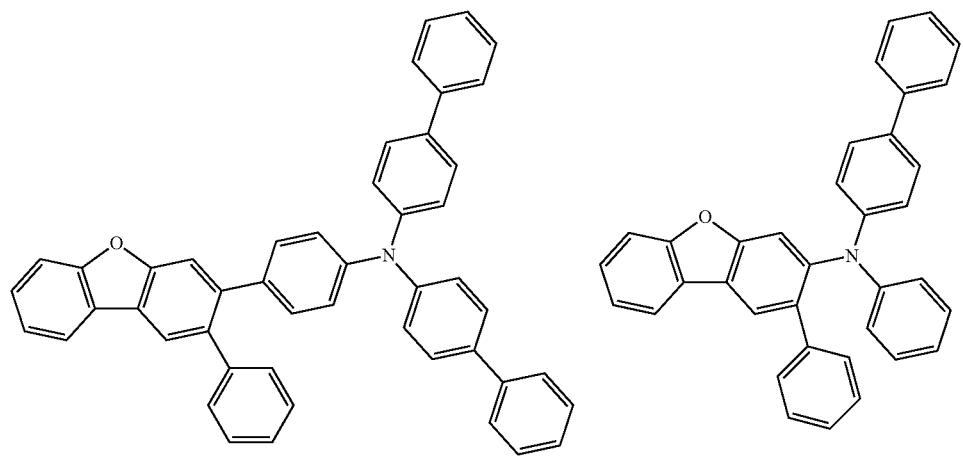

-continued
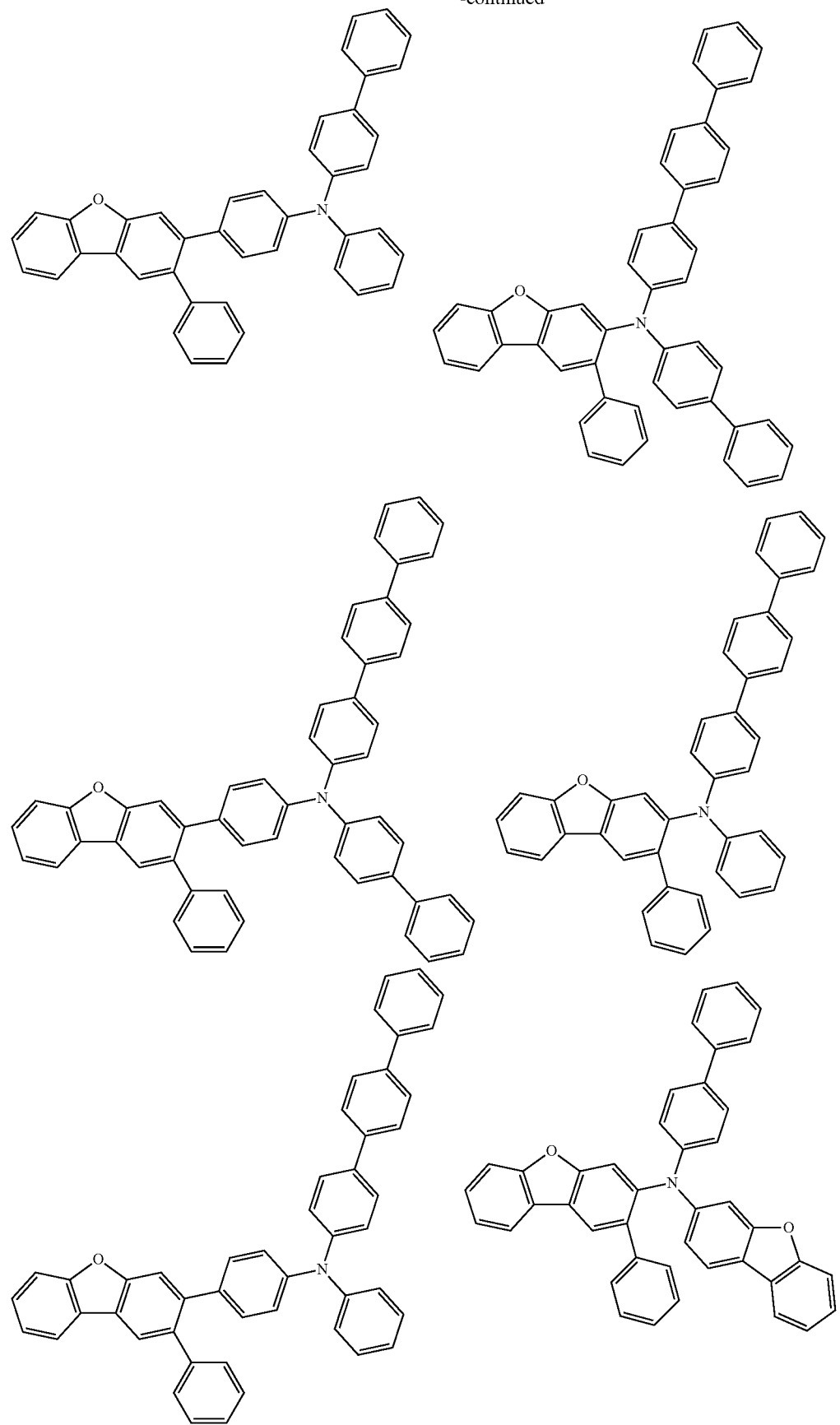

-continued
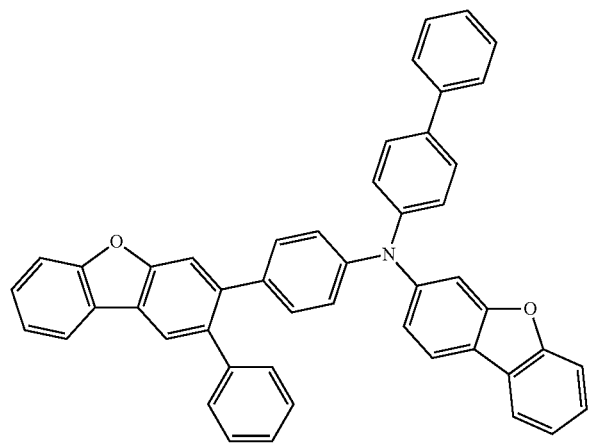
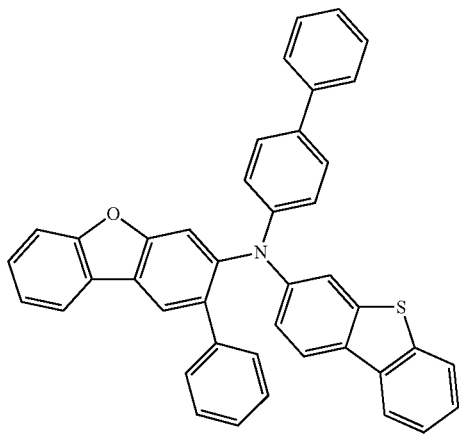
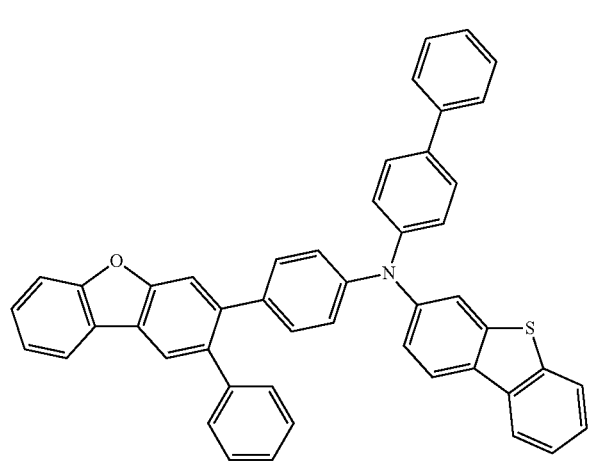
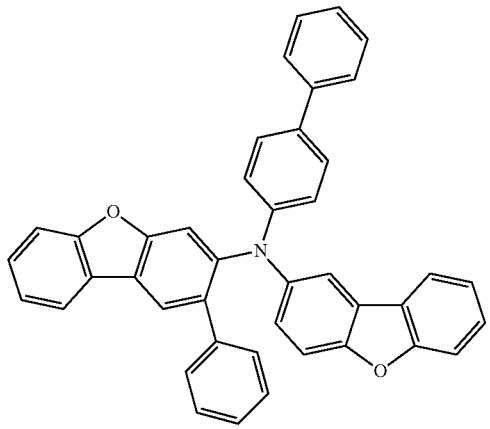
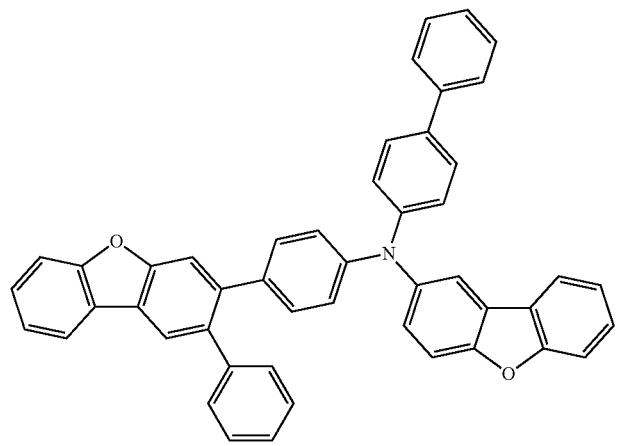
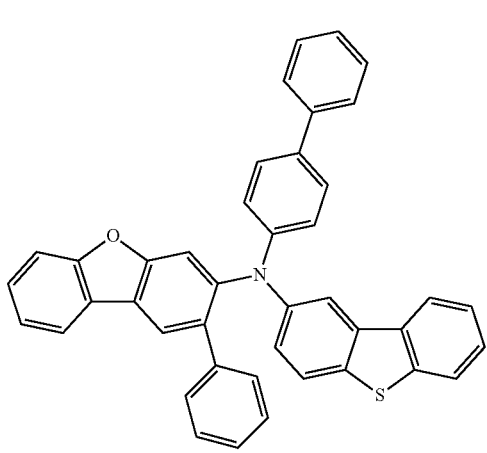

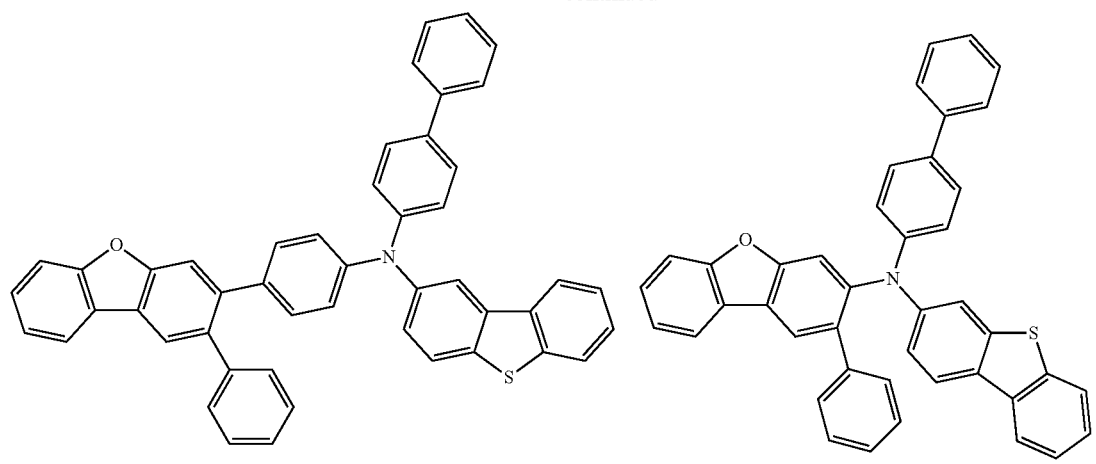
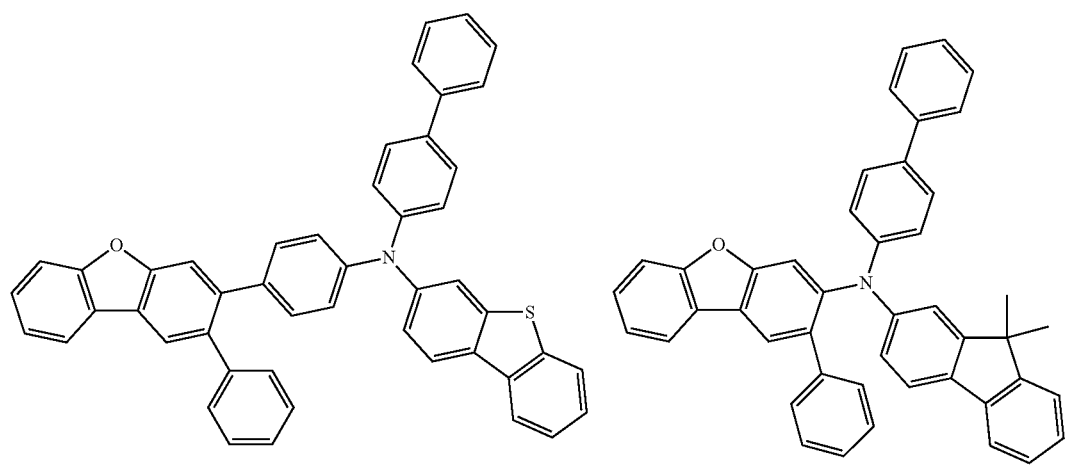
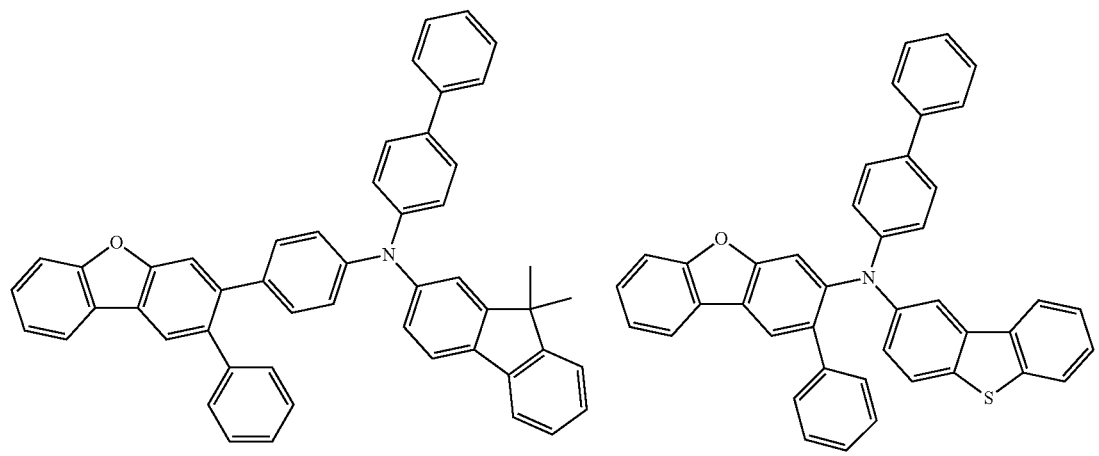

-continued
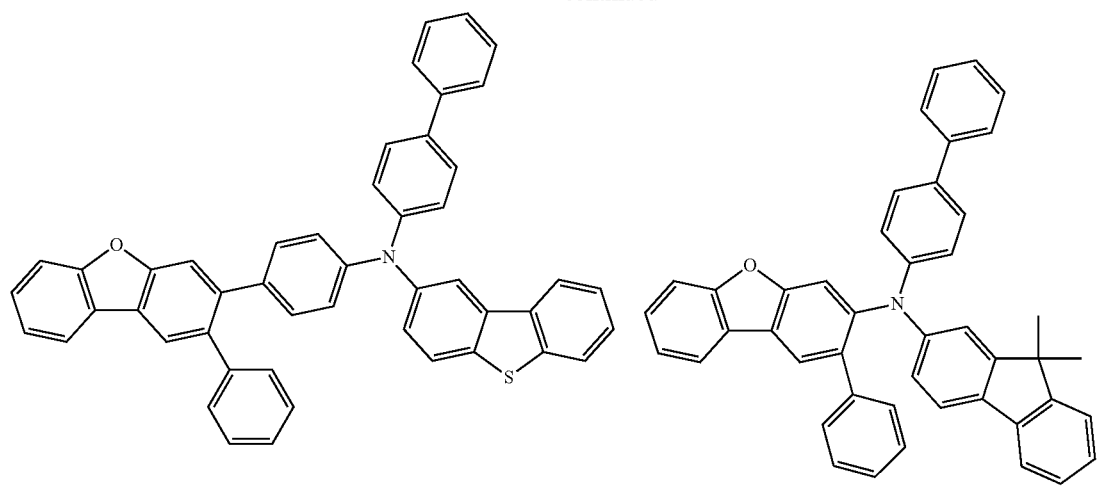
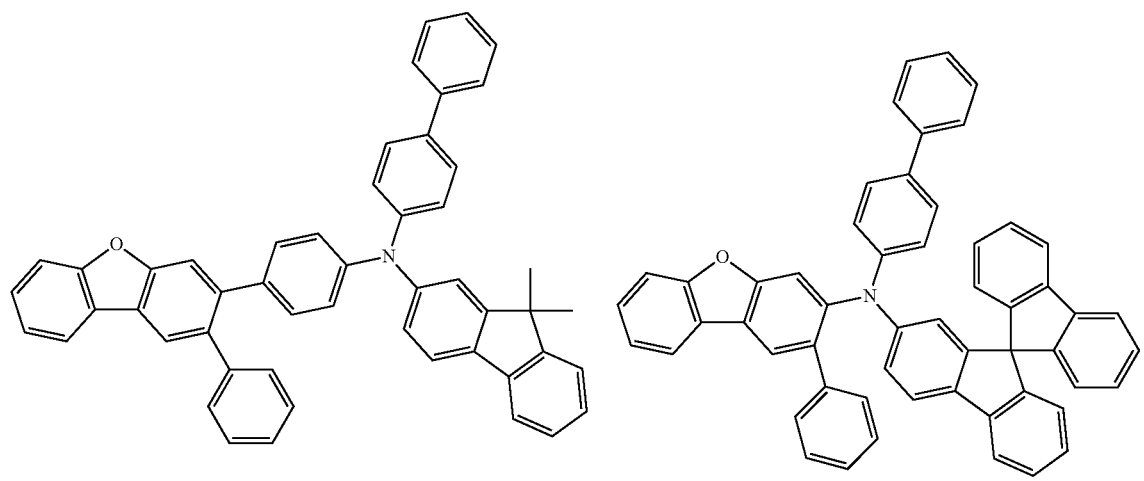
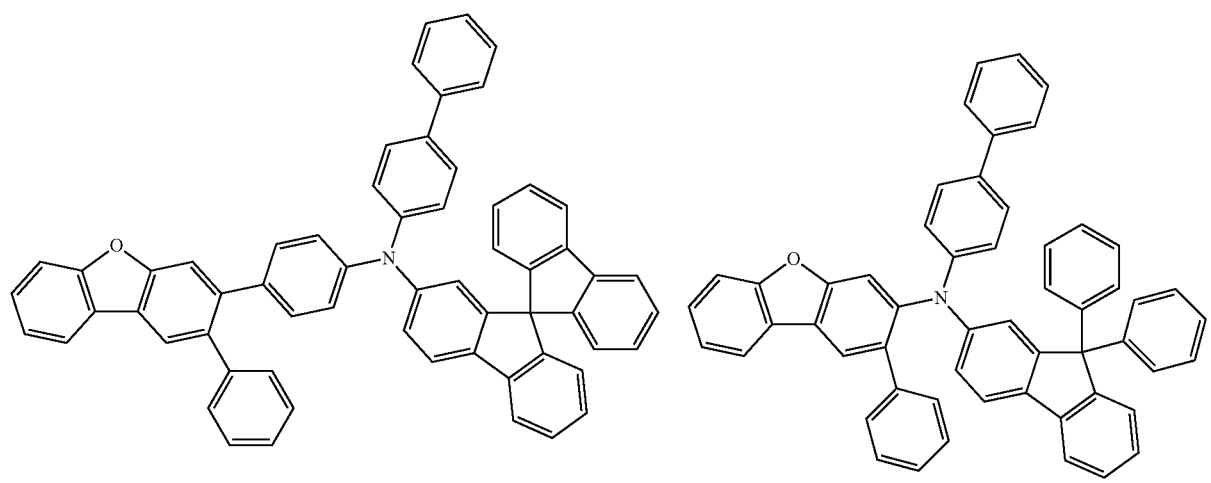

-continued
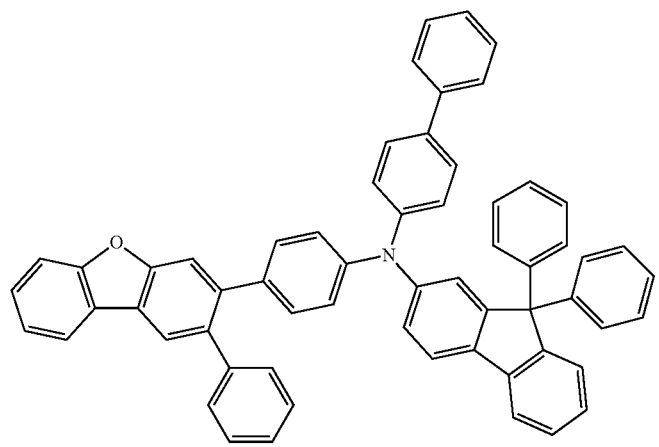
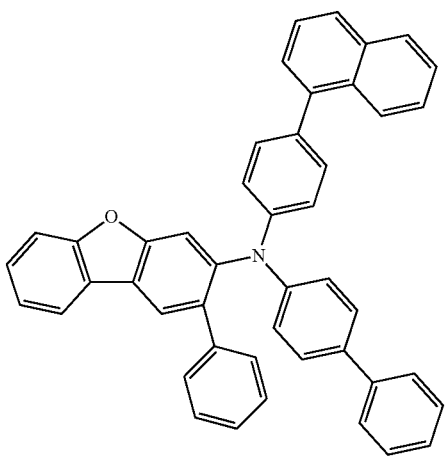
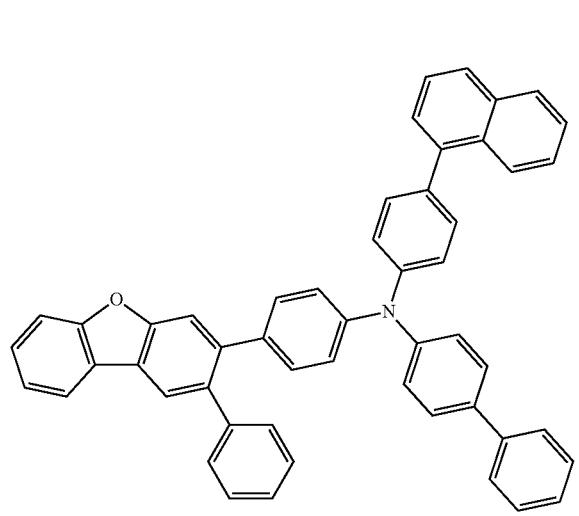
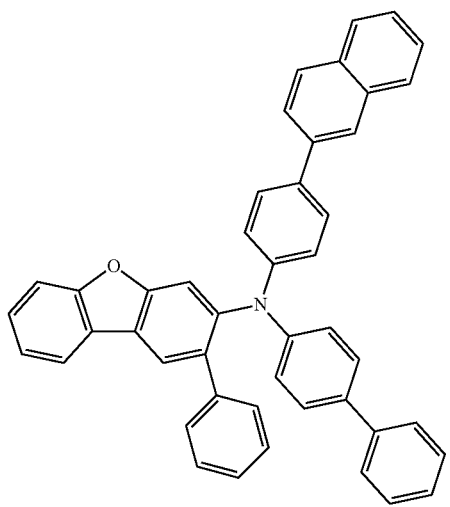
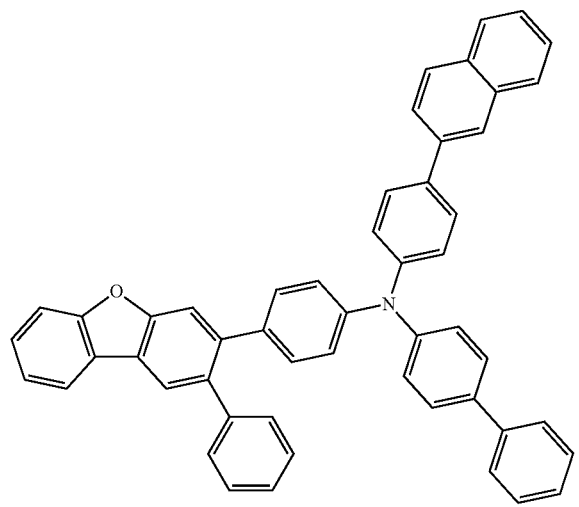
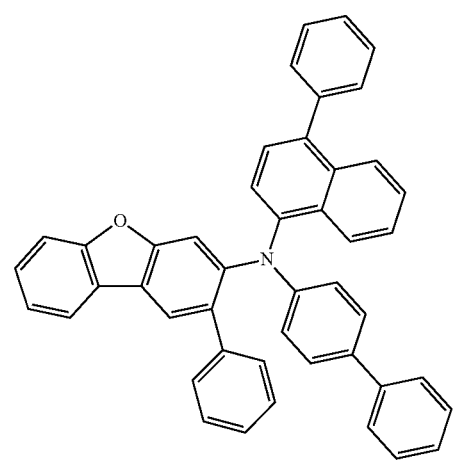

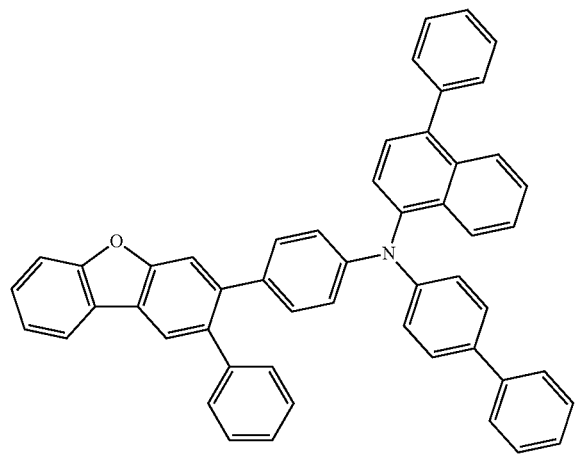
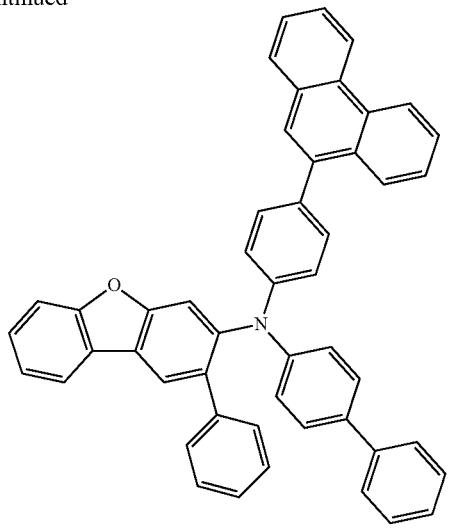
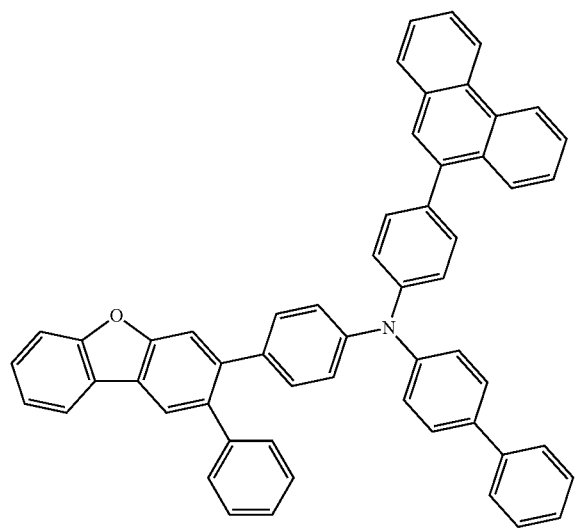
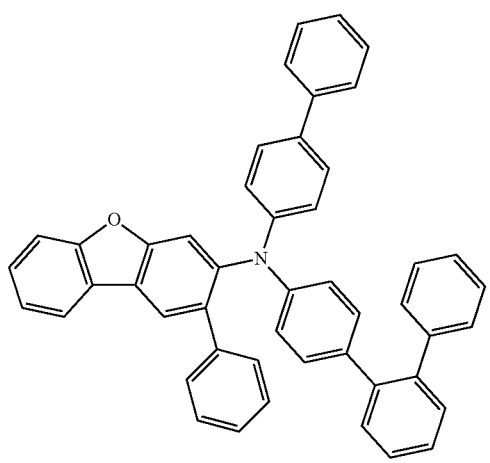
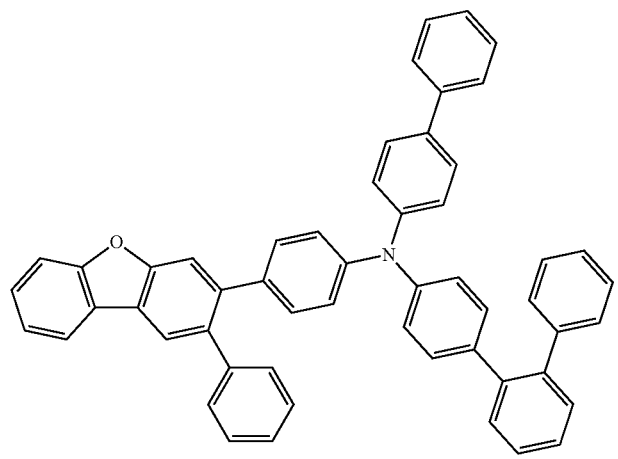
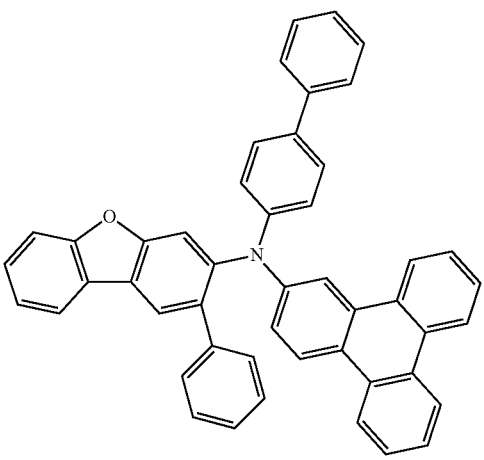

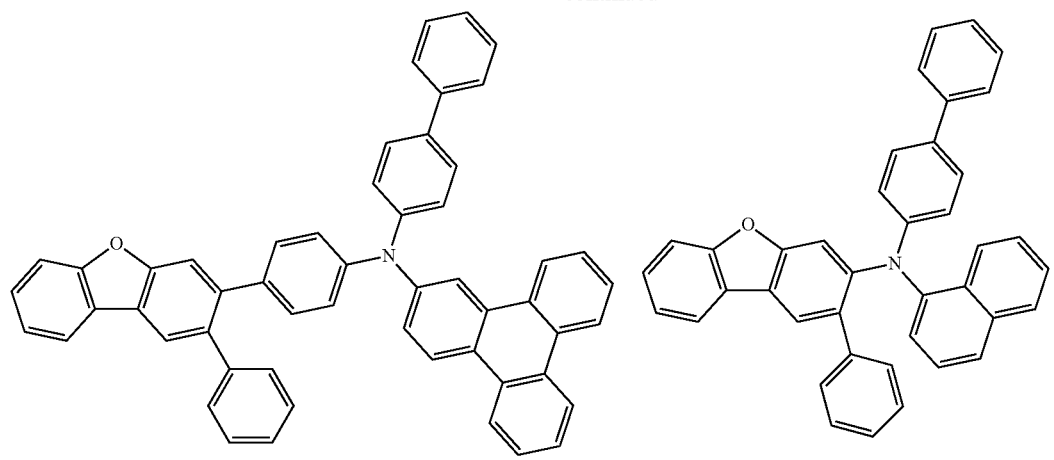
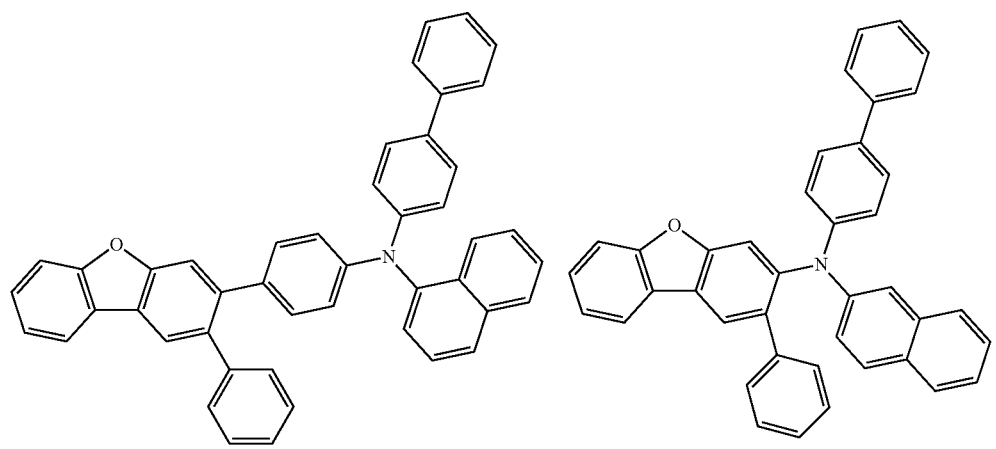
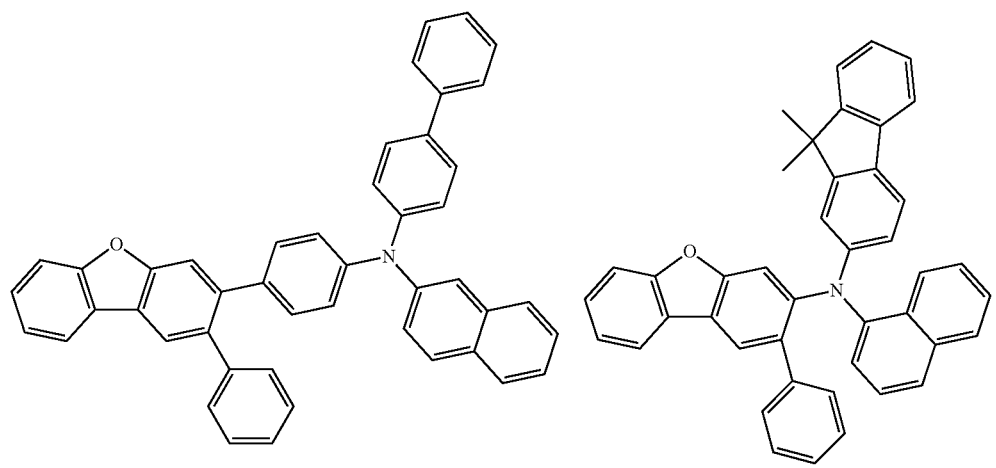

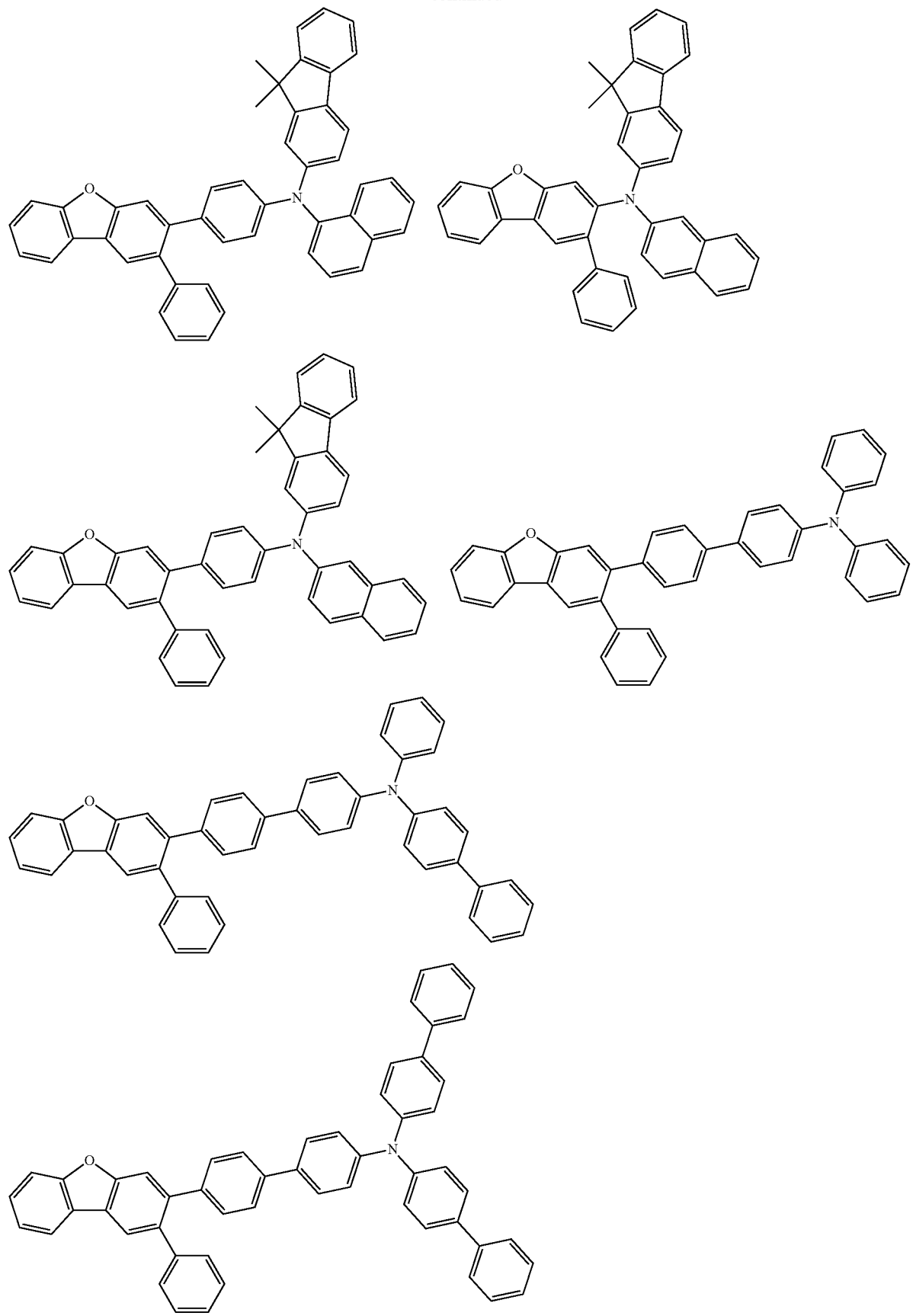

-continued
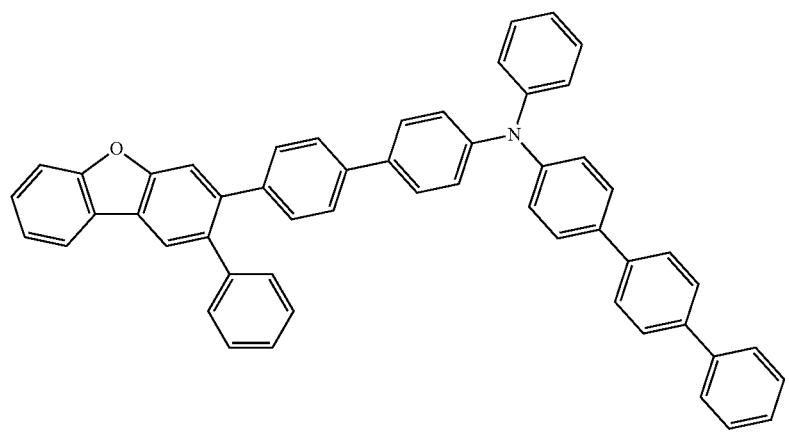
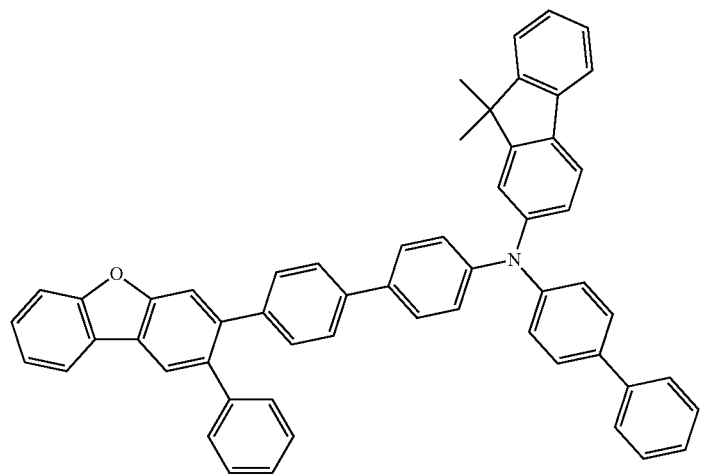
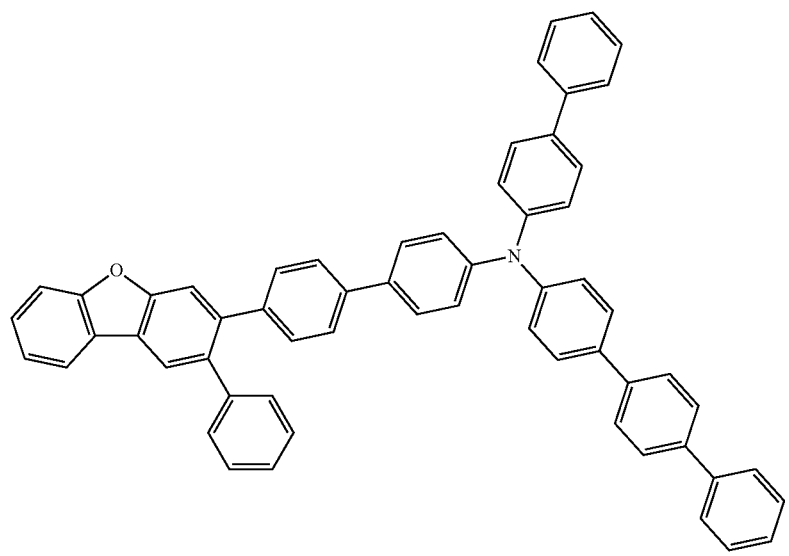

-continued
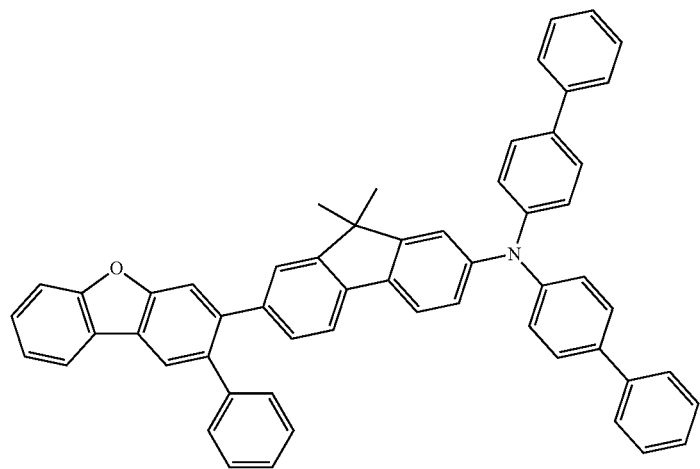
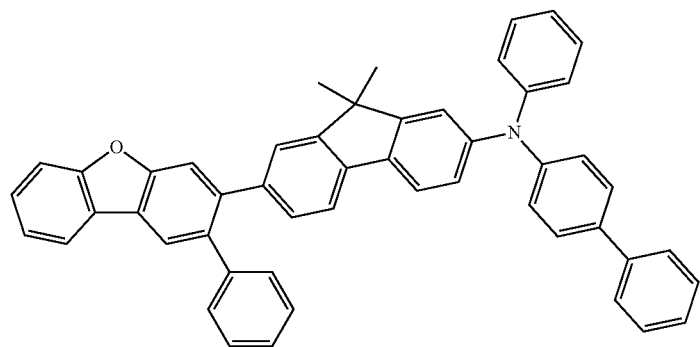
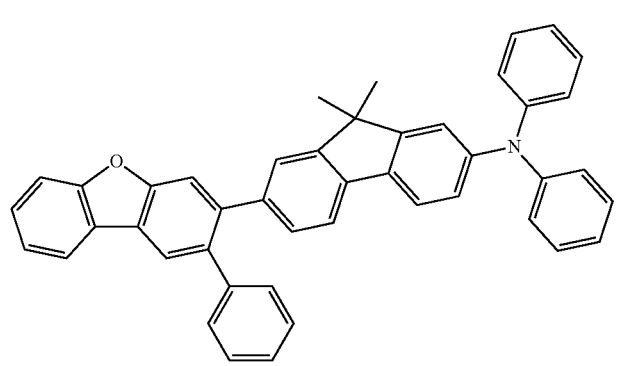
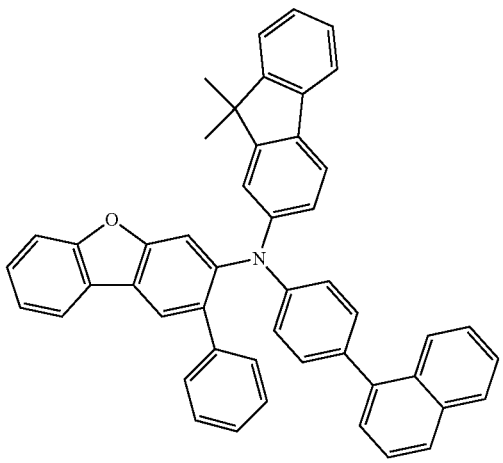

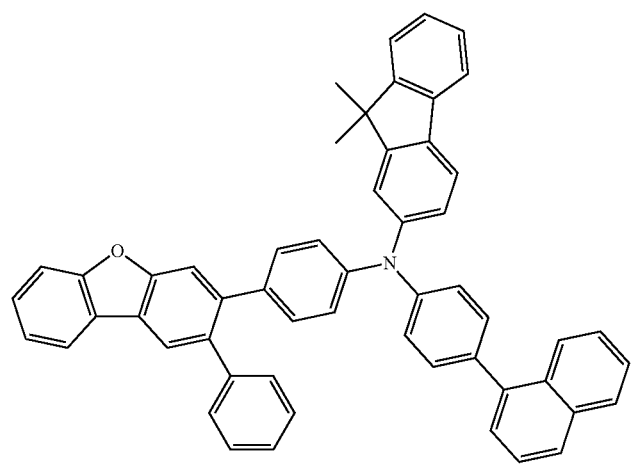
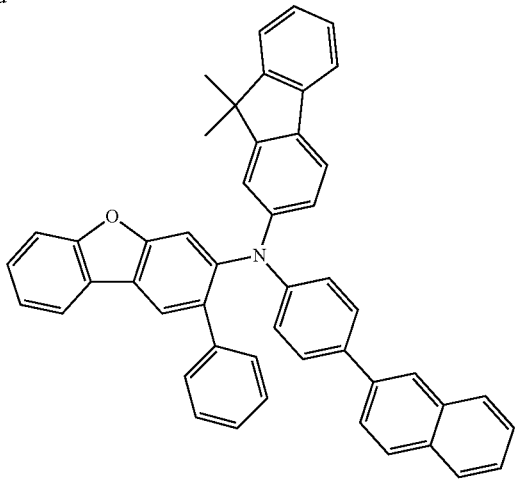
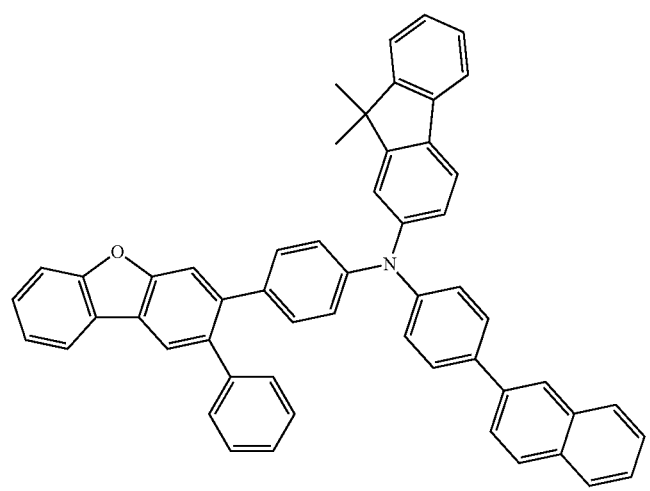
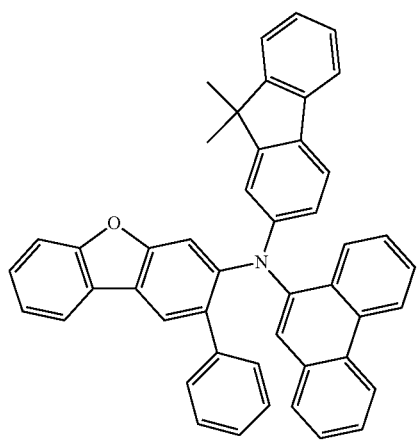
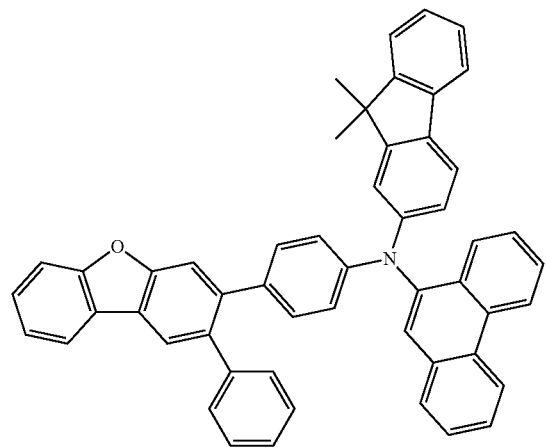
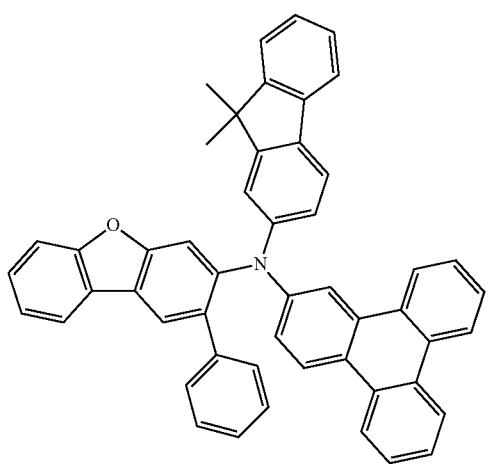

-continued
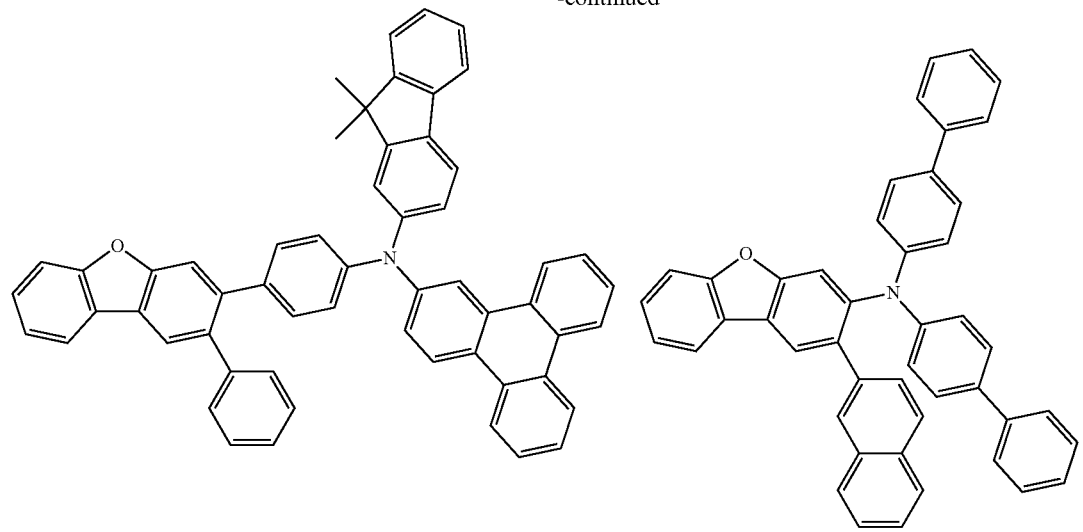
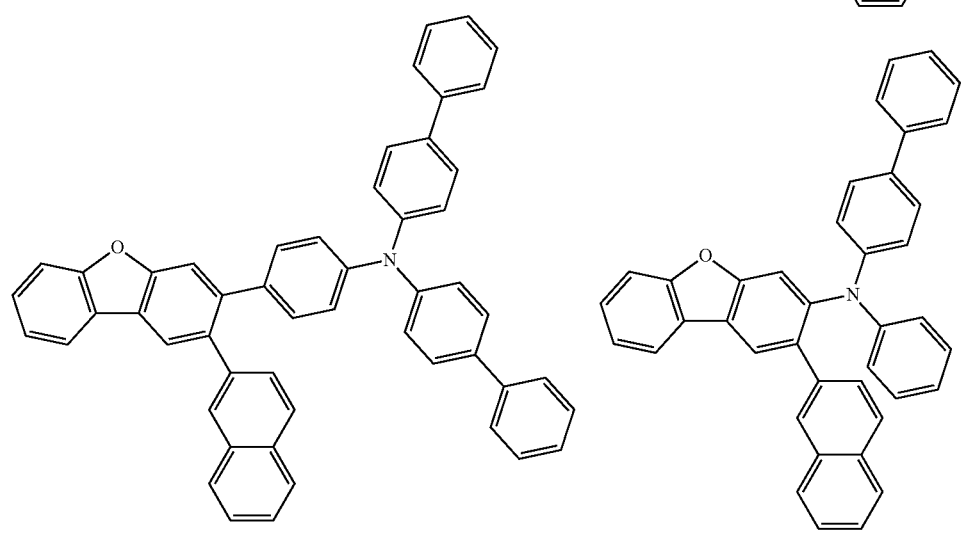
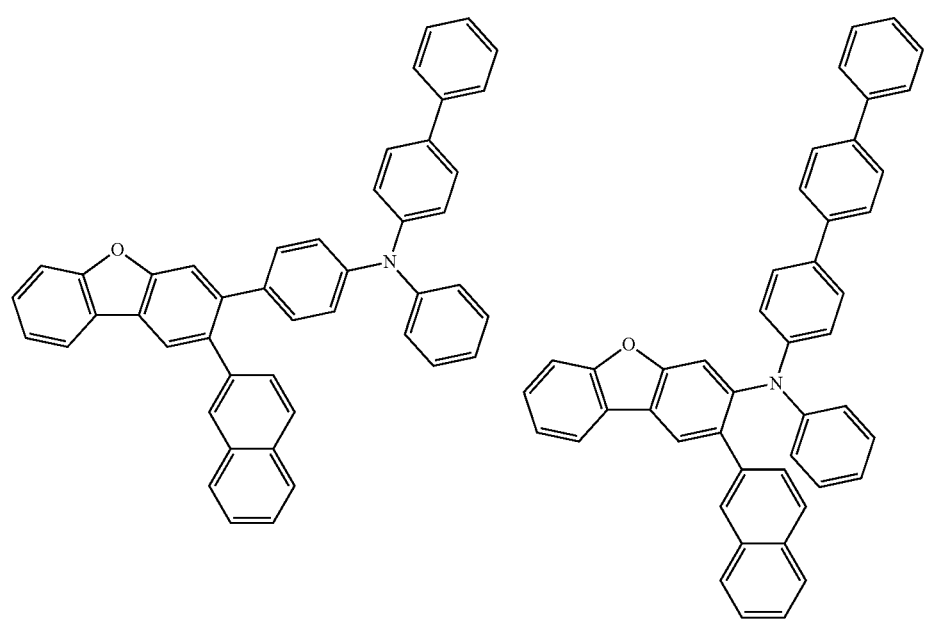

-continued
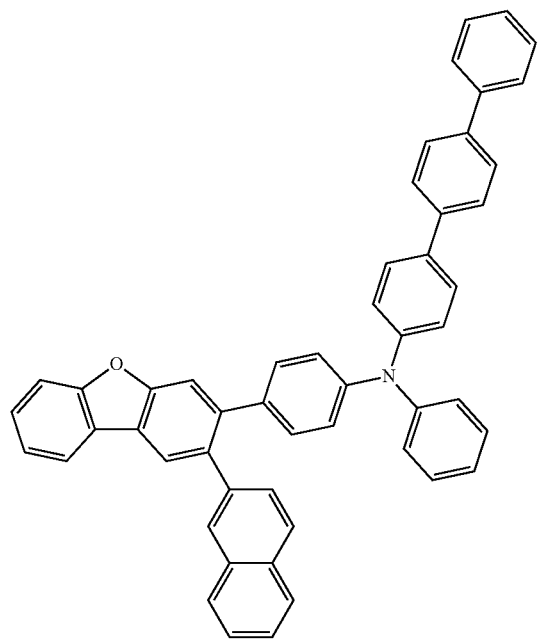
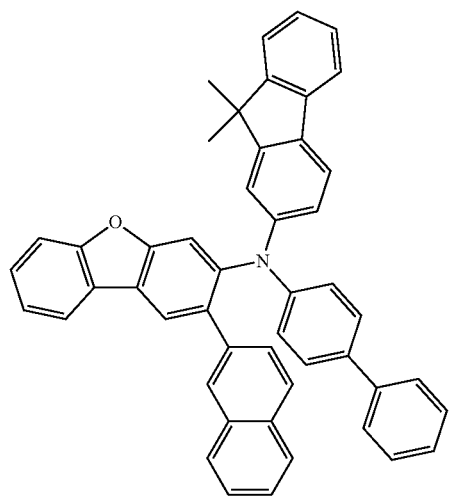
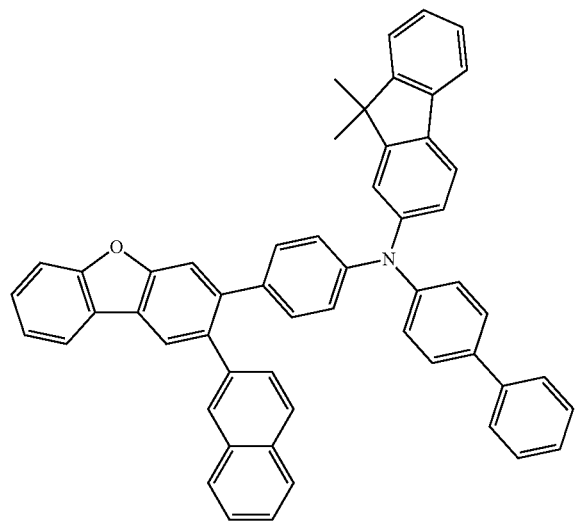
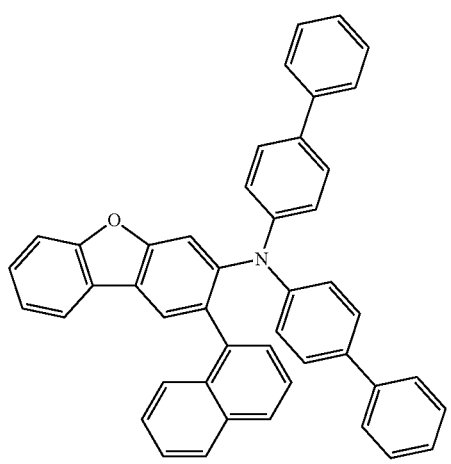
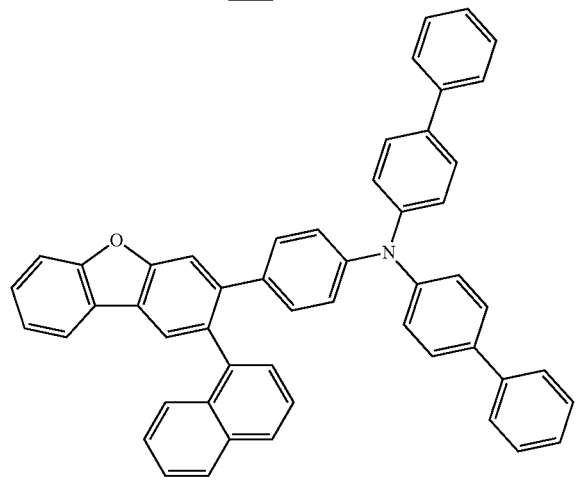
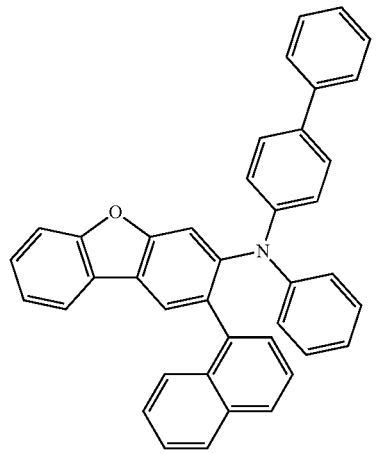

-continued
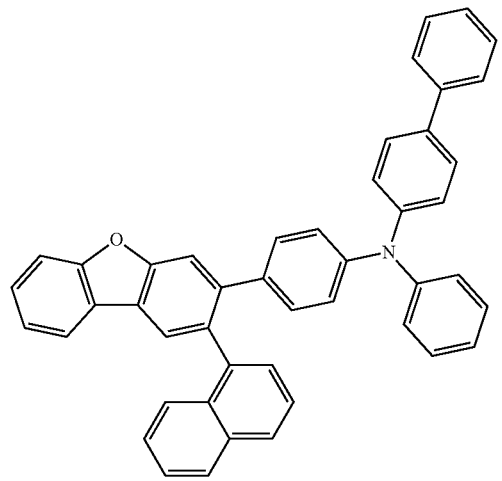
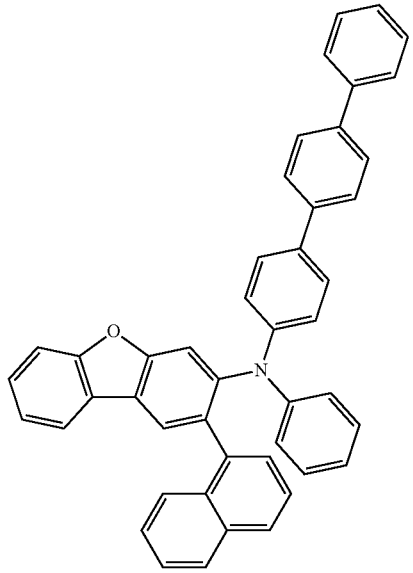
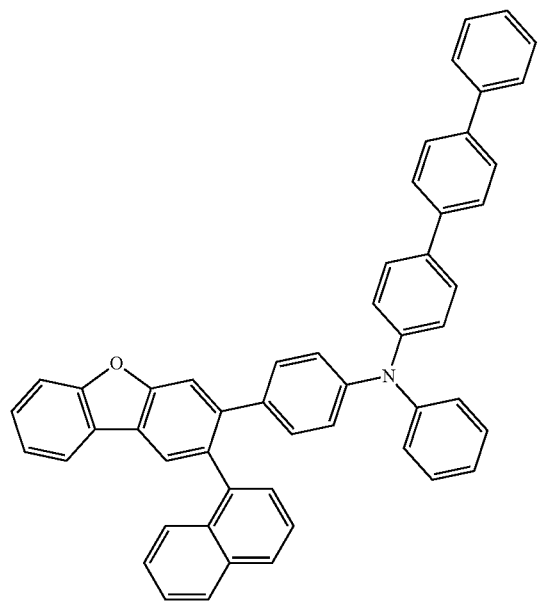
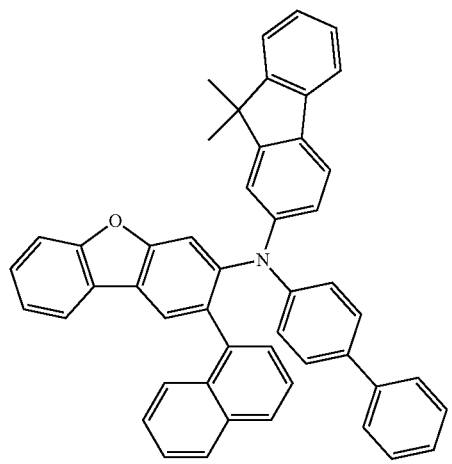
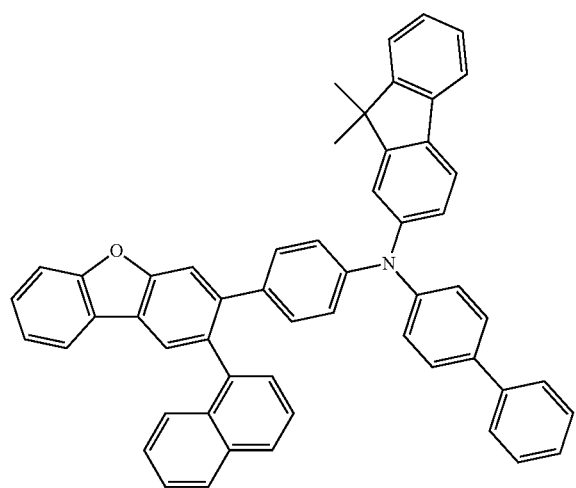
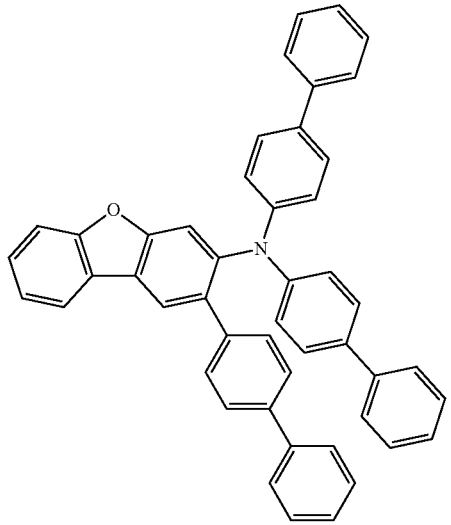

53 54
-continued
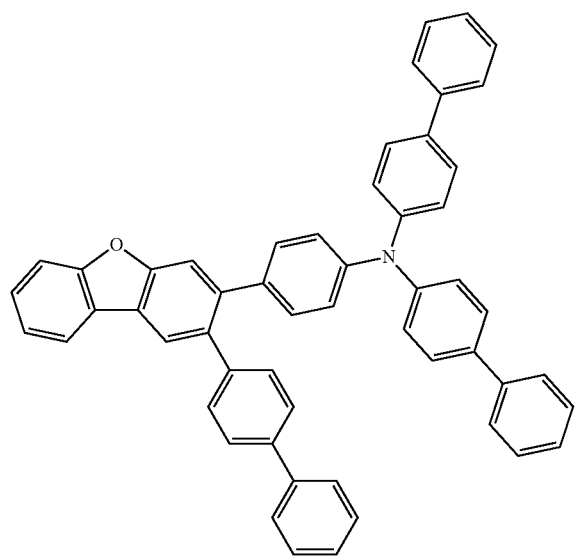
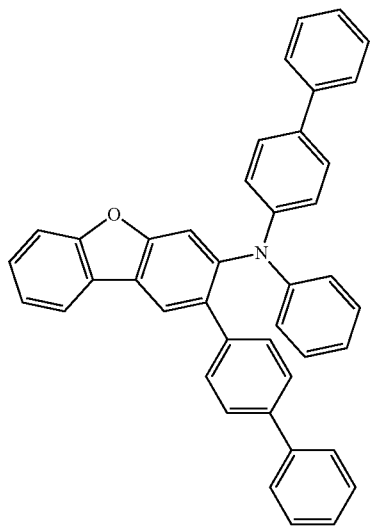
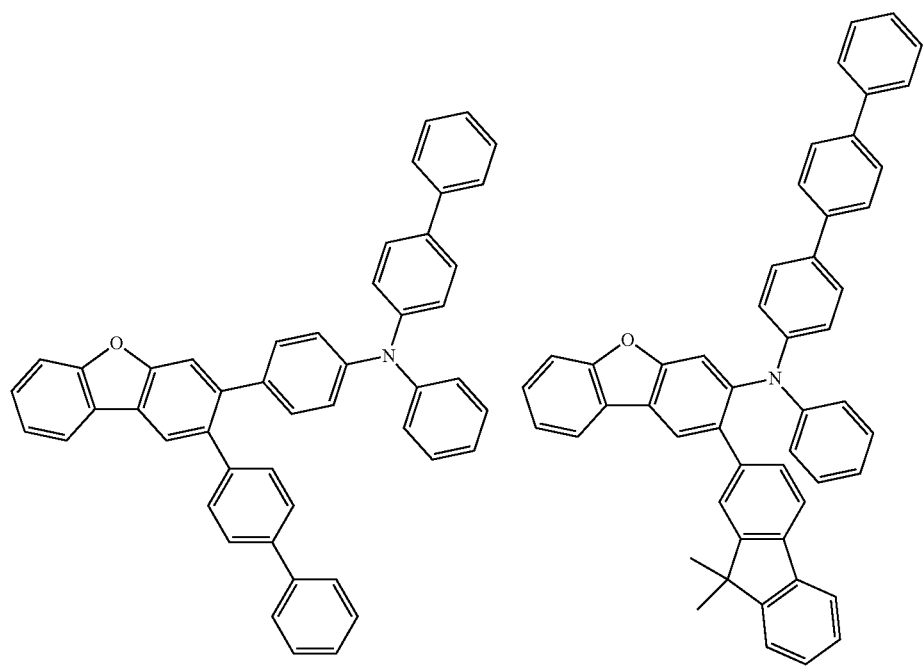

-continued
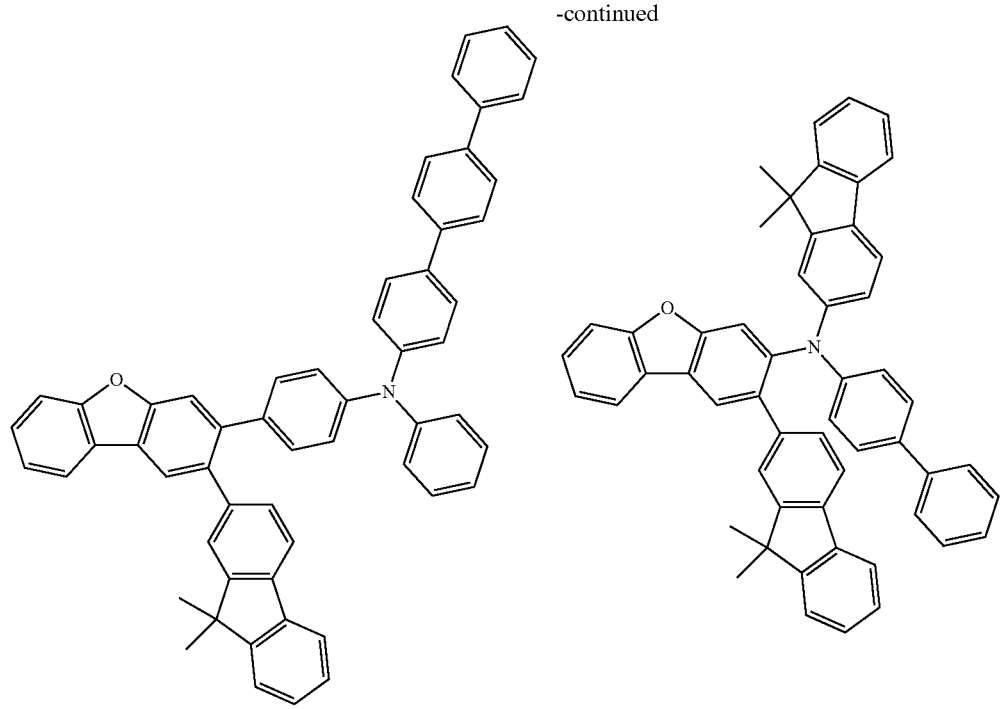
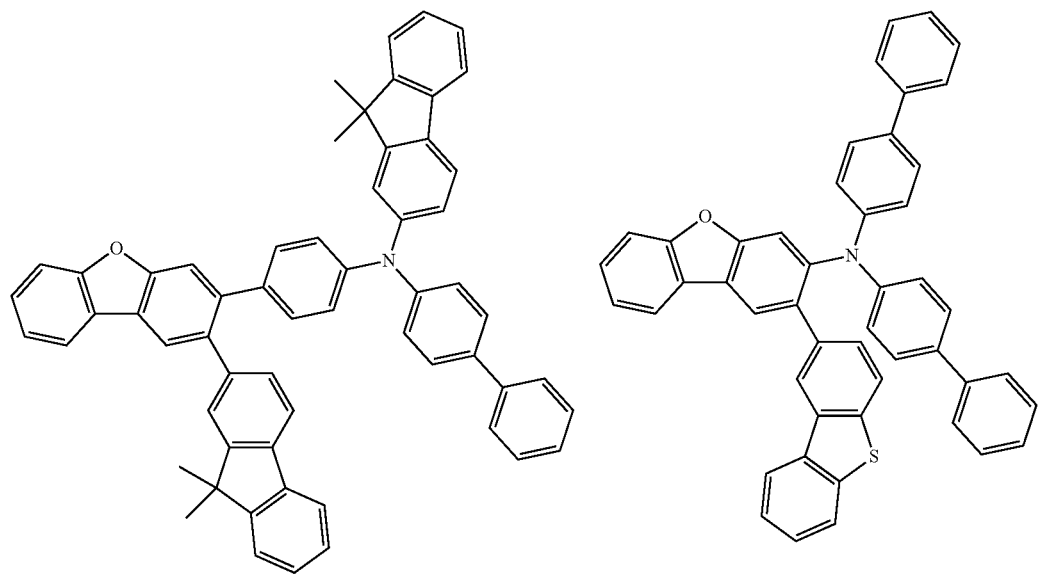

-continued
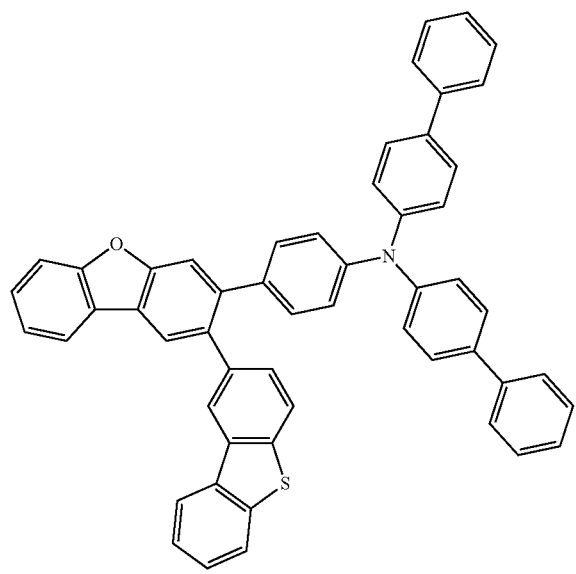
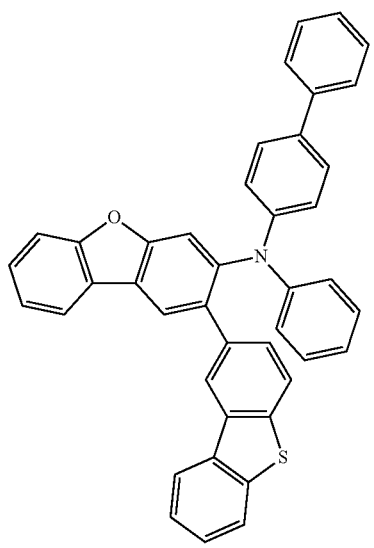
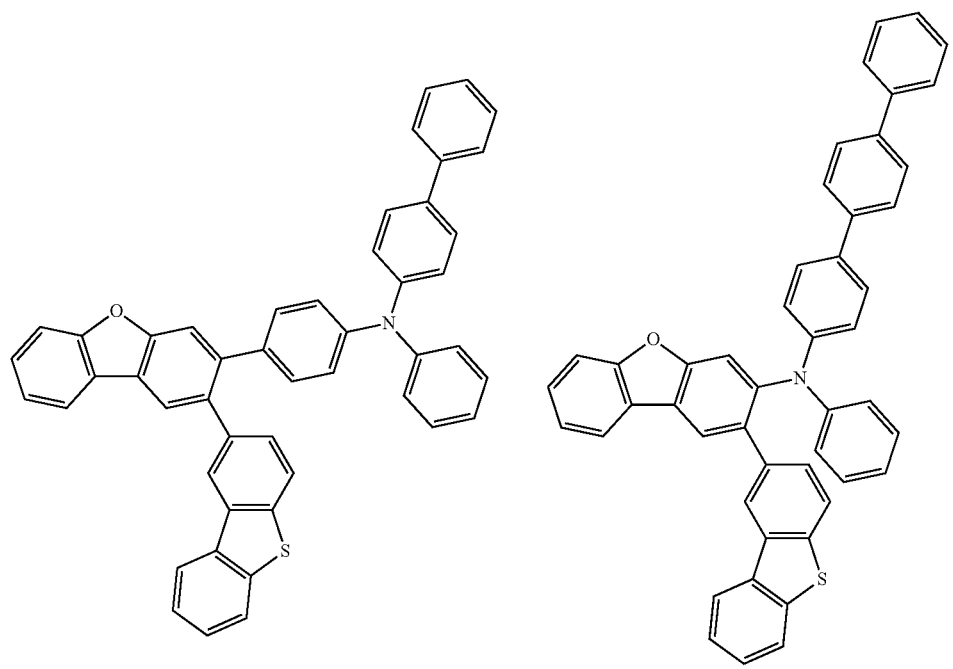

-continued
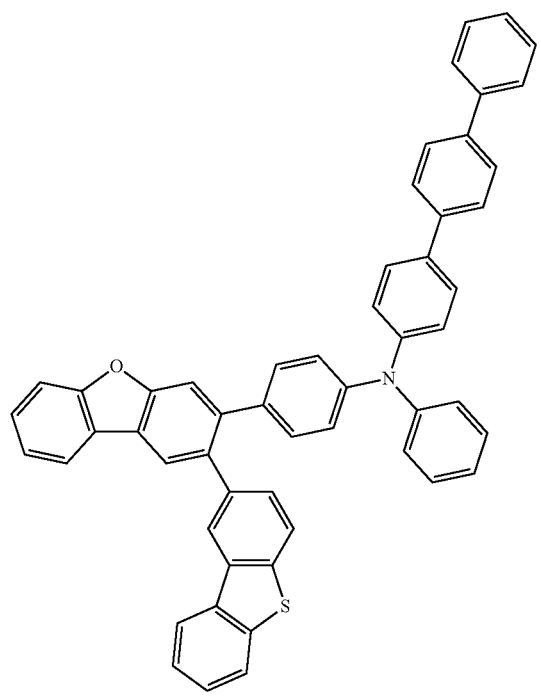
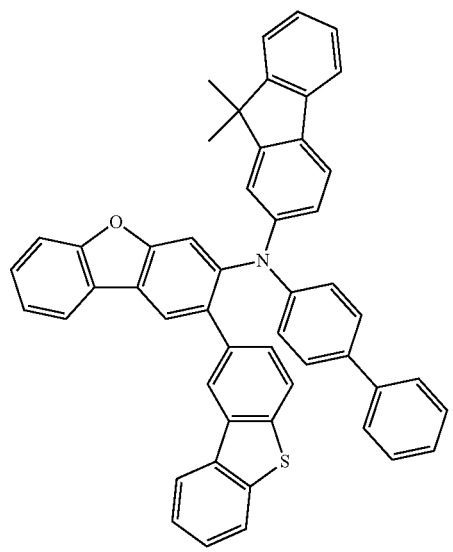
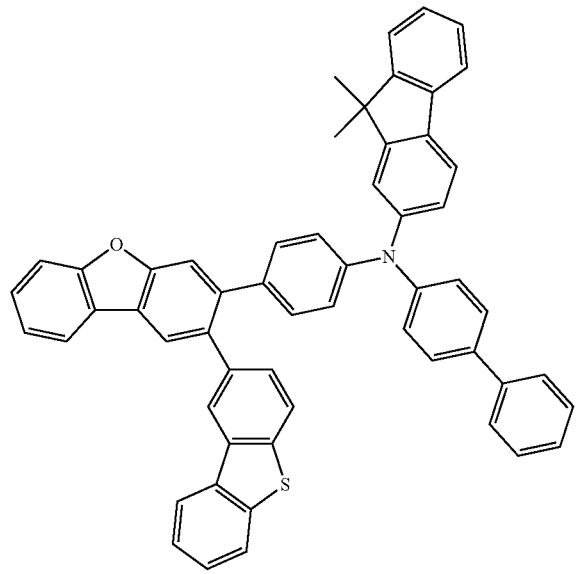
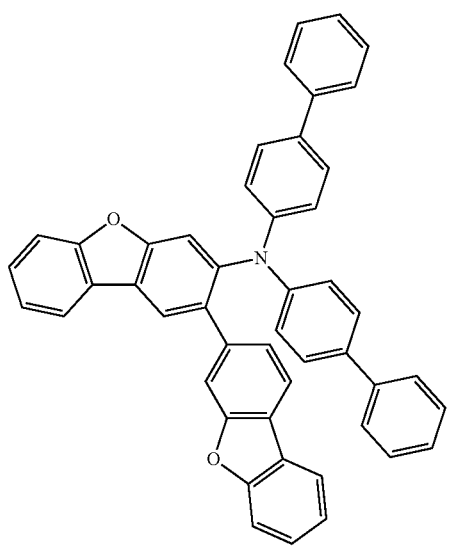

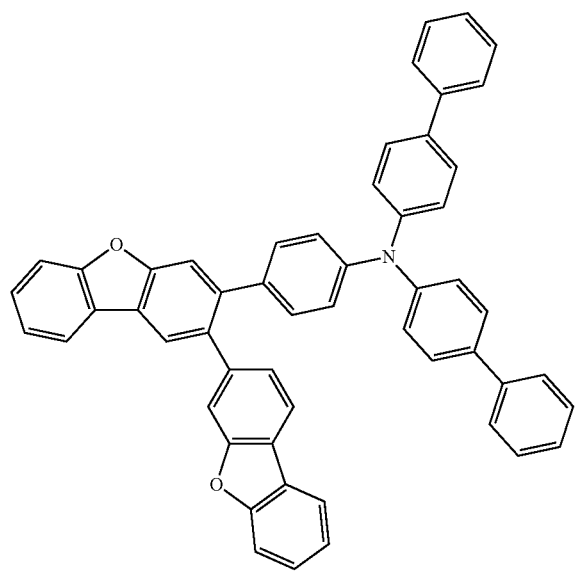
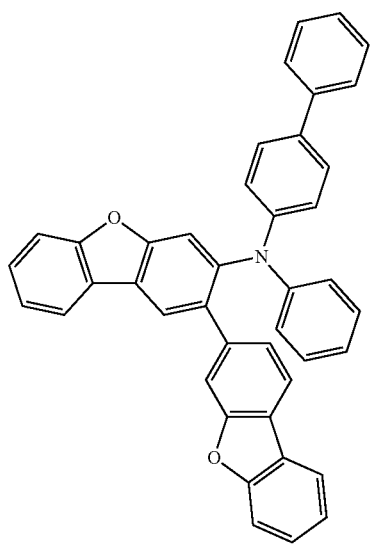
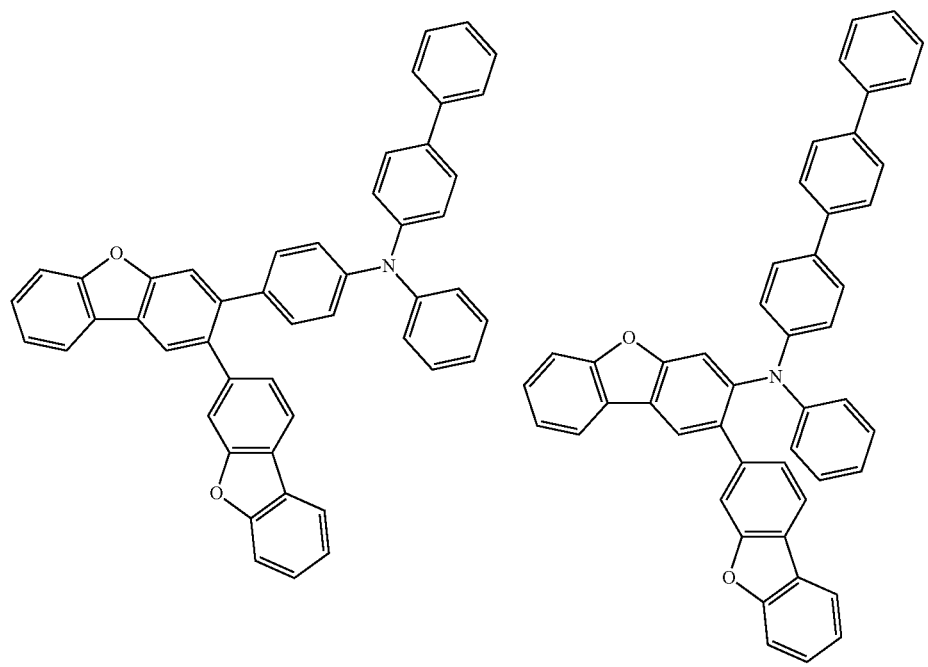

-continued
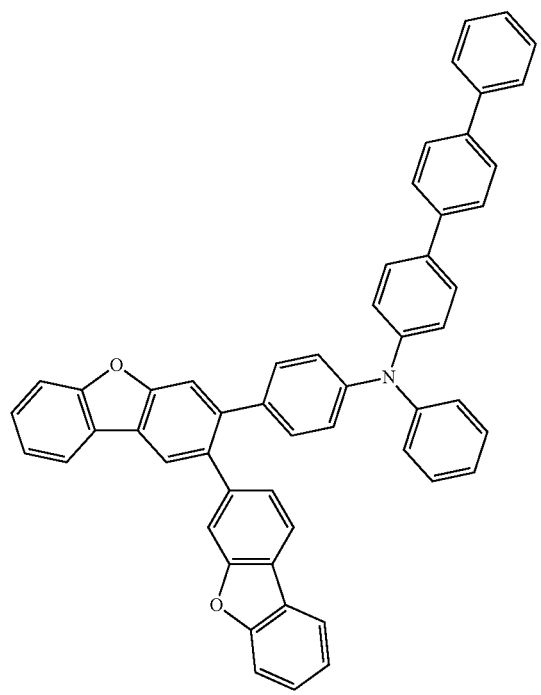
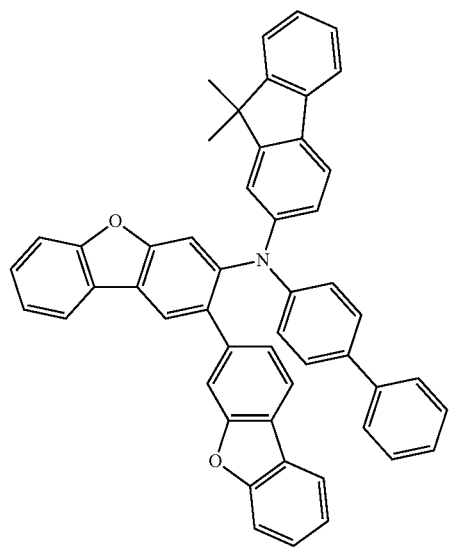
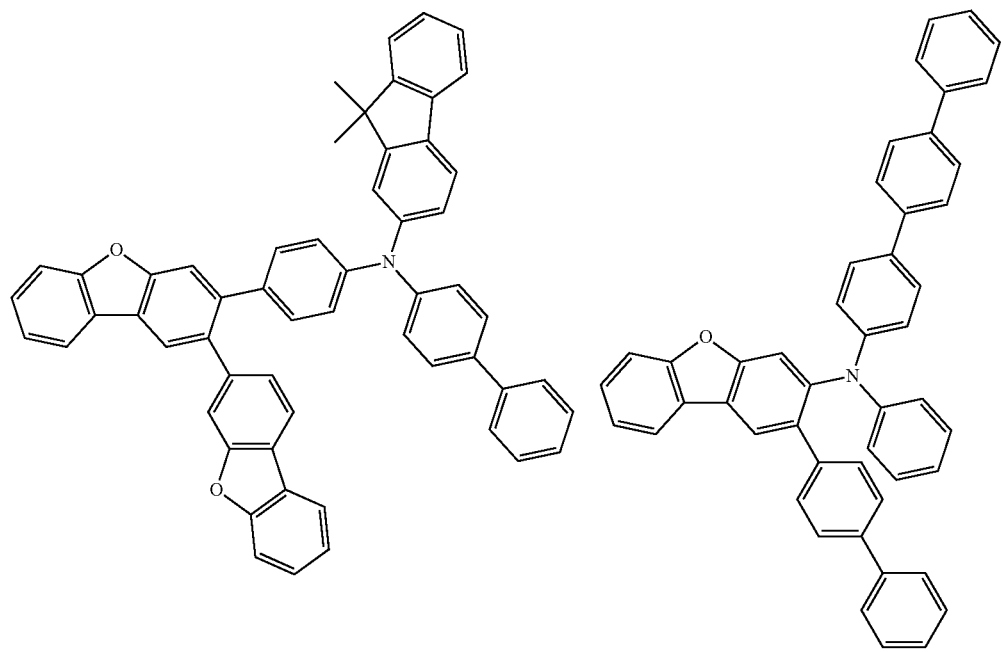

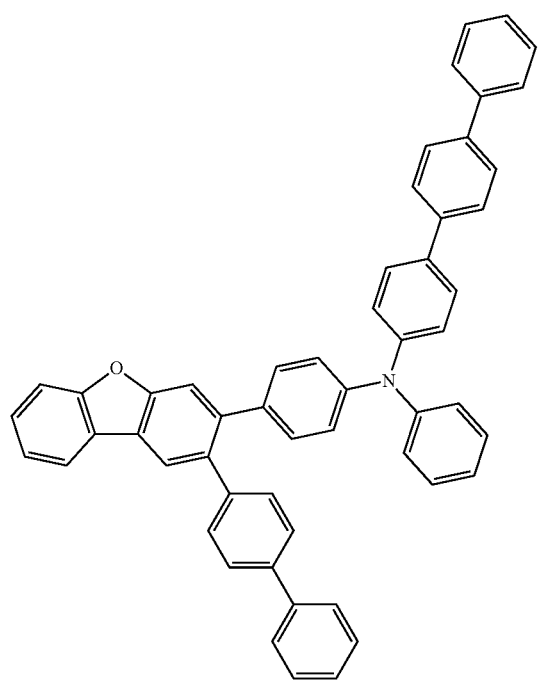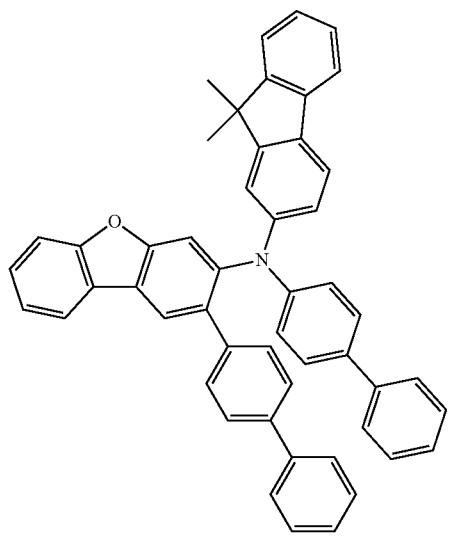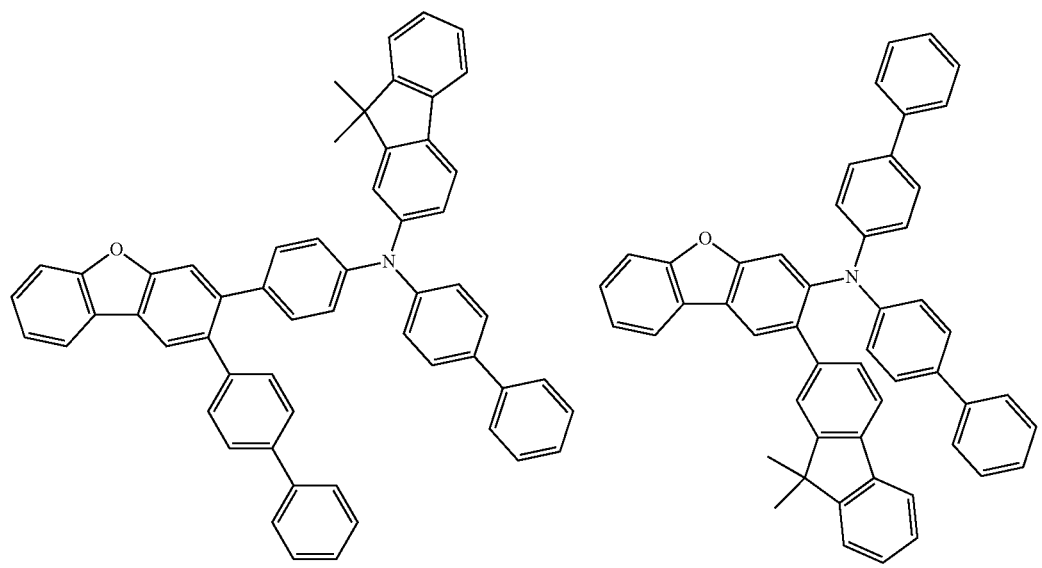

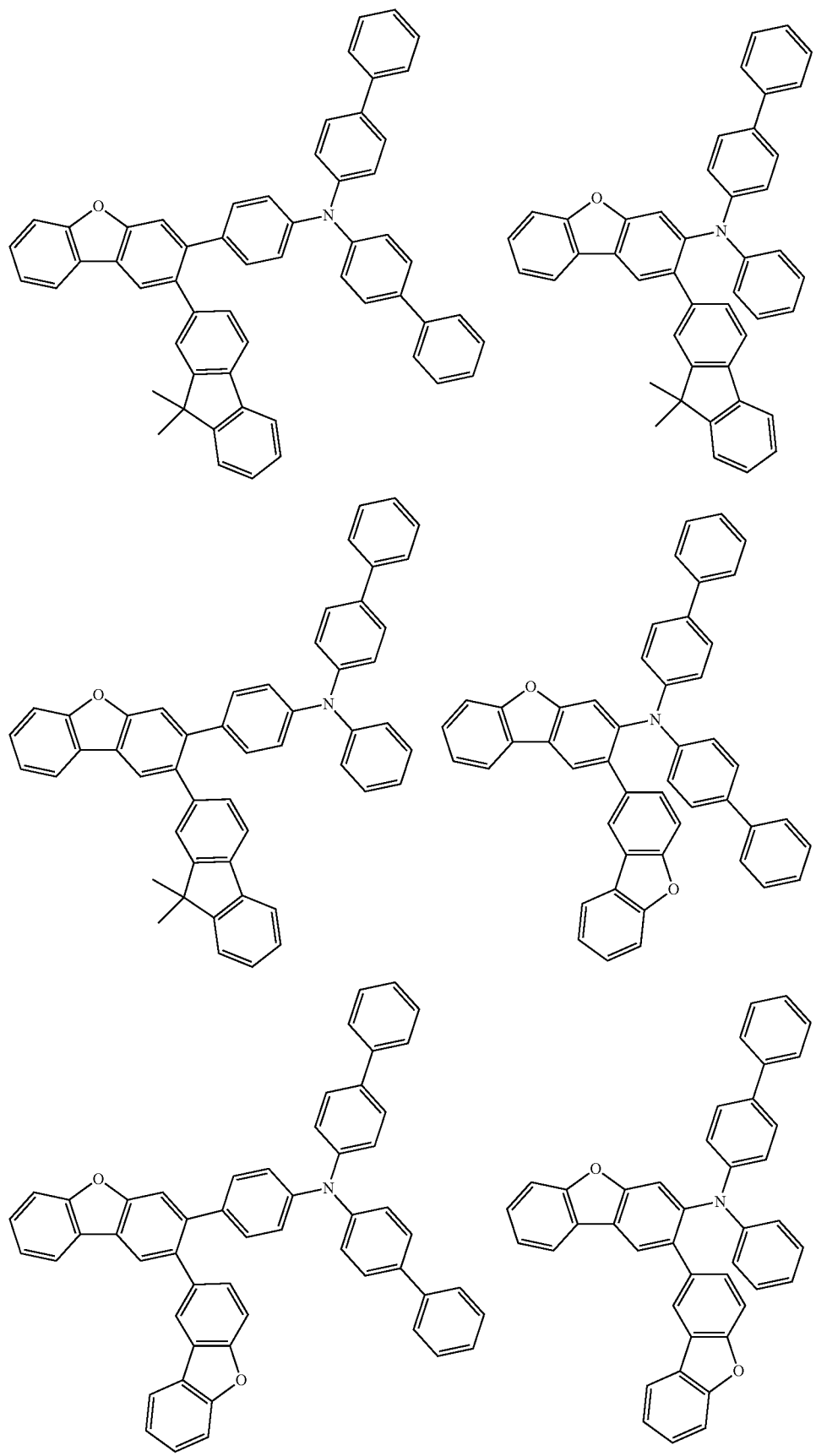

-continued
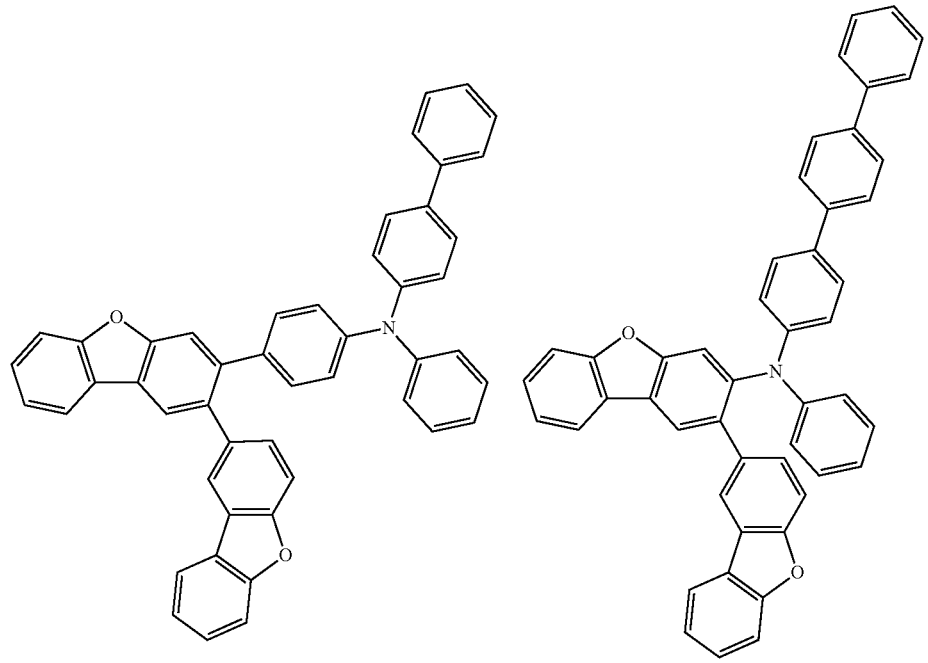
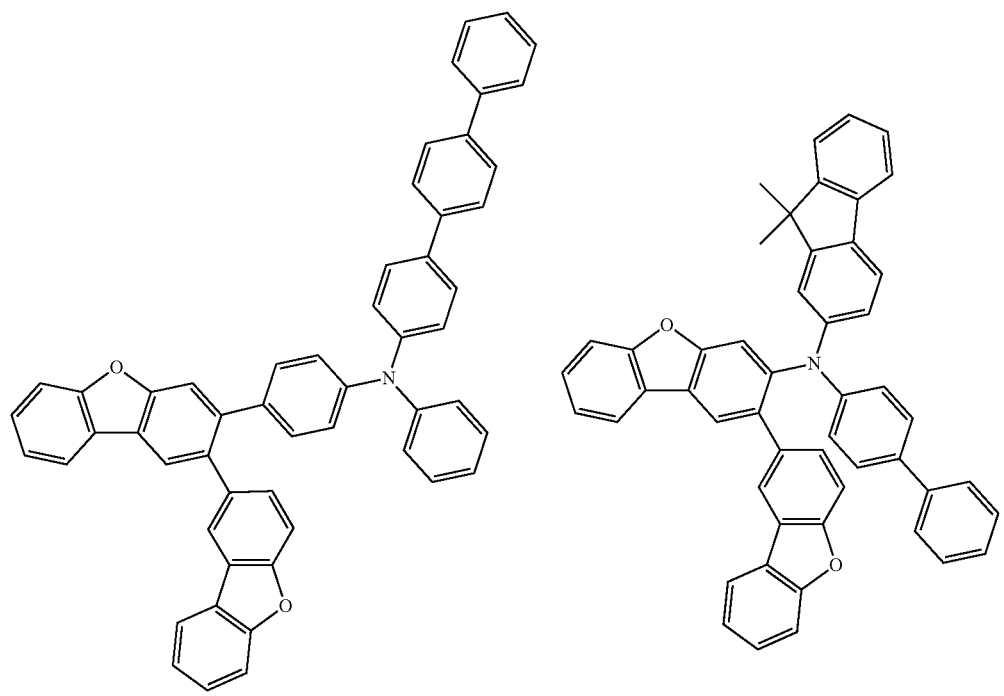

-continued
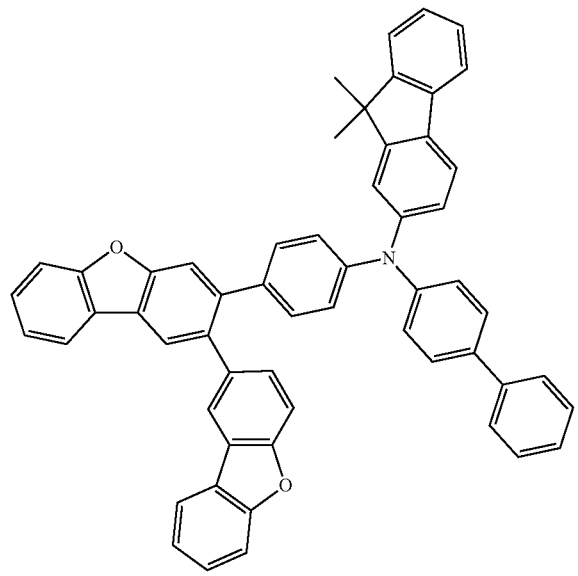
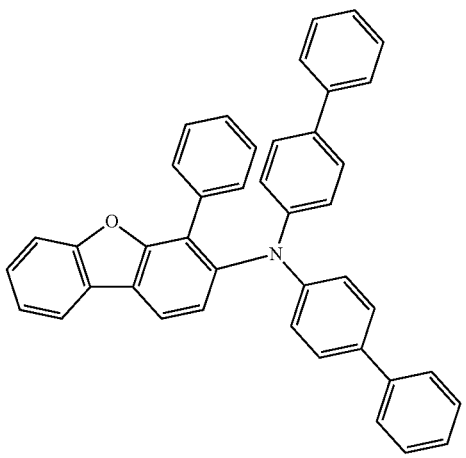
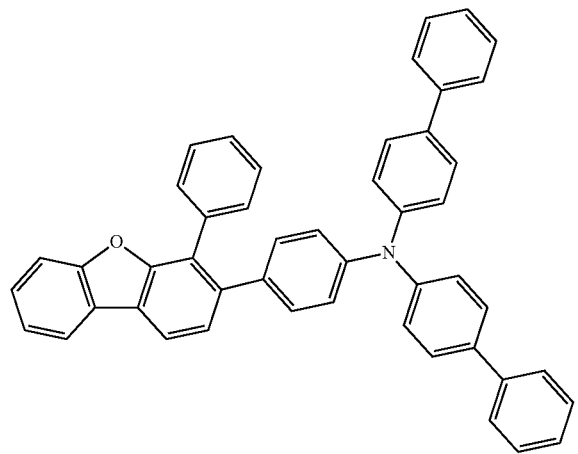
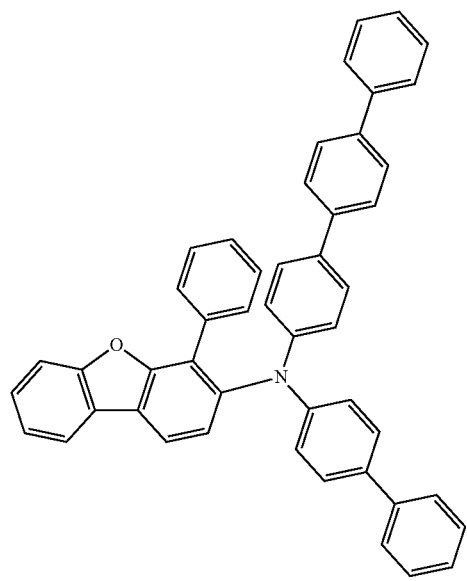
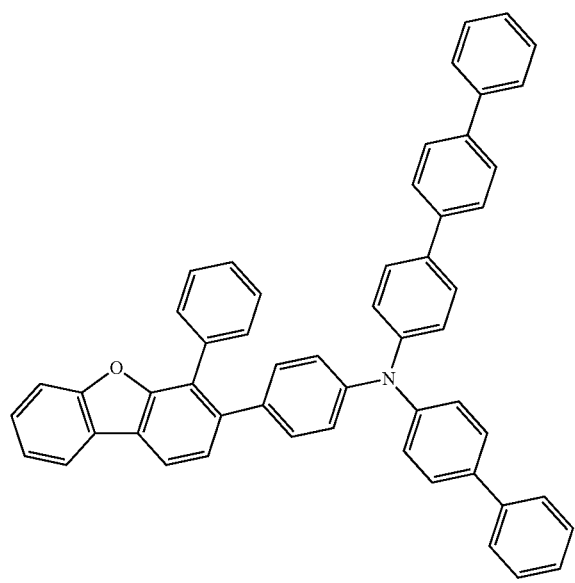

-continued
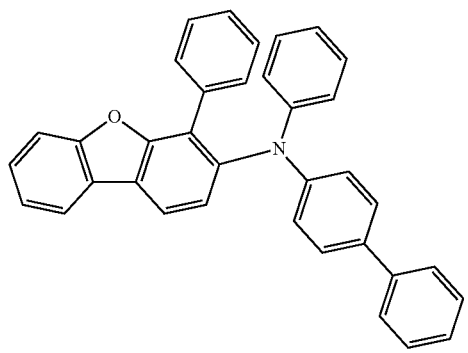
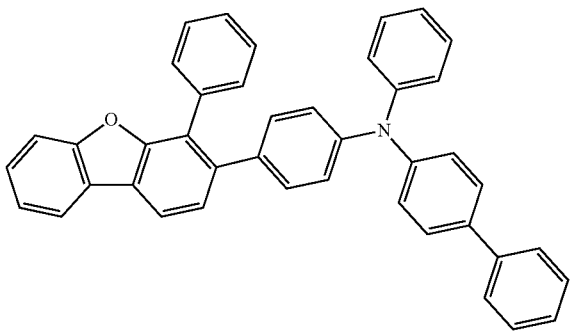
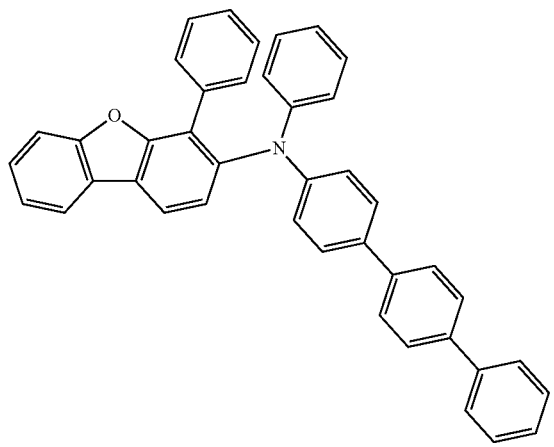
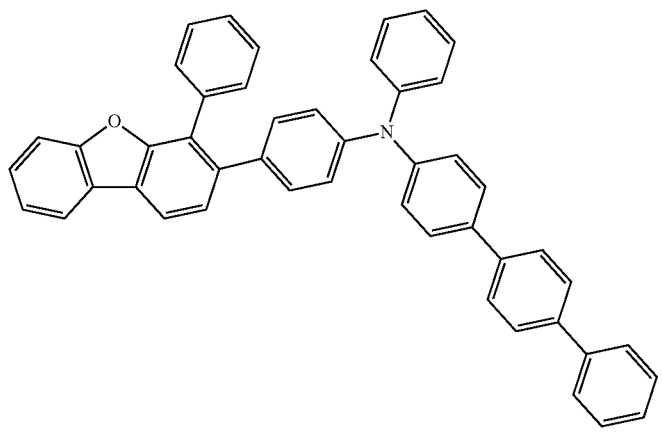
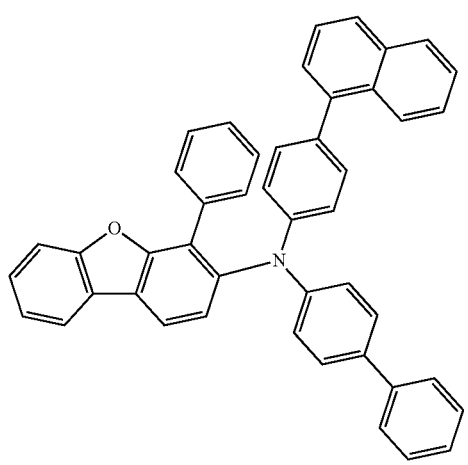
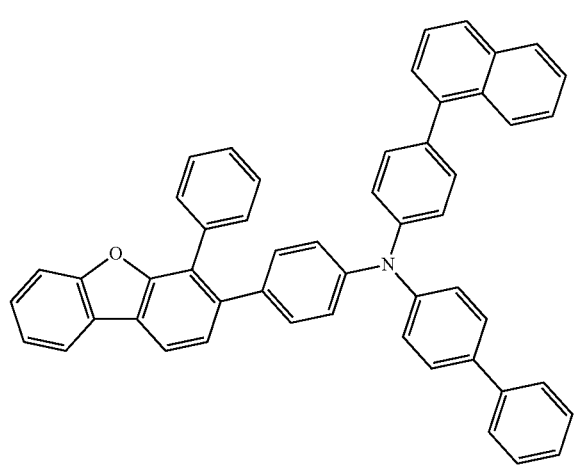

-continued
75
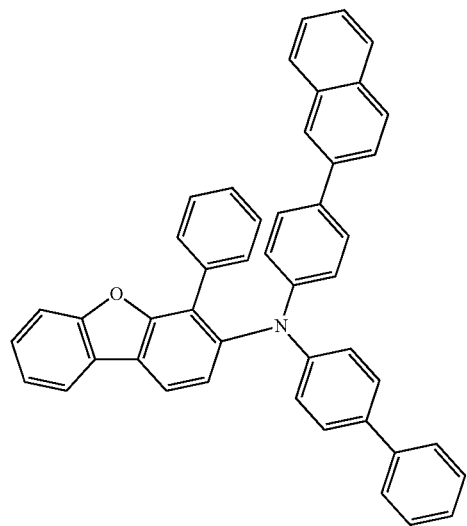
76
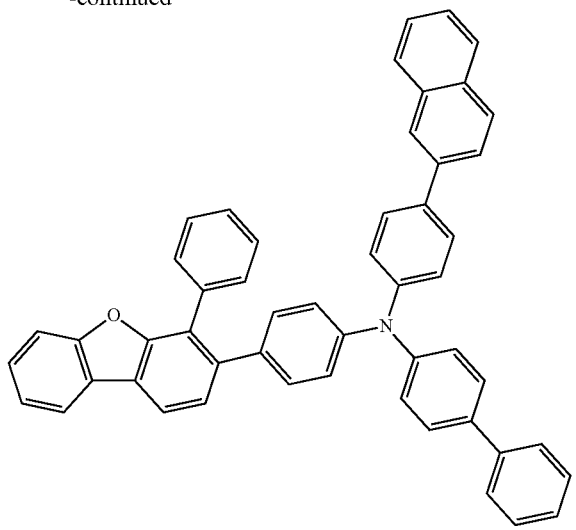
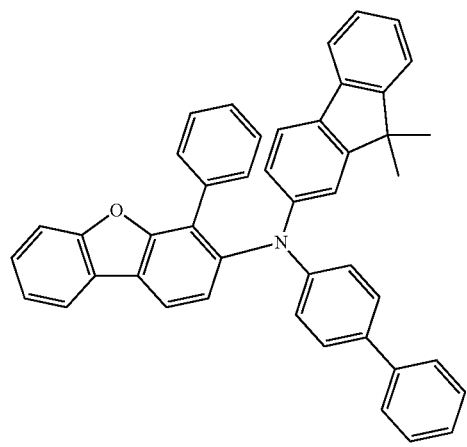
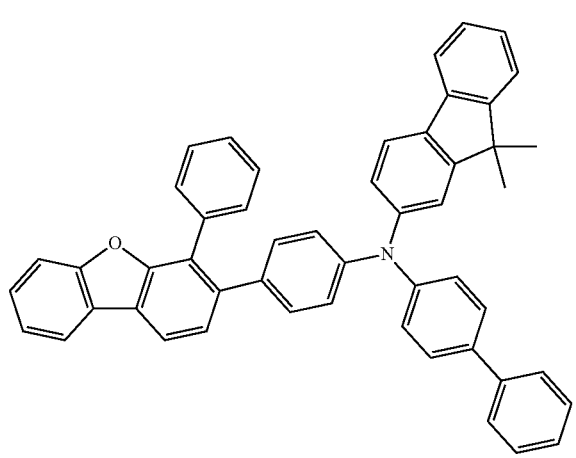
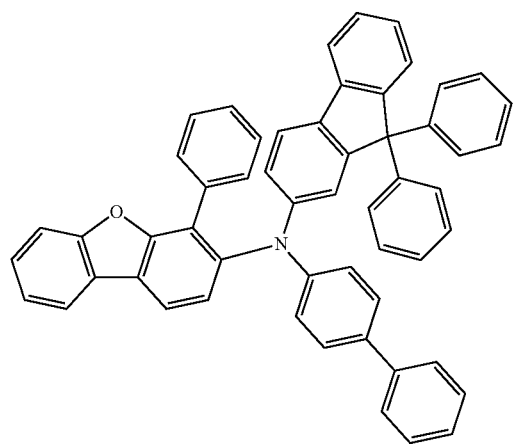
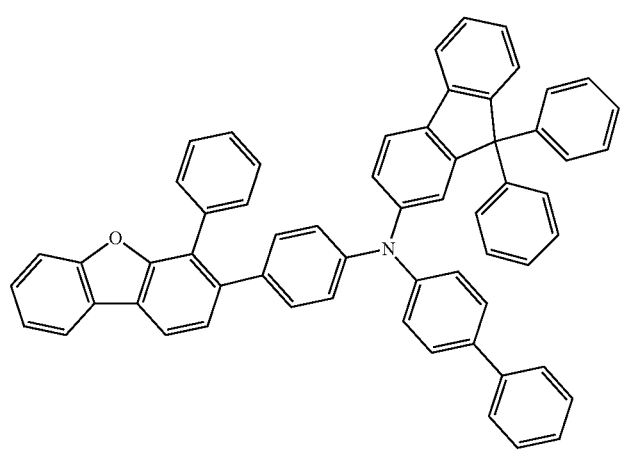

-continued
77
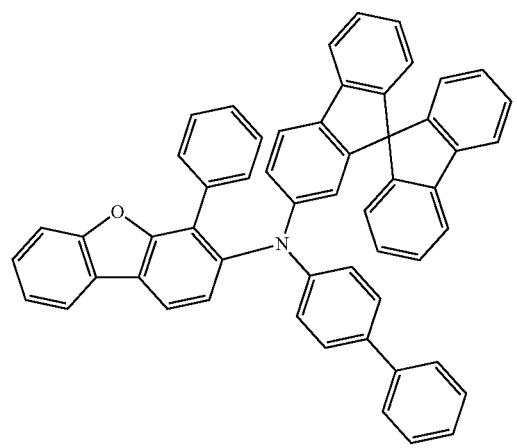
78
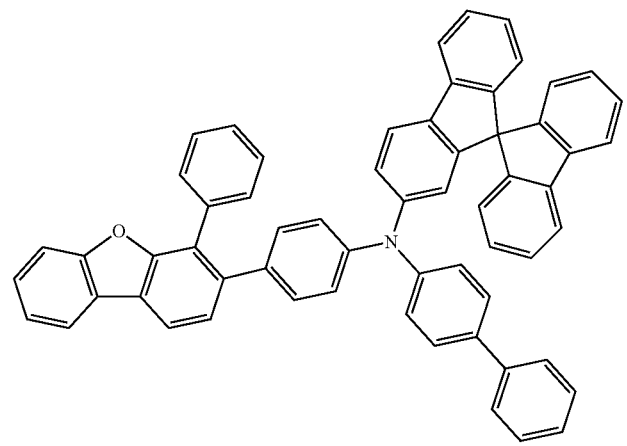
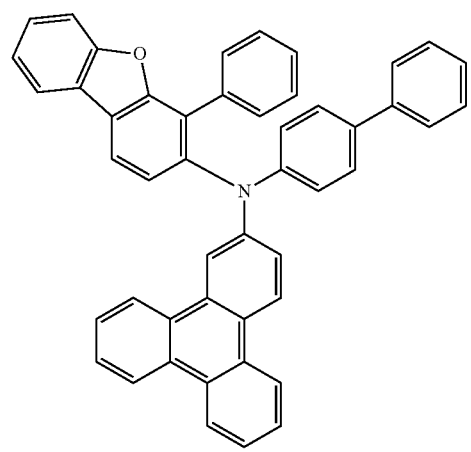
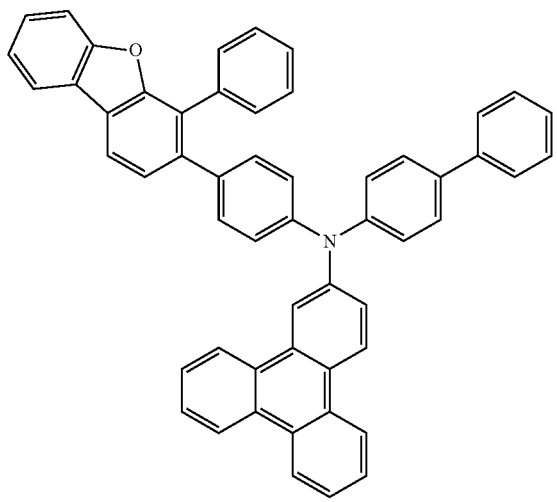
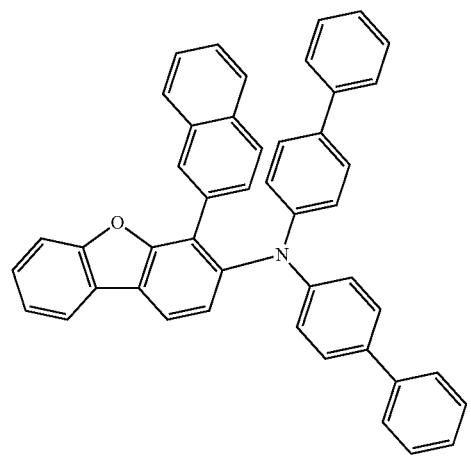
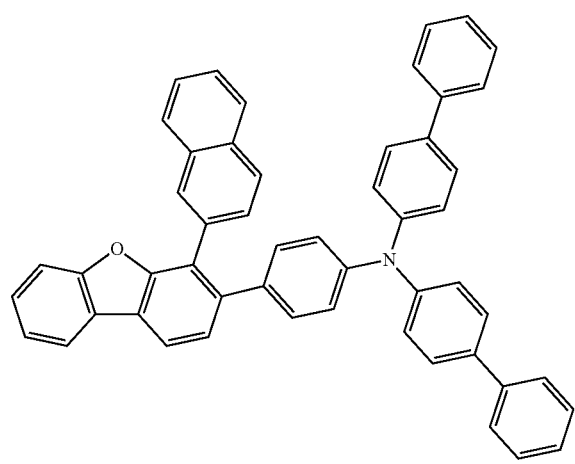

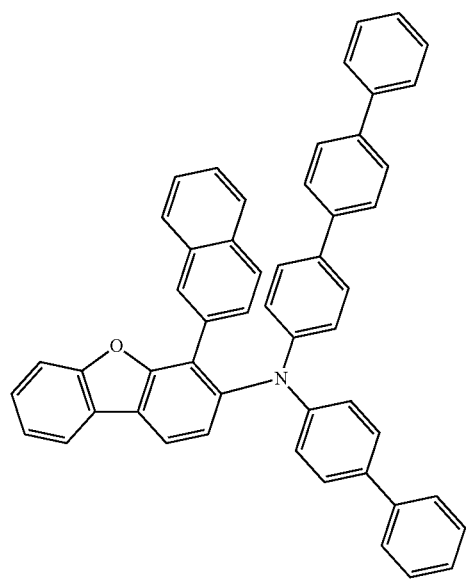
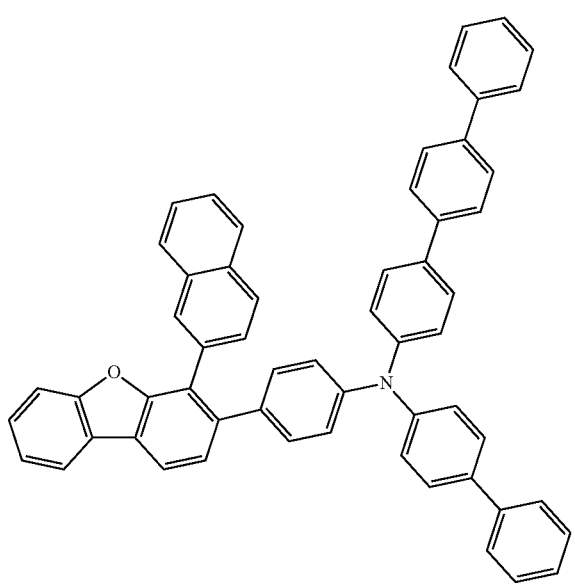
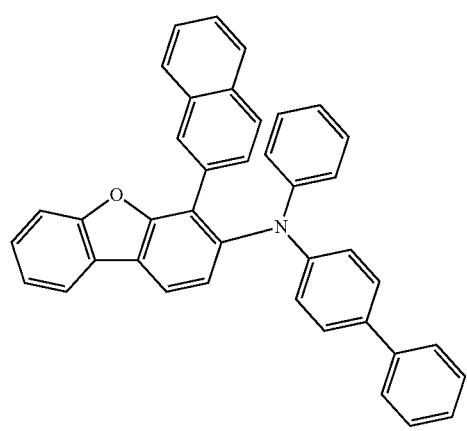
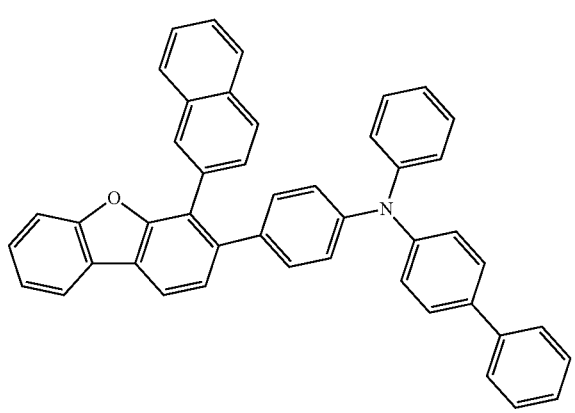
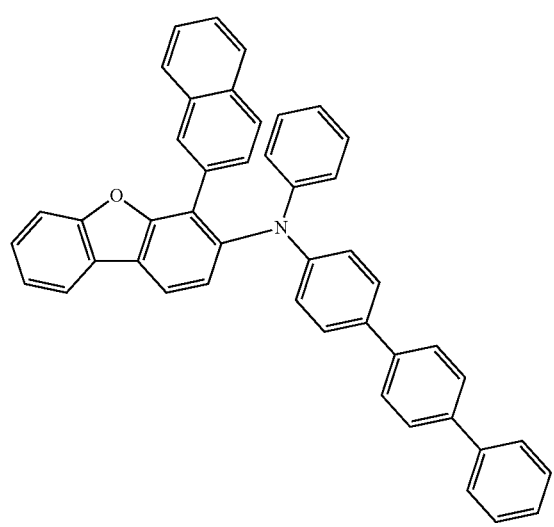

81 82
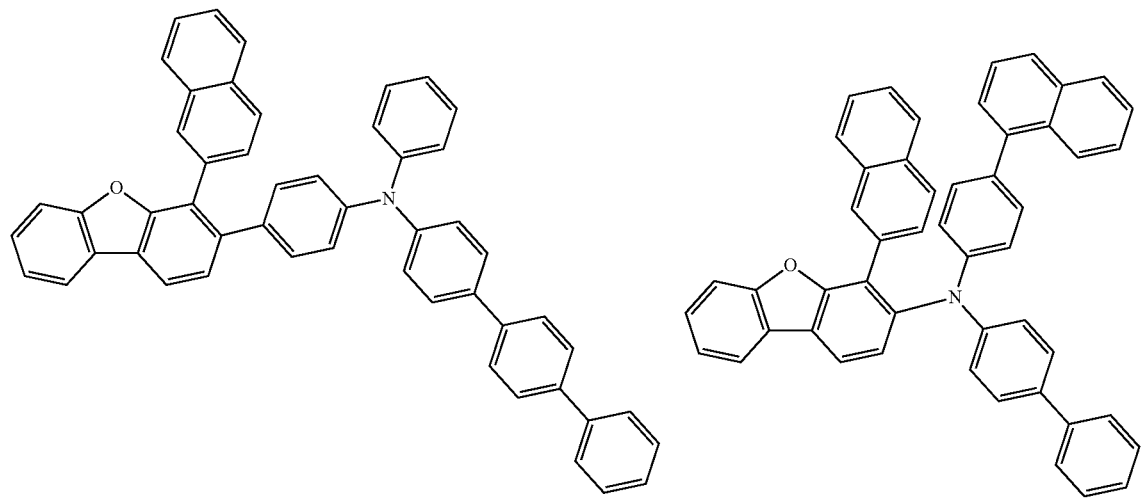
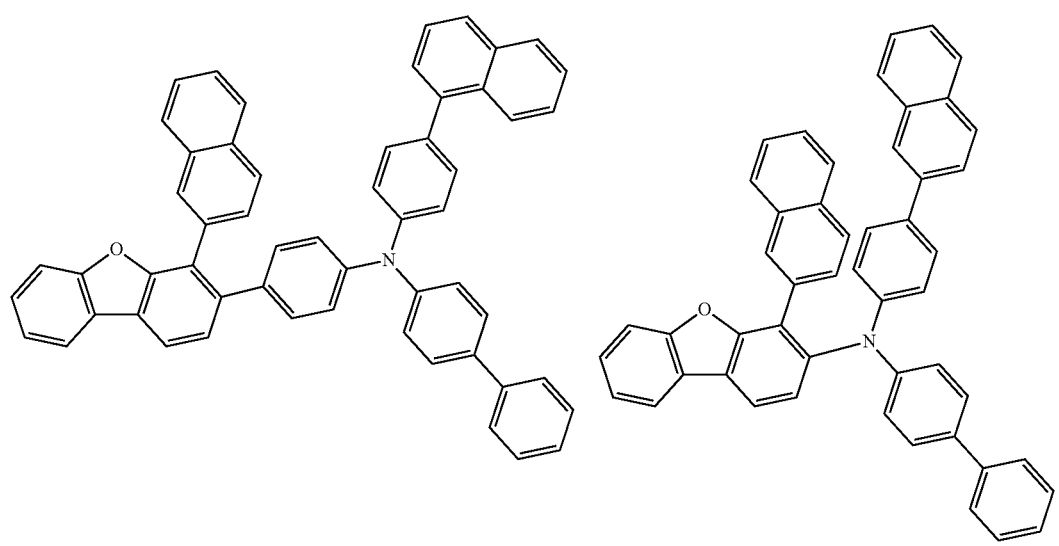
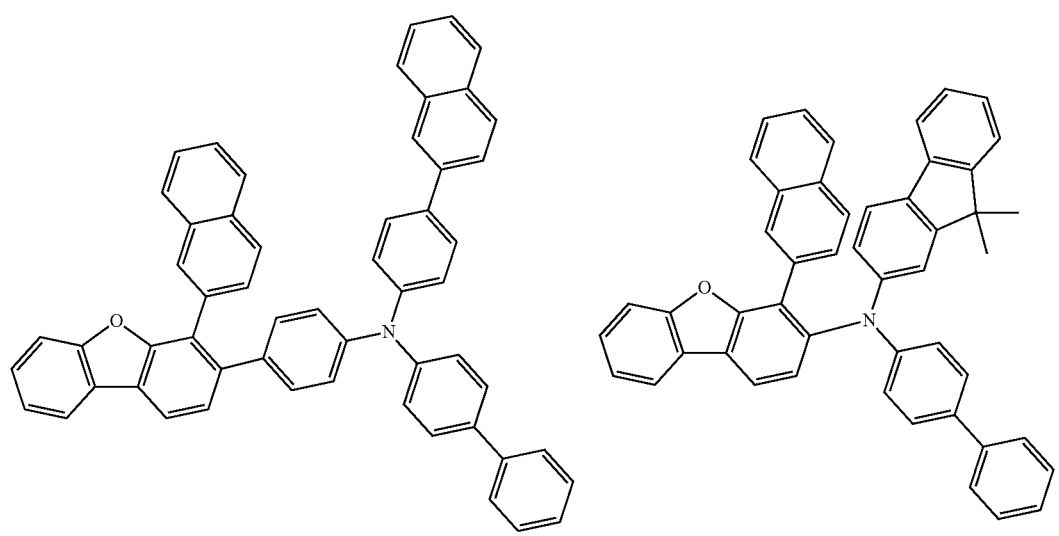

-continued
83
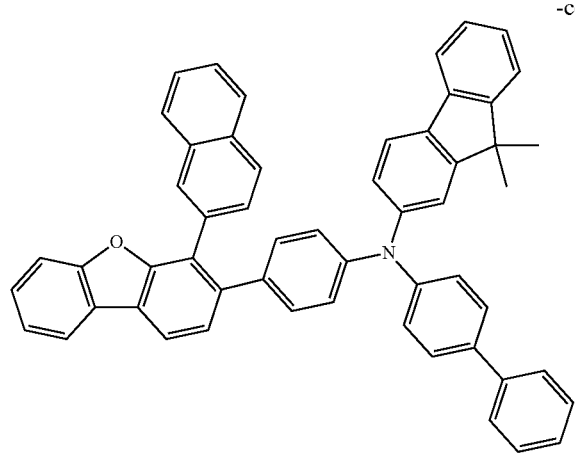
84
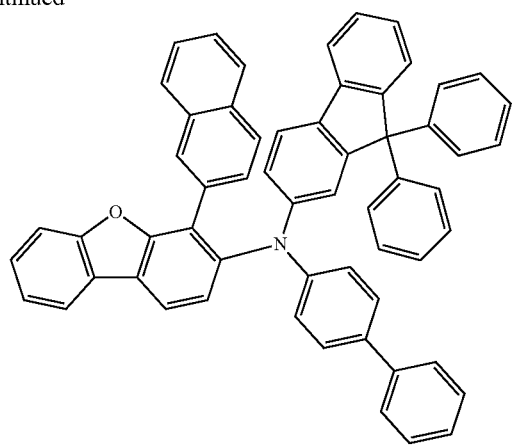
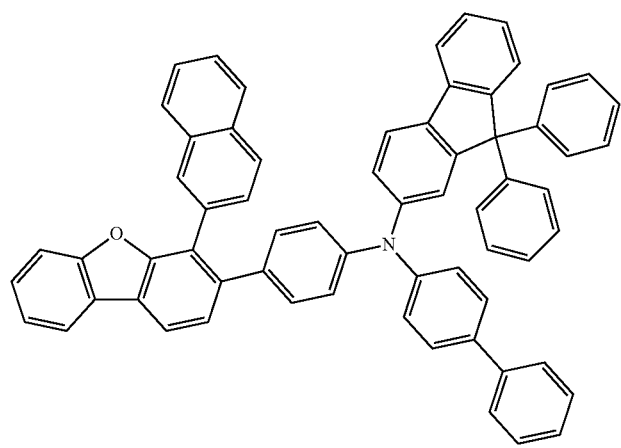
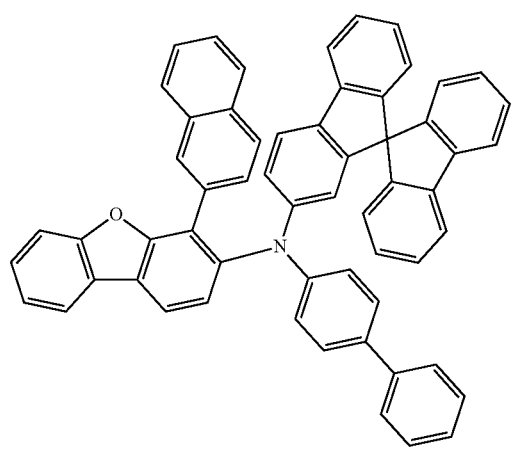
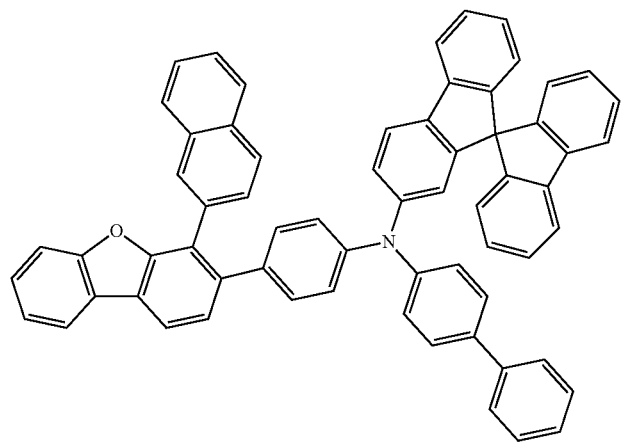
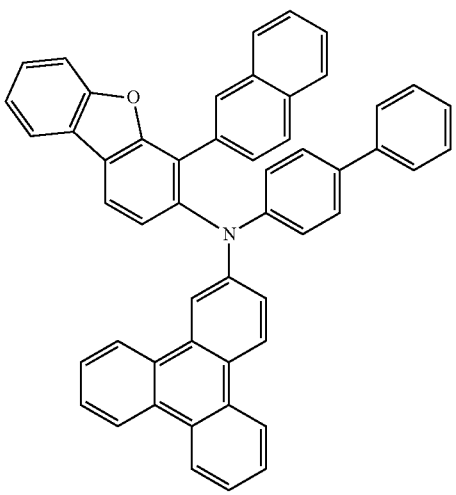

85
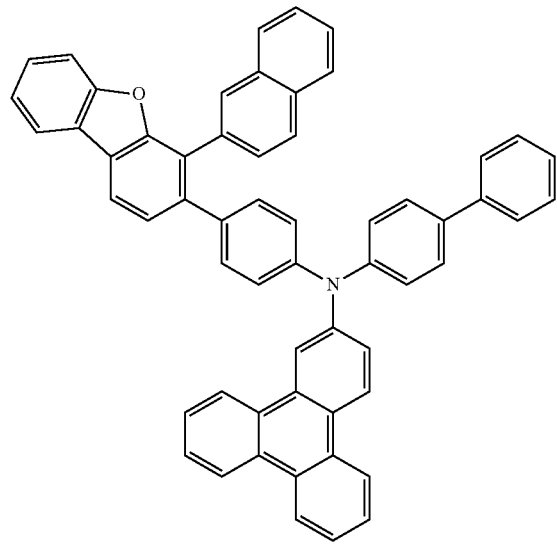
86
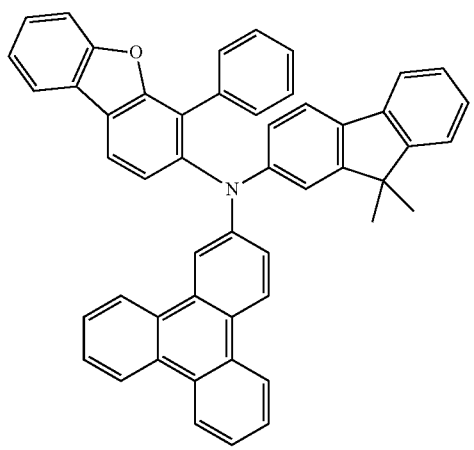
-continued
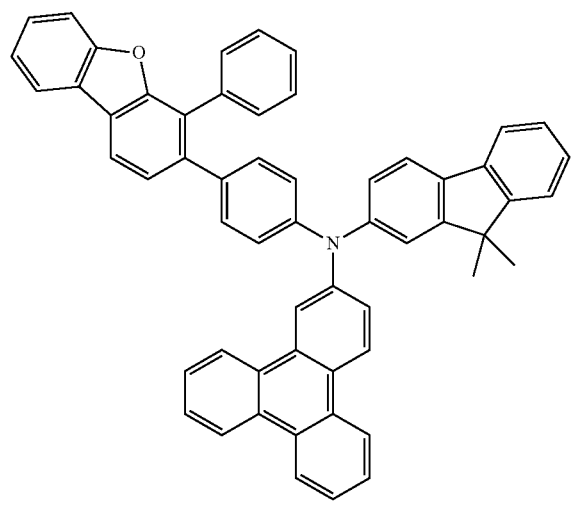
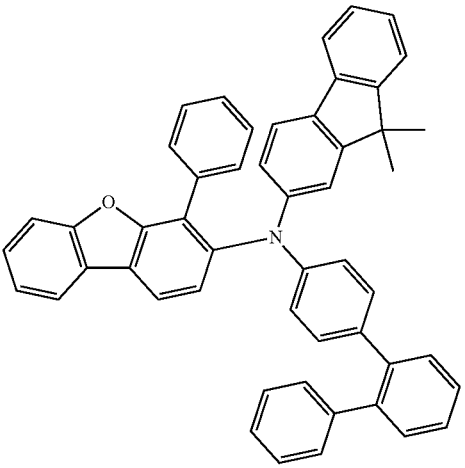
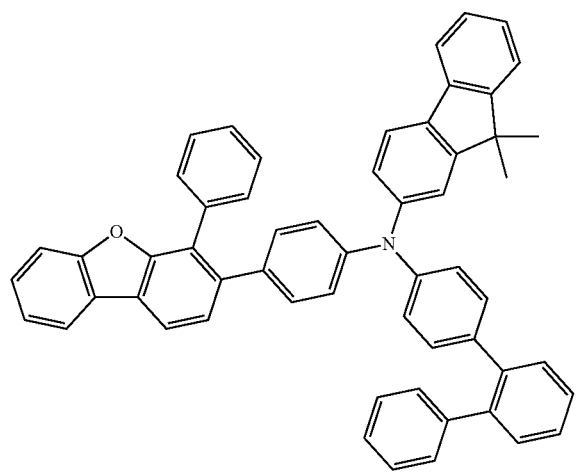
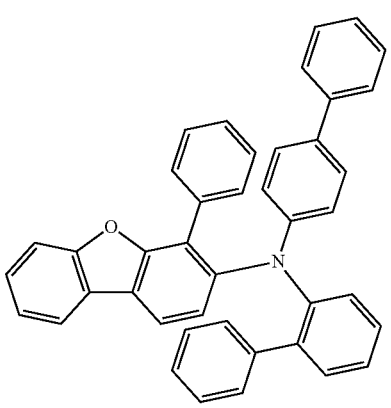

87
88
-continued
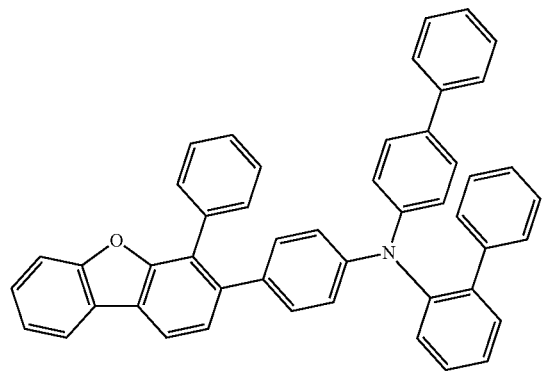
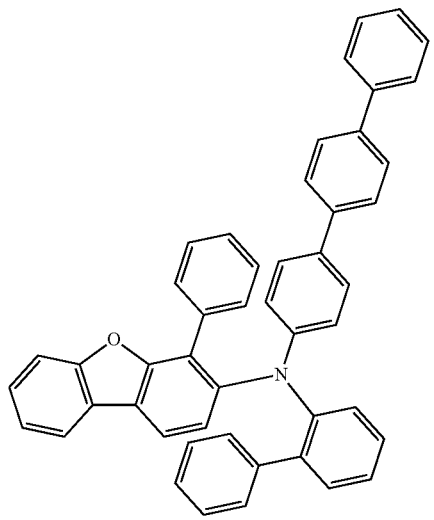
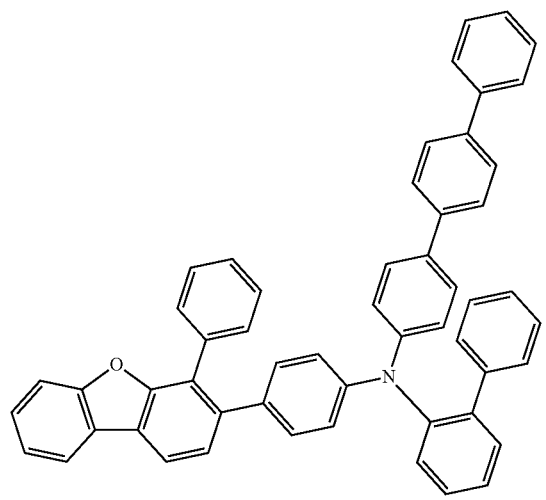
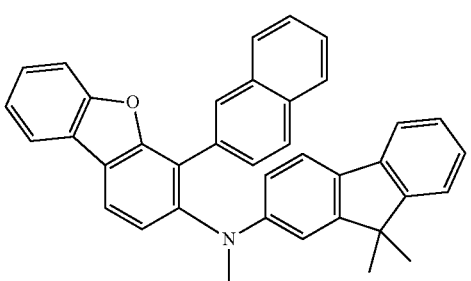
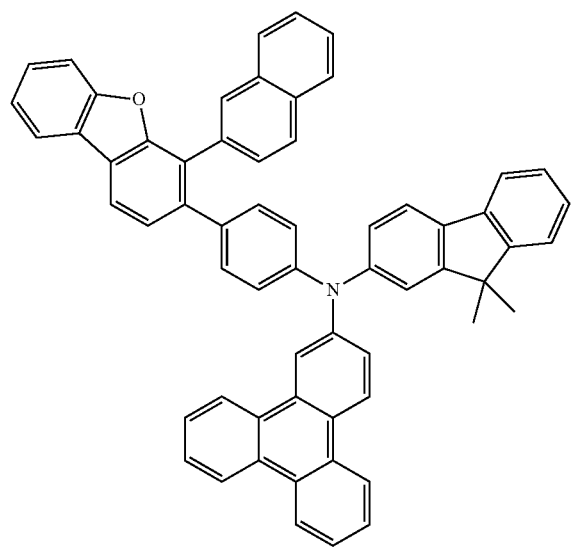
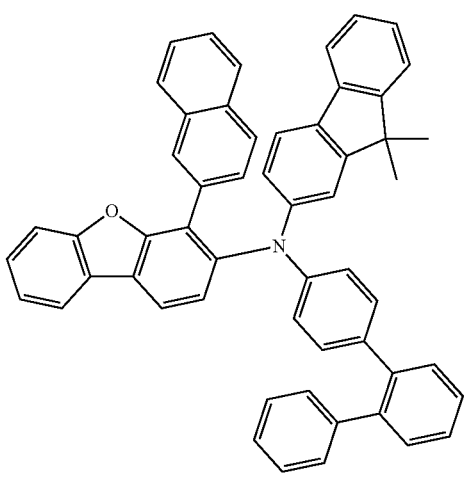

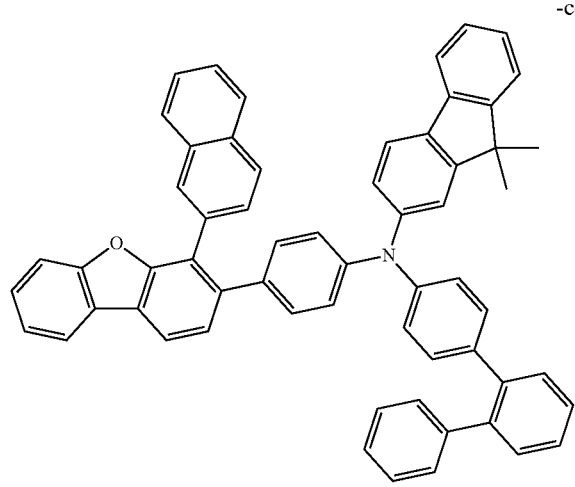
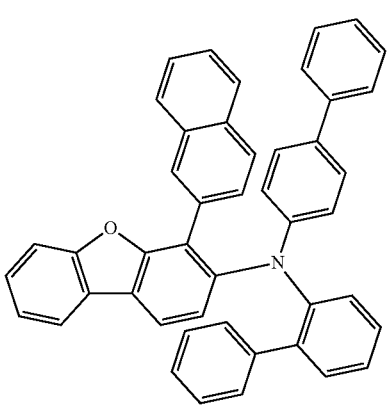
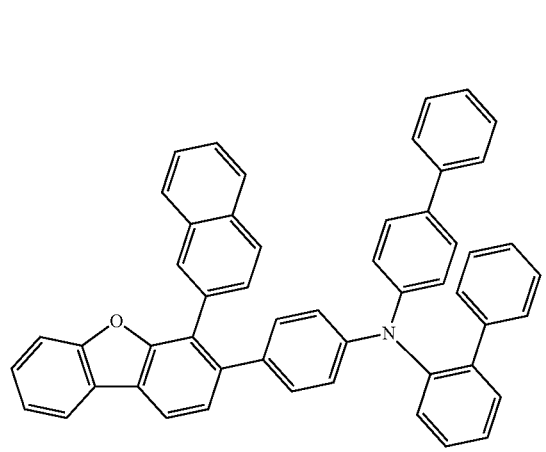
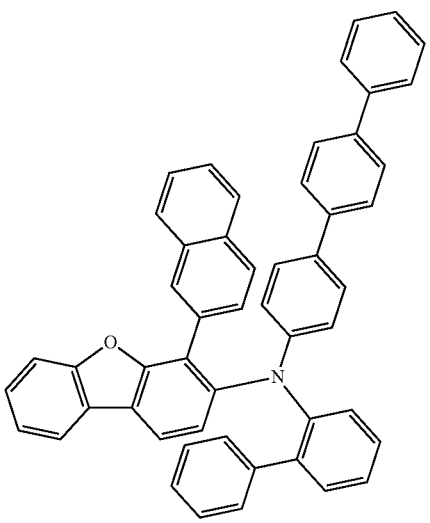
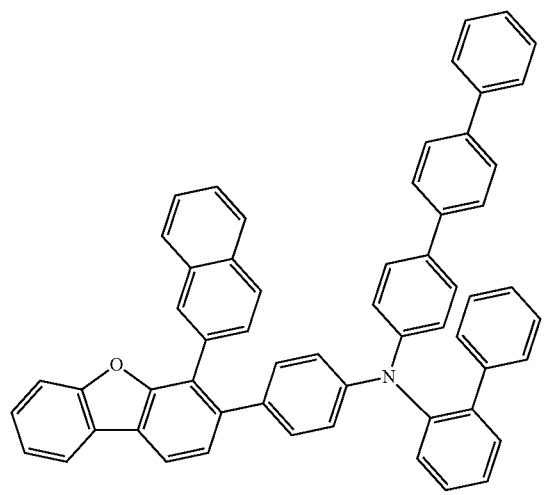 [SMILES: c1ccc(-c2ccc(-c3ccc(N(c4ccc(-c5ccc6c(oc7ccccc76)c5-c5ccc6ccccc6c5)cc4)c4ccccc4-c4ccccc4)cc3)cc2)cc1]

91
92
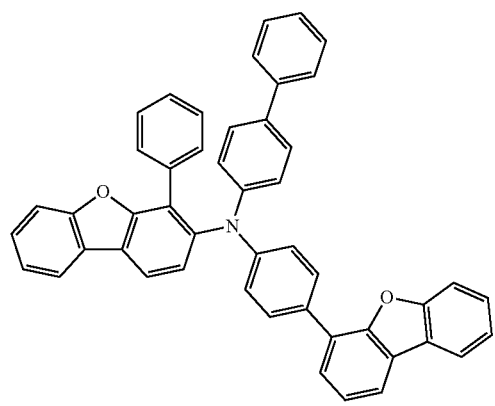
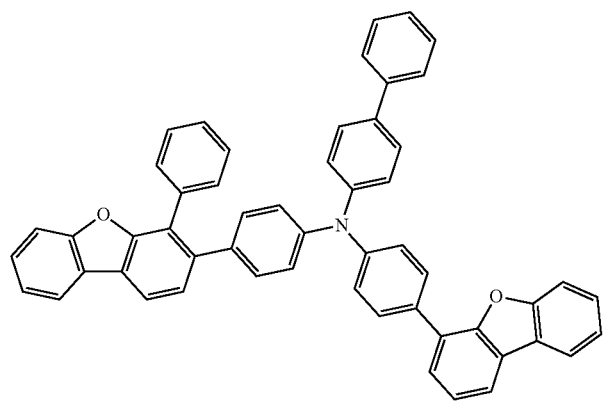
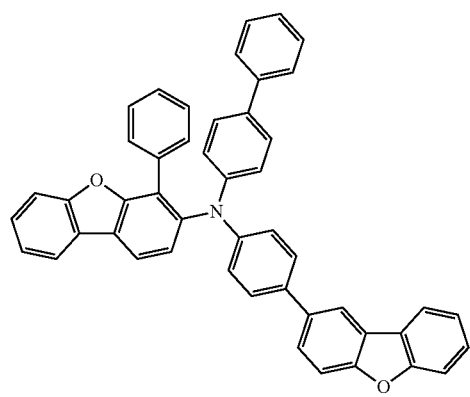
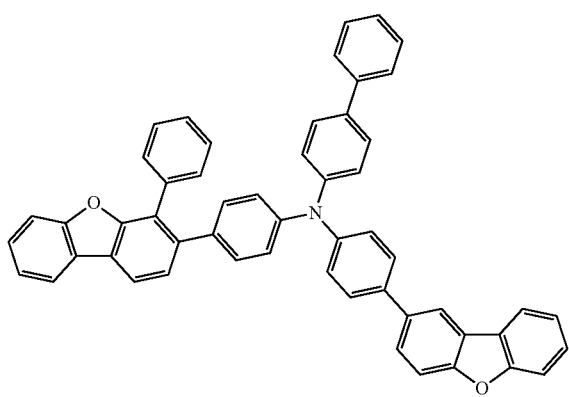
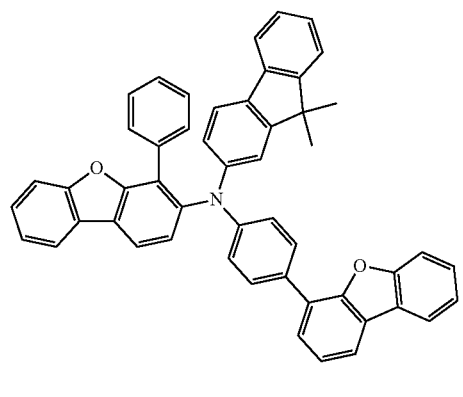
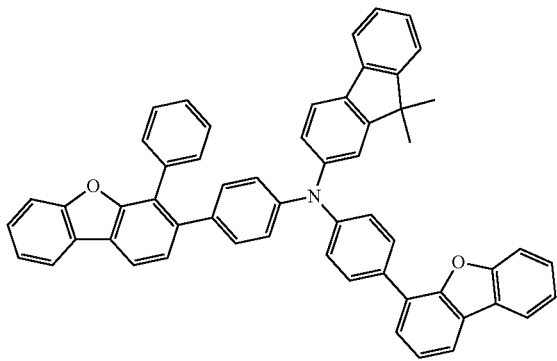
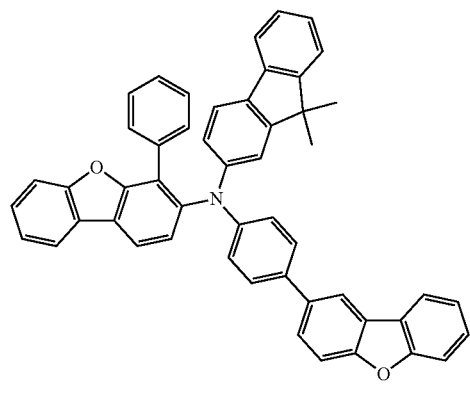
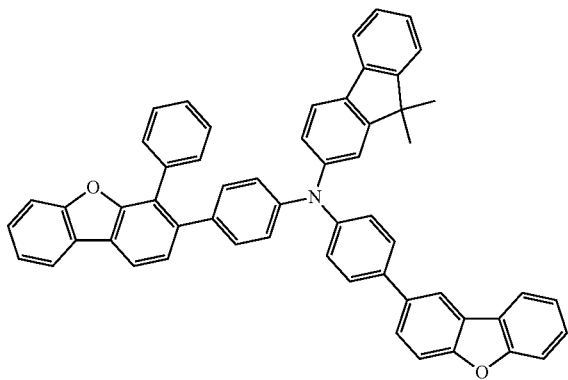

-continued
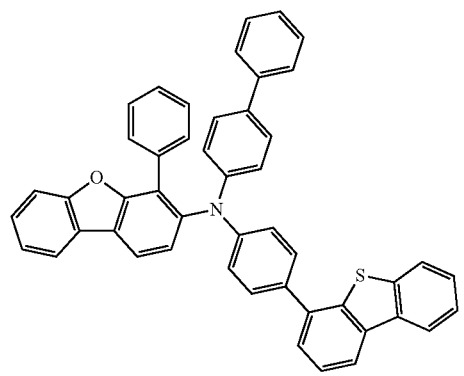
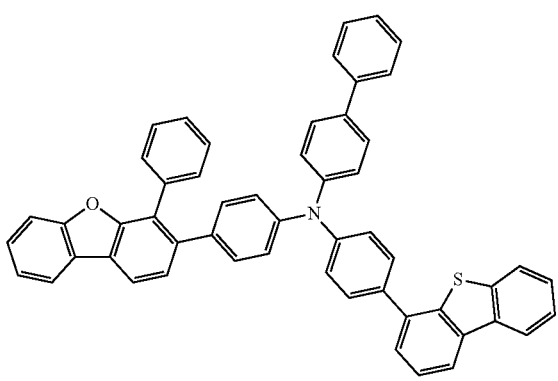
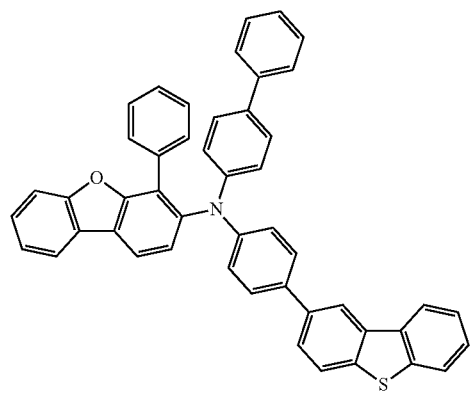
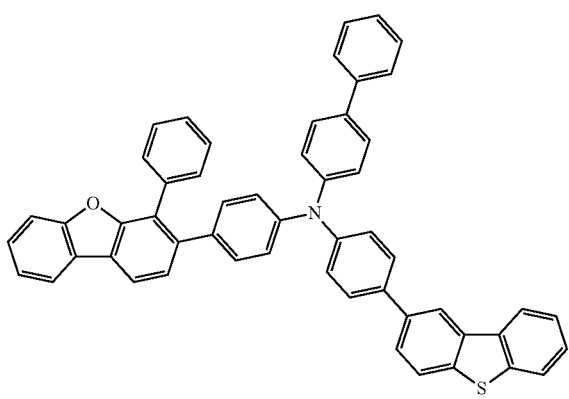
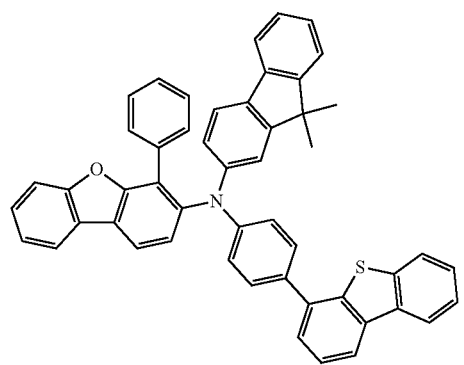
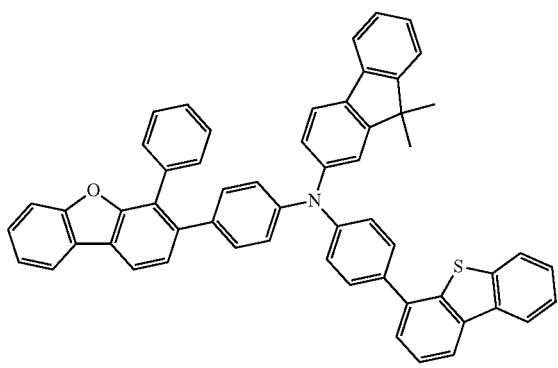
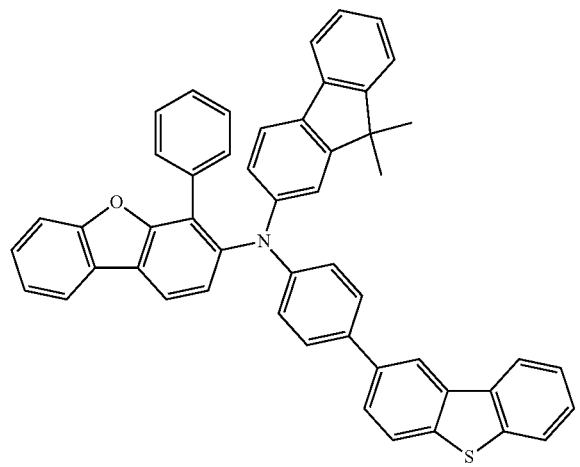

-continued
95
96
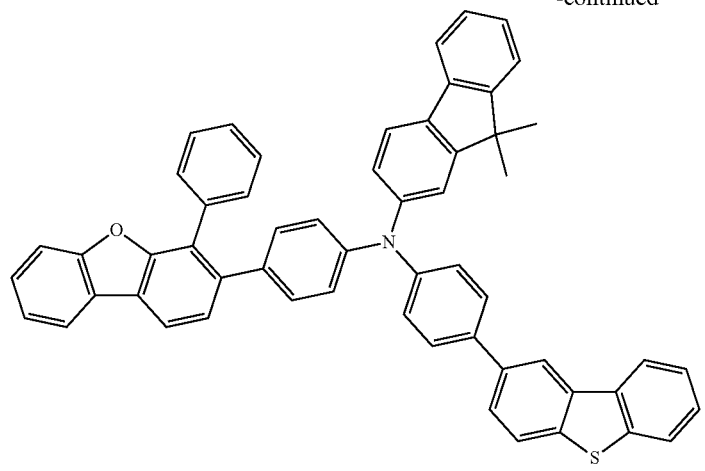
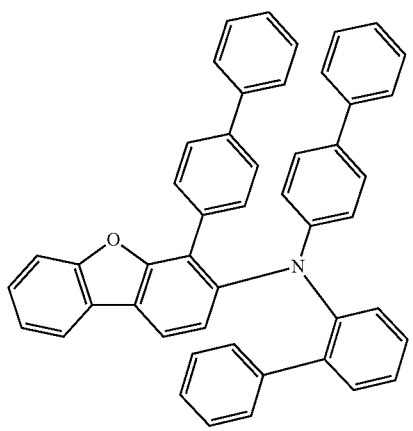
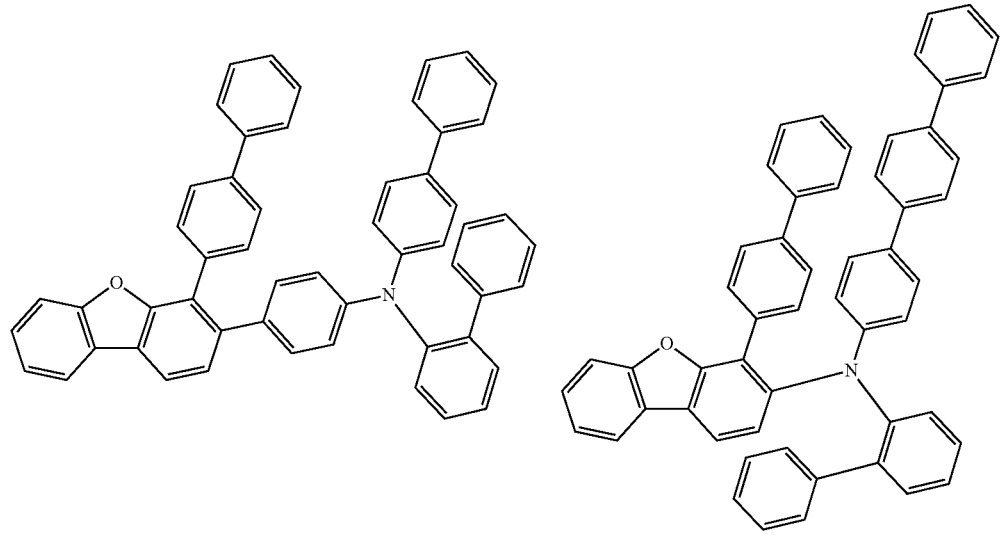
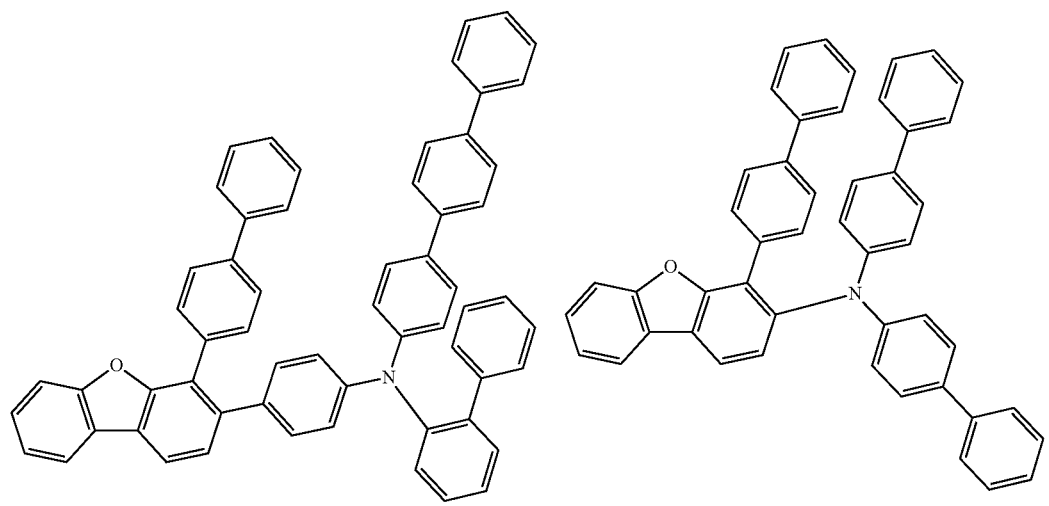

-continued
97
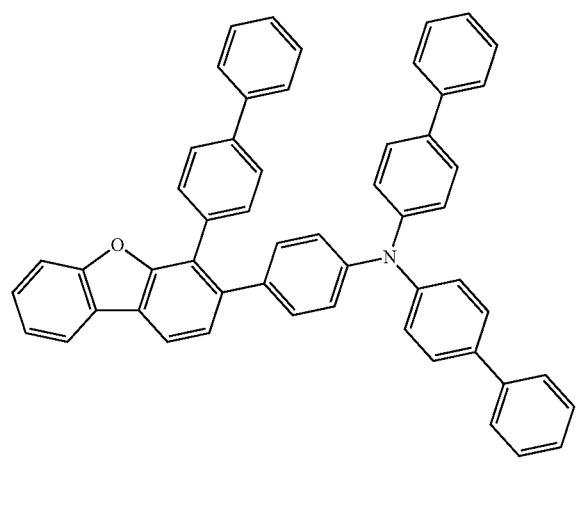
98
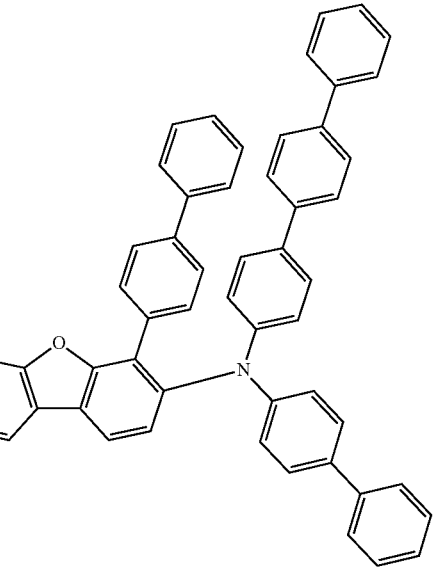
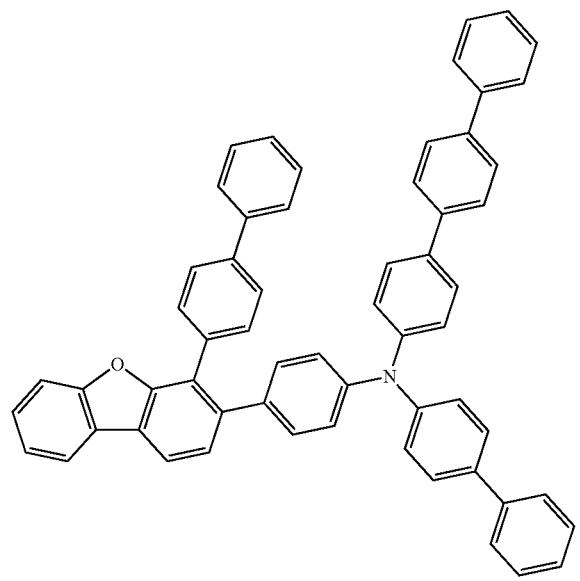
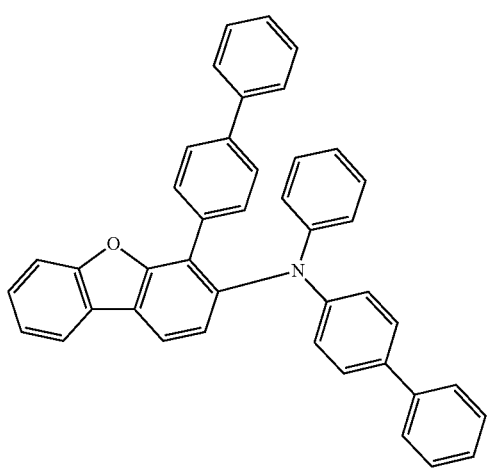
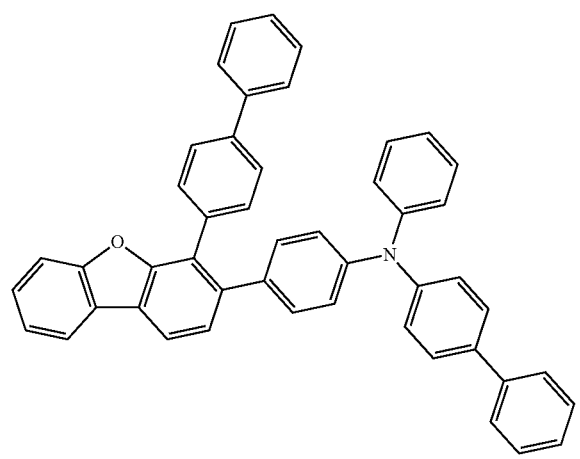
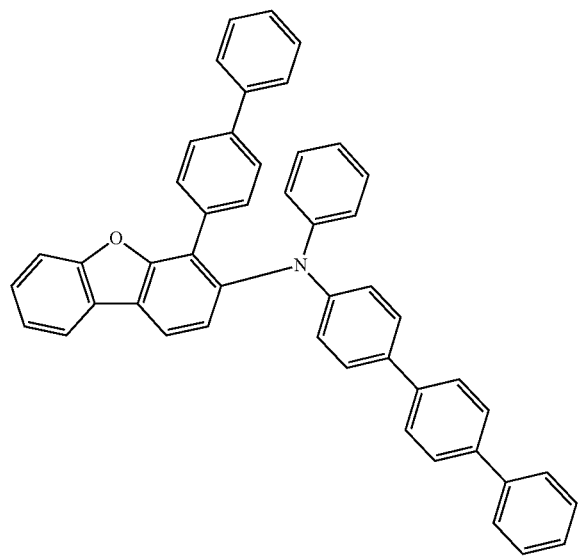

-continued
99
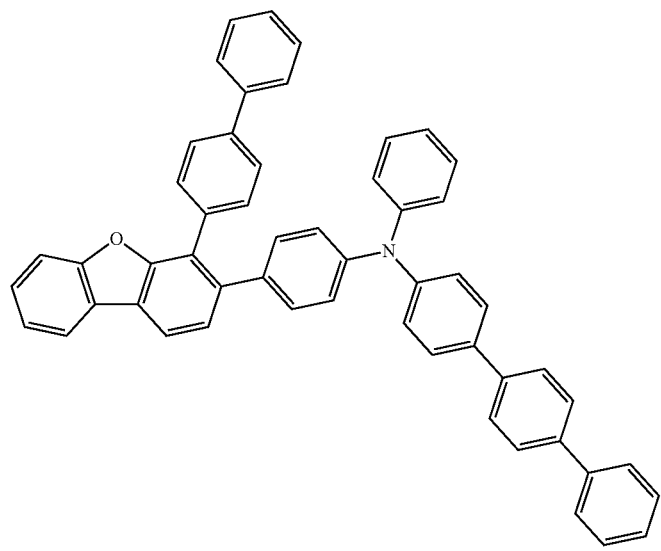
100
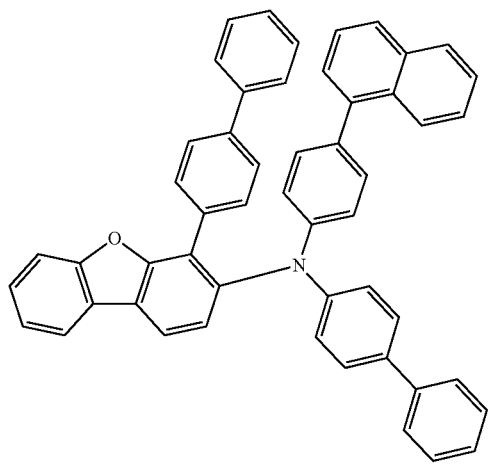
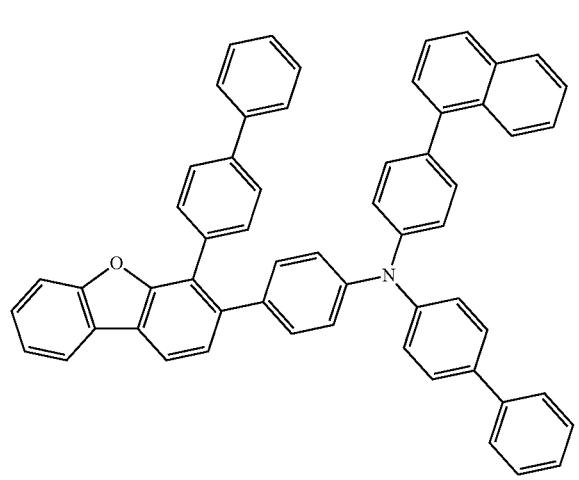
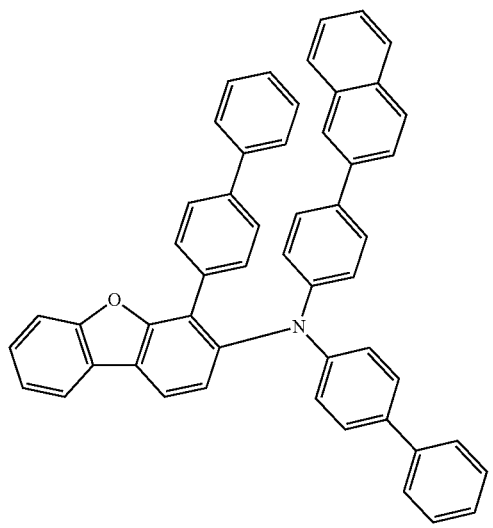
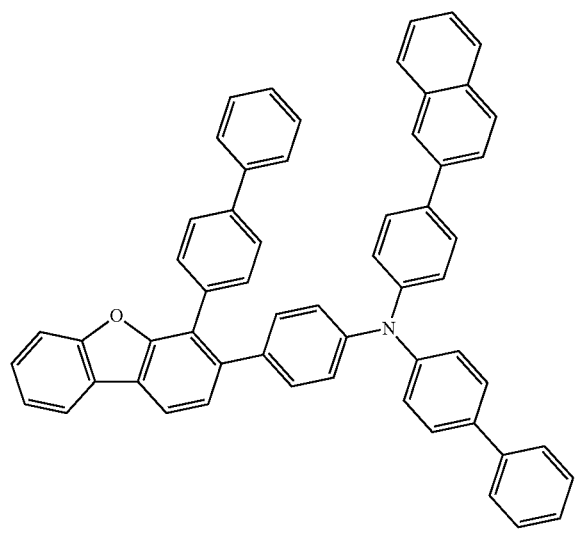
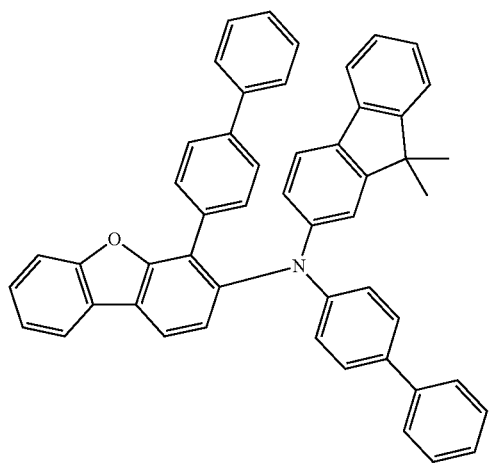

-continued
101
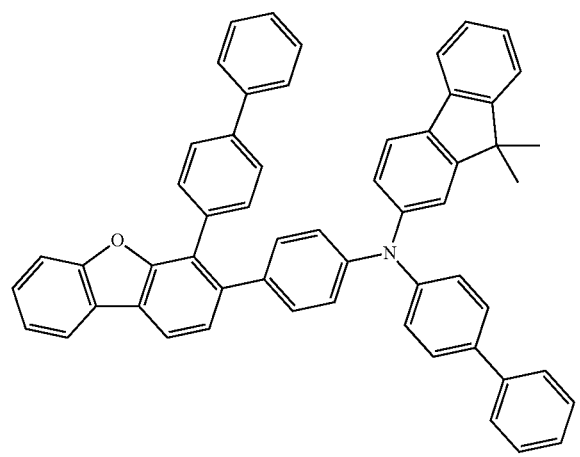
102
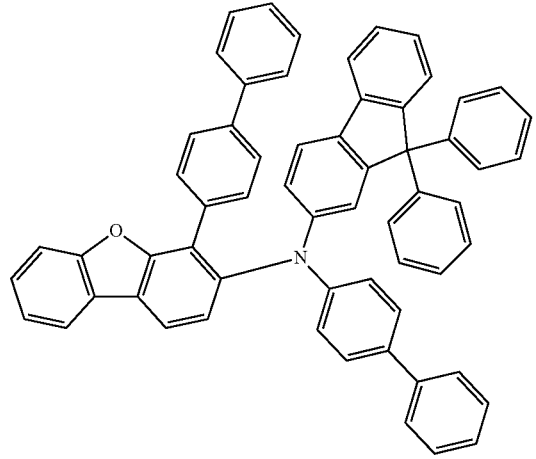
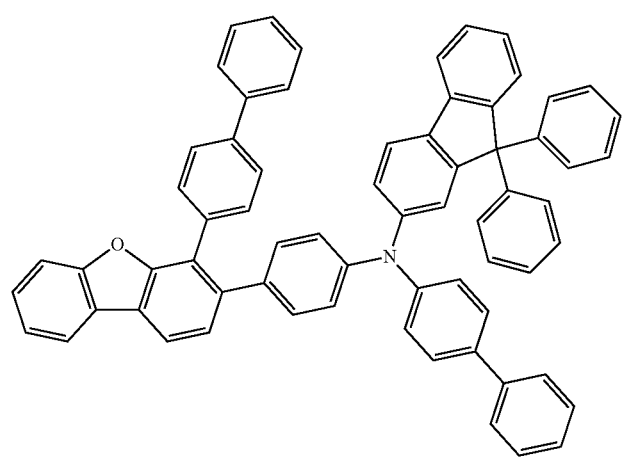
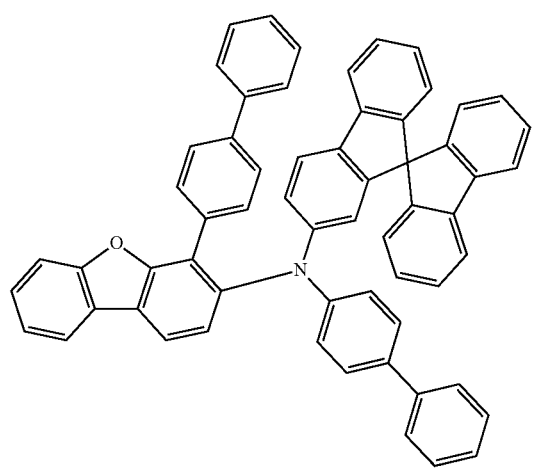
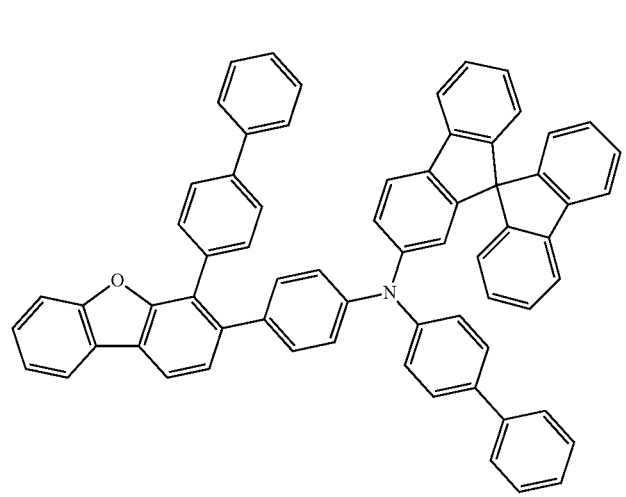
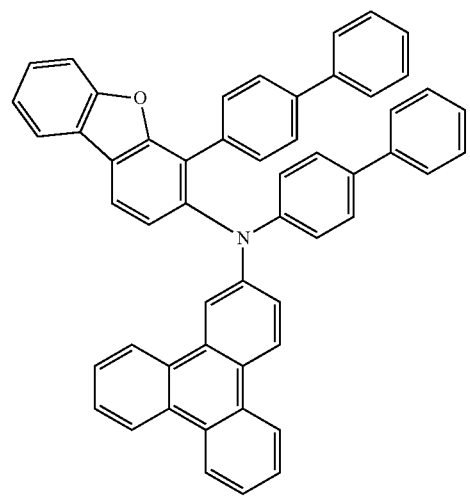

103
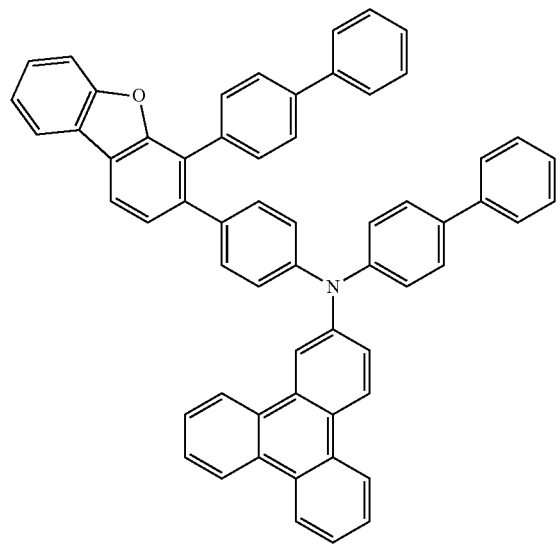
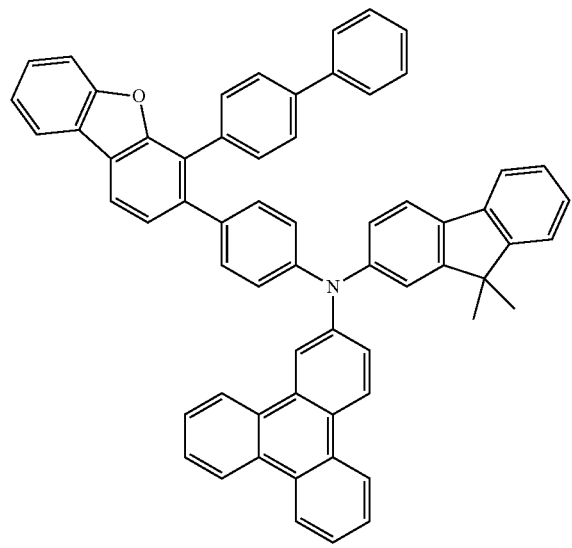
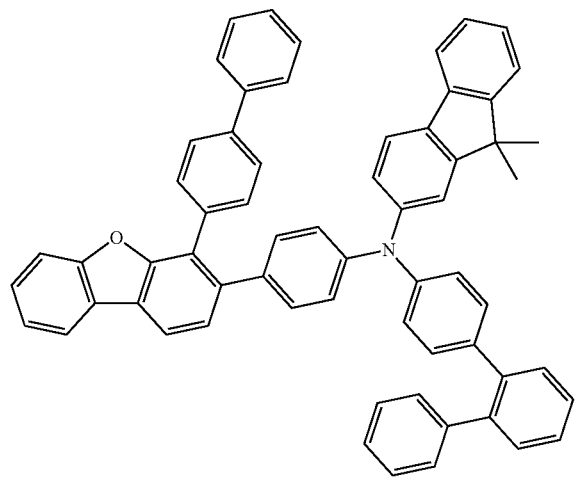
104
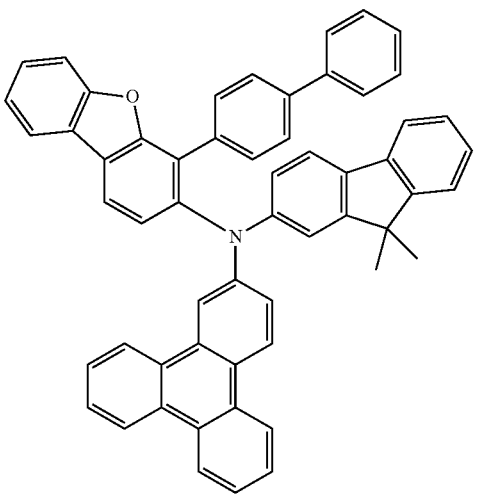
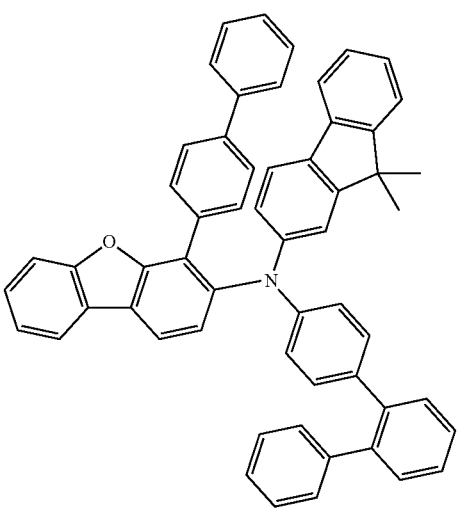
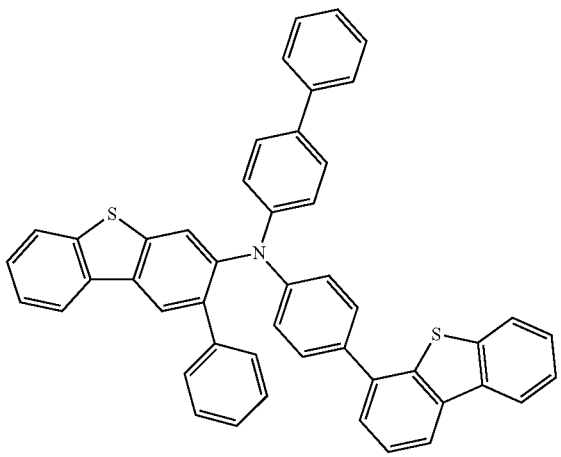

105
106
-continued
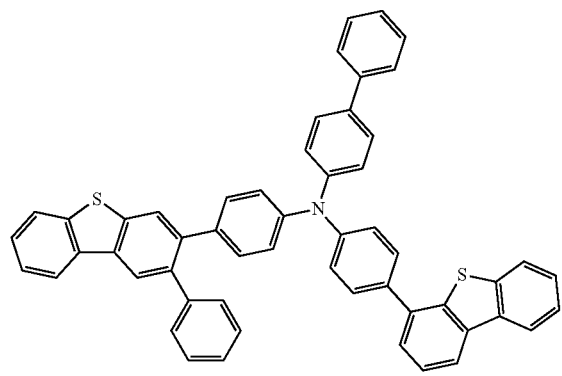
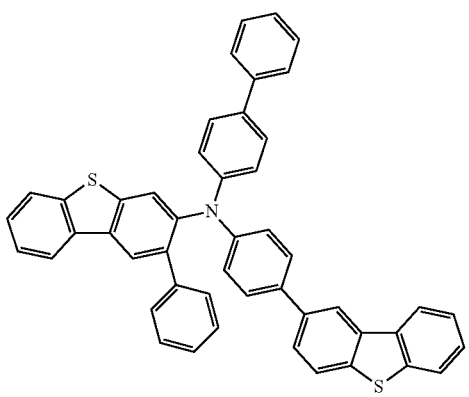
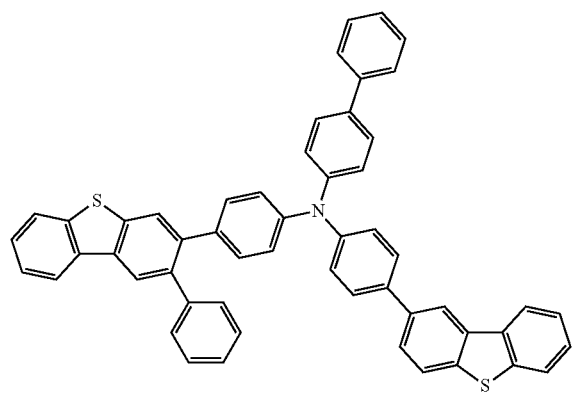
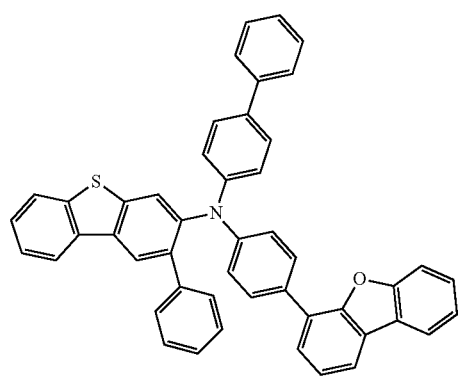
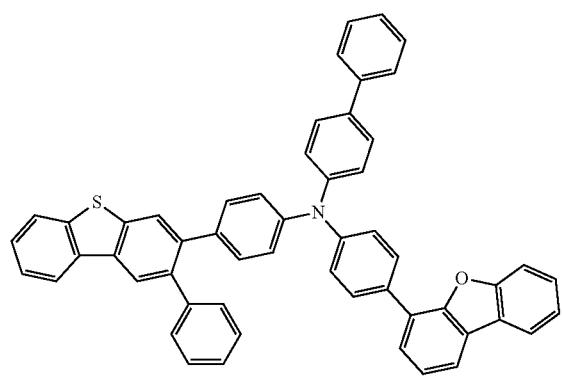
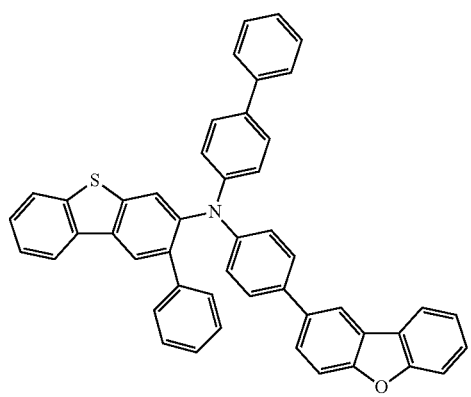
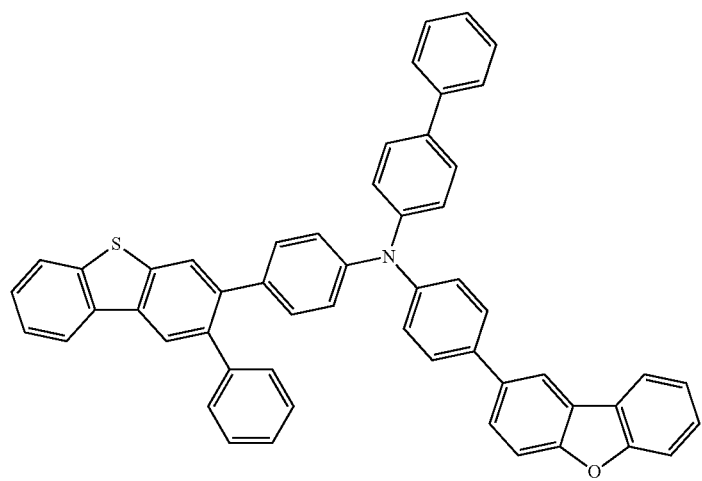
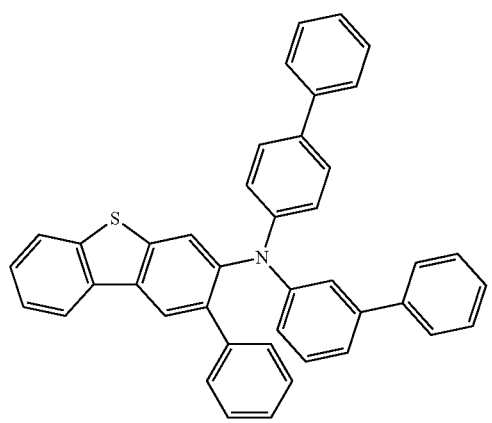

107
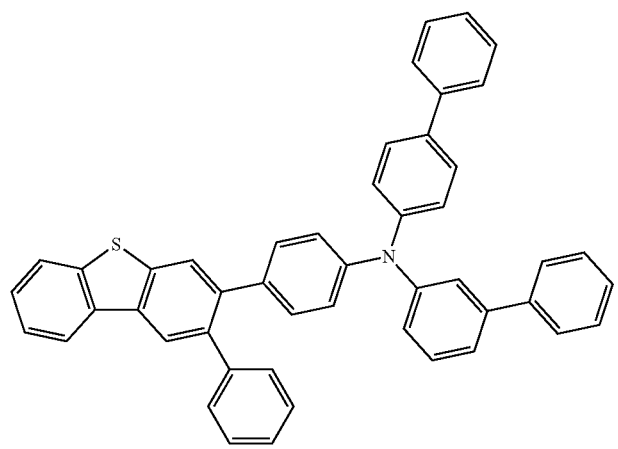
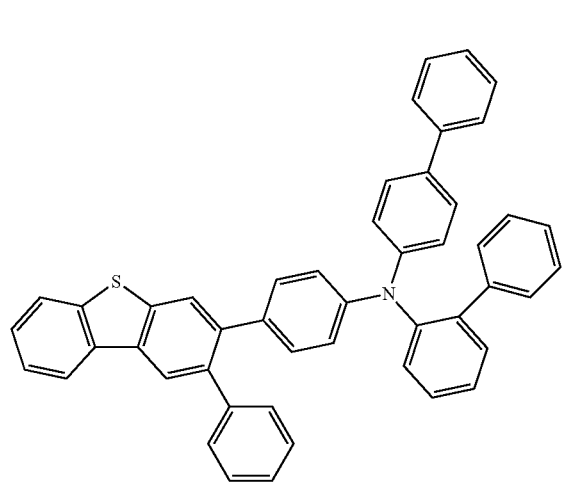
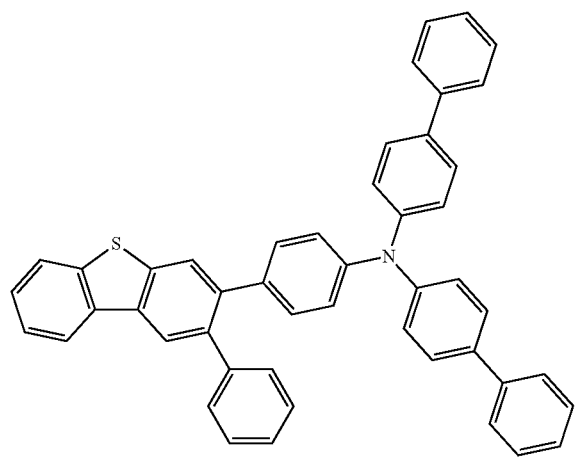
108
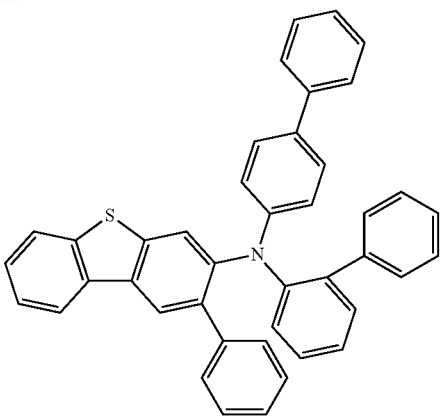
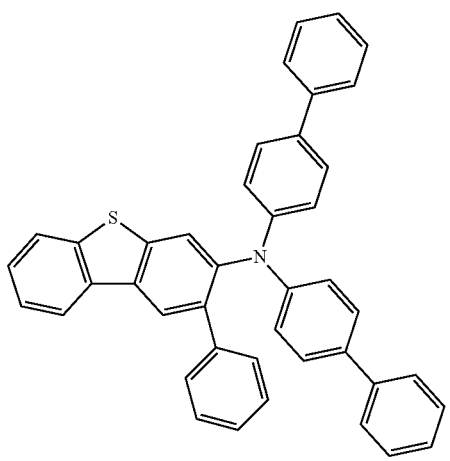
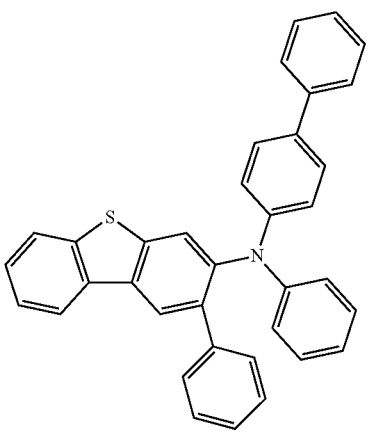

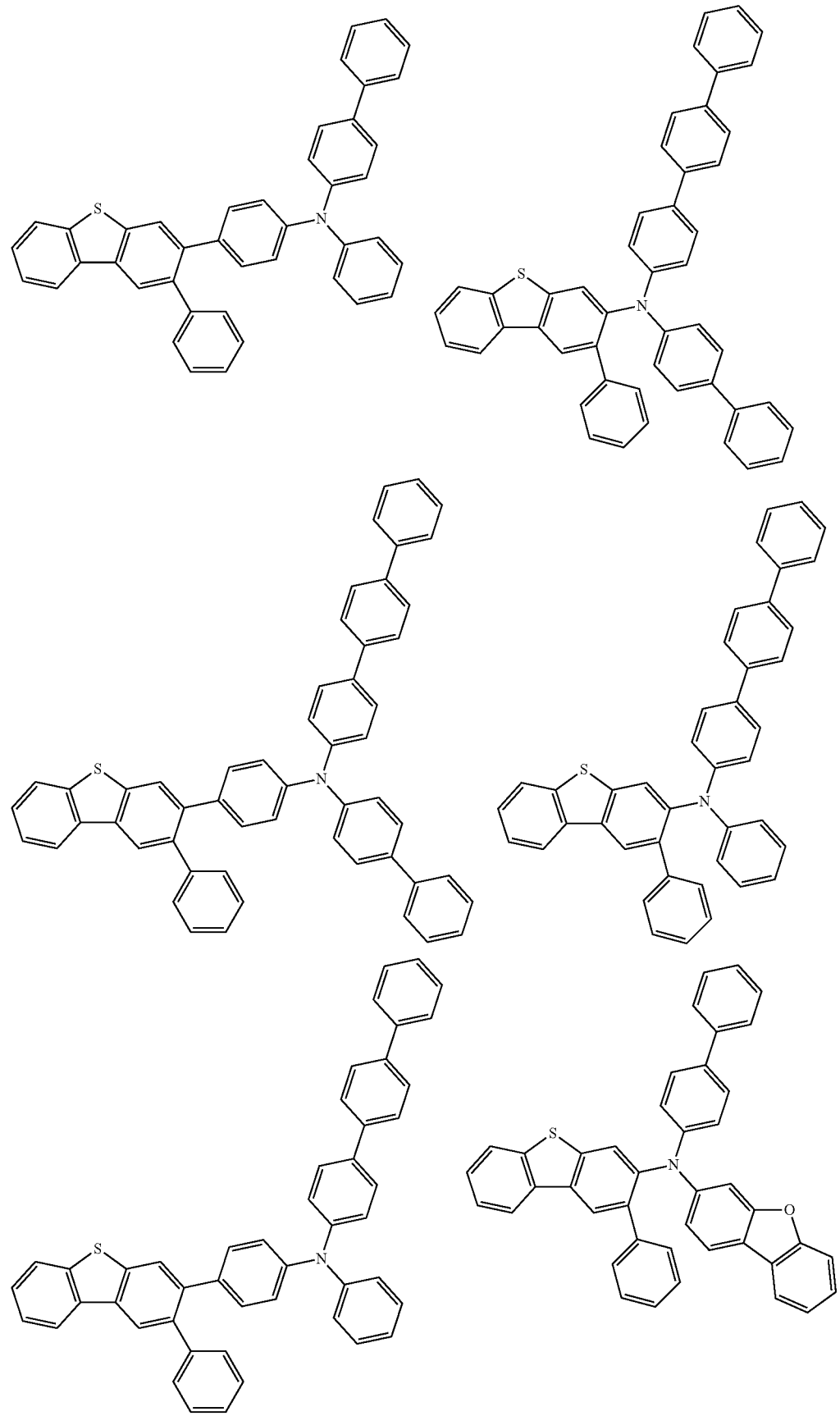

-continued
111
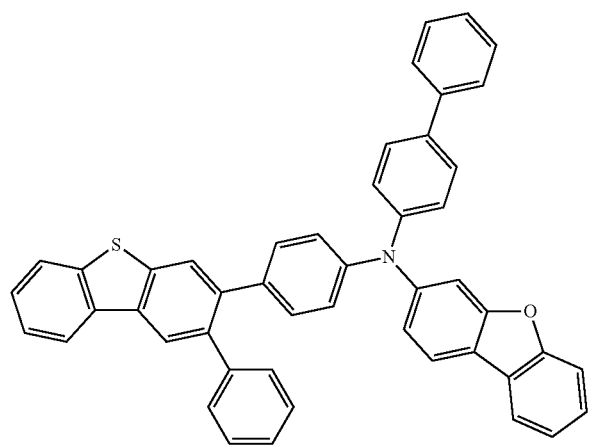
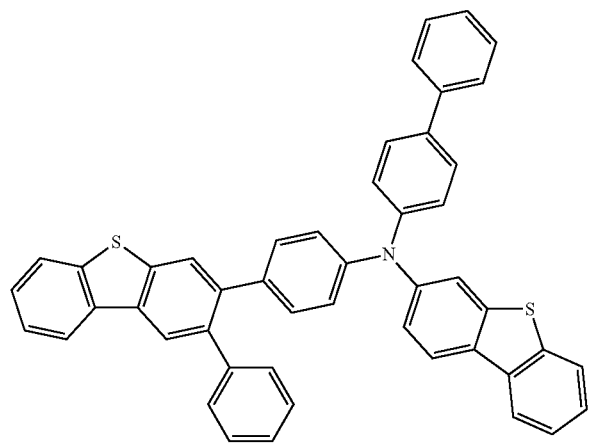
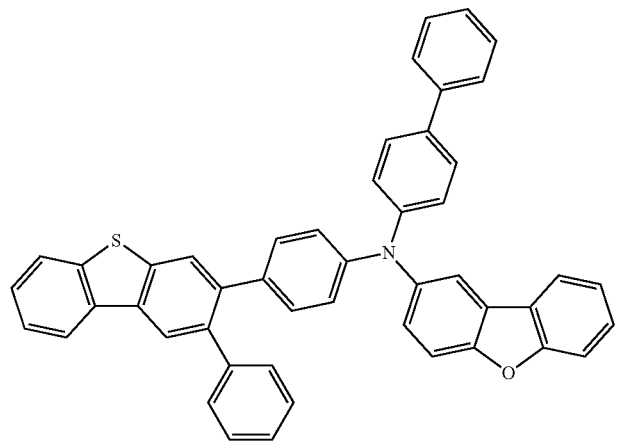
112
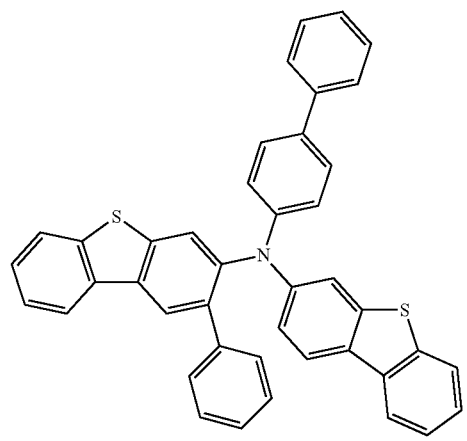
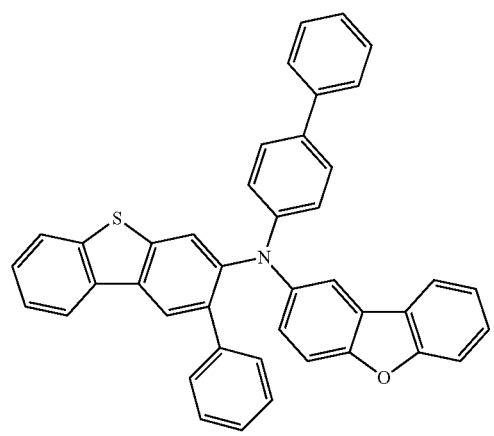
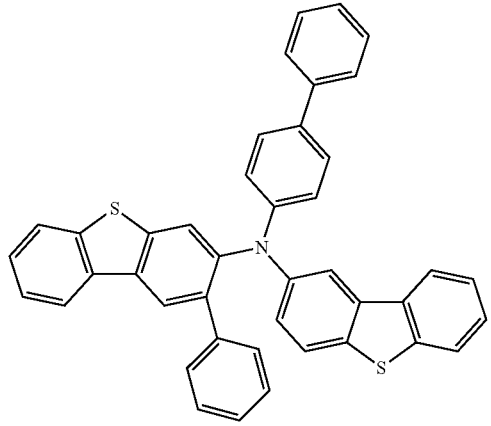

113 114
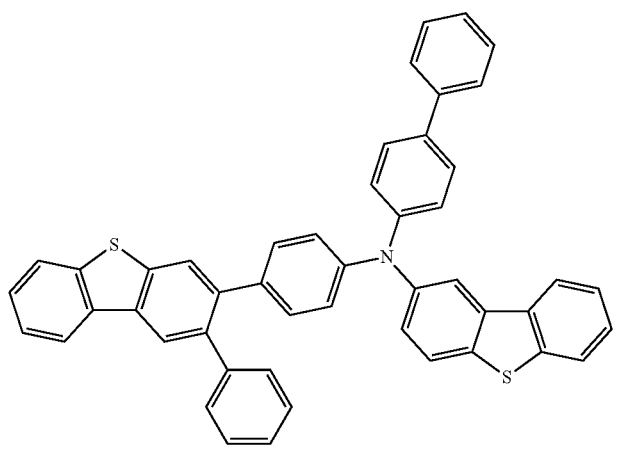 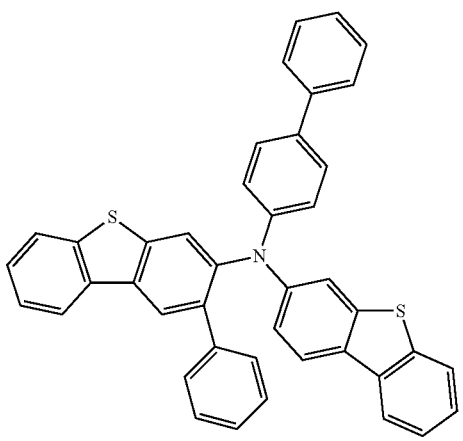
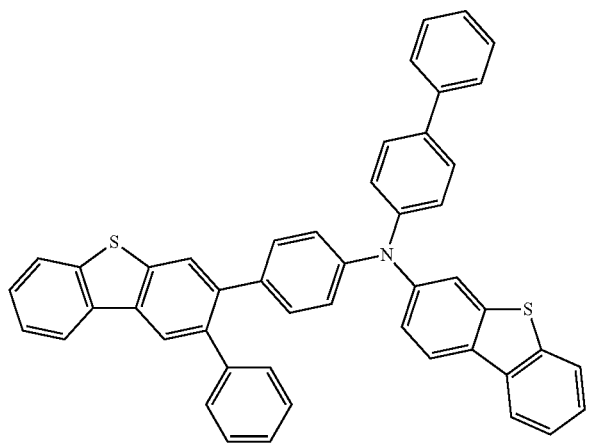 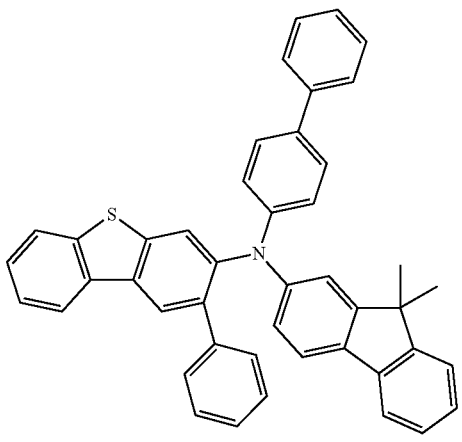
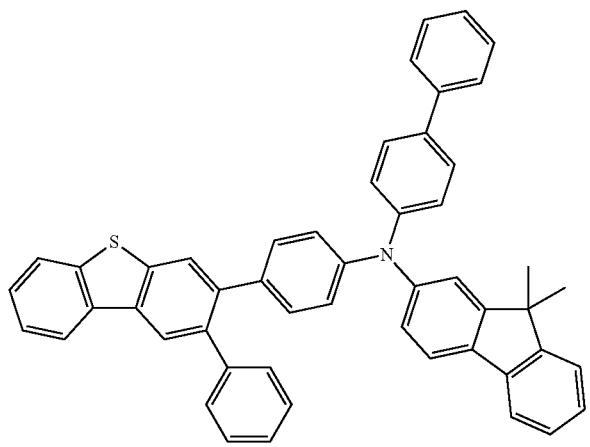 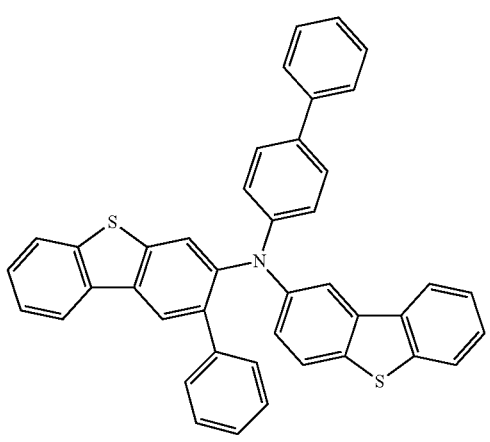

115 116
-continued
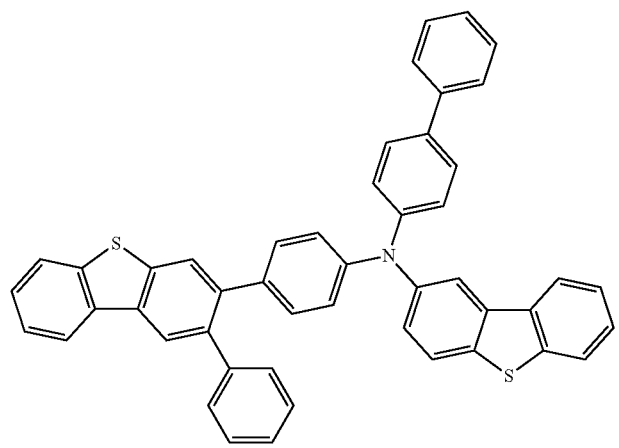
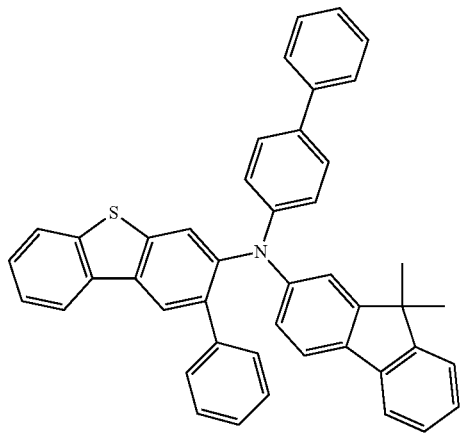
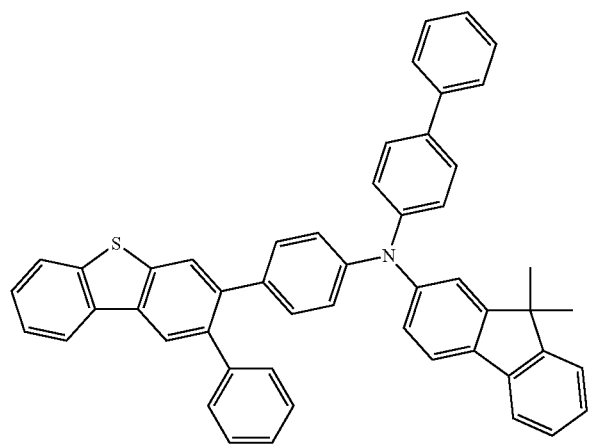
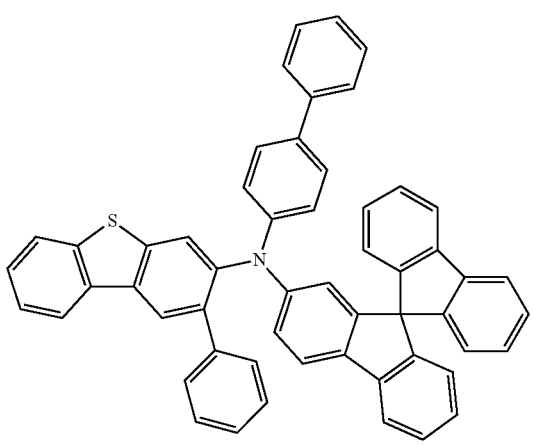
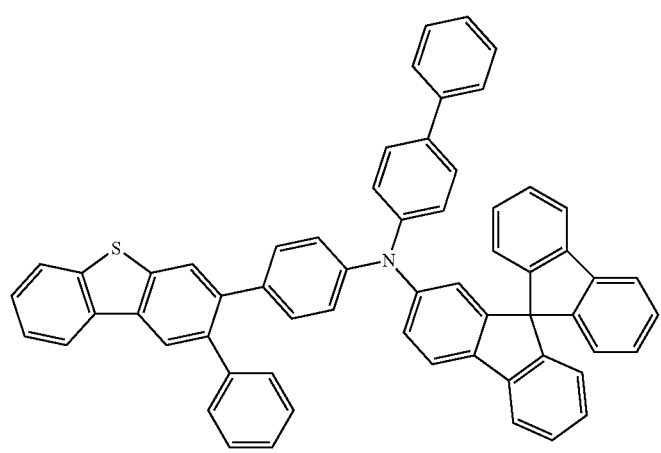
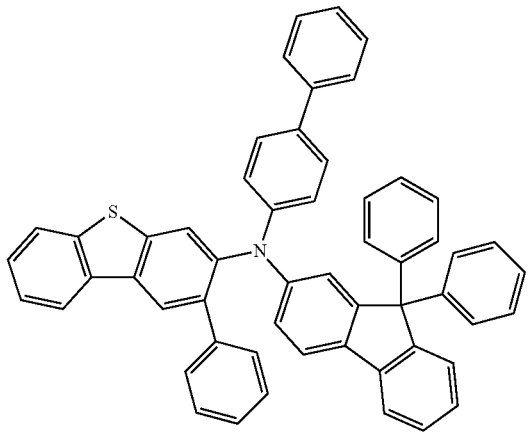

-continued
117
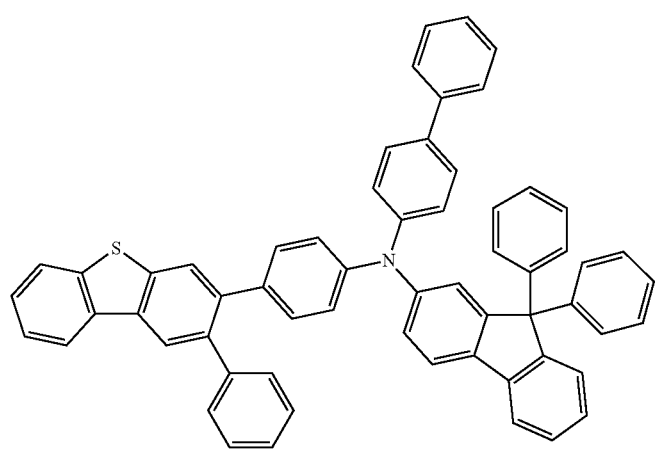
118
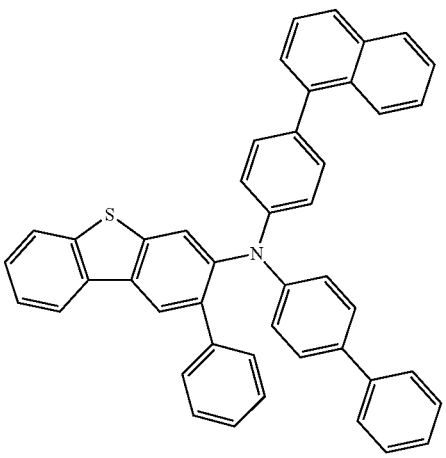
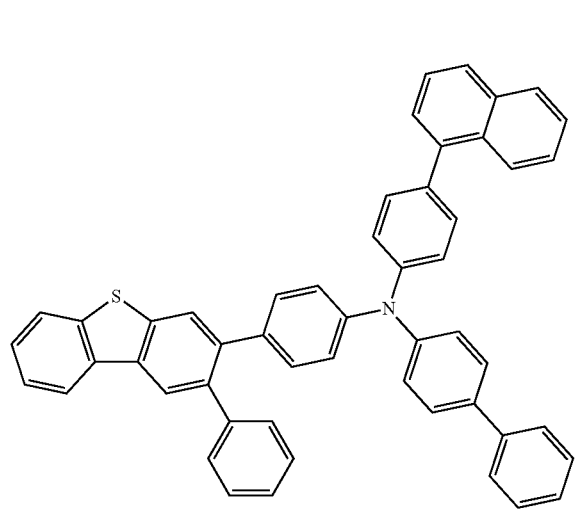
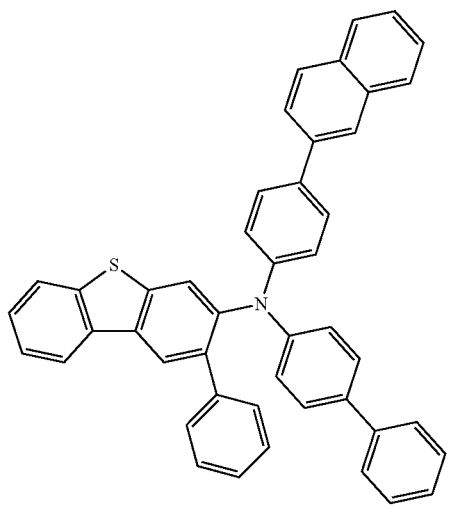
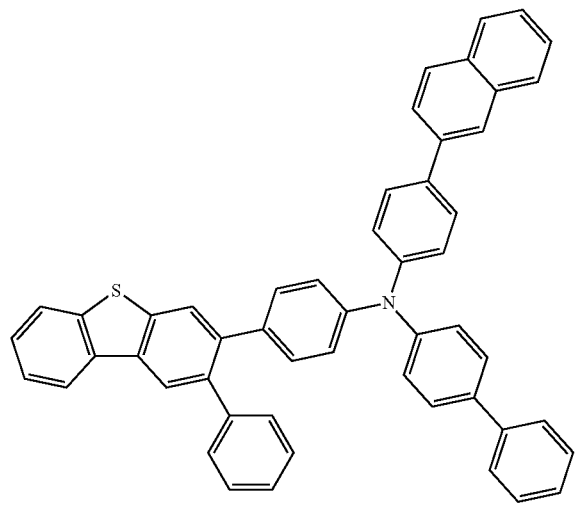
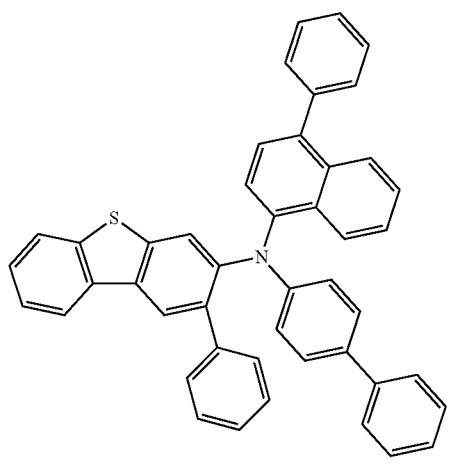

119 120
-continued
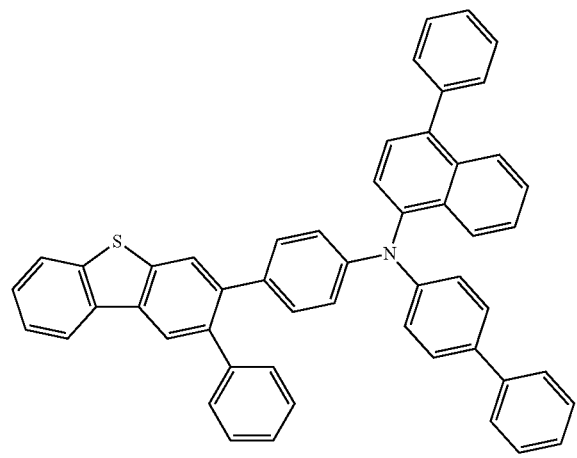
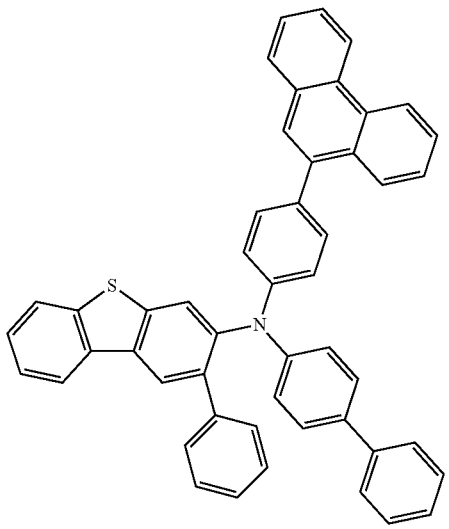
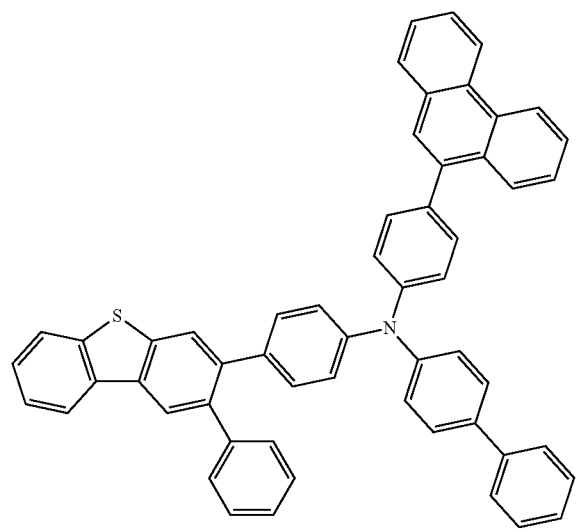
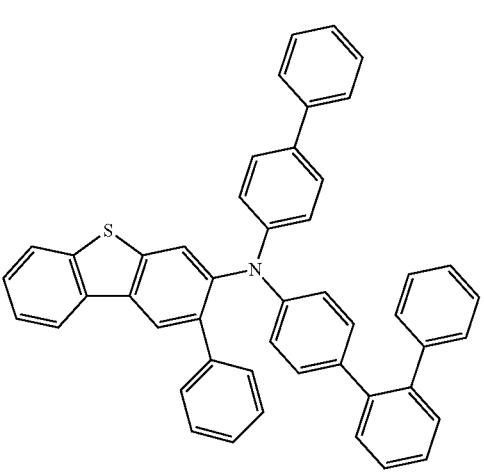
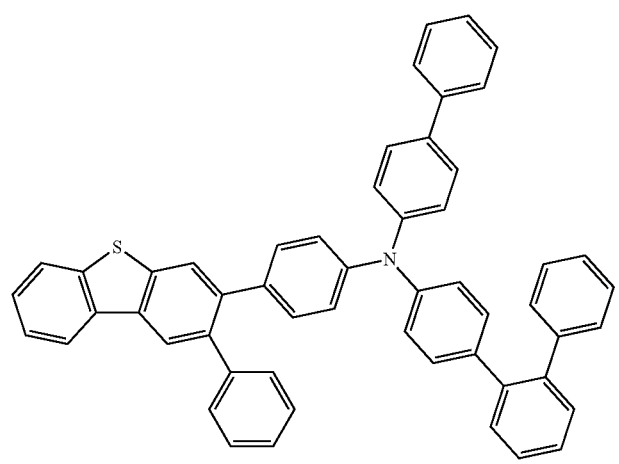
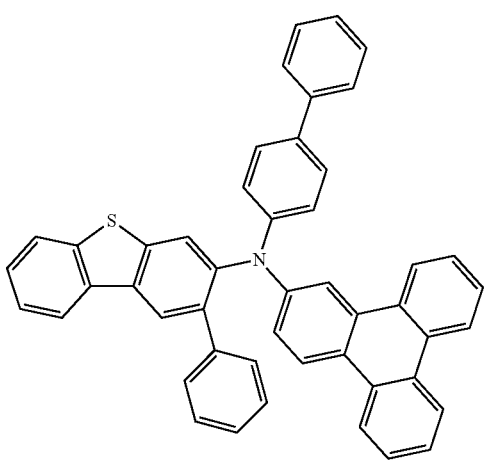

-continued
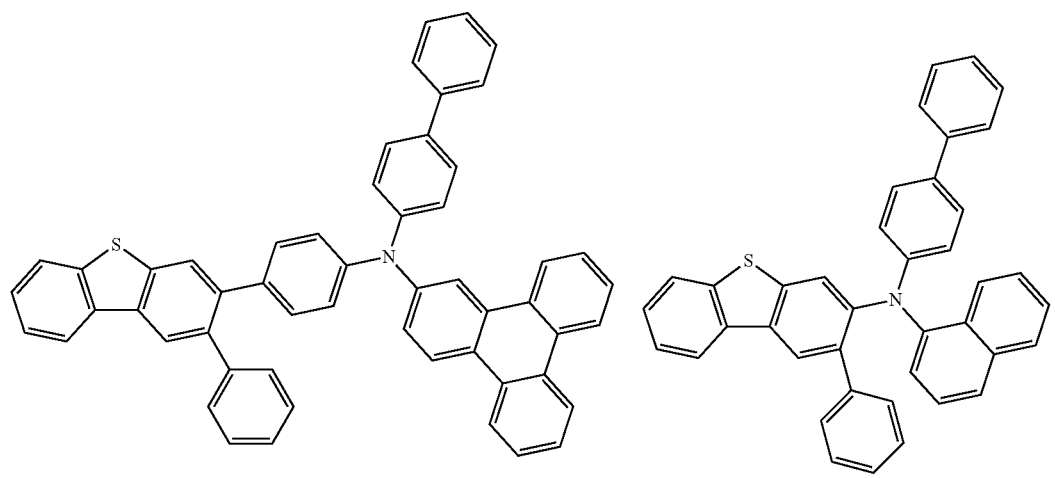
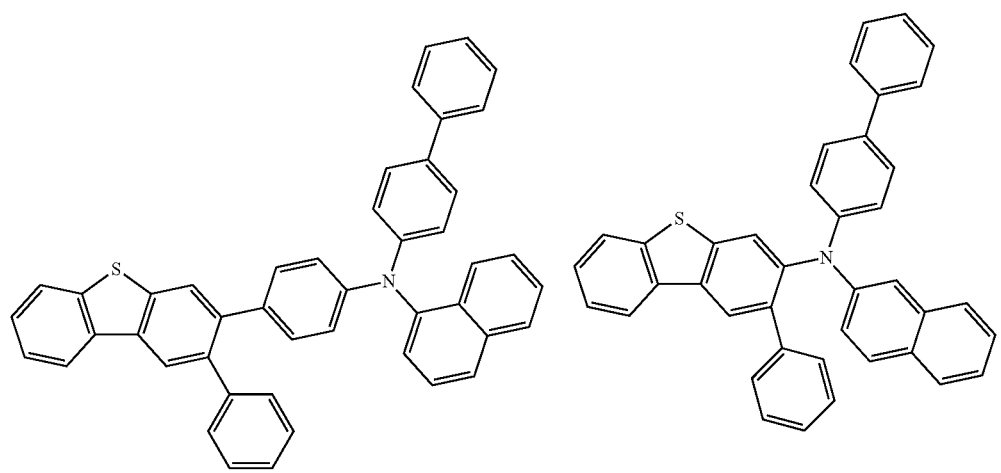
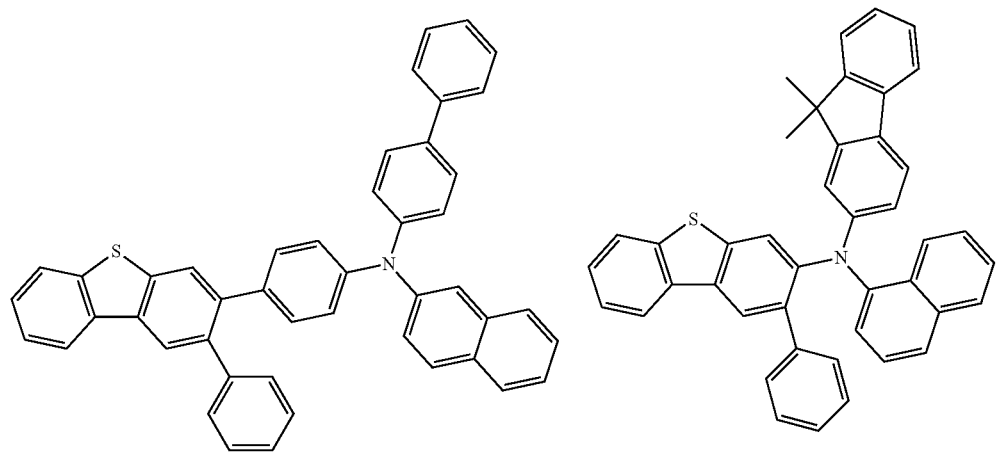

-continued
| 123 | 124 |
|---|---|
| 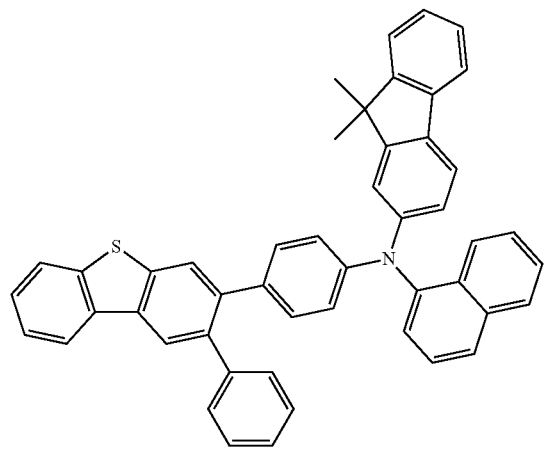 | 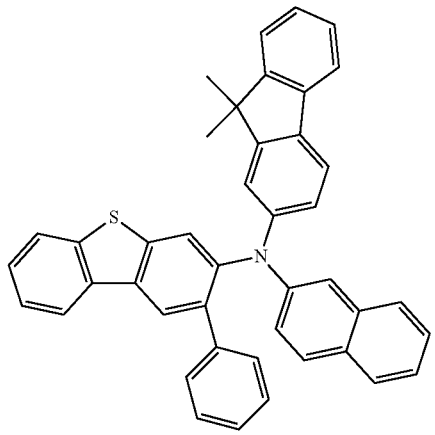 |
| 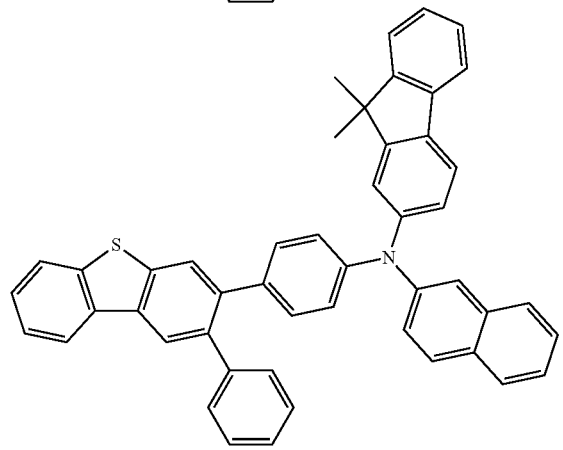 | 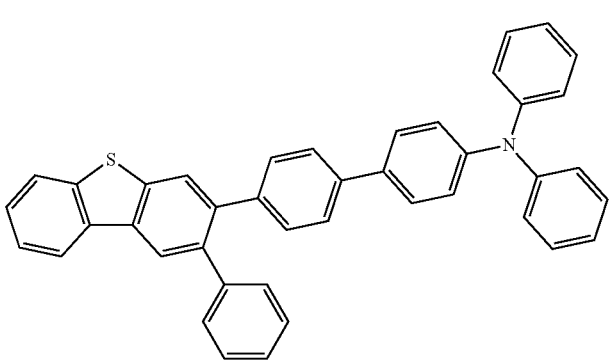 |
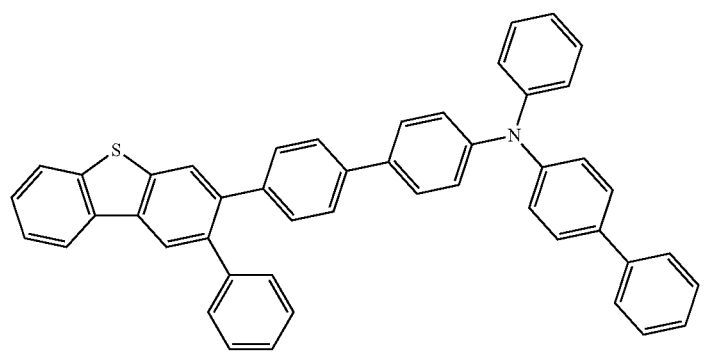
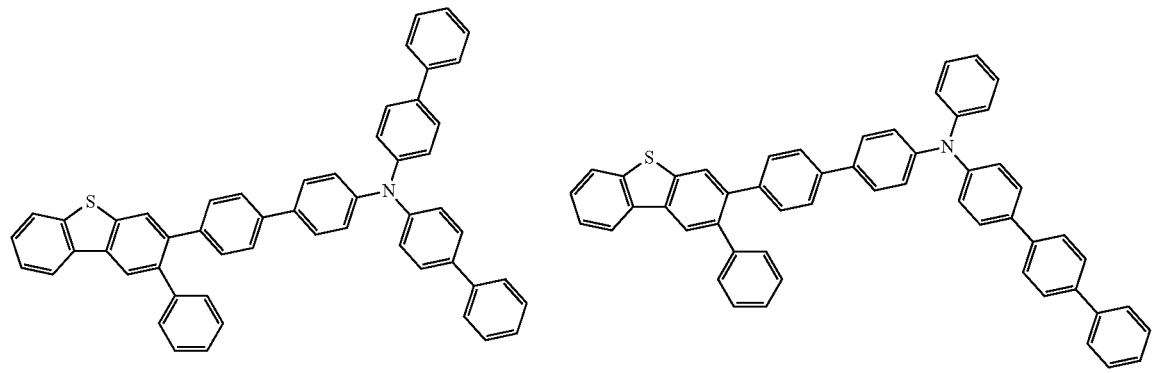 [SMILES: c1ccc(-c2ccc(N(c3ccc(-c4ccccc4)cc3)c3ccc(-c4ccc(-c5cc6sc7ccccc7c6cc5-c5ccccc5)cc4)cc3)cc2)cc1 ; c1ccc(-c2ccc(-c3ccc(N(c4ccccc4)c4ccc(-c5ccc(-c6cc7sc8ccccc8c7cc6-c6ccccc6)cc5)cc4)cc3)cc2)cc1]

-continued
125
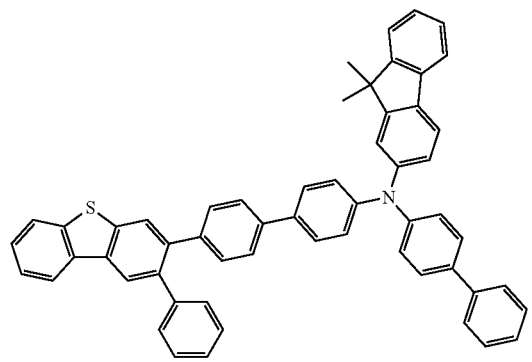
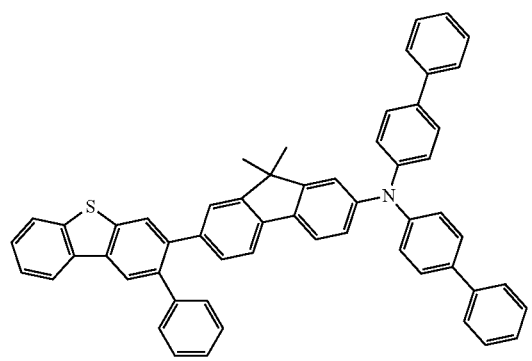
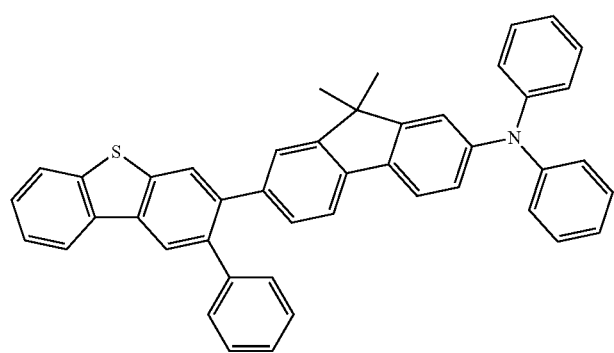
126
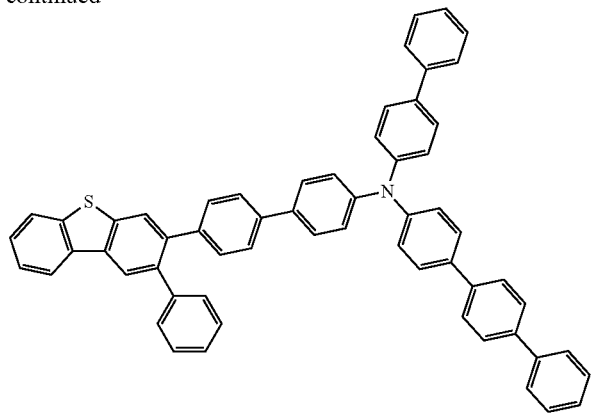
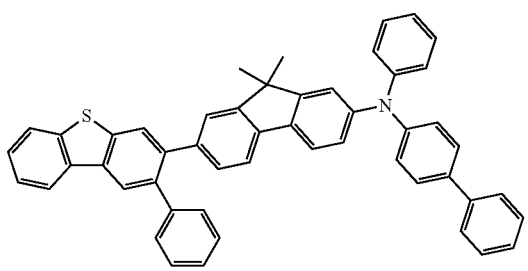
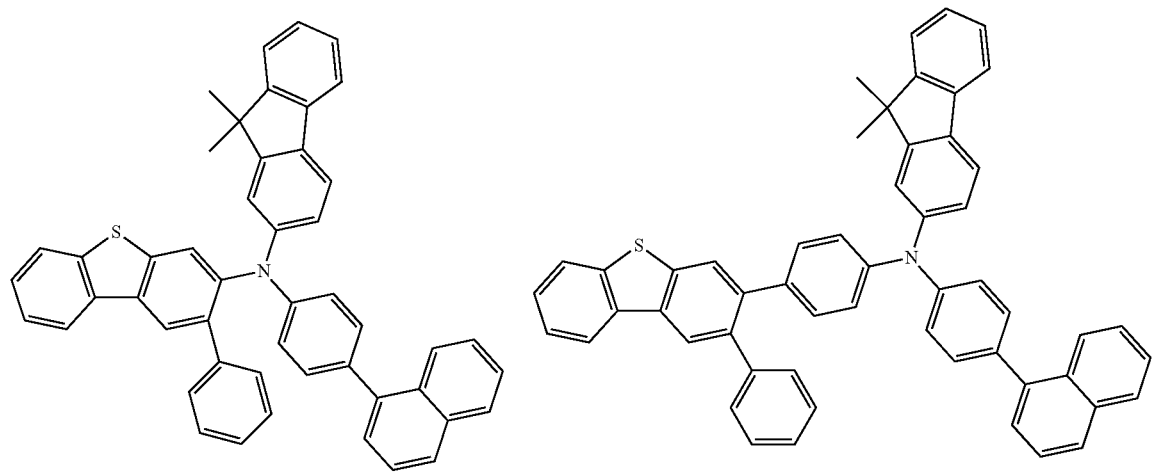

-continued
127
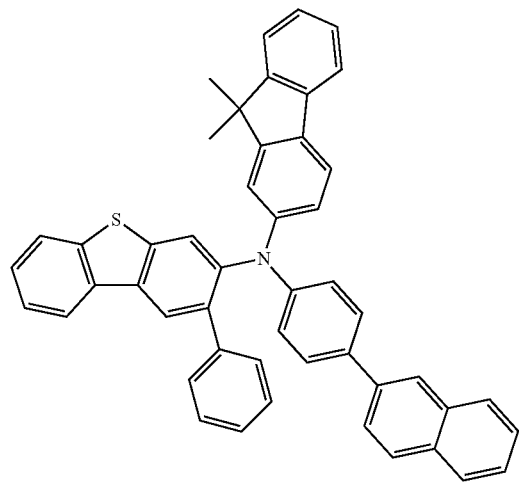
128
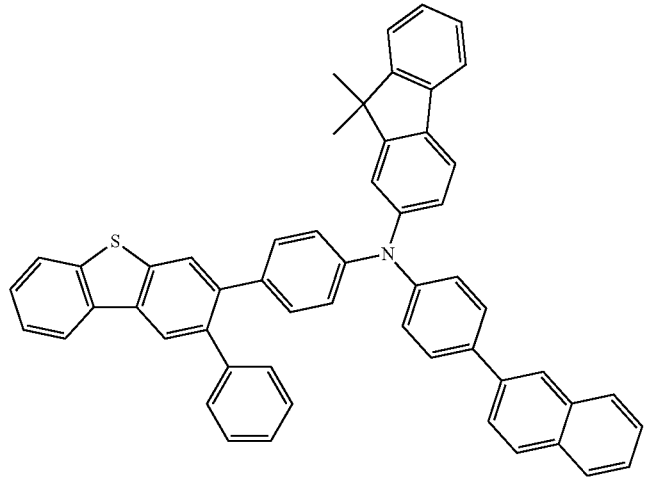
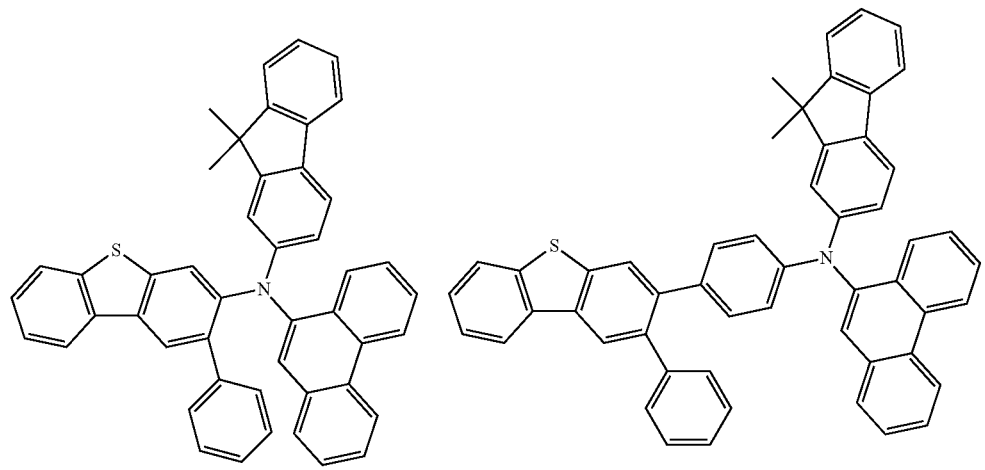
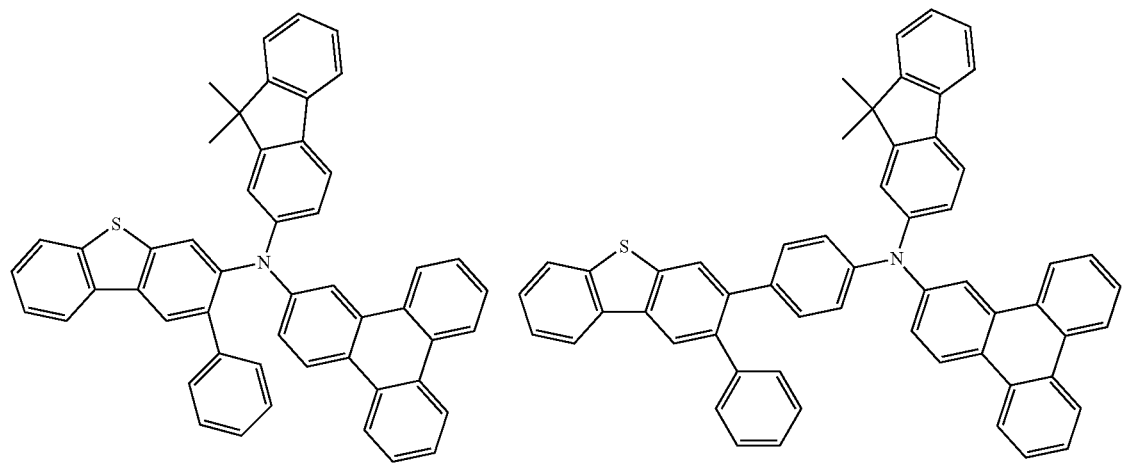

129
130
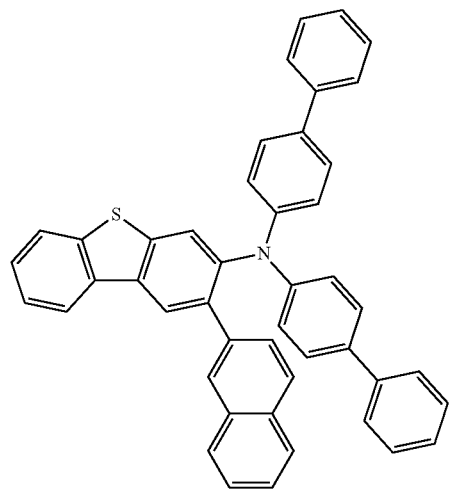
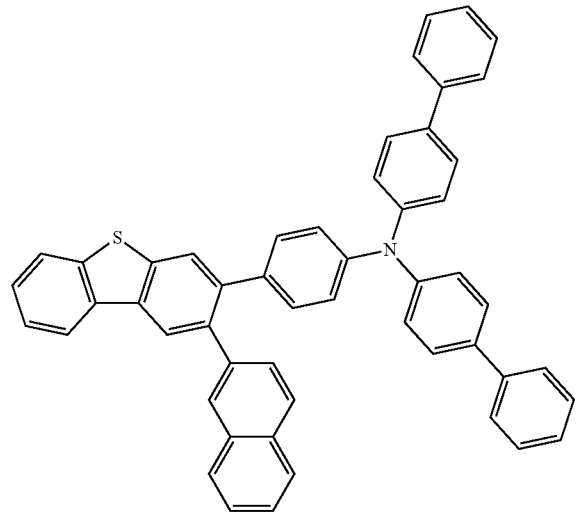
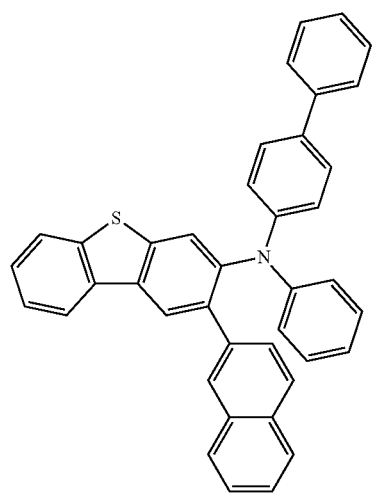
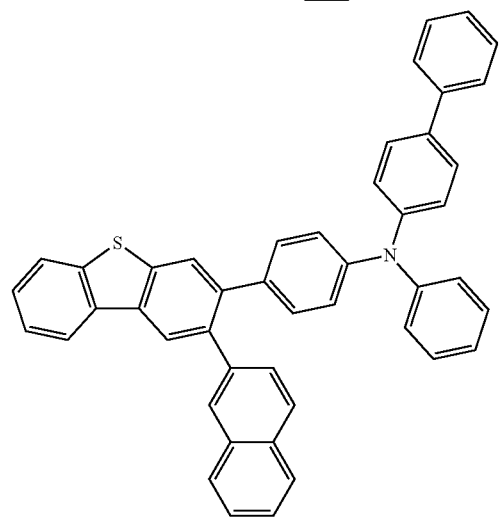
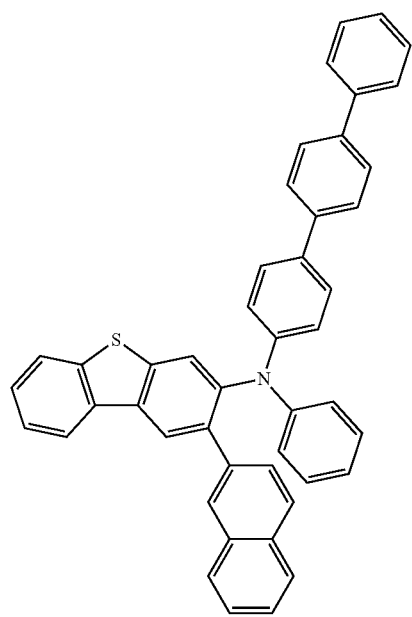
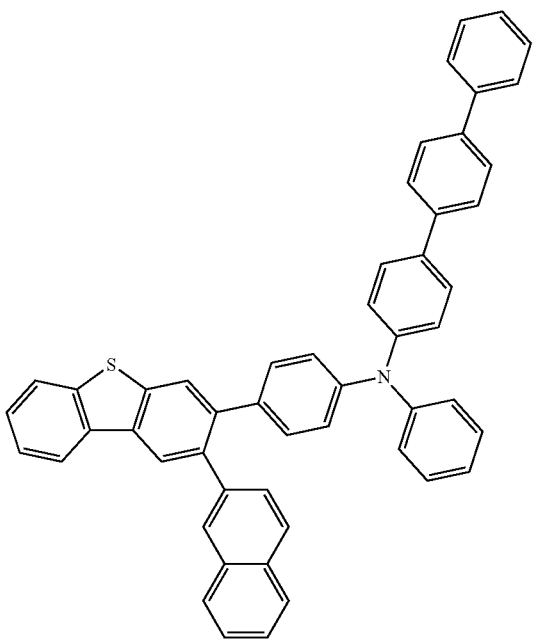

-continued
131
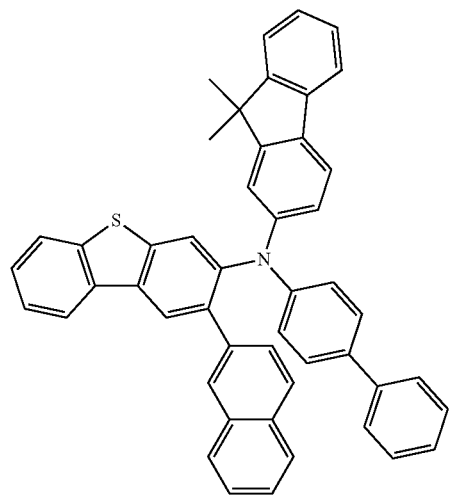
132
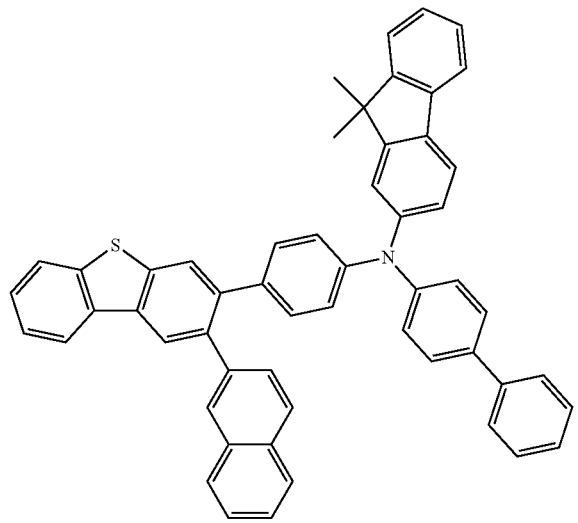
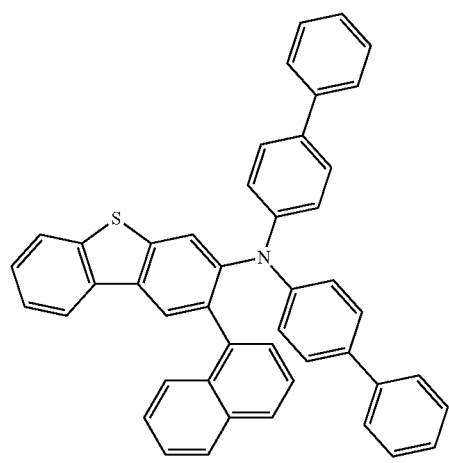
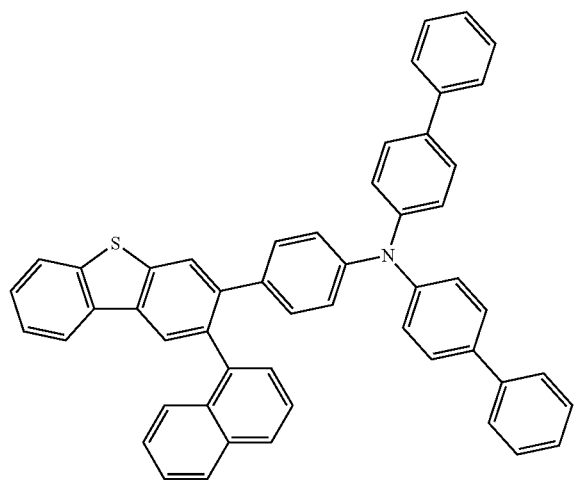
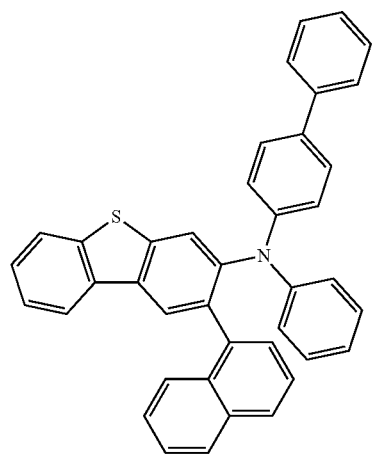
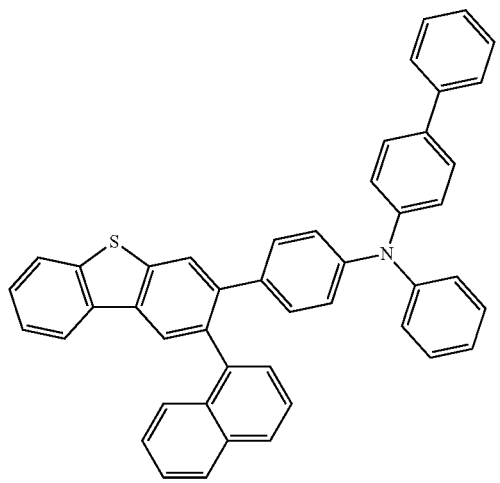

-continued
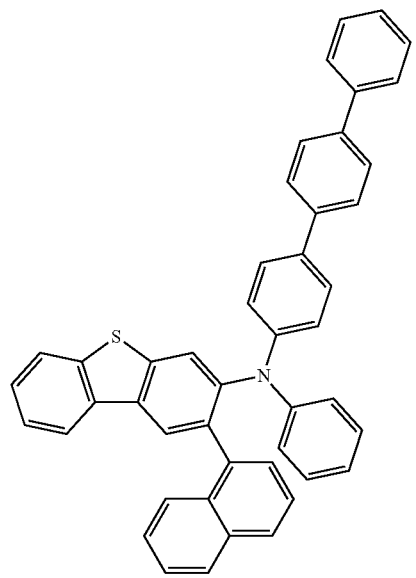
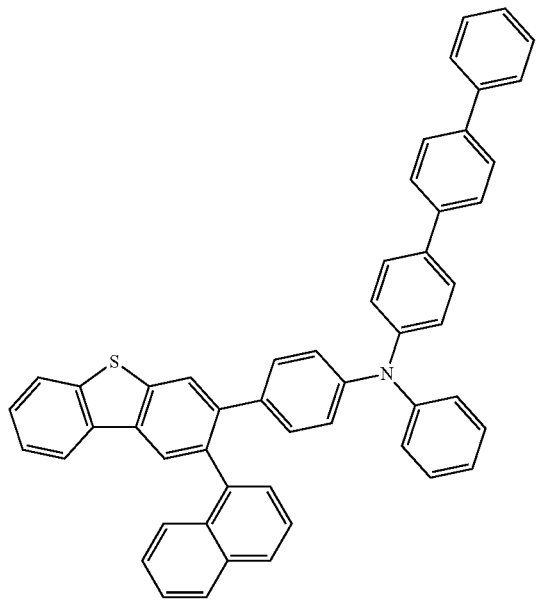
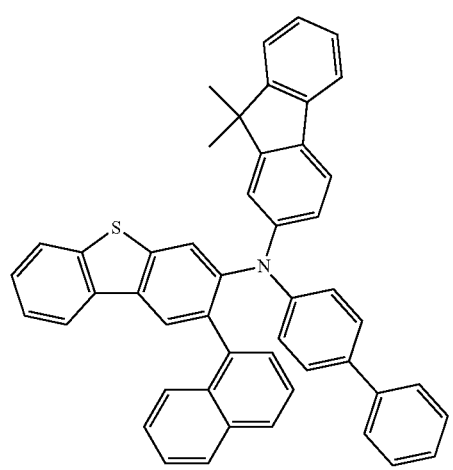
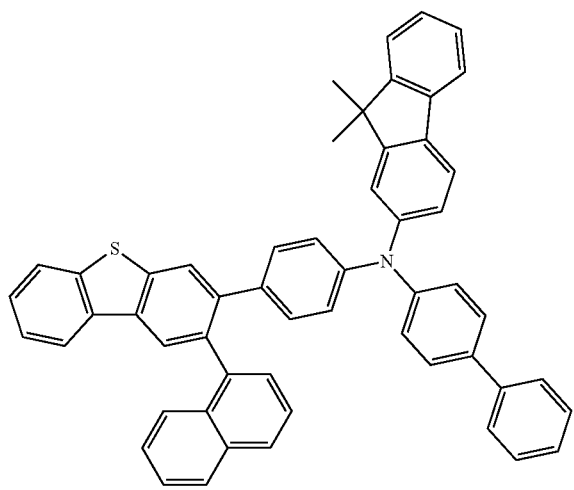
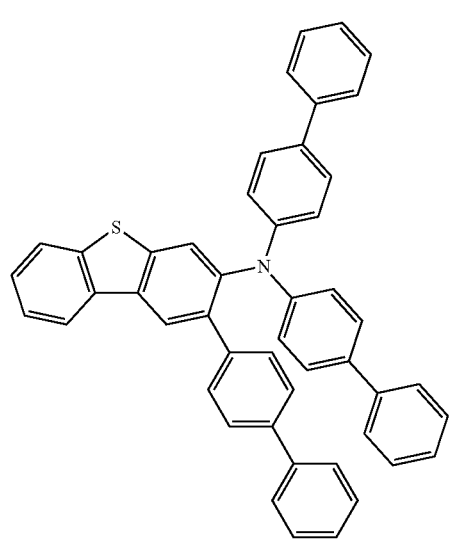
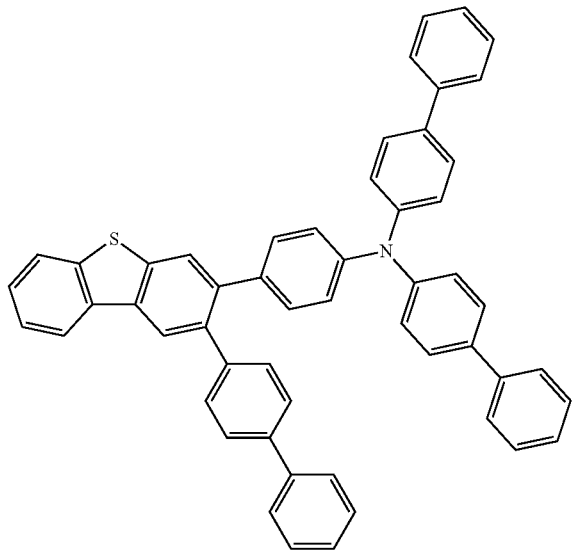

135 136
-continued
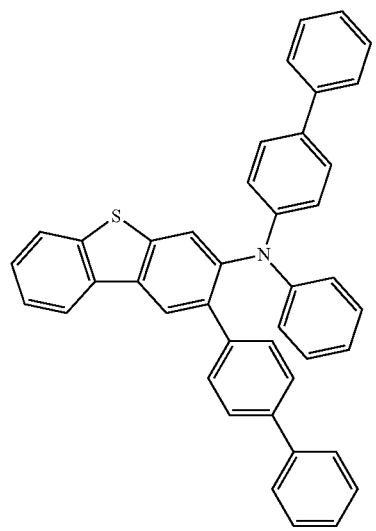 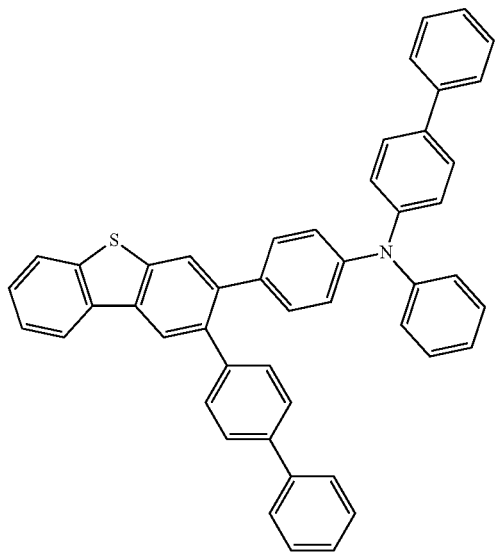
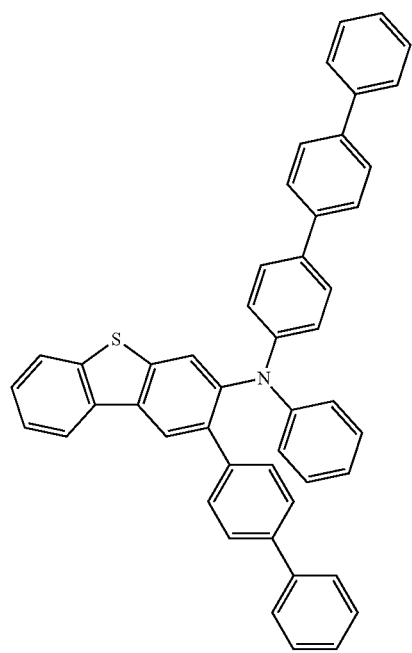 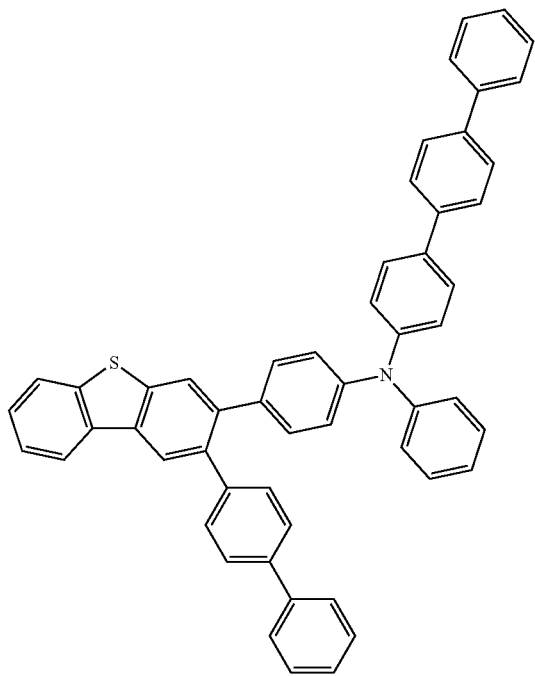

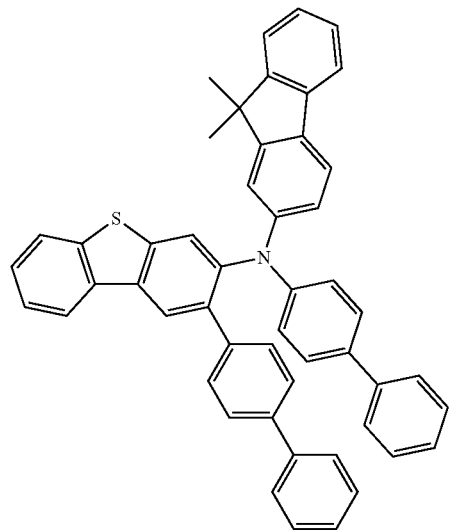
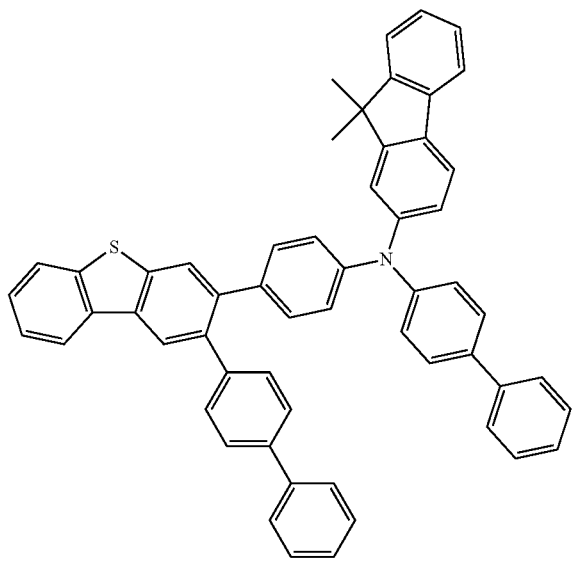
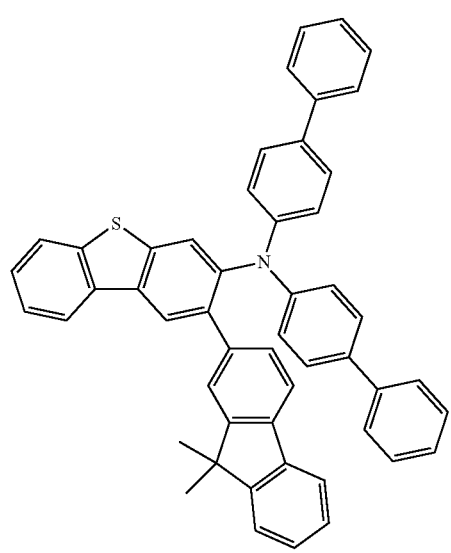
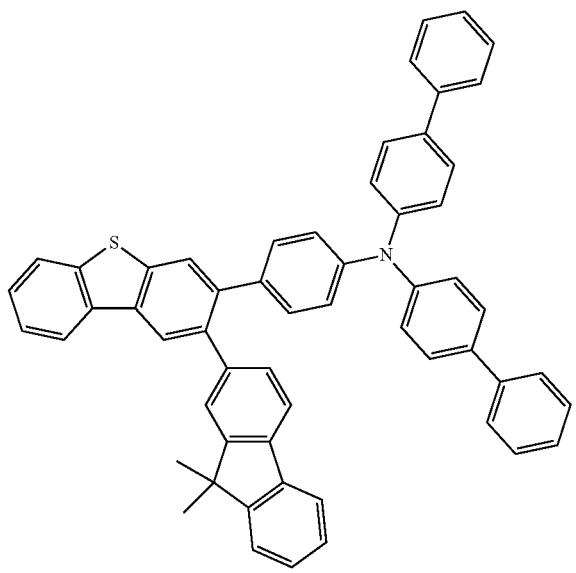
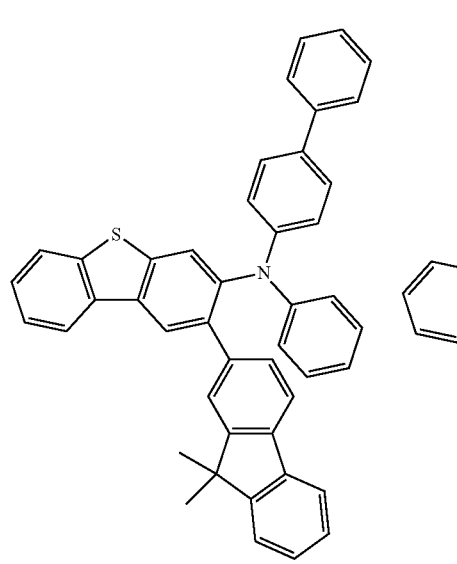
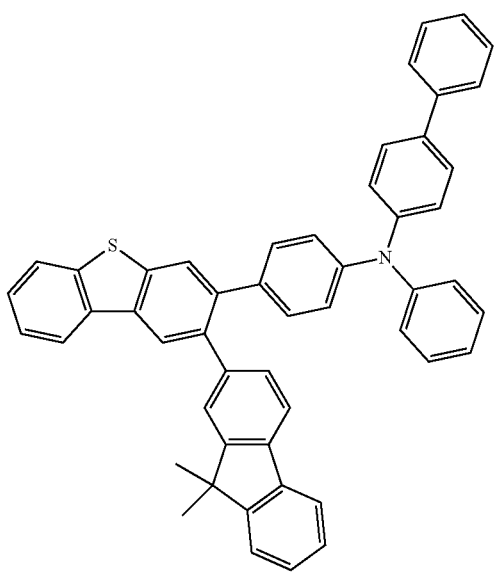

139
140
-continued
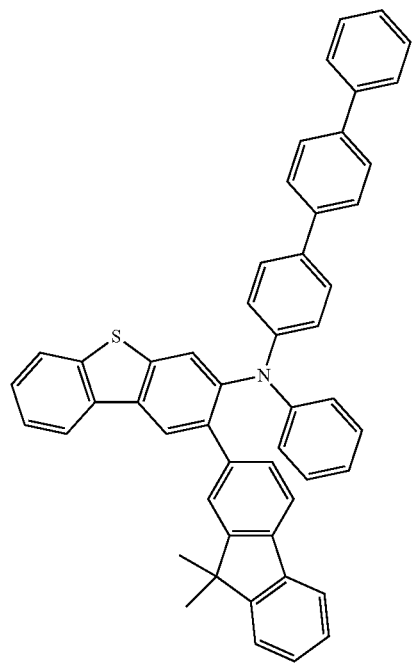 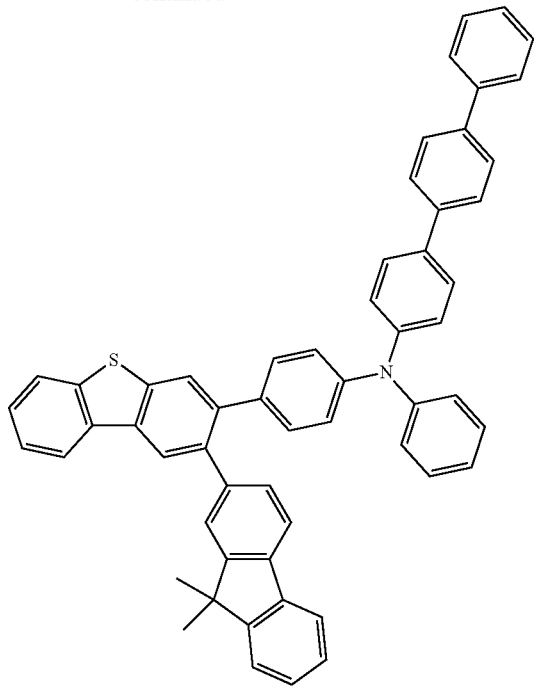
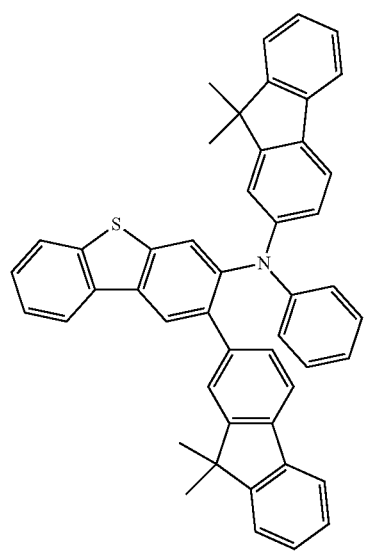 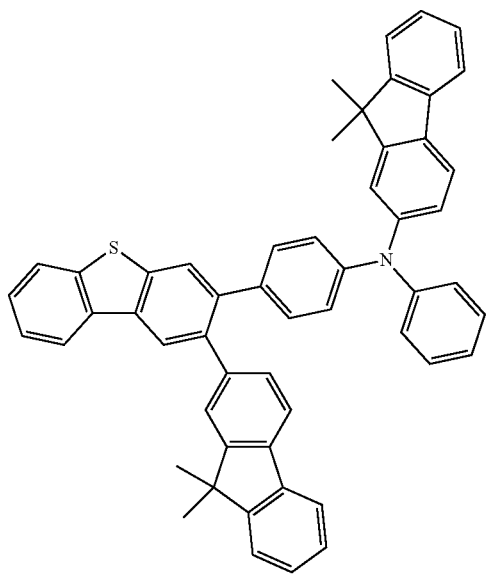

141 142
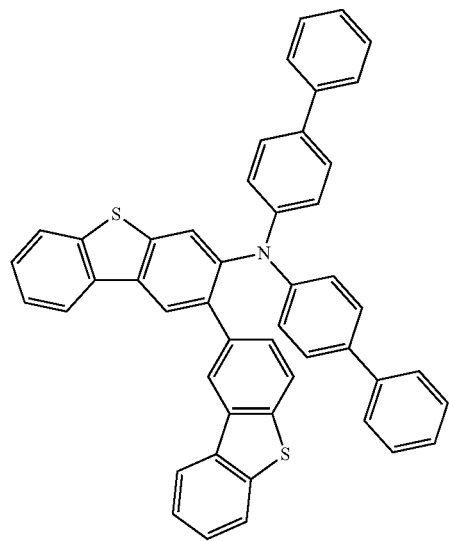
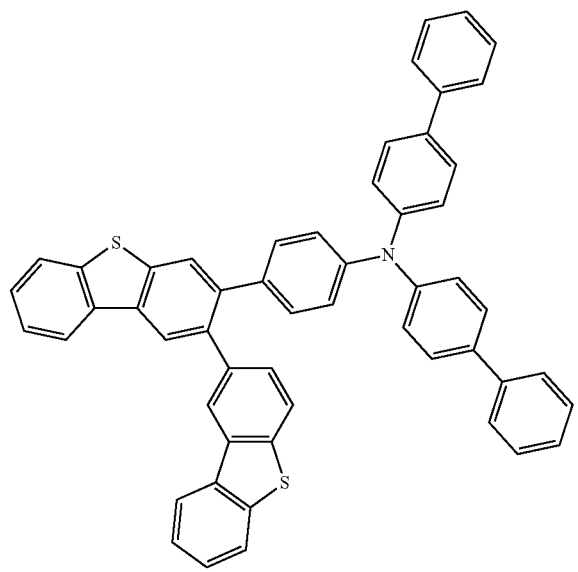
-continued
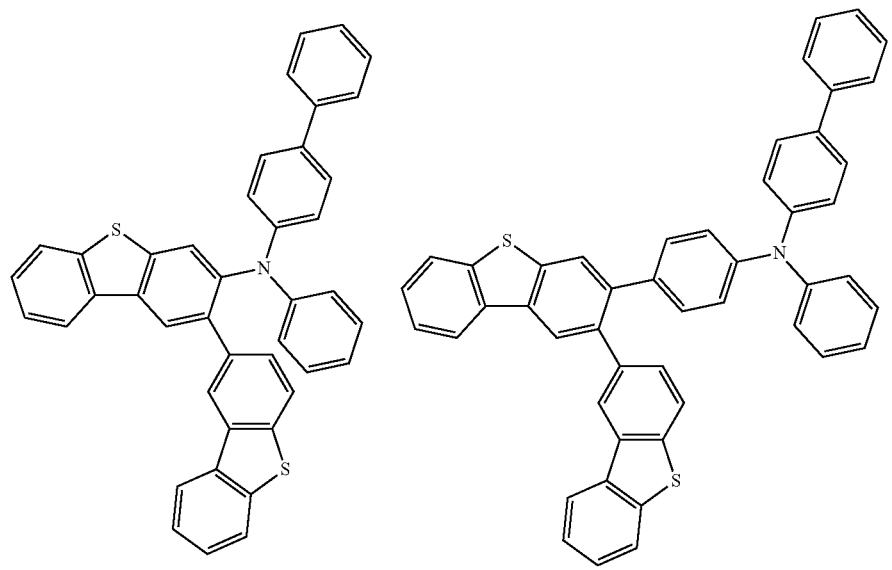

143 144
-continued
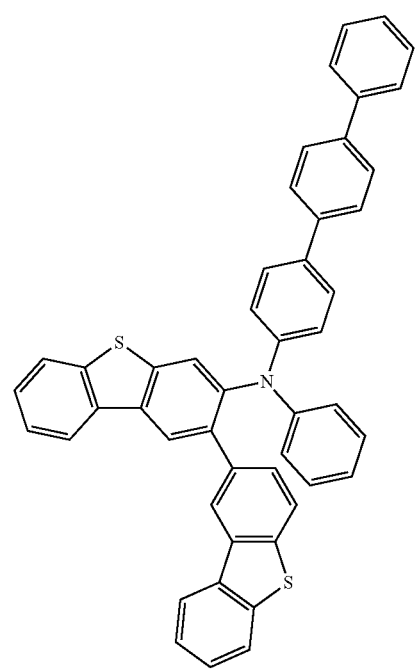
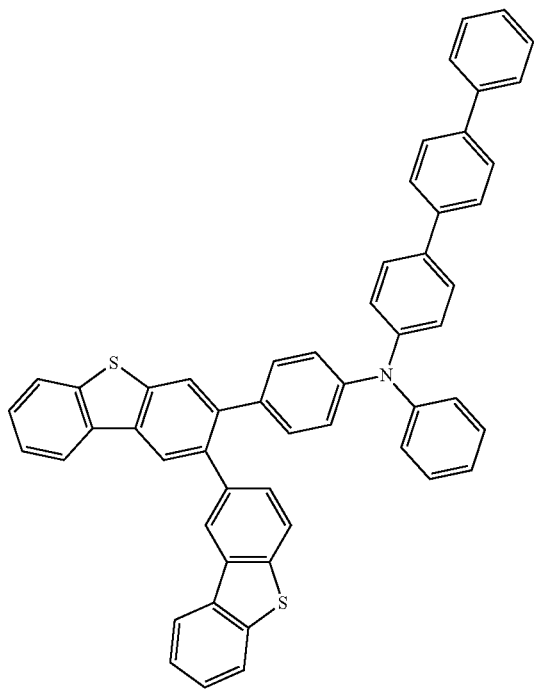
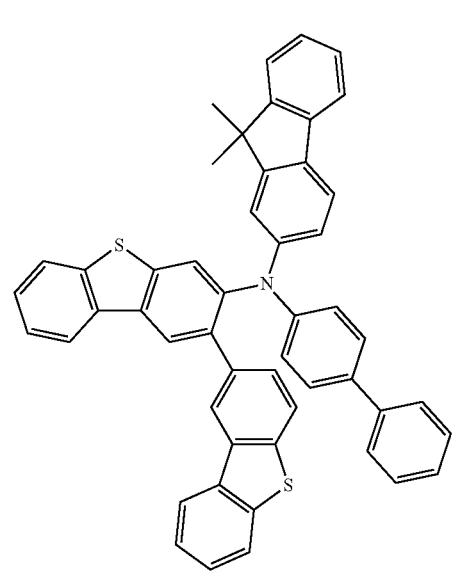
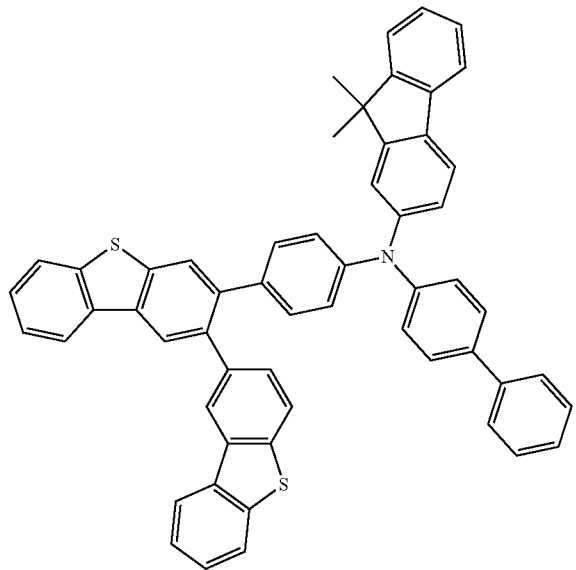

-continued
145
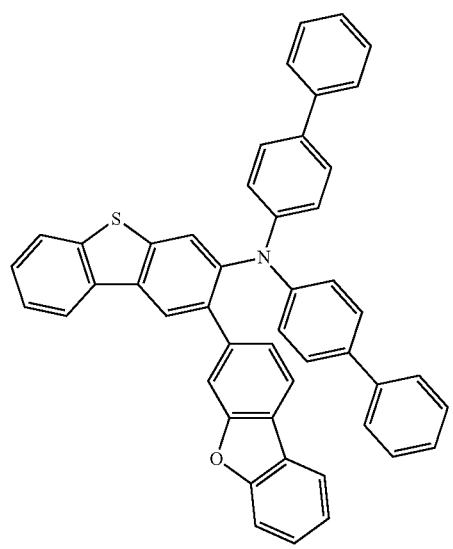
146
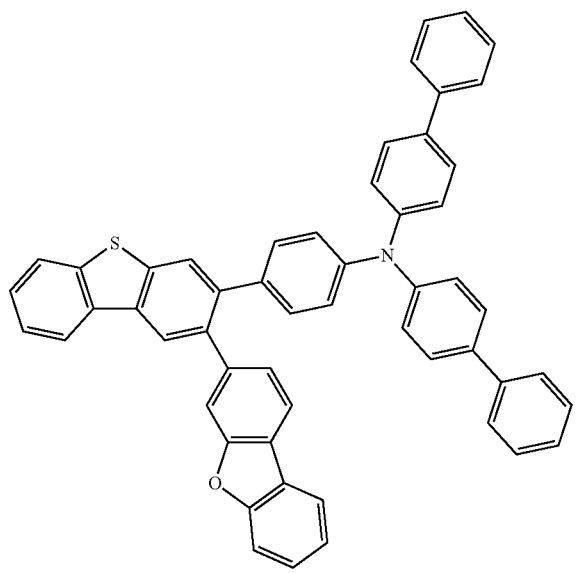
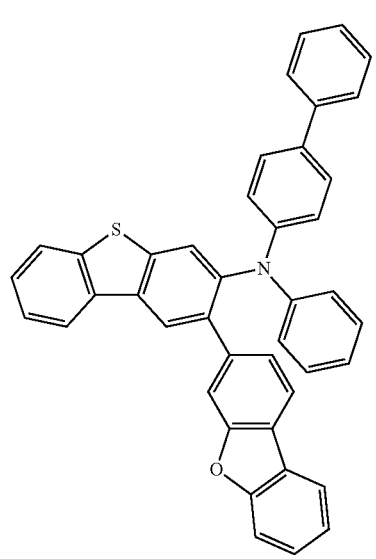
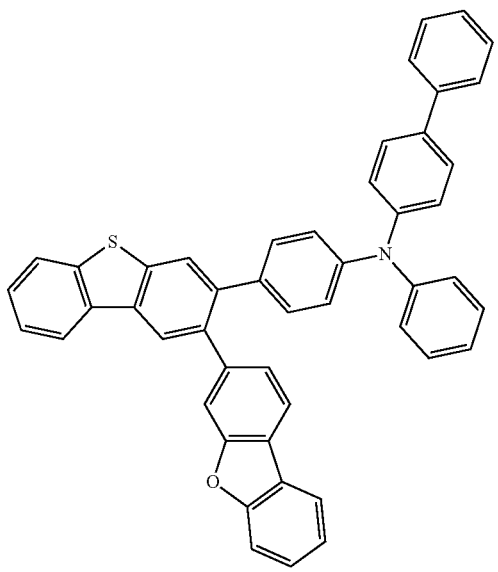

-continued
147
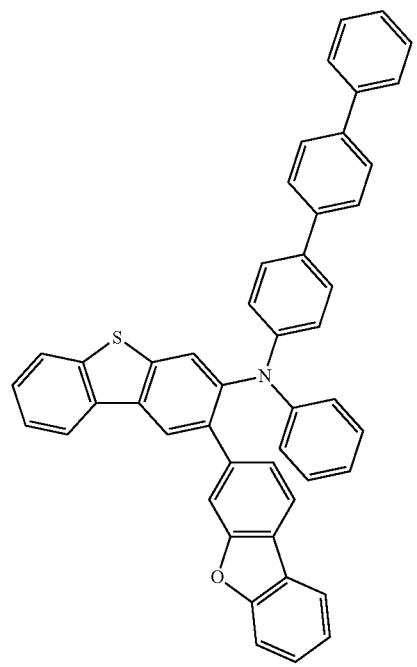
148
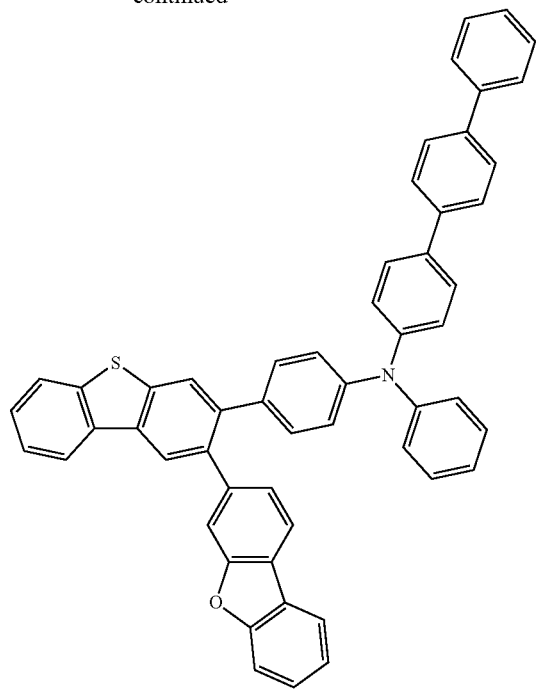
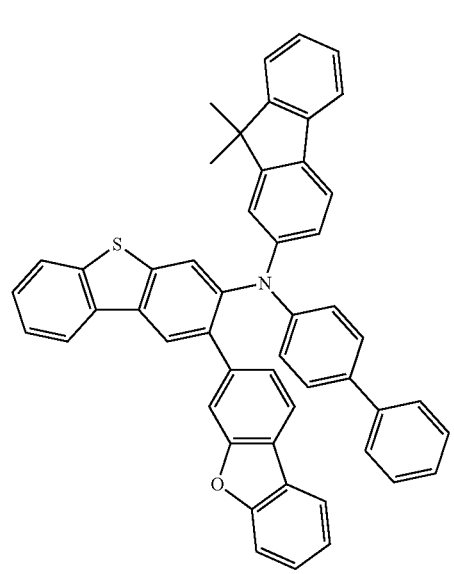
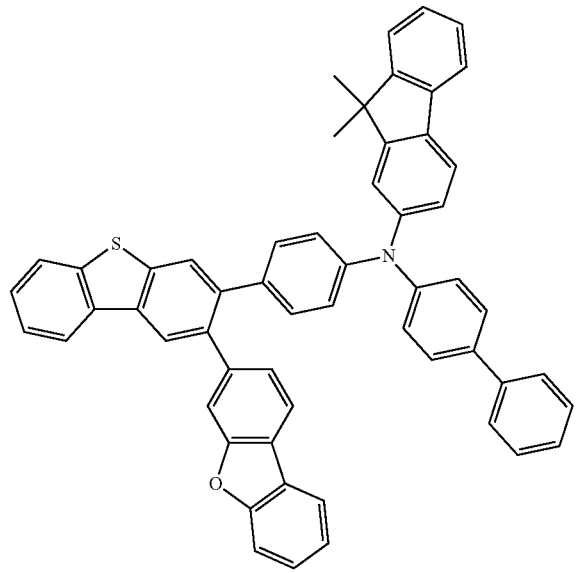

149 150
-continued
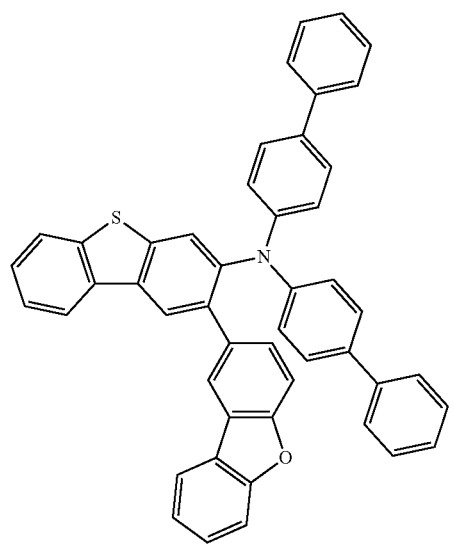
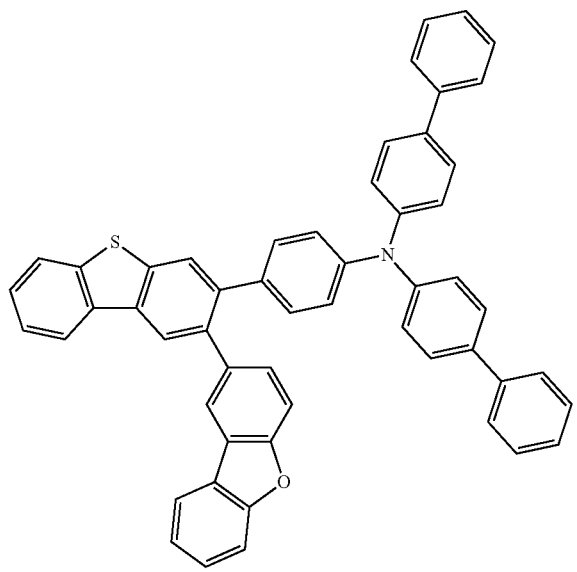
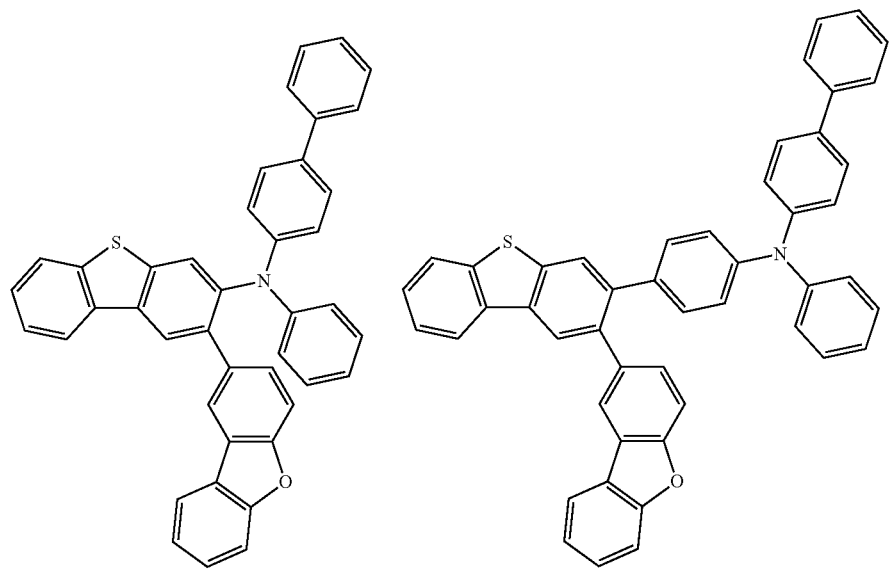

-continued
151
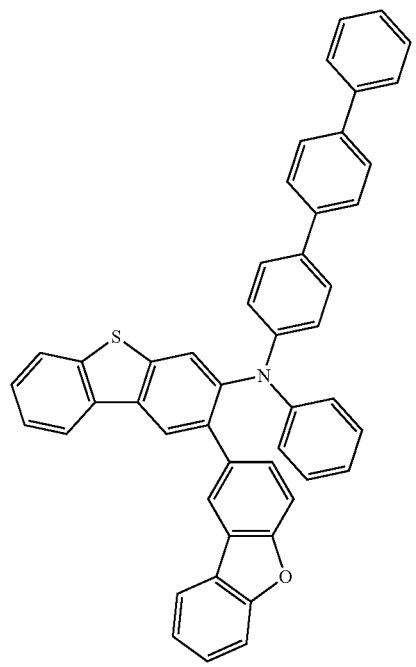
152
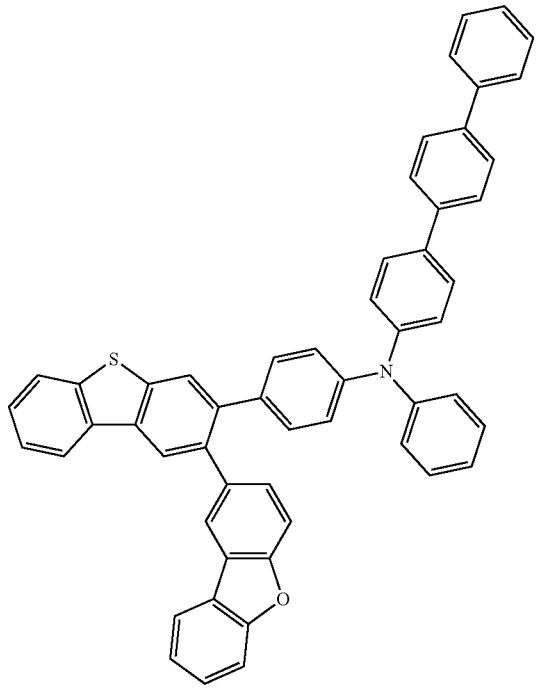
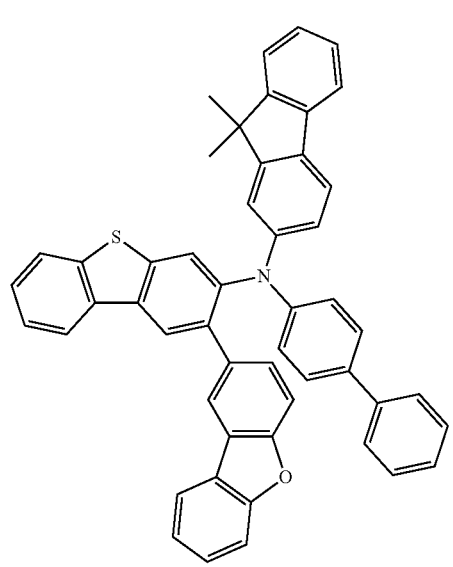
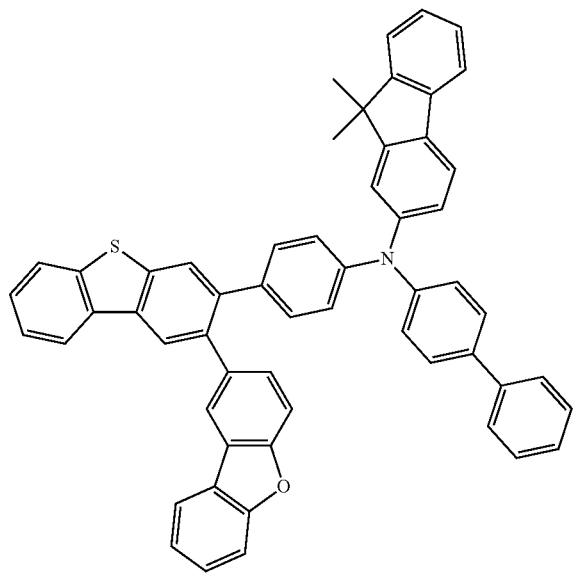

-continued
| 153 | 154 |
|---|---|
| 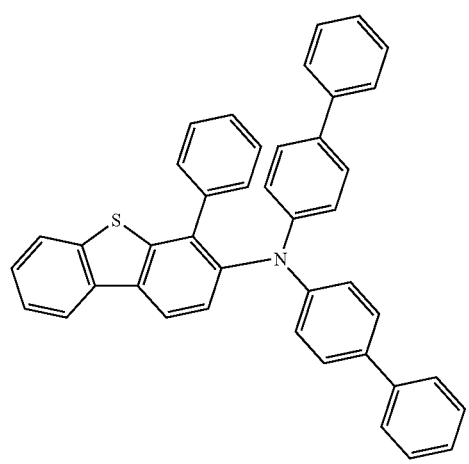 | 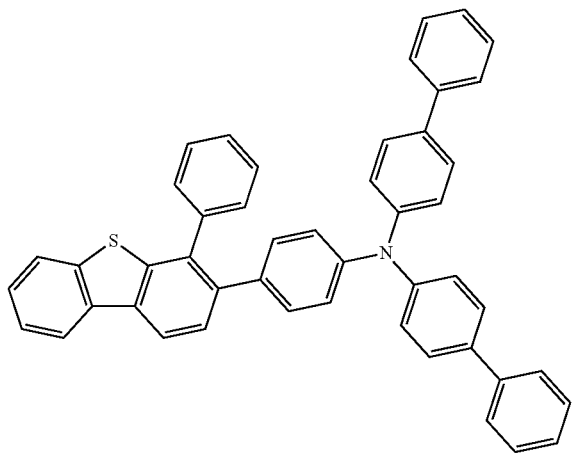 |
| 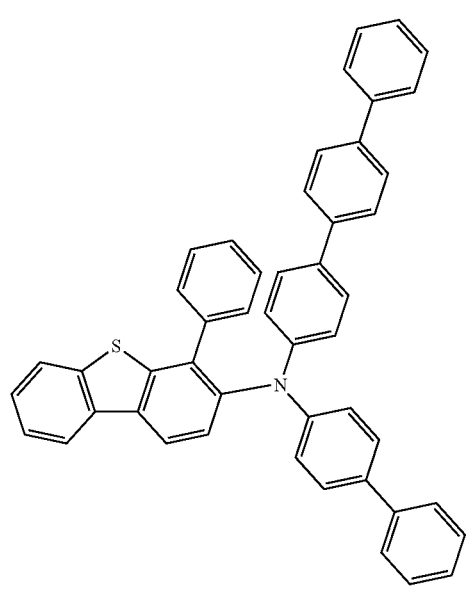 | 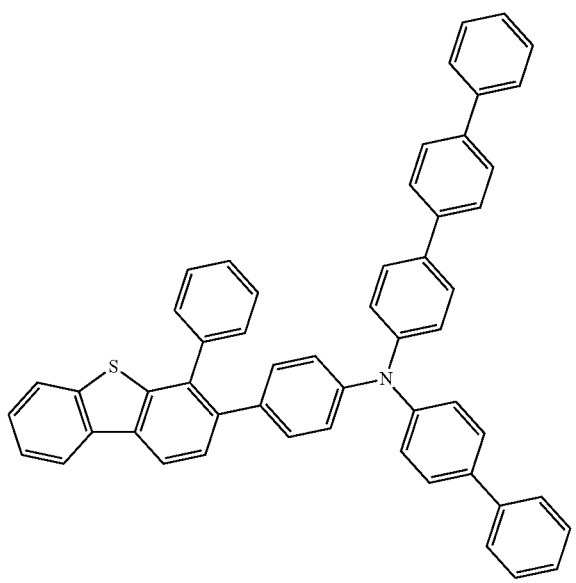 |
| 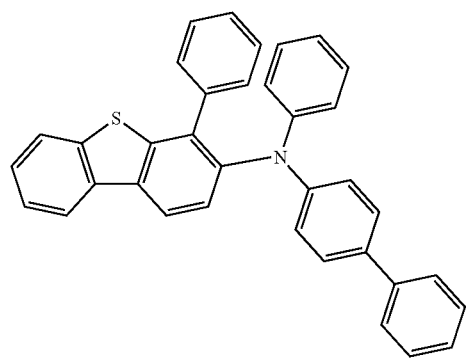 | 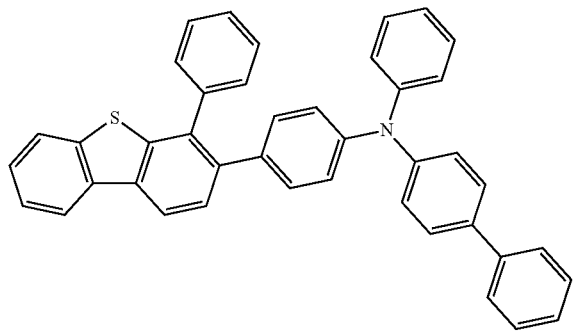 |

-continued
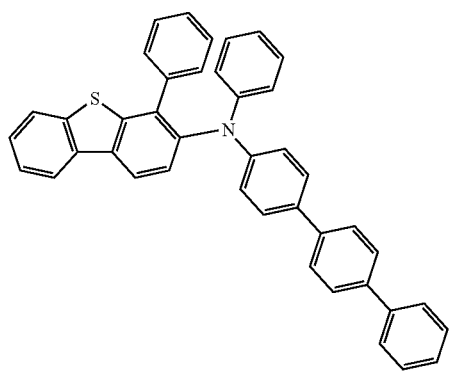
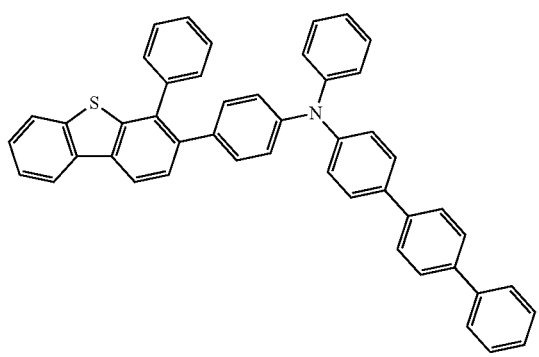
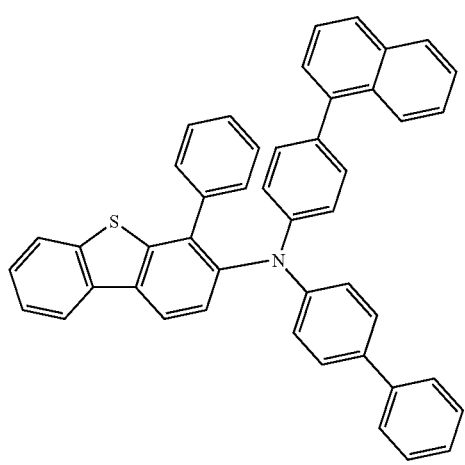
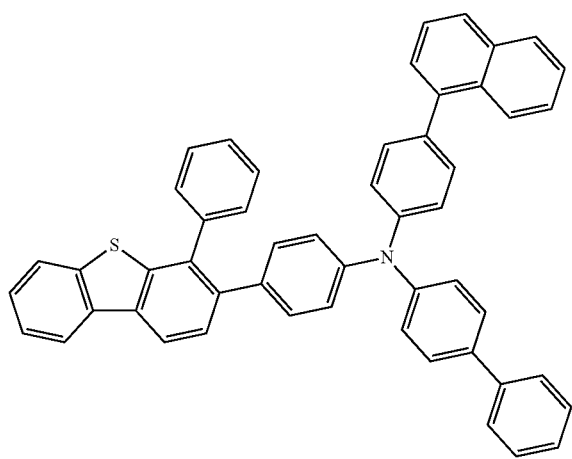
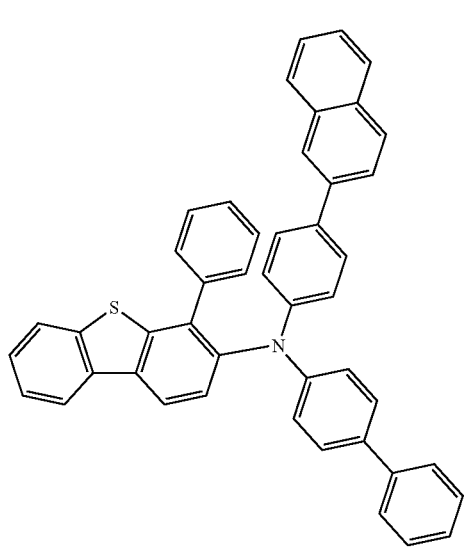
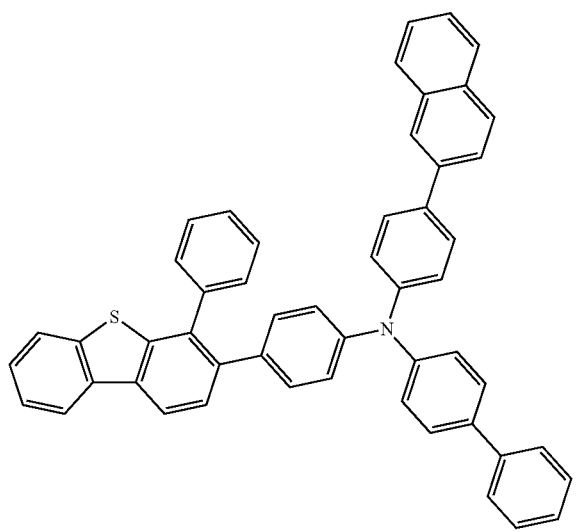

157 158
-continued
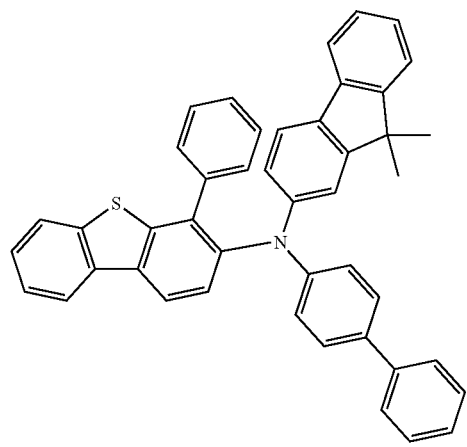
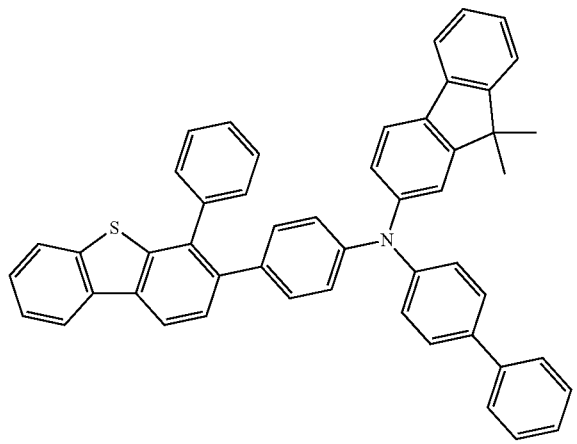
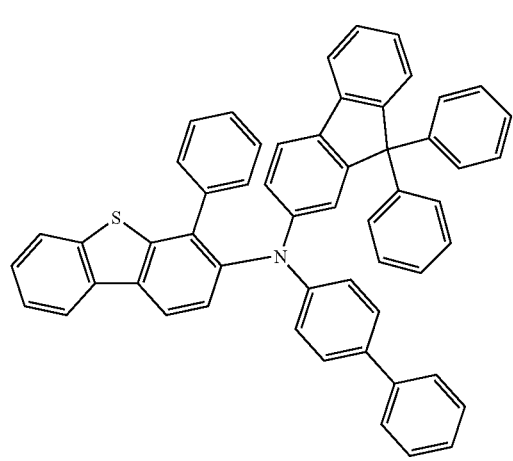
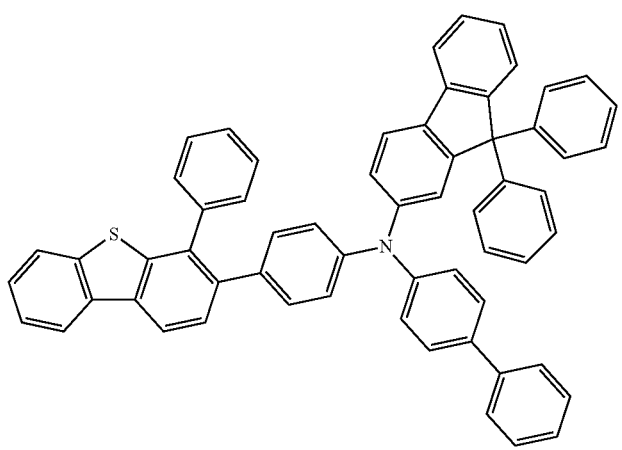
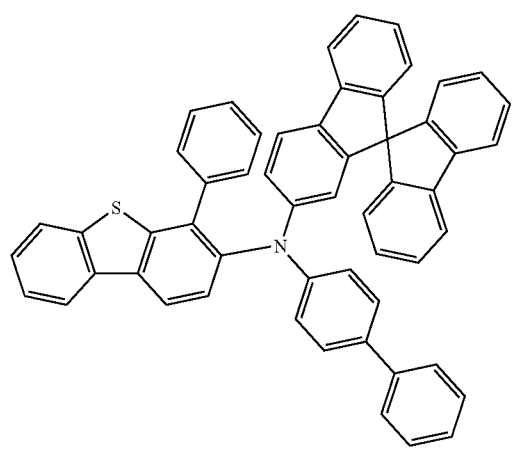
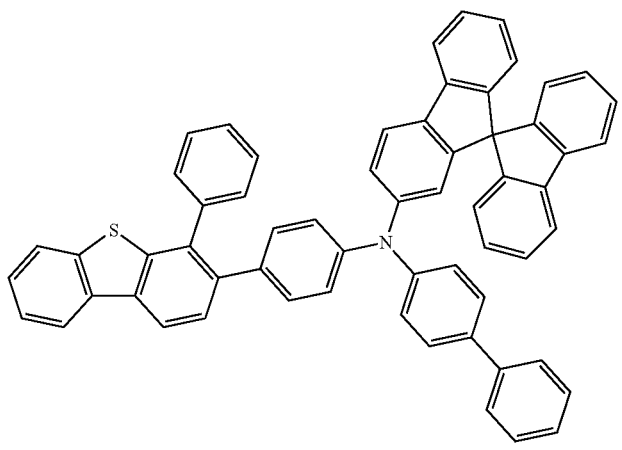

159
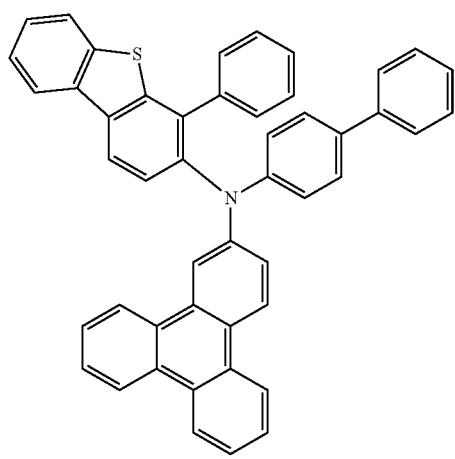
160
-continued
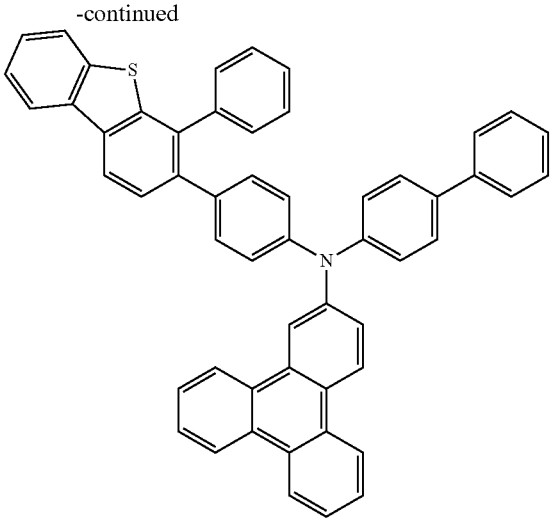
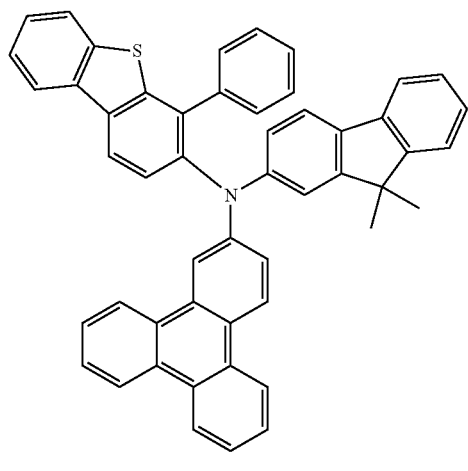
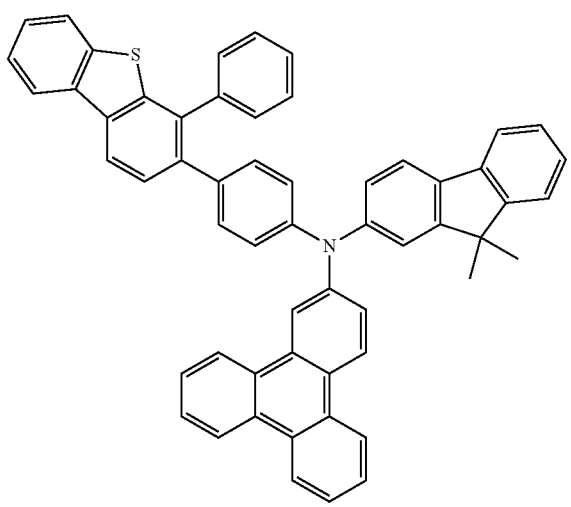
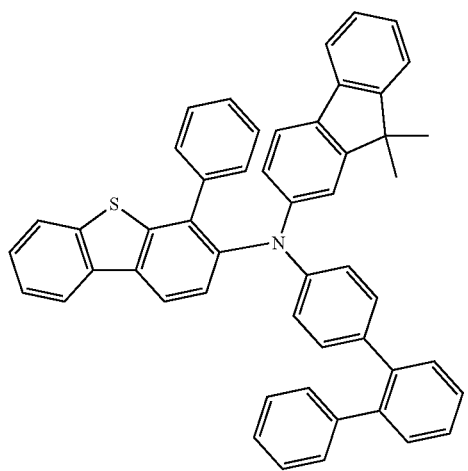
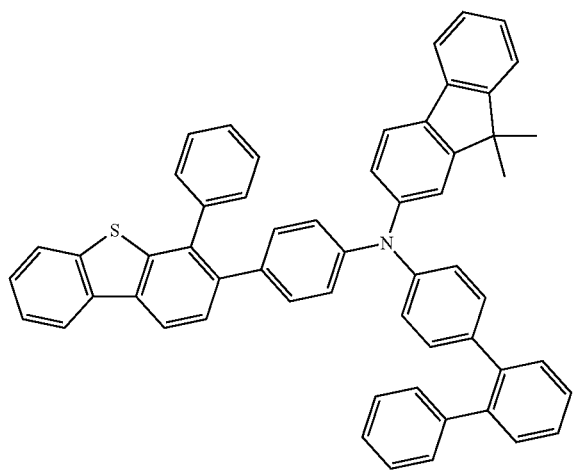

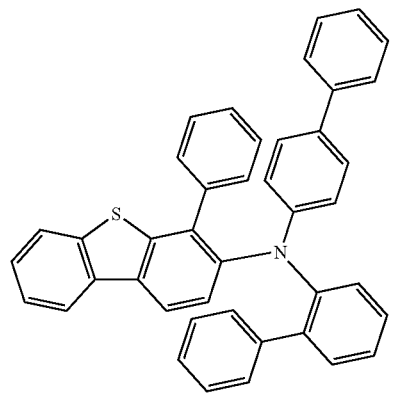
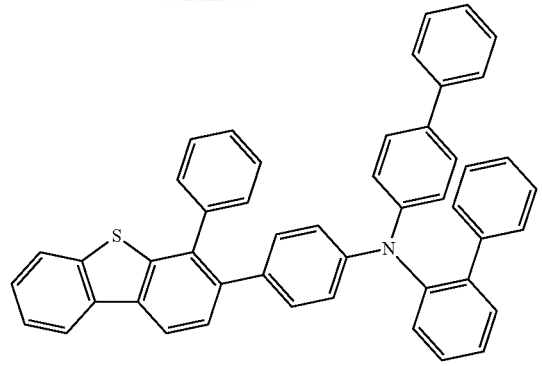
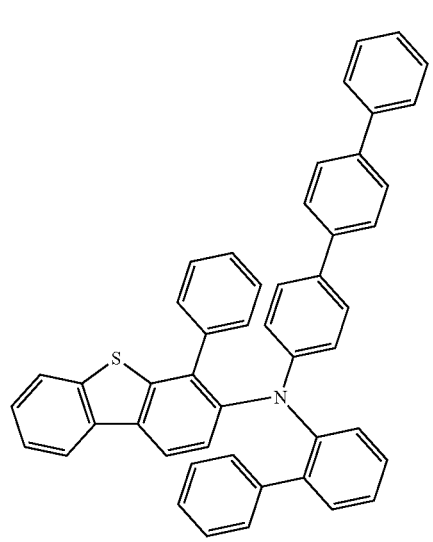
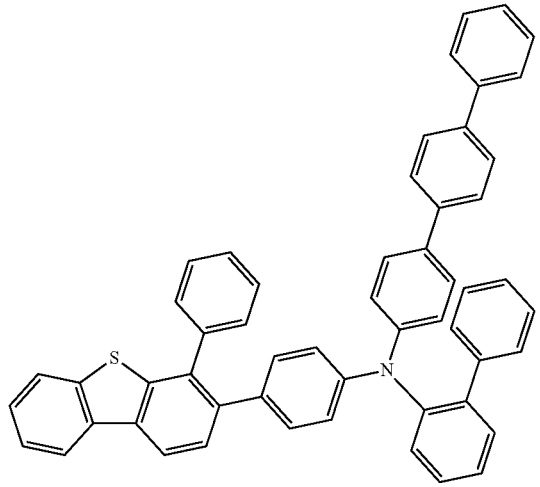
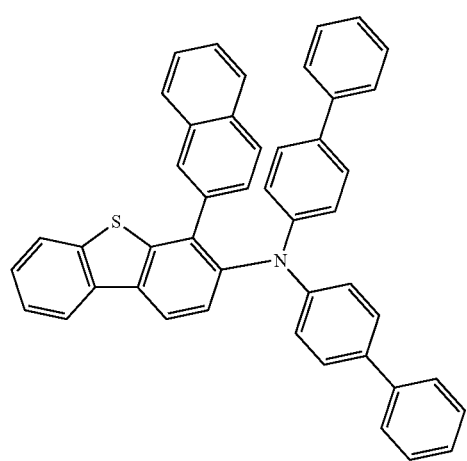
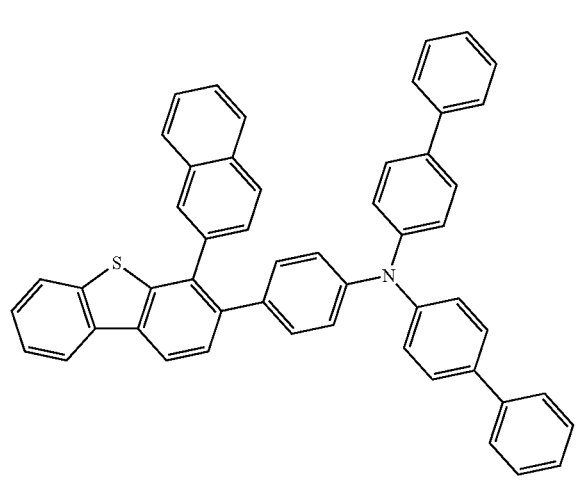

-continued
163
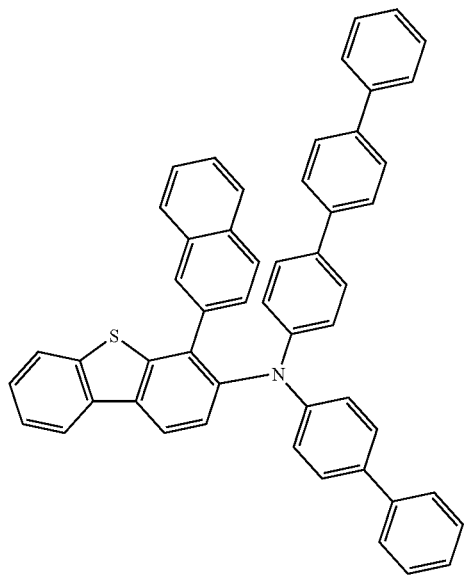
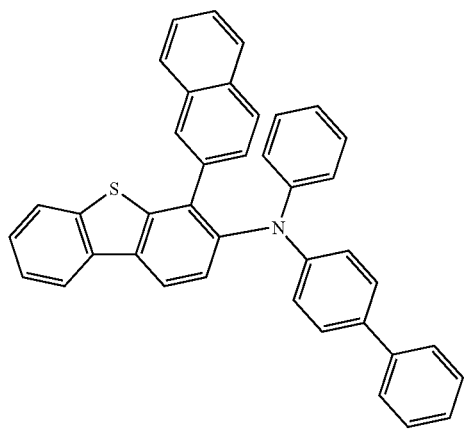
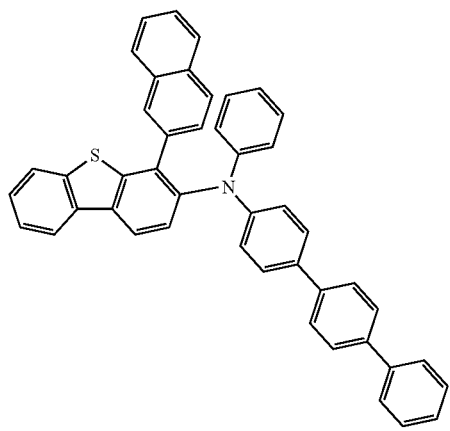
164
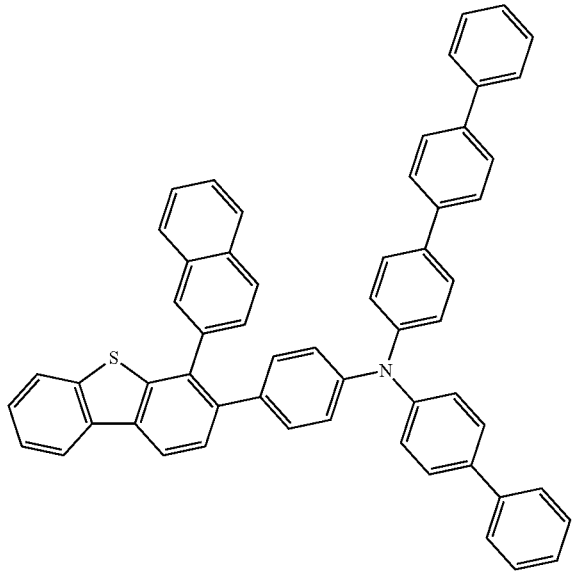
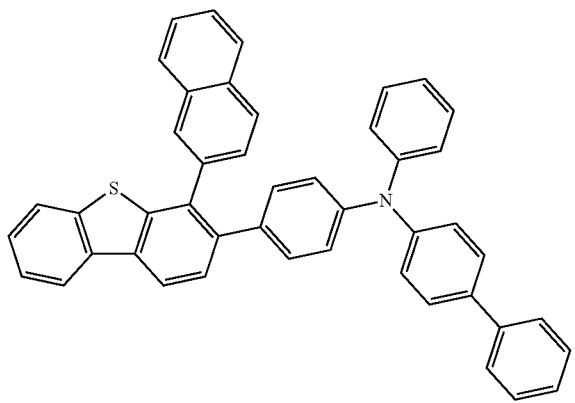
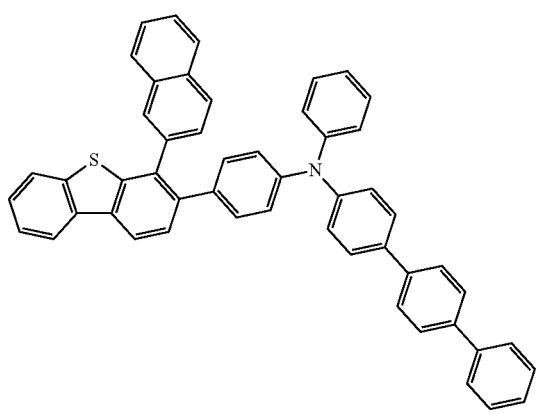

-continued
| 165 | 166 |
|---|---|
| 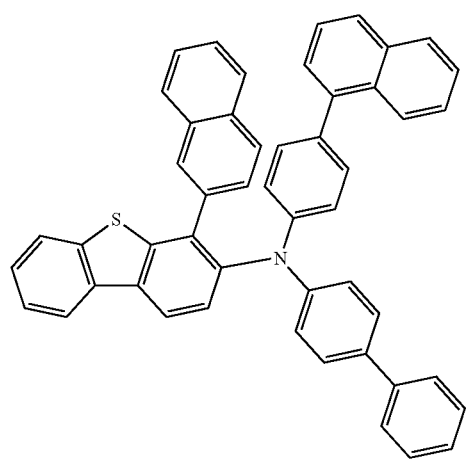 | 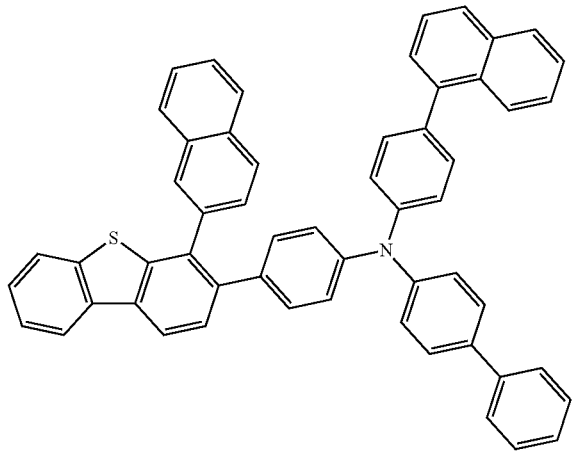 |
| 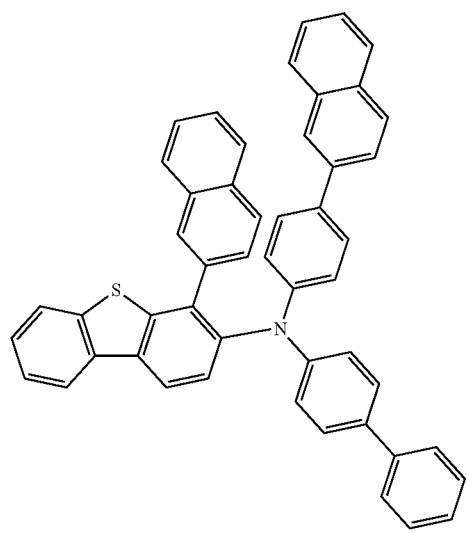 | 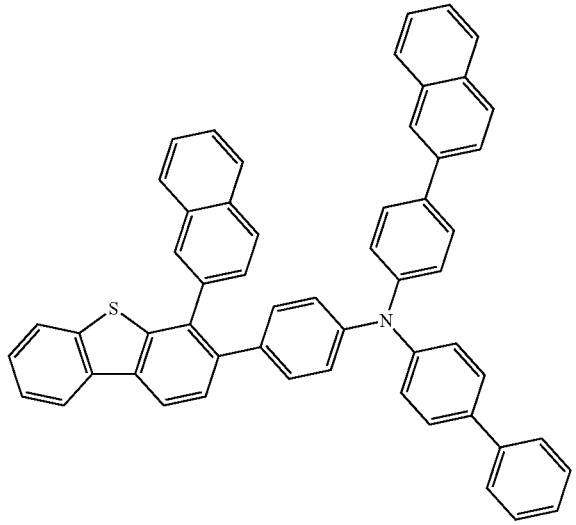 |
| 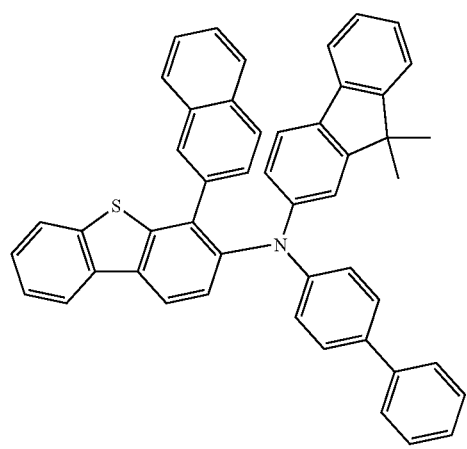 | 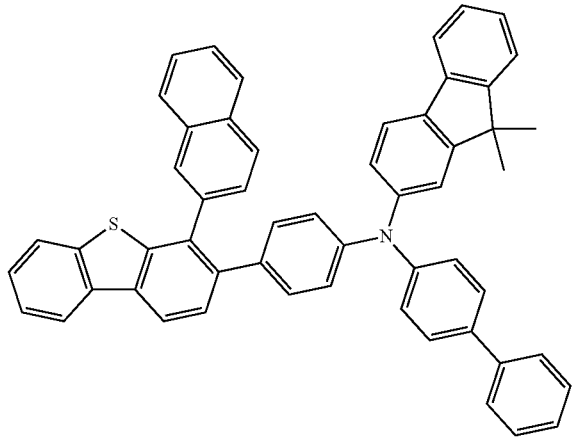 |

-continued
167
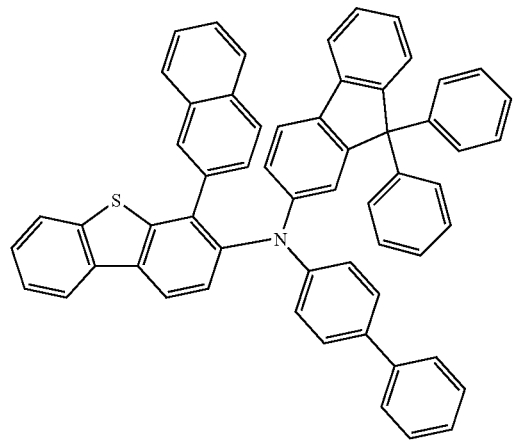
168
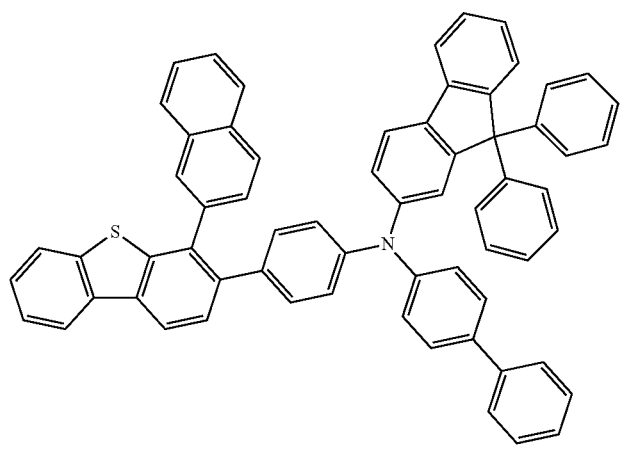
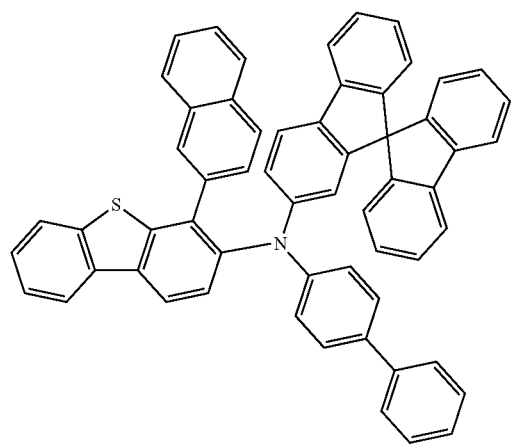
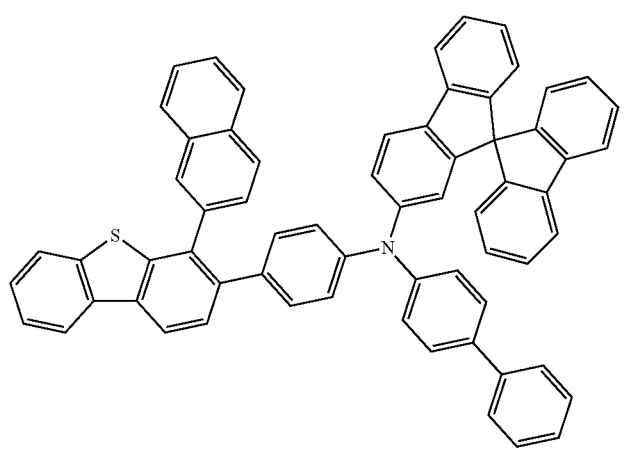
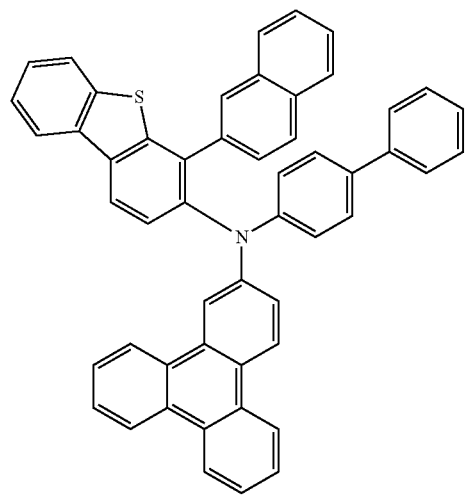
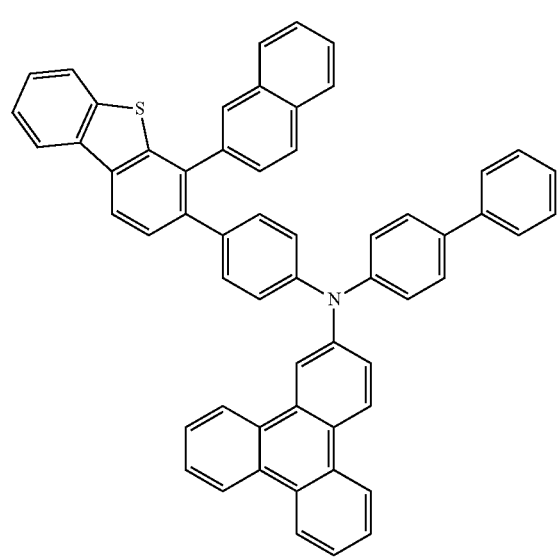

169
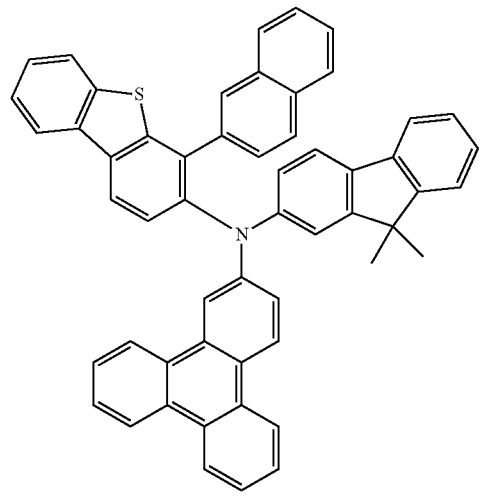
170
-continued
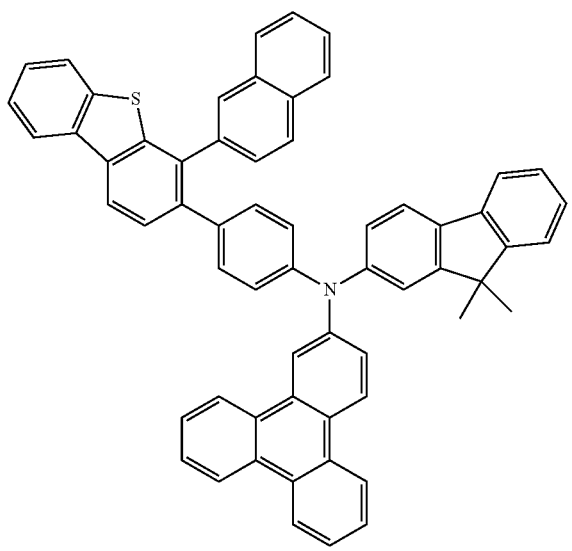
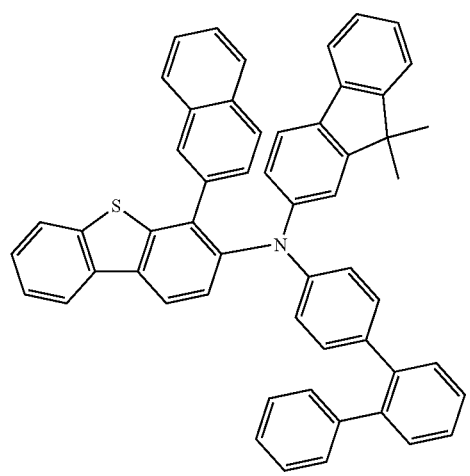
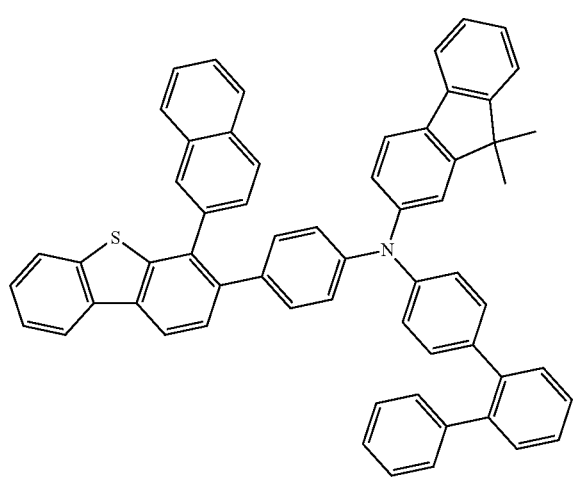
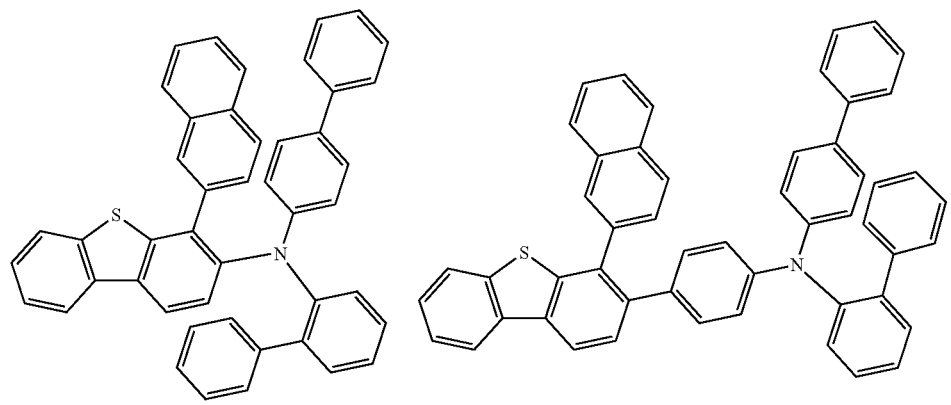

171
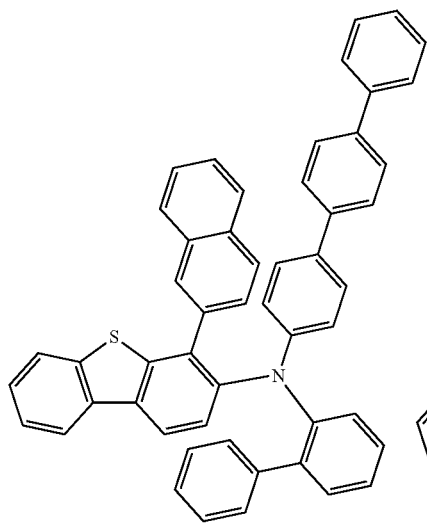
172
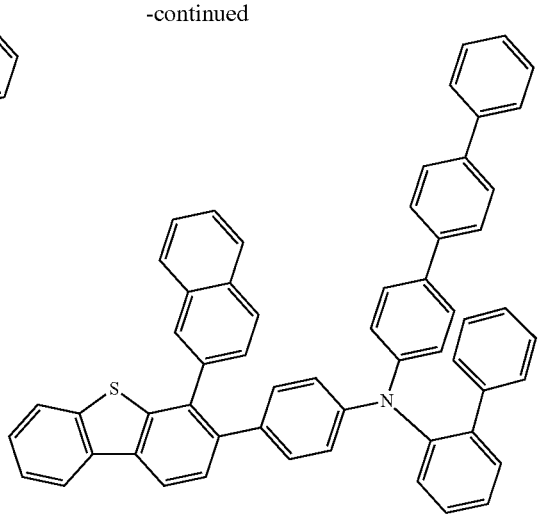
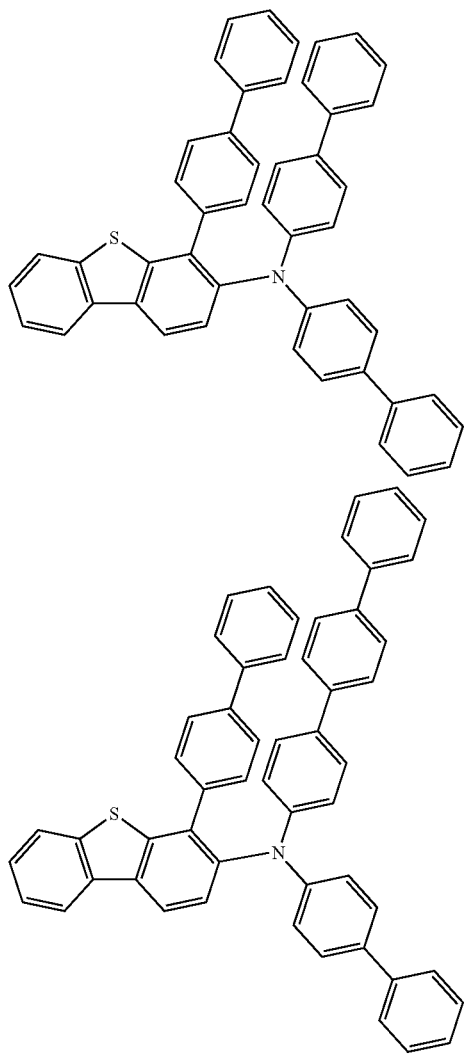
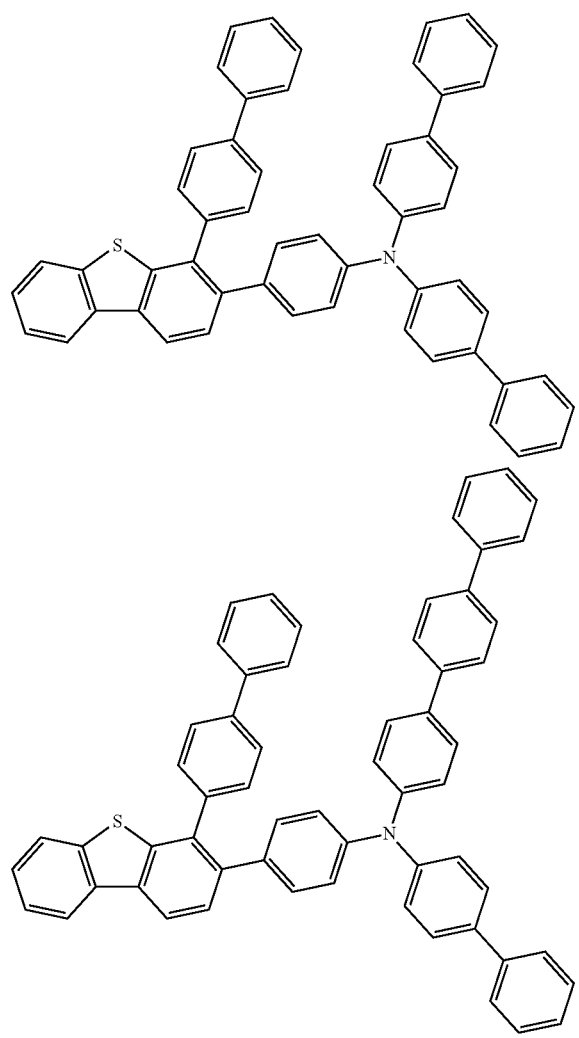

-continued
173
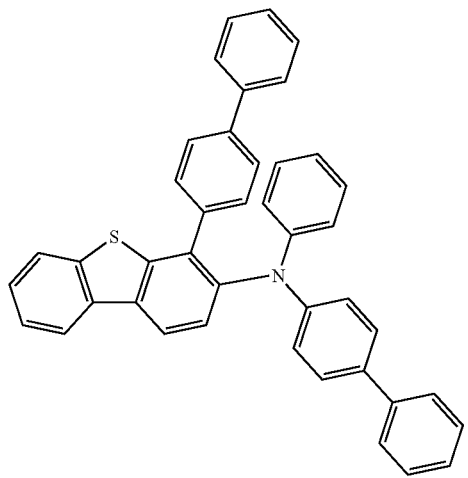
174
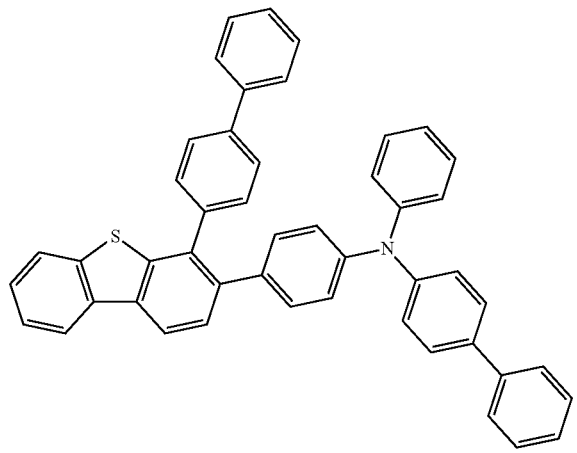
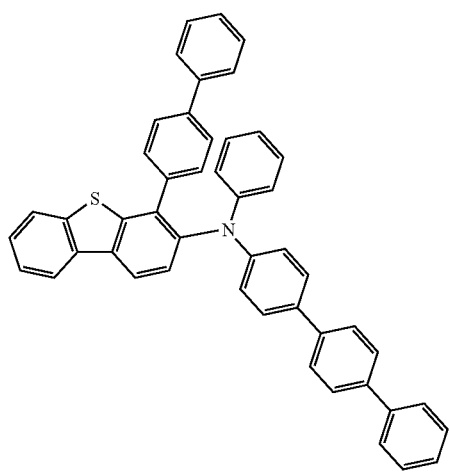
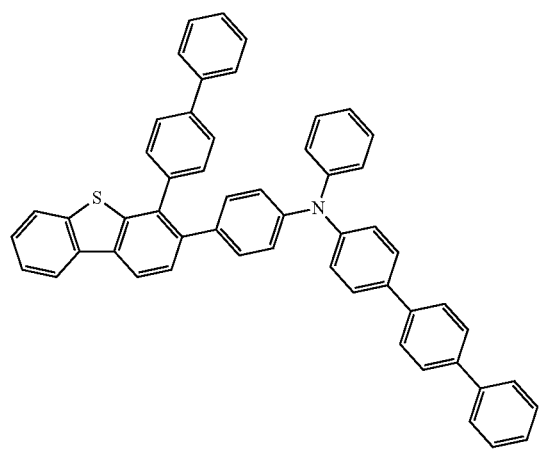
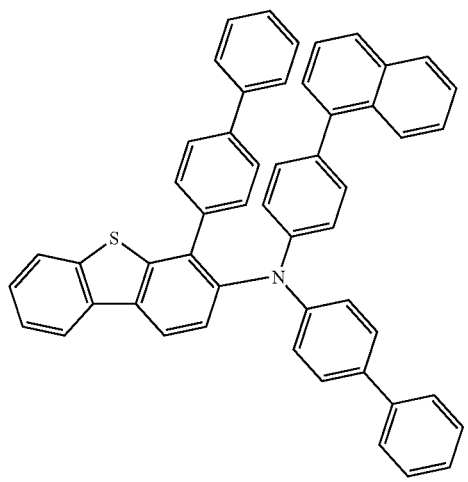
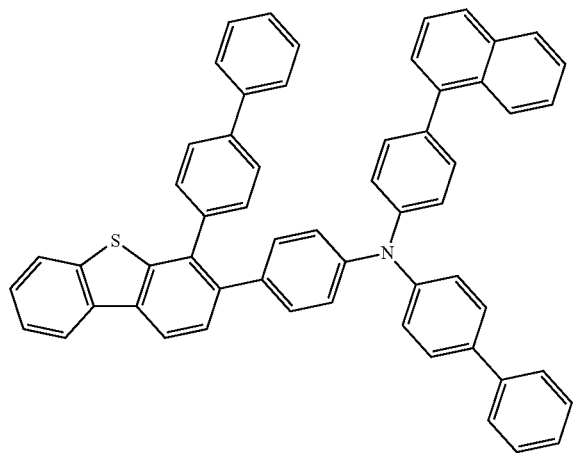

-continued
| 175 | 176 |
|---|---|
| 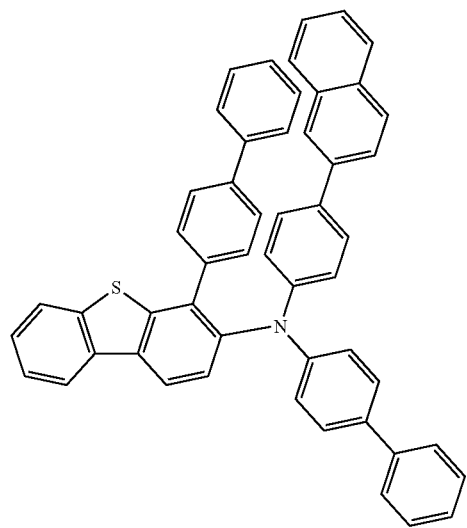 | 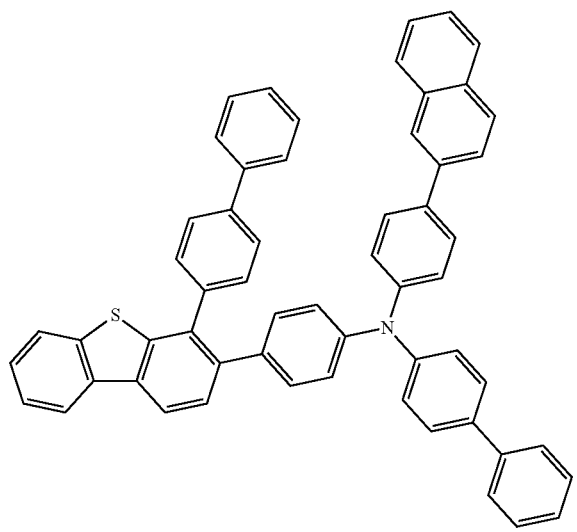 |
| 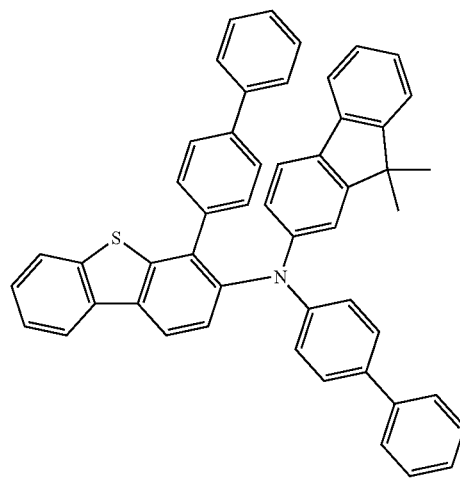 | 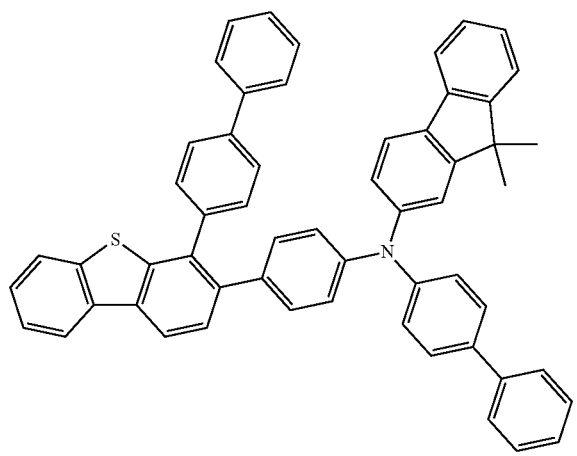 |
| 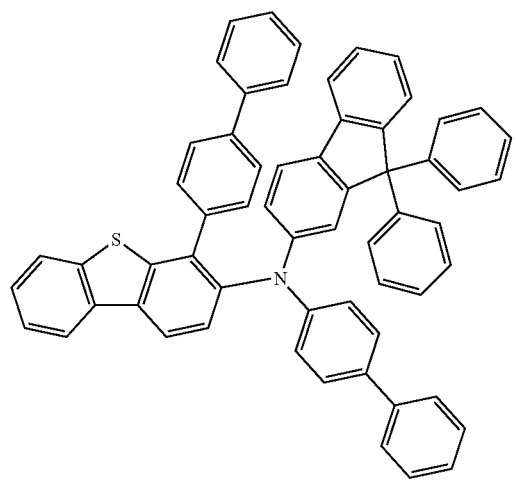 | 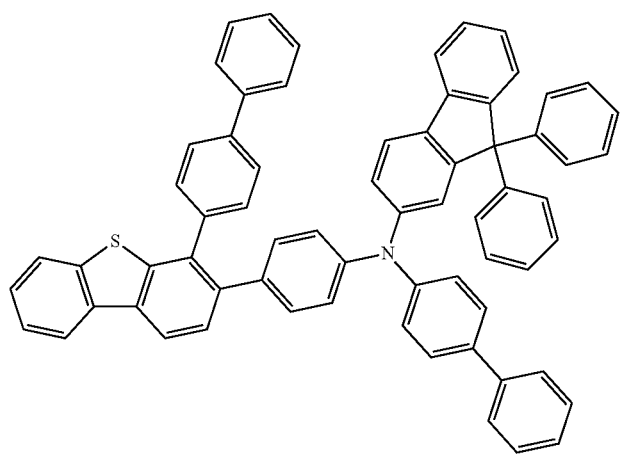 |

-continued
177
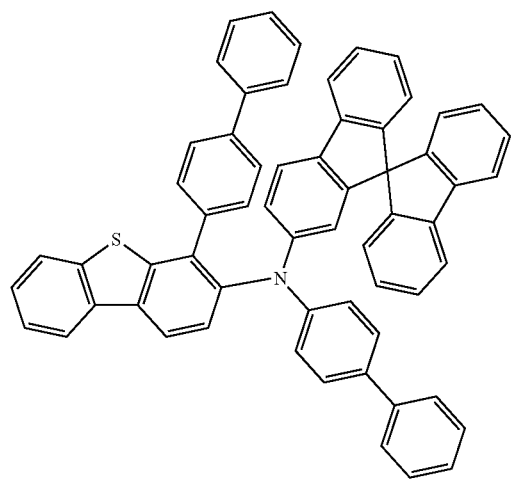
178
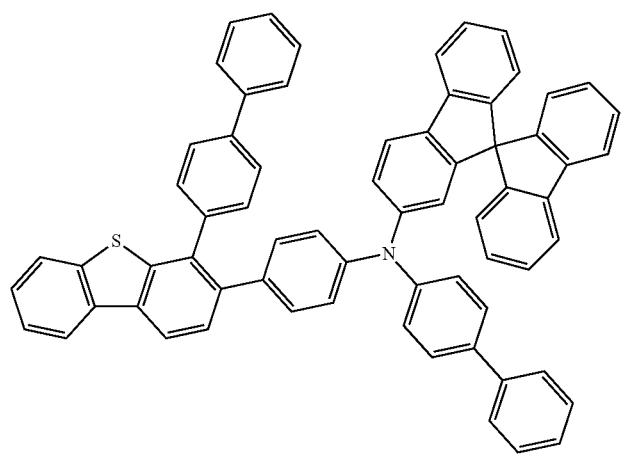
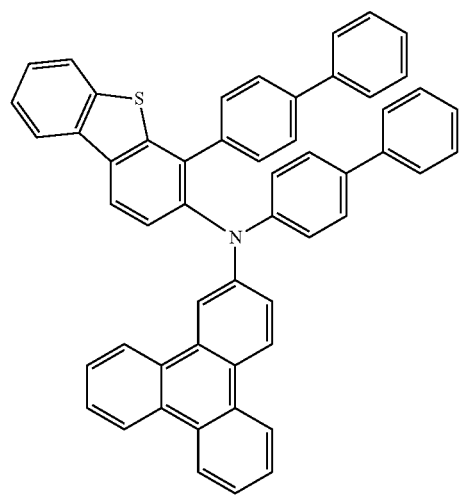
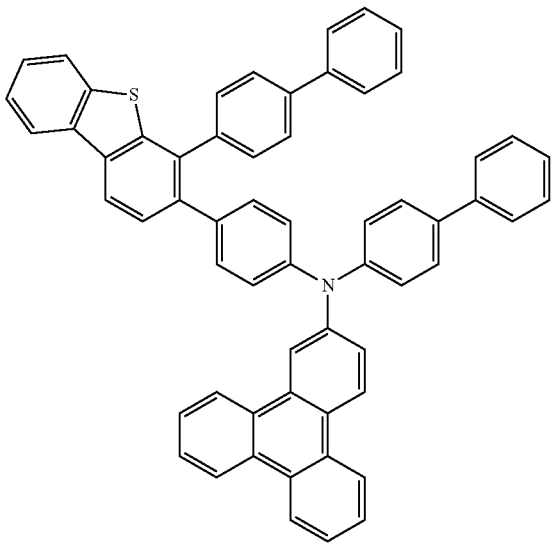
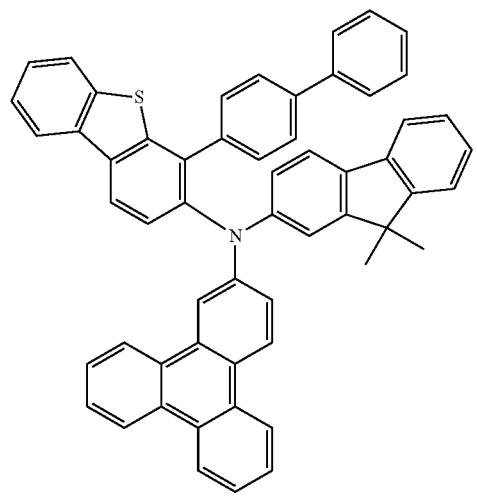
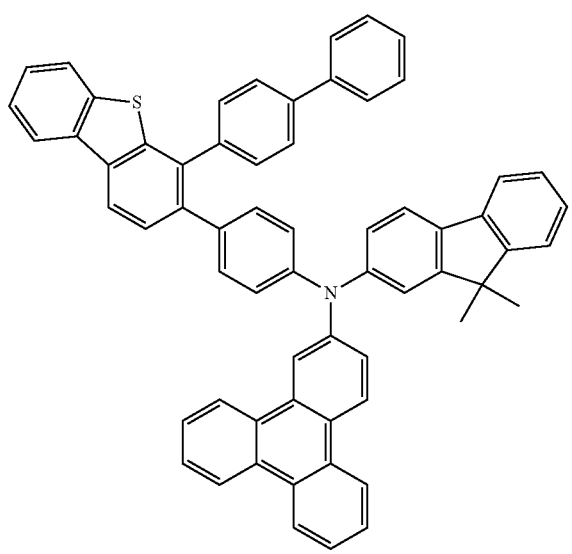

-continued
| 179 | 180 |
|---|---|
| 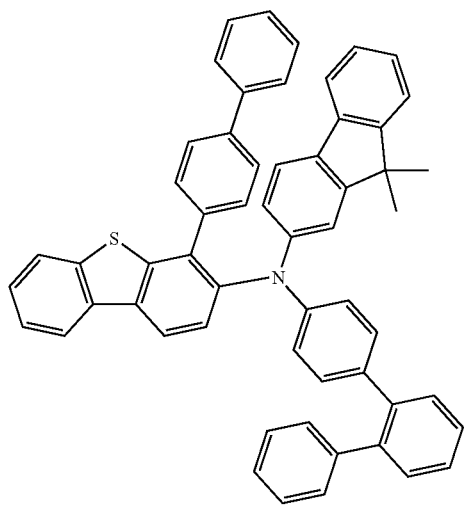 | 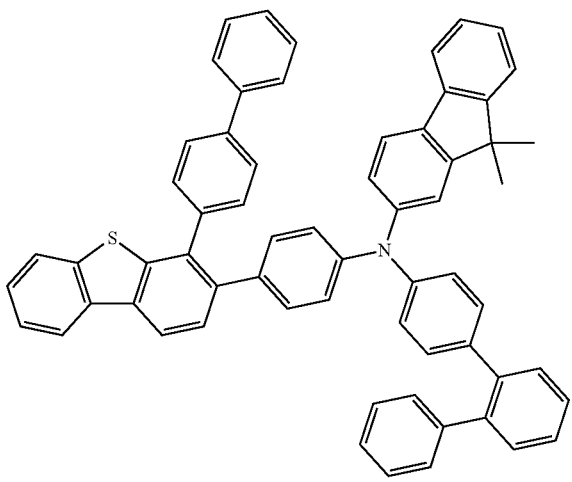 |
| 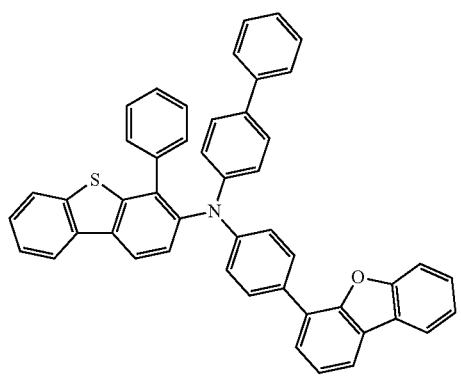 | 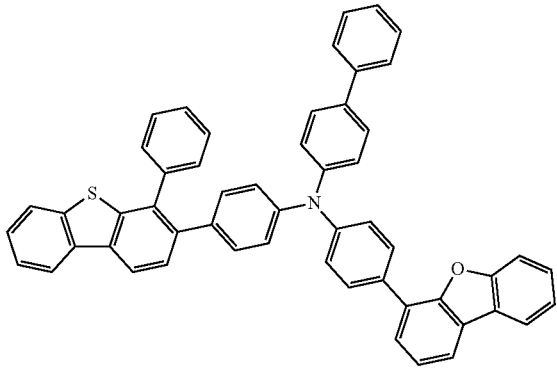 |
| 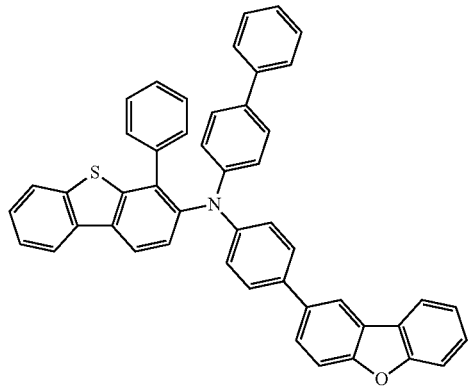 | 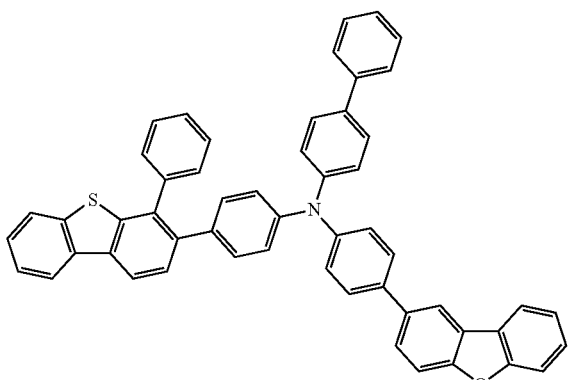 |
| 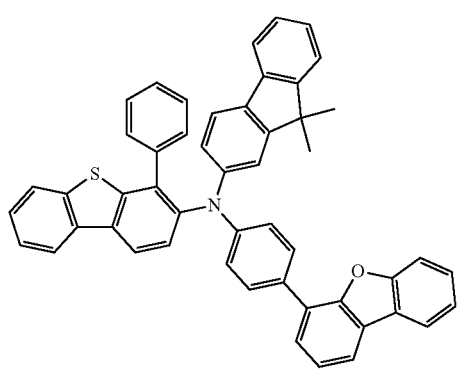 | 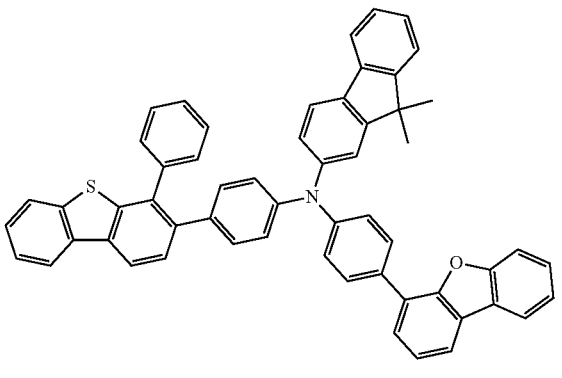 |

-continued
181
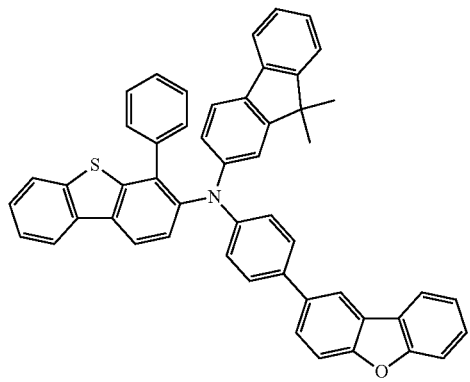
182
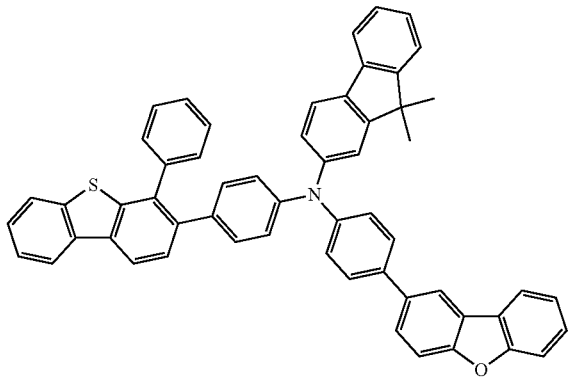
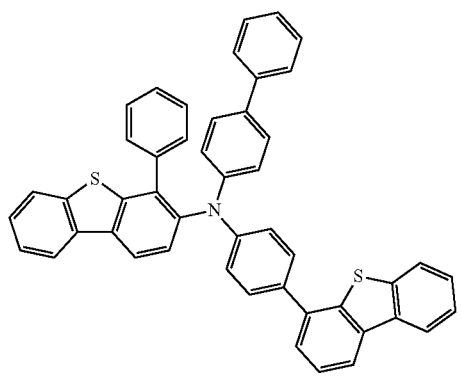
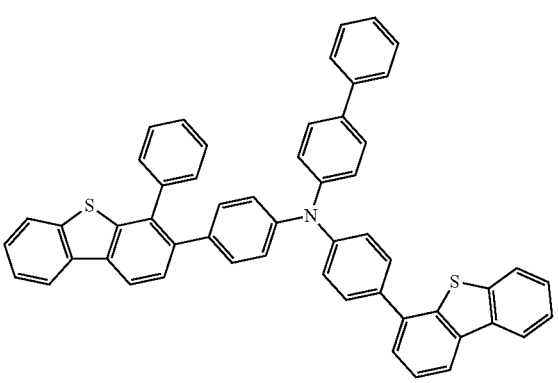
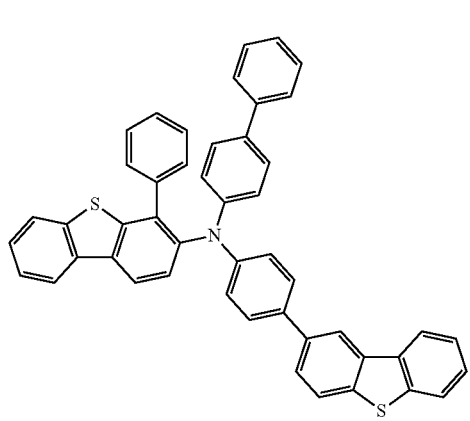
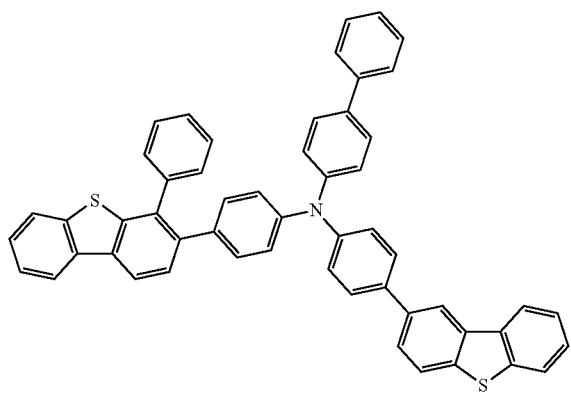
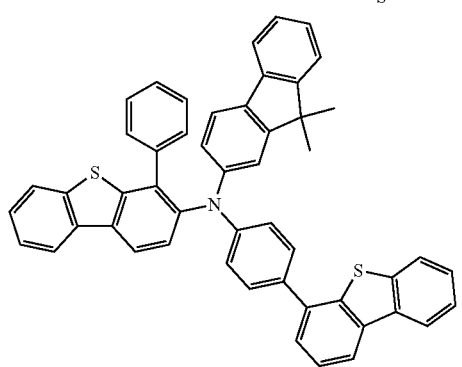
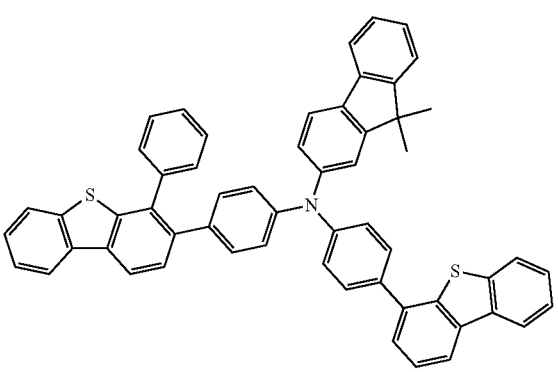

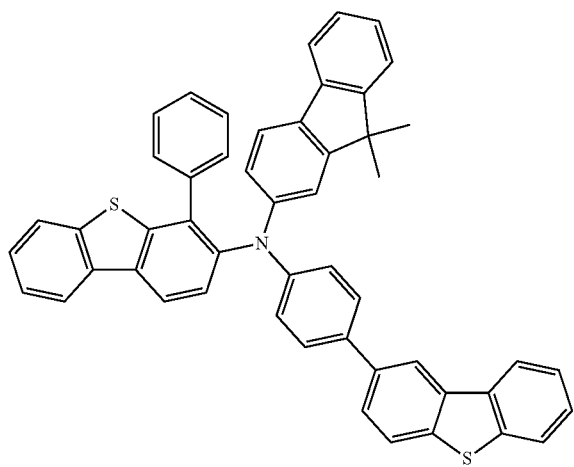
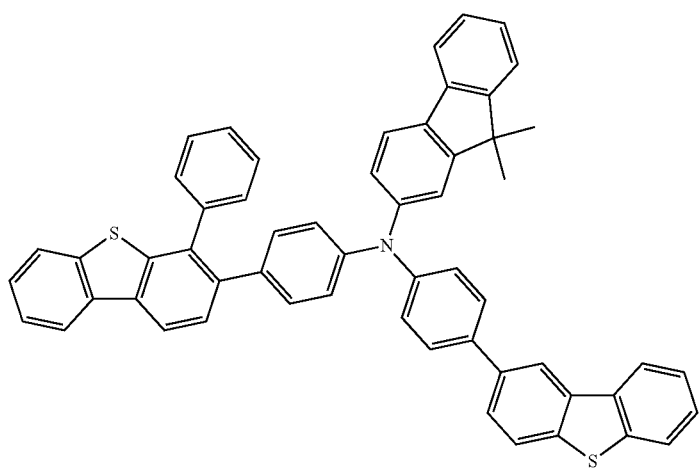
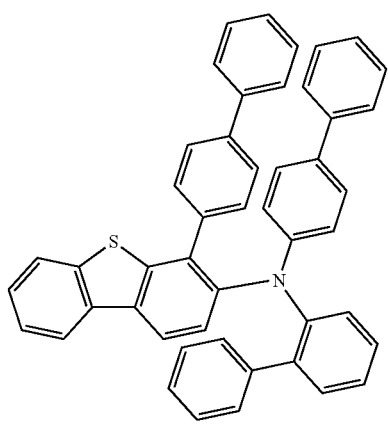
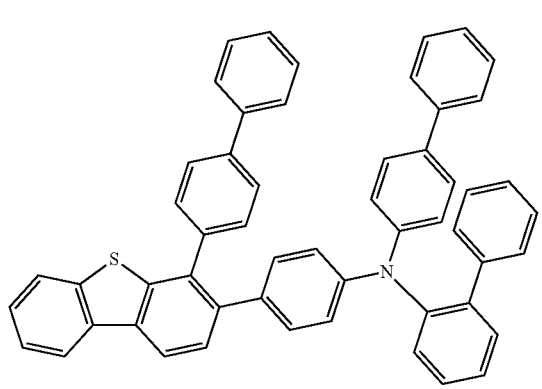
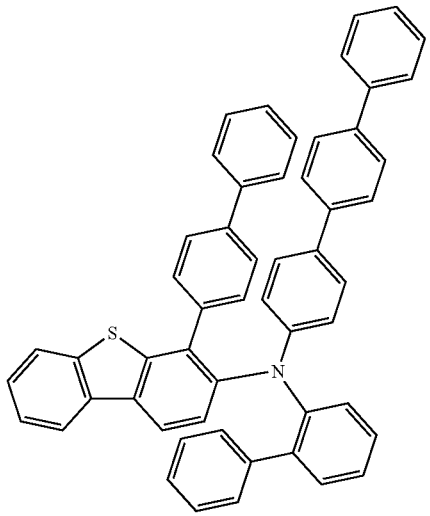

-continued

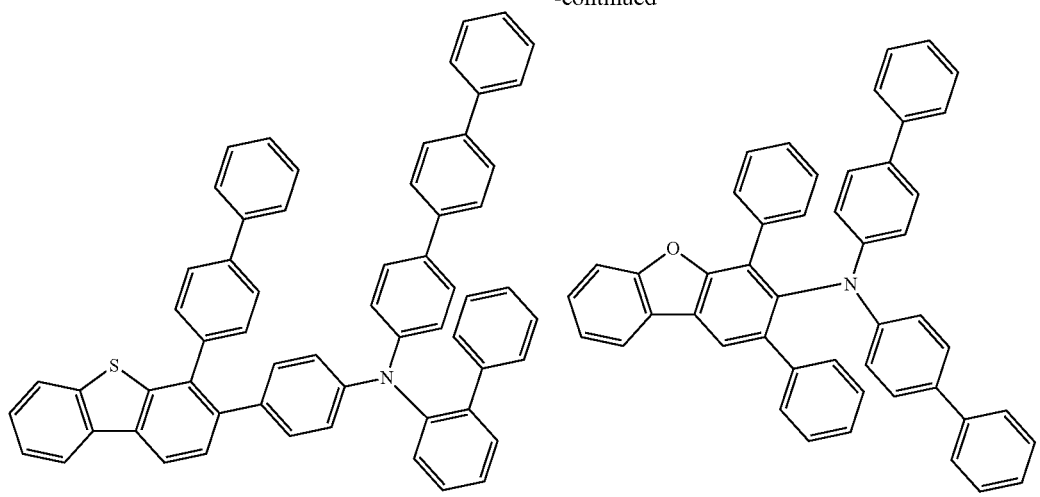

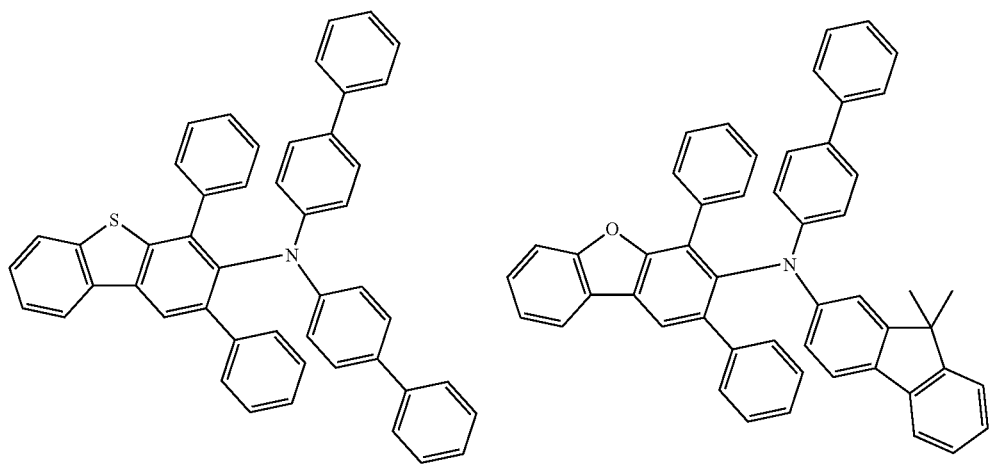

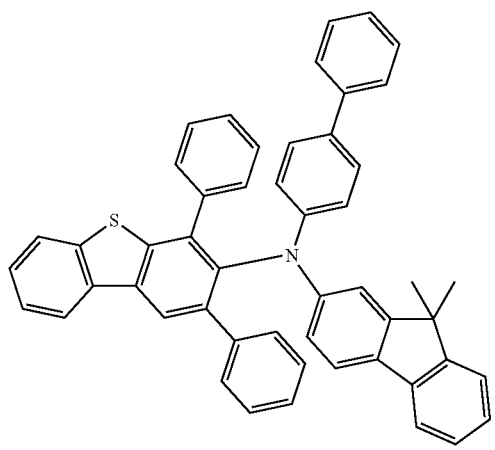

The compound represented by Chemical Formula 1 has a structure in which A or B and an arylamine substituent are linked to a specific position of a dibenzofuran/dibenzothiophene core, and thereby, the organic light emitting device using the same can have high efficiency, a low driving voltage, high luminance, and a long lifetime.

Meanwhile, the compound represented by Chemical Formula 1A can be prepared, for example, by the preparation method as shown in the following Reaction Scheme 1, and the compound represented by Chemical Formula 1B can be prepared, for example, by the preparation method as shown in the following Reaction Scheme 2.

[Reaction Scheme 1]
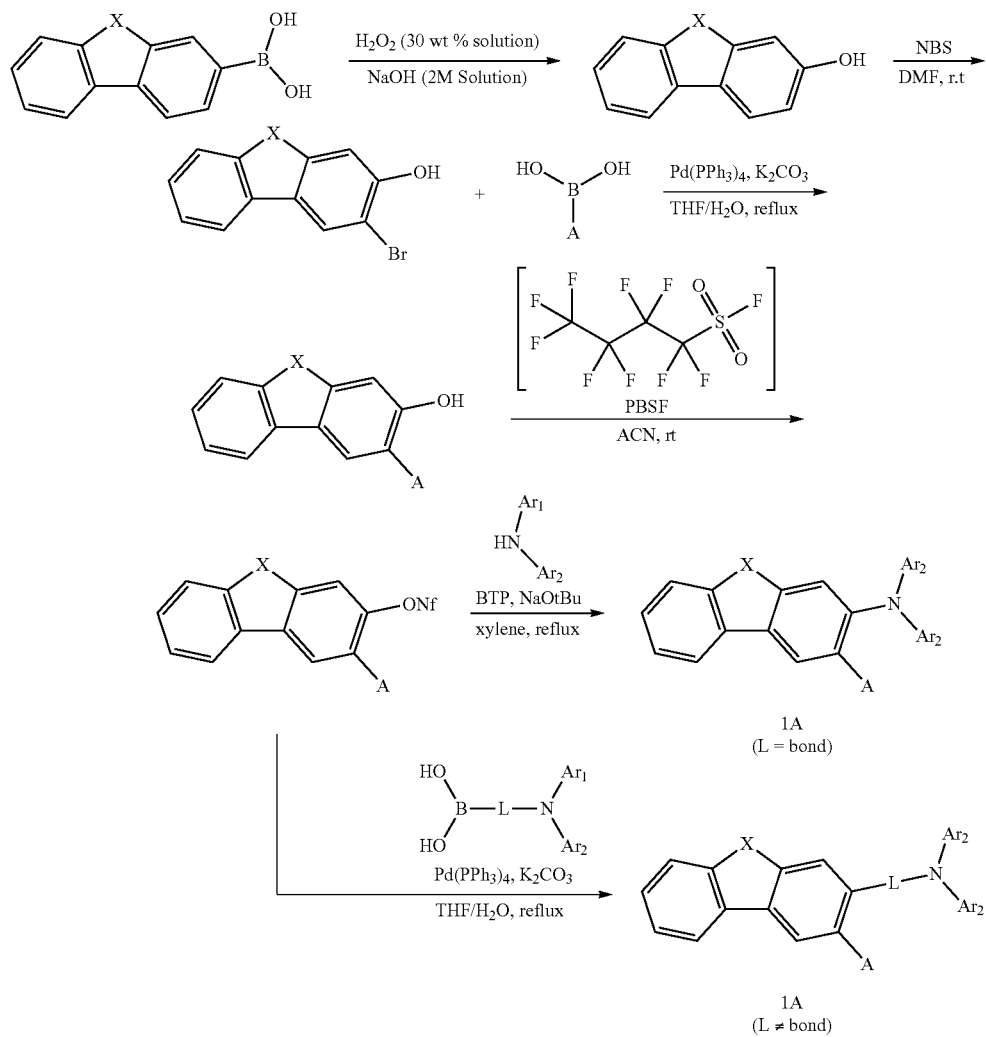
[Reaction Scheme 2]
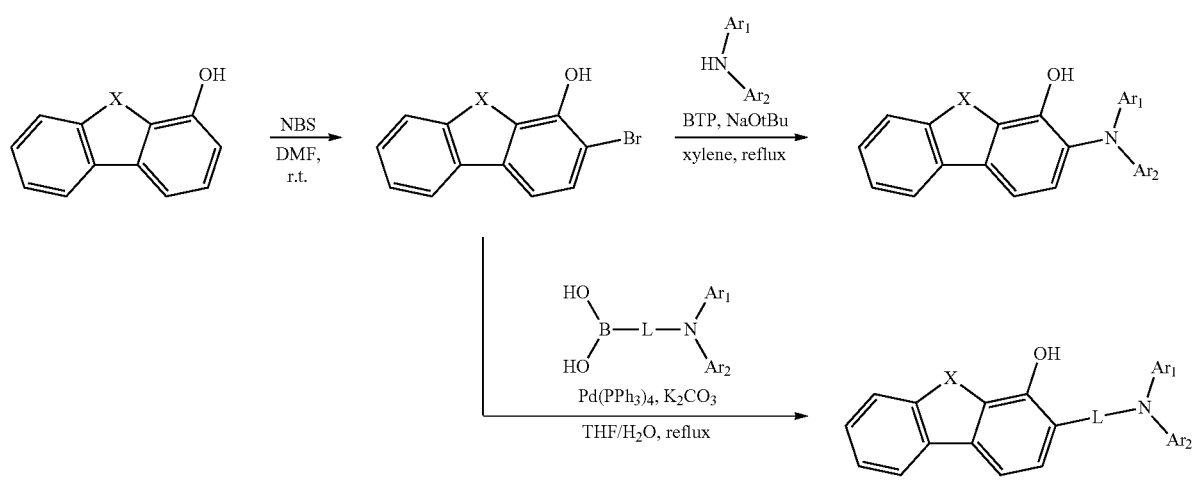

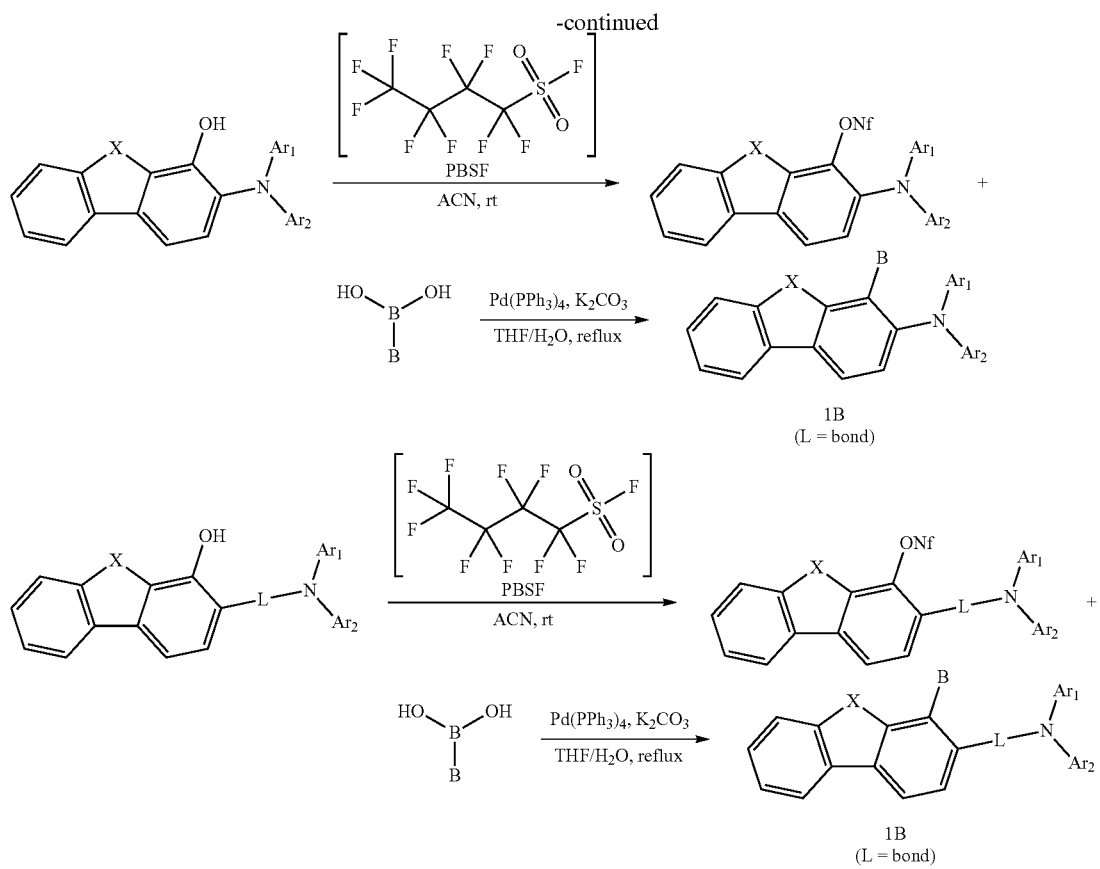

In Reaction Schemes 1 and 2, X, A, B, L, Ar₁, and Ar₂ are the same as defined in Chemical Formula 1 above.

The compound represented by Chemical Formula 1 can be prepared by appropriately substituting the starting material in accordance with the structure of the compound to be prepared with reference to Reaction Schemes 1 and 2.

Meanwhile, the present invention provides an organic light emitting device including the compound represented by Chemical Formula 1. In one example, the present invention provides an organic light emitting device including: a first electrode; a second electrode provided to face to the first electrode; and at least one of organic material layers provided between the first electrode and the second electrode, wherein the at least one of the organic material layers includes the compound represented by Chemical Formula 1.

The organic material layer may include a hole injection layer, a hole transport layer, and a layer simultaneously performing hole injection and hole transport.

Further, the organic material layer may include a light emitting layer, wherein the light emitting layer may include the compound represented by Chemical Formula 1.

Further, the organic material layer may include an electron transport layer, an electron injection layer, or a layer simultaneously performing electron transport and electron injection.

In addition to the organic material layer, the organic light emitting device may further include an electron blocking layer (EBL) disposed between the hole transport layer and the light emitting layer, and/or a hole blocking layer (HBL) disposed between the light emitting layer and the electron transport layer. The electron blocking layer and the hole blocking layer may be organic layers adjacent to the light emitting layer, respectively.

In this case, the compound represented by Chemical Formula 1 may be included in the hole transport layer and/or the electron blocking layer.

The organic material layer of the organic light emitting device according to the present invention may have a single layer structure, or alternatively, a multilayered structure in which at least two organic material layers are stacked. For example, the organic light emitting device of the present invention may include a hole injection layer, a hole transport layer, a light emitting layer, an electron transport layer, and an electron injection layer as the organic material layers. However, the structure of the organic light emitting device is not limited thereto, and may include a smaller number of organic material layers.

The organic material layer of the organic light emitting device according to the present invention may have a single layer structure, or alternatively, a multilayered structure in which at least two organic material layers are stacked. For example, the organic light emitting device of the present invention may, in addition to the light emitting layer, include a hole injection layer and a hole transport layer disposed between the first electrode and the light emitting layer, and an electron transport layer and an electron injection layer disposed between the light emitting layer and the second electrode. However, the structure of the organic light emitting device is not limited thereto, and may include a smaller number or a larger number of organic material layers.

Further, the organic light emitting device according to the present invention may be a normal type of organic light emitting device in which an anode, at least one organic material layer, and a cathode are sequentially stacked on a substrate. Further, the organic light emitting device according to the present invention may be an inverted type of organic light emitting device in which a cathode, at least one organic material layer, and an anode are sequentially stacked on a substrate. For example, the structure of an organic light emitting device according to an embodiment of the present invention is illustrated in FIGS. 1 and 2.

FIG. 1 shows an example of an organic light emitting device including a substrate 1, an anode 2, a light emitting layer 3, and a cathode 4. In such a structure, the compound represented by Chemical Formula 1 may be included in the light emitting layer.

FIG. 2 shows an example of an organic light emitting device including a substrate 1, an anode 2, a hole injection layer 5, a hole transport layer 6, a light emitting layer 7, an electron transport layer 8, and a cathode 4. In such a structure, the compound represented by Chemical Formula 1 may be included in at least one of the hole injection layer, the hole transport layer, the light emitting layer, and the electron transport layer.

The organic light emitting device according to the present invention may be manufactured by materials and methods known in the art, except that at least one layer of the organic material layers includes the compound represented by Chemical Formula 1. In addition, when the organic light emitting device includes a plurality of organic material layers, the organic material layers may be formed of the same material or different materials.

For example, the organic light emitting device according to the present invention can be manufactured by sequentially stacking a first electrode, an organic material layer, and a second electrode on a substrate. In this case, the organic light emitting device may be manufactured by depositing a metal, metal oxides having conductivity, or an alloy thereof on the substrate by using a PVD (physical vapor deposition) method such as a sputtering method or an e-beam evaporation method to form the anode, forming an organic material layer including the hole injection layer, the hole transport layer, the light emitting layer, and the electron transport layer thereon, and then depositing a material that can be used as the cathode thereon.

In addition to such a method, the organic light emitting device may be manufactured by sequentially depositing a cathode material, an organic material layer, and an anode material on a substrate.

In addition, the compound represented by Chemical Formula 1 may be formed into an organic layer by a solution coating method as well as a vacuum deposition method at the time of manufacturing an organic light emitting device. Herein, the solution coating method means spin coating, dip coating, doctor blading, inkjet printing, screen printing, a spray method, roll coating, or the like, but is not limited thereto.

In addition to such a method, the organic light emitting device may be manufactured by sequentially depositing a cathode material, an organic material layer, and an anode material on a substrate (International Publication WO 2003/012890). However, the manufacturing method is not limited thereto.

For example, the first electrode is an anode and the second electrode is a cathode, or the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SNO_2$:Sb; conductive polymers such as poly(3-methylthiophene), poly[3,4-(ethylene-1,2-dioxy)thiophene] (PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has an ability of transporting the holes, thus a hole injecting effect in the anode and an excellent hole injecting effect to the light emitting layer or the light emitting material, prevents movement of an exciton generated in the light emitting layer to the electron injection layer or the electron injection material, and has an excellent thin film forming ability. It is preferable that a HOMO (highest occupied molecular orbital) of the hole injection material is between the work function of the anode material and a HOMO of a peripheral organic material layer. Specific examples of the hole injection material include a metal porphyrin, an oligothiophene, an arylamine-based organic material, a hexanitrilehexaazatriphenylene-based organic material, a quinacridone-based organic material, a perylene-based organic material, anthraquinone, polyaniline, and an polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is a material capable of emitting light in the visible light region by combining holes and electrons respectively transported from the hole transport layer and the electron transport layer, and having good quantum efficiency for fluorescence or phosphorescence. Specific examples thereof include an 8-hydroxy-quinoline aluminum complex ($Alq_3$); carbazole-based compounds; dimerized styryl compounds; BAlq; 10-hydroxybenzoquinoline-metal compounds; benzoxazole, benzothiazole and benzimidazole-based compounds; poly(p-phenylene vinylene) (PPV)-based polymers; spiro compounds; polyfluorene; rubrene; and the like, but are not limited thereto.

The light emitting layer may include a host material and a dopant material as described above. The host material may further include a fused aromatic ring derivative, a heterocycle-containing compound, or the like. Specific examples of the fused aromatic ring derivatives include anthracene derivatives, pyrene derivatives, naphthalene derivatives, pentacene derivatives, phenanthrene compounds, fluoranthene compounds, and the like. Examples of heterocyclic compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specific examples of the aromatic amine derivatives include substituted or unsubstituted fused aromatic ring derivatives having an arylamino group, and examples thereof include pyrene, anthracene, chrysene, and periflanthene having the arylamino group, and the like. The styrylamine compound is a compound where at least one arylvinyl group is substituted in substituted or unsubstituted arylamine, in which one or more substituents selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport layer is a layer receiving the electrons from the electron injection layer and transporting the electrons to the light emitting layer, and the electron transport material is a material that can receive the electrons well from the cathode and transport the electrons to the light emitting layer, and a material having large mobility to the electrons is suitable. Specific examples thereof include an 8-hydroxyquinoline Al complex; a complex including Alq$_3$; an organic radical compound; a hydroxyflavone-metal complex, and the like, but are not limited thereto. The electron transport layer may be used together with a predetermined desired cathode material as used according to the prior art. In particular, an example of an appropriate cathode material is a general material having the low work function and followed by an aluminum layer or a silver layer. Specific examples thereof include cesium, barium, calcium, ytterbium, and samarium, and each case is followed by the aluminum layer or the silver layer.

The electron injection layer is a layer injecting the electrons from the electrode, and a compound which has an ability of transporting the electrons, an electron injecting effect from the cathode, and an excellent electron injecting effect to the light emitting layer or the light emitting material, prevents movement of an exciton generated in the light emitting layer to the hole injection layer, and has an excellent thin film forming ability is preferable. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and their derivatives, a metal complex compound, a nitrogen-containing 5-membered cycle derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present invention may be a front side emission type, a back side light emitting type, or a double side light emitting type according to the used material.

In addition, the compound represented by Chemical Formula 1 may be included in an organic solar cell or an organic transistor in addition to an organic light emitting device.

The preparation of the compound represented by Chemical Formula 1 and the organic light emitting device including the same will be described in detail in the following examples. However, these examples are presented for illustrative purposes only, and the scope of the present invention is not limited thereto.

Preparation Example A: Preparation of Intermediate Compound A

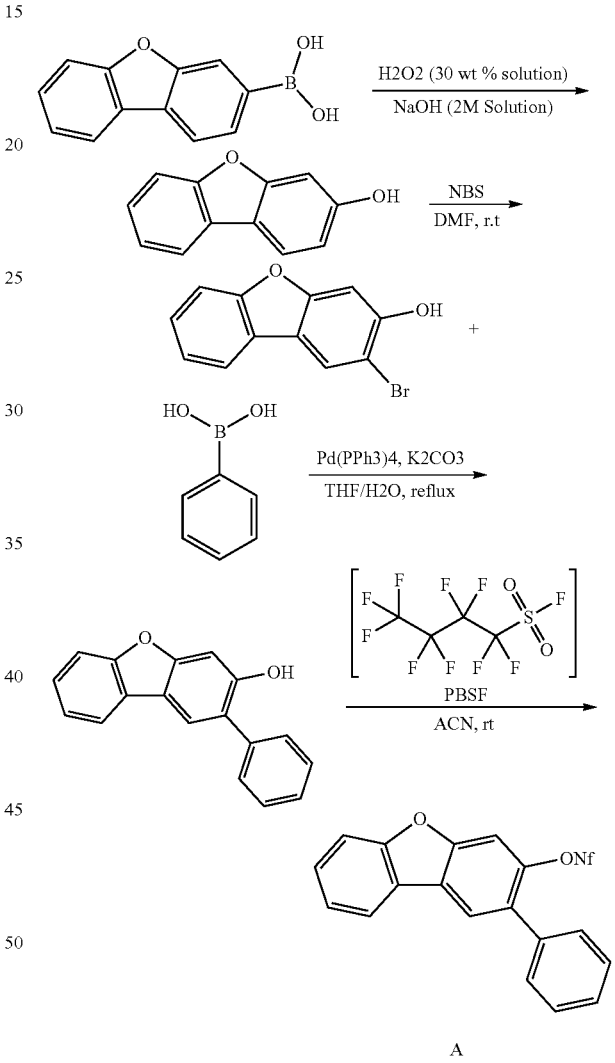

A

Preparation Example B: Preparation of Intermediate Compound B

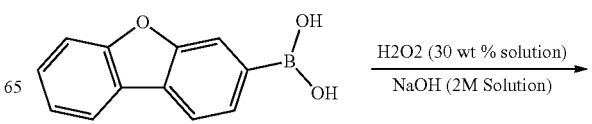

195
-continued
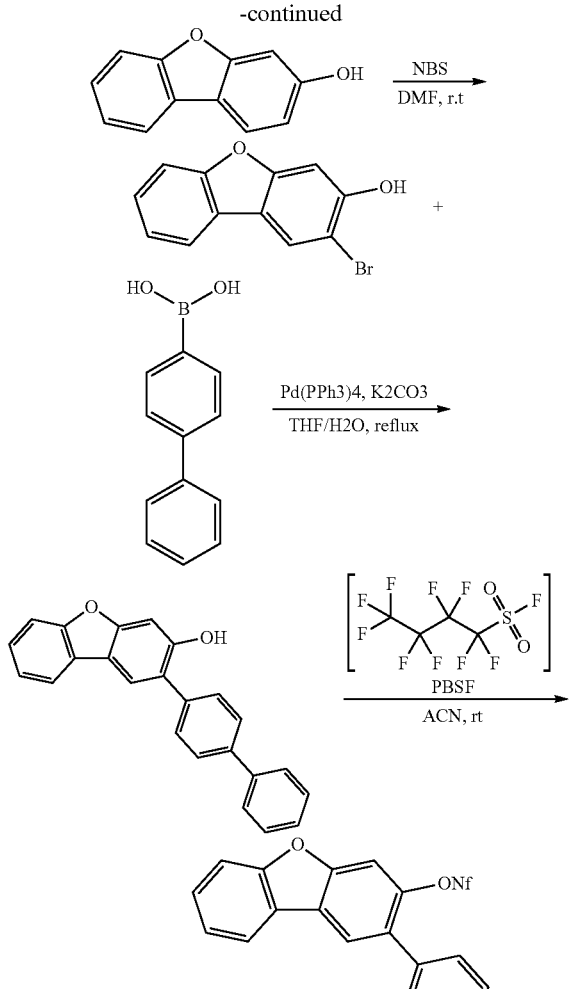
B
Preparation Example C: Preparation of Intermediate Compound C
196
-continued
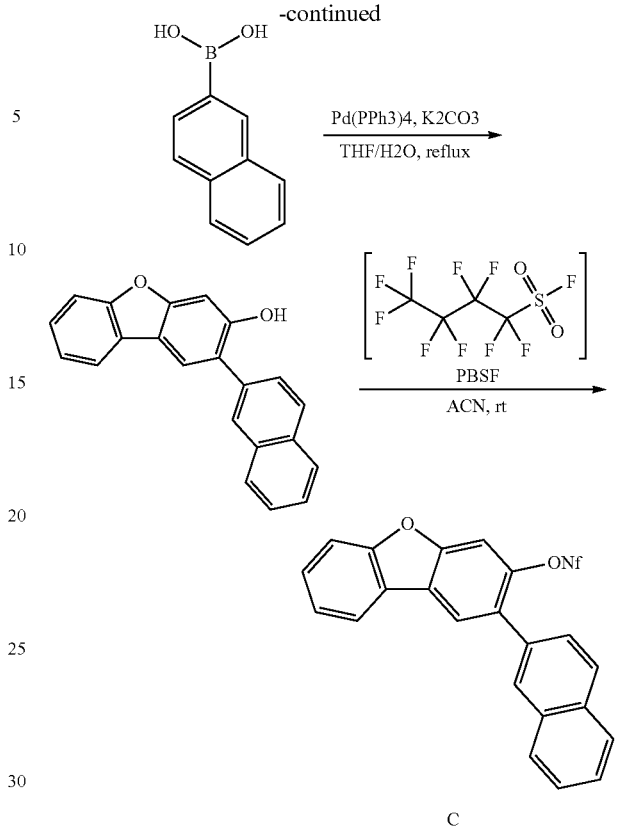
C
Preparation Example D: Preparation of Intermediate Compound D
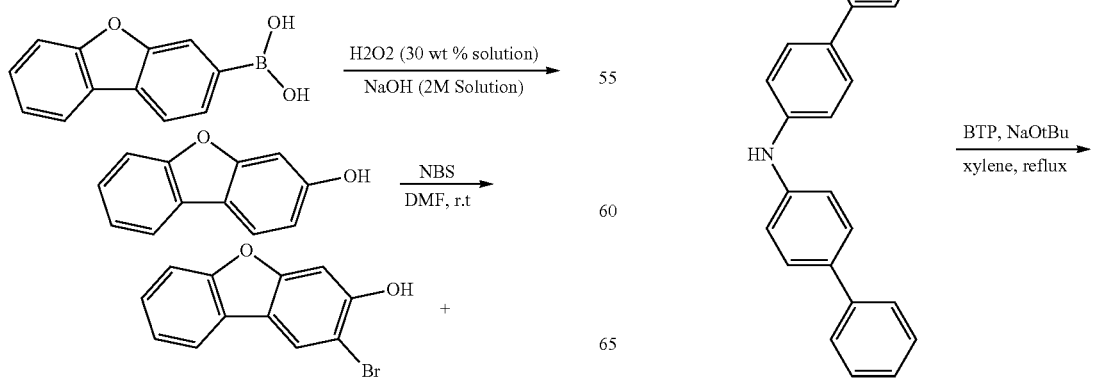

197
-continued
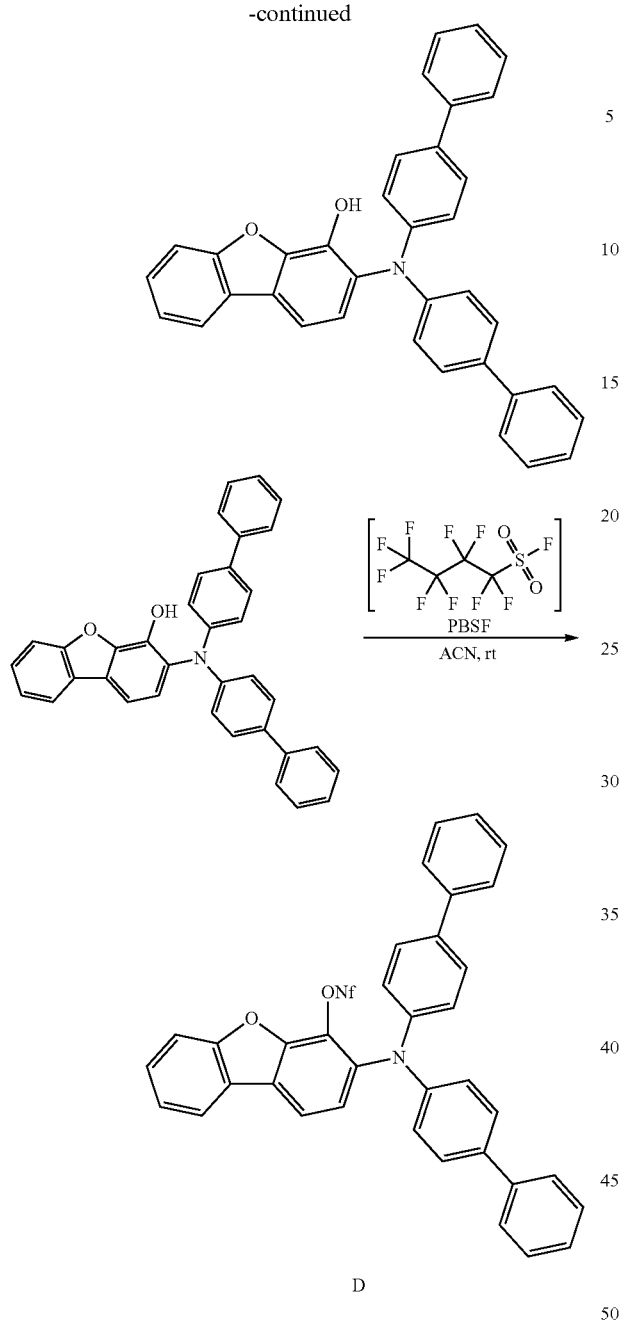
Preparation Example E: Preparation of Intermediate Compound E
198
-continued
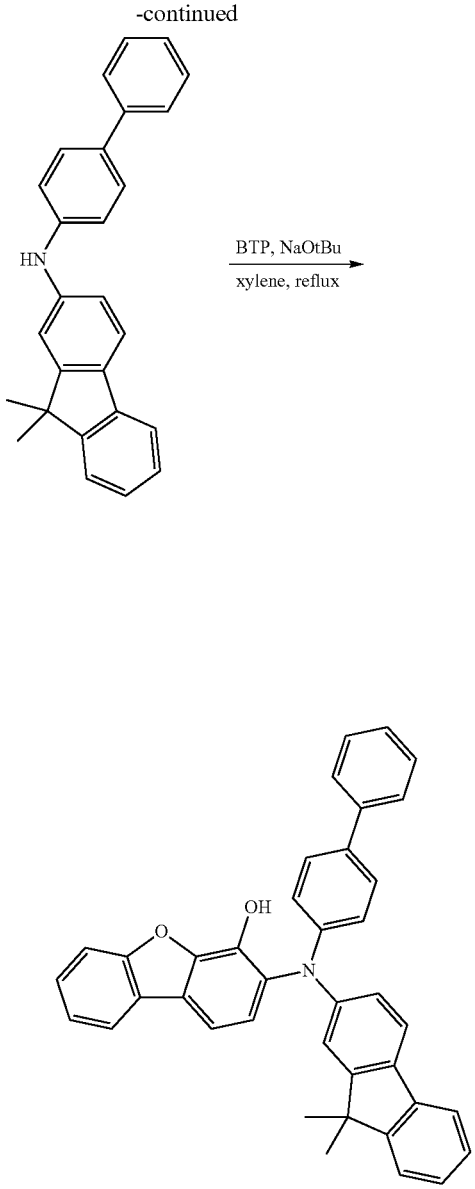
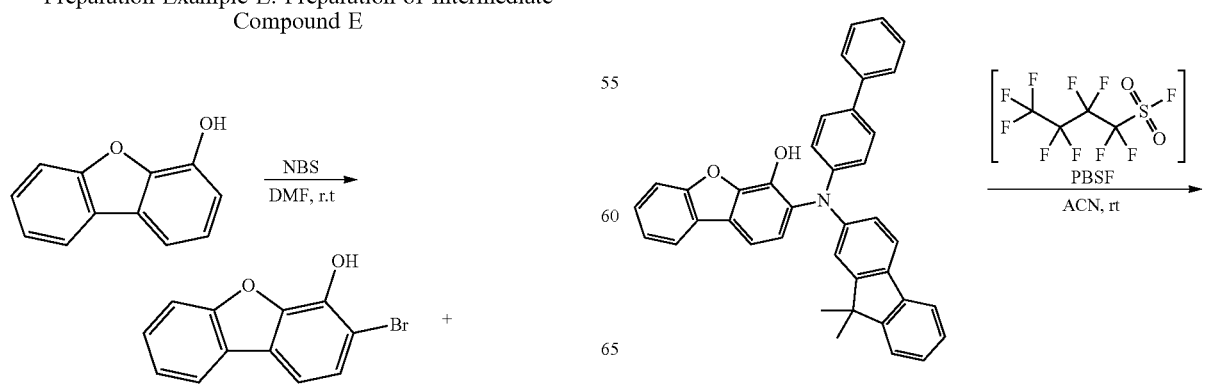

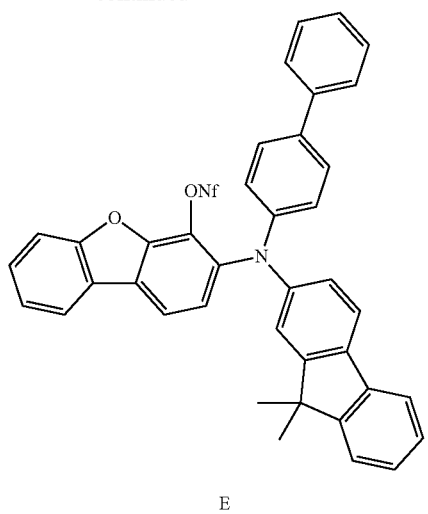
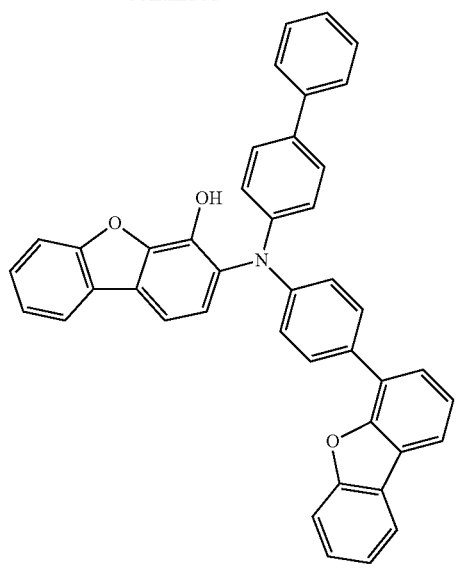
Preparation Example F: Preparation of Intermediate Compound F
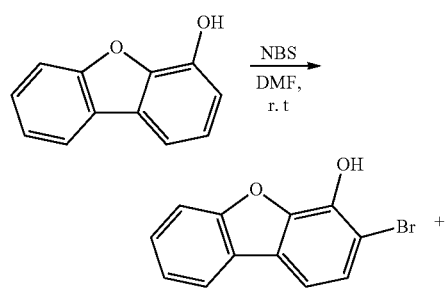
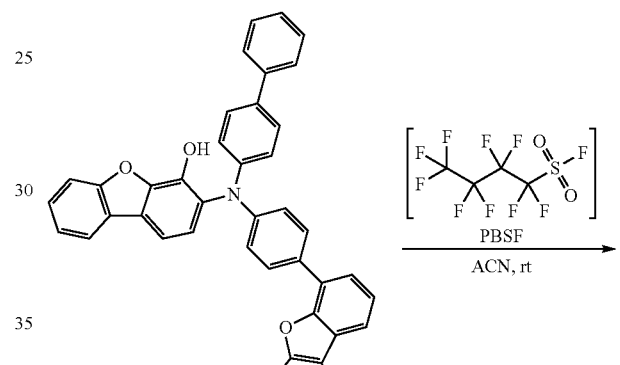
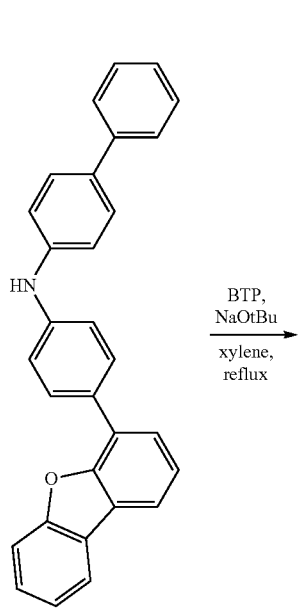
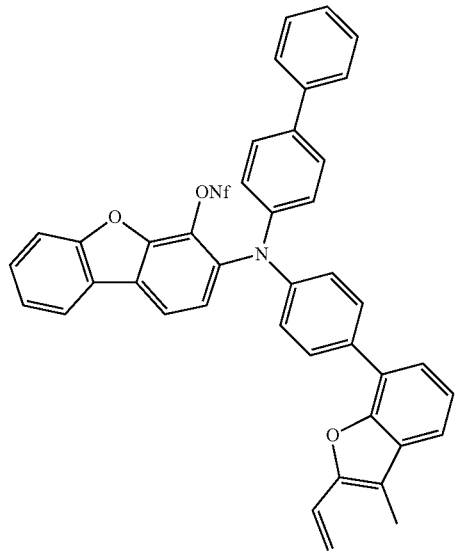
F

Preparation Example G: Preparation of Intermediate Compound G
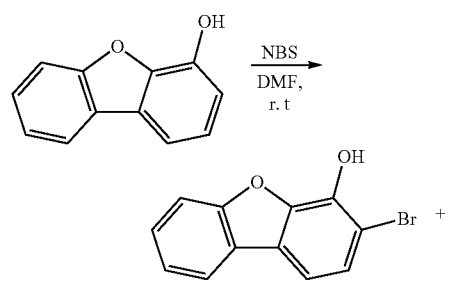
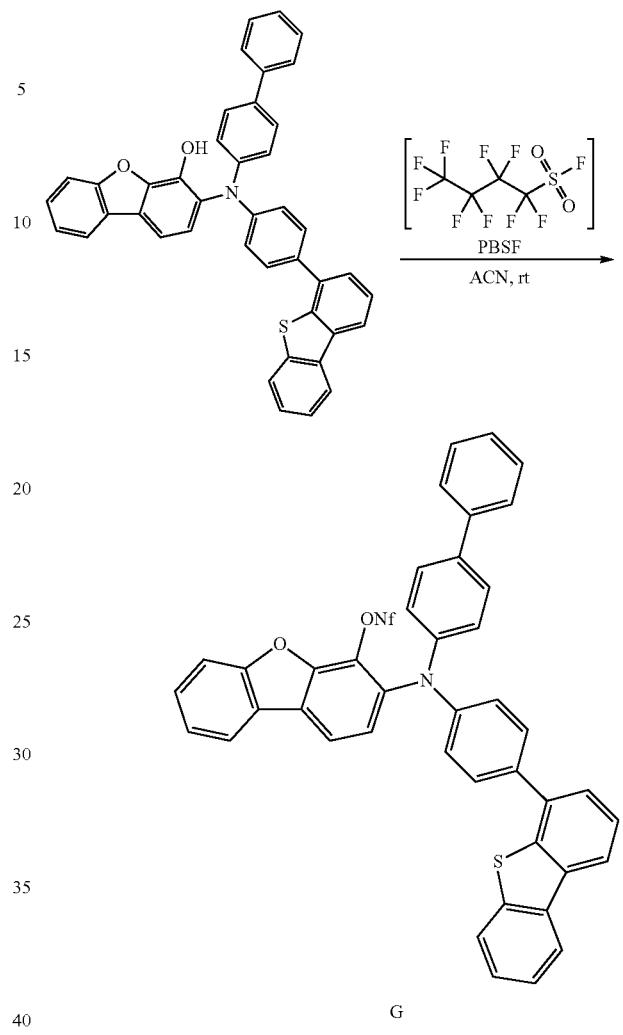
Preparation Example H: Preparation of Intermediate Compound H
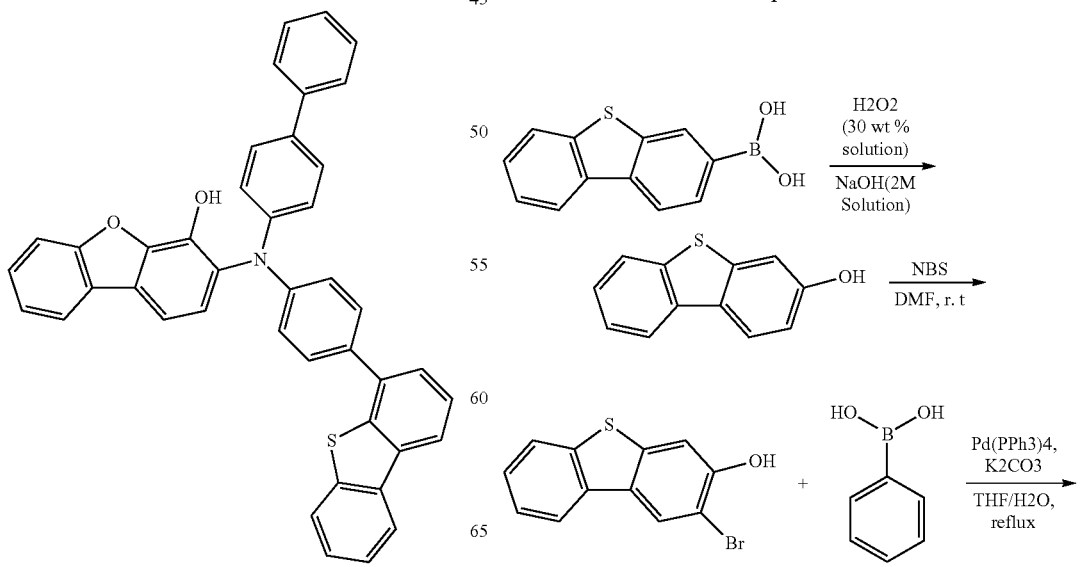

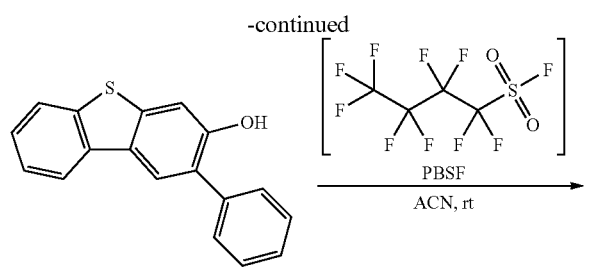
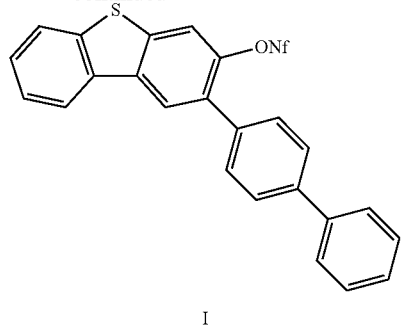
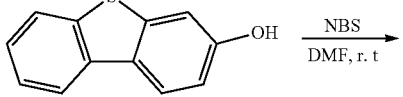
Preparation Example J: Preparation of Intermediate Compound J
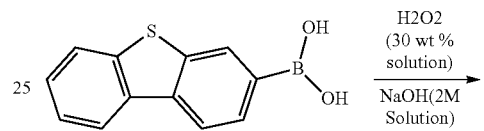
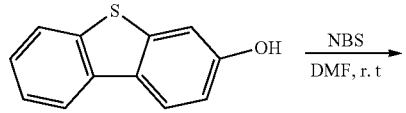
Preparation Example I: Preparation of Intermediate Compound I
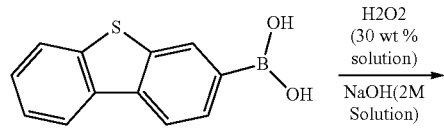
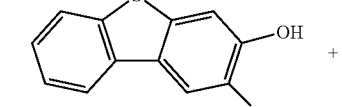
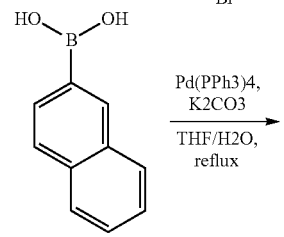
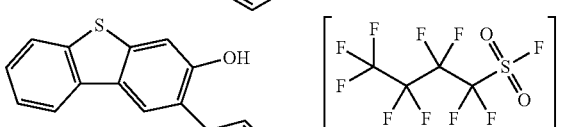

Preparation Example K: Preparation of Intermediate Compound K
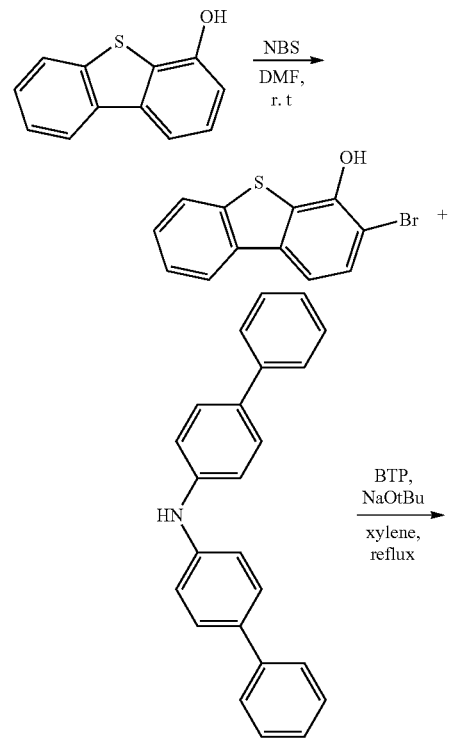
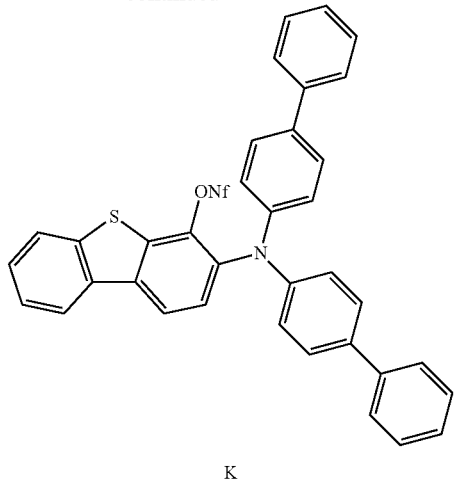
Preparation Example L: Preparation of Intermediate Compound L
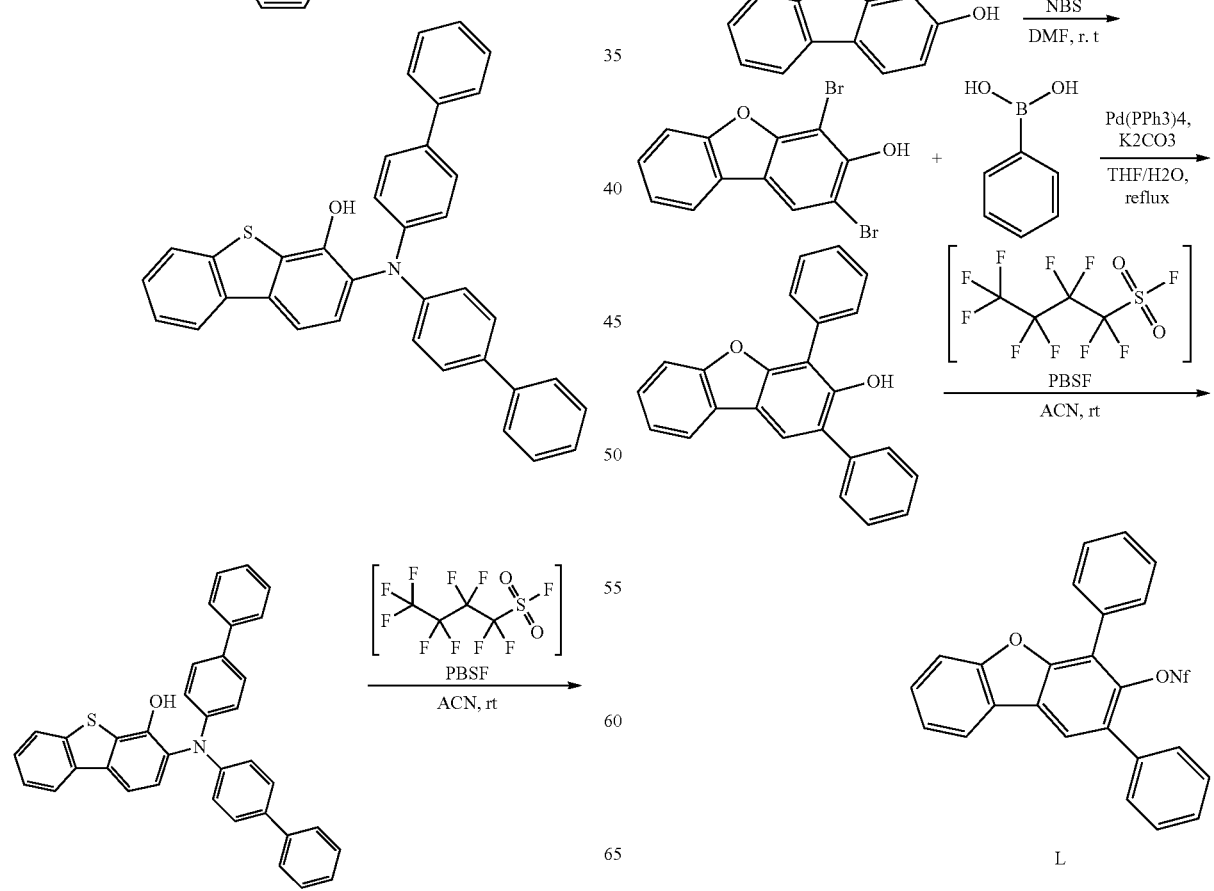

Preparation Example M: Preparation of Intermediate Compound M

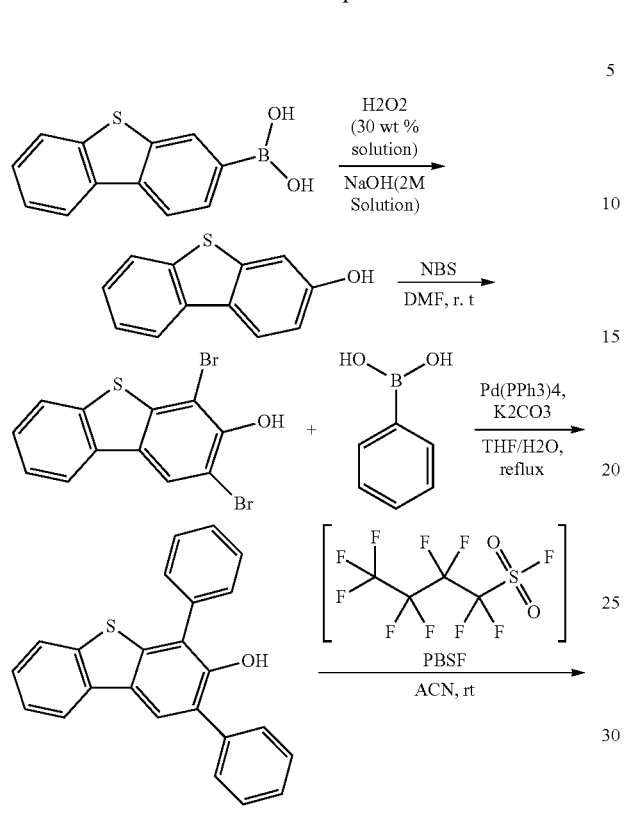

M

Preparation Example 1: Preparation of Compound 1

[Compound 1]

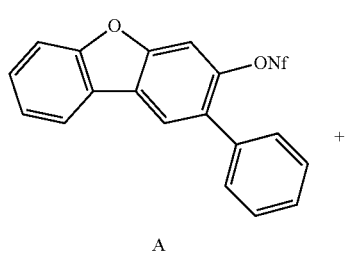

A

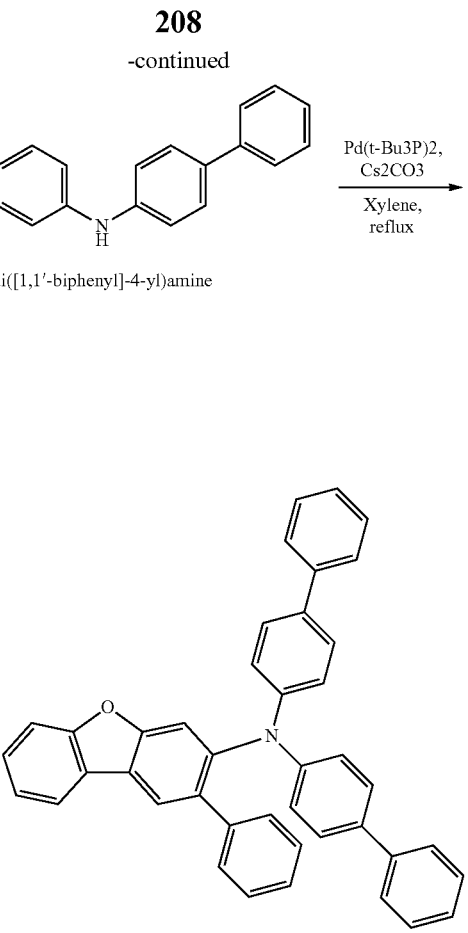

di([1,1'-biphenyl]-4-yl)amine

Compound A (7.56 g, 31.11 mmol) and di([1,1'-biphenyl]-4-yl)amine (10.99 g, 34.22 mmol) were completely dissolved in 220 ml of xylene in a 500 ml round bottom flask under a nitrogen atmosphere, to which cesium carbonate (12.13 g, 37.33 mmol) was added and bis(tri-tert-butylphosphine)palladium(0) (0.08 g, 0.16 mmol) was added, and then the mixture was heated and stirred for 3 hours. After lowering the temperature to room temperature, the reaction mixture was filtered to remove the base. Xylene was then concentrated under reduced pressure and recrystallized from 180 ml of ethyl acetate to prepare Compound 1 (12.46 g, yield: 71%).

MS[M+H]⁺=564

Preparation Example 2: Preparation of Compound 2

[Compound 2]

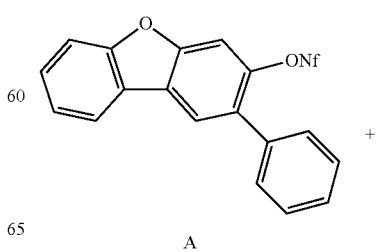

A

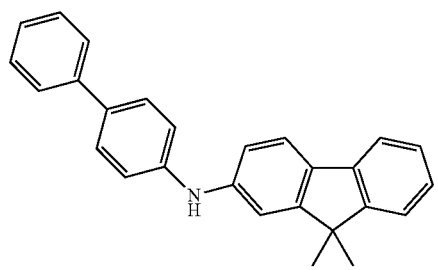

N-([1,1'-biphenyl]-4-yl)-9,9-
dimethyl-9H-fluoren-2-amine

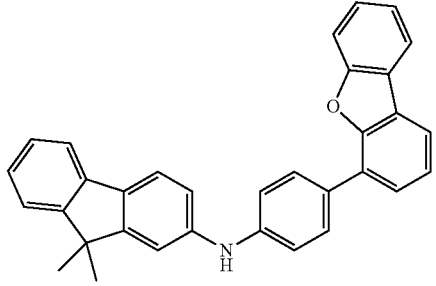

N-(4-(dibenzo[b,d]furan-4-yl)phenyl)-9,9-
dimethyl-9H-fluoren-2-amine

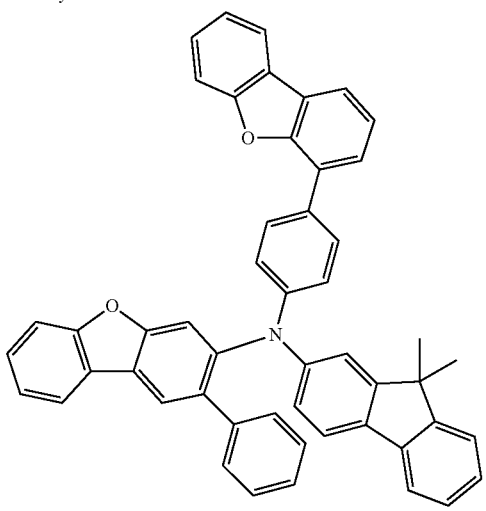

Compound A (8.22 g, 33.83 mmol) and N-([1,1'-biphenyl]-4-yl)-9,9-dimethyl-9H-fluoren-2-amine (13.43 g, 37.21 mmol) were completely dissolved in 250 ml of xylene in a 500 ml round bottom flask under a nitrogen atmosphere, to which cesium carbonate (13.19 g, 40.59 mmol) was added and bis(tri-tert-butylphosphine)palladium(0) (0.09 g, 0.17 mmol) was added, and then the mixture was heated and stirred for 2 hours. After lowering the temperature to room temperature, the reaction mixture was filtered to remove the base. Xylene was then concentrated under reduced pressure and recrystallized from 130 ml of ethyl acetate to prepare Compound 2 (10.45 g, yield: 51%).

MS[M+H]$^+$=604

Preparation Example 3: Preparation of Compound 3

[Compound 3]

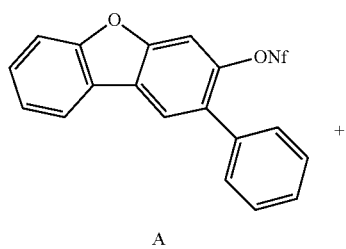

A

Compound A (6.73 g, 27.70 mmol) and N-(4-(dibenzo[b,d]furan-4-yl)phenyl)-9,9-dimethyl-9H-fluoren-2-amine (13.74 g, 30.47 mmol) were completely dissolved in 300 ml of xylene in a 500 ml round bottom flask under a nitrogen atmosphere, to which cesium carbonate (10.80 g, 33.23 mmol) was added and bis(tri-tert-butylphosphine)palladium (0) (0.07 g, 0.14 mmol) was added, and then the mixture was heated and stirred for 6 hours. After lowering the temperature to room temperature, the reaction mixture was filtered to remove the base. Xylene was then concentrated under reduced pressure and recrystallized from 260 ml of tetrahydrofuran to prepare Compound 3 (13.29 g, yield: 69%).

MS[M+H]$^+$=694

Preparation Example 4: Preparation of Compound 4

[Compound 4]

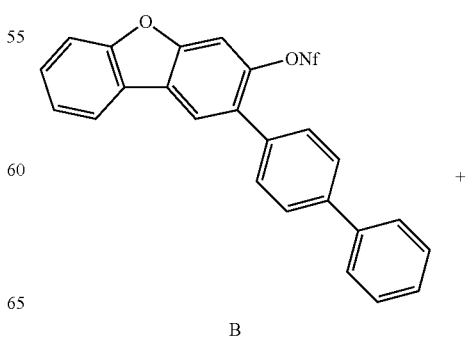

B

211

-continued

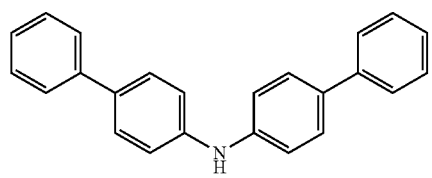

di([1,1'-biphenyl]-4-yl)amine

Pd(t-Bu3P)2,
Cs2CO3
Xylene,
reflux

212

-continued

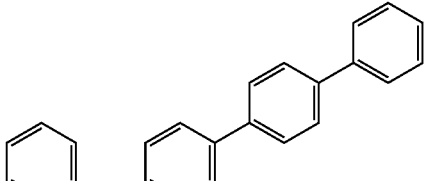

N-phenyl-[1,1':4',1''terphenyl]-4-amine

Pd(t-Bu3P)2,
Cs2CO3
Xylene,
reflux

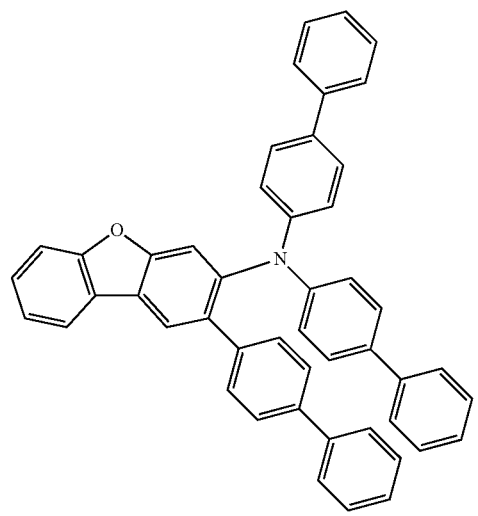

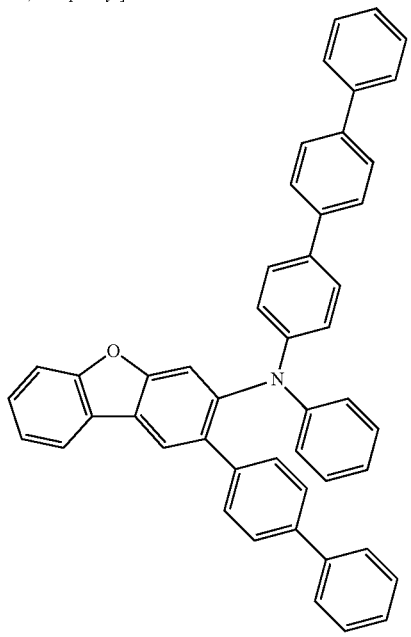

Compound B (4.96 g, 15.55 mmol) and di([1,1'-biphenyl]-4-yl)amine (5.49 g, 17.10 mmol) were completely dissolved in 260 ml of xylene in a 500 ml round bottom flask under a nitrogen atmosphere, to which cesium carbonate (6.06 g, 18.66 mmol) was added and bis(tri-tert-butylphosphine)palladium(0) (0.04 g, 0.08 mmol) was added, and then the mixture was heated and stirred for 6 hours. After lowering the temperature to room temperature, the reaction mixture was filtered to remove the base. Xylene was then concentrated under reduced pressure and recrystallized from 220 ml of ethyl acetate to prepare Compound 4 (7.19 g, yield: 67%).

MS[M+H]$^+$=640

Preparation Example 5: Preparation of Compound 5

[Compound 5]

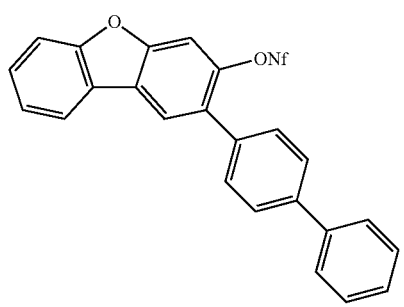

B

Compound B (4.96 g, 15.55 mmol) and N-phenyl-[1,1':4',1''-terphenyl]-4-amine (5.49 g, 17.10 mmol) were completely dissolved in 260 ml of xylene in a 500 ml round bottom flask under a nitrogen atmosphere, to which cesium carbonate (6.06 g, 18.66 mmol) was added and bis(tri-tert-butylphosphine)palladium(0) (0.04 g, 0.08 mmol) was added, and then the mixture was heated and stirred for 5 hours. After lowering the temperature to room temperature, the reaction mixture was filtered to remove the base. Xylene was then concentrated under reduced pressure and recrystallized from 250 ml of ethyl acetate to prepare Compound 5 (6.08 g, yield: 56%).

MS[M+H]$^+$=640

Preparation Example 6: Preparation of Compound 6

[Compound 6]

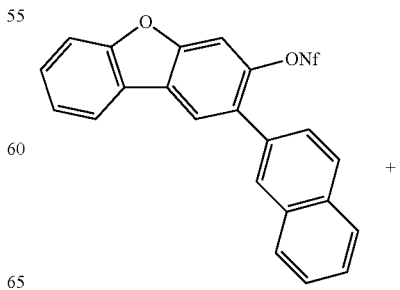

C

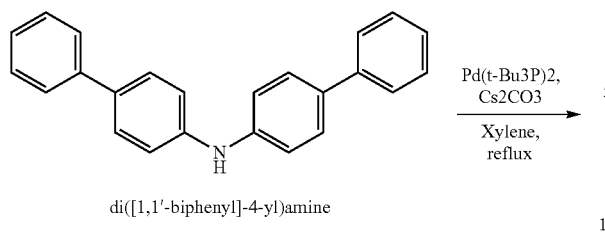

di([1,1'-biphenyl]-4-yl)amine

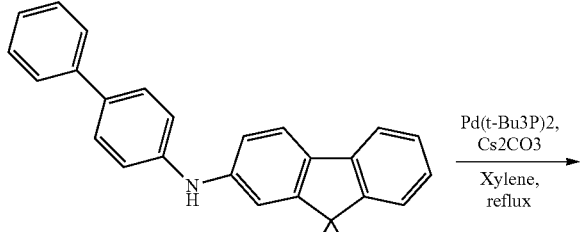

N-([1,1'-biphenyl]-4-yl)-9,9-dimethyl-9H-fluoren-2-amine

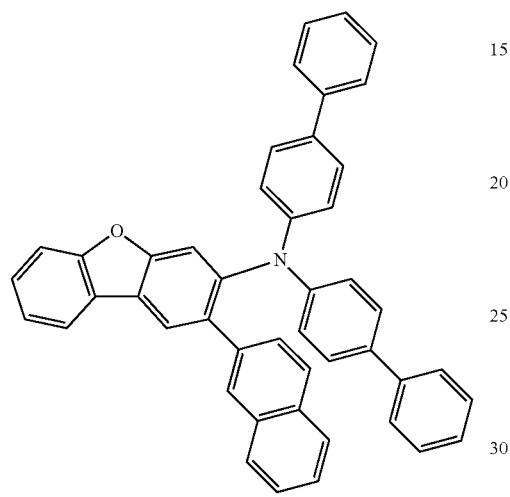

Compound C (5.13 g, 17.51 mmol) and di([1,1'-biphenyl]-4-yl)amine (6.18 g, 19.26 mmol) were completely dissolved in 190 ml of xylene in a 500 ml round bottom flask under a nitrogen atmosphere, to which cesium carbonate (6.83 g, 21.01 mmol) was added and bis(tri-tert-butylphosphine)palladium(0) (0.04 g, 0.08 mmol) was added, and then the mixture was heated and stirred for 4 hours. After lowering the temperature to room temperature, the reaction mixture was filtered to remove the base. Xylene was then concentrated under reduced pressure and recrystallized from 250 ml of ethyl acetate to prepare Compound 6 (7.82 g, yield: 73%).

MS[M+H]$^+$=614

Preparation Example 7: Preparation of Compound 7

[Compound 7]

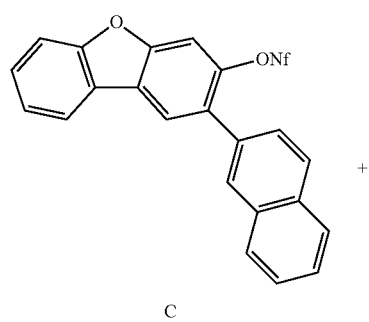

C

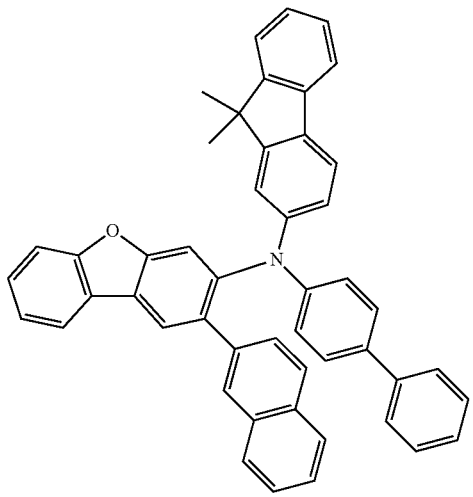

Compound C (4.29 g, 14.64 mmol) and N-([1,1'-biphenyl]-4-yl)-9,9-dimethyl-9H-fluoren-2-amine (5.81 g, 16.11 mmol) were completely dissolved in 280 ml of xylene in a 500 ml round bottom flask under a nitrogen atmosphere, to which cesium carbonate (5.71 g, 17.57 mmol) was added and bis(tri-tert-butylphosphine)palladium(0) (0.04 g, 0.07 mmol) was added, and then the mixture was heated and stirred for 3 hours. After lowering the temperature to room temperature, the reaction mixture was filtered to remove the base. Xylene was then concentrated under reduced pressure and recrystallized from 130 ml of ethyl acetate to prepare Compound 7 (5.17 g, yield: 58%).

MS[M+H]$^+$=604

Preparation Example 8: Preparation of Compound 8

[Compound 8]

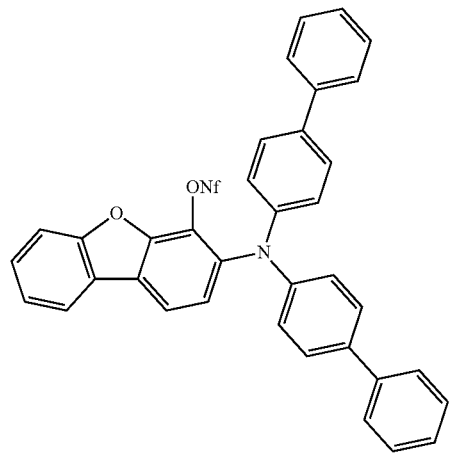

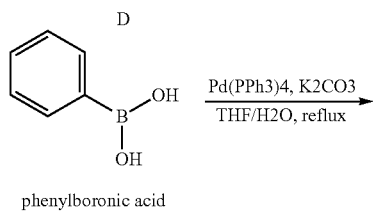

phenylboronic acid

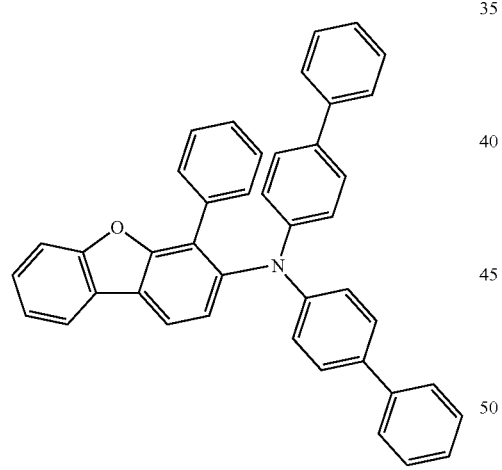

Compound D (7.38 g, 15.19 mmol) and phenylboronic acid (2.13 g, 17.46 mmol) were completely dissolved in 240 ml of tetrahydrofuran in a 500 ml round bottom flask under a nitrogen atmosphere, to which a 2M aqueous potassium carbonate solution (120 ml) was added and tetrakis-(triphenylphosphine)palladium (0.62 g, 0.58 mmol) was added, and then the mixture was heated and stirred for 5 hours. After lowering the temperature to room temperature, the water layer was removed, and the resultant was dried with anhydrous magnesium sulfate, concentrated under reduced pressure, and recrystallized from 250 ml of ethyl acetate to prepare Compound 8 (6.27 g, yield: 73%).

MS[M+H]$^+$=564

Preparation Example 9: Preparation of Compound 9

[Compound 9]

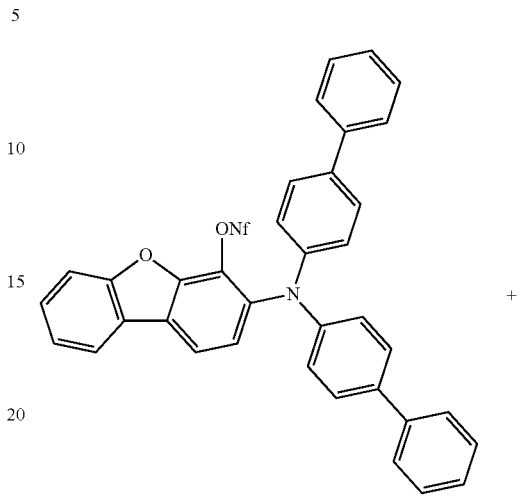

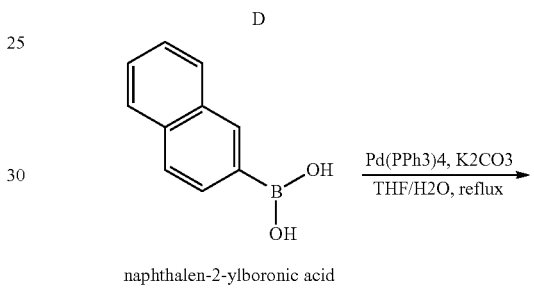

naphthalen-2-ylboronic acid

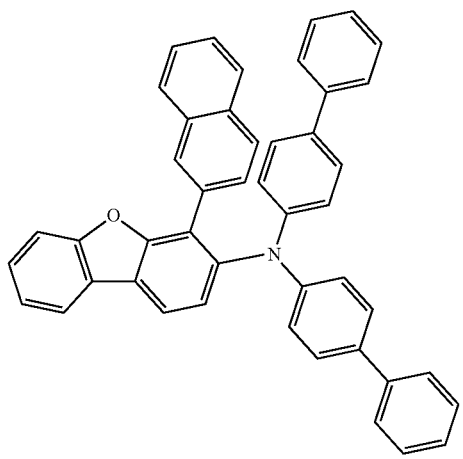

Compound D (7.38 g, 15.19 mmol) and naphthalen-2-ylboronic acid (2.13 g, 17.46 mmol) were completely dissolved in 280 ml of tetrahydrofuran in a 500 ml round bottom flask under a nitrogen atmosphere, to which a 2M aqueous potassium carbonate solution (140 ml) was added and tetrakis-(triphenylphosphine)palladium (0.61 g, 0.57 mmol) was added, and then the mixture was heated and stirred for 4 hours. After lowering the temperature to room temperature, the water layer was removed, and the resultant was dried with anhydrous magnesium sulfate, concentrated under reduced pressure, and recrystallized from 250 ml of ethyl acetate to prepare Compound 9 (7.01 g, yield: 75%).

MS[M+H]$^+$=614

Preparation Example 10: Preparation of Compound 10

[Compound 10]

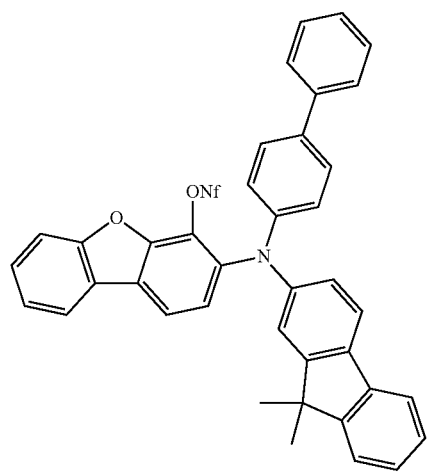

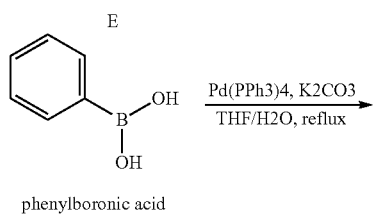

phenylboronic acid

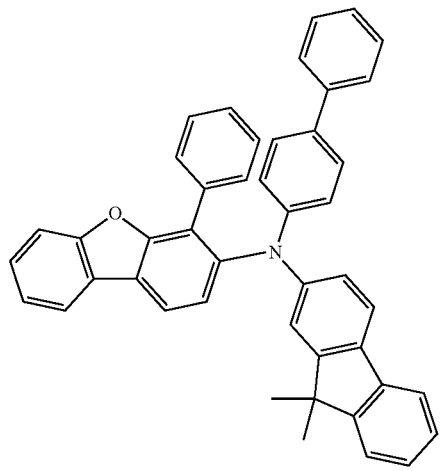

Compound E (7.38 g, 15.19 mmol) and phenylboronic acid (2.13 g, 17.46 mol) were completely dissolved in 240 ml of tetrahydrofuran in a 500 ml round bottom flask under a nitrogen atmosphere, to which a 2M aqueous potassium carbonate solution (120 ml) was added and tetrakis-(triphenylphosphine)palladium (0.49 g, 0.46 mmol) was added, and then the mixture was heated and stirred for 6 hours. After lowering the temperature to room temperature, the water layer was removed, and the resultant was dried with anhydrous magnesium sulfate, concentrated under reduced pressure, and recrystallized from 240 ml of ethyl acetate to prepare Compound 10 (8.26 g, yield: 79%).

MS[M+H]$^+$=604

Preparation Example 11: Preparation of Compound 11

[Compound 11]

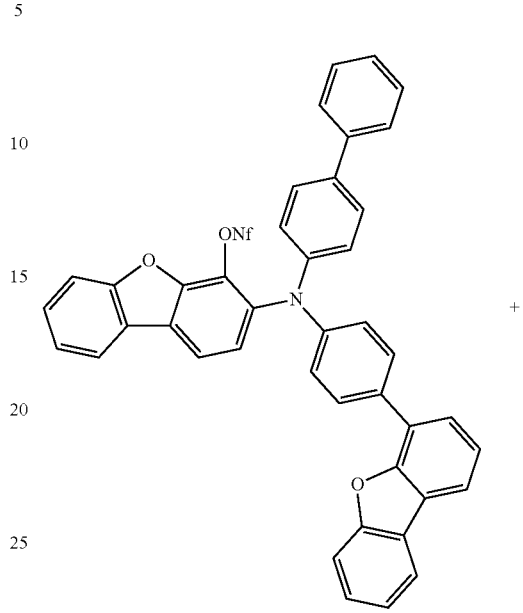

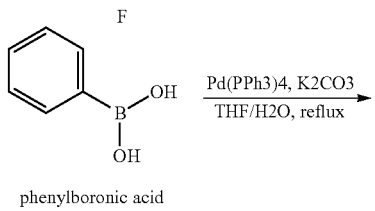

phenylboronic acid

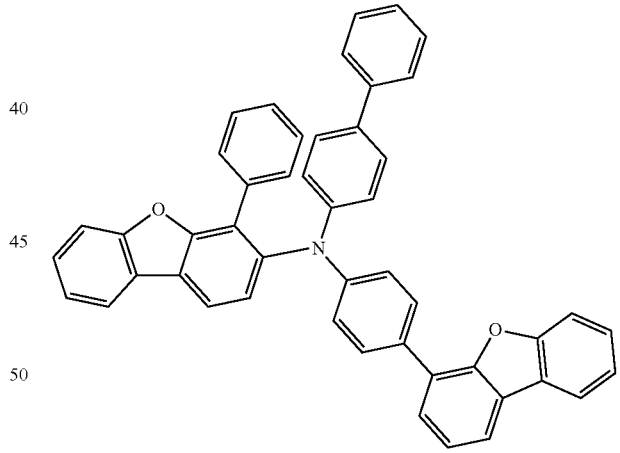

Compound F (7.77 g, 13.49 mmol) and phenylboronic acid (1.89 g, 15.51 mol) were completely dissolved in 200 ml of tetrahydrofuran in a 500 ml round bottom flask under a nitrogen atmosphere, to which a 2M aqueous potassium carbonate solution (100 ml) was added and tetrakis-(triphenylphosphine)palladium (0.47 g, 0.40 mmol) was added, and then the mixture was heated and stirred for 6 hours. After lowering the temperature to room temperature, the water layer was removed, and the resultant was dried with anhydrous magnesium sulfate, concentrated under reduced pressure and recrystallized from 260 ml of ethyl acetate to prepare Compound 11 (8.26 g, yield: 79%).

MS[M+H]$^+$=654

Preparation Example 12: Preparation of Compound 12

[Compound 12]

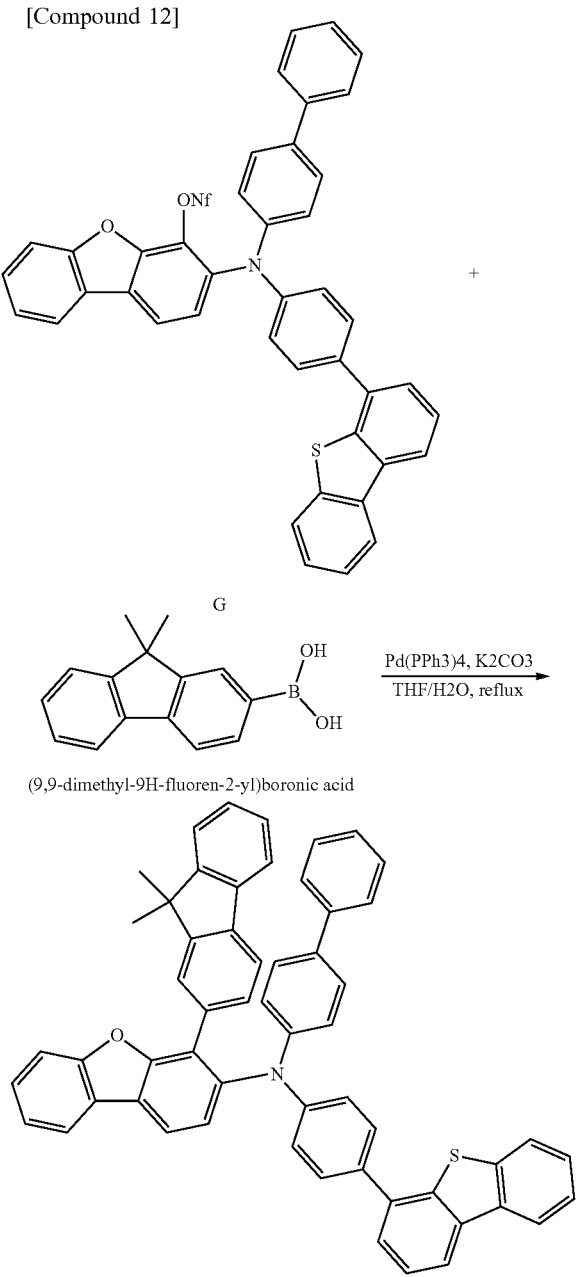

(9,9-dimethyl-9H-fluoren-2-yl)boronic acid

Compound G (6.64 g, 11.22 mmol) and (9,9-dimethyl-9H-fluoren-2-yl)boronic acid (3.07 g, 12.90 mmol) were completely dissolved in 240 ml of tetrahydrofuran in a 500 ml round bottom flask under a nitrogen atmosphere, to which a 2M aqueous potassium carbonate solution (120 ml) was added and tetrakis-(triphenylphosphine)palladium (0.39 g, 0.34 mmol) was added, and then the mixture was heated and stirred for 4 hours. After lowering the temperature to room temperature, the water layer was removed, and the resultant was dried with anhydrous magnesium sulfate, concentrated under reduced pressure, and recrystallized from 310 ml of ethyl acetate to prepare Compound 12 (8.26 g, yield: 79%).

MS[M+H]$^+$=786

Preparation Example 13: Preparation of Compound 13

[Compound 13]

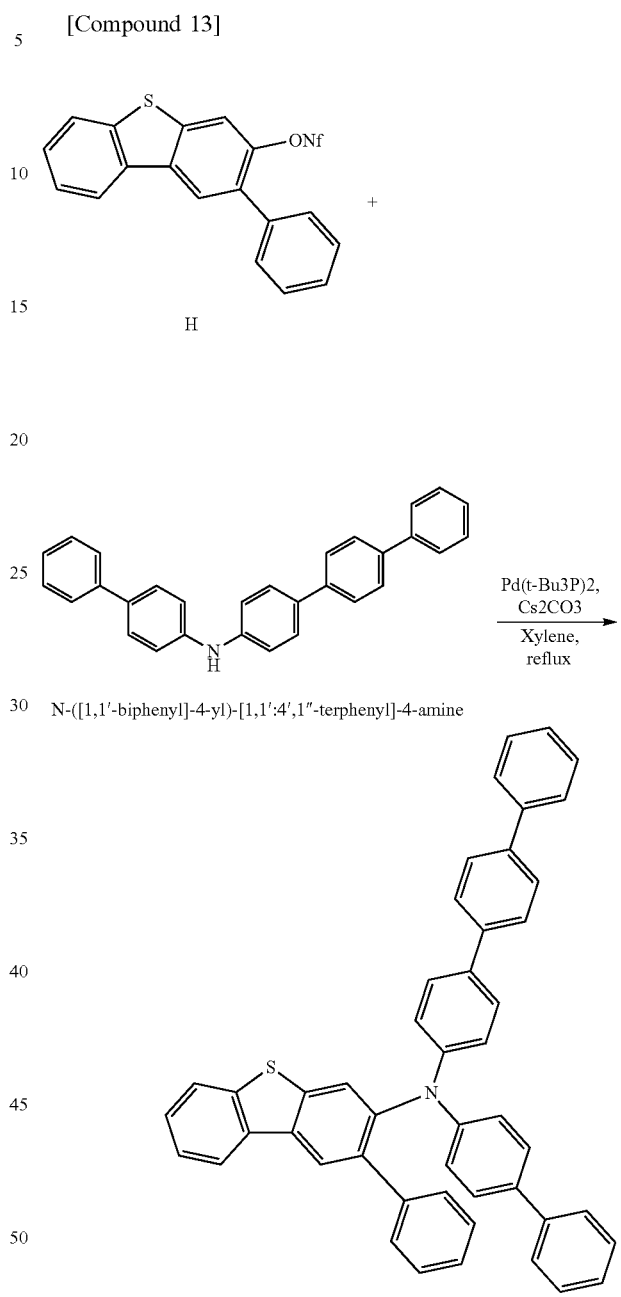

N-([1,1'-biphenyl]-4-yl)-[1,1':4',1''-terphenyl]-4-amine

Compound H (5.39 g, 20.81 mmol) and N-([1,1'-biphenyl]-4-yl)-[1,1':4',1''-terphenyl]-4-amine (9.17 g, 23.10 mmol) were completely dissolved in 250 ml of xylene in a 500 ml round bottom flask under a nitrogen atmosphere, to which cesium carbonate (8.66 g, 27.05 mmol) was added and bis(tri-tert-butylphosphine)palladium(0) (0.11 g, 0.21 mmol) was added, and then the mixture was heated and stirred for 5 hours. After lowering the temperature to room temperature, the reaction mixture was filtered to remove the base. Xylene was then concentrated under reduced pressure and recrystallized from 250 ml of tetrahydrofuran to prepare Compound 13 (11.67 g, yield: 70%).

MS[M+H]$^+$=656

Preparation Example 14: Preparation of Compound 14

[Compound 14]

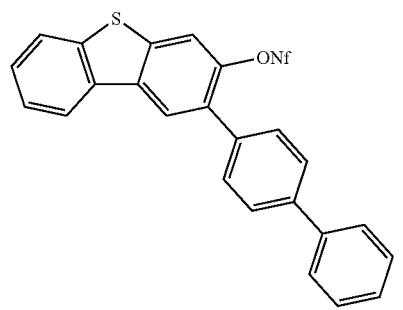

I

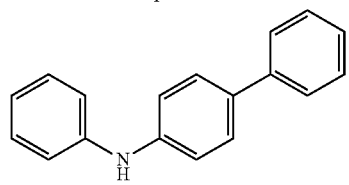

N-phenyl-[1,1'-biphenyl]-4-amine

Pd(t-Bu3P)2, Cs2CO3
Xylene, reflux
→

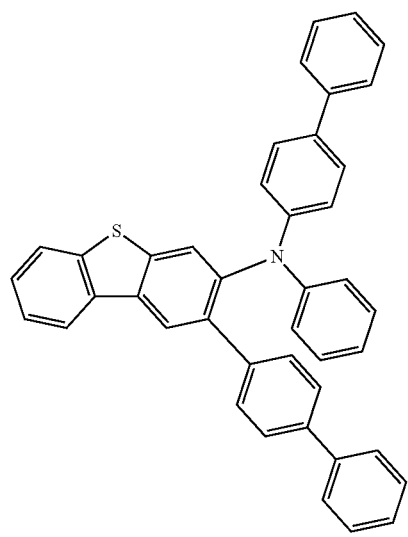

Preparation Example 15: Preparation of Compound 15

[Compound 15]

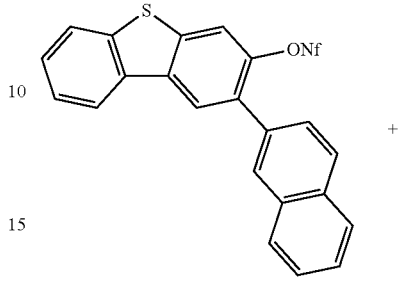

I

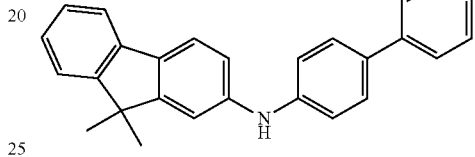

N-([1,1'-biphenyl]-4-yl)-9,9-dimethyl-9H-fluoren-2-amine

Pd(t-Bu3P)2, Cs2CO3
Xylene, reflux
→

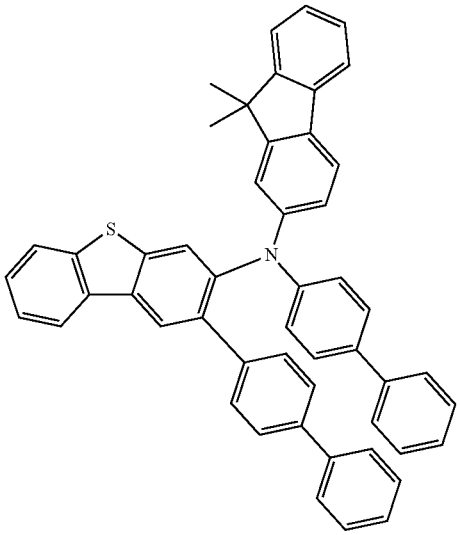

Compound I (7.16 g, 20.81 mmol) and N-phenyl-[1,1'-biphenyl]-4-amine (5.81 g, 23.72 mmol) were completely dissolved in 300 ml of xylene in a 500 ml round bottom flask under a nitrogen atmosphere, to which cesium carbonate (8.89 g, 27.79 mmol) was added and bis(tri-tert-butylphosphine)palladium(0) (0.11 g, 0.21 mmol) was added, and then the mixture was heated and stirred for 3 hours. After lowering the temperature to room temperature, the reaction mixture was filtered to remove the base. Xylene was then concentrated under reduced pressure and recrystallized from 200 ml of tetrahydrofuran to prepare Compound 14 (8.88 g, yield: 72%).

MS[M+H]$^+$=580

Compound I (4.28 g, 13.85 mmol) and N-([1,1'-biphenyl]-4-yl)-9,9-dimethyl-9H-fluoren-2-amine (5.55 g, 15.37 mmol) were completely dissolved in 280 ml of xylene in a 500 ml round bottom flask under a nitrogen atmosphere, to which cesium carbonate (5.76 g, 18.01 mmol) was added and bis(tri-tert-butylphosphine)palladium(0) (0.07 g, 0.14 mmol) was added, and then the mixture was heated and stirred for 4 hours. After lowering the temperature to room temperature, the reaction mixture was filtered to remove the base. Xylene was then concentrated under reduced pressure and recrystallized from 220 ml of tetrahydrofuran to prepare Compound 15 (4.39 g, yield: 46%).

MS[M+H]$^+$=696

Preparation Example 16: Preparation of Compound 16

[Compound 16]

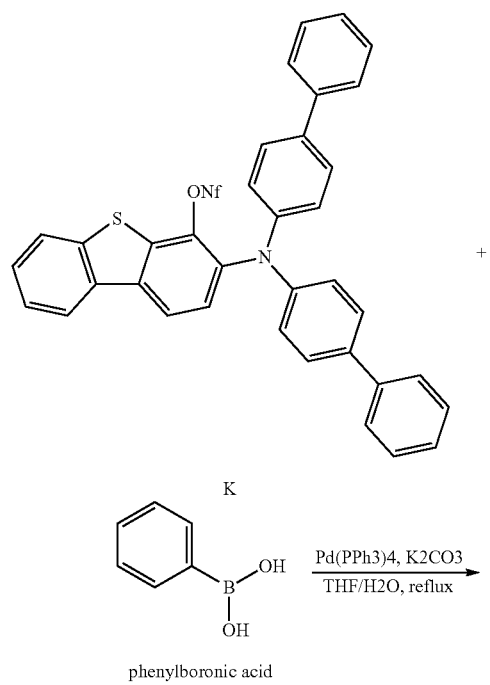

Preparation Example 17: Preparation of Compound 17

[Compound 17]

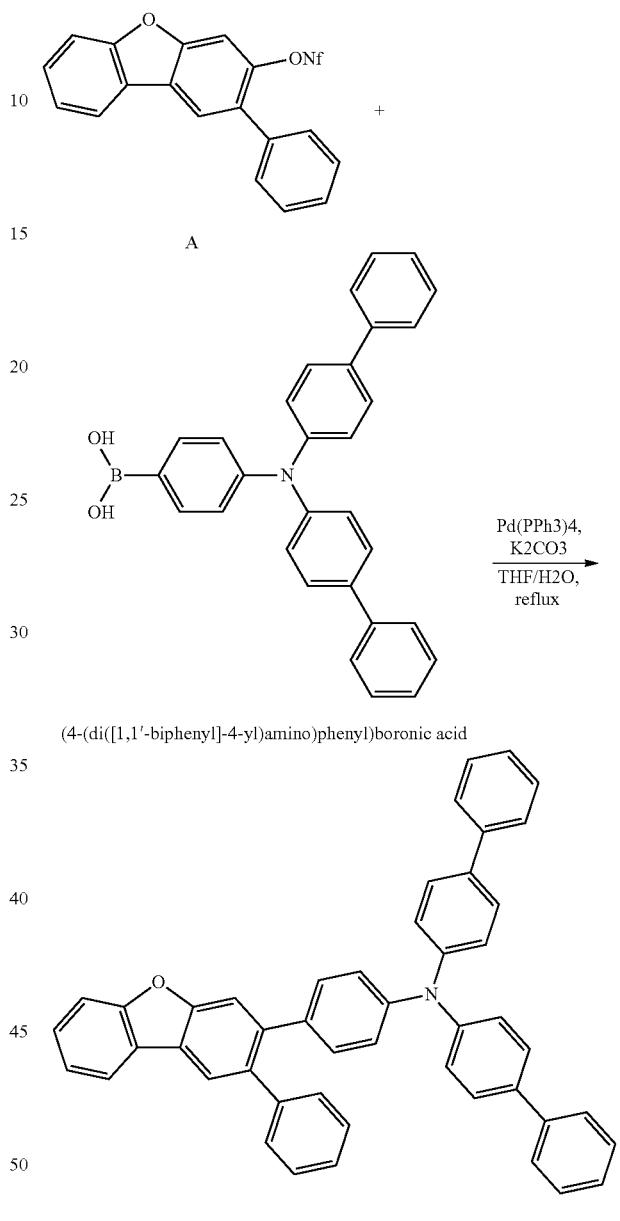

Compound K (9.68 g, 19.28 mmol) and phenylboronic acid (2.61 g, 21.40 mmol) were completely dissolved in 240 ml of tetrahydrofuran in a 500 ml round bottom flask under a nitrogen atmosphere, to which a 2M aqueous potassium carbonate solution (120 ml) was added and tetrakis-(triphenylphosphine)palladium (0.67 g, 0.58 mmol) was added, and then the mixture was heated and stirred for 4 hours. After lowering the temperature to room temperature, the water layer was removed, and the resultant was dried with anhydrous magnesium sulfate, concentrated under reduced pressure, and recrystallized from 220 ml of ethyl acetate to prepare Compound 16 (6.09 g, yield: 54%).

MS[M+H]$^+$=580

Compound A (5.32 g) and (4-(di([1,1'-biphenyl]-4-yl)amino)phenyl)boronic acid (10.72 g, 24.30 mmol) were completely dissolved in 240 ml of tetrahydrofuran in a 500 ml round bottom flask under a nitrogen atmosphere, to which a 2M aqueous potassium carbonate solution (120 ml) was added and tetrakis-(triphenylphosphine)palladium (0.76 g, 0.66 mmol) was added, and then the mixture was heated and stirred for 4 hours. After lowering the temperature to room temperature, the water layer was removed, and the resultant was dried with anhydrous magnesium sulfate, concentrated under reduced pressure, and recrystallized from 250 ml of ethyl acetate to prepare Compound 17 (7.12 g, yield: 51%).

MS[M+H]$^+$=640

Preparation Example 18: Preparation of Compound 18

[Compound 18]

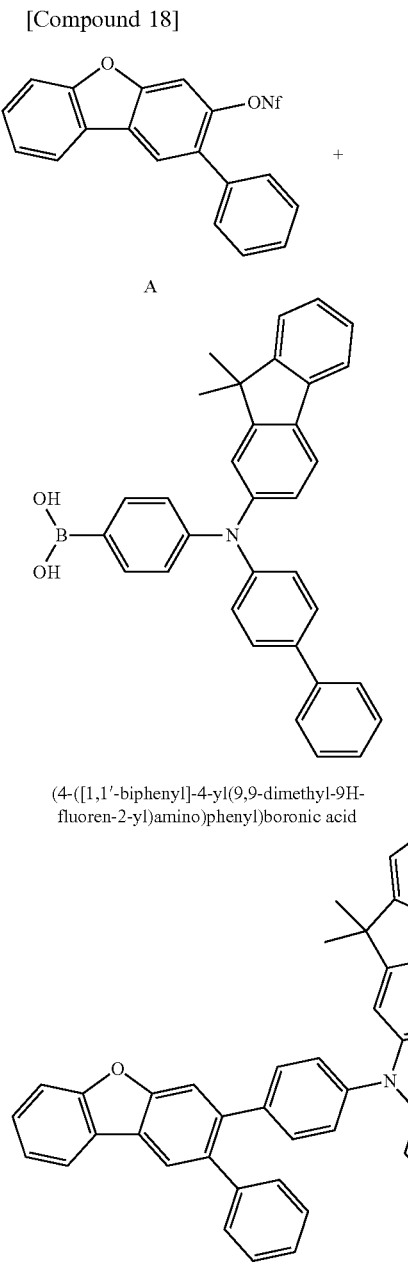

(4-([1,1'-biphenyl]-4-yl(9,9-dimethyl-9H-fluoren-2-yl)amino)phenyl)boronic acid

Compound A (6.67 g, 27.45 mmol) and (4-([1,1'-biphenyl]-4-yl(9,9-dimethyl-9H-fluoren-2-yl)amino)phenyl)boronic acid (10.72 g, 24.30 mol) were completely dissolved in 240 ml of tetrahydrofuran in a 500 ml round bottom flask under a nitrogen atmosphere, to which a 2M aqueous potassium carbonate solution (120 ml) was added and tetrakis-(triphenylphosphine)palladium (0.76 g, 0.66 mmol) was added, and then the mixture was heated and stirred for 4 hours. After lowering the temperature to room temperature, the water layer was removed, and the resultant was dried with anhydrous magnesium sulfate, concentrated under reduced pressure, and recrystallized from 250 ml of ethyl acetate to prepare Compound 18 (7.12 g, yield: 51%).
MS[M+H]$^+$=680

Preparation Example 19: Preparation of Compound 19

[Compound 19]

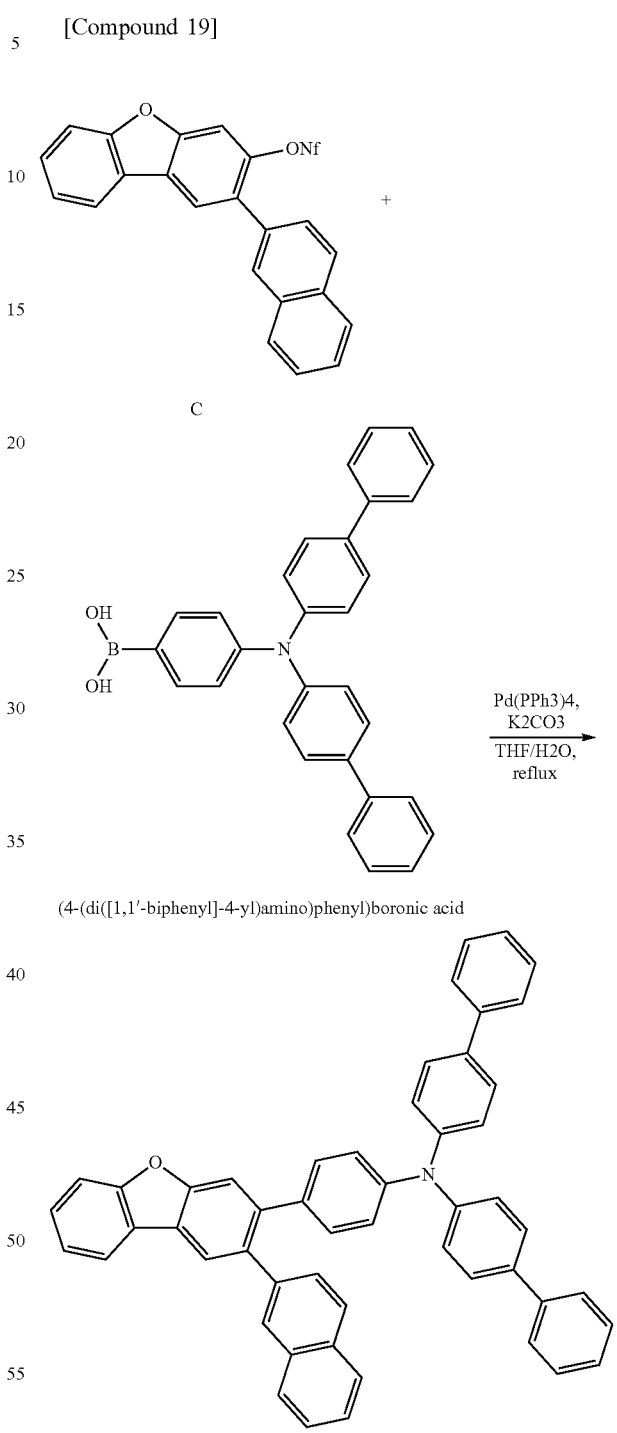

(4-(di([1,1'-biphenyl]-4-yl)amino)phenyl)boronic acid

Compound C (7.75 g, 27.45 mmol) and (4-([1,1'-biphenyl]-4-yl(9,9-dimethyl-9H-fluoren-2-yl)amino)phenyl)boronic acid (13.41 g, 30.42 mol) were completely dissolved in 280 ml of tetrahydrofuran in a 500 ml round bottom flask under a nitrogen atmosphere, to which a 2M aqueous potassium carbonate solution (140 ml) was added and tetrakis-(triphenylphosphine)palladium (0.92 g, 0.79 mmol) was added, and then the mixture was heated and stirred for 3 hours. After lowering the temperature to room temperature, the water layer was removed, and the resultant was dried with anhydrous magnesium sulfate, concentrated under reduced pressure, and recrystallized from 250 ml of ethyl acetate to prepare Compound 19 (15.26 g, yield: 84%).

MS[M+H]$^+$=690

Preparation Example 20: Preparation of Compound 20

[Compound 20]

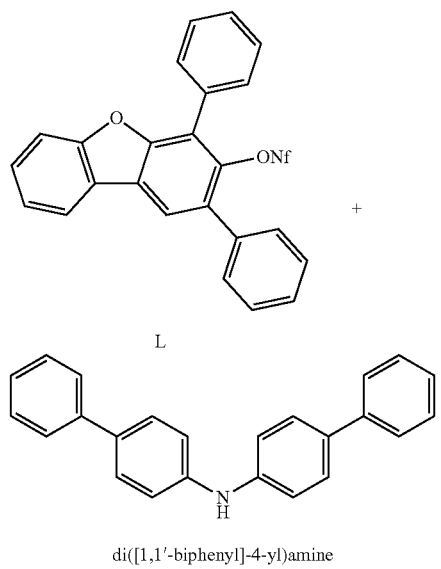

L

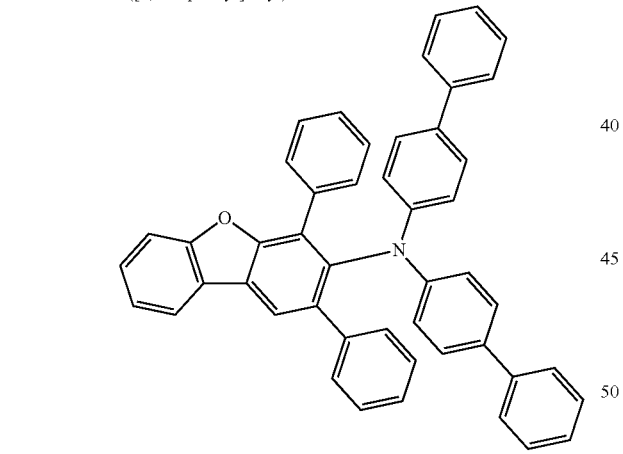

di([1,1'-biphenyl]-4-yl)amine

Pd(t-Bu3P)2, Cs2CO3
Xylene, reflux

Preparation Example 21: Preparation of Compound 21

[Compound 21]

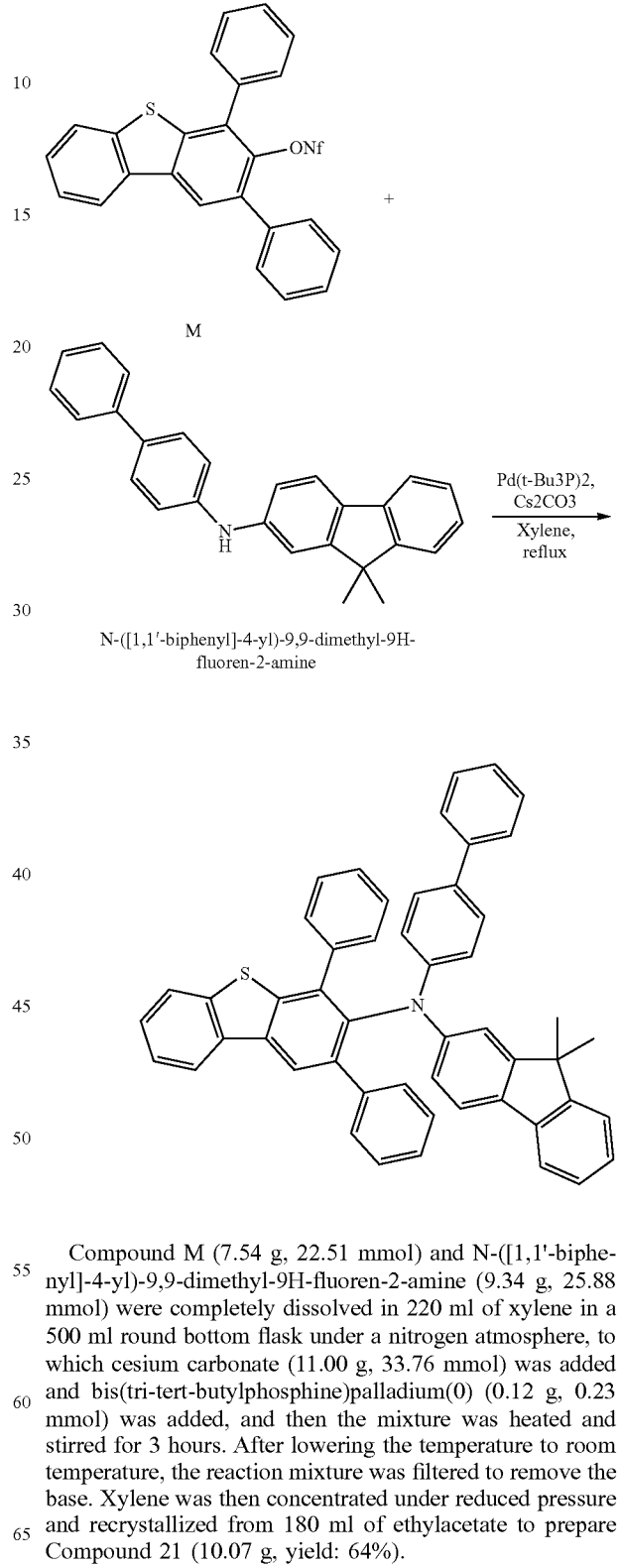

M

N-([1,1'-biphenyl]-4-yl)-9,9-dimethyl-9H-fluoren-2-amine

Pd(t-Bu3P)2, Cs2CO3
Xylene, reflux

Compound L (5.47 g, 17.15 mmol) and di([1,1'-biphenyl]-4-yl)amine (6.33 g, 19.72 mmol) were completely dissolved in 180 ml of xylene in a 500 ml round bottom flask under a nitrogen atmosphere, to which cesium carbonate (8.38 g, 25.72 mmol) was added and bis(tri-tert-butylphosphine)palladium(0) (0.09 g, 0.17 mmol) was added, and then the mixture was heated and stirred for 6 hours. After lowering the temperature to room temperature, the reaction mixture was filtered to remove the base. Xylene was then concentrated under reduced pressure and recrystallized from 250 ml of ethylacetate to prepare Compound 20 (6.77 g, yield: 62%).

MS[M+H]$^+$=640

Compound M (7.54 g, 22.51 mmol) and N-([1,1'-biphenyl]-4-yl)-9,9-dimethyl-9H-fluoren-2-amine (9.34 g, 25.88 mmol) were completely dissolved in 220 ml of xylene in a 500 ml round bottom flask under a nitrogen atmosphere, to which cesium carbonate (11.00 g, 33.76 mmol) was added and bis(tri-tert-butylphosphine)palladium(0) (0.12 g, 0.23 mmol) was added, and then the mixture was heated and stirred for 3 hours. After lowering the temperature to room temperature, the reaction mixture was filtered to remove the base. Xylene was then concentrated under reduced pressure and recrystallized from 180 ml of ethylacetate to prepare Compound 21 (10.07 g, yield: 64%).

MS[M+H]$^+$=696

Example 1-1

A glass substrate on which ITO (indium tin oxide) was coated as a thin film to a thickness of 1000 Å was put into distilled water in which a detergent was dissolved, and ultrasonically washed. In this case, a product manufactured by Fischer Co. was used as the detergent, and as the distilled water, distilled water filtered twice using a filter manufactured by Millipore Co., was used. After the ITO was washed for 30 minutes, ultrasonic washing was conducted twice using distilled water for 10 minutes each. After the washing using distilled water was completed, ultrasonic washing was conducted using solvents of isopropyl alcohol, acetone, and methanol, and then it was dried and transferred to a plasma cleaner. In addition, the substrate was cleaned for 5 minutes using oxygen plasma, and then transferred to a vacuum depositor.

On the ITO transparent electrode thus prepared, hexanitrile hexaazatriphenylene (HAT) of the following chemical formula was thermally vacuum-deposited in a thickness of 150 Å to form a hole injection layer.

[HAT]

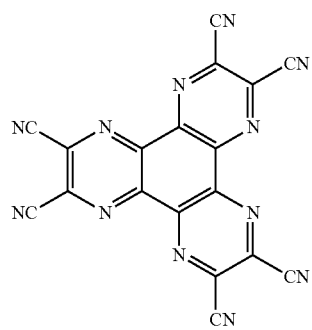

The following compound HT1 (1150 Å), a material transporting holes, was vacuum deposited on the hole injection layer to form a hole transport layer.

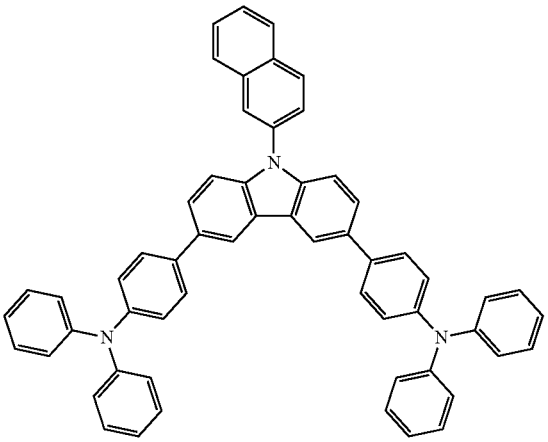 [SMILES: c1ccc(N(c2ccccc2)c2ccc(-c3ccc4c(c3)c3cc(-c5ccc(N(c6ccccc6)c6ccccc6)cc5)ccc3n4-c3ccc4ccccc4c3)cc2)cc1]

Then, Compound 1 prepared in Preparation Example 1 was vacuum deposited to a film thickness of 150 Å on the hole transport layer to form an electron blocking layer.

Next, BH and BD shown below were vacuum deposited in a weight ratio of 25:1 on the electron blocking layer to a film thickness of 300 Å to form a light emitting layer.

[BH]                                    [BD]

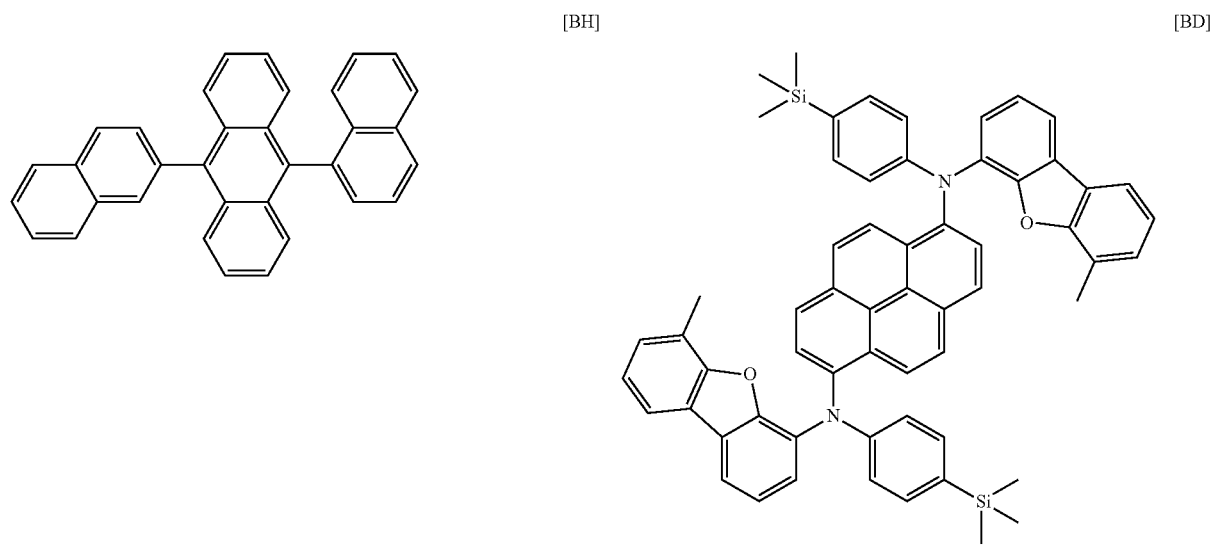

-continued

[ET]

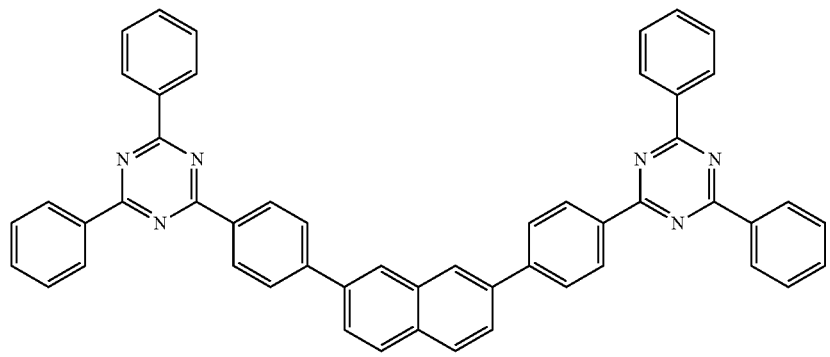

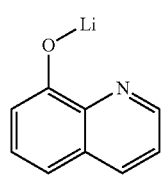

[LiQ]

The above Compound ET and the above Compound LiQ (Lithium Quinolate) was vacuum deposited in a weight ratio of 1:1 on the light emitting layer to form an electron transport layer at a thickness of 300 Å. Lithium fluoride (LiF) with a thickness of 12 Å and aluminum with a thickness of 2000 Å was sequentially deposited on the electron transport layer to form an electron injection layer and a cathode.

In the aforementioned process, the deposition rate of the organic material was maintained at 0.4 to 0.7 Å/s, the deposition rate of lithium fluoride of the cathode at 0.3 Å/s, the deposition rate of aluminum at 2 Å/s, and the degree of vacuum during the deposition at $2 \times 10^{-7}$ tor to $5 \times 10^{-6}$ tor, thereby manufacturing an organic light emitting device.

Example 1-2 to Example 1-15

The organic light emitting devices of Examples 1-2 to 1-15 were respectively manufactured in the same manner as in Example 1-1, except that when forming the electron blocking layer, Compound 1 was changed to those as shown in Table 1 below.

Comparative Example 1-1

An organic light emitting device was manufactured in the same manner as in Example 1-1, except that when forming the electron blocking layer, EB-1 shown below was used instead of Compound 1.

[EB-1]

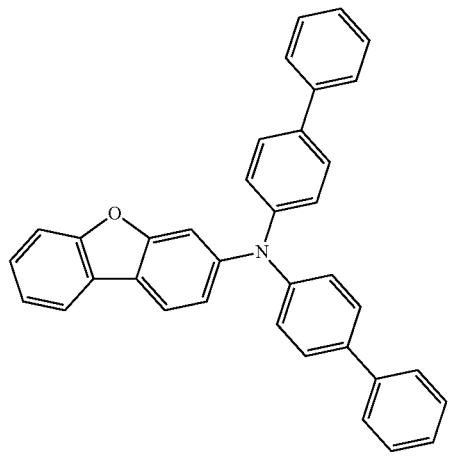

Comparative Example 1-2

An organic light emitting device was manufactured in the same manner as in Example 1-1, except that when forming the electron blocking layer, EB-2 shown below was used instead of Compound 1.

[EB-2]

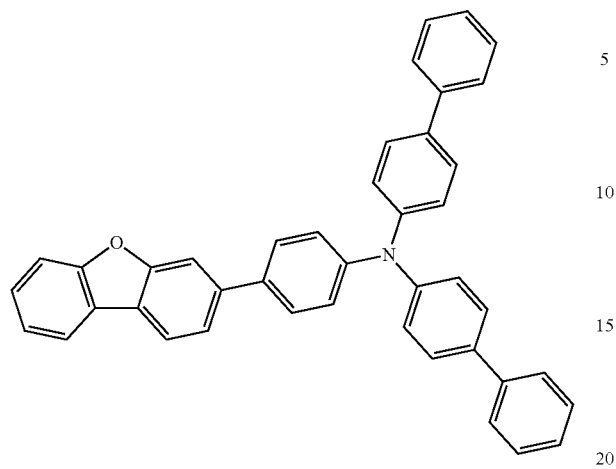

Comparative Example 1-3

An organic light emitting device was manufactured in the same manner as in Example 1-1, except that when forming the electron blocking layer, EB-3 shown below was used instead of Compound 1.

[EB-3]

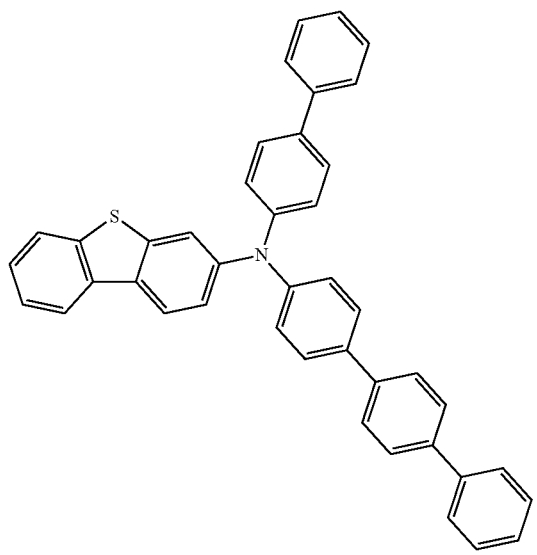

Comparative Example 1-4

An organic light emitting device was manufactured in the same manner as in Example 1-1, except that when forming the electron blocking layer, EB-4 shown below was used instead of Compound 1.

[EB-4]

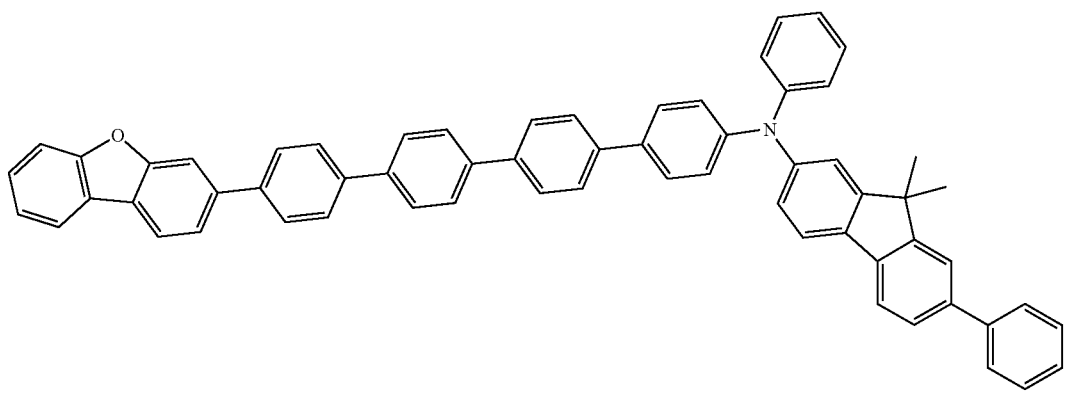

Experimental Example 1

A voltage, efficiency, luminance, color coordinates, and lifetime were measured by applying a current to the organic light emitting devices manufactured in Examples 1-1 to 1-15 and Comparative Examples 1-1 to 1-4, and the results are shown in Table 1 below. T95 means the time taken for the luminance to be reduced to 95% of the initial luminance (650 nit).

TABLE 1

| | Electron blocking layer Compound | Voltage (V@10 mA/cm$^2$) | Efficiency (cd/A@10 mA/cm$^2$) | Color coordinates (x, y) | Lifetime (T95, h) |
|---|---|---|---|---|---|
| Example 1-1 | Compound 1 | 3.72 | 5.47 | (0.140, 0.045) | 225 |
| Example 1-2 | Compound 4 | 3.86 | 5.32 | (0.140, 0.045) | 215 |
| Example 1-3 | Compound 5 | 3.88 | 5.31 | (0.139, 0.046) | 210 |
| Example 1-4 | Compound 6 | 3.87 | 5.38 | (0.139, 0.047) | 230 |
| Example 1-5 | Compound 8 | 3.74 | 5.41 | (0.138, 0.044) | 220 |
| Example 1-6 | Compound 9 | 3.85 | 5.28 | (0.140, 0.042) | 200 |
| Example 1-7 | Compound 11 | 3.81 | 5.29 | (0.140, 0.041) | 205 |
| Example 1-8 | Compound 12 | 3.72 | 5.45 | (0.141, 0.045) | 210 |
| Example 1-9 | Compound 13 | 3.77 | 5.42 | (0.142, 0.045) | 205 |
| Example 1-10 | Compound 14 | 3.98 | 5.11 | (0.137, 0.047) | 245 |
| Example 1-11 | Compound 16 | 3.94 | 5.18 | (0.136, 0.048) | 240 |
| Example 1-12 | Compound 17 | 3.88 | 5.31 | (0.137, 0.044) | 250 |
| Example 1-13 | Compound 19 | 3.74 | 5.28 | (0.136, 0.045) | 215 |
| Example 1-14 | Compound 20 | 3.68 | 5.57 | (0.142, 0.042) | 250 |
| Example 1-15 | Compound 21 | 3.64 | 5.58 | (0.143, 0.043) | 215 |
| Comparative Example 1-1 | EB-1 | 4.05 | 4.87 | (0.136, 0.047) | 165 |
| Comparative Example 1-2 | EB-2 | 4.16 | 4.77 | (0.136, 0.048) | 170 |
| Comparative Example 1-3 | EB-3 | 4.10 | 4.82 | (0.136, 0.046) | 185 |
| Comparative Example 1-4 | EB-4 | 5.12 | 4.13 | (0.136, 0.047) | 115 |

As shown in Table 1, it can be confirmed that in the case of an organic light emitting device manufactured by using the compound according to the present invention as an electron blocking layer, it exhibited superior performance in terms of driving voltage, current efficiency, lifetime, and stability as compared with the organic light emitting device of the comparative examples.

Specifically, in the case of the organic light emitting device manufactured by using the compounds of Comparative Examples 1-1 to 1-3 having no substituent in the 1$^{st}$ and 3$^{rd}$ directions while having the same structure as the core of the present invention as an electron blocking layer, it resulted in decreasing the efficiency by 10% or more and the lifetime by 30% or more, compared to the examples.

On the other hand, the compound of Comparative Example 1-4 showed the result that the distance between the core and the arylamine group was too far, and thus the characteristics of the organic light emitting device were greatly deteriorated.

Consequently, it was confirmed that in the case of the compound of the examples of the present invention, the efficiency of the device was increased and at the same time the stability was remarkably increased.

Example 2-1

A glass substrate on which ITO (indium tin oxide) was coated as a thin film to a thickness of 1000 Å was put into distilled water in which a detergent was dissolved, and ultrasonically washed. In this case, a product manufactured by Fischer Co., was used as the detergent, and as the distilled water, distilled water filtered twice using a filter manufactured by Millipore Co., was used. After the ITO was washed for 30 minutes, ultrasonic washing was conducted twice using distilled water for 10 minutes each. After the washing using distilled water was completed, ultrasonic washing was conducted using solvents of isopropyl alcohol, acetone, and methanol, and then it was dried transferred to a plasma cleaner. In addition, the substrate was cleaned for 5 minutes using oxygen plasma, and then transferred to a vacuum depositor.

On the ITO transparent electrode thus prepared, the HAT was thermally vacuum-deposited at a thickness of 150 Å to form a hole injection layer.

The compound prepared in Preparation Example 1, which is a material transporting holes, was vacuum deposited to a film thickness of 1150 Å on the hole injection layer to form a hole transport layer.

Subsequently, the following Compound EB was vacuum deposited to a film thickness of 150 Å on the hole transport layer to form an electron blocking layer.

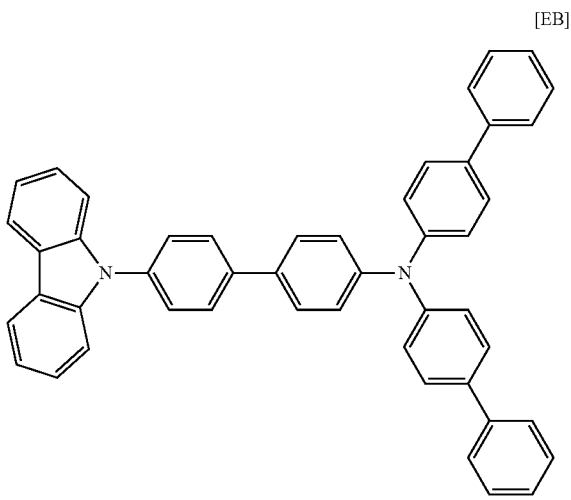 [SMILES: c1ccc(-c2ccc(N(c3ccc(-c4ccccc4)cc3)c3ccc(-c4ccc(-n5c6ccccc6c6ccccc65)cc4)cc3)cc2)cc1]

[EB]

Next, the BH and BD were vacuum deposited in a weight ratio of 25:1 on the electron blocking layer to a film thickness of 300 Å to form a light emitting layer.

The above Compound ET and the above Compound LiQ (Lithium Quinolate) were vacuum deposited at a weight ratio of 1:1 on the light emitting layer to form an electron transport layer in a thickness of 300 Å. Lithium fluoride (LiF) with a thickness of 12 Å and aluminum with a thickness of 2000 Å was sequentially deposited on the electron transport layer to form an electron injection layer and a cathode.

In the aforementioned process, the deposition rate of the organic material was maintained at 0.4 to 0.7 Å/s, the deposition rate of lithium fluoride of the cathode at 0.3 Å/s, the deposition rate of aluminum at 2 Å/s, and the degree of vacuum during the deposition at $2\times10^{-7}$ tor to $5\times10^{-6}$ tor, thereby manufacturing an organic light emitting device.

Example 2-2 to Example 2-12

The organic light emitting devices of Examples 2-2 to 1-12 were respectively manufactured in the same manner as in Example 2-1, except that when forming the hole transport layer, Compound 1 was changed to those shown in Table 2 below.

Comparative Example 2-1

An organic light emitting device was manufactured in the same manner as in Example 2-1, except that when forming the hole transport layer, HT-1 shown below was used instead of Compound 1 as the electron transport material.

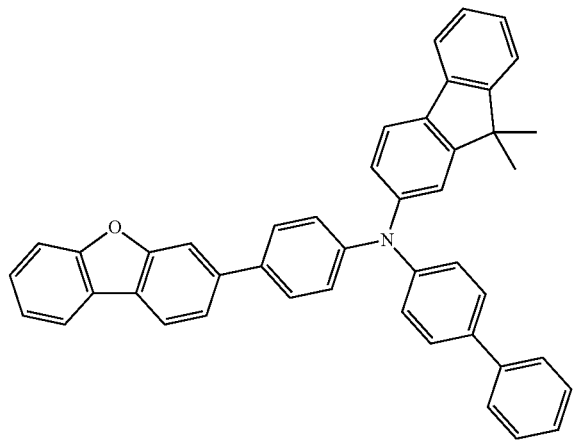

[HT-2]

Comparative Example 2-3

An organic light emitting device was manufactured in the same manner as in Example 2-1, except that when forming the hole transport layer, HT-3 shown below was used instead of Compound 1 as the electron transport material.

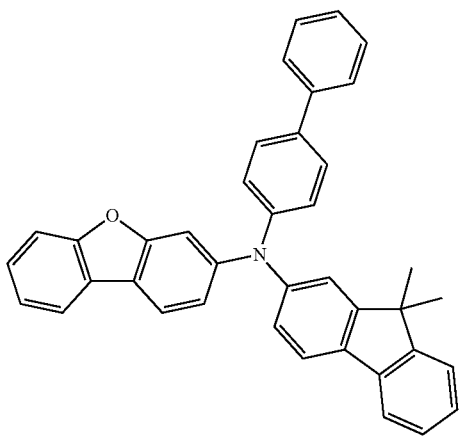

[HT-1]

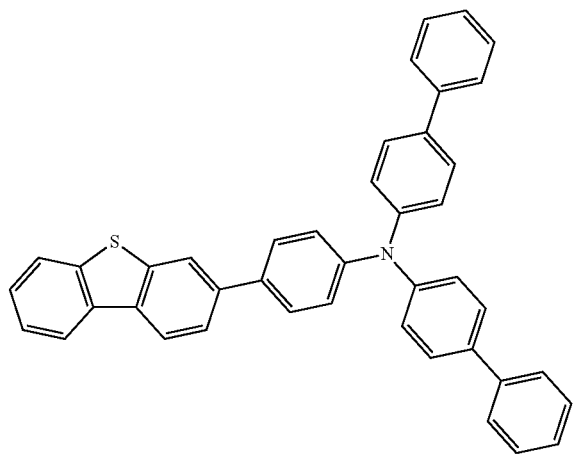

[HT-3]

Comparative Example 2-2

An organic light emitting device was manufactured in the same manner as in Example 2-1, except that when forming the hole transport layer, HT-2 shown below was used instead of Compound 1 as the electron transport material.

Comparative Example 2-4

An organic light emitting device was manufactured in the same manner as in Example 2-1, except that when forming the hole transport layer, HT-4 shown below was used instead of Compound 1 as the electron transport material.

[HT-4]

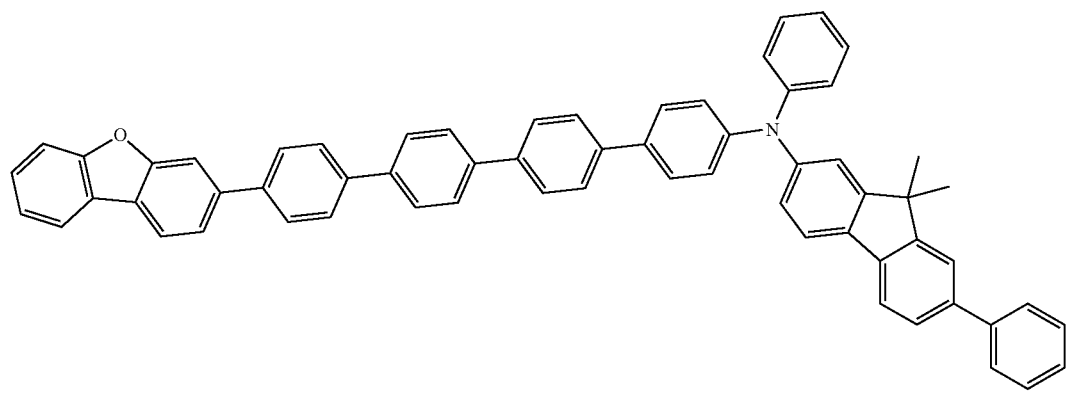

Experimental Example 2

A voltage, efficiency, luminance, color coordinates, and lifetime were measured by applying a current to the organic light emitting devices manufactured in Examples 2-1 to 2-12 and Comparative Examples 2-1 to 2-4, and the results are shown in Table 2 below. T95 means the time taken for the luminance to be reduced to 95% of the initial luminance (650 nit).

TABLE 2

| | Hole transport layer compound | Voltage (V@10 mA/cm$^2$) | Efficiency (cd/A@10 mA/cm$^2$) | Color coordinates (x, y) | Lifetime (T95, h) |
|---|---|---|---|---|---|
| Example 2-1 | Compound 1 | 3.81 | 5.53 | (0.140, 0.045) | 260 |
| Example 2-2 | Compound 2 | 3.95 | 5.42 | (0.140, 0.045) | 250 |
| Example 2-3 | Compound 3 | 3.94 | 5.44 | (0.139, 0.046) | 255 |
| Example 2-4 | Compound 4 | 3.96 | 5.45 | (0.139, 0.047) | 275 |
| Example 2-5 | Compound 6 | 3.87 | 5.57 | (0.138, 0.044) | 265 |
| Example 2-6 | Compound 7 | 3.99 | 5.38 | (0.140, 0.042) | 245 |
| Example 2-7 | Compound 9 | 3.91 | 5.39 | (0.140, 0.041) | 240 |
| Example 2-8 | Compound 10 | 3.82 | 5.59 | (0.141, 0.045) | 255 |
| Example 2-9 | Compound 15 | 3.85 | 5.55 | (0.142, 0.045) | 240 |
| Example 2-10 | Compound 18 | 4.01 | 5.26 | (0.137, 0.047) | 280 |
| Example 2-11 | Compound 20 | 3.86 | 5.43 | (0.142, 0.041) | 270 |
| Example 2-12 | Compound 21 | 3.73 | 5.42 | (0.143, 0.042) | 265 |
| Comparative Example 2-1 | HT-1 | 4.13 | 4.83 | (0.136, 0.047) | 200 |
| Comparative Example 2-2 | HT-2 | 4.21 | 4.74 | (0.136, 0.048) | 215 |
| Comparative Example 2-3 | HT-3 | 4.29 | 4.87 | (0.136, 0.046) | 220 |
| Comparative Example 2-4 | HT-4 | 4.92 | 4.10 | (0.143, 0.042) | 110 |

As shown in Table 2, it can be confirmed that in the case of an organic light emitting device manufactured by using the compound according to the present invention as a hole transport layer, it exhibited superior performance in terms of current efficiency, driving voltage, lifetime, and stability as compared with the organic light emitting device of the comparative examples.

Specifically, in the case of the organic light emitting device manufactured by using the compounds of Comparative Examples 2-1 to 2-3 having no substituent in the 1$^{st}$ and 3$^{rd}$ directions while having the same structure as the core of the present invention as a hole transport layer, it resulted in decreasing the efficiency by 10% or more and the lifetime by 30% or more, compared to the examples.

On the other hand, the compound of Comparative Example 2-4 showed the result that the distance between the core and the arylamine group was too far, and thus the characteristics of the organic light emitting device were greatly deteriorated.

Consequently, it was confirmed that in the case of the compounds of the examples of the present invention, the efficiency of the device was increased and at the same time the stability was remarkably increased.

Therefore, it can be seen that the compound according to the present invention is excellent not only in the electron blocking ability but also in the hole transporting ability, so is applicable to an electron blocking layer and/or a hole transport layer of an organic light emitting device.

[Description of symbols]

| | |
|---|---|
| 1: substrate | 2: anode |
| 3: light emitting layer | 4: cathode |
| 5: hole injection layer | |
| 6: hole transport layer | |
| 7: light emitting layer | |
| 8: electron transport layer | |

The invention claimed is:
1. A compound represented by the following Chemical Formula 1:

[Chemical Formula 1]

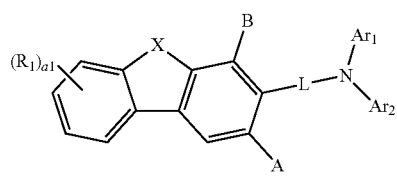

wherein, in Chemical Formula 1,
X is O or S,
A and B are each independently hydrogen; a substituted or unsubstituted $C_{6-60}$ aryl; or a substituted or unsubstituted $C_{2-60}$ heteroaryl containing 1 to 3 heteroatoms selected from the group consisting of O and S,
at least one of A and B is not hydrogen,
L is a single bond; a substituted or unsubstituted $C_{6-60}$ arylene; or a substituted or unsubstituted $C_{2-60}$ heteroarylene containing one or more heteroatoms selected from the group consisting of O, N, Si, and S,
$R_1$ is hydrogen; deuterium; a halogen; a cyano; a nitro; an amino; a substituted or unsubstituted $C_{1-60}$ alkyl; a substituted or unsubstituted $C_{1-60}$ haloalkyl; a substituted or unsubstituted $C_{1-60}$ alkoxy; a substituted or unsubstituted $C_{1-60}$ haloalkoxy; a substituted or unsubstituted $C_{3-60}$ cycloalkyl; a substituted or unsubstituted $C_{2-60}$ alkenyl; a substituted or unsubstituted $C_{6-60}$ aryl; a substituted or unsubstituted $C_{6-60}$ aryloxy; or a substituted or unsubstituted $C_{2-60}$ heterocyclic group containing one or more heteroatoms selected from the group consisting of N, O, and S,
a1 is an integer of 0 to 4, and
$Ar_1$ and $Ar_2$ are each independently any one selected from the croup consisting of the following:

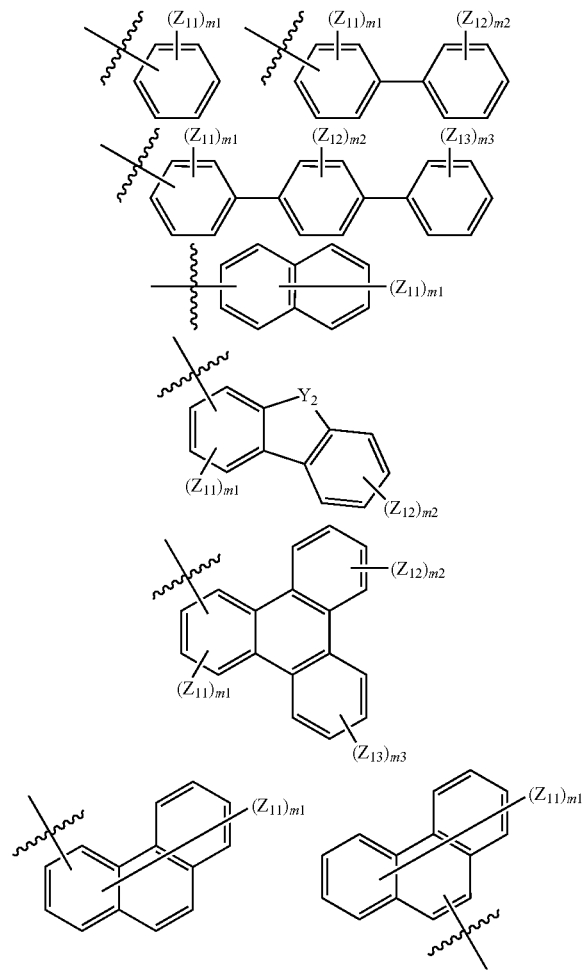

wherein,
$Y_2$ is O, S, or $CZ_{14}Z_{15}$, $Z_{11}$ to $Z_{15}$ are each independently hydrogen; deuterium; a halogen; a cyano; a nitro; an amino; a silyl; a $C_{1-20}$ alkyl; a $C_{1-20}$ haloalkyl; a $C_{6-20}$ aryl; or a $C_{2-20}$ heteroaryl containing one or more heteroatoms of O or S,
$Z_{14}$ and $Z_{15}$ are optionally linked to each other to form a monocyclic or polycyclic ring, and
m1 to m3 are each independently an integer of 0 to 3.

2. The compound of claim 1, wherein A and B are each independently hydrogen or any one selected from the croup consisting of the following:

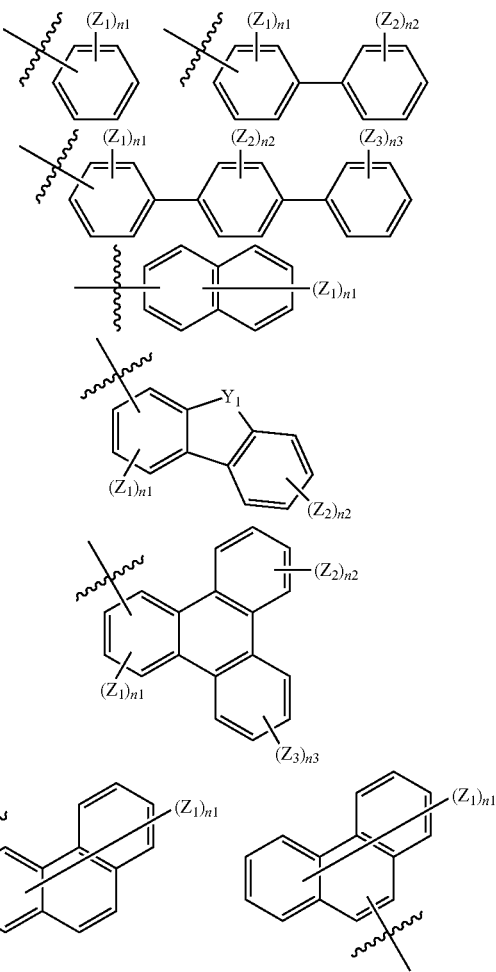

wherein,
$Y_1$ is O, S, or $CZ_4Z_5$,
$Z_1$ to $Z_5$ are each independently hydrogen; deuterium; a halogen; a cyano; a nitro; an amino; a $C_{1-20}$ alkyl; a $C_{1-20}$ haloalkyl; a $C_{6-20}$ aryl; or a $C_{2-20}$ heteroaryl containing one or more heteroatoms of O or S, and
n1 to n3 are each independently an integer of 0 to 3.

3. The compound of claim 2, wherein A and B are each independently hydrogen or any one selected from the group consisting of the following:

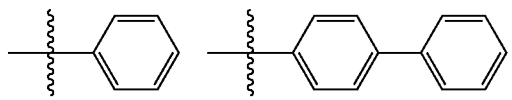

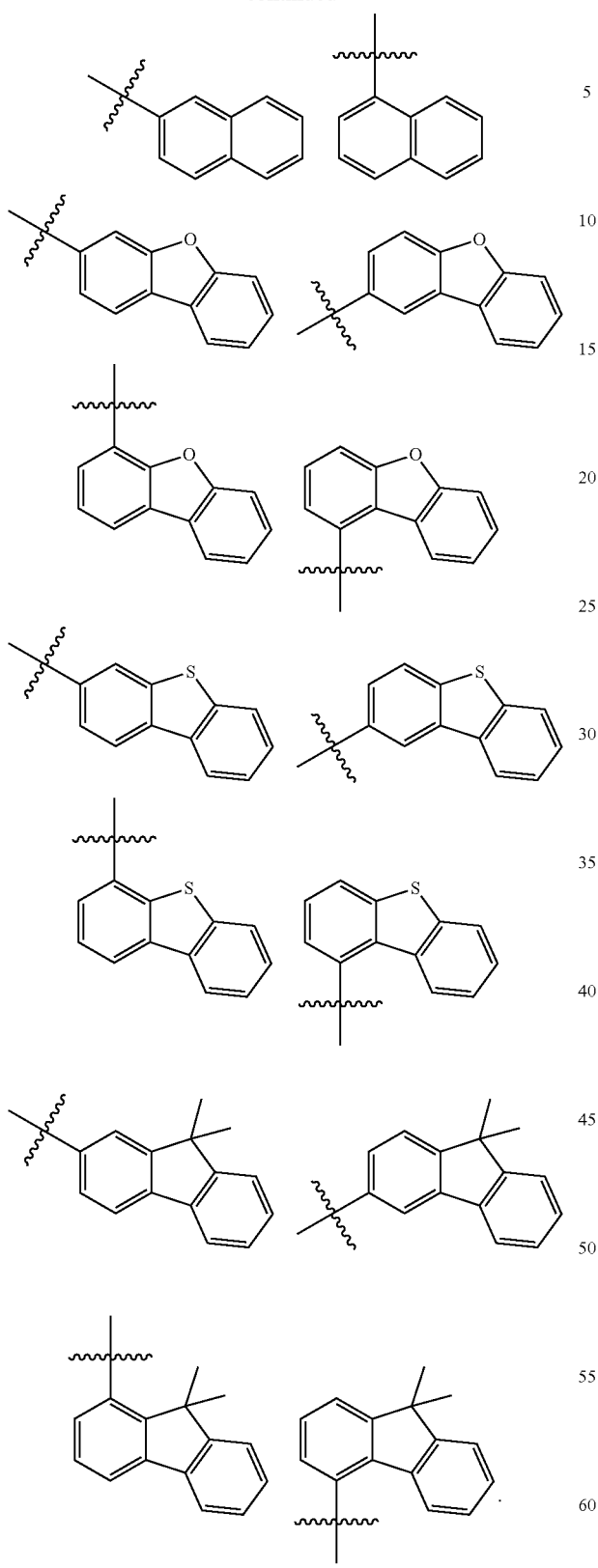
4. The compound of claim 1, wherein L is a single bond, or any one selected from the group consisting of the following:
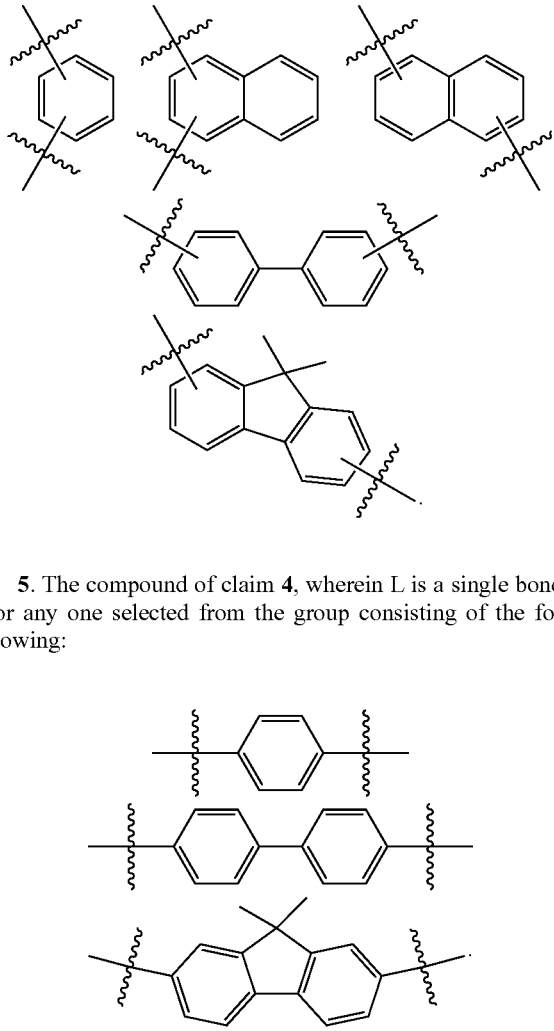
5. The compound of claim 4, wherein L is a single bond, or any one selected from the group consisting of the following:
6. The compound of claim 1, wherein $Ar_1$ and $Ar_2$ are each independently any one selected from the group consisting of the following:
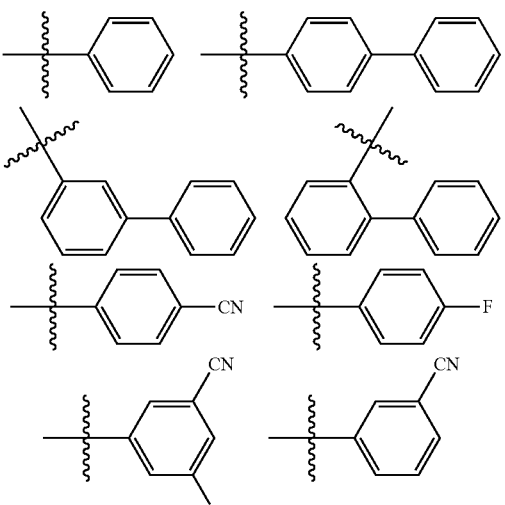

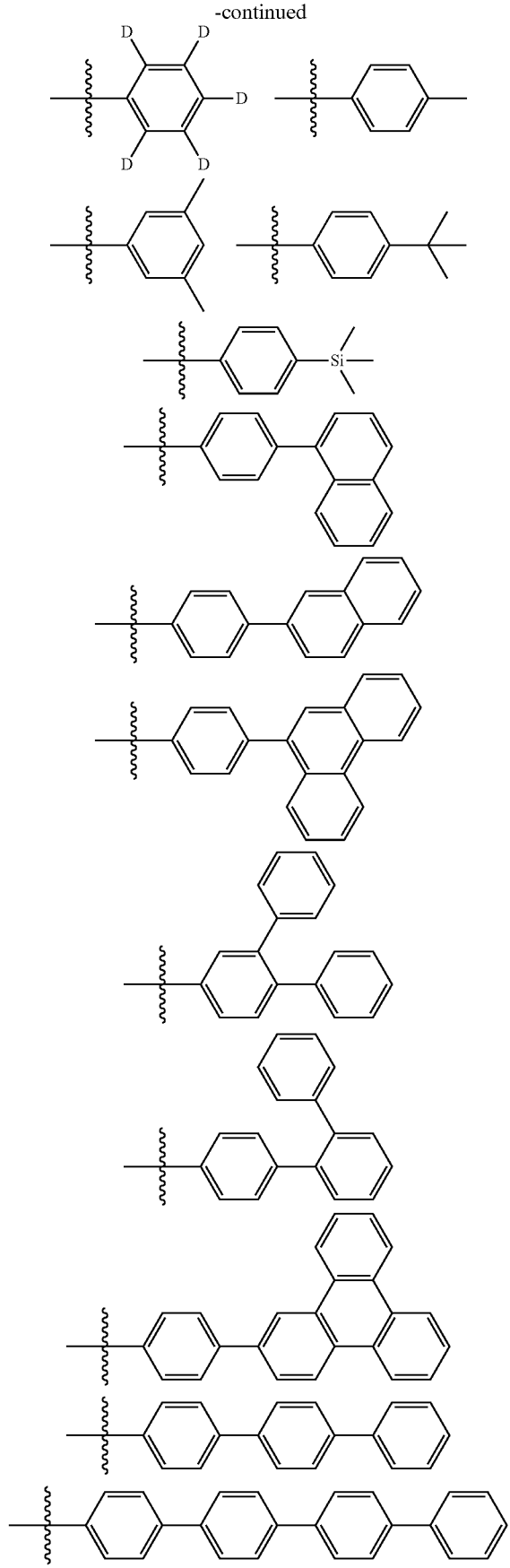
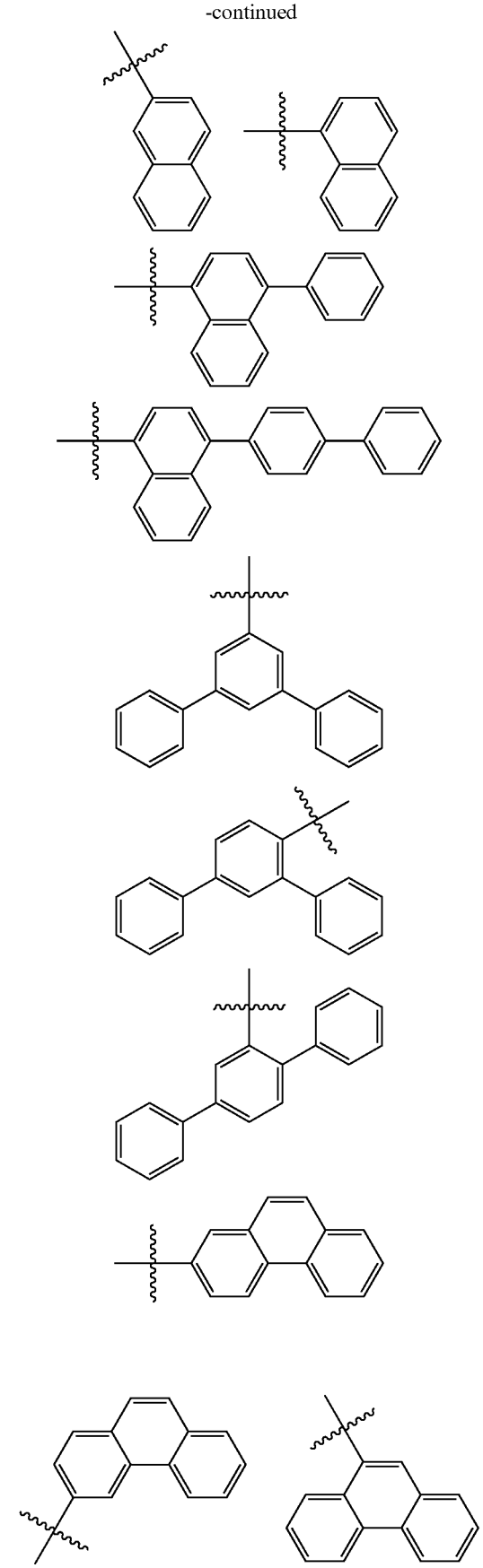

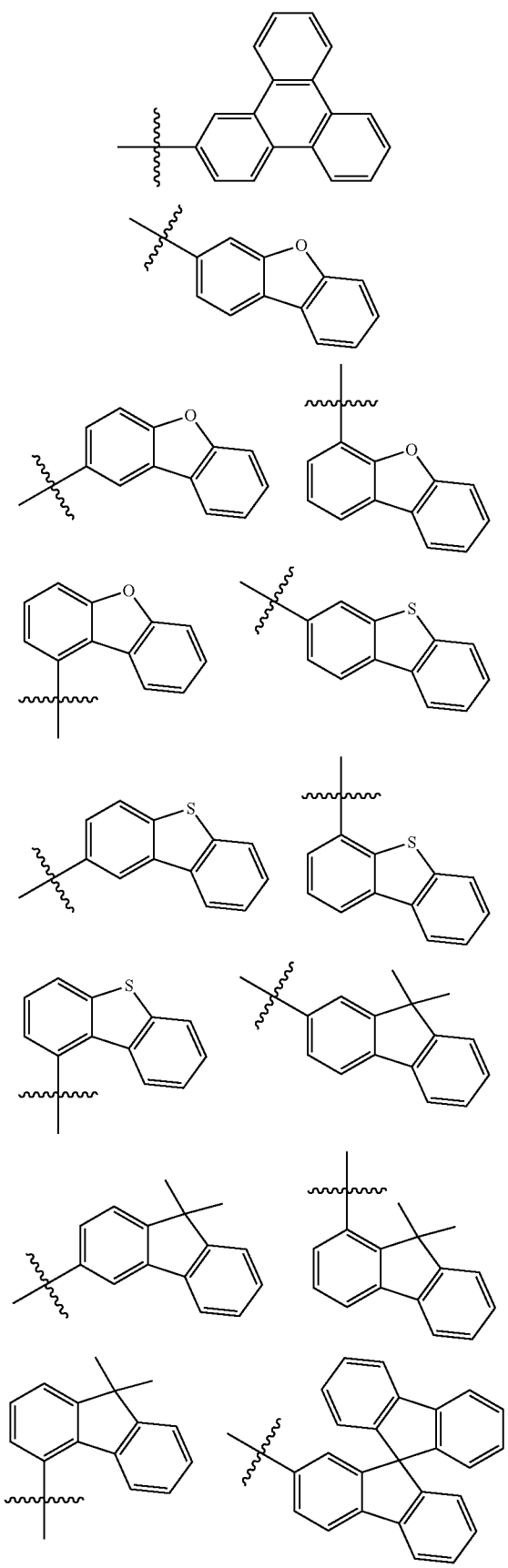
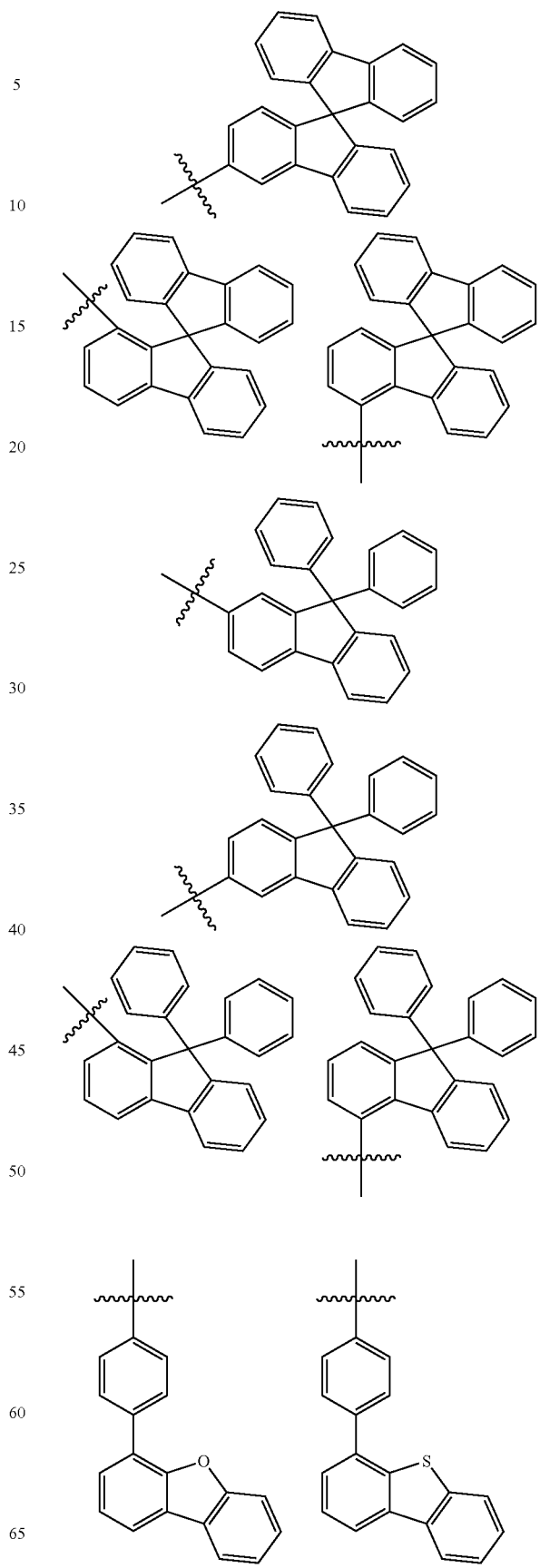

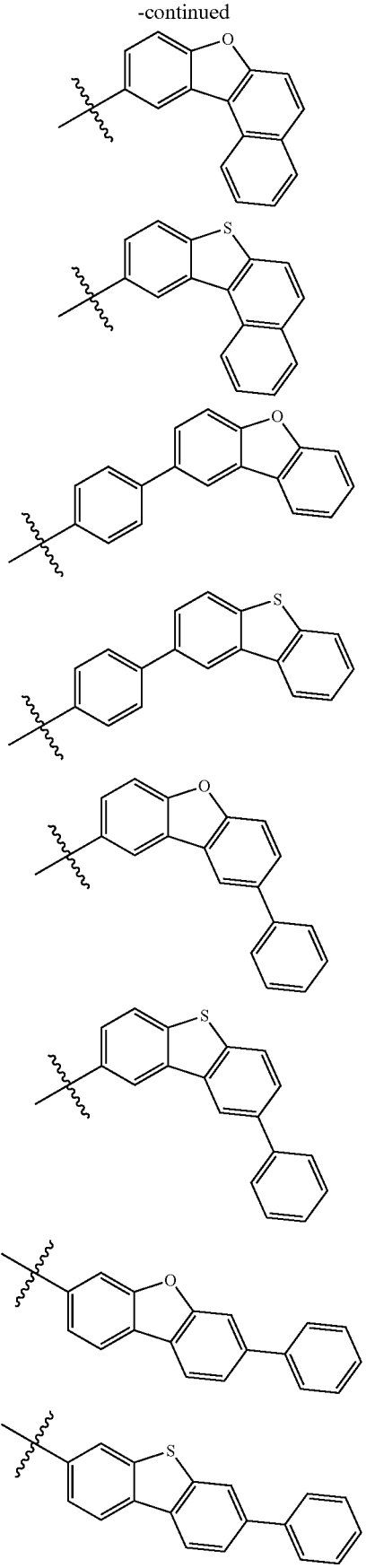

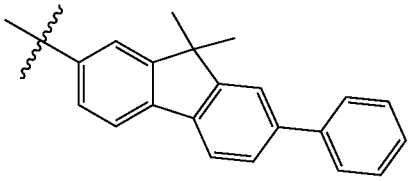
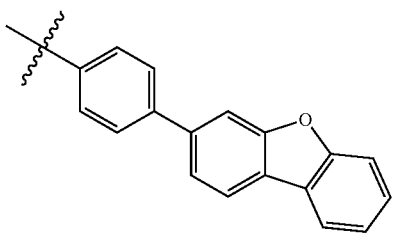
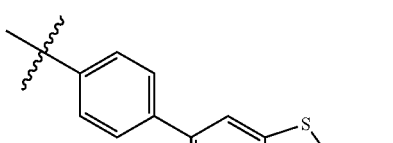
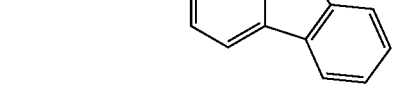
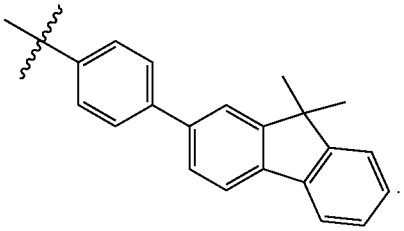

7. The compound of claim 1, wherein $R_1$ is hydrogen; deuterium; a halogen, cyano, a nitro, a methyl, or a phenyl, and a1 is 0 or 1.

8. The compound of claim 1, wherein the compound is represented by the following Chemical Formula 1A or 1B:

[Chemical Formula 1A]

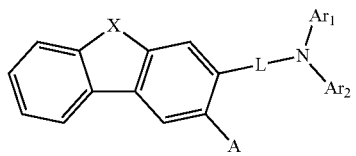

[Chemical Formula 1B]

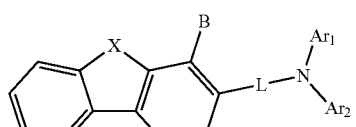

wherein, in Chemical Formula 1A and 1B, X, A, B, L, $A_1$, and $Ar_2$ are the same as defined in claim 1.

9. The compound of claim 1, wherein the compound is any one selected from the group consisting of the following:

251
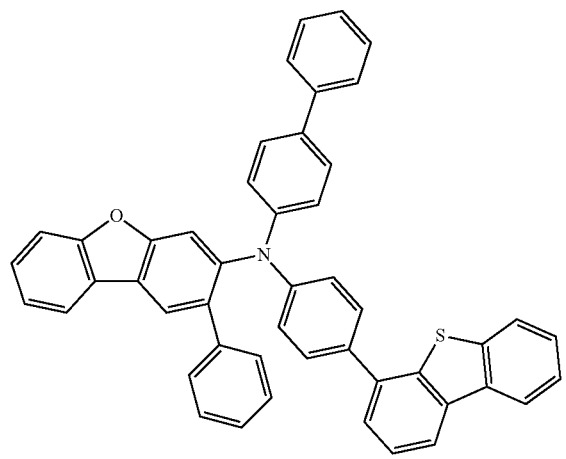
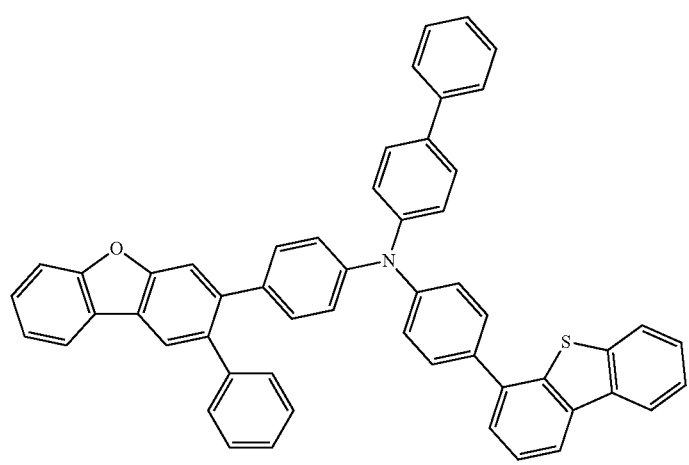
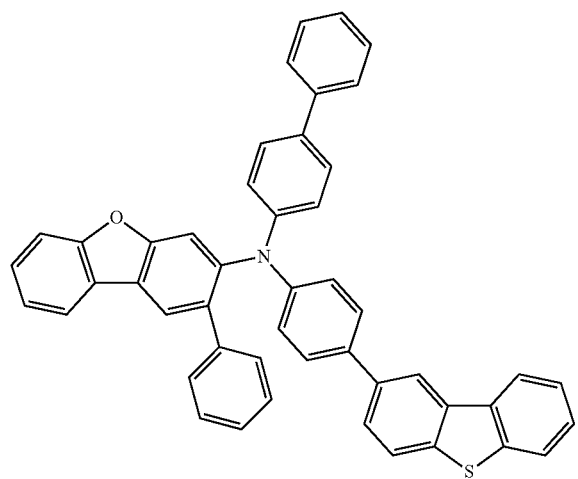
252

-continued
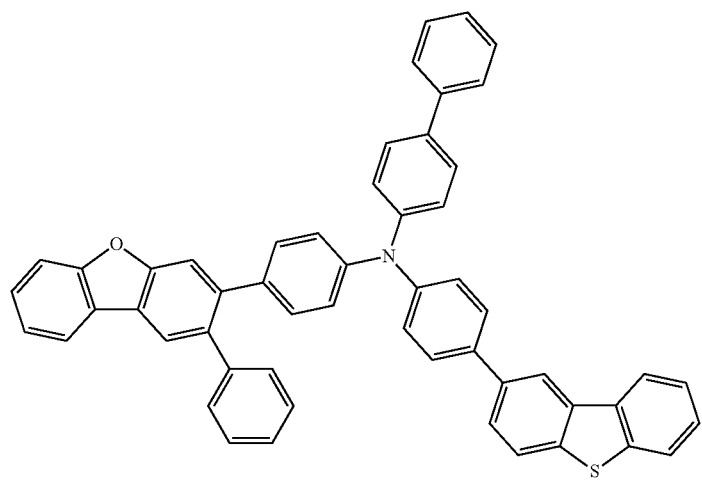
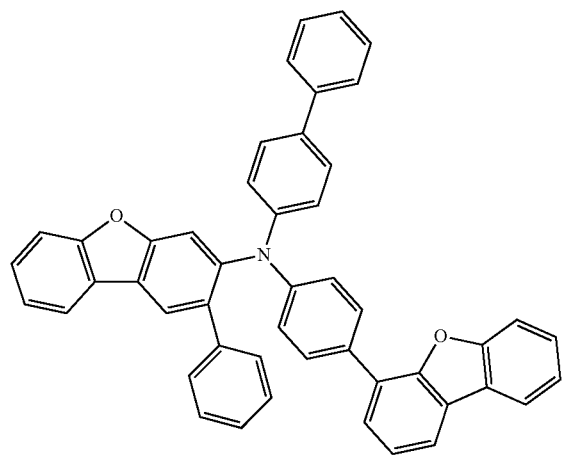
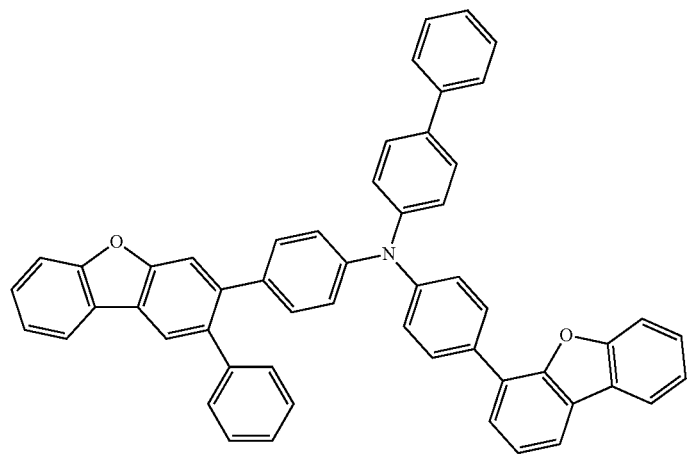

255 256
-continued
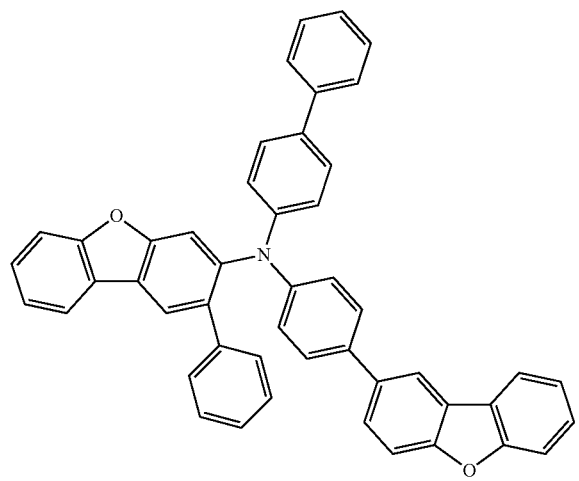
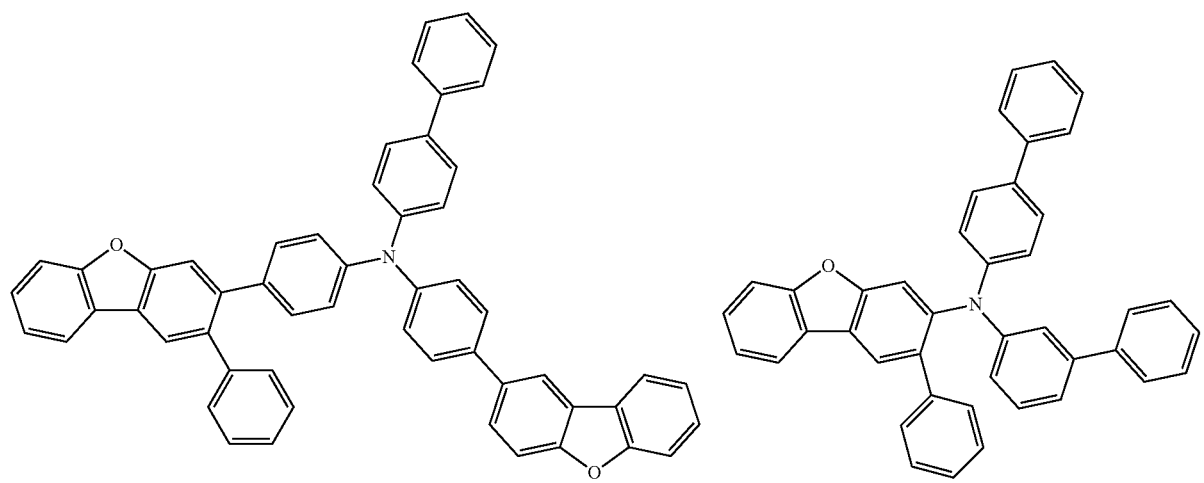
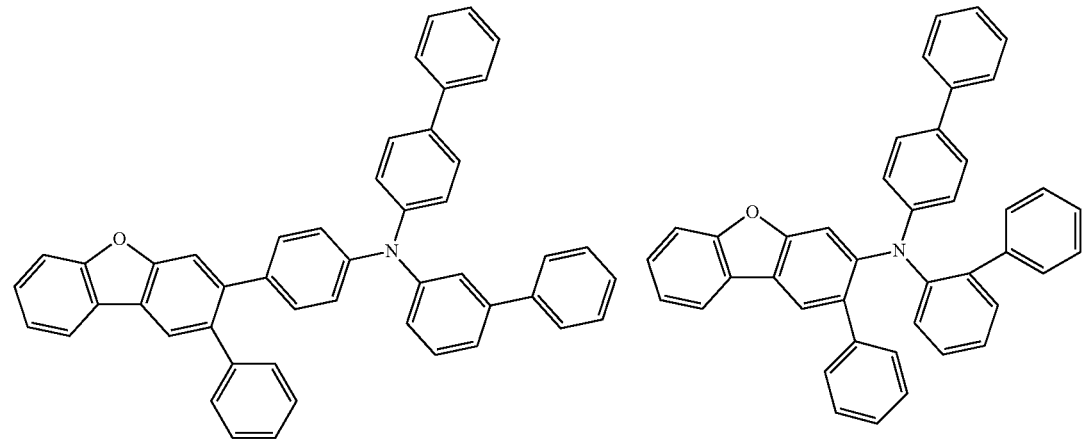

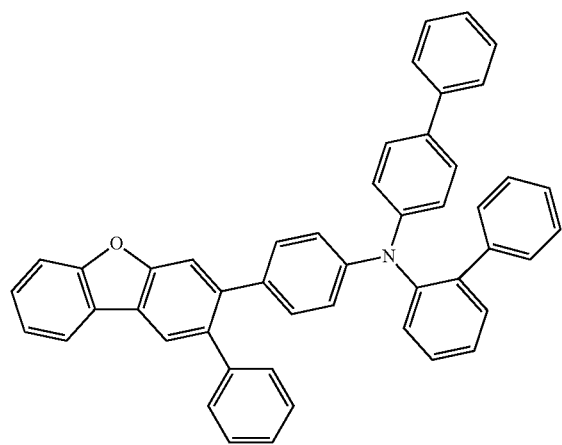
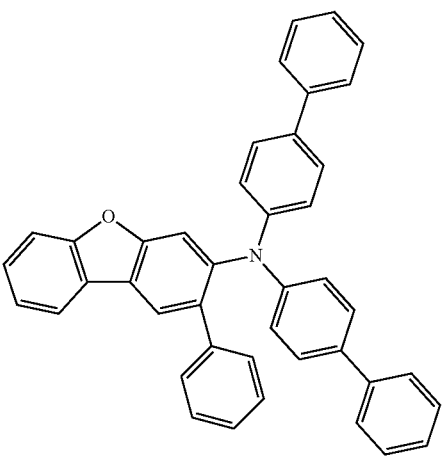
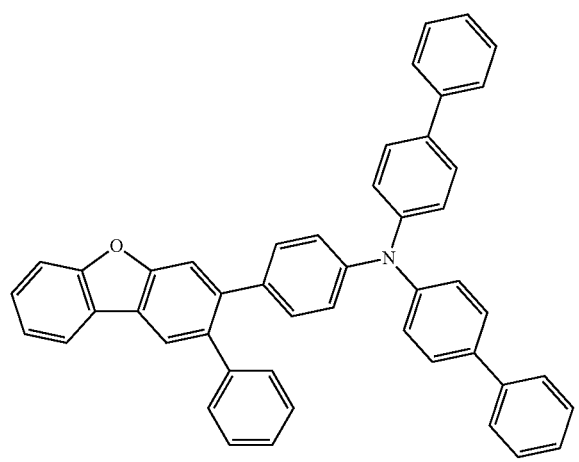
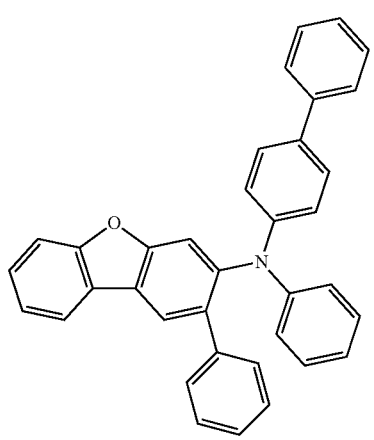
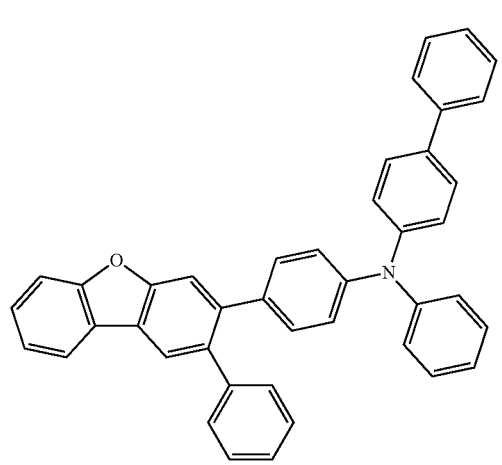
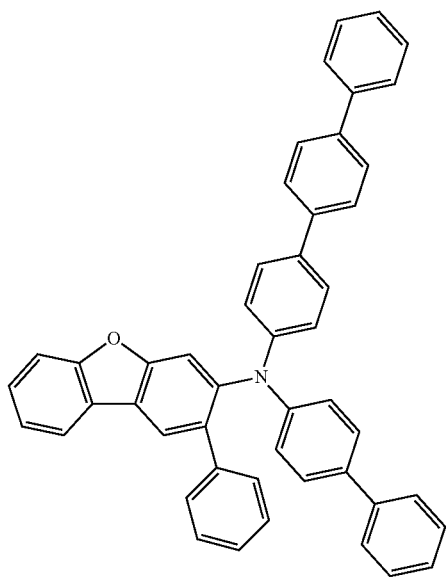

259
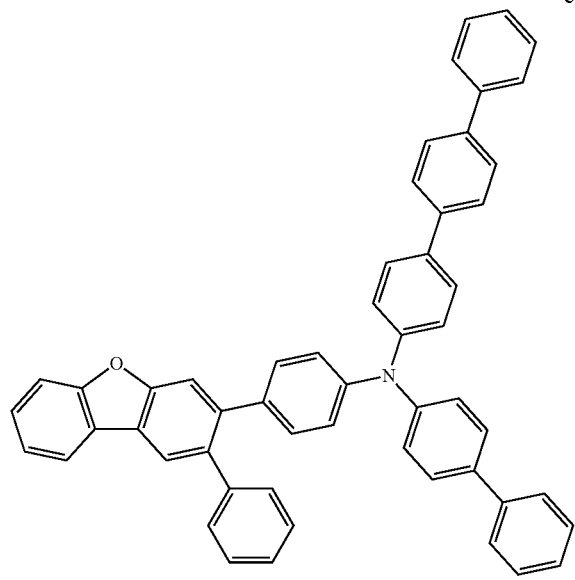
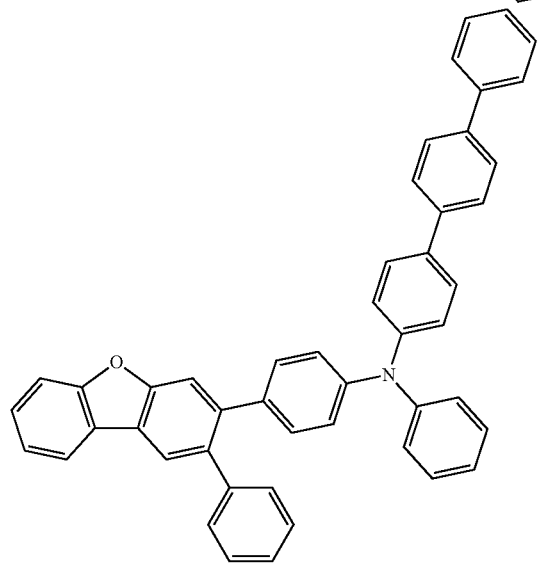
260
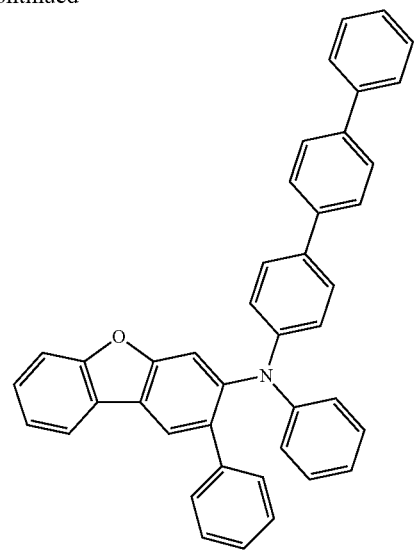
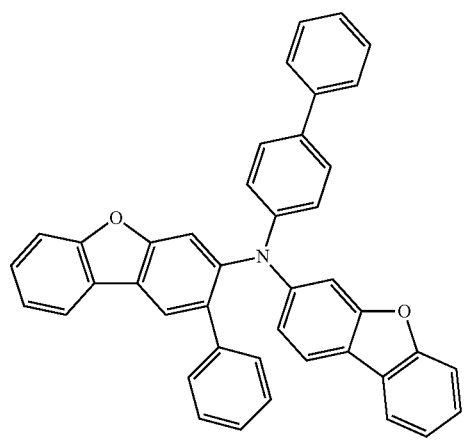
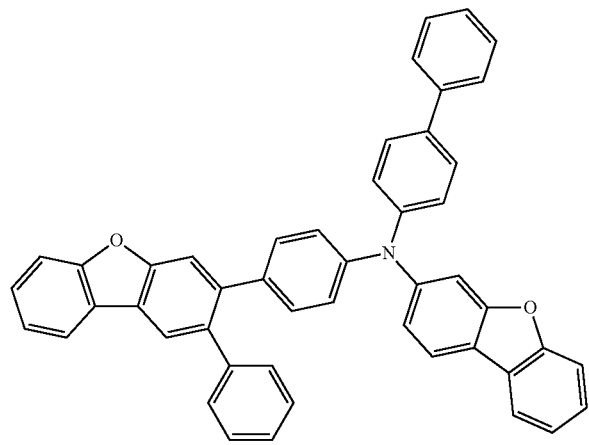
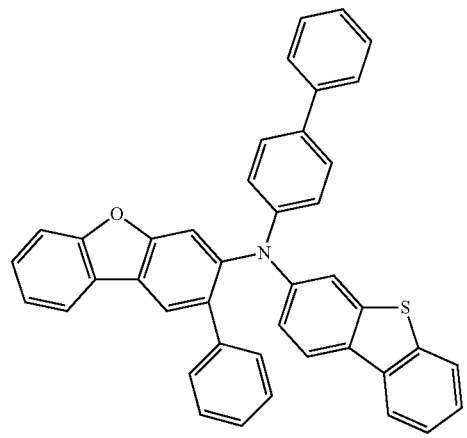

-continued
261
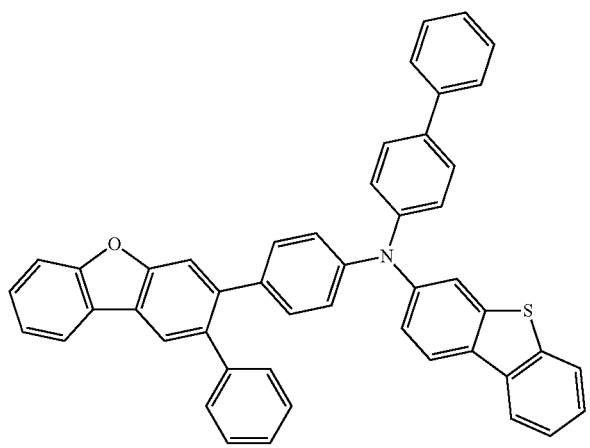
262
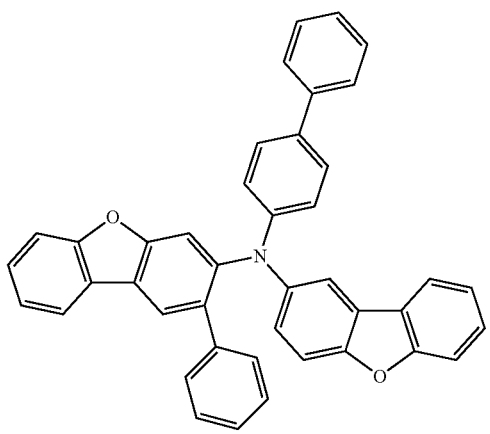
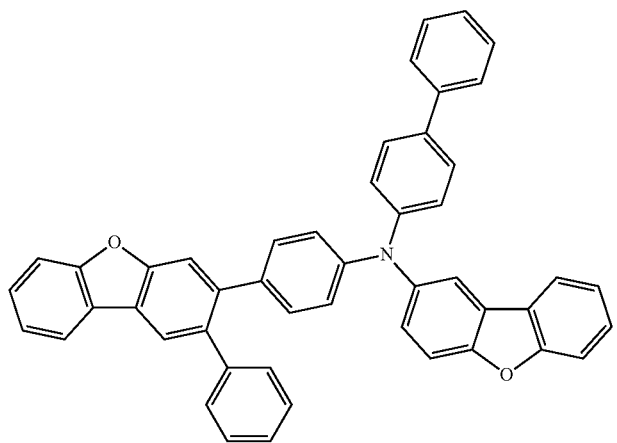
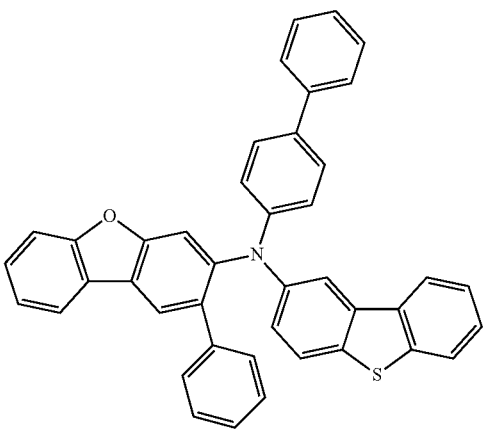
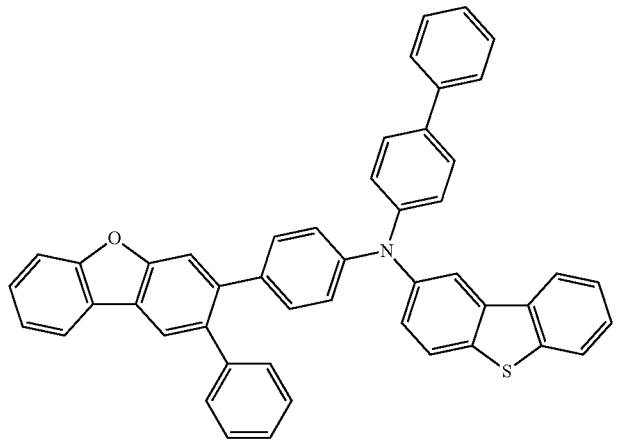
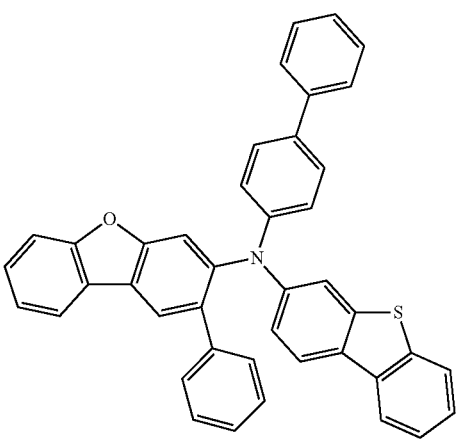

263
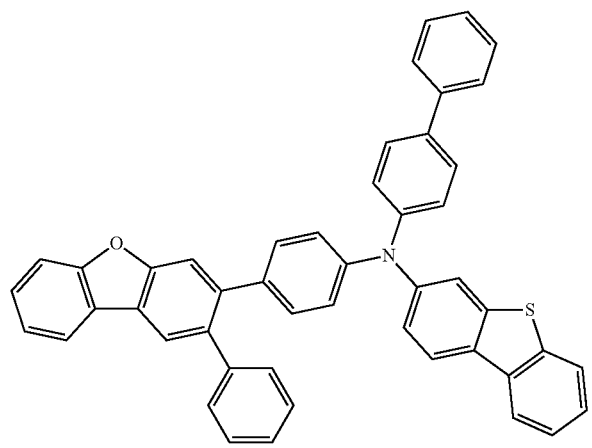
264
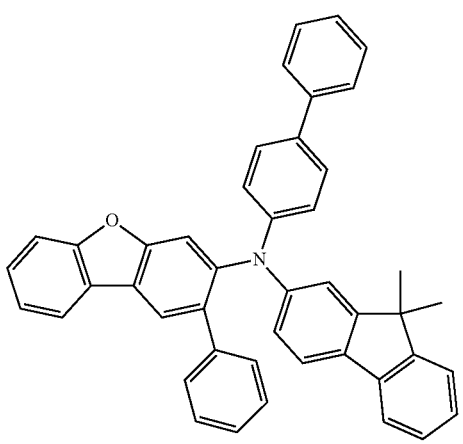
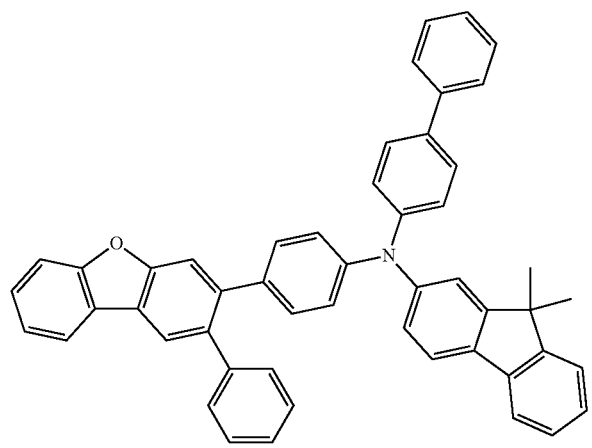
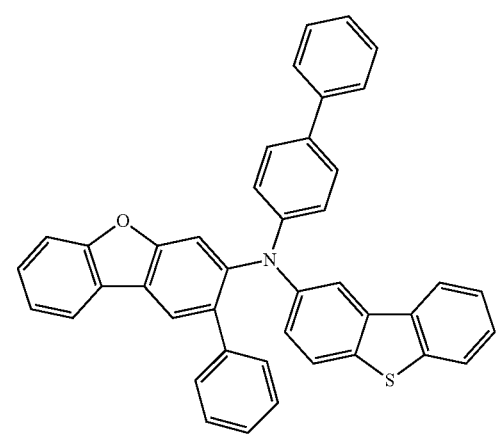
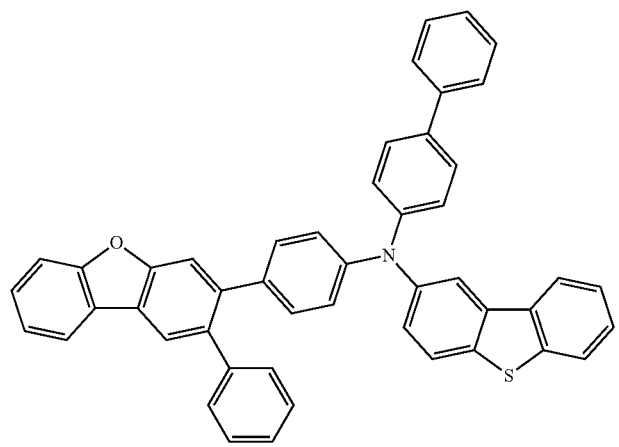
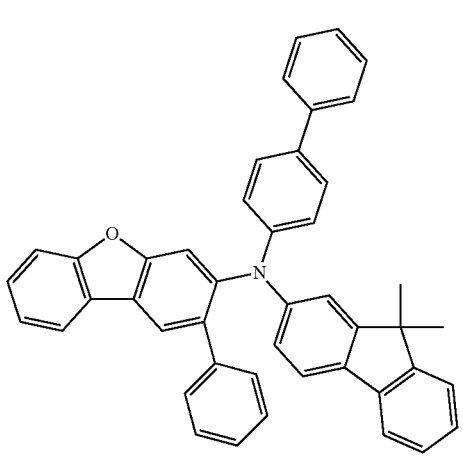

-continued
265
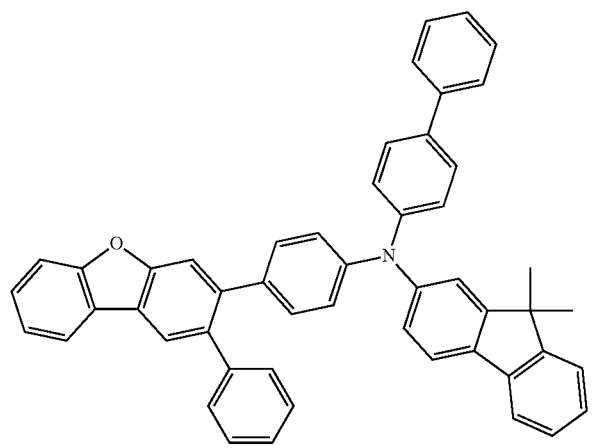
266
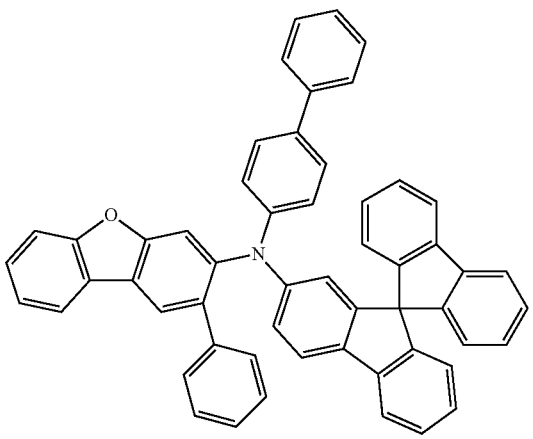
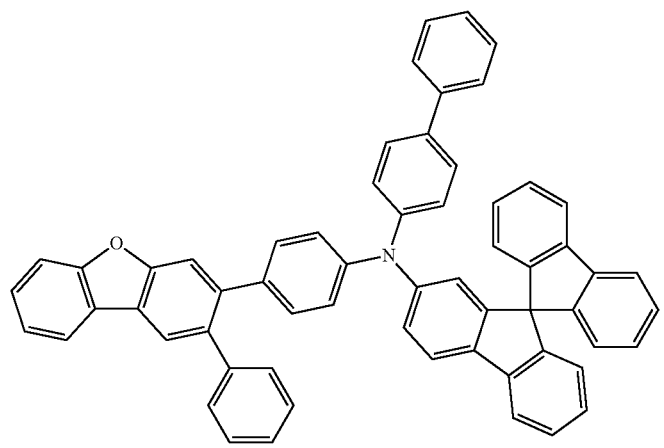
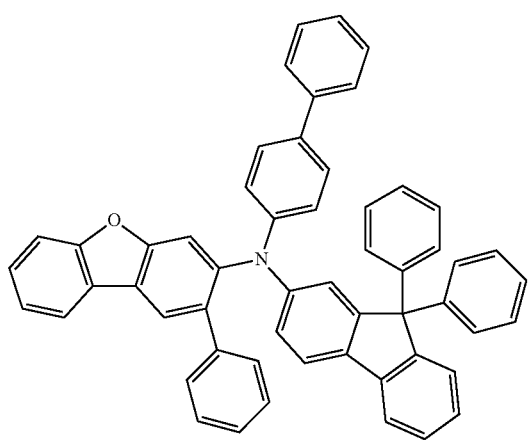
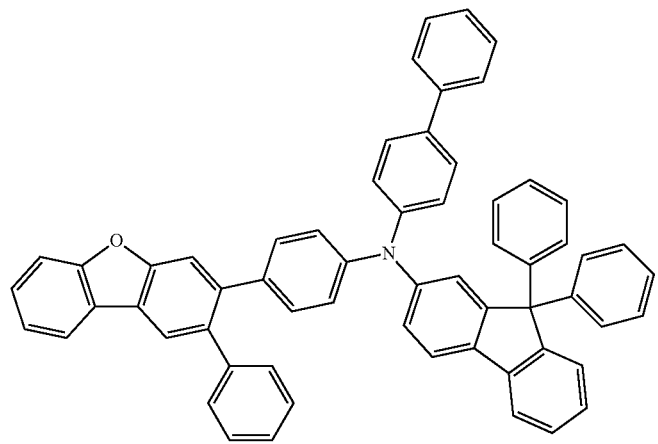
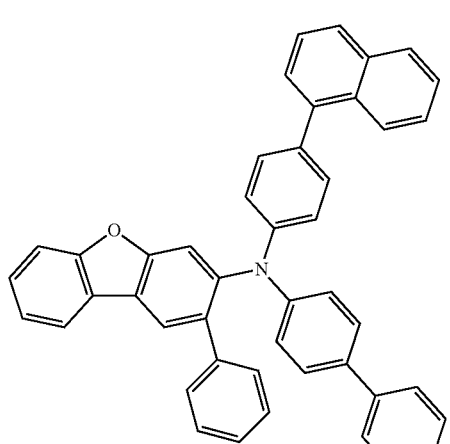

267 268
-continued
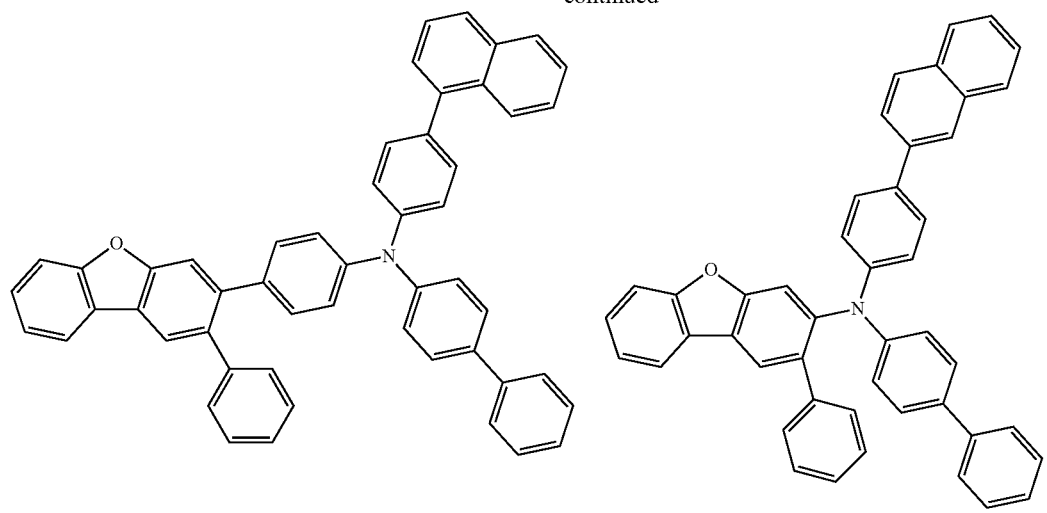
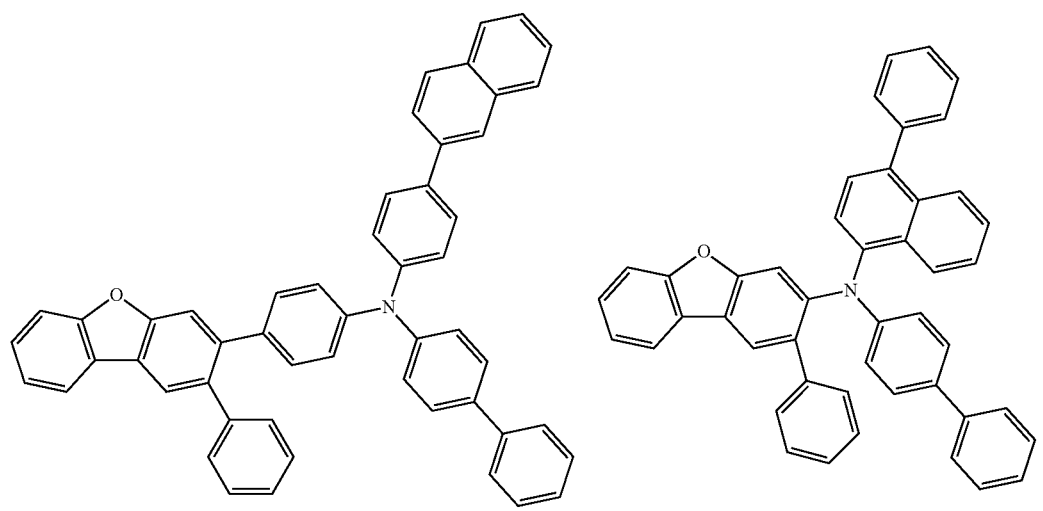
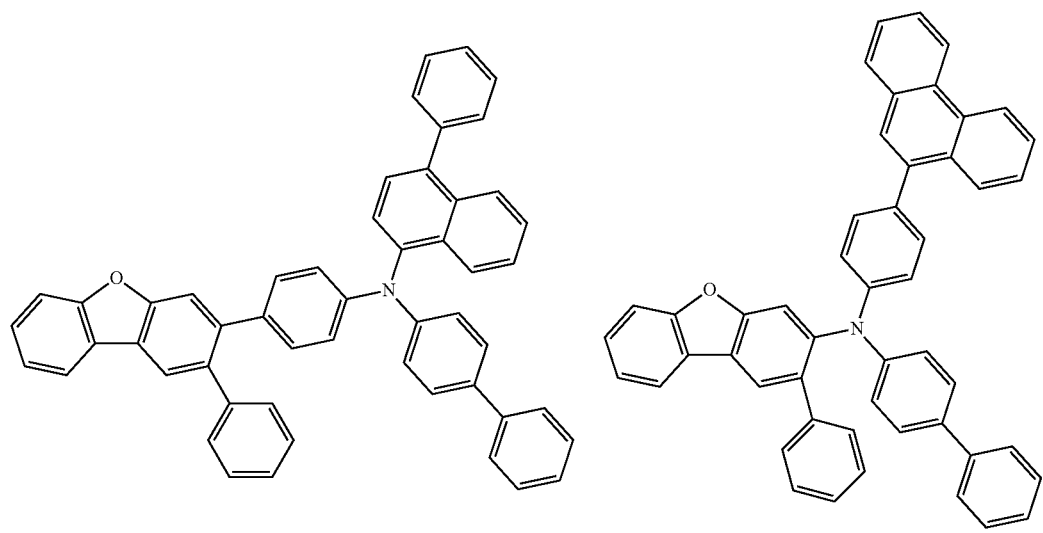

269
270
-continued
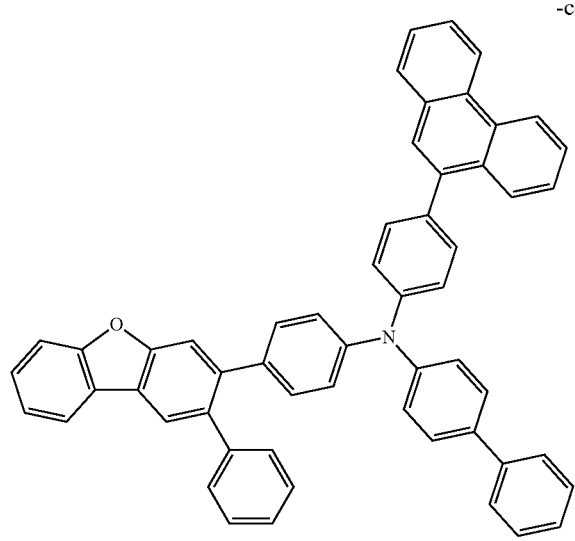
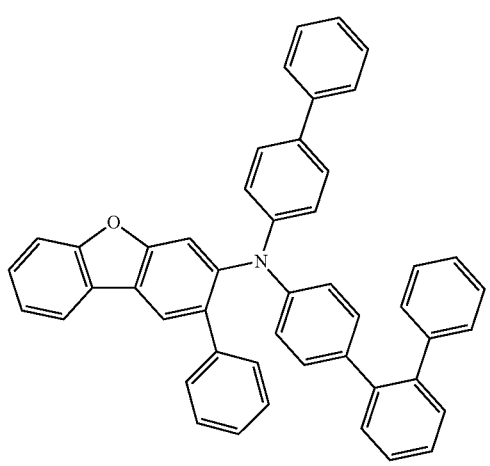
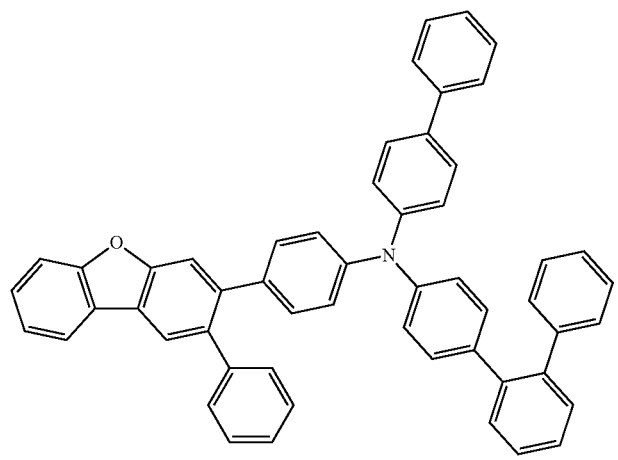
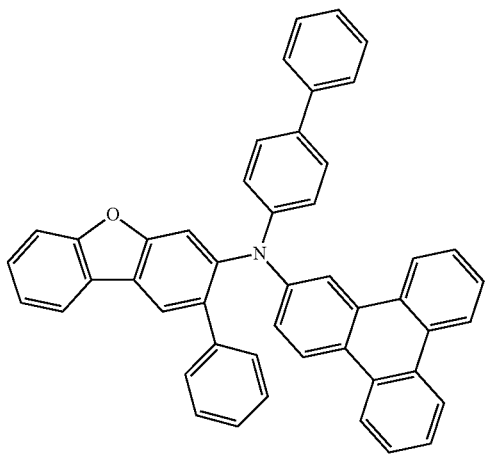
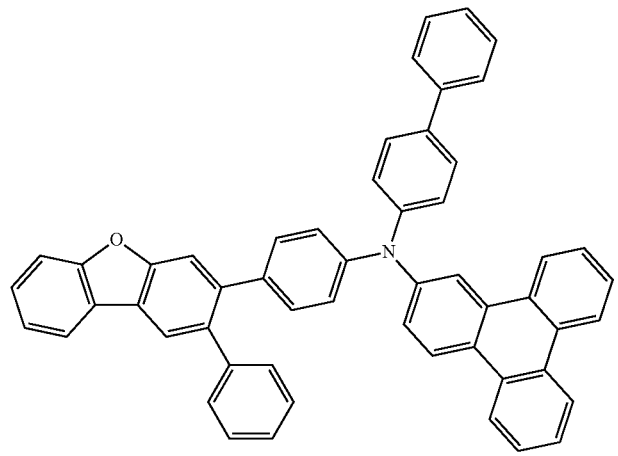
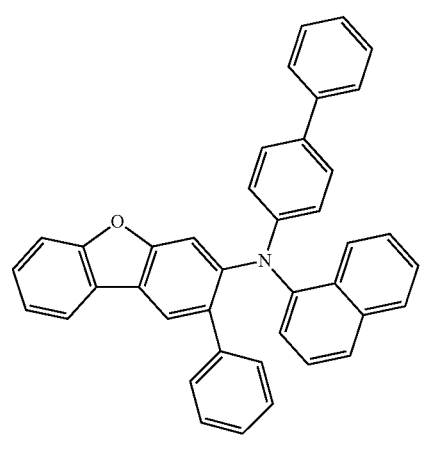

271 272
-continued
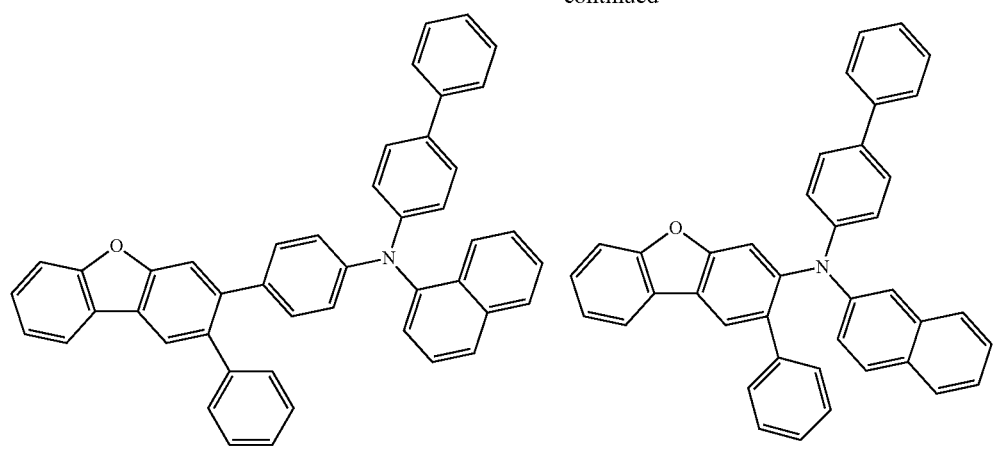
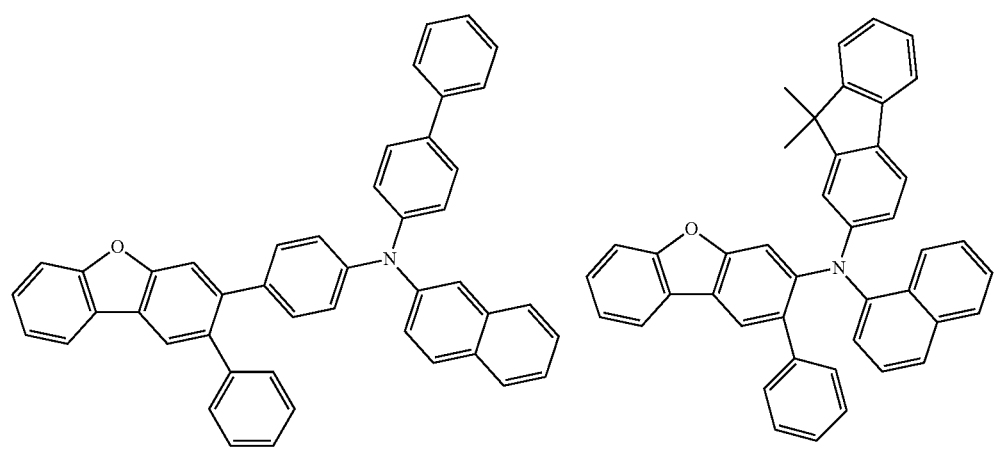
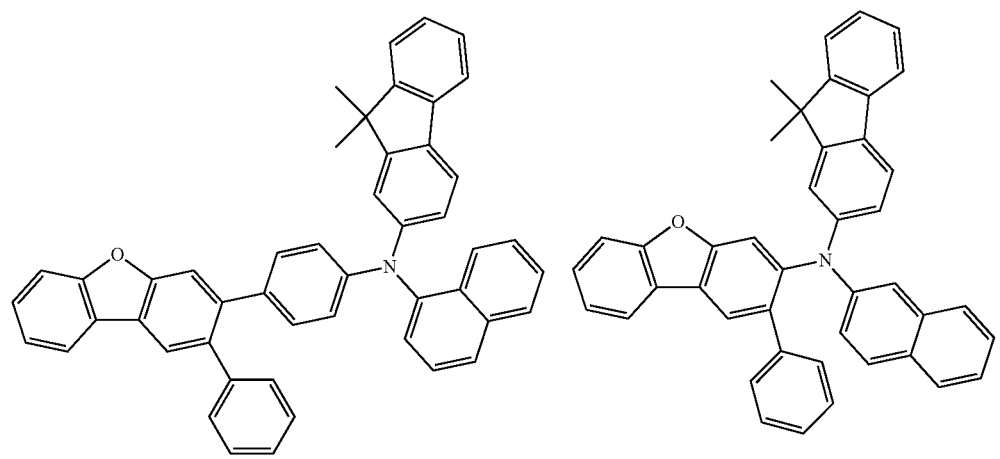

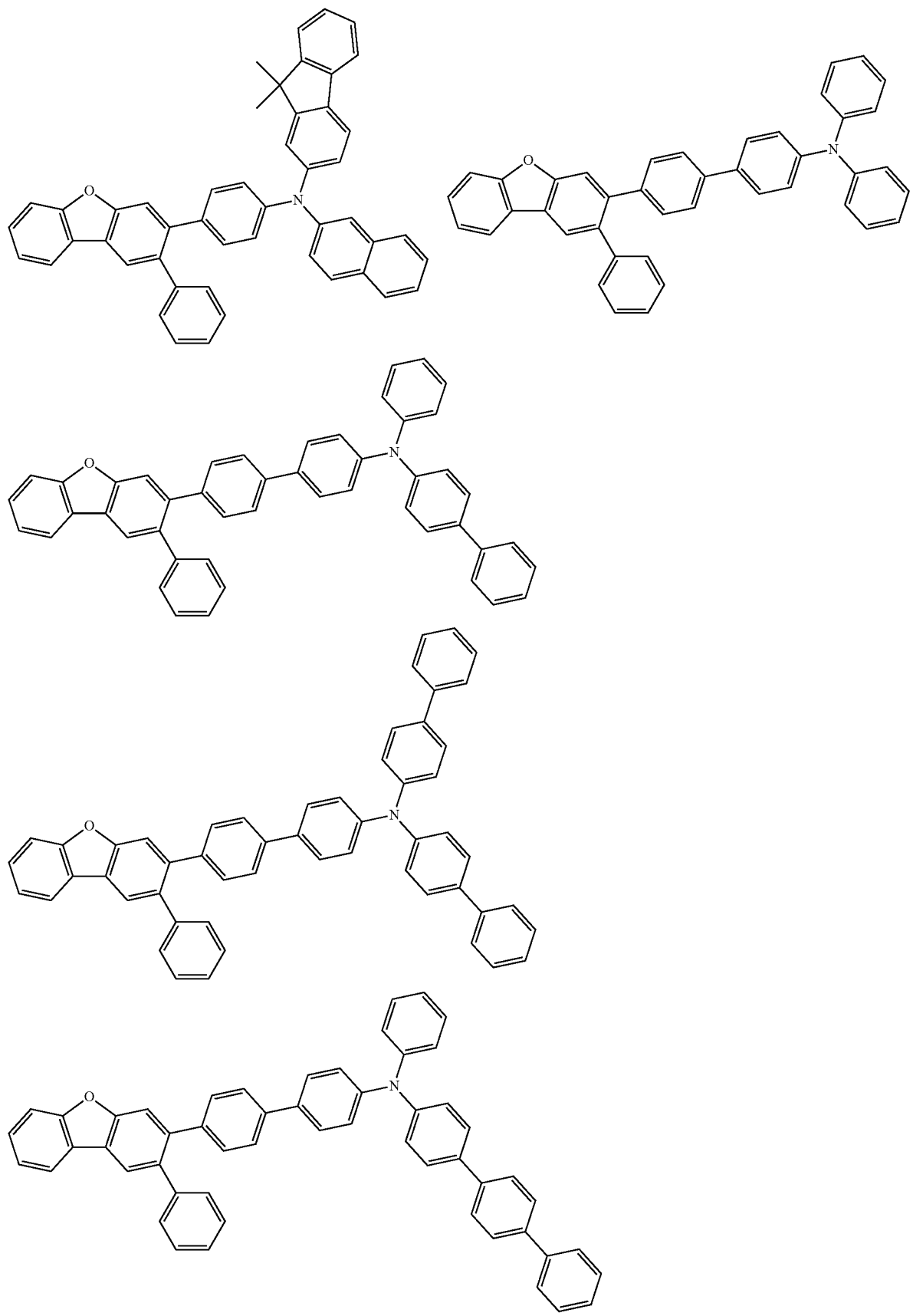

-continued
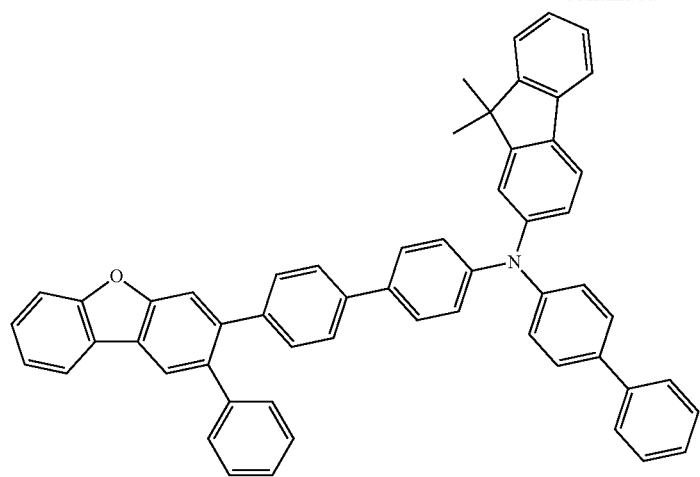
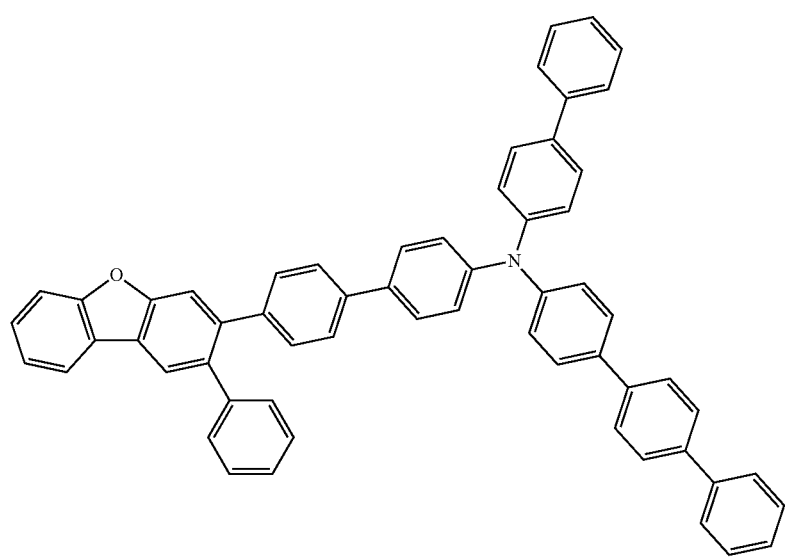
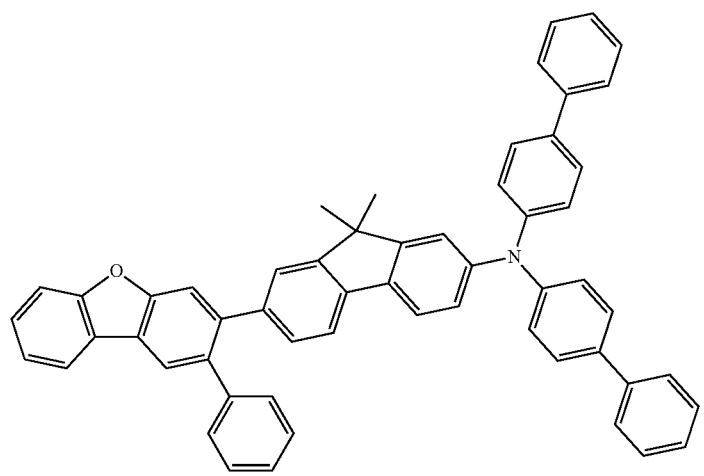

-continued
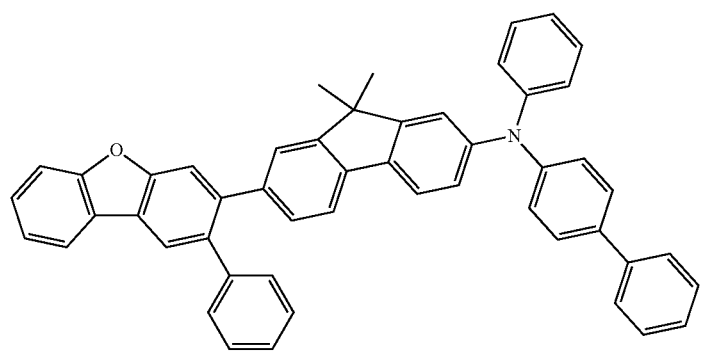
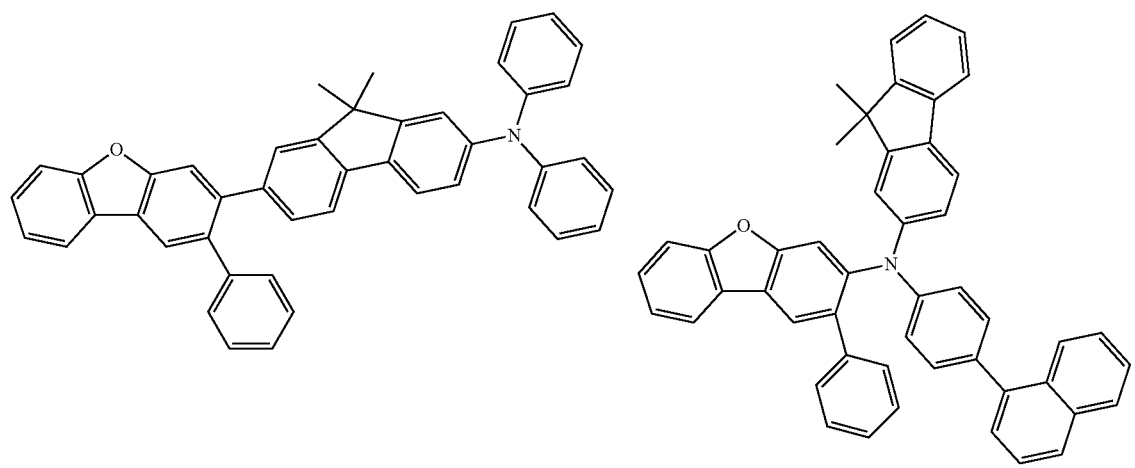
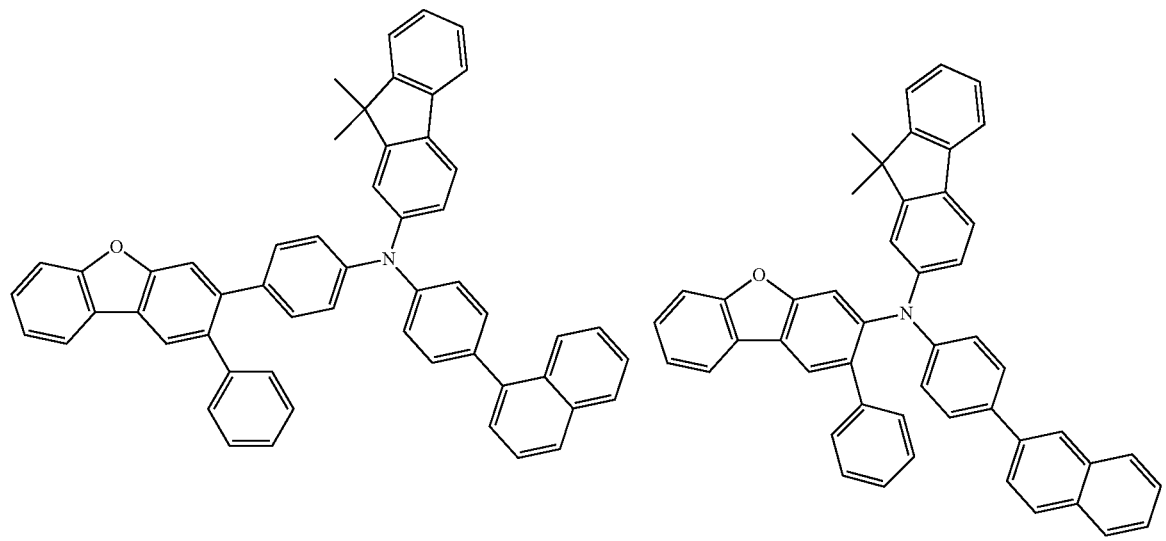

279 280
-continued
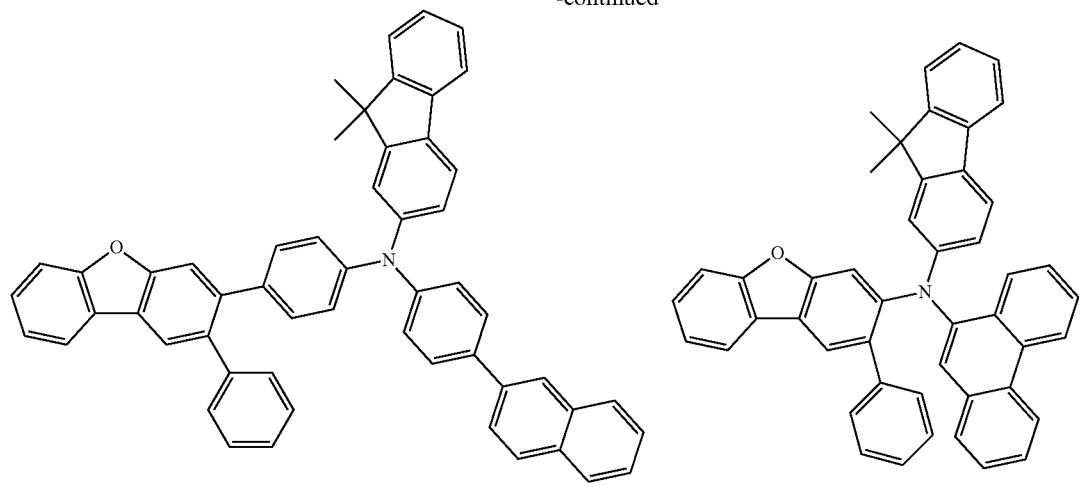
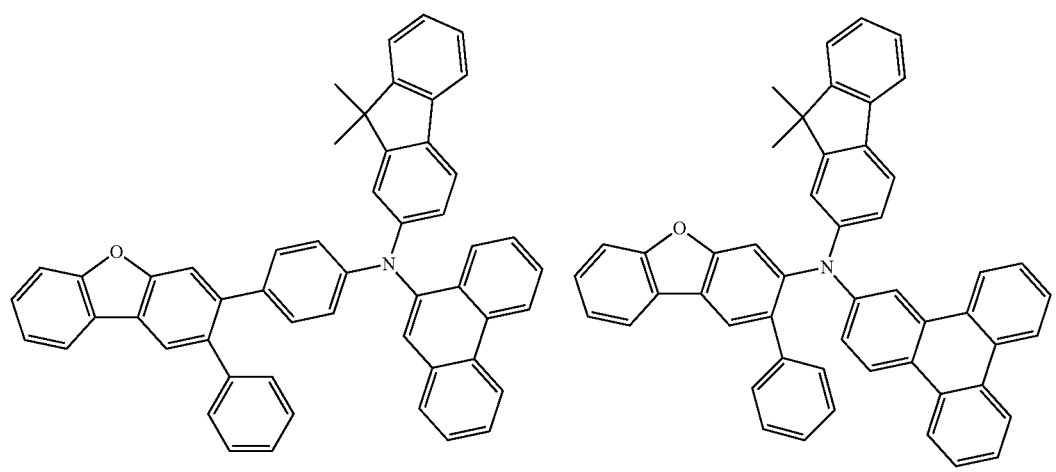
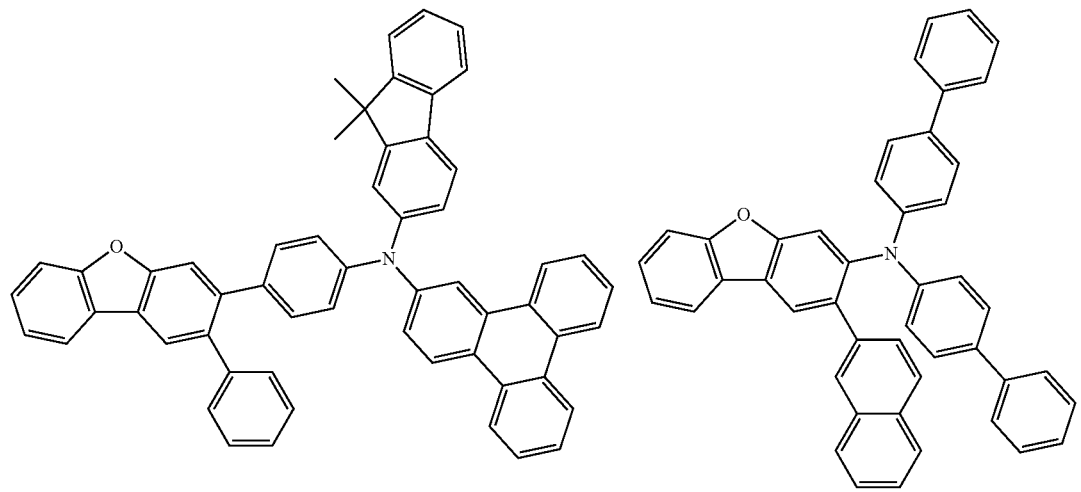

-continued
281
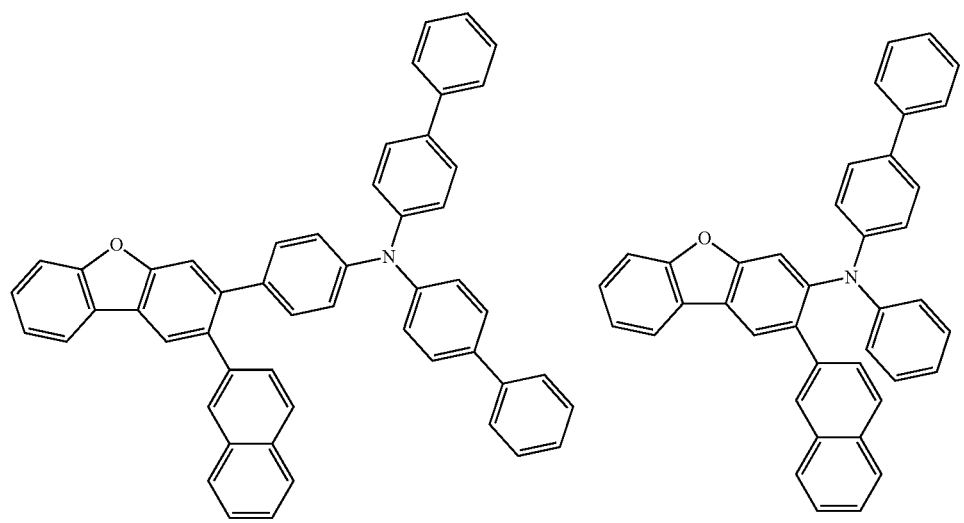
282
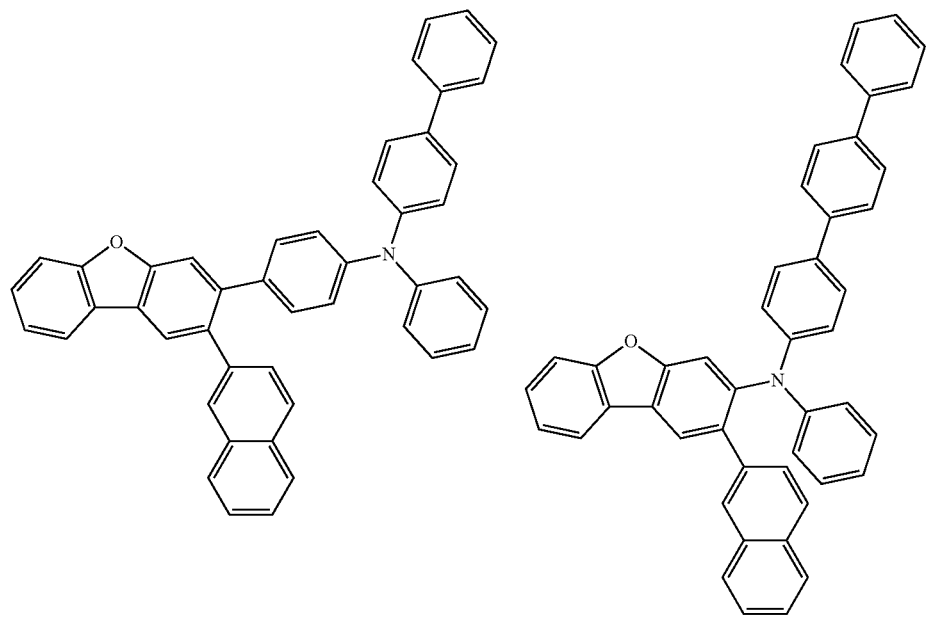

-continued
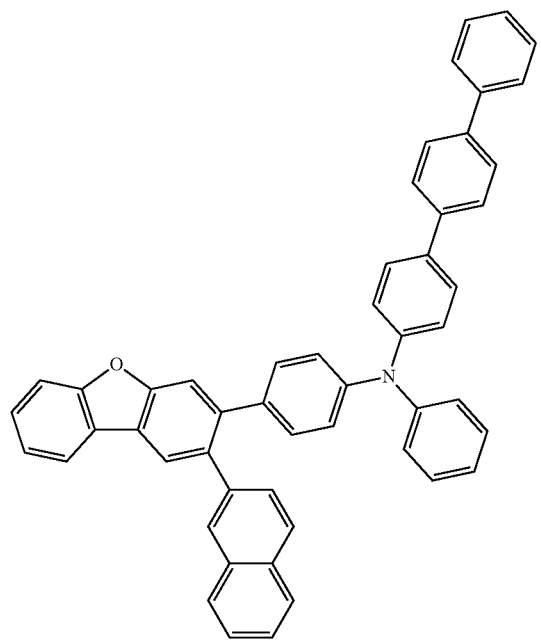
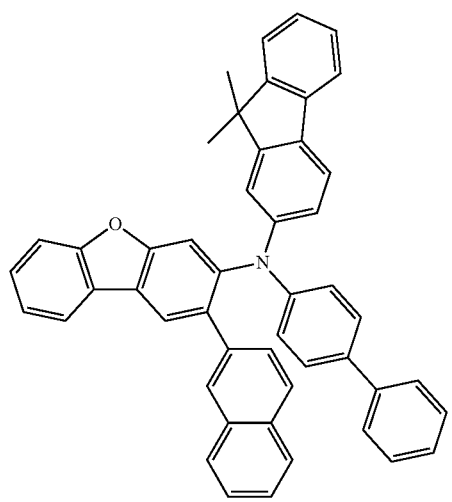
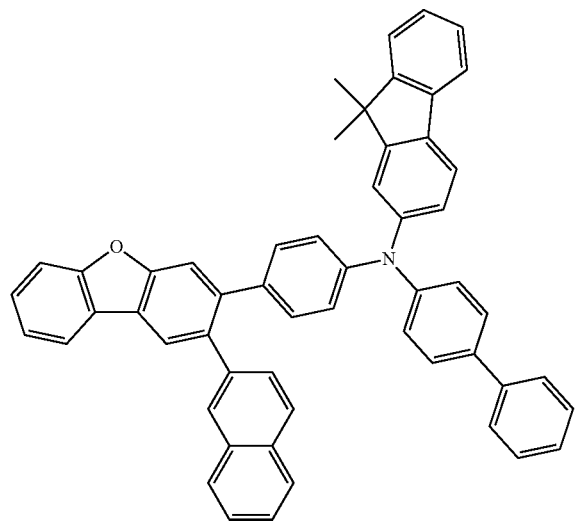
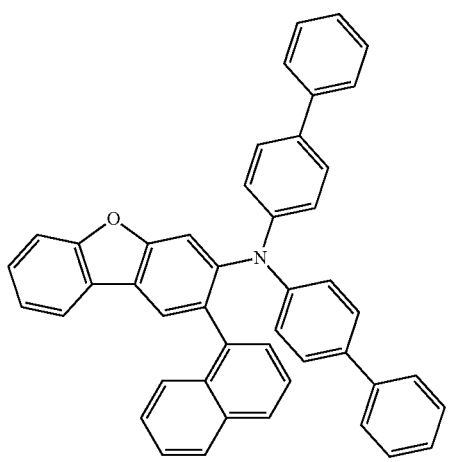
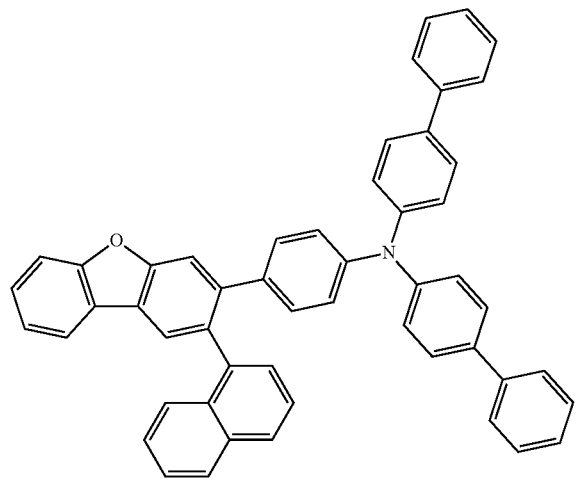
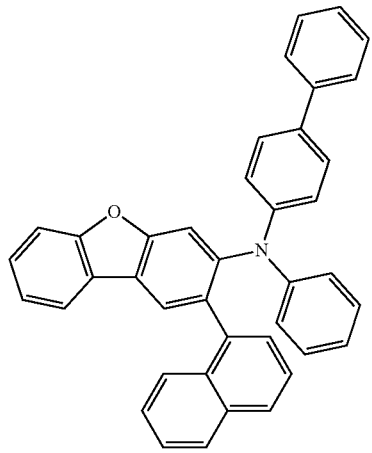

285 286
-continued
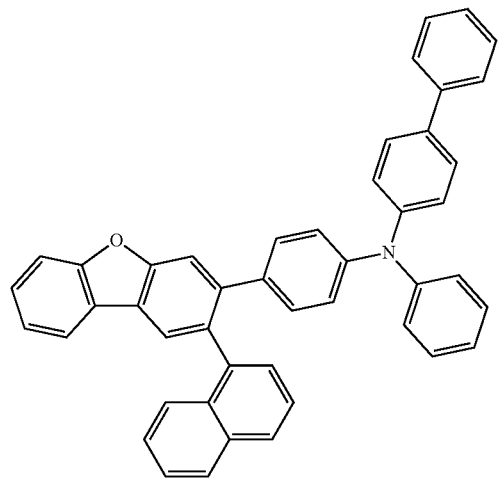
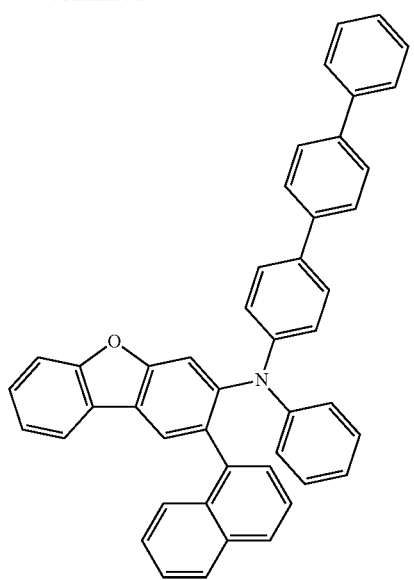
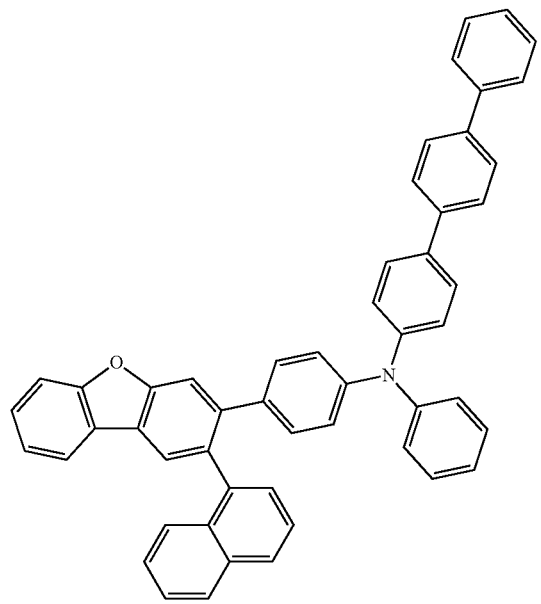
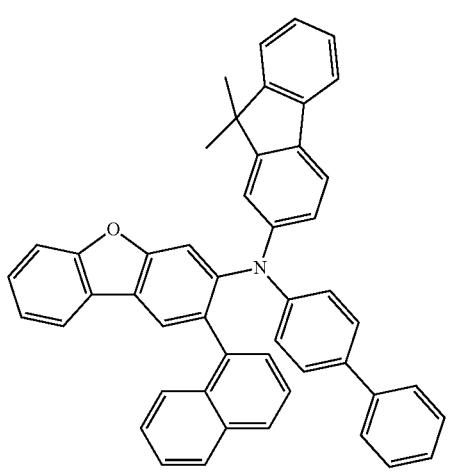
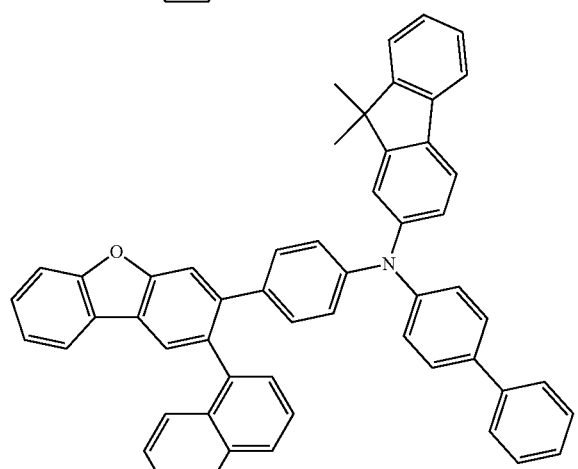
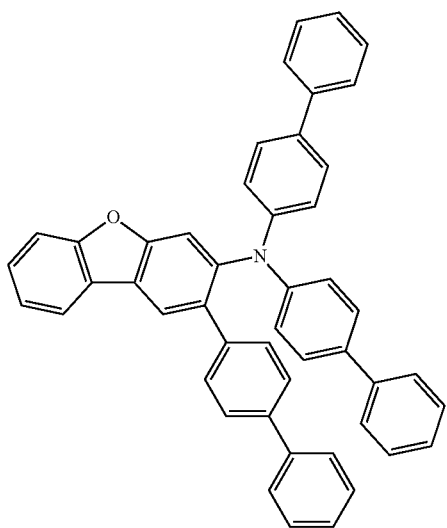

287 288
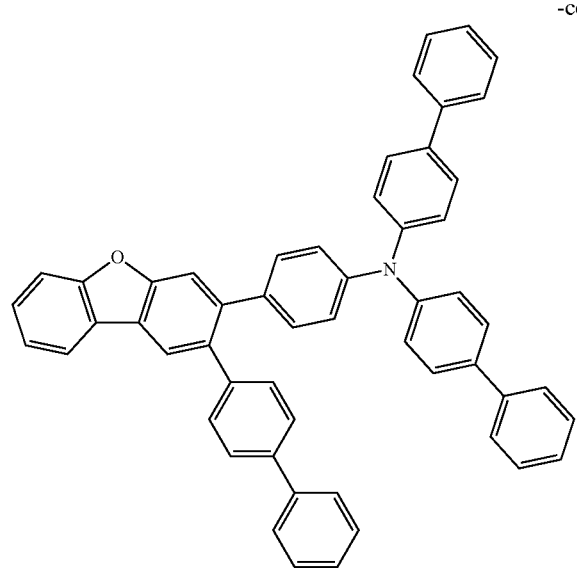
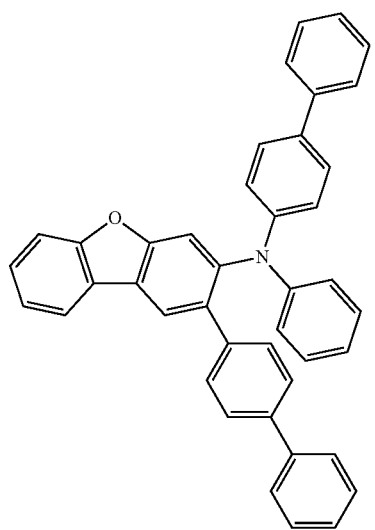
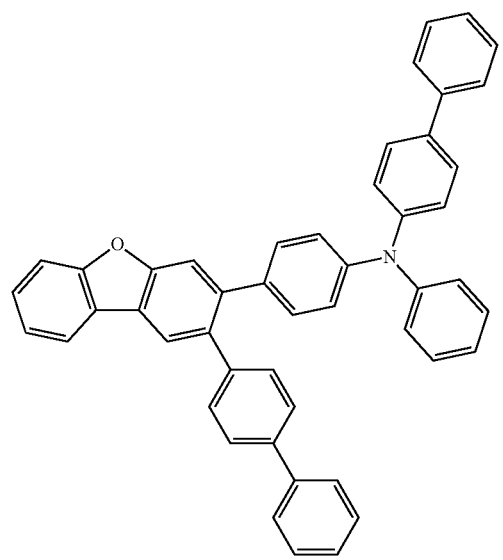
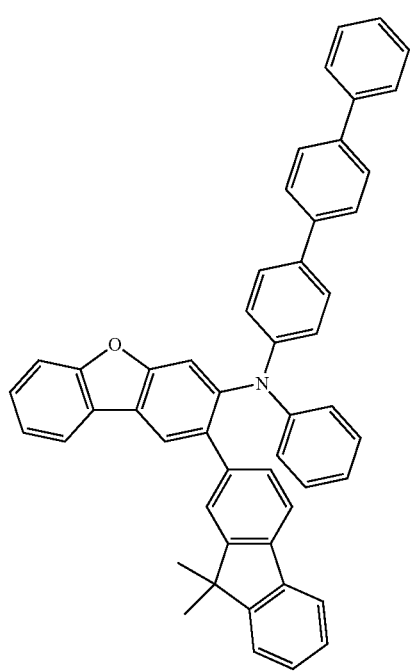

289 290
-continued
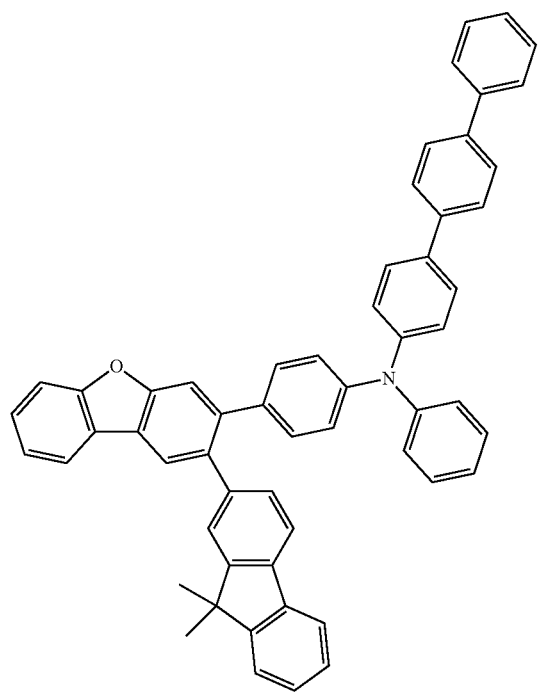
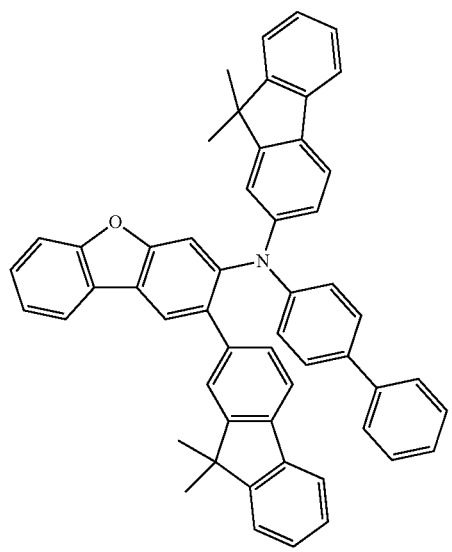
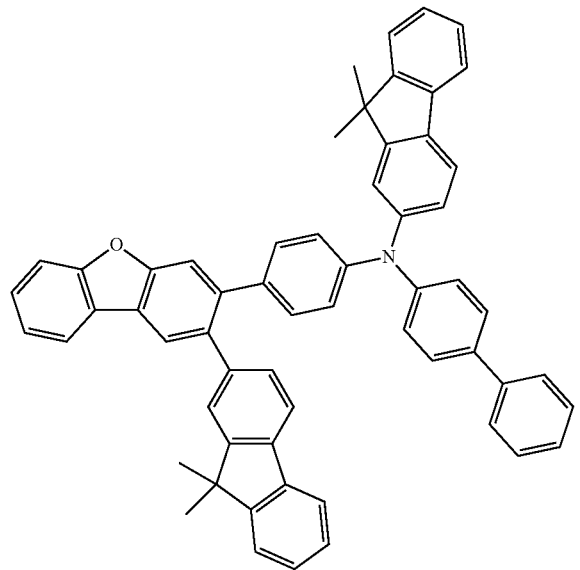
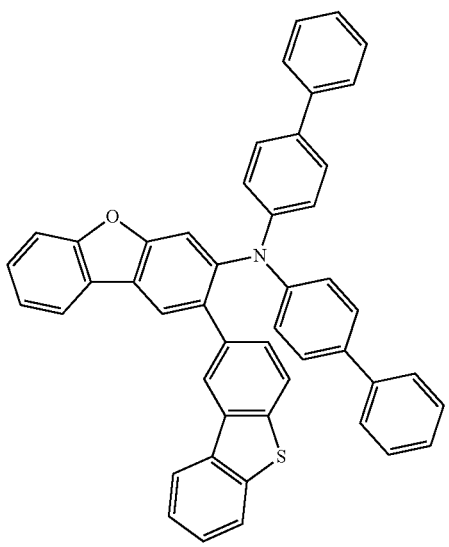

291
292
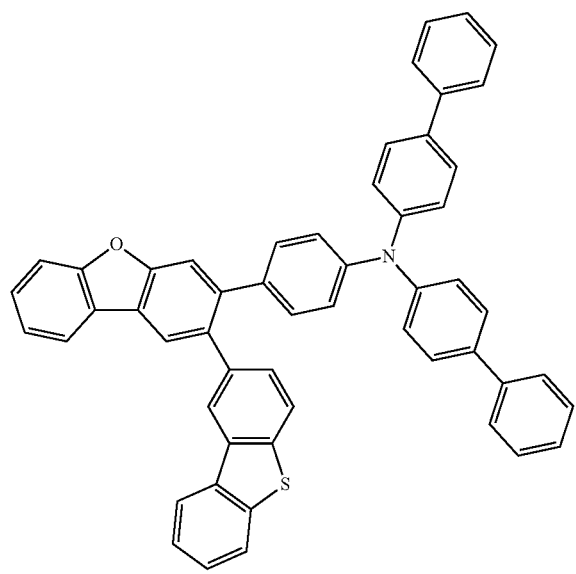
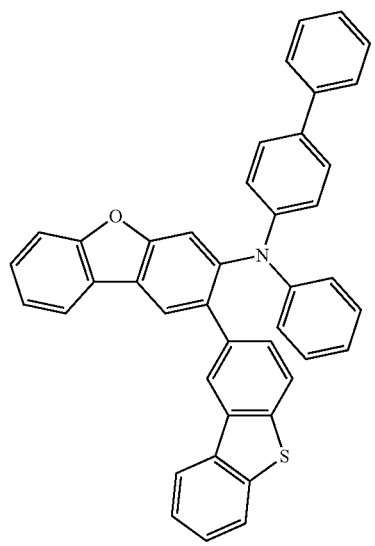
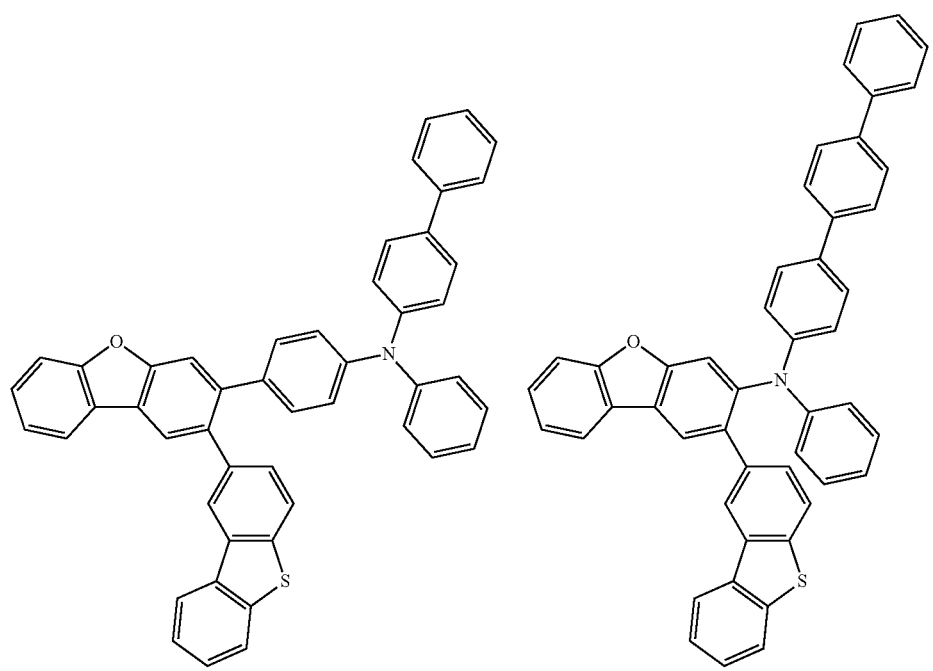

-continued
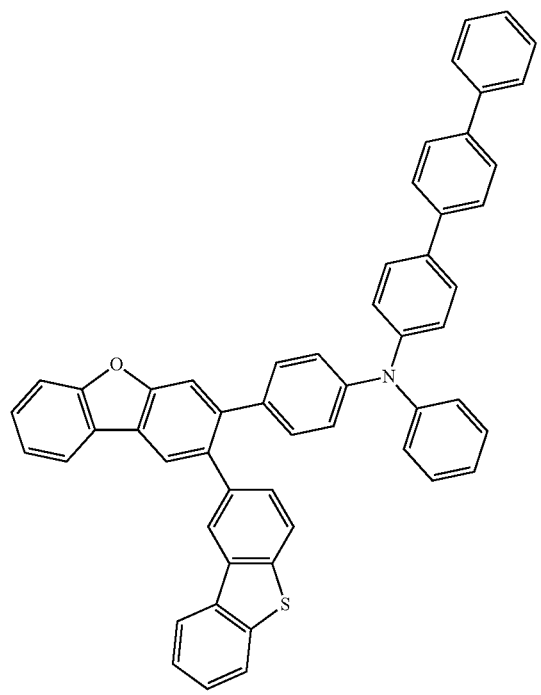
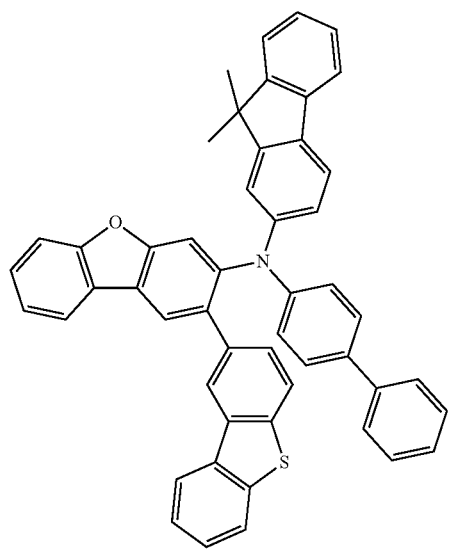
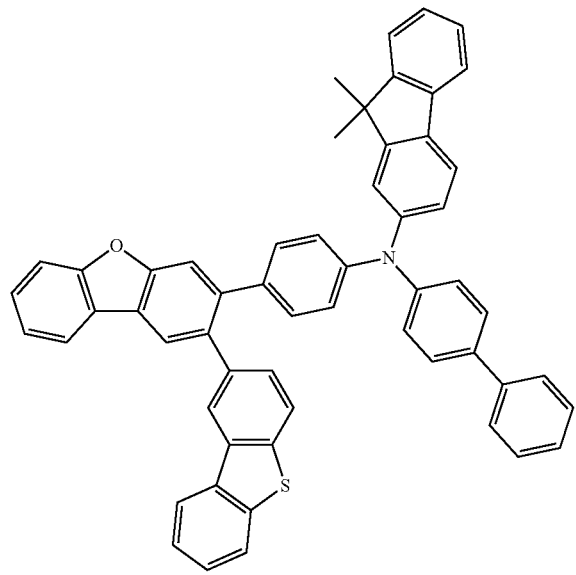
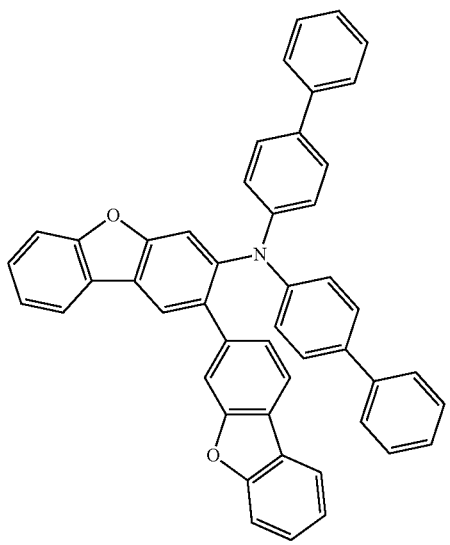

295 296
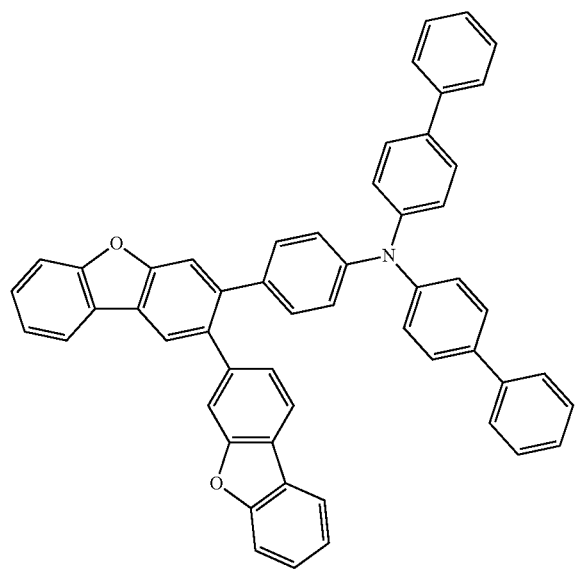 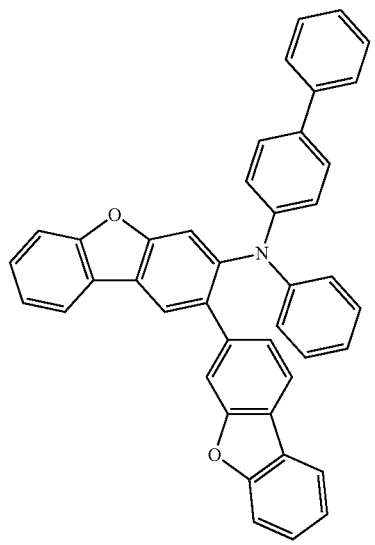
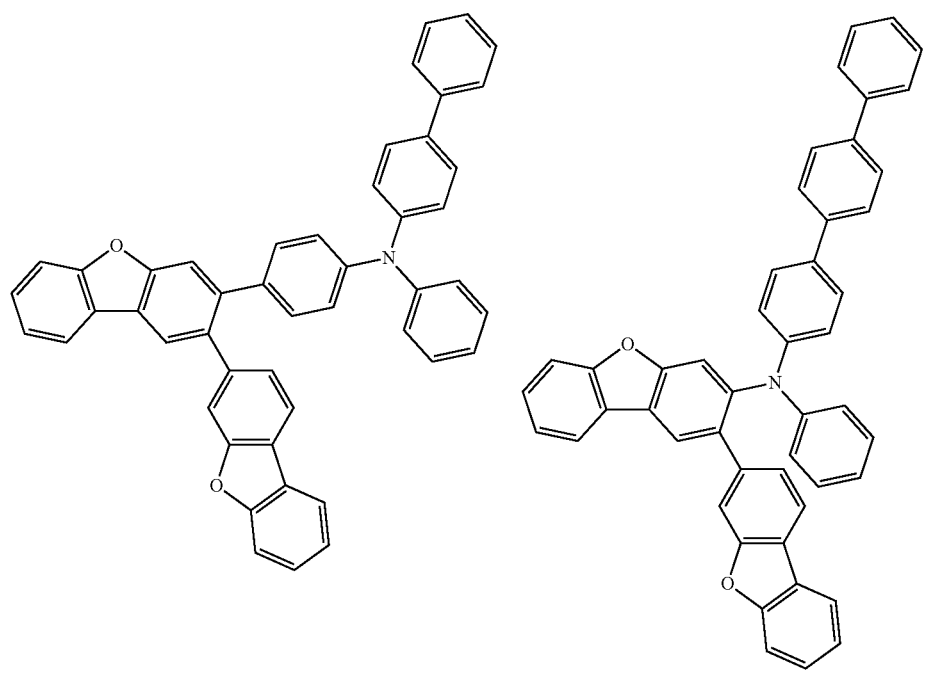

297 298
-continued
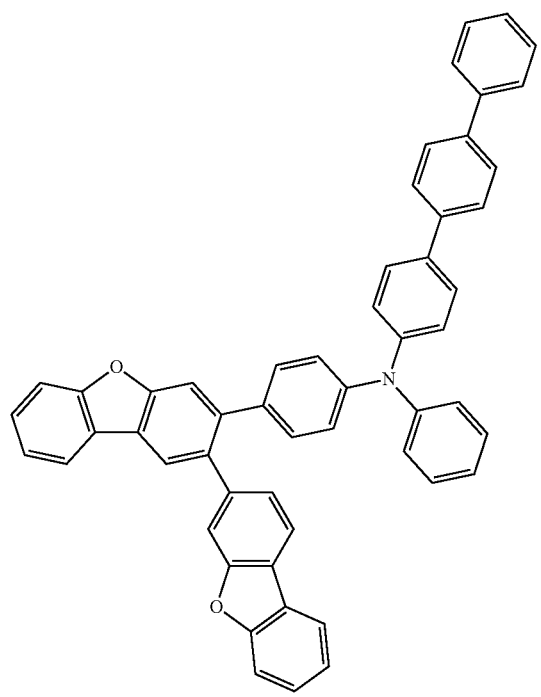
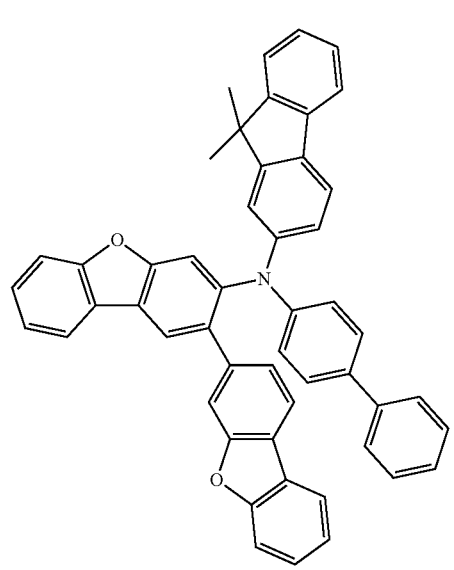
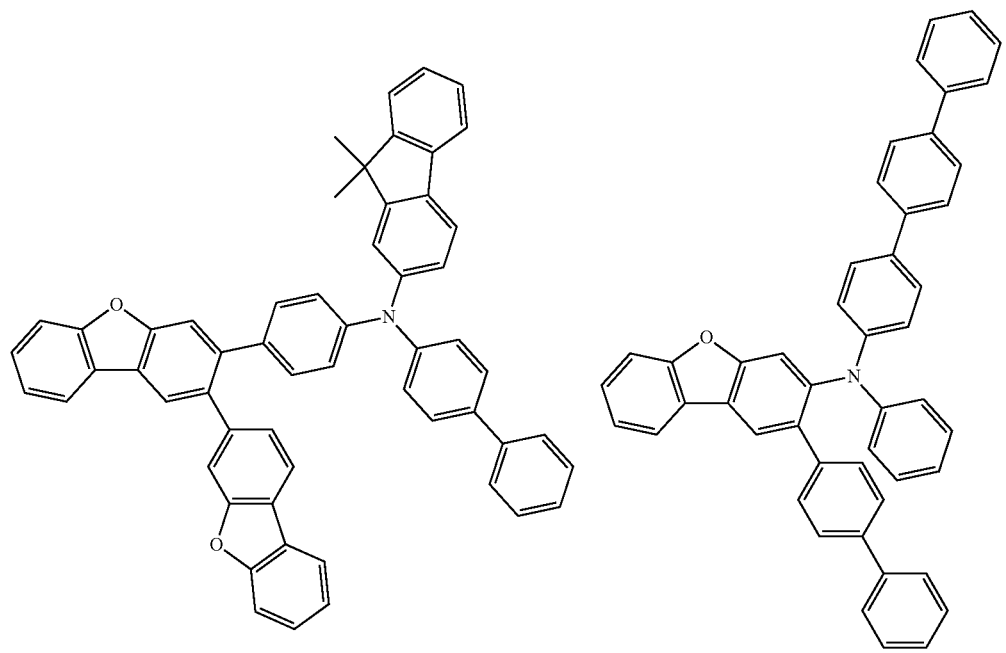

-continued
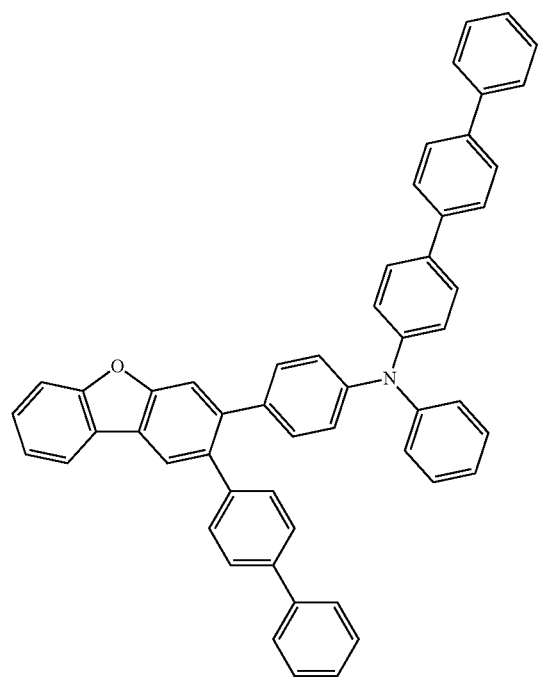
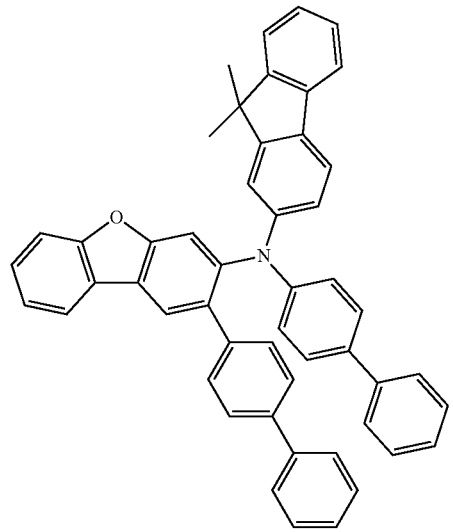
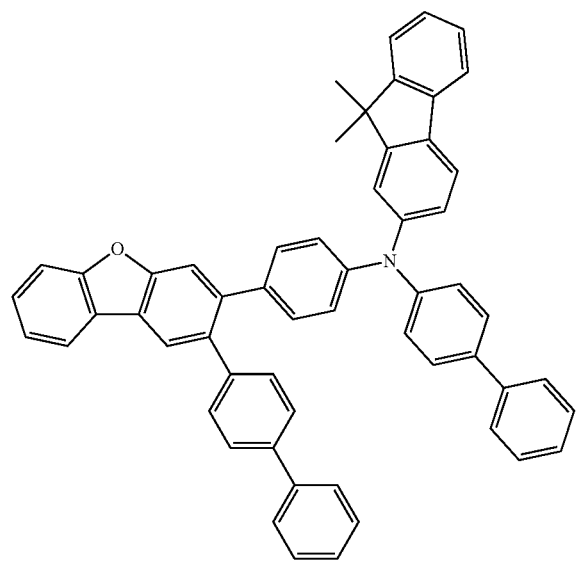
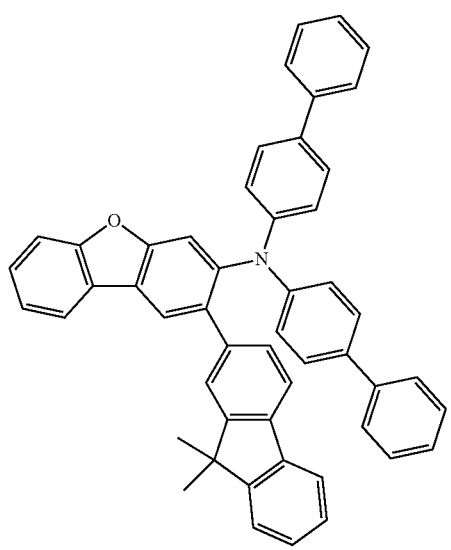

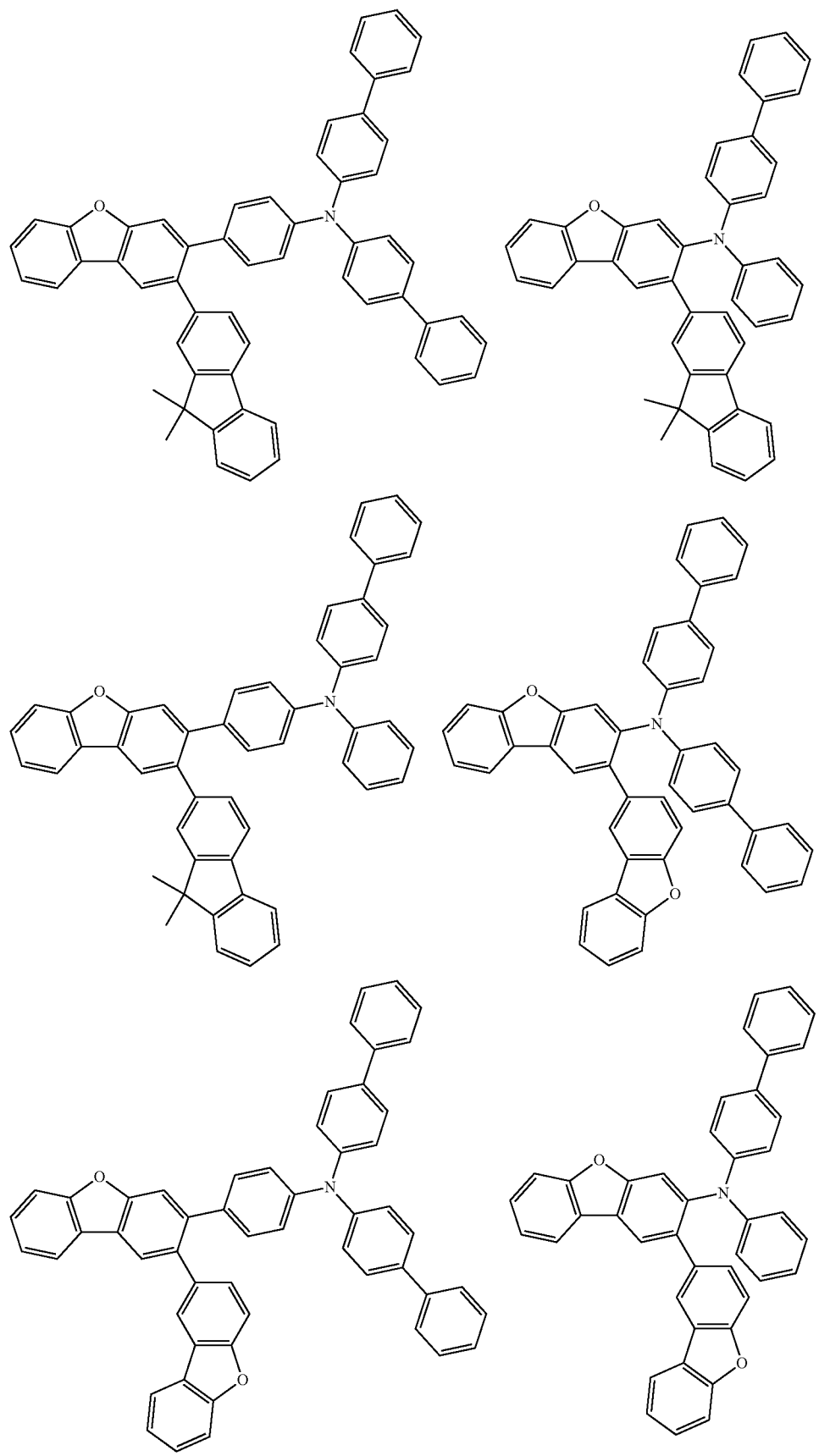

-continued
303
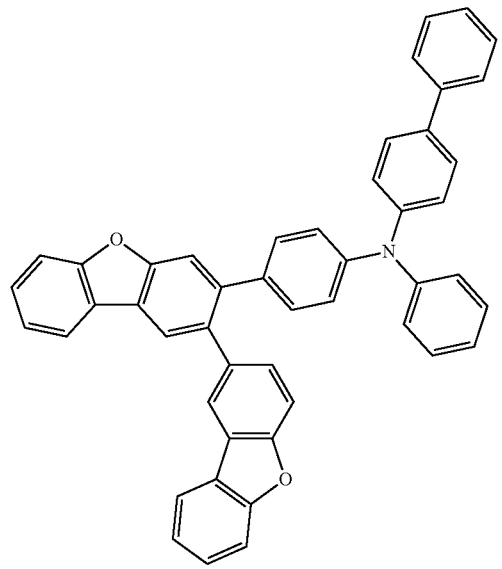
304
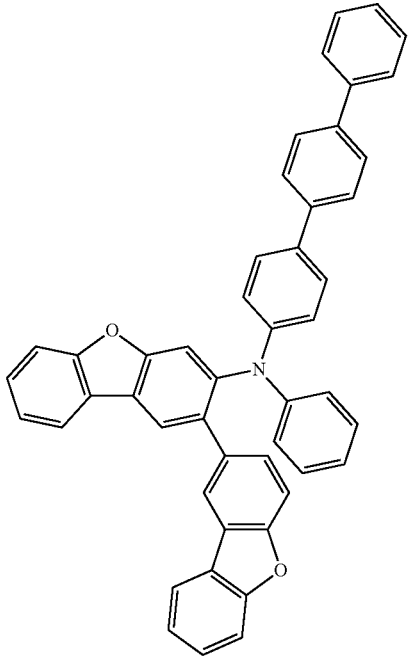
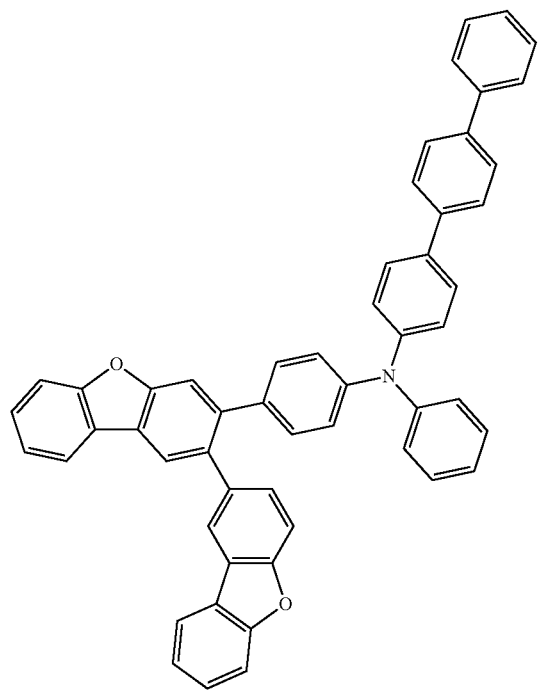
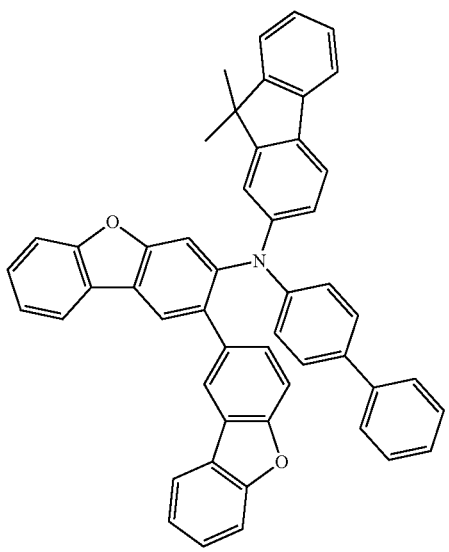

305
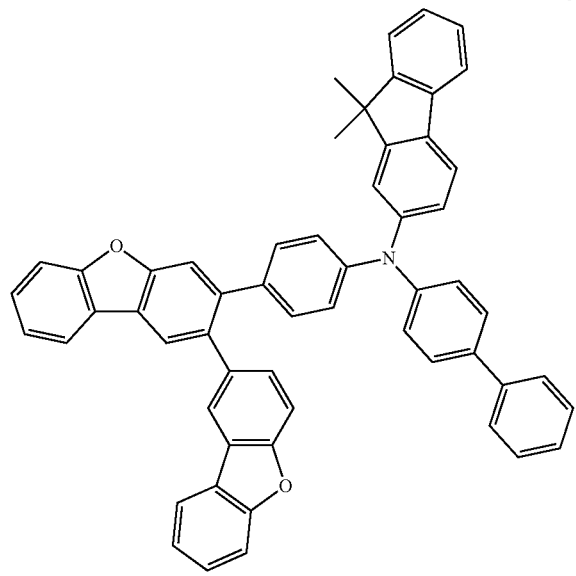
306
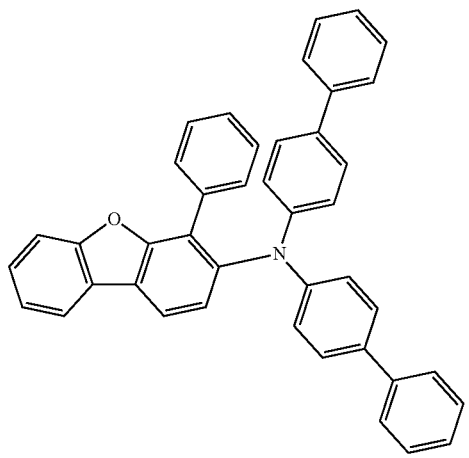
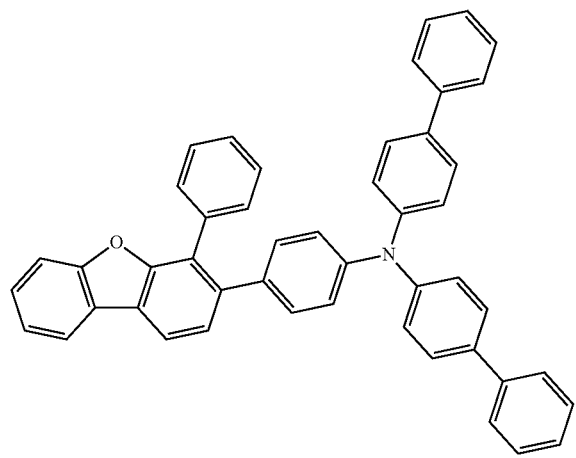
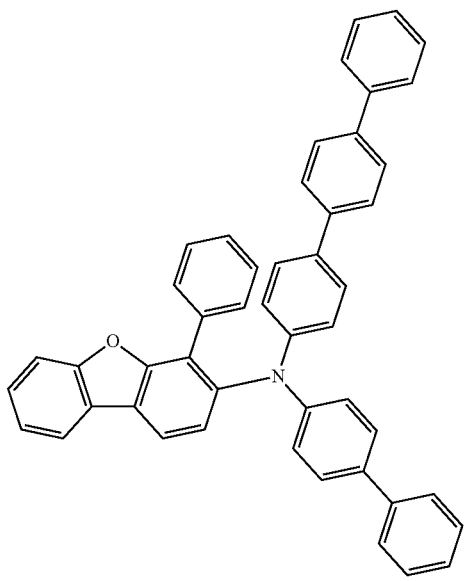
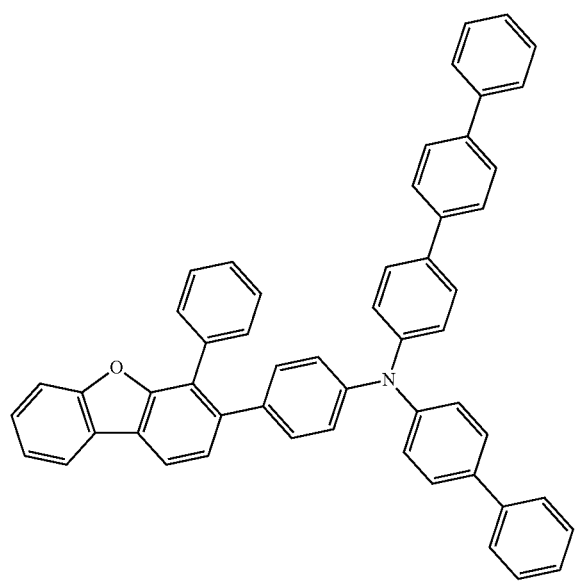
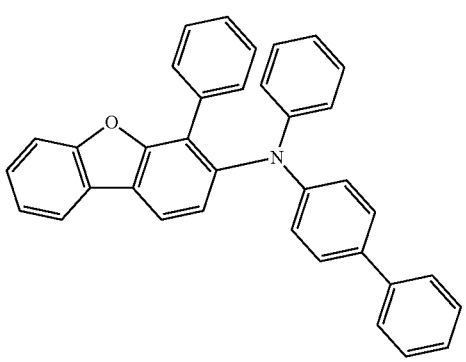

-continued
| 307 | 308 |
|---|---|
| 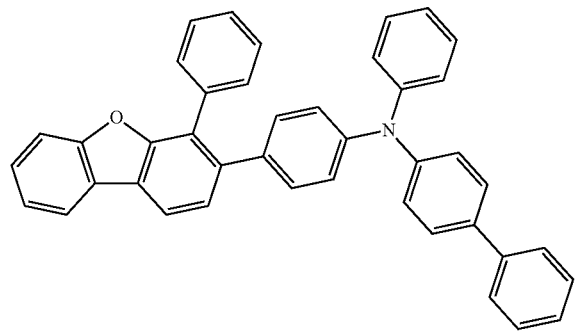 | 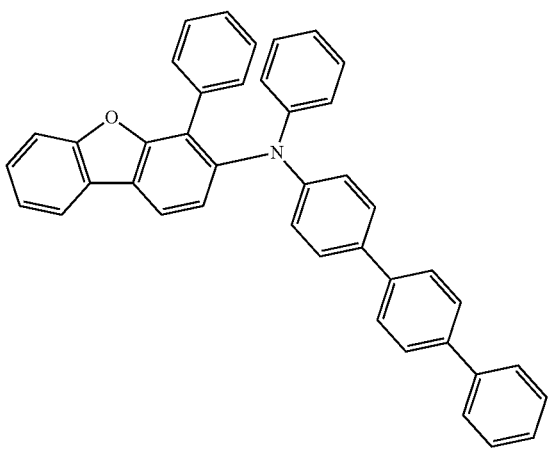 |
| 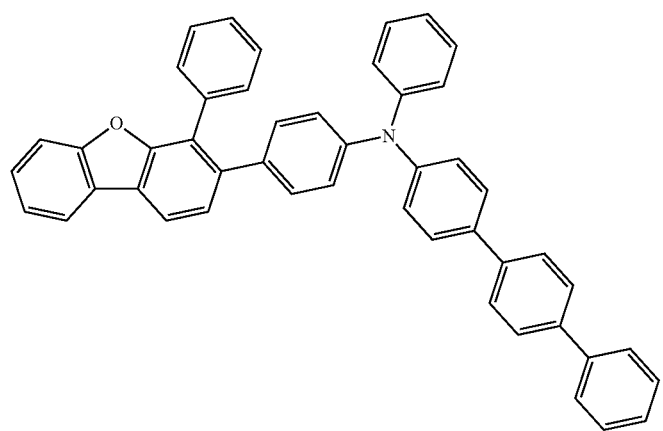 | 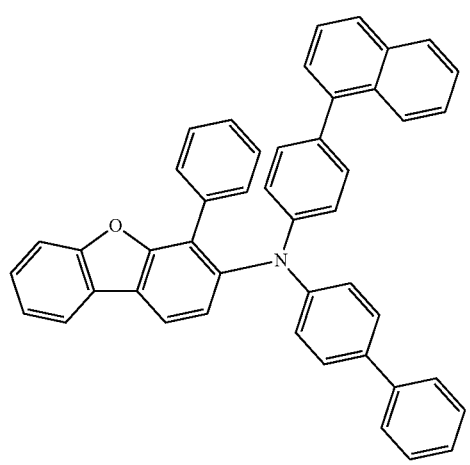 |
| 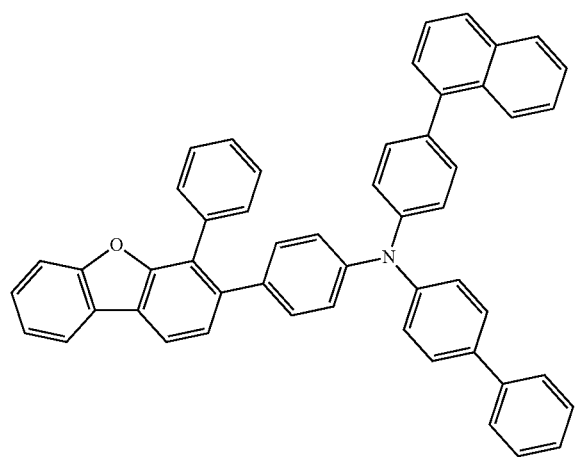 | 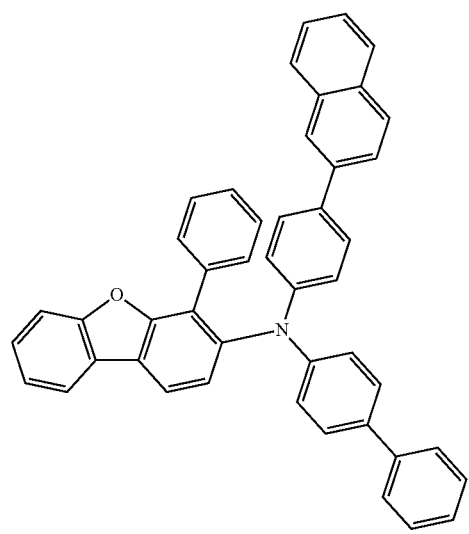 |

| 309 | 310 |
|---|---|
| 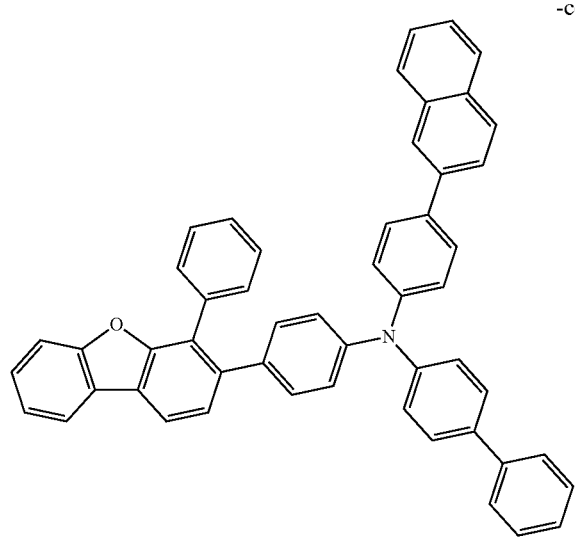 | 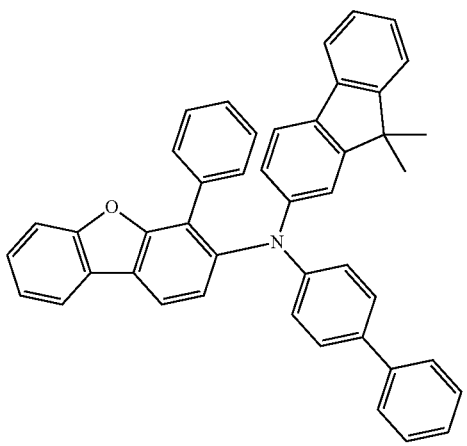 |
| 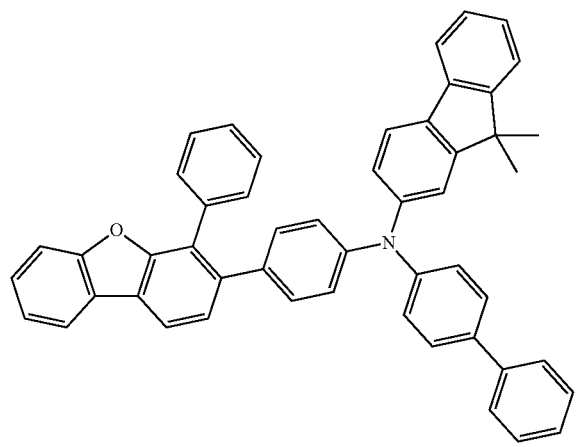 | 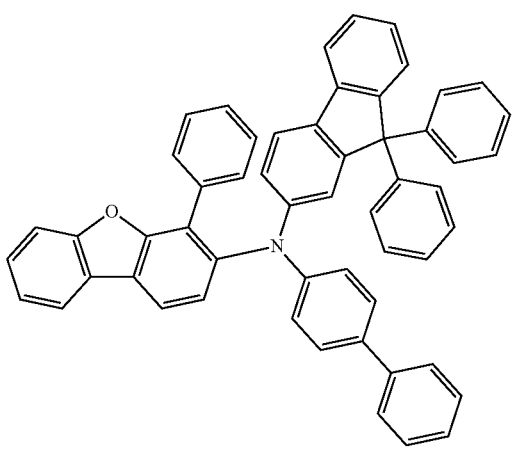 |
| 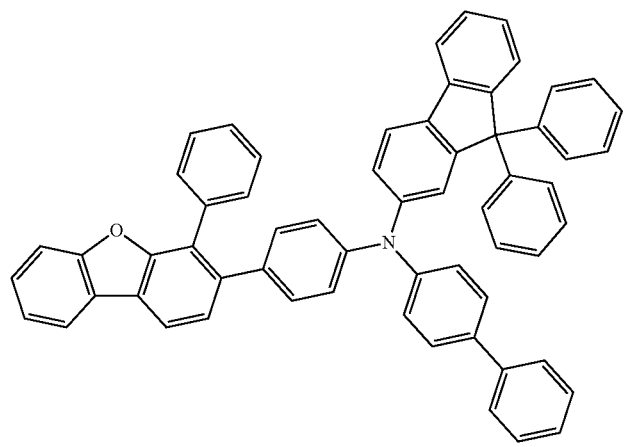 | 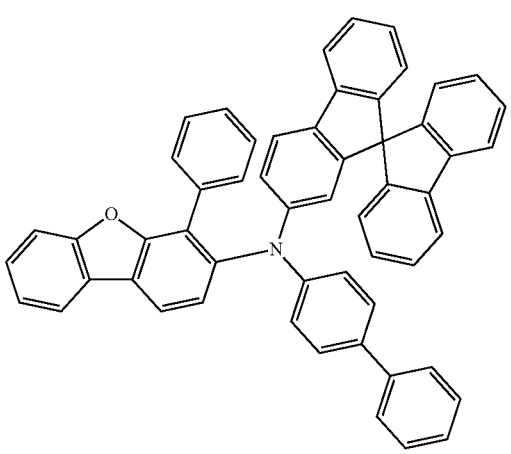 |

-continued
311 312
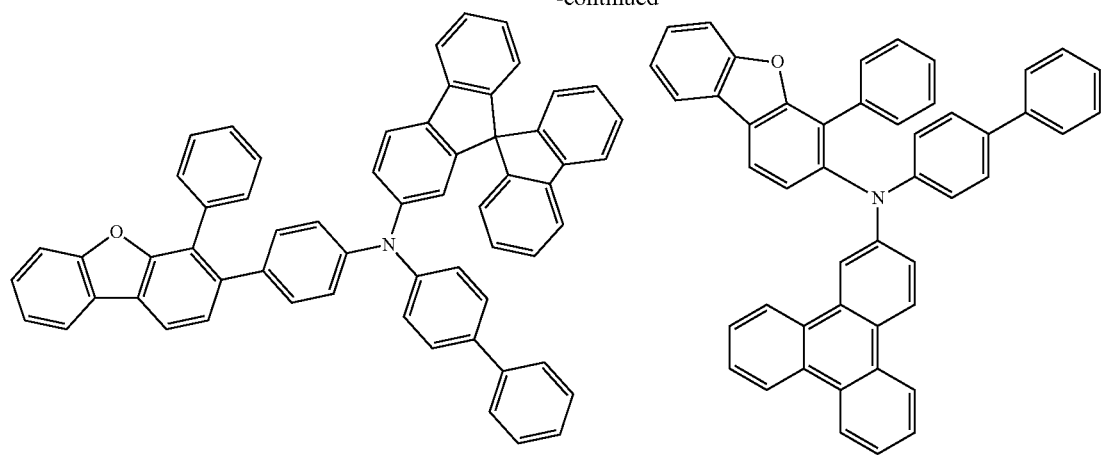
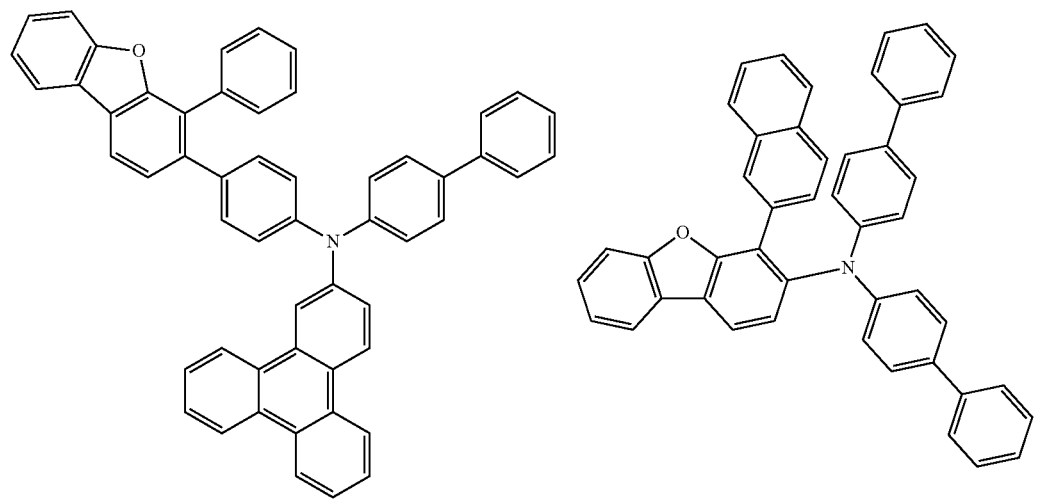
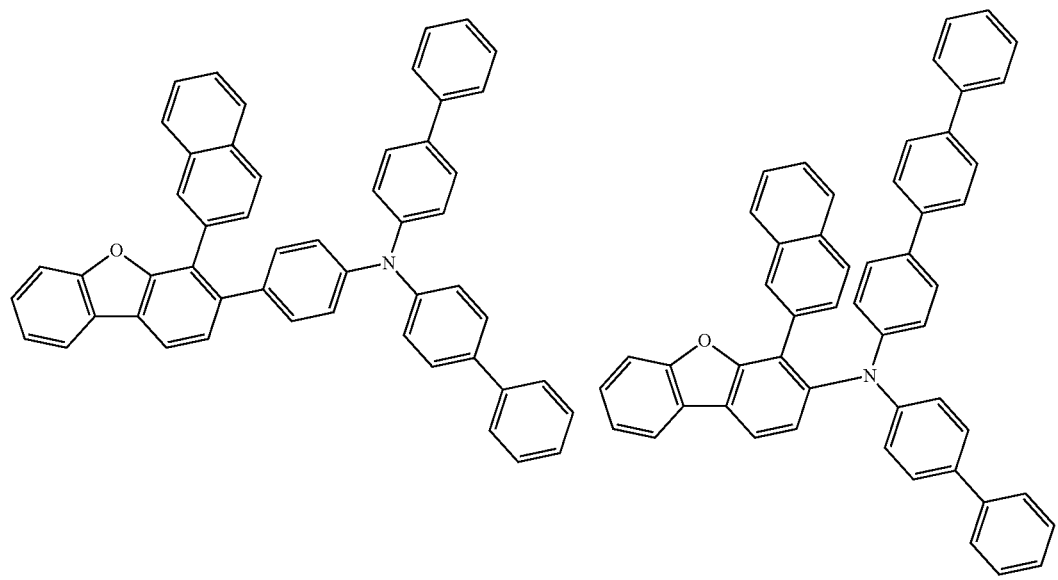

-continued
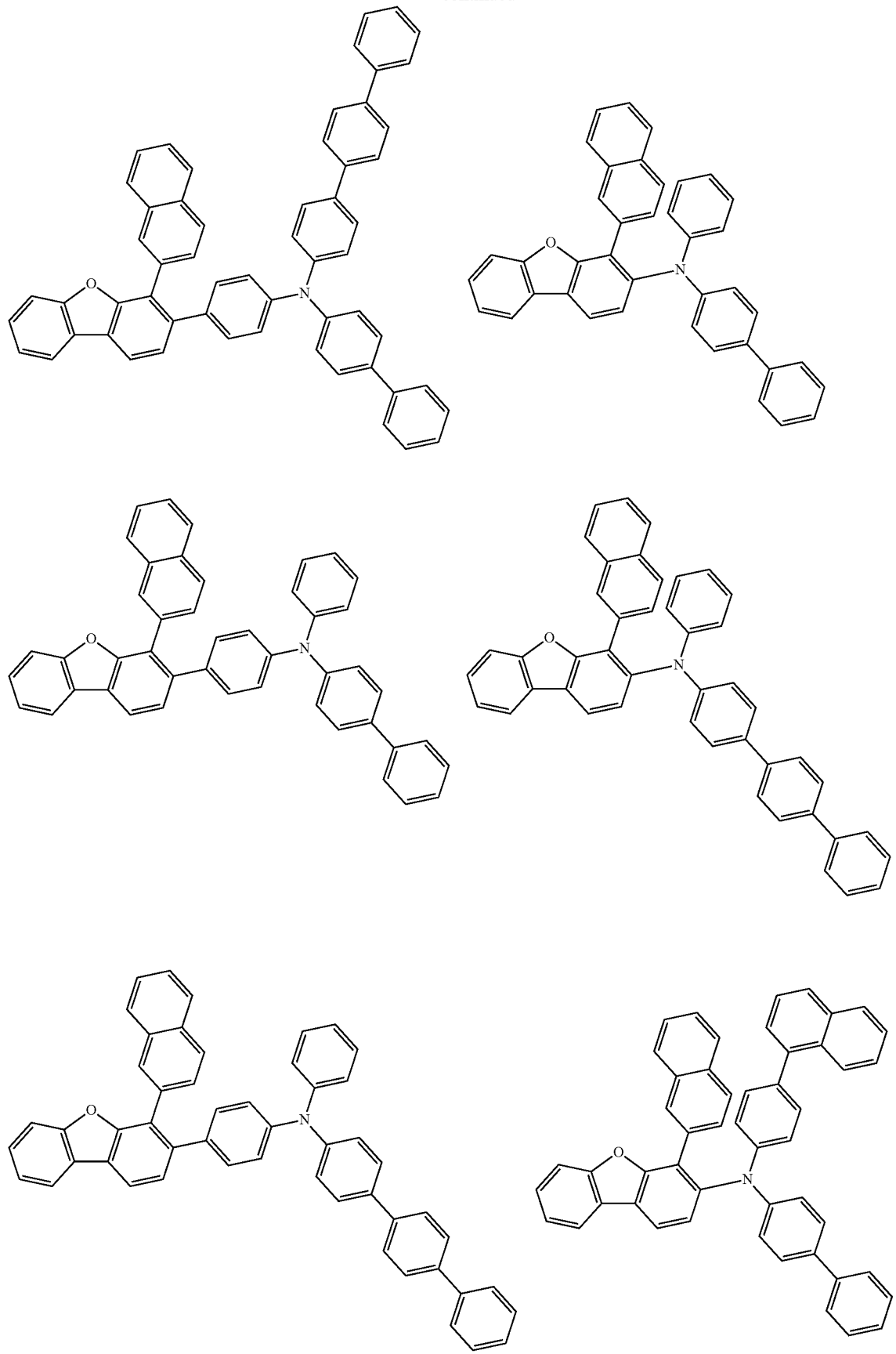

315        316
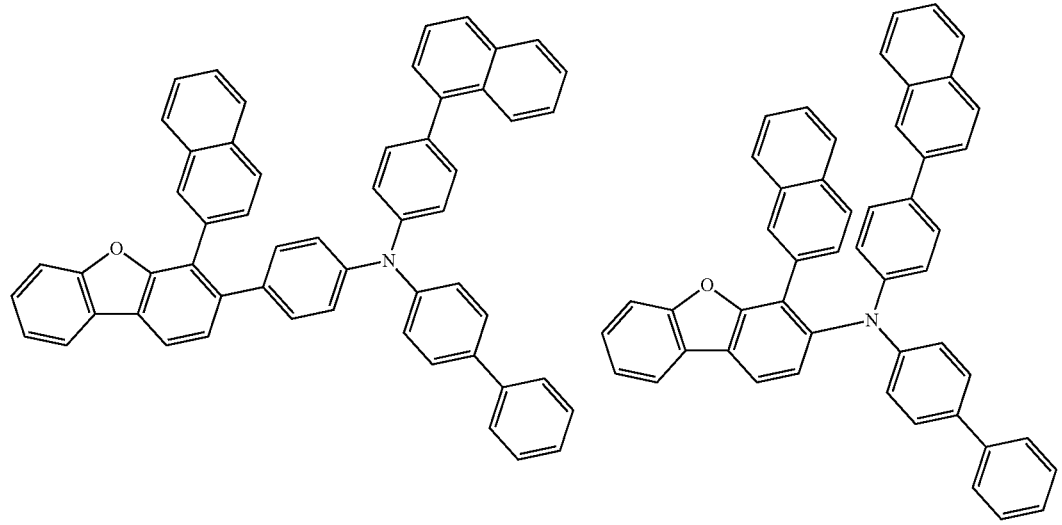
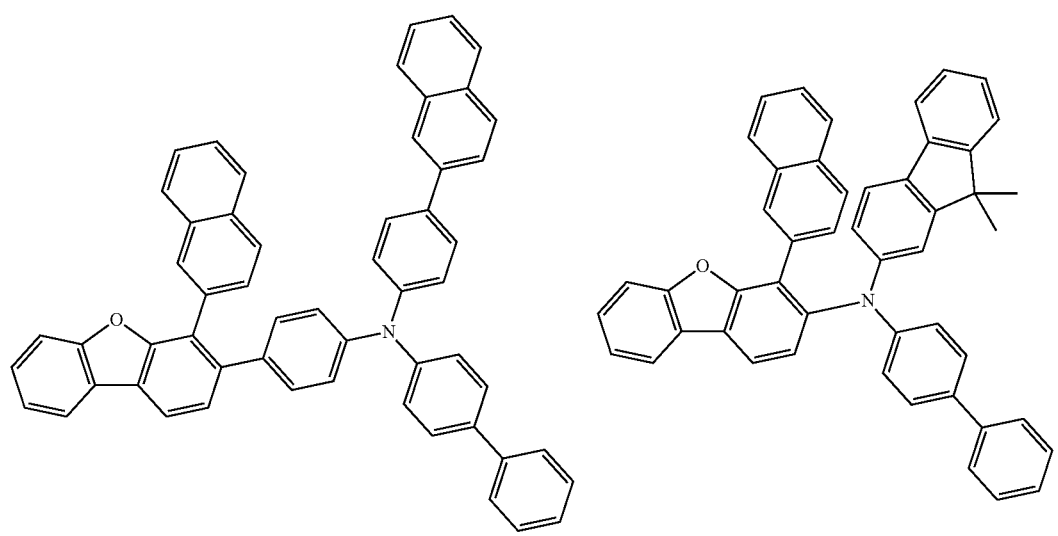
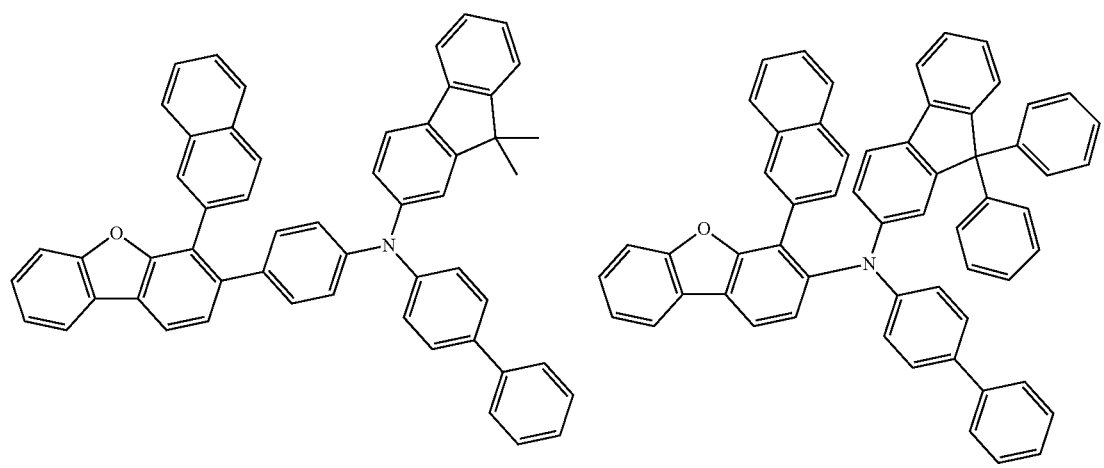

317 318
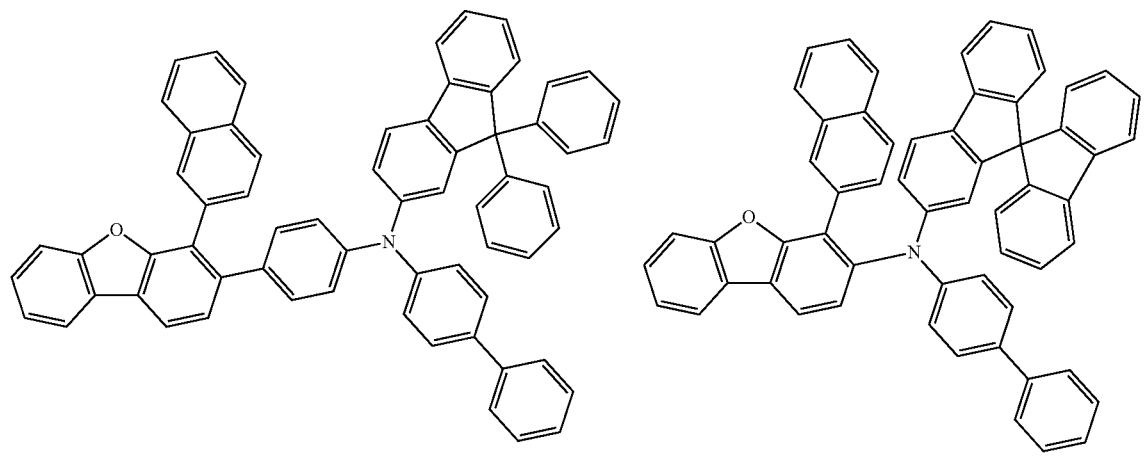
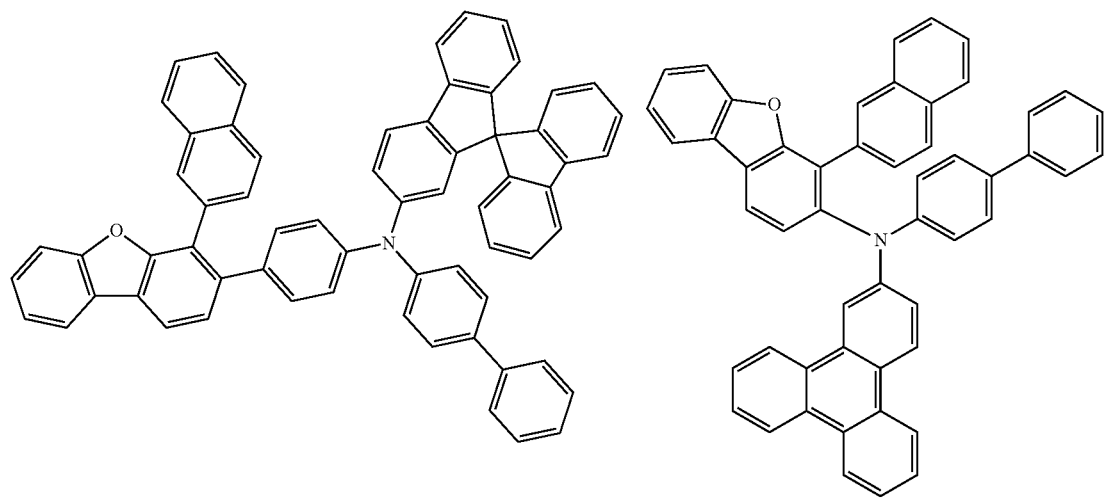
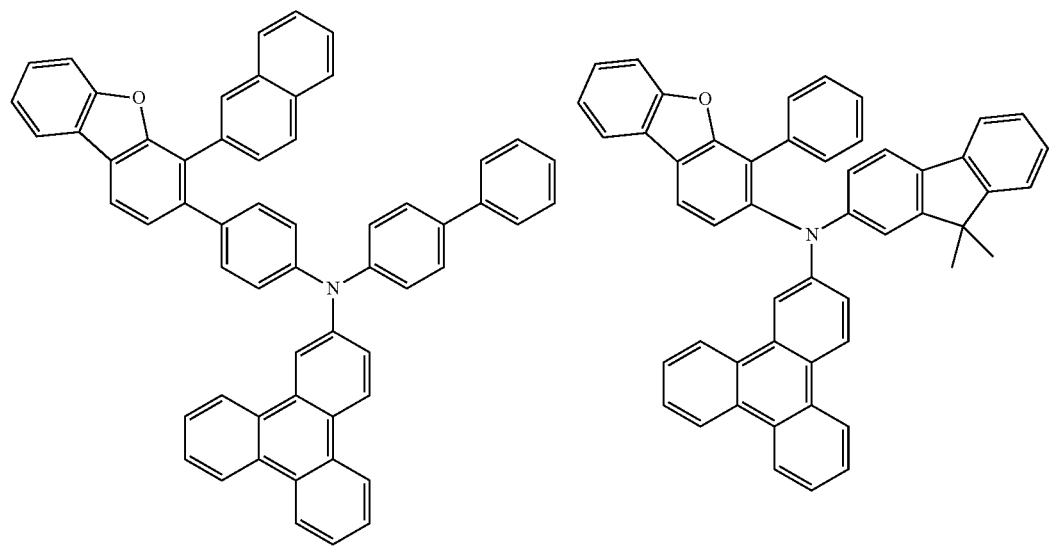

319
320
-continued
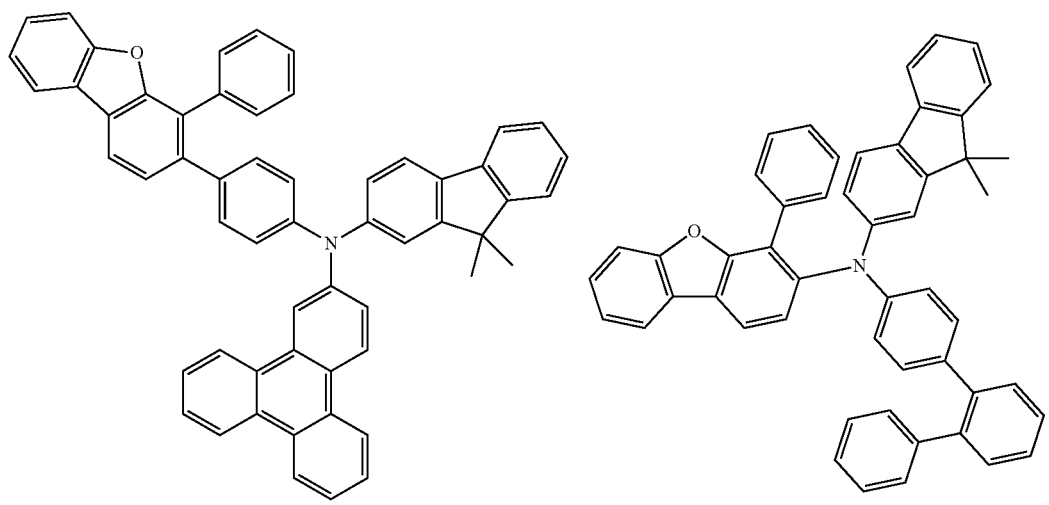
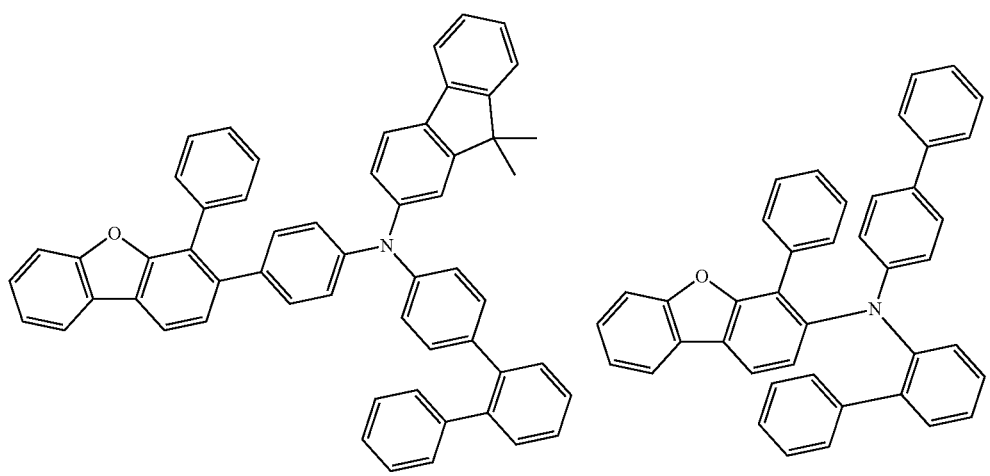
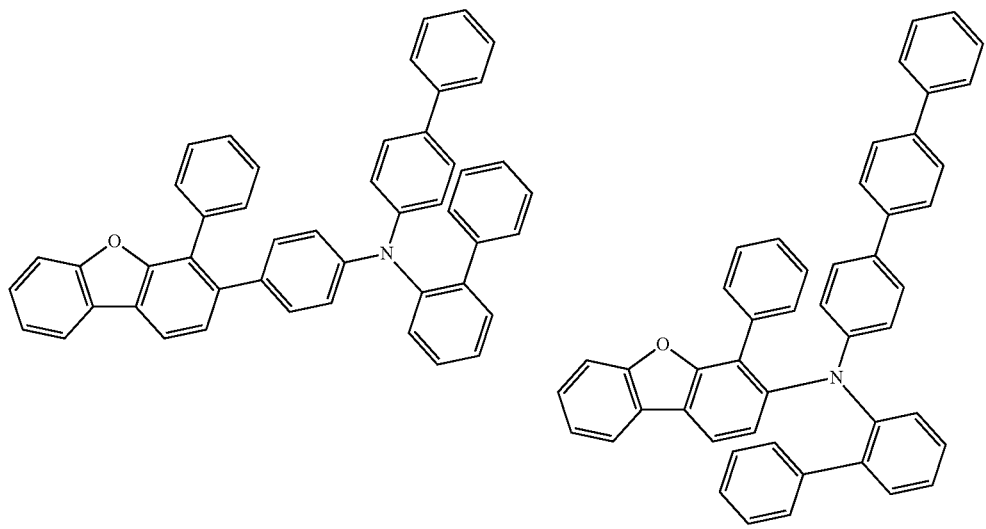

-continued
321
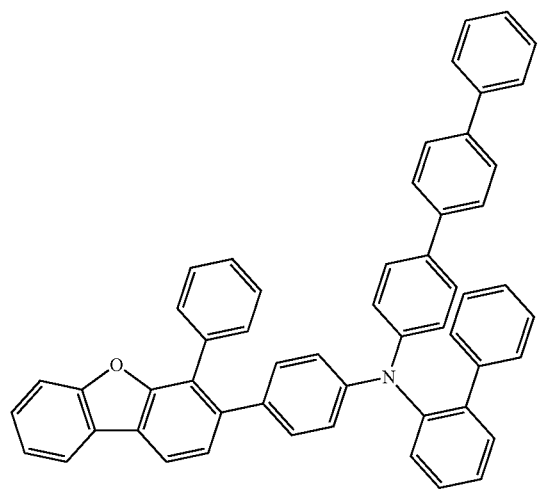
322
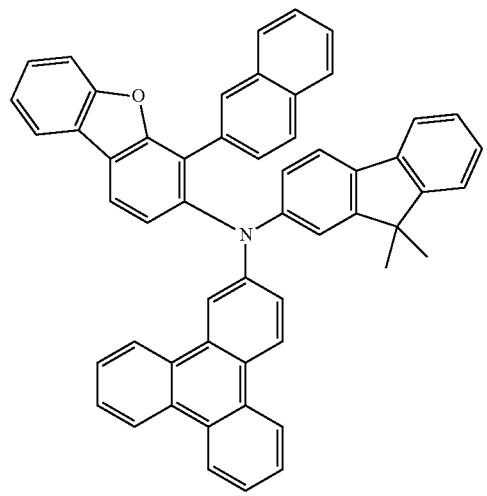
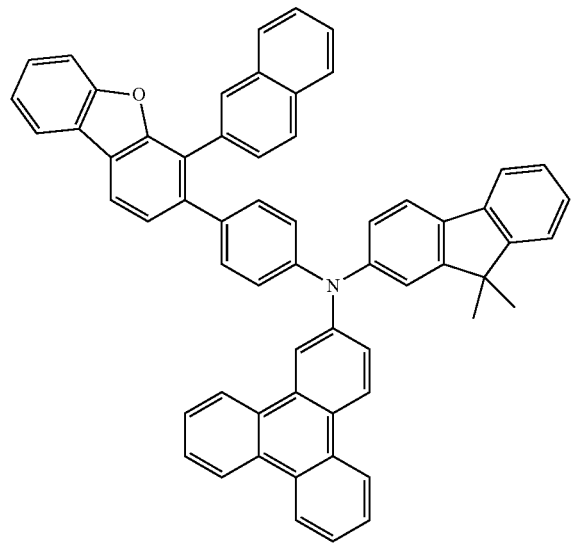
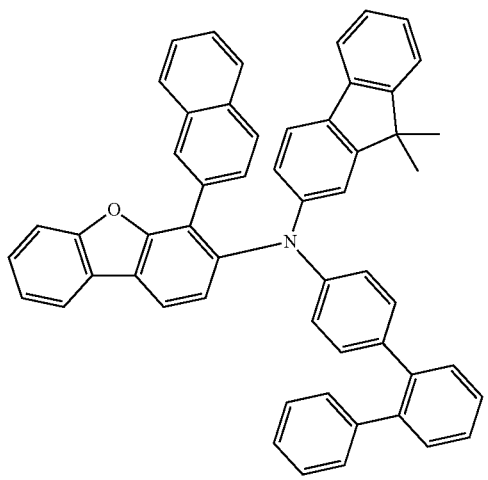
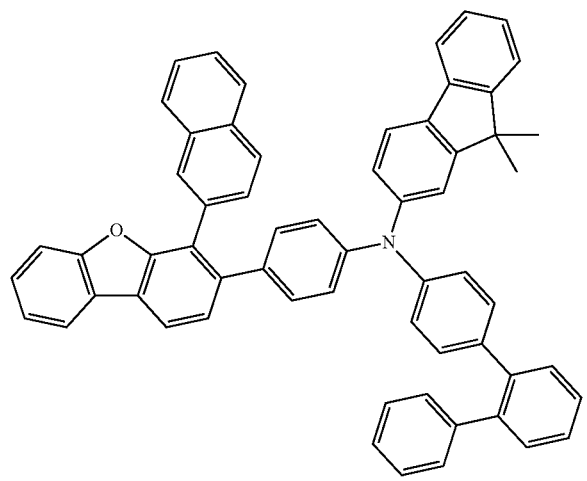
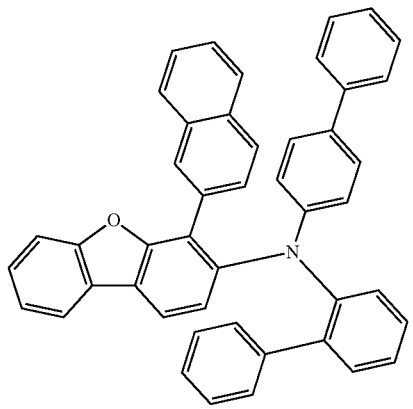

323
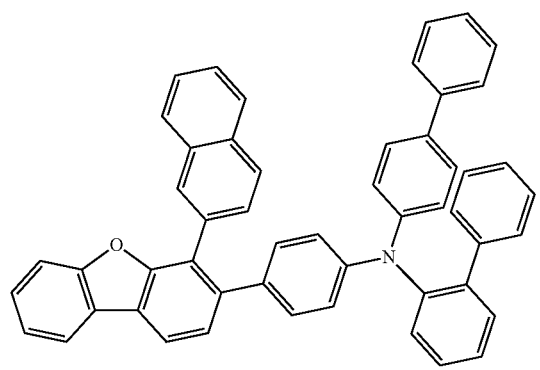
324
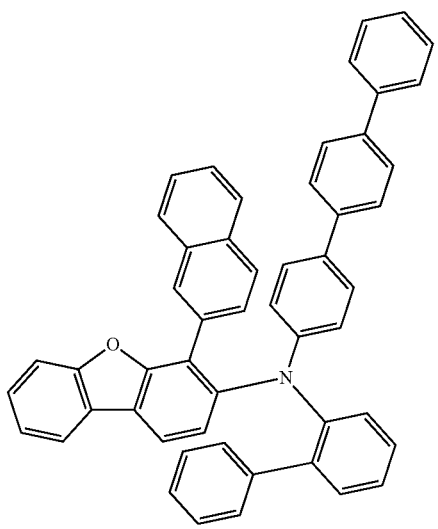
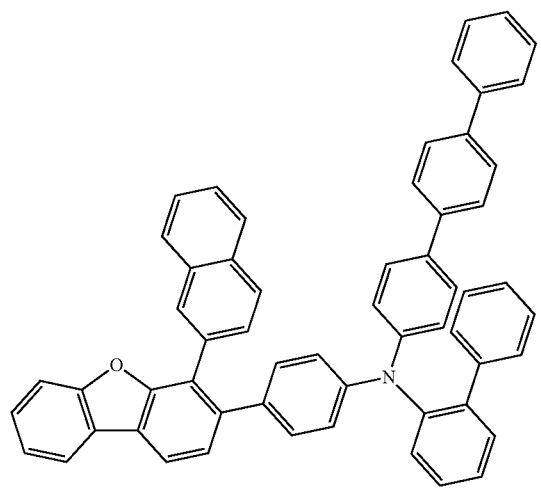
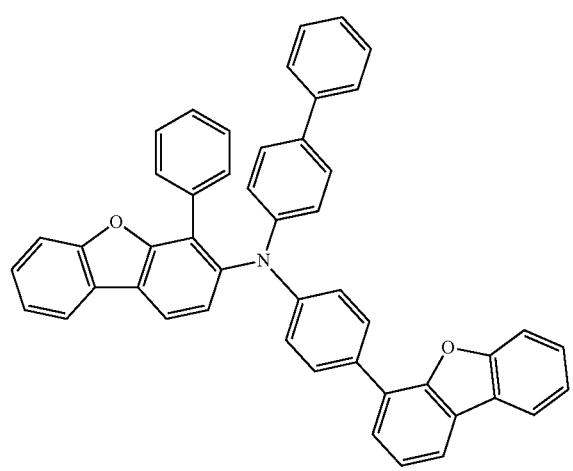
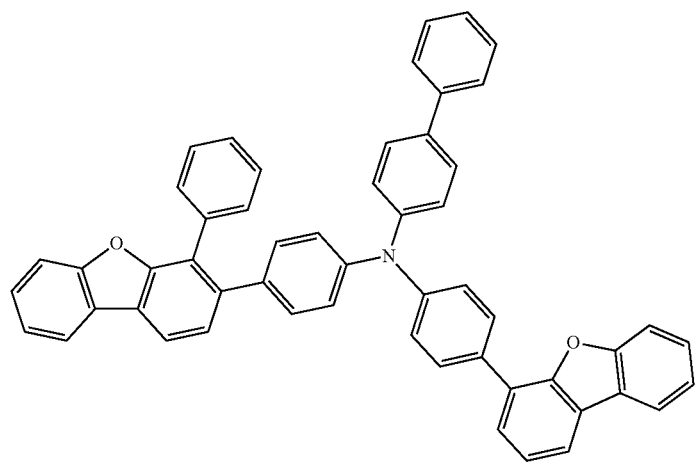

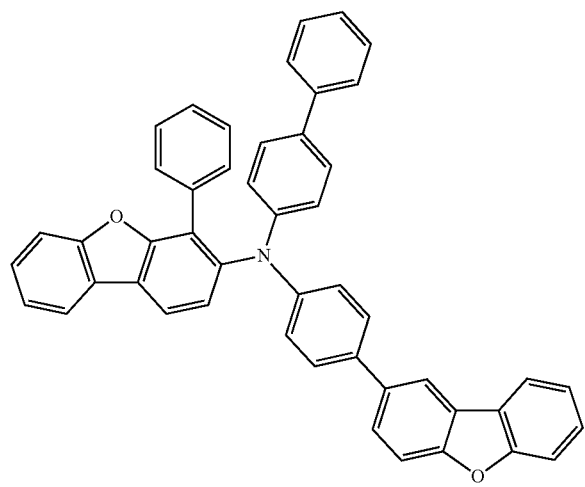
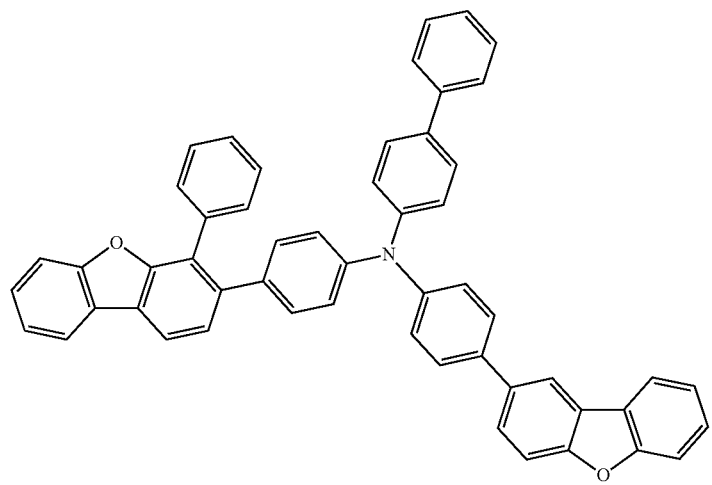
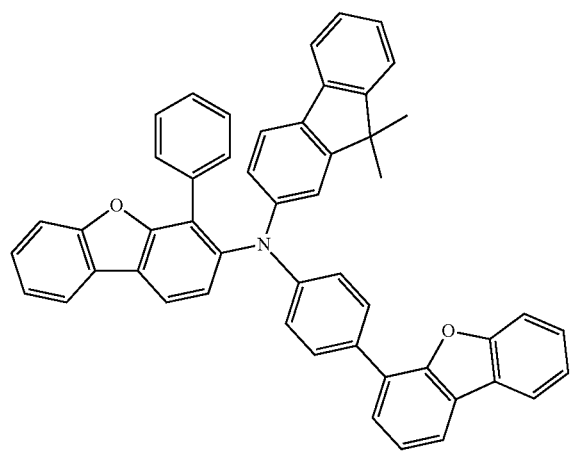

-continued
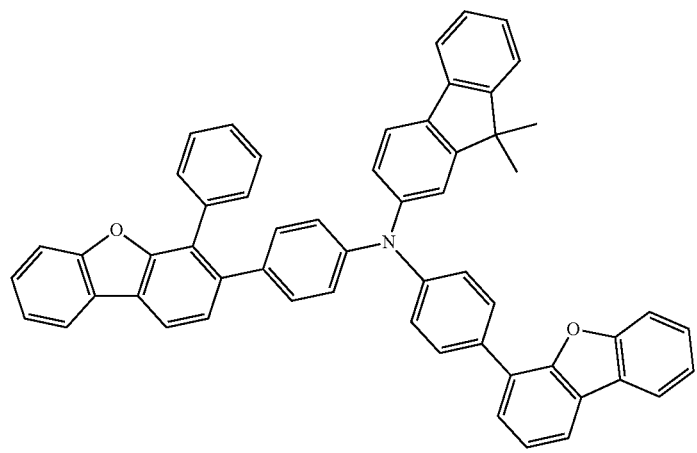
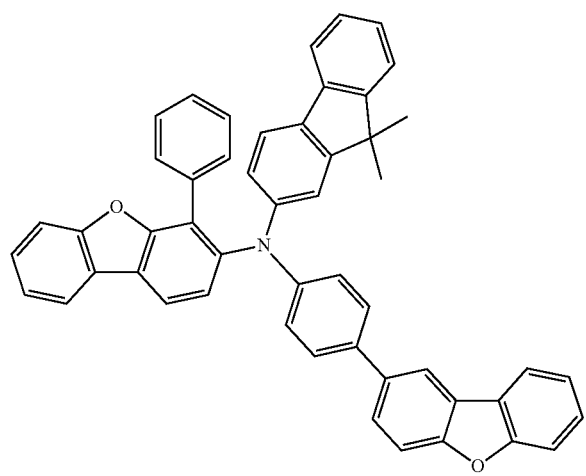
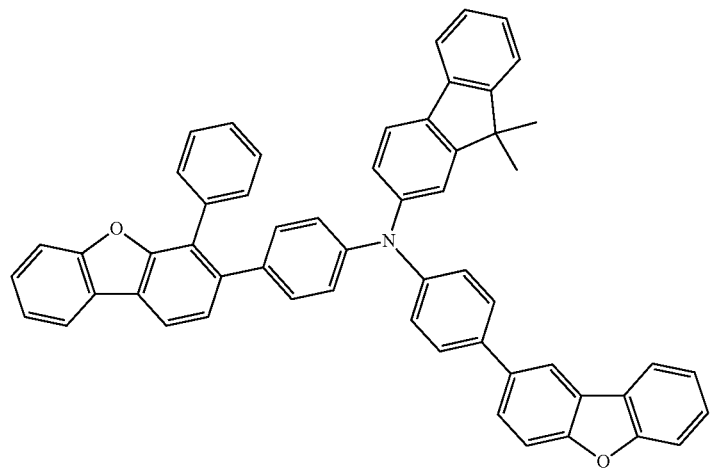

-continued
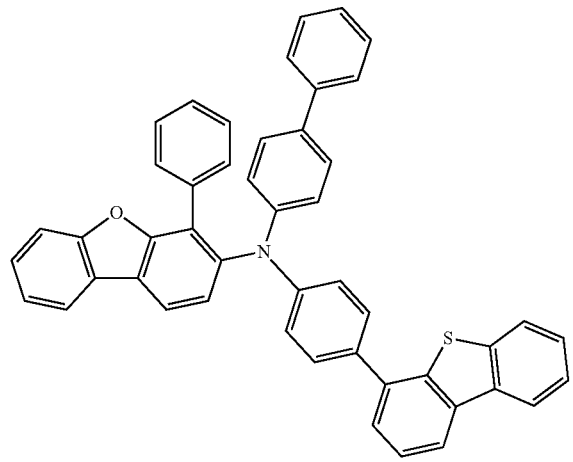
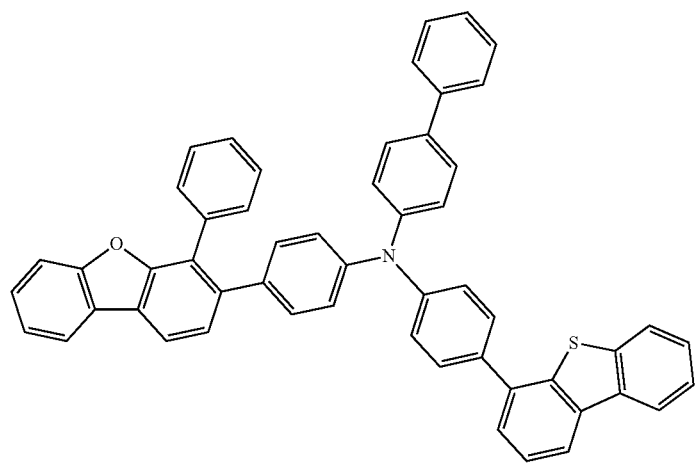
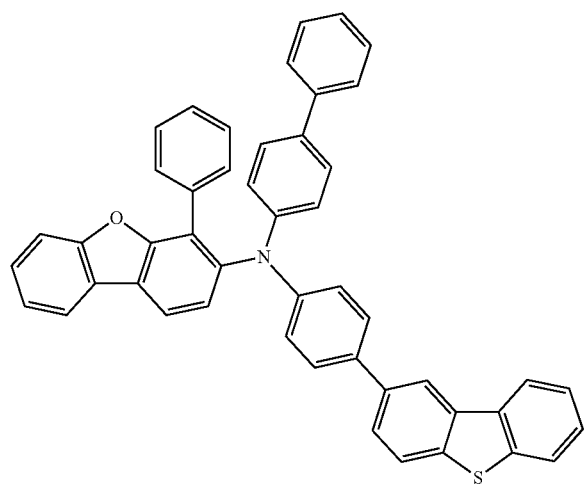

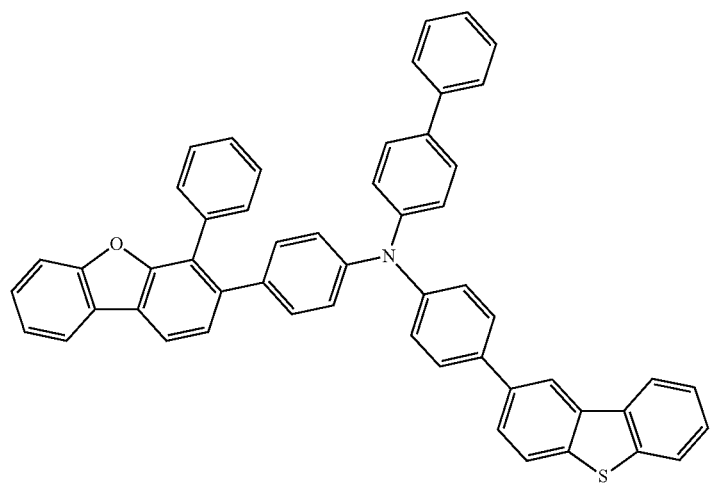
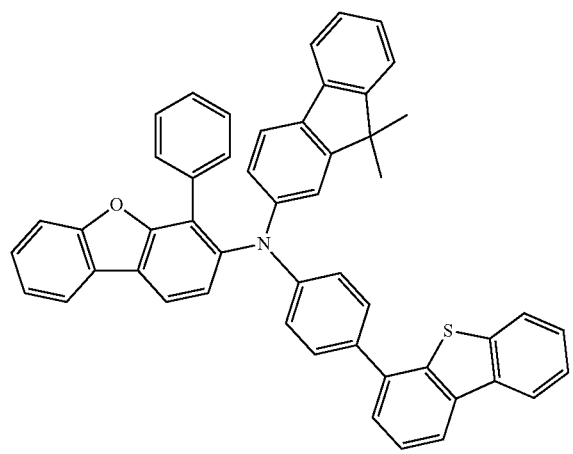
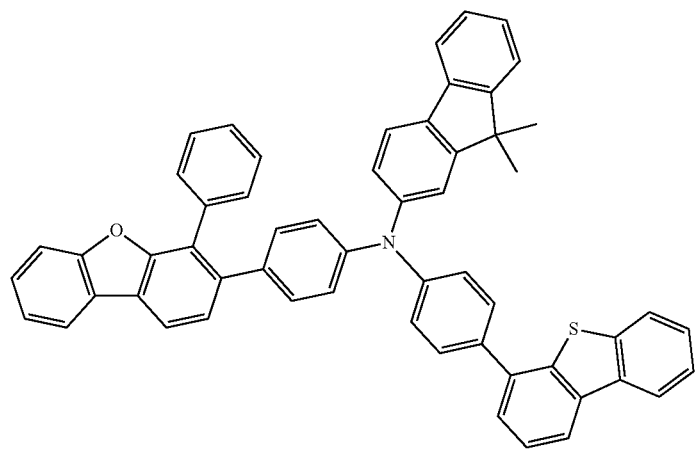

-continued
333
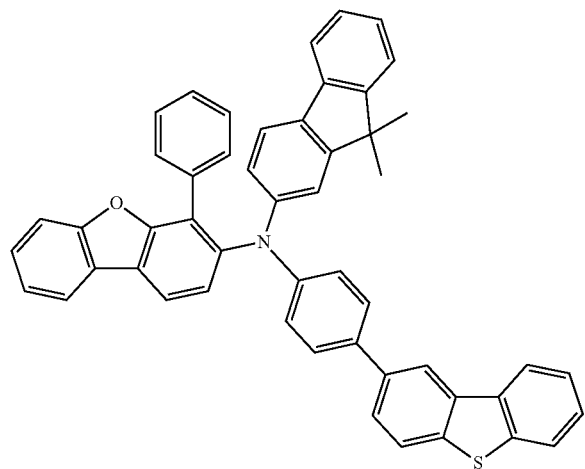
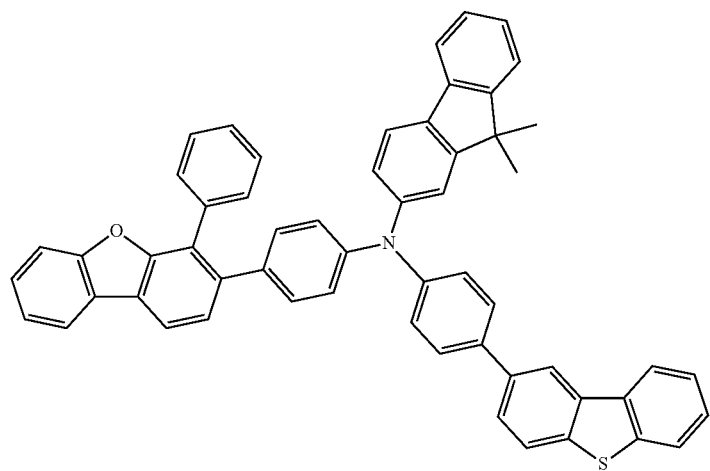
334
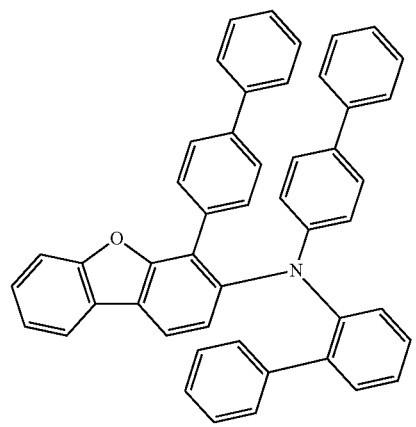
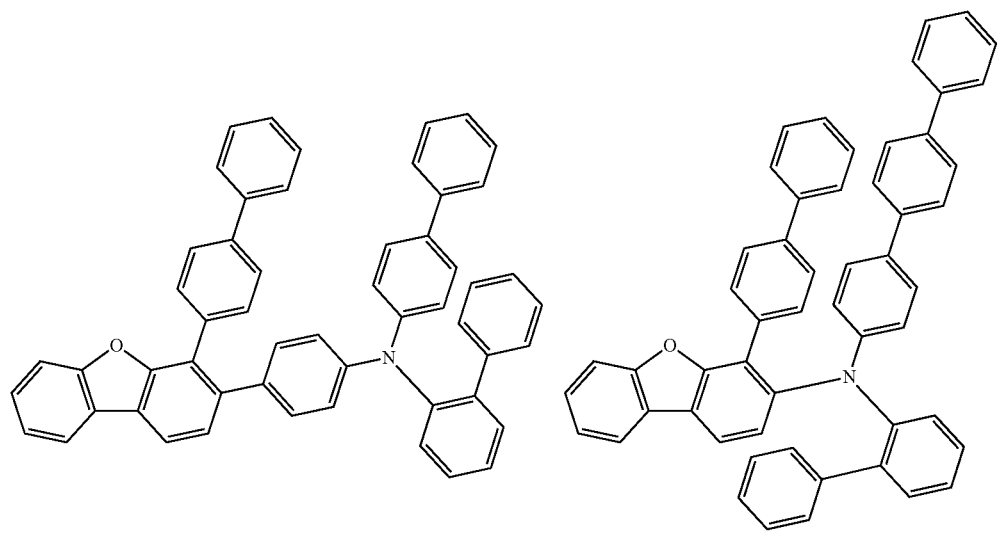

-continued
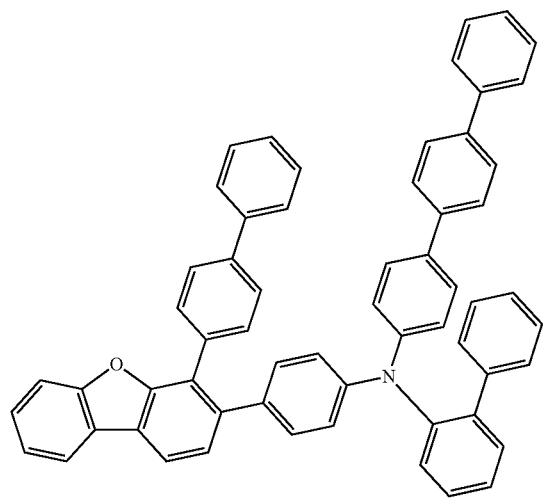
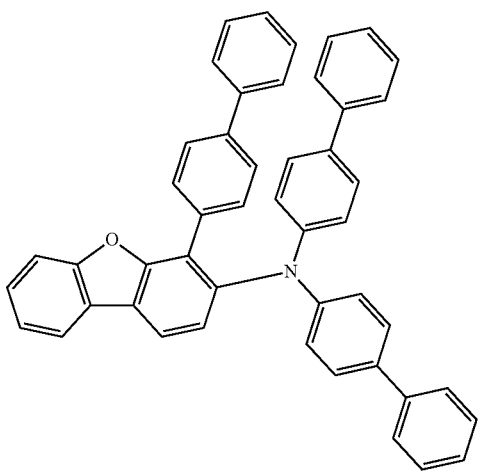
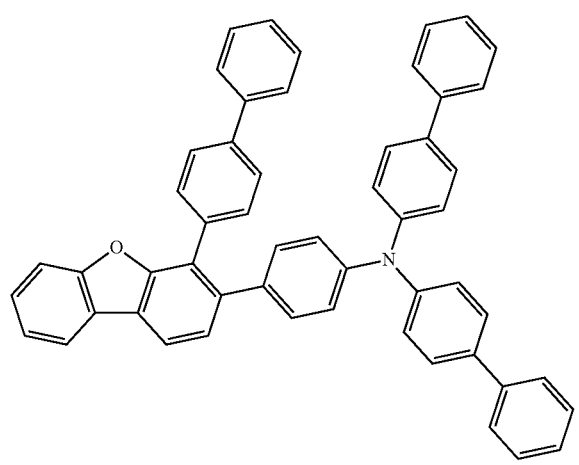
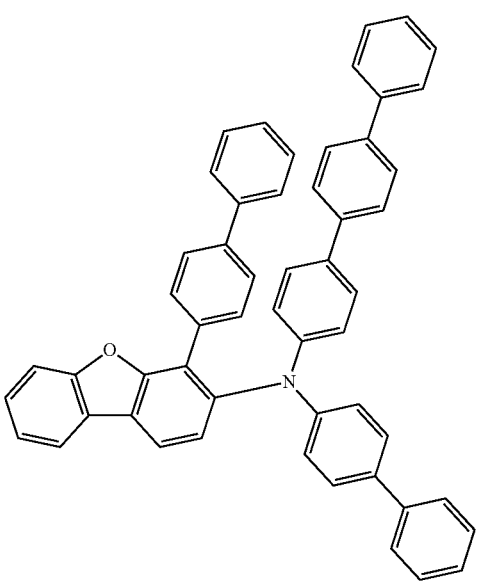
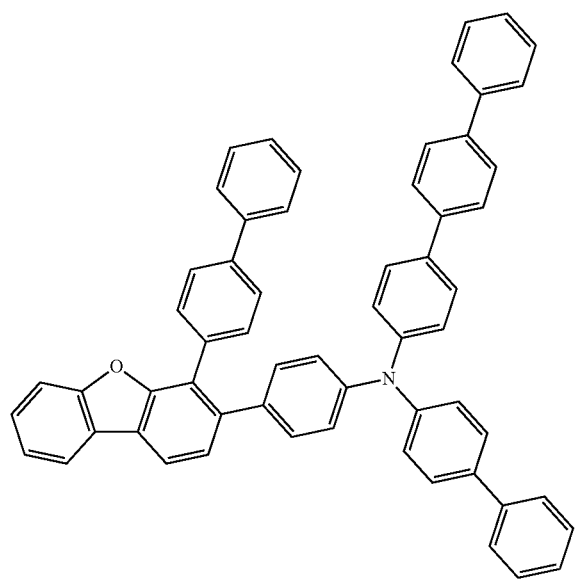
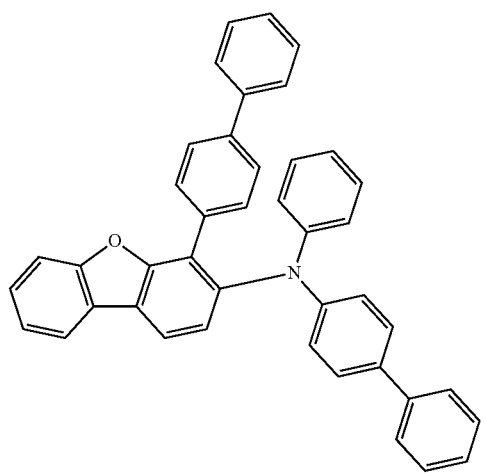

-continued
337
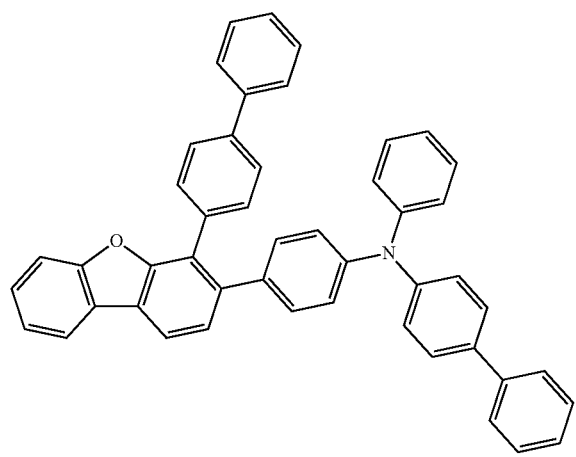
338
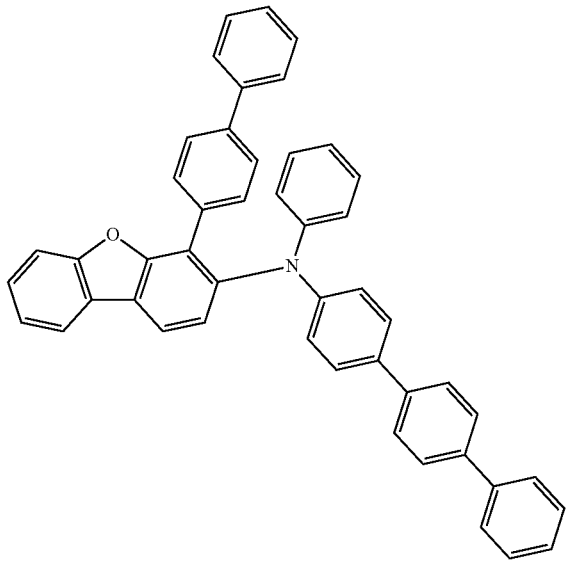
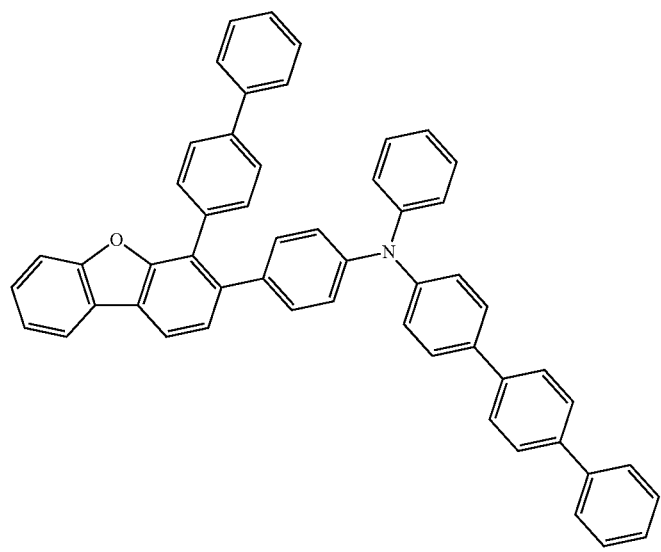
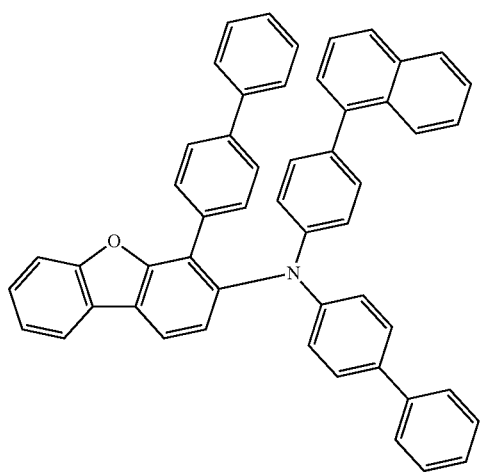
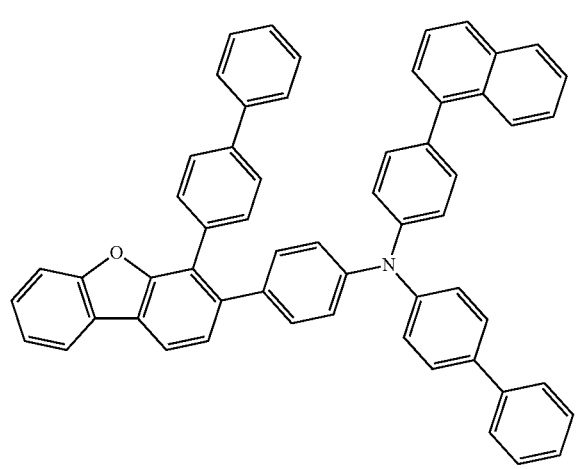
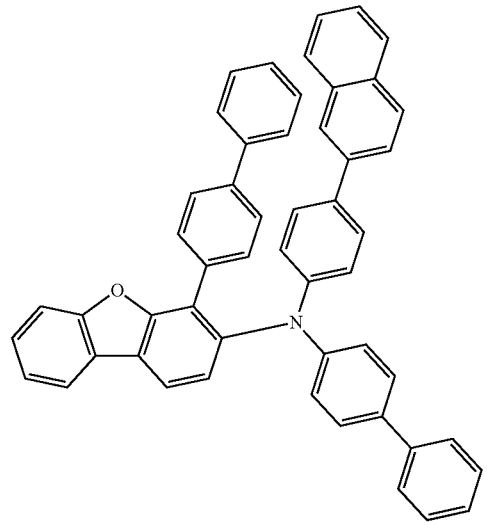

-continued
339
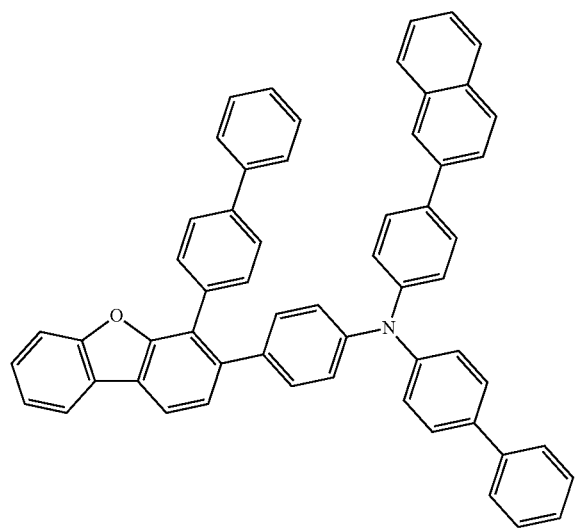
340
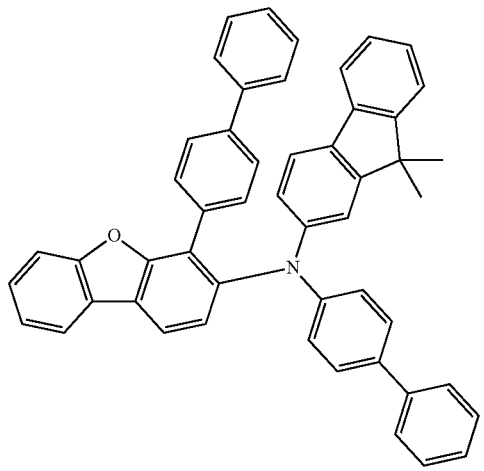
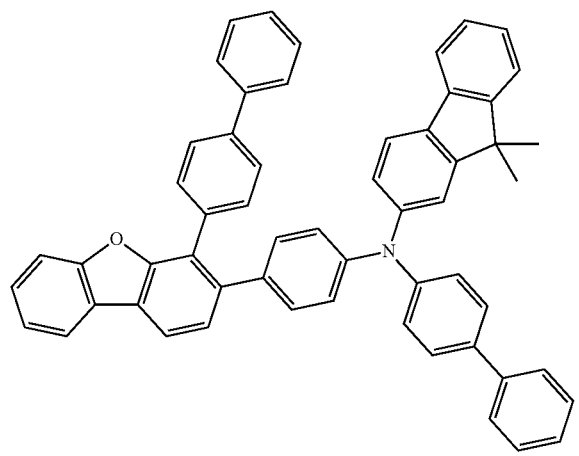
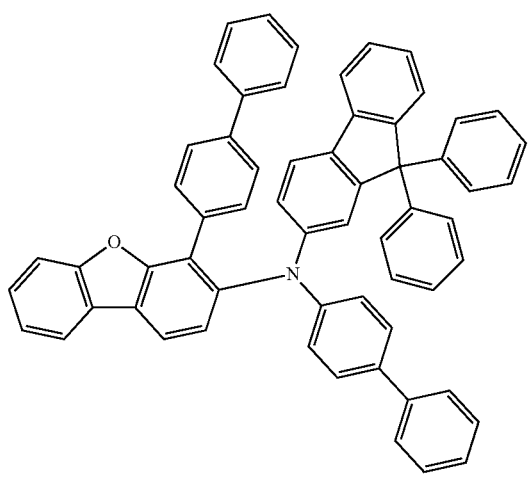
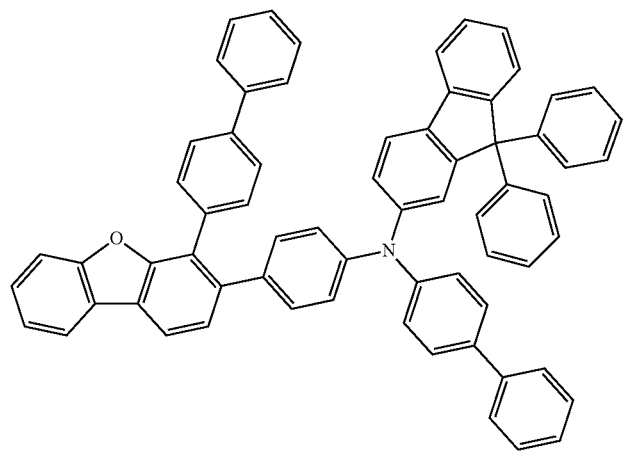
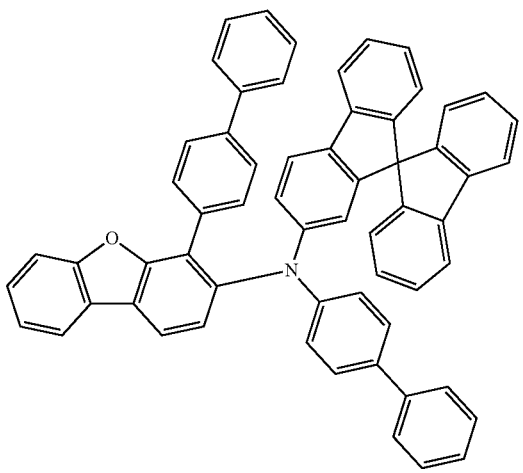

341
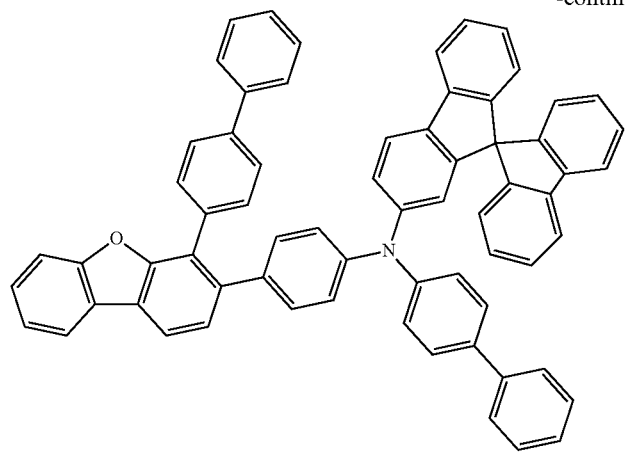
342
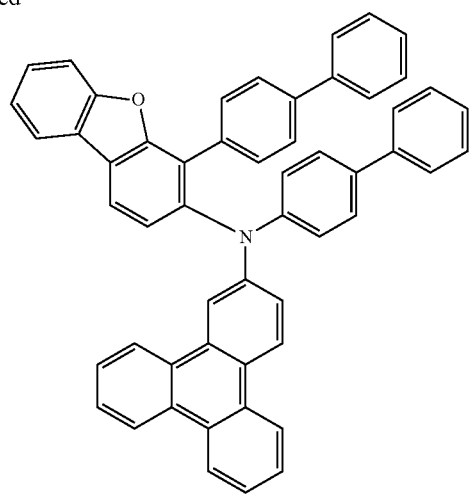
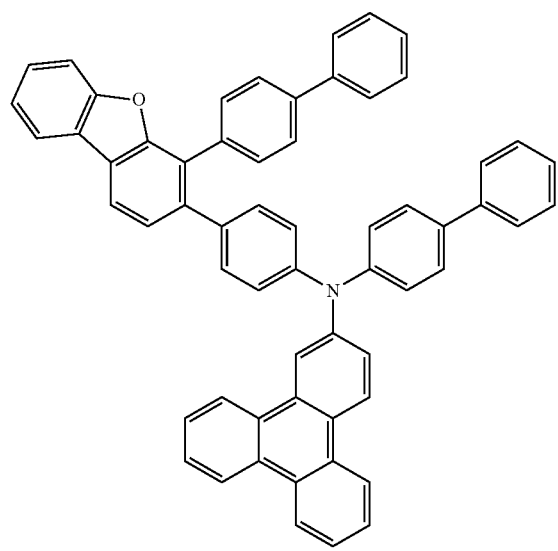
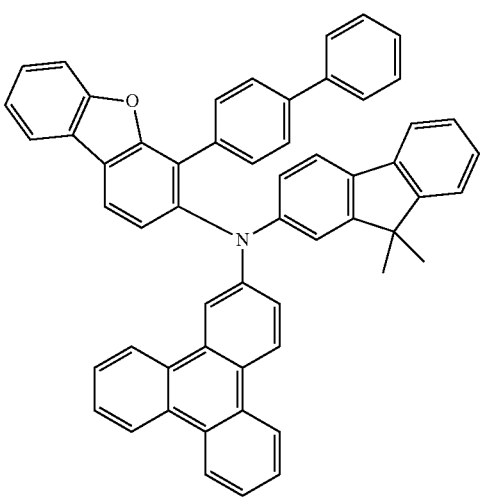
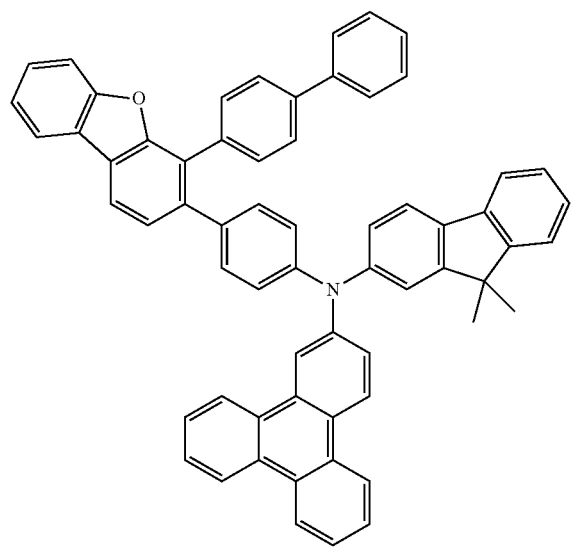
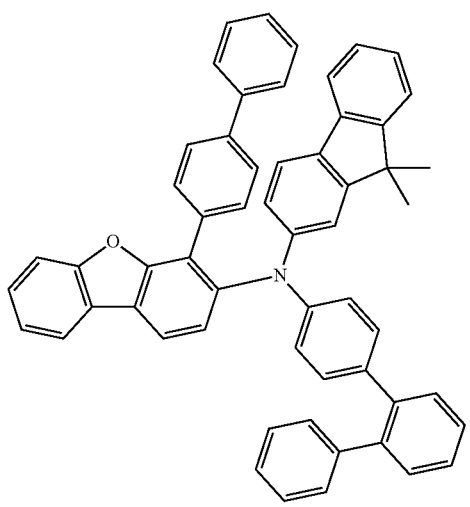

343 344
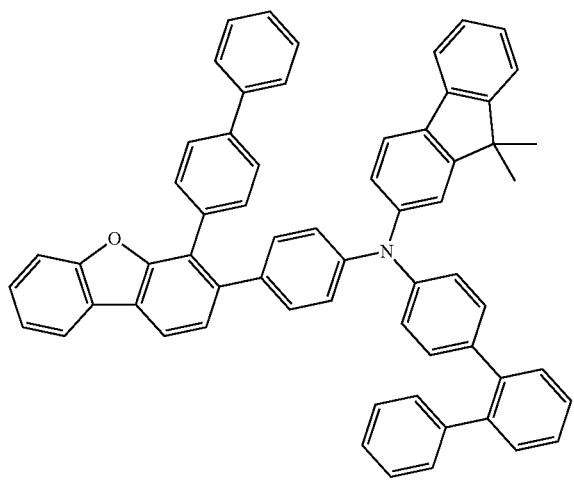 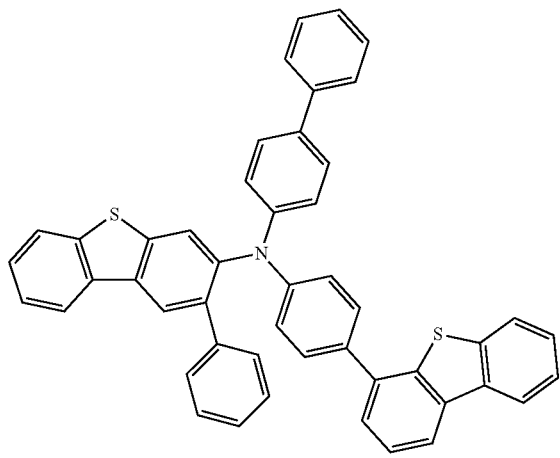
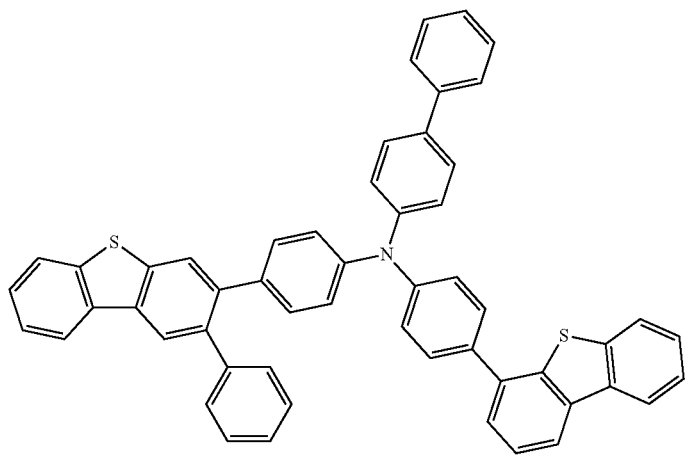
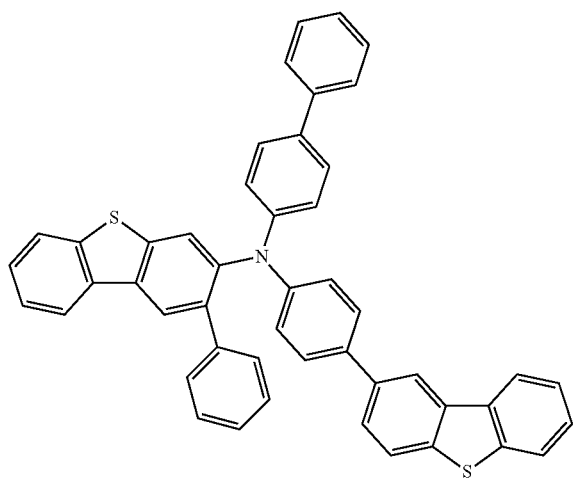

-continued
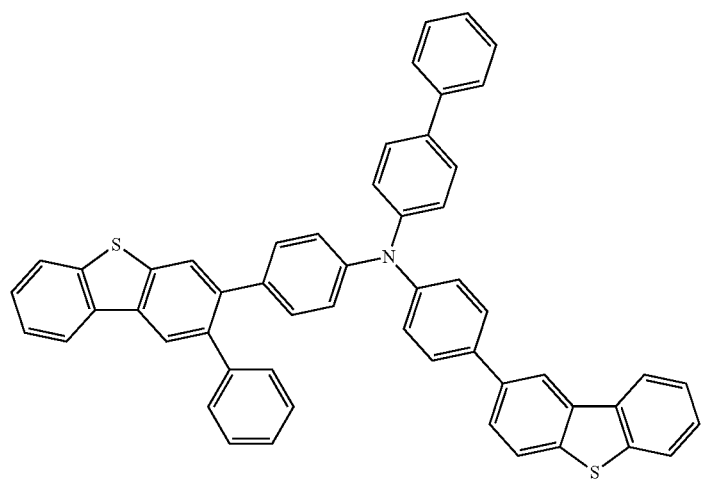
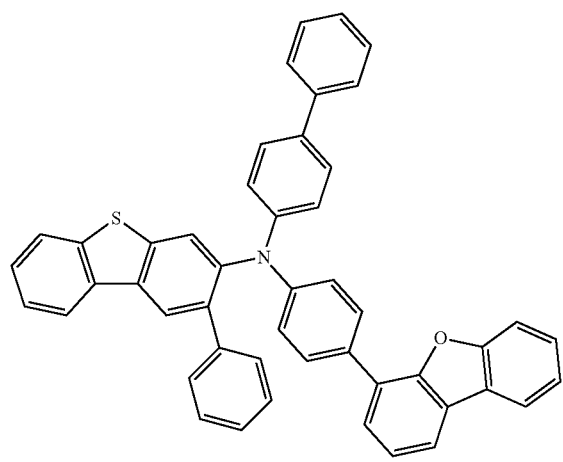
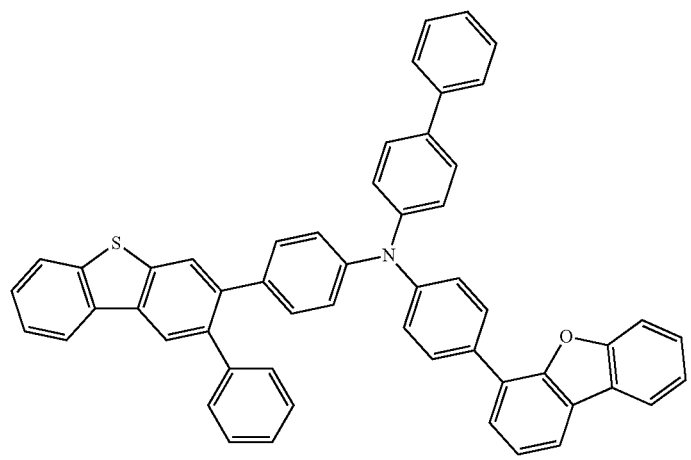

-continued
347
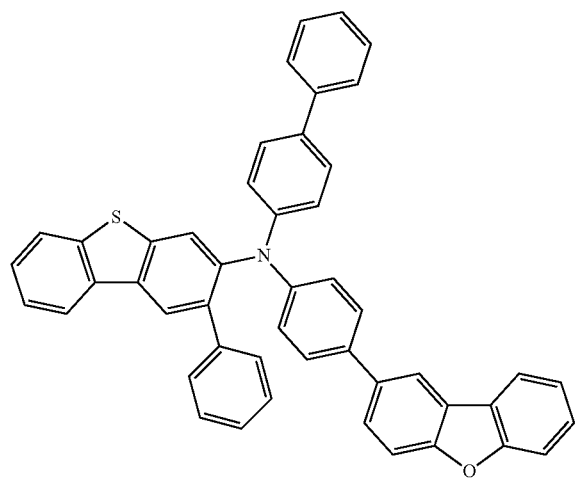
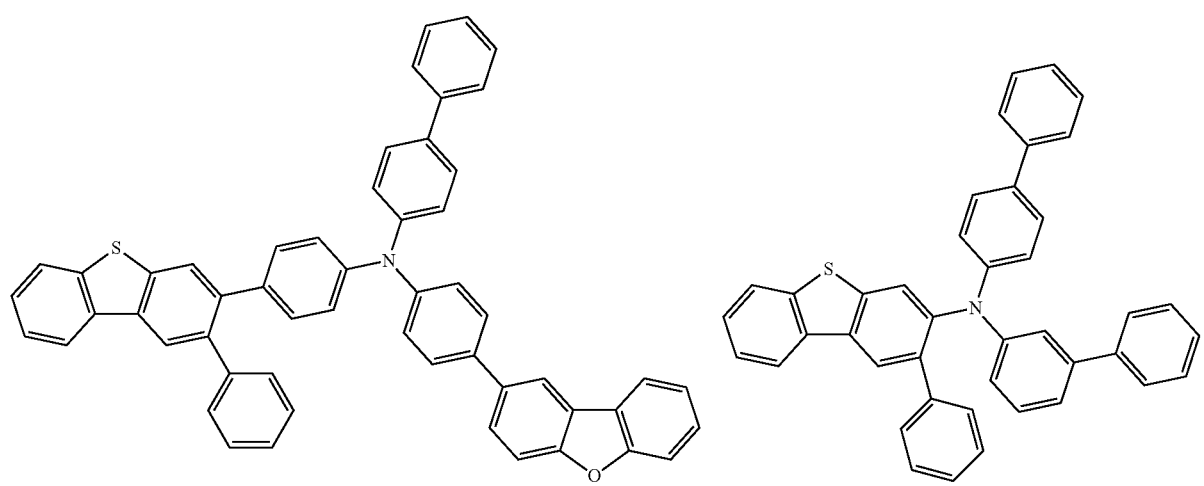
348
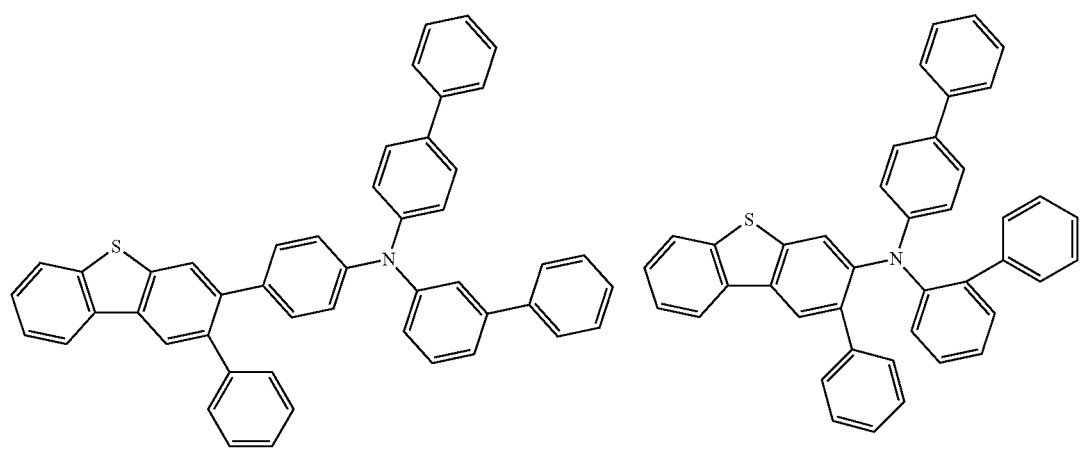

349 350
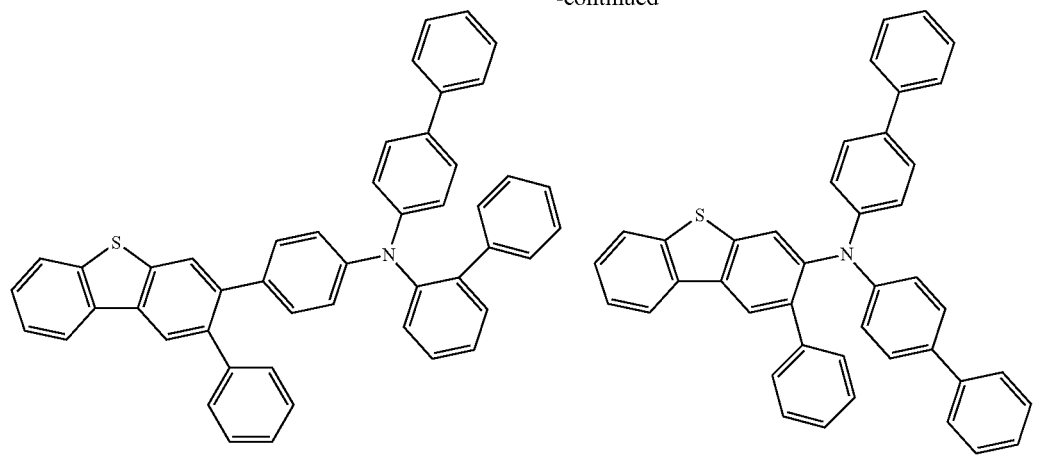
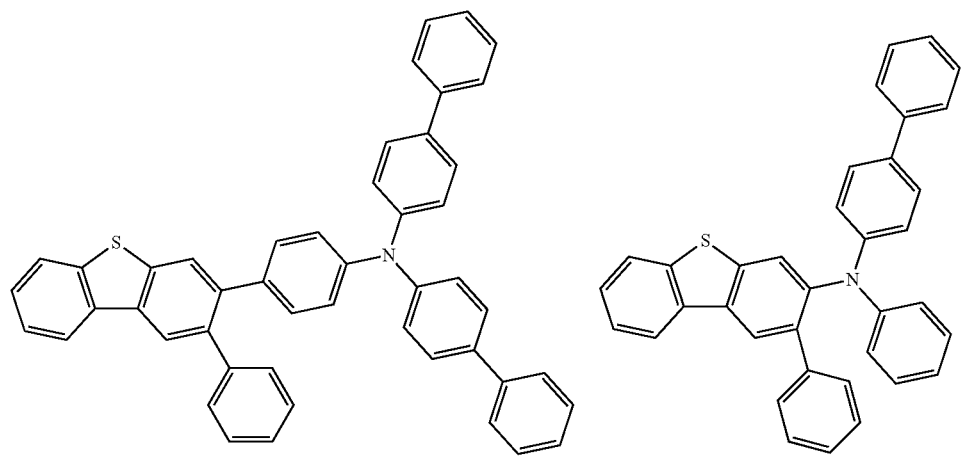
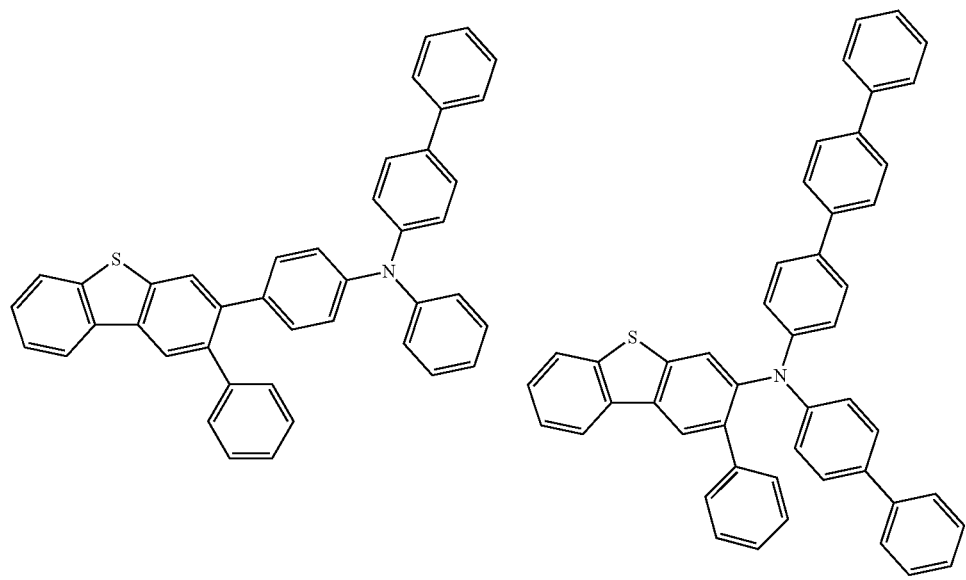

351
352
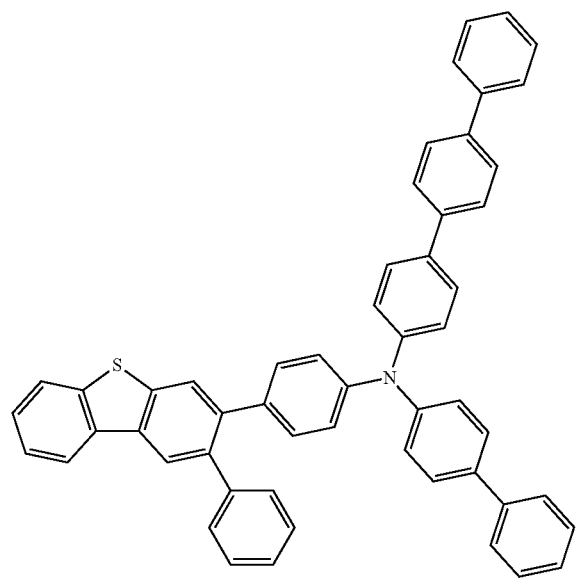
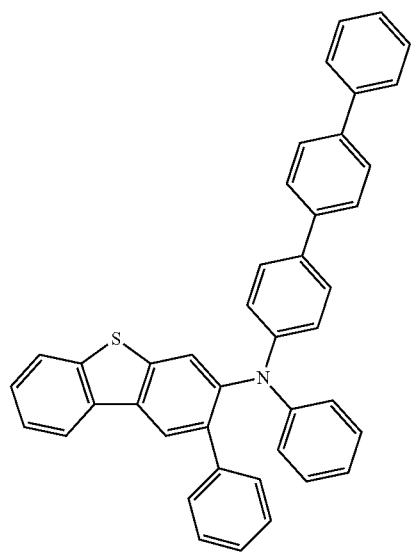
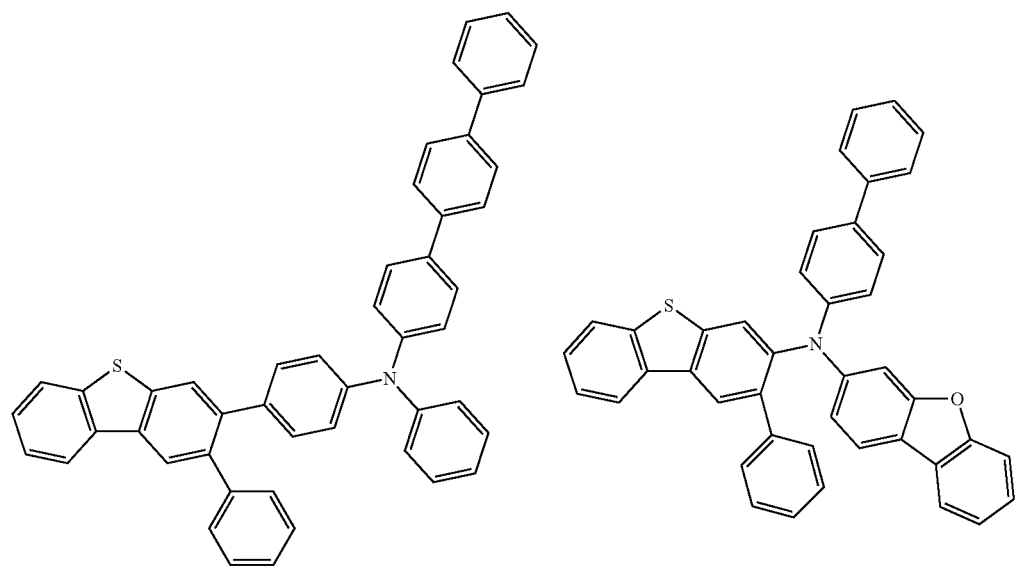
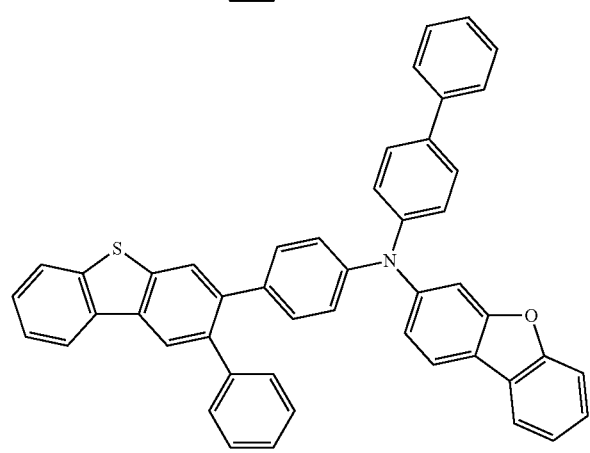
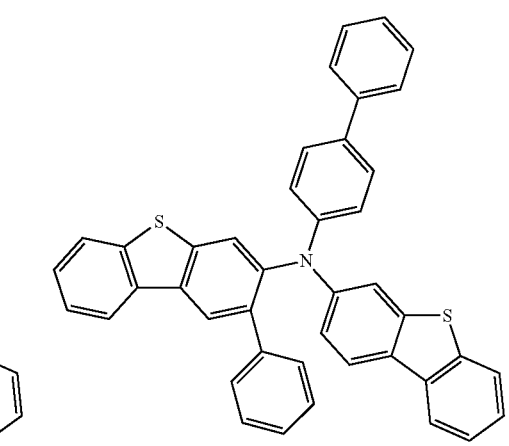

353
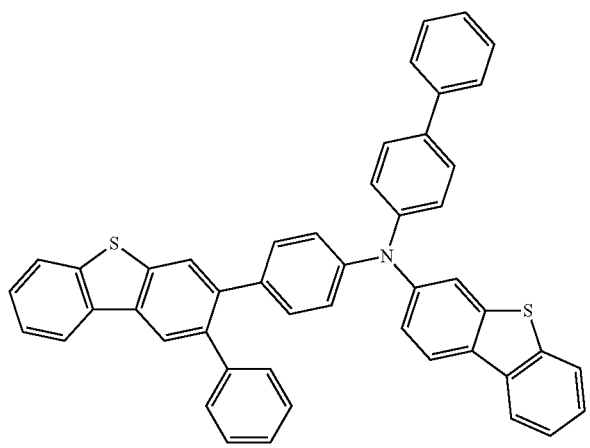
354
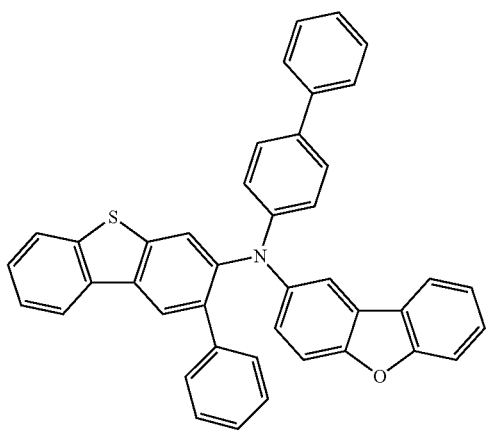
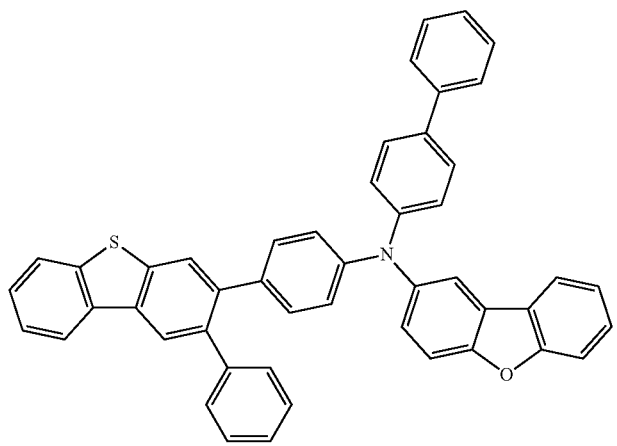
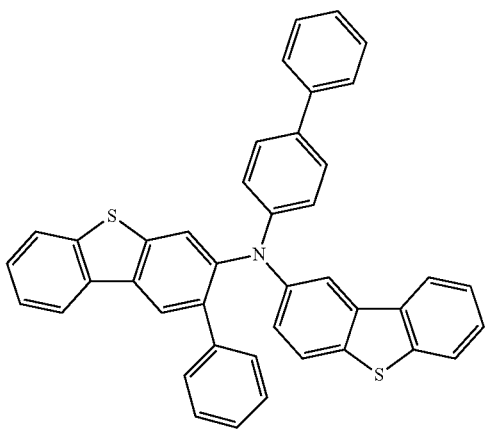
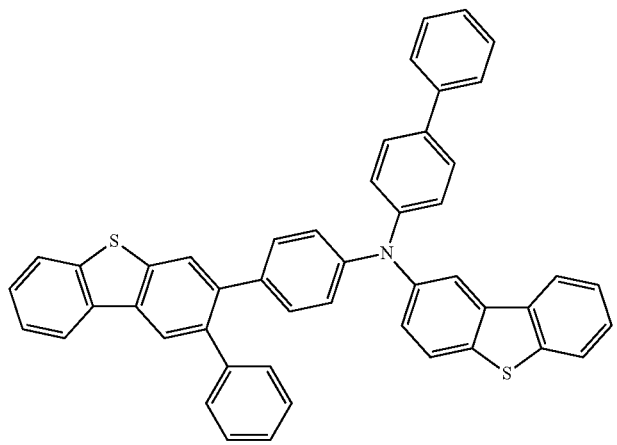
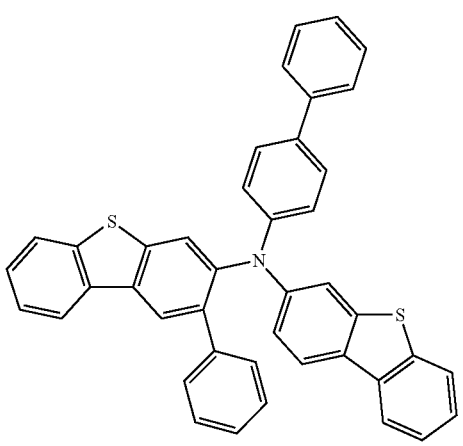

355
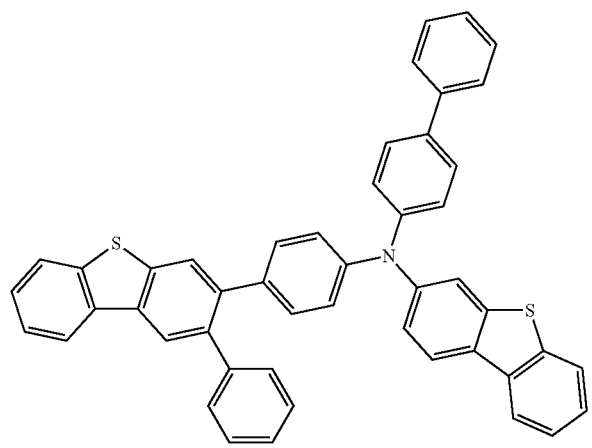
356
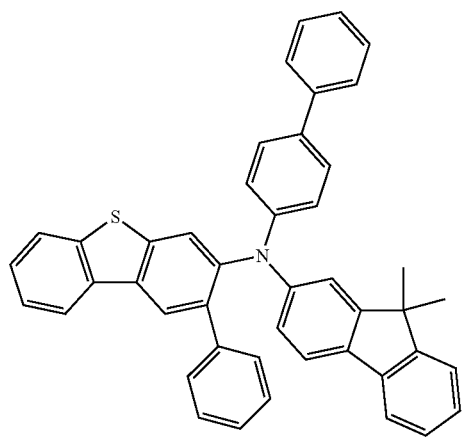
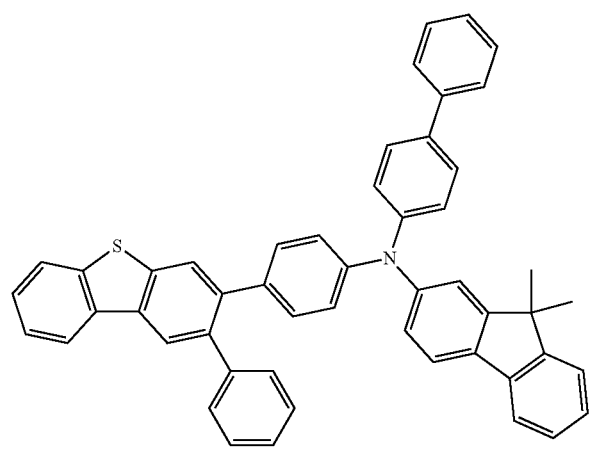
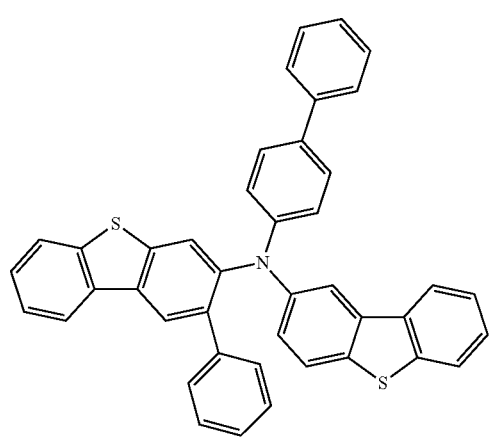
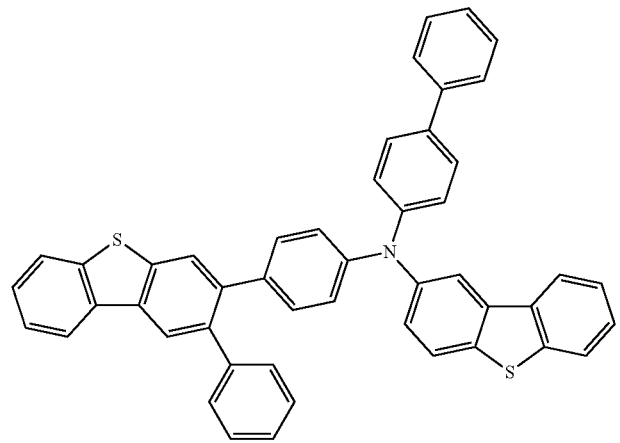
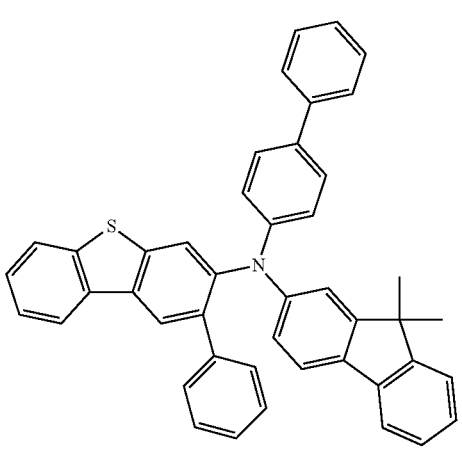

-continued
357
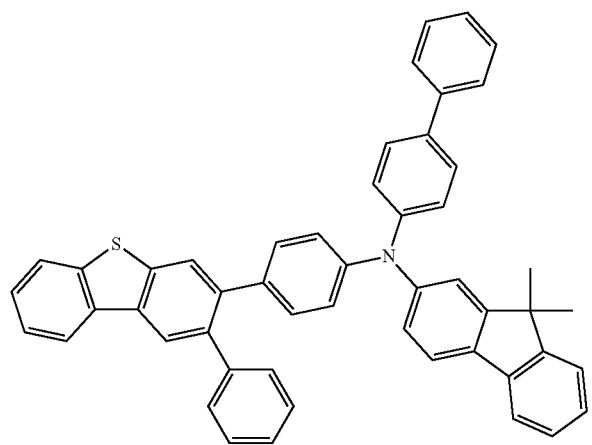
358
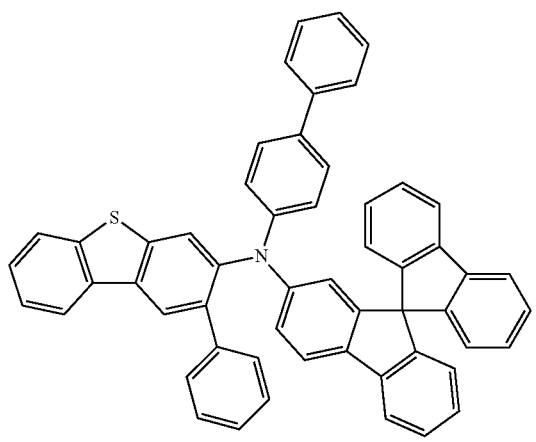
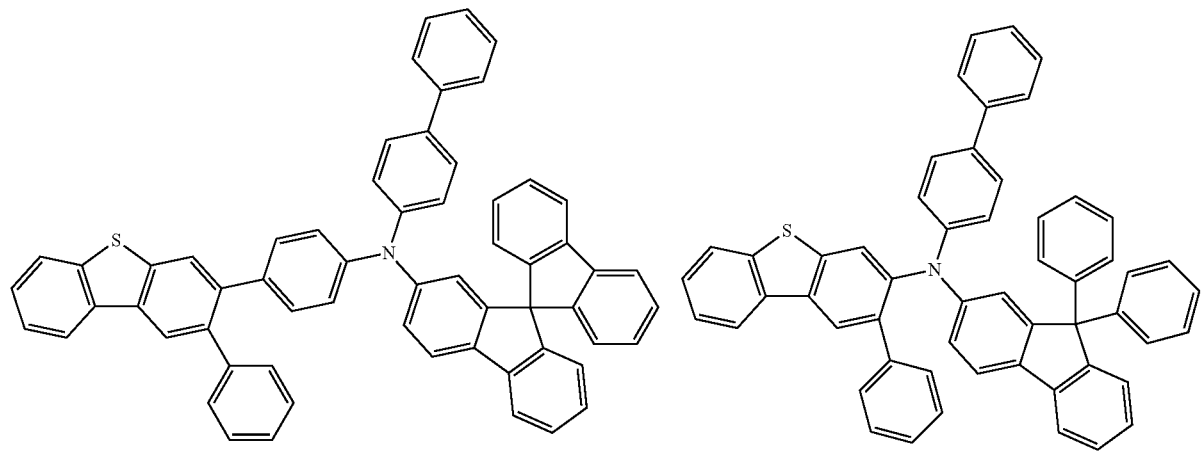
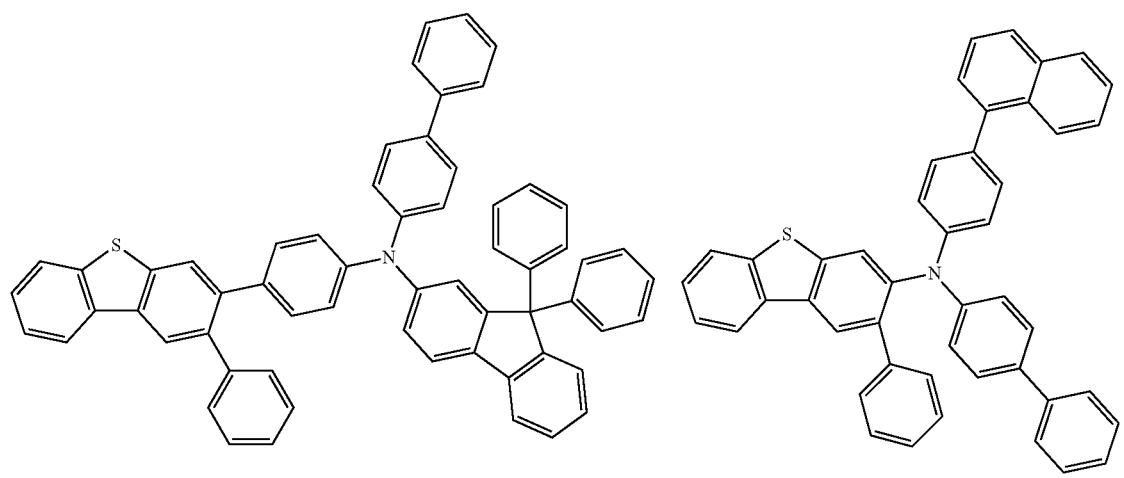

359 360
-continued
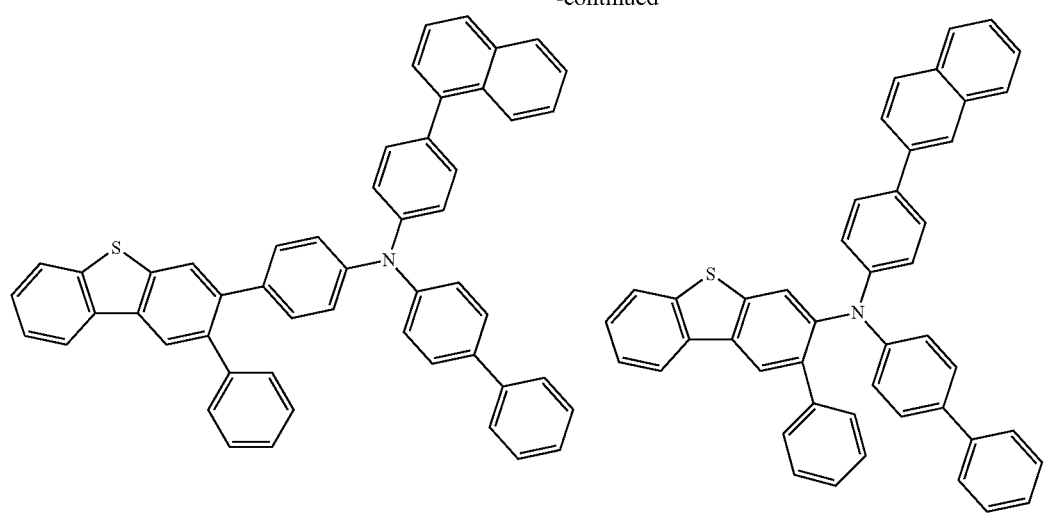
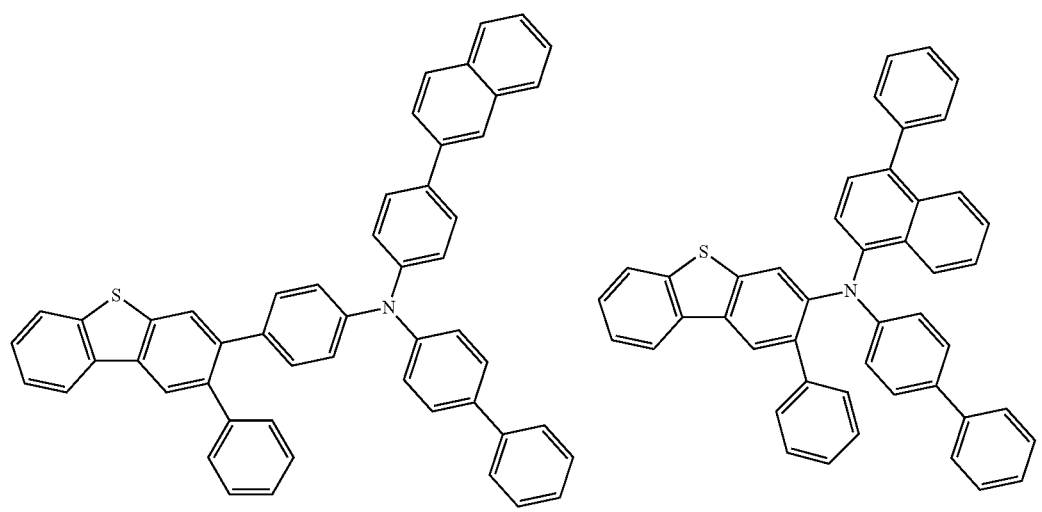
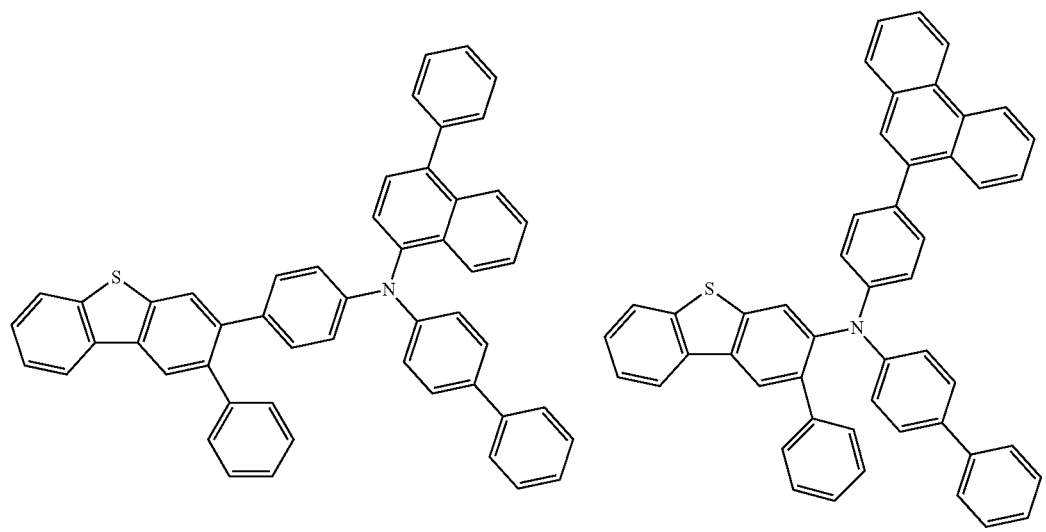

-continued
361
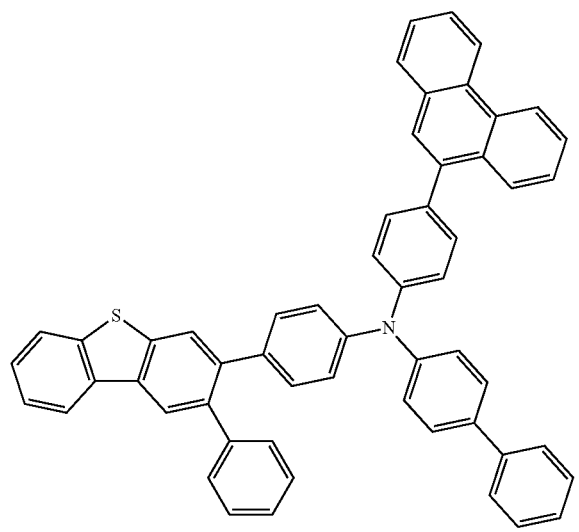
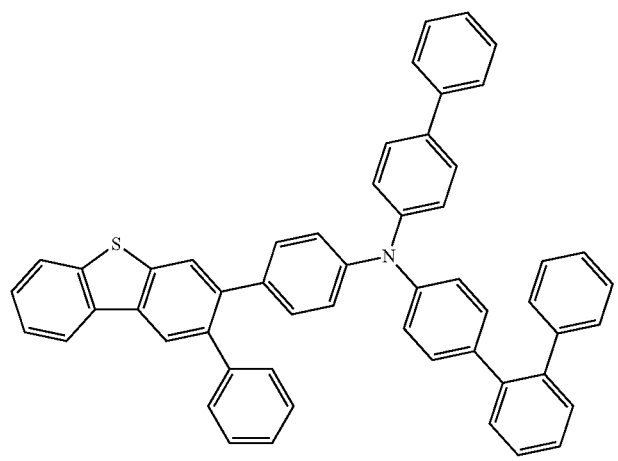
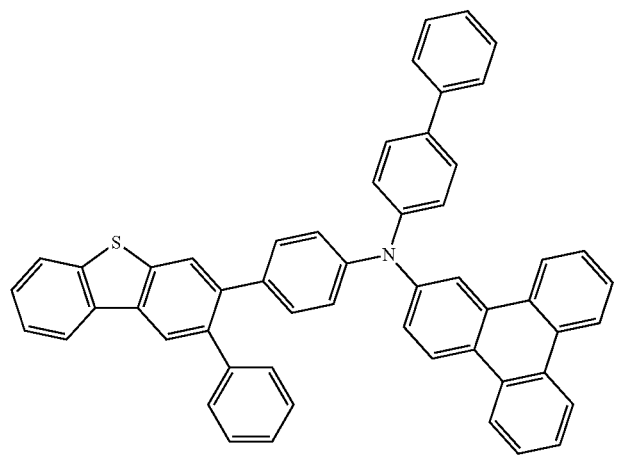
362
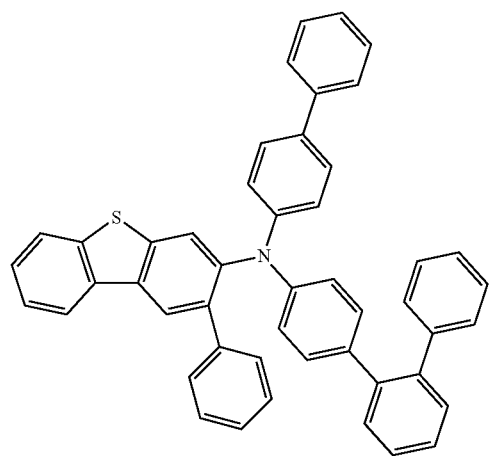
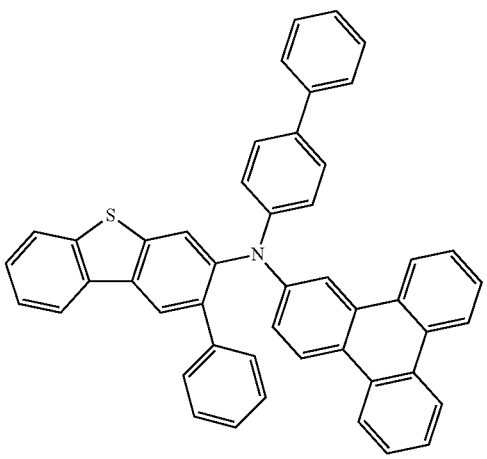
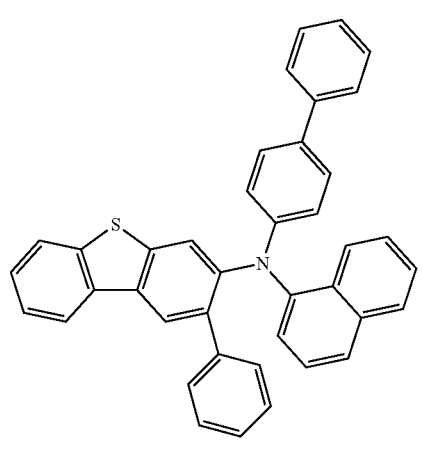

-continued
363
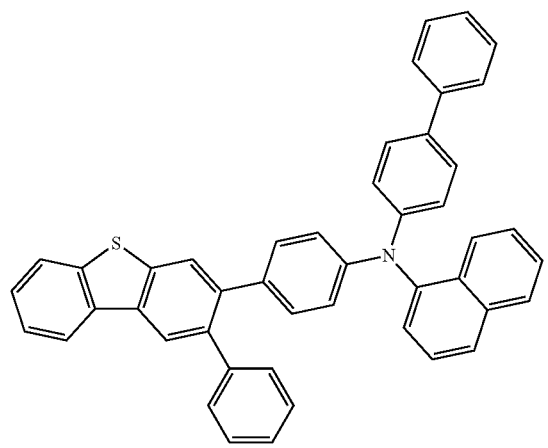
364
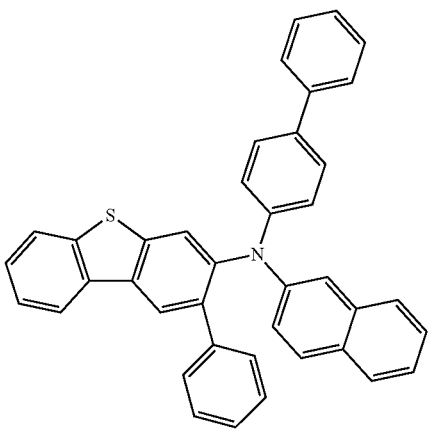
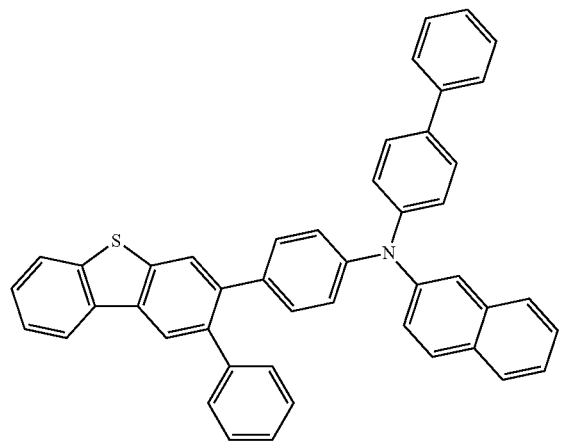
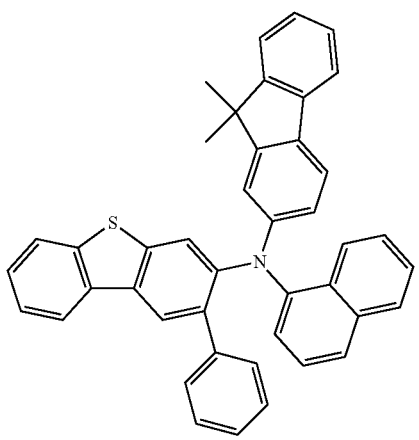
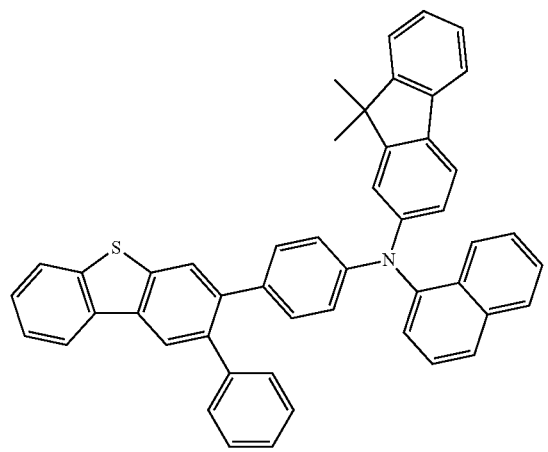
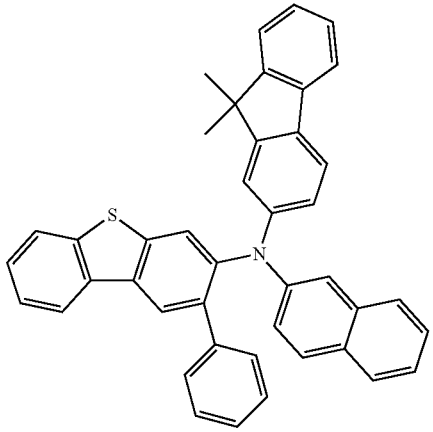

-continued
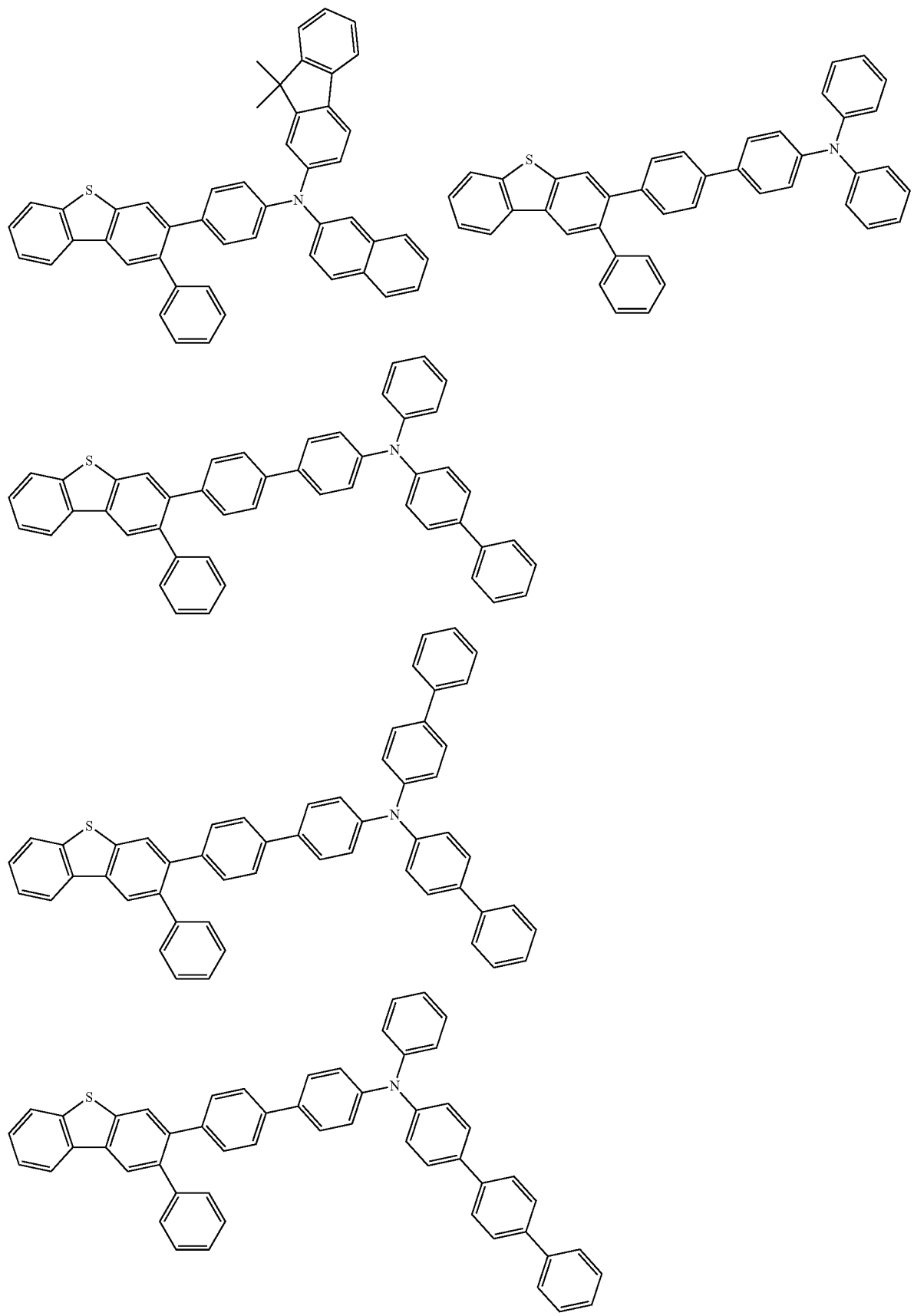

-continued
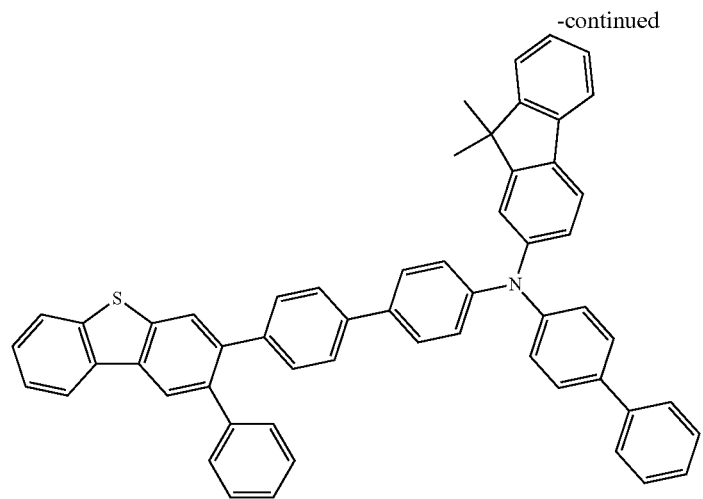
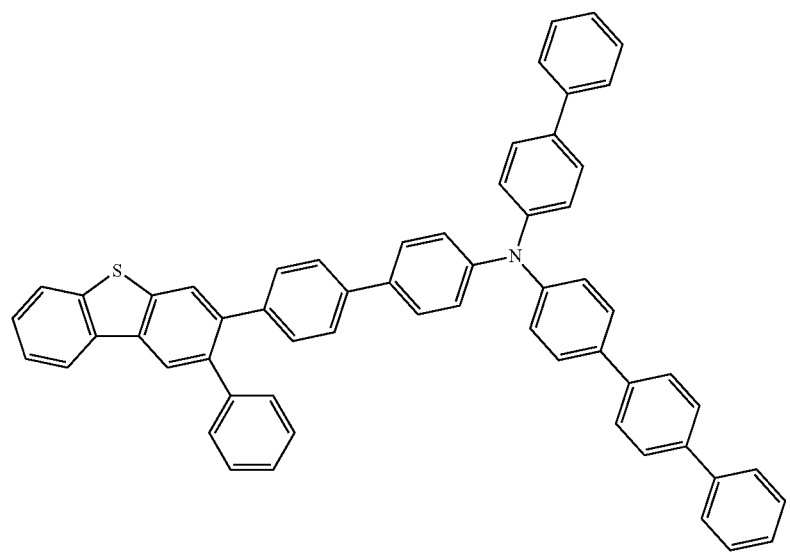
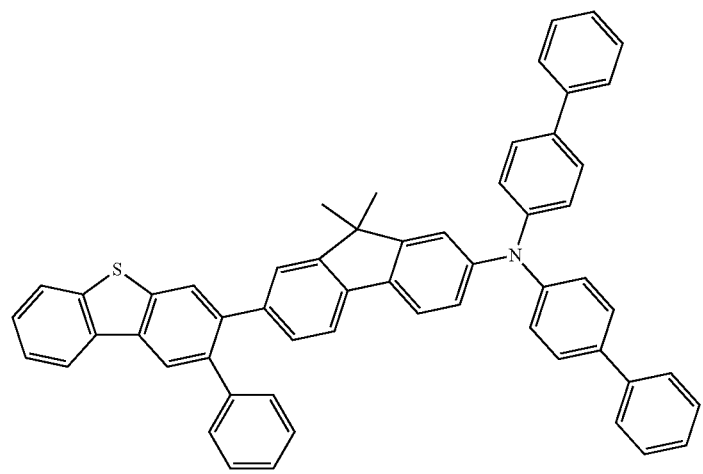

-continued
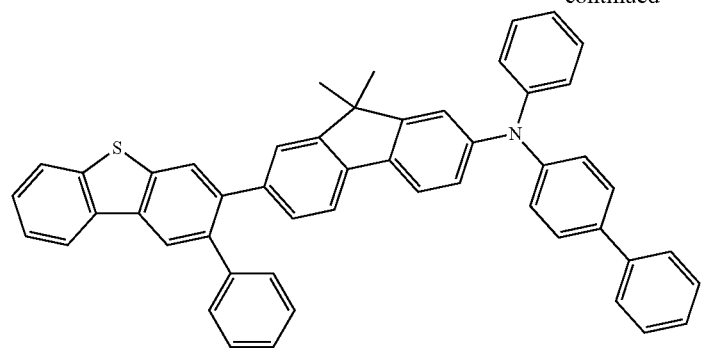
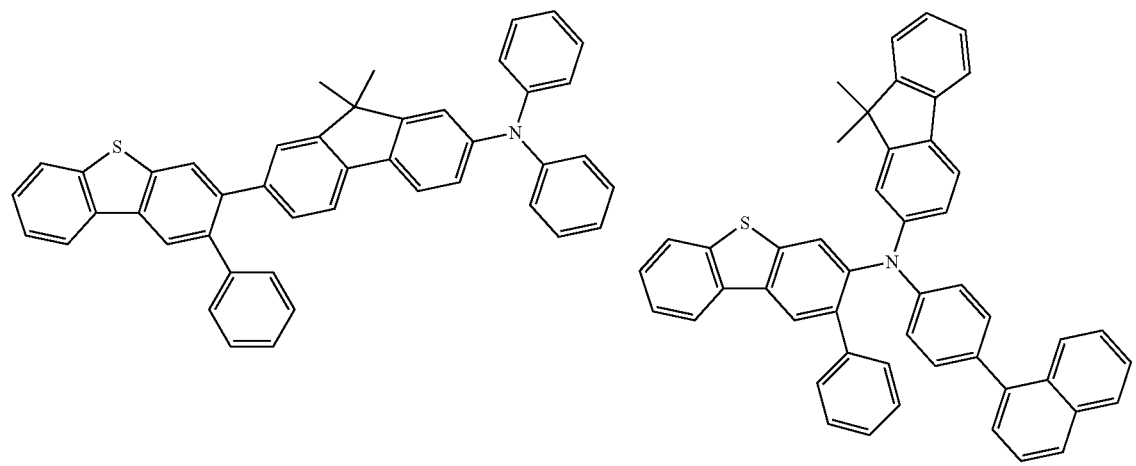
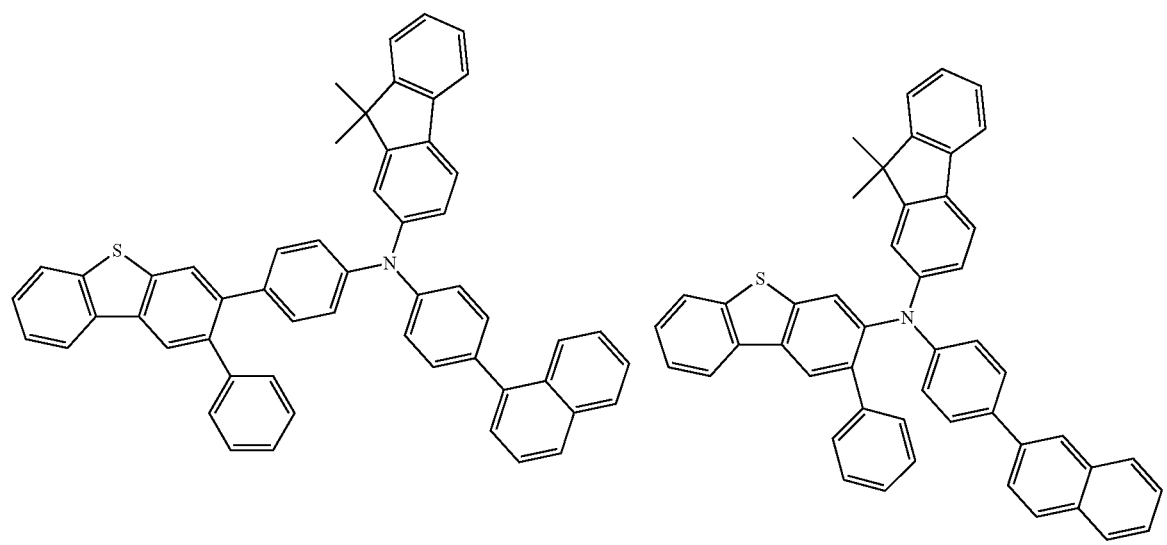

371  372
-continued
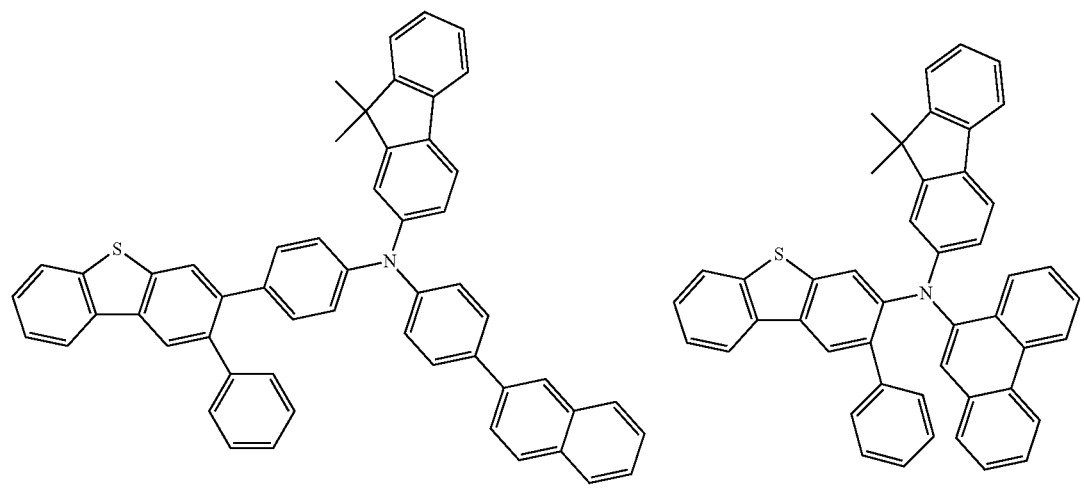
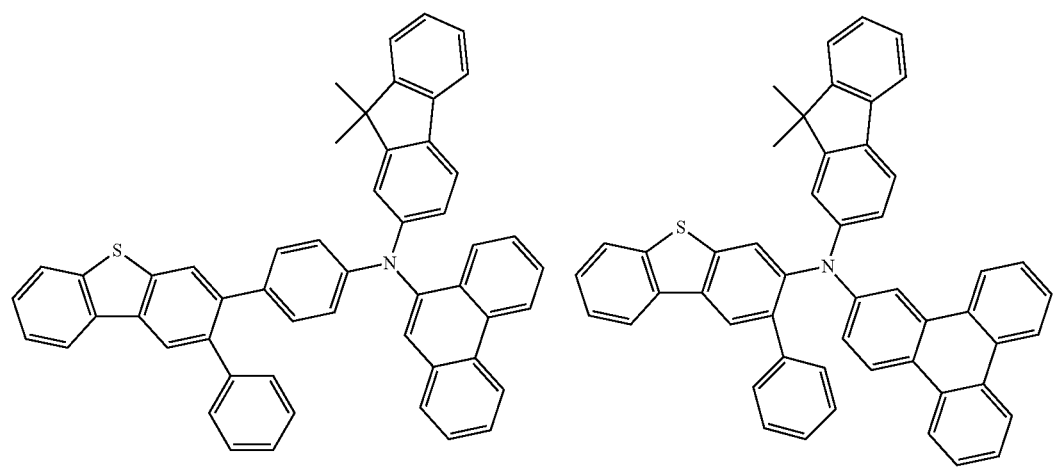
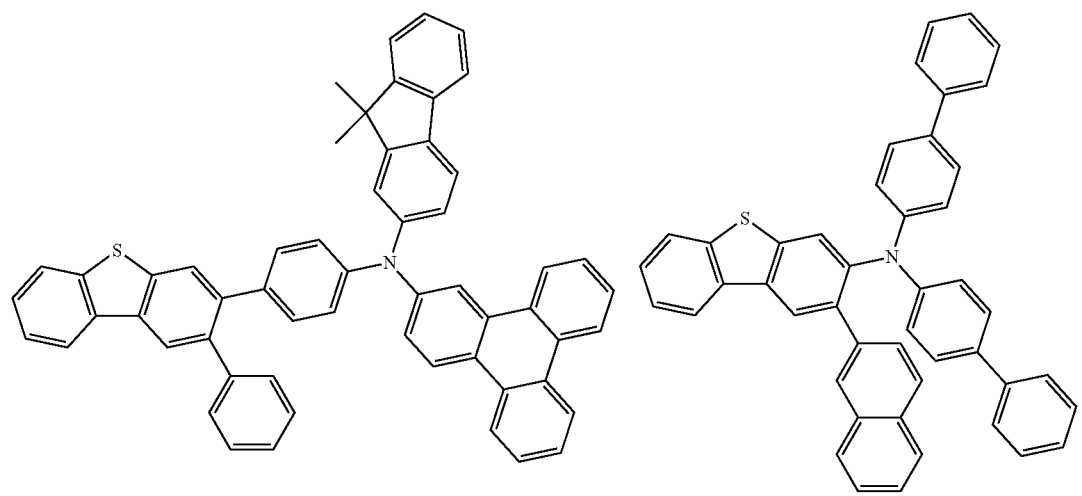

373 374
-continued
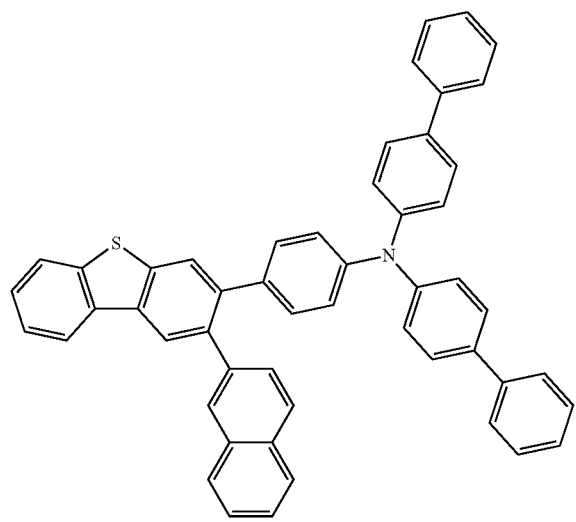 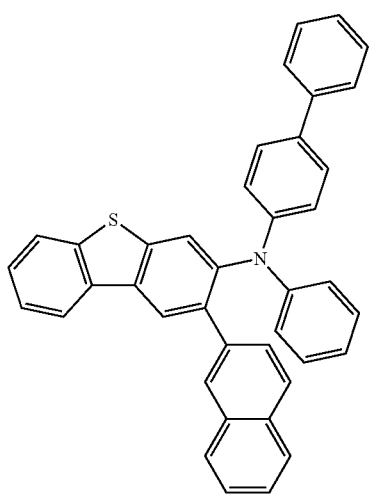
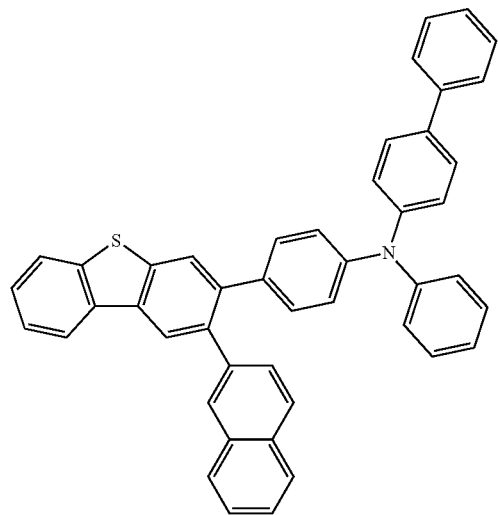 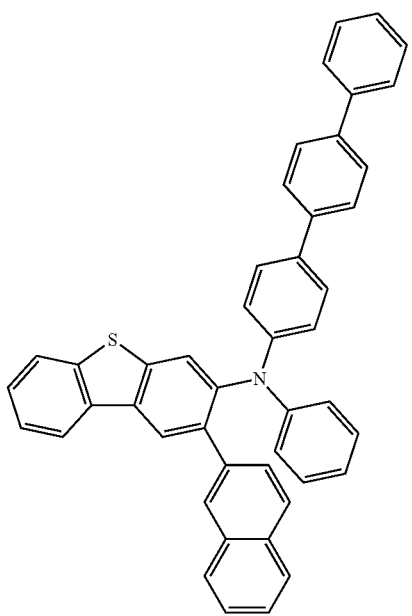

-continued
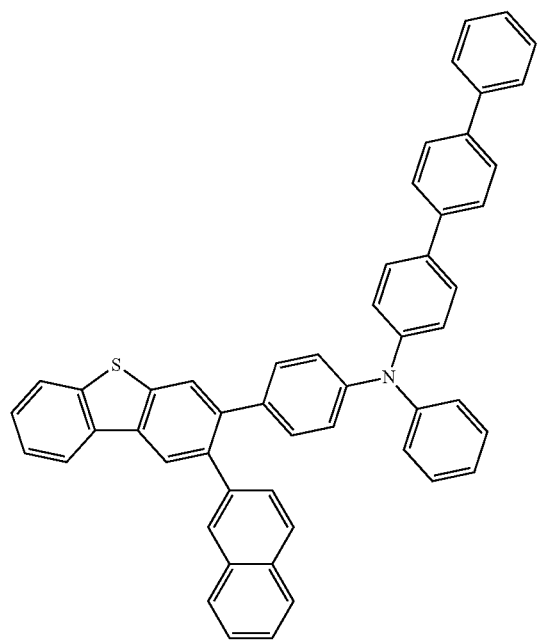
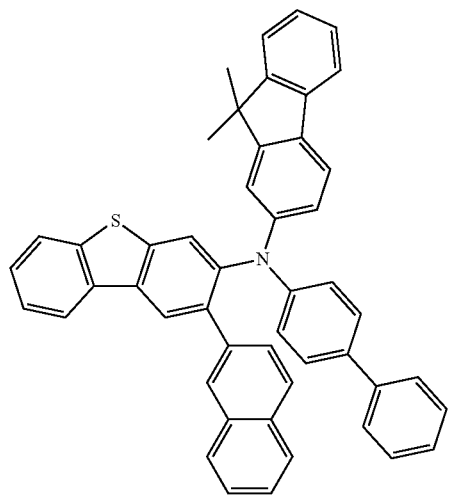
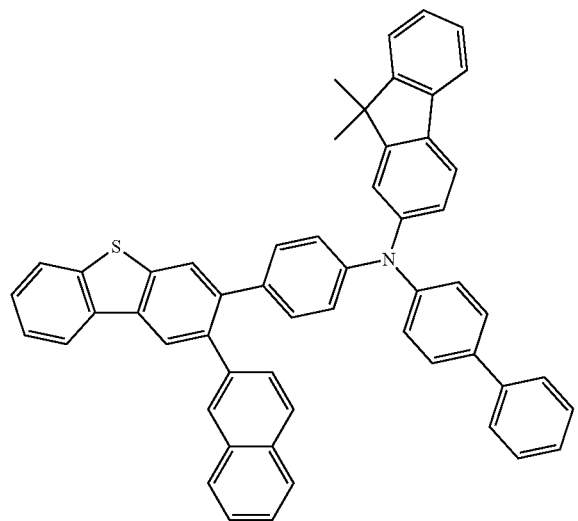
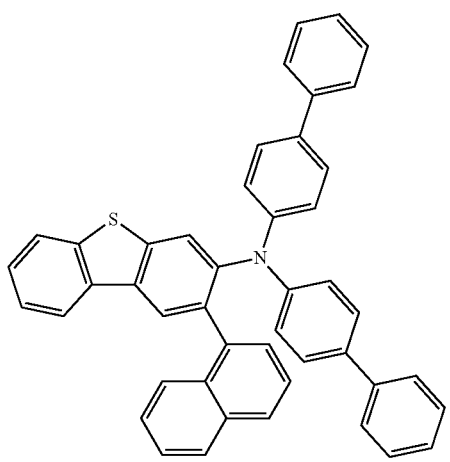
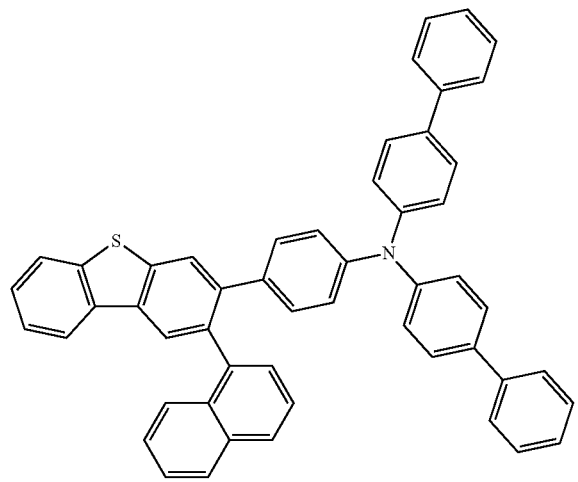
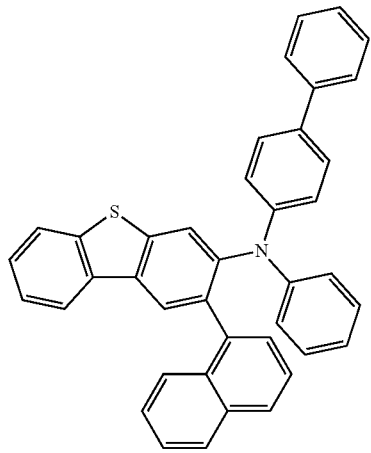

-continued
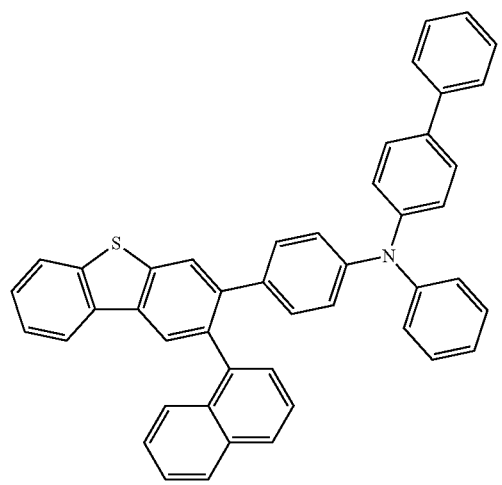
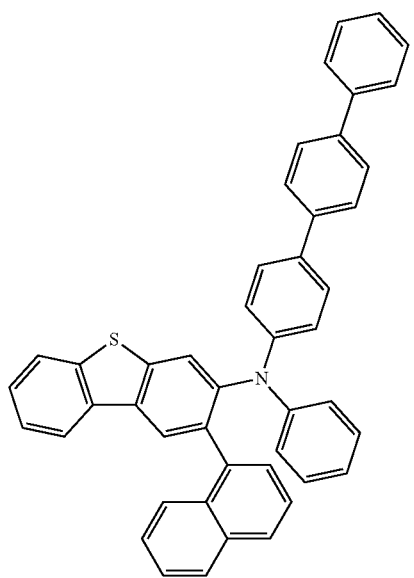
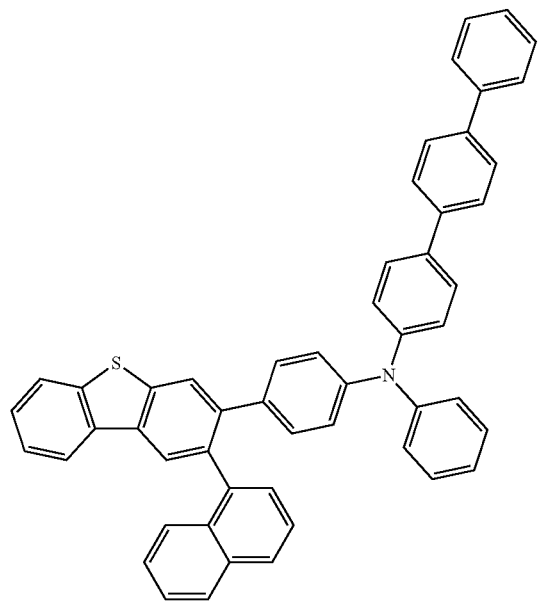
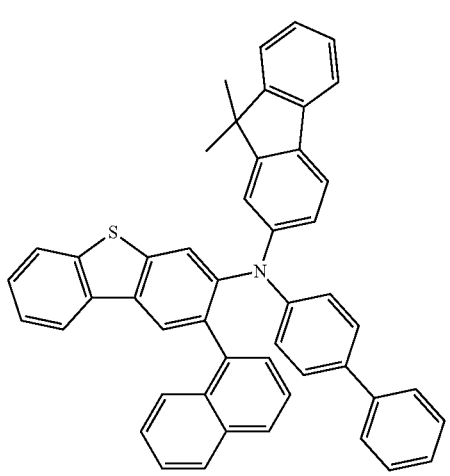
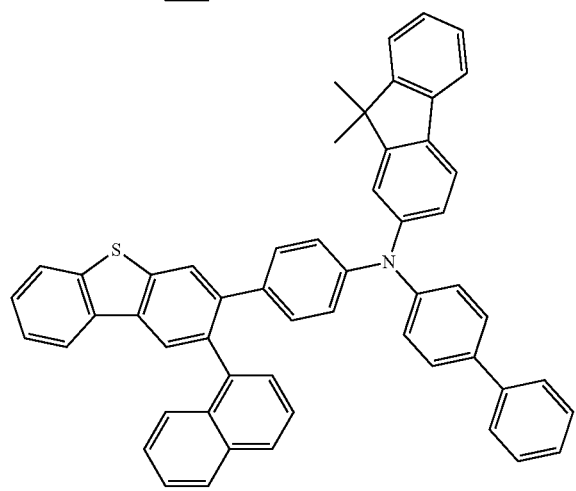
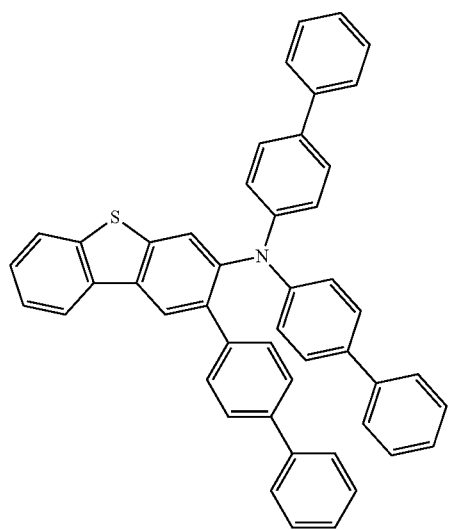

-continued
379
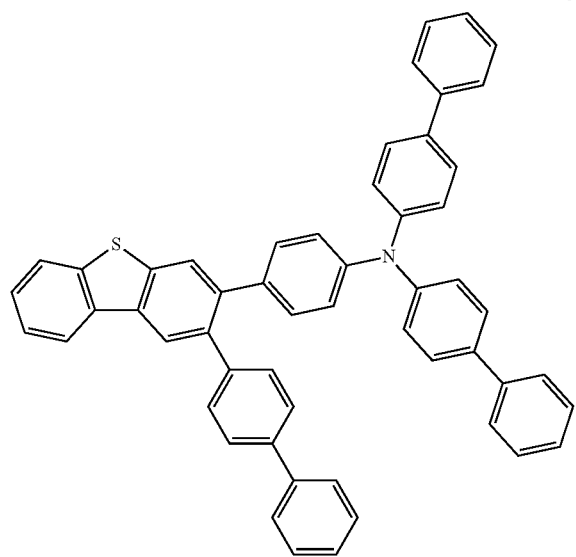
380
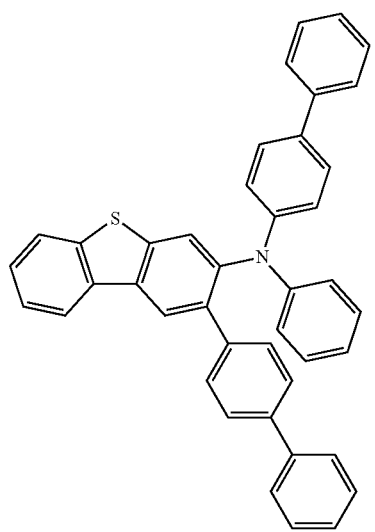
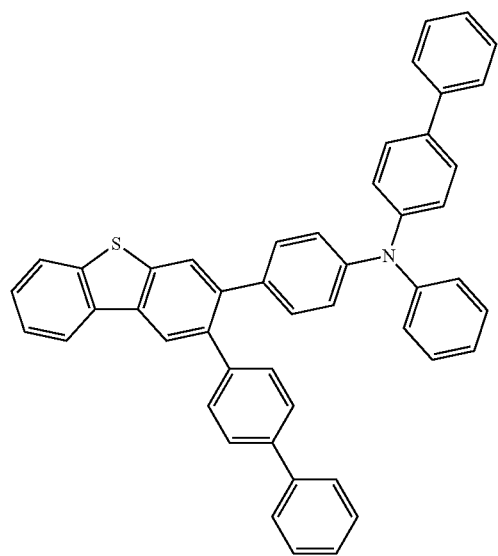
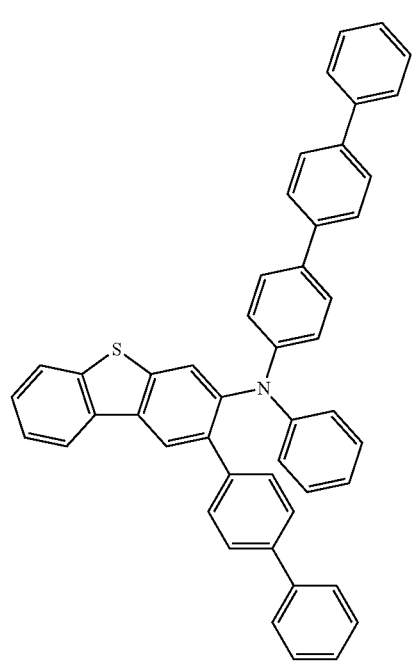

-continued
| 381 | 382 |
|---|---|
| 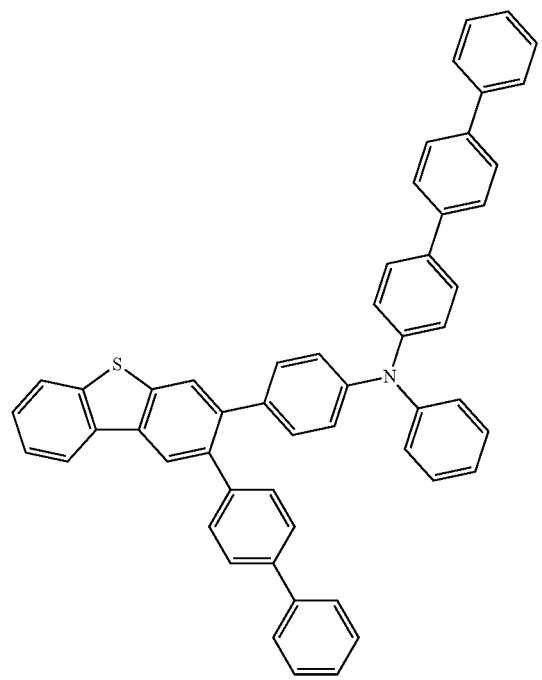 | 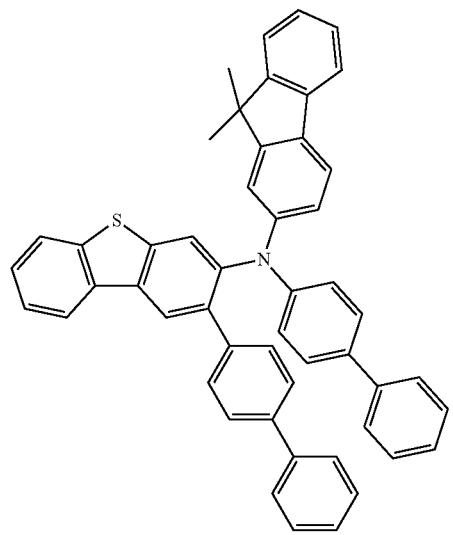 |
| 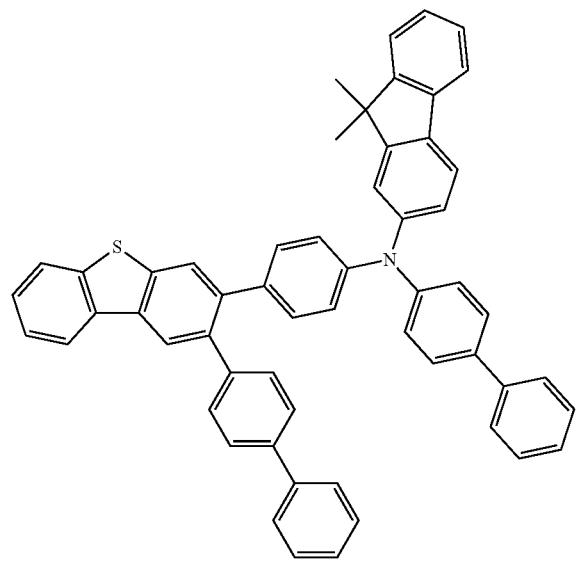 | 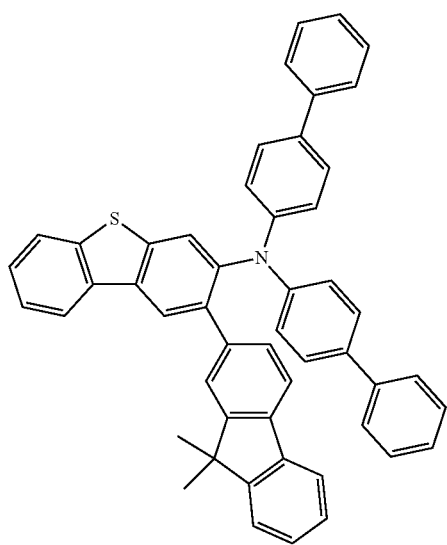 |

-continued
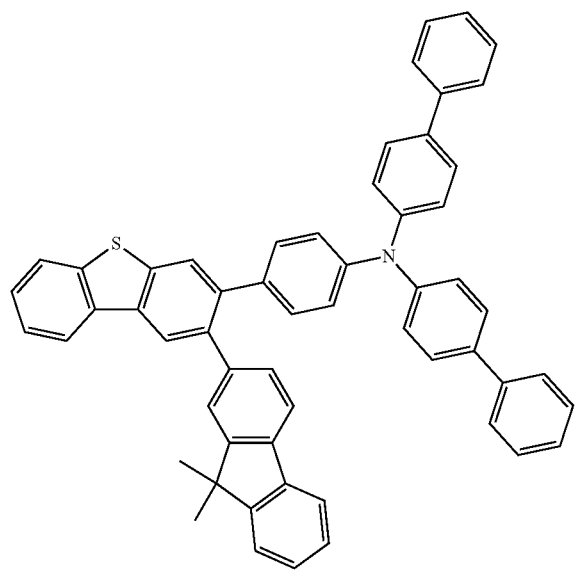 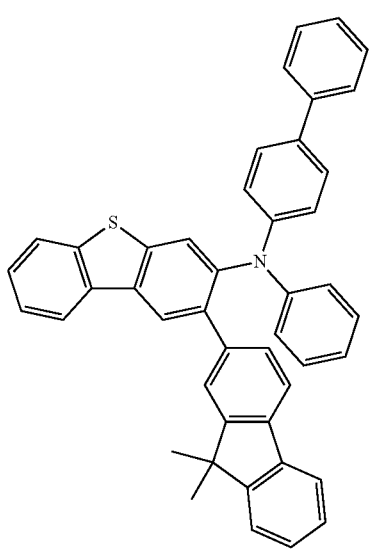
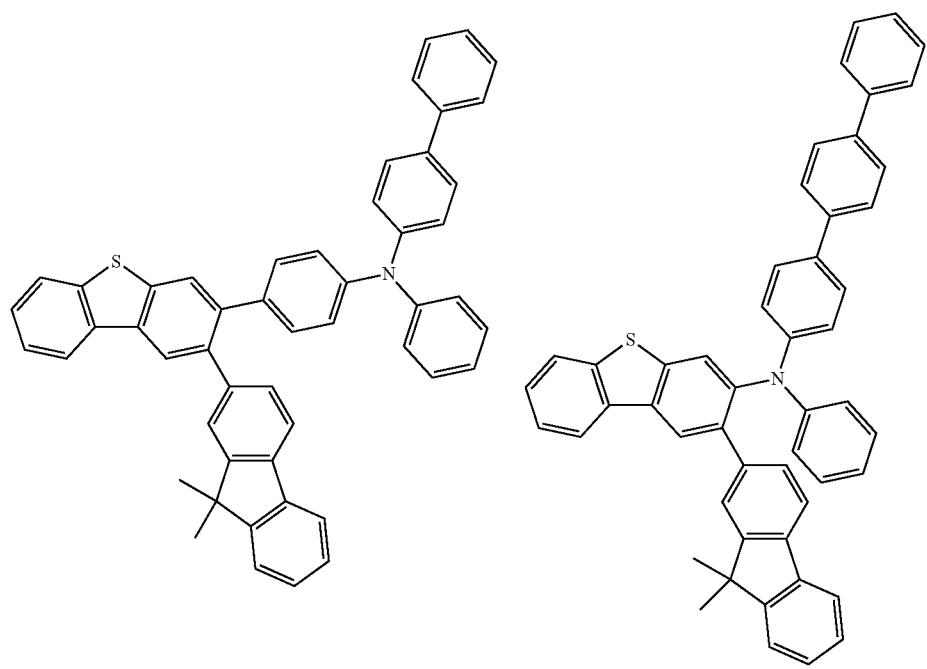

-continued
| 385 | 386 |
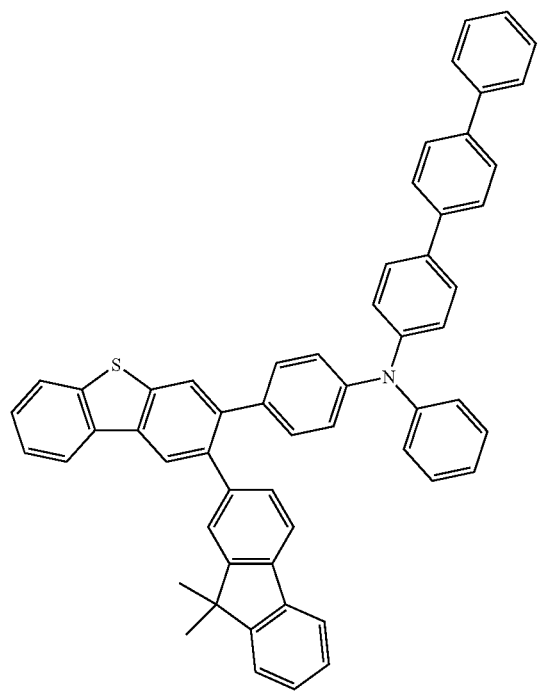
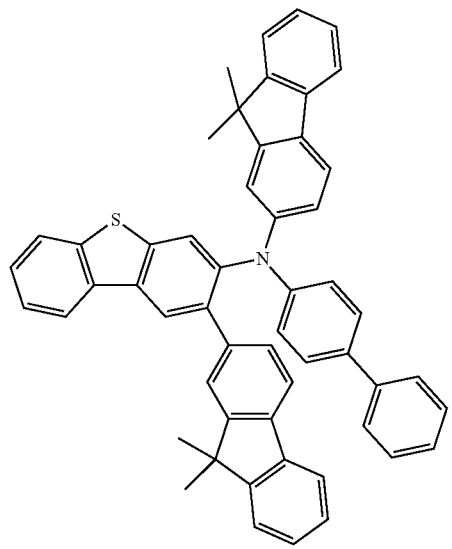
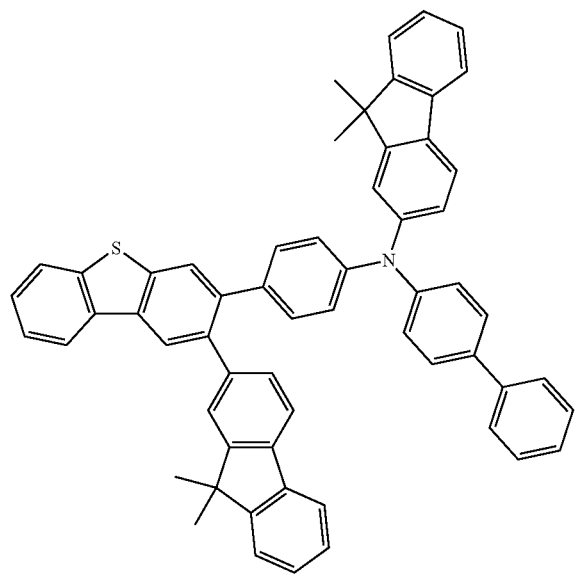
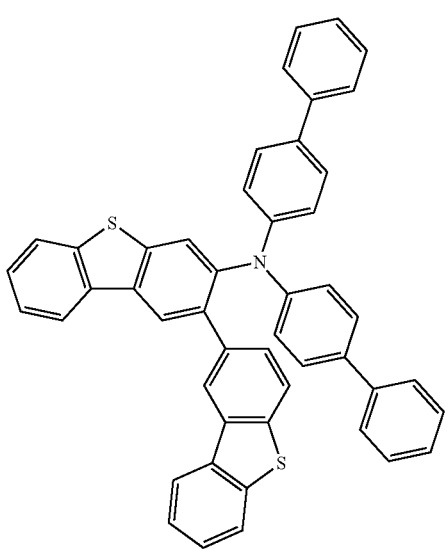

387
388
-continued
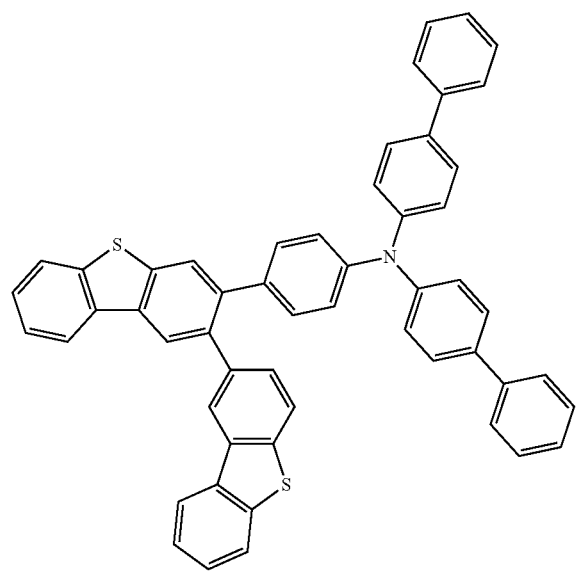
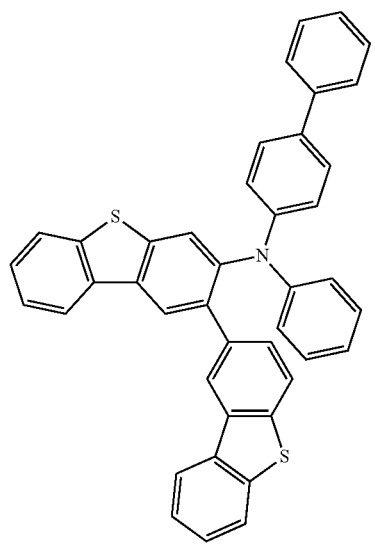
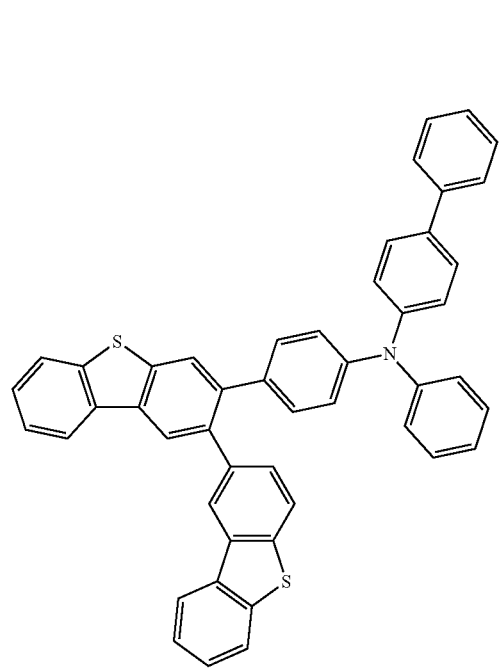
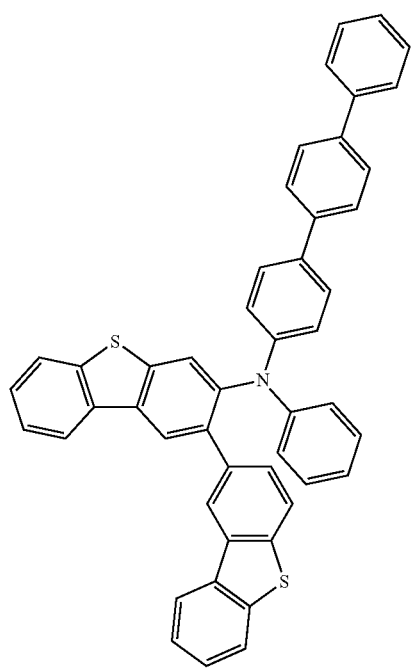

389
390
-continued
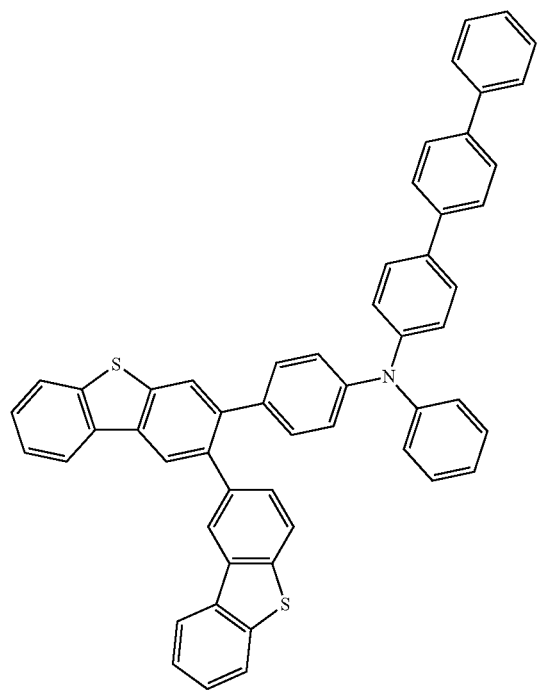
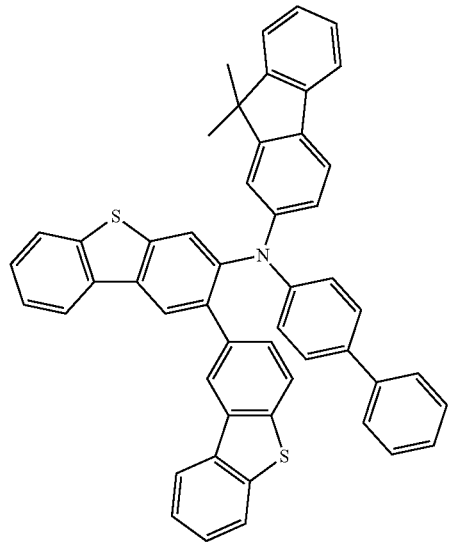
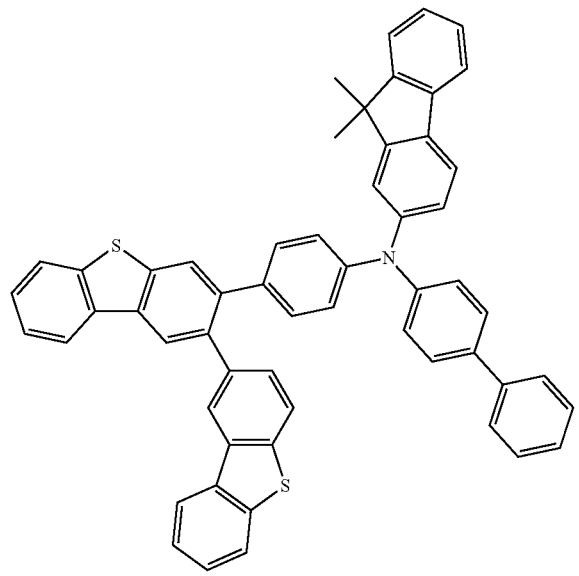
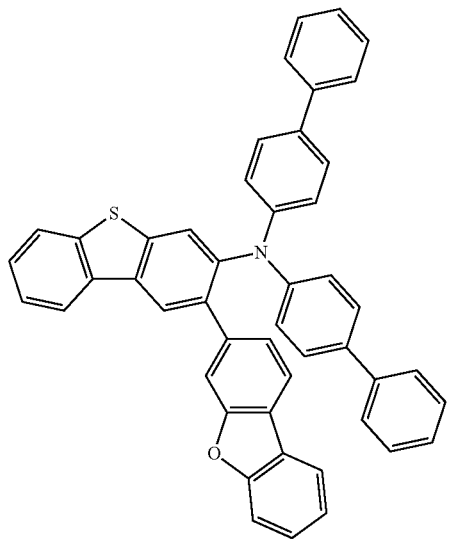

391 392
-continued
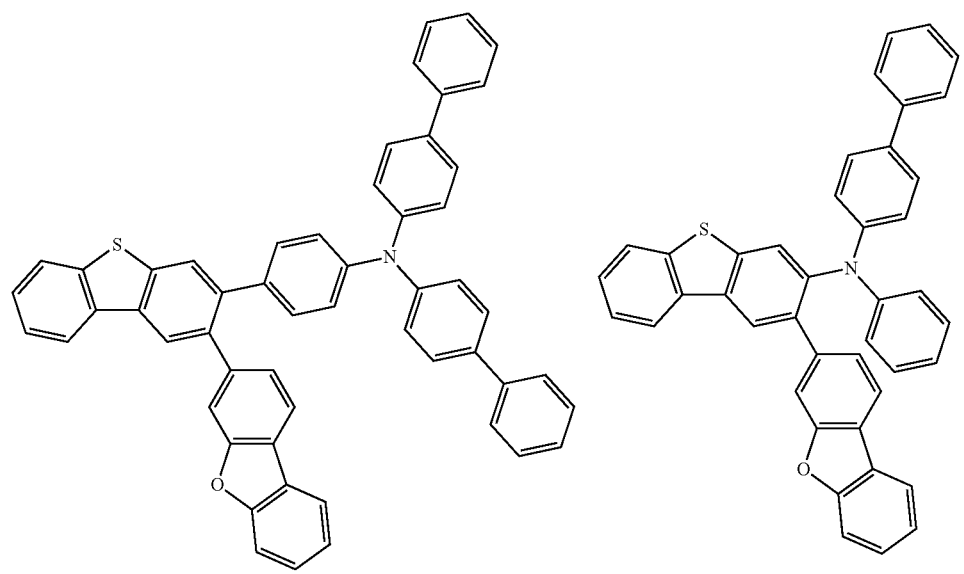
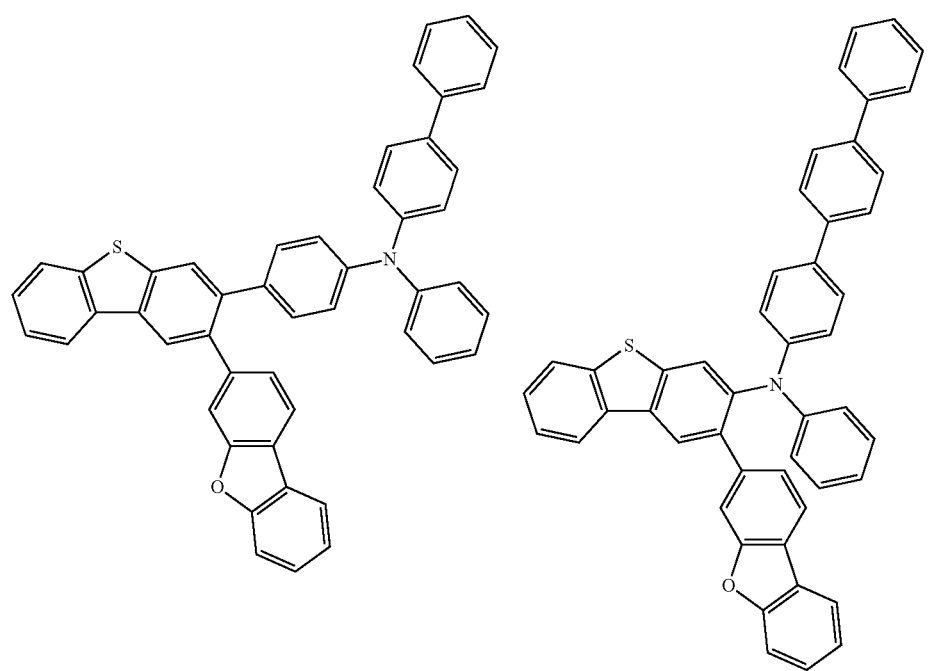

-continued
393
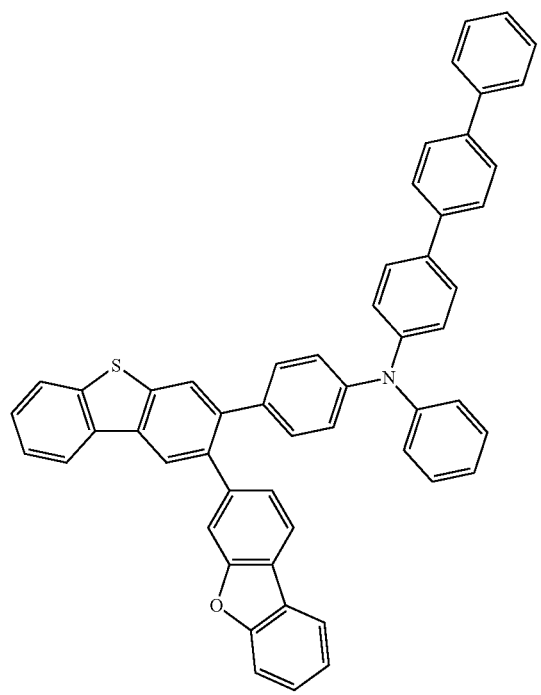
394
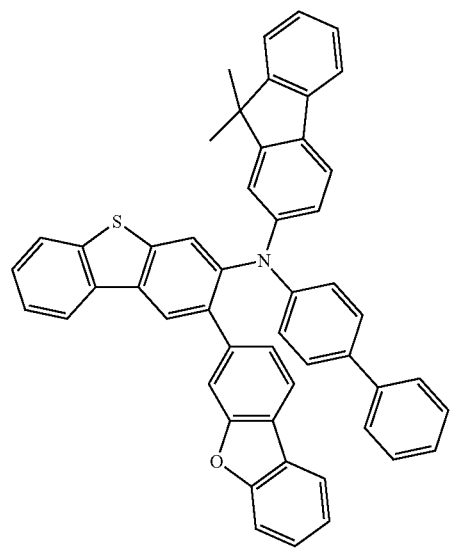
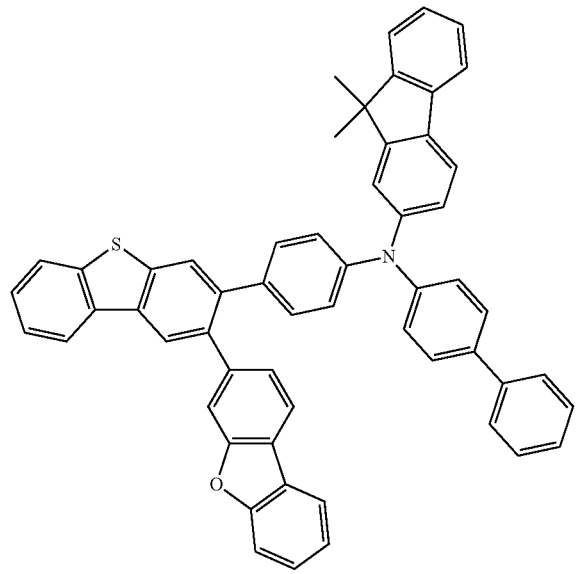
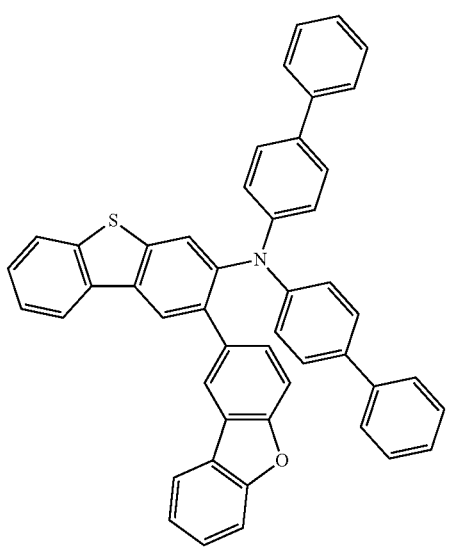

395 396
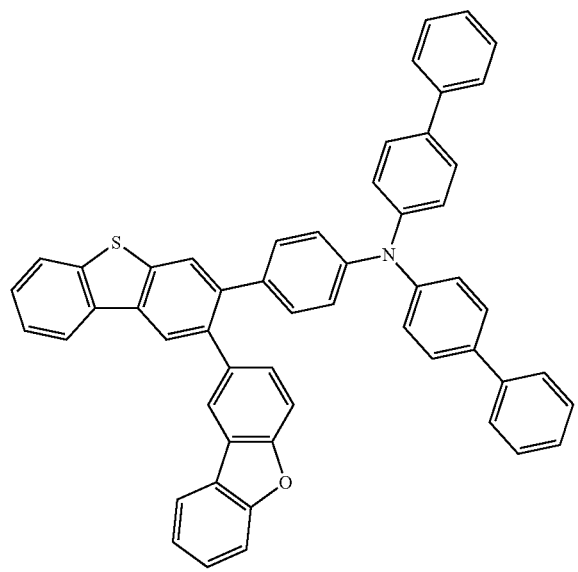 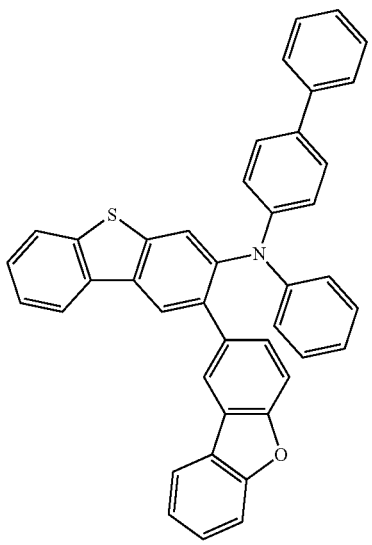
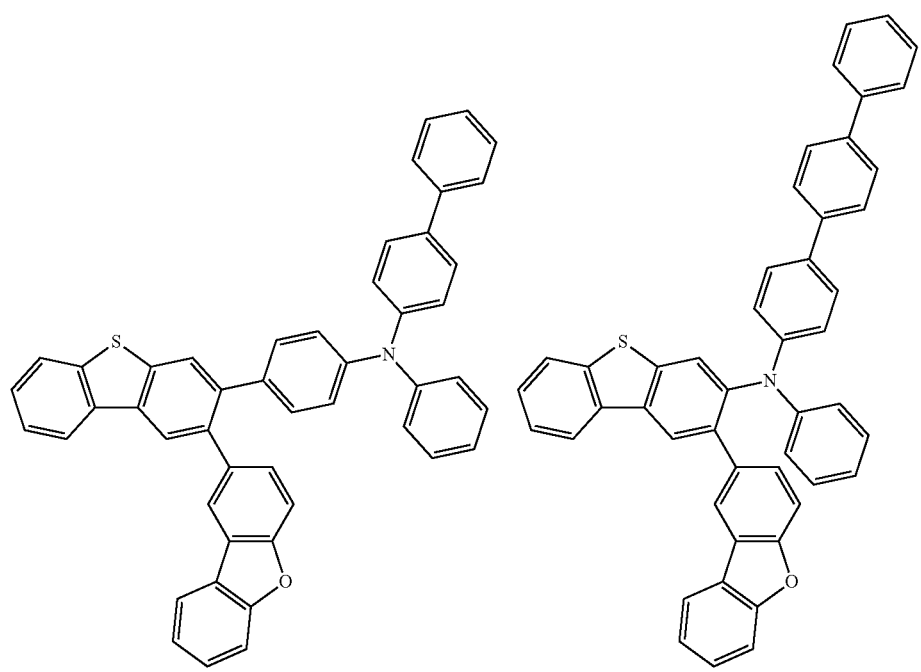

397 398
-continued
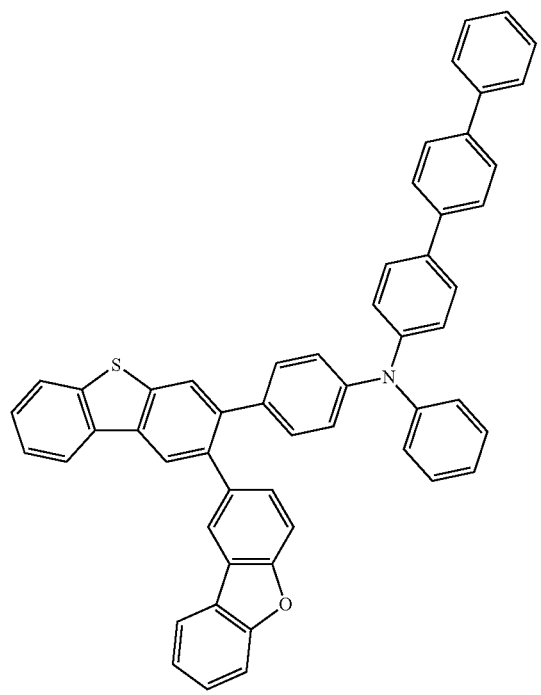 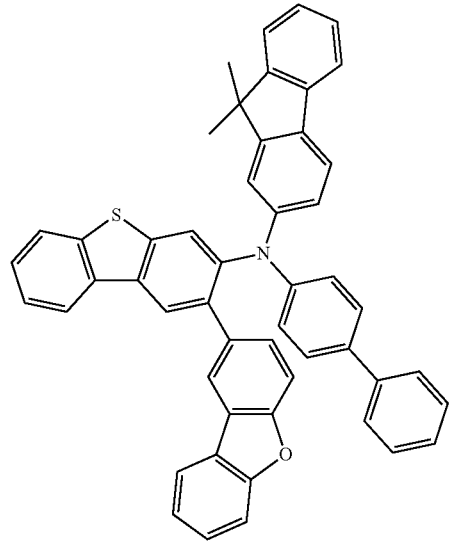
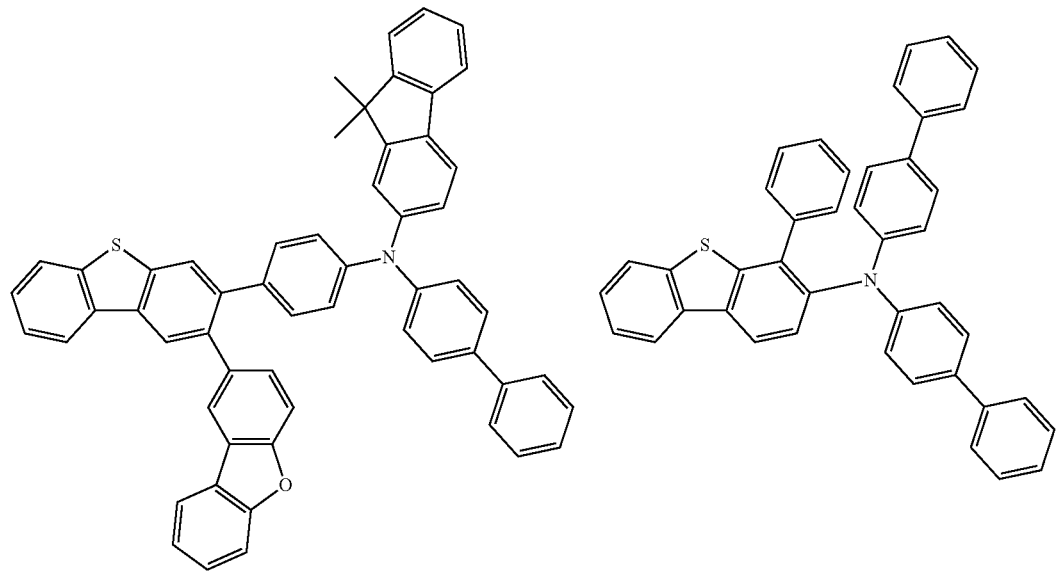

399
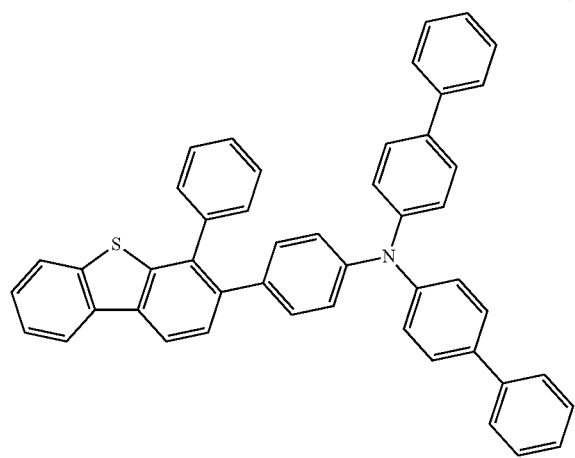
400
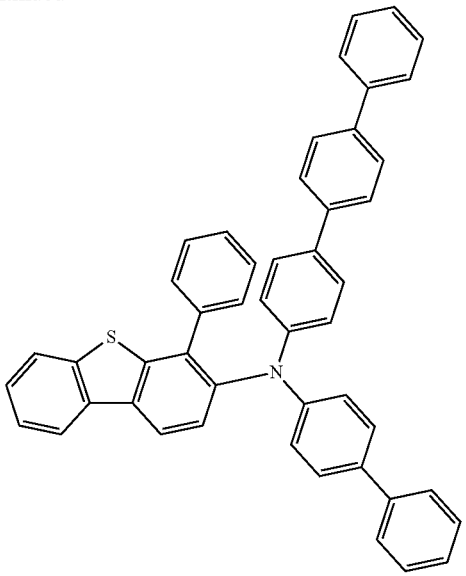
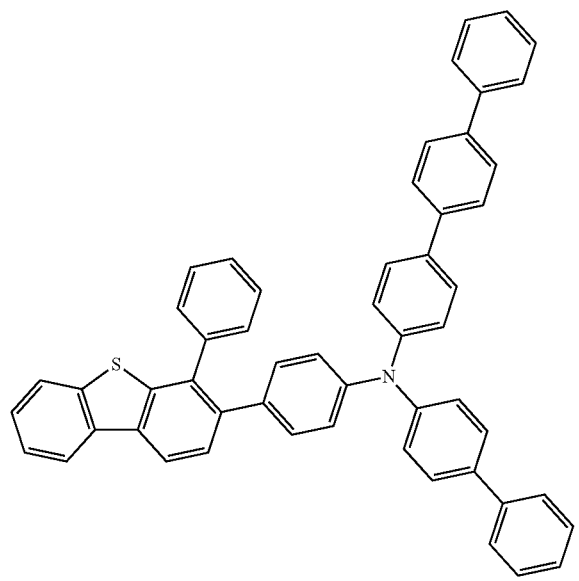
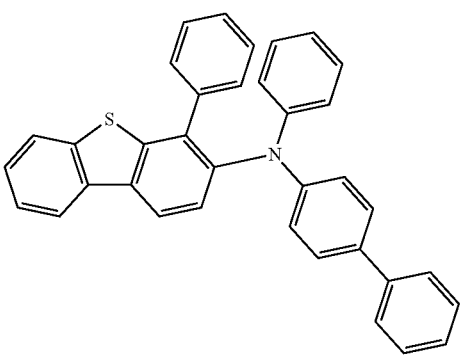
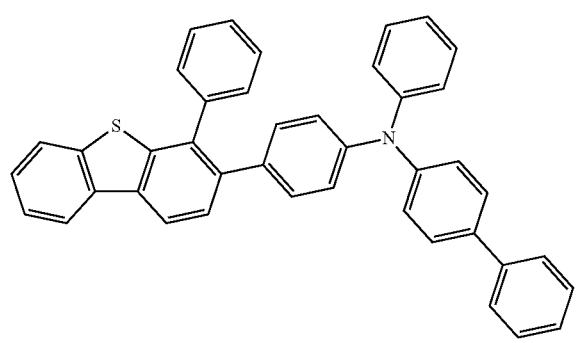
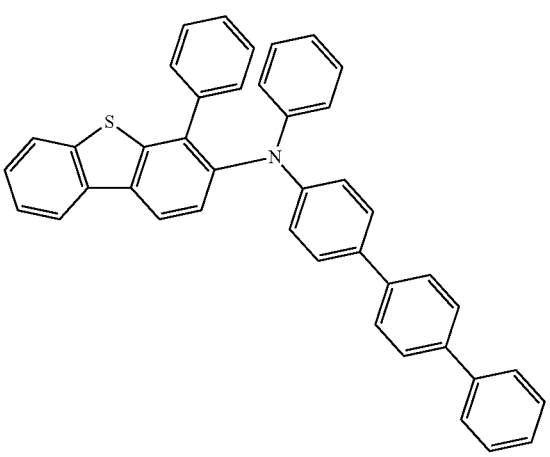

-continued
| 401 | 402 |
|---|---|
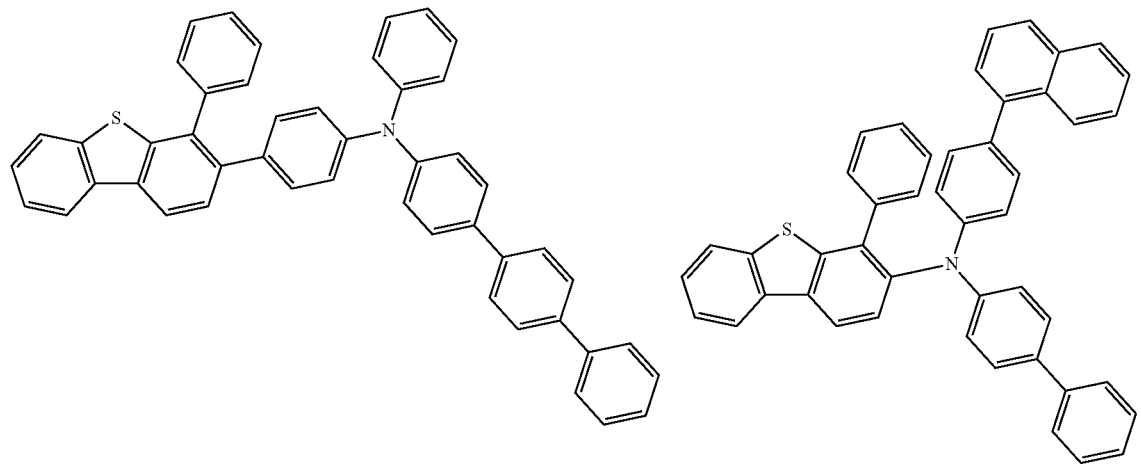
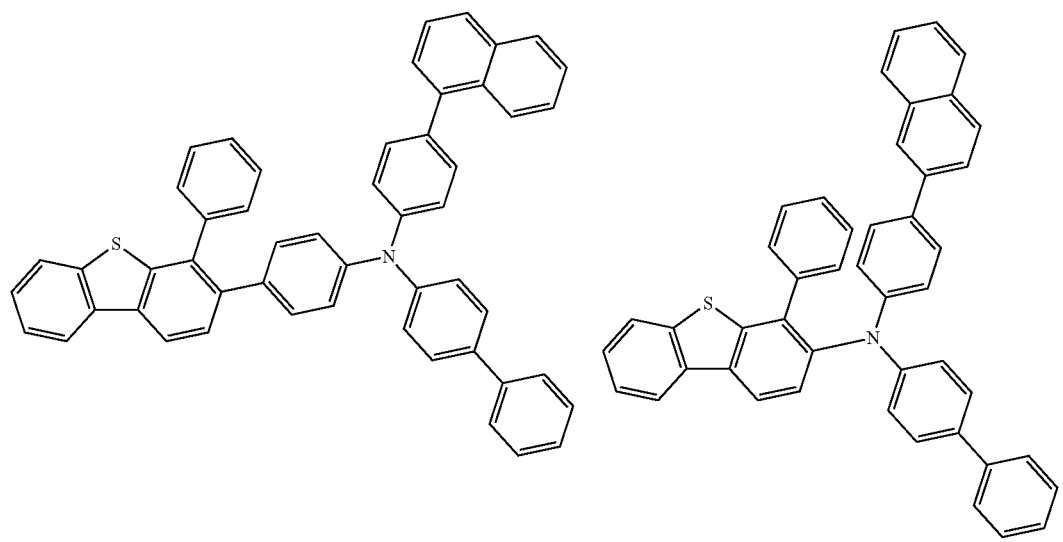
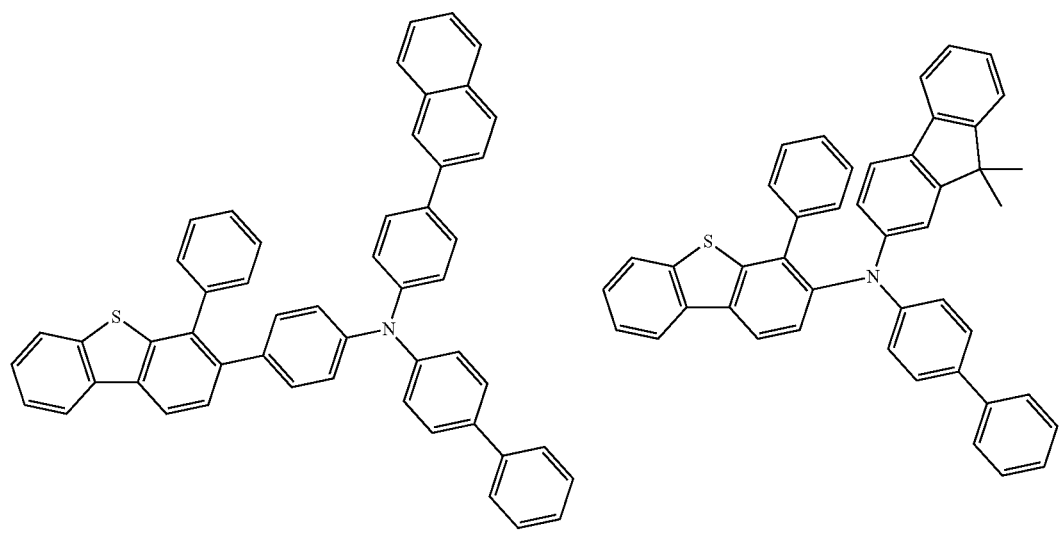

-continued
403
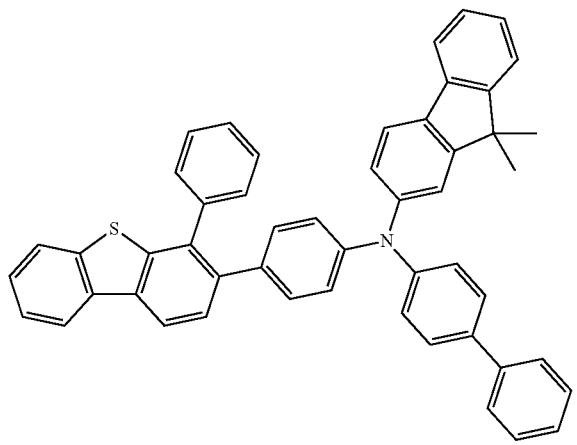
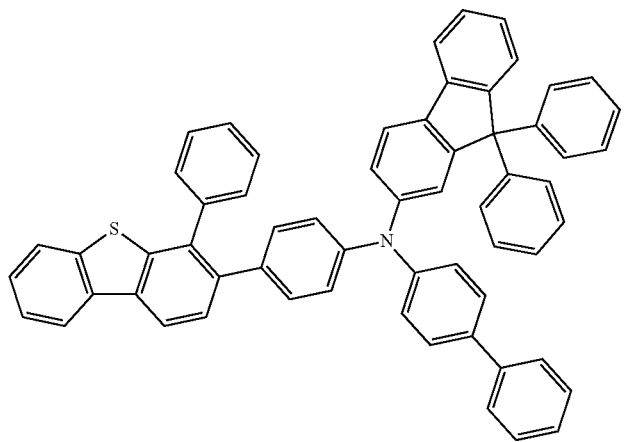
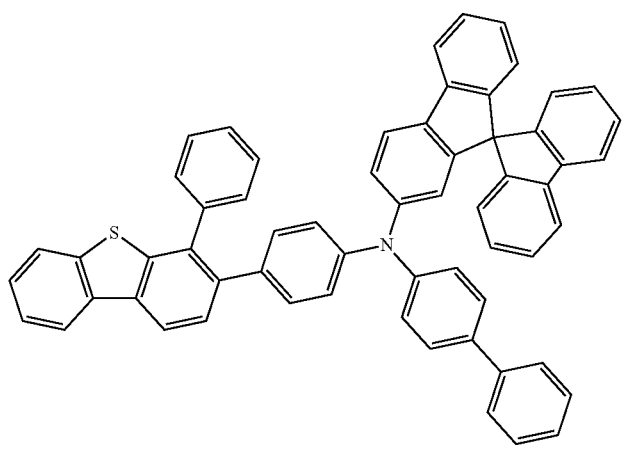
404
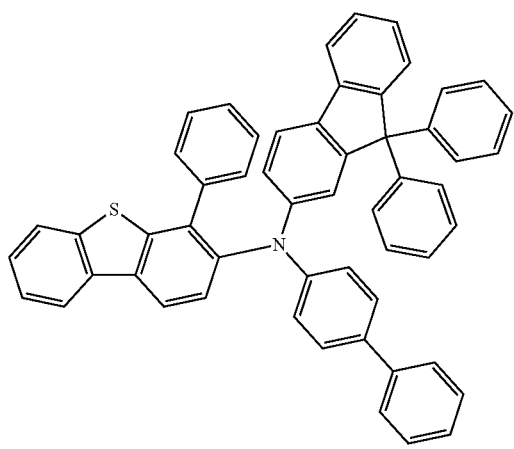
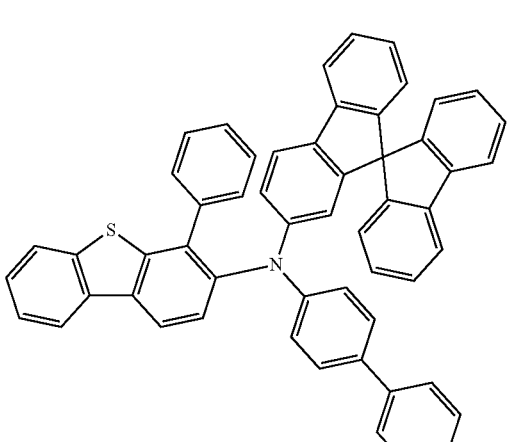
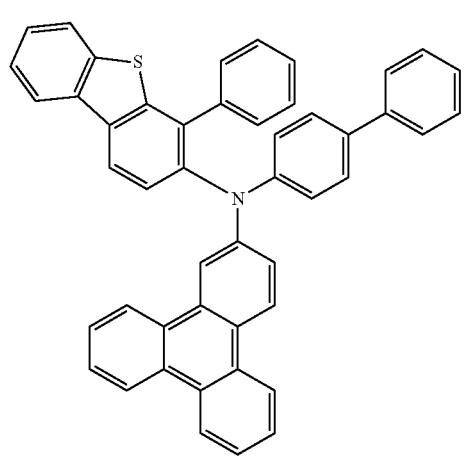

405 406
-continued
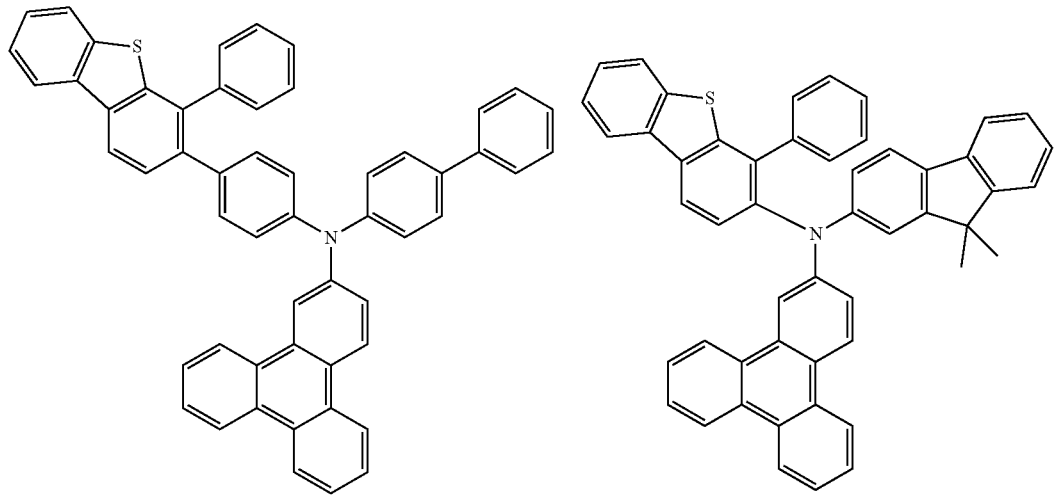
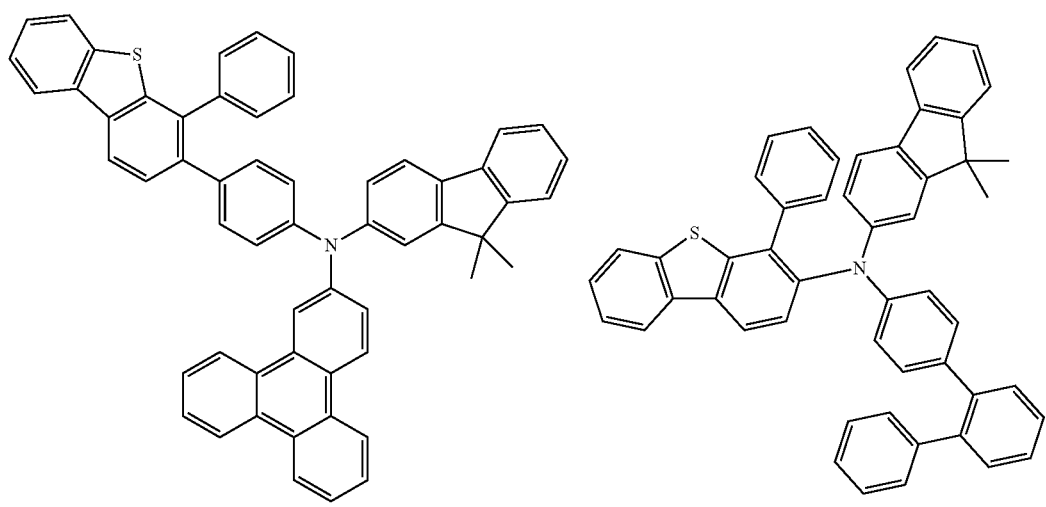
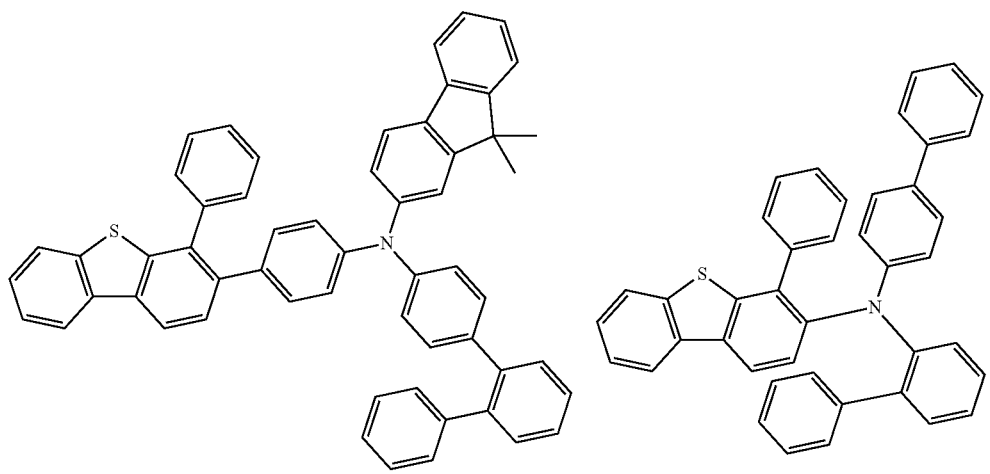

-continued
407
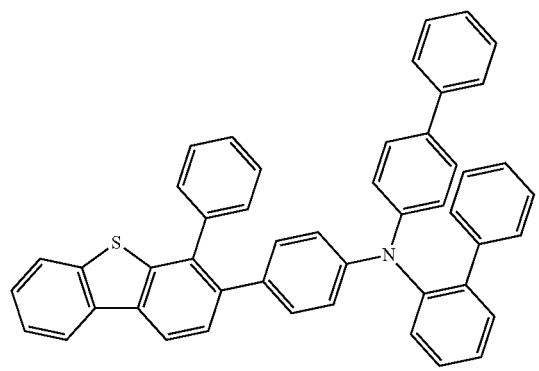
408
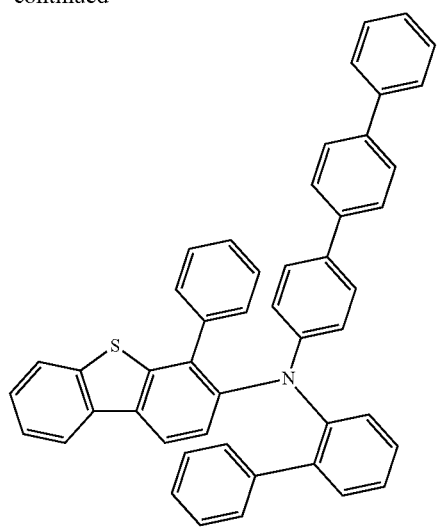
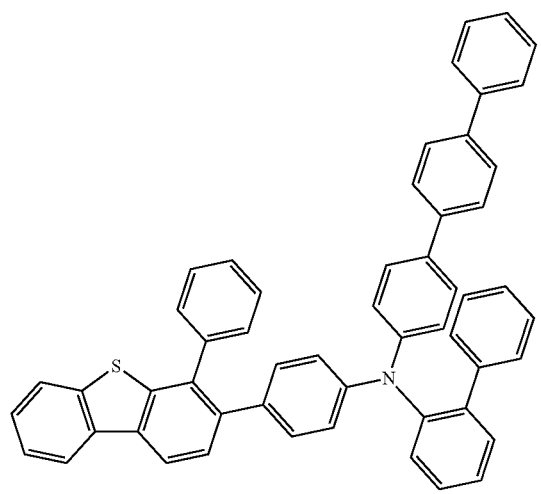
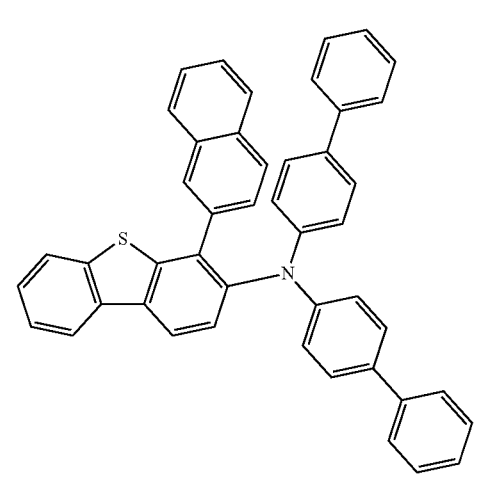
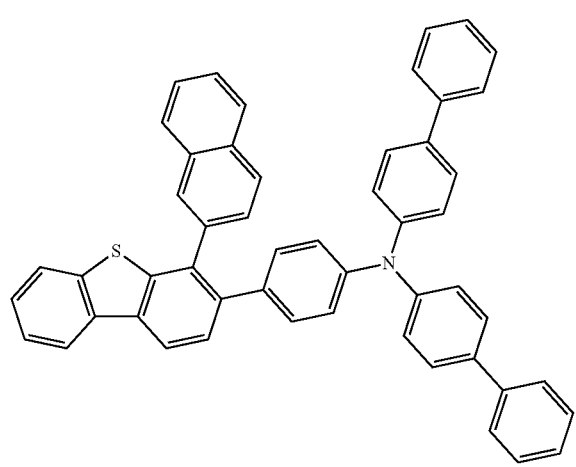
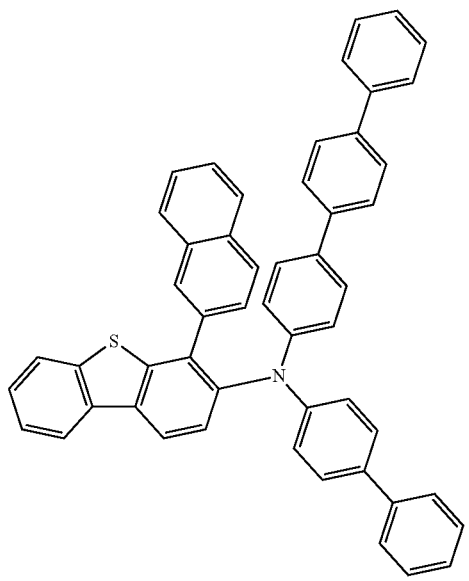

-continued
409
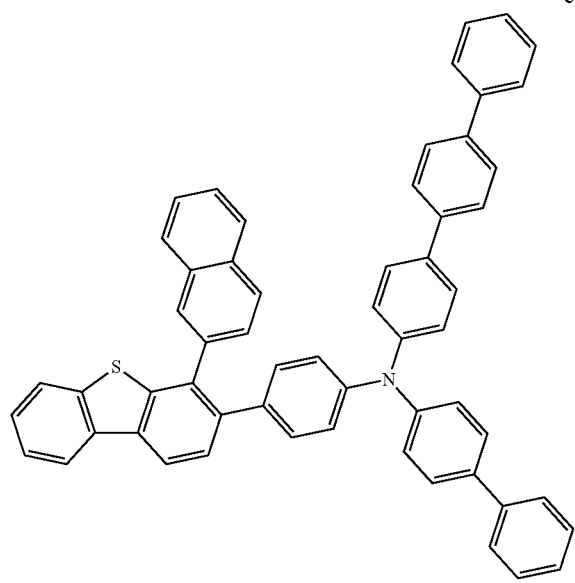
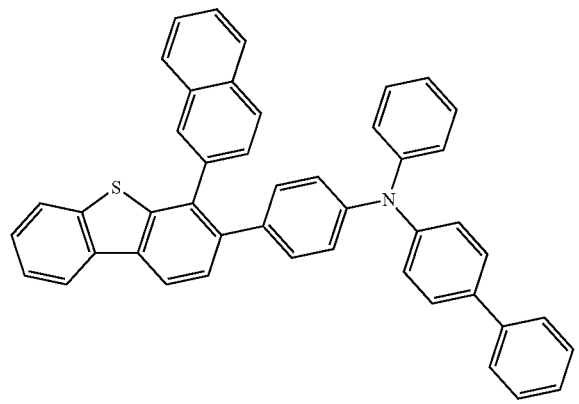
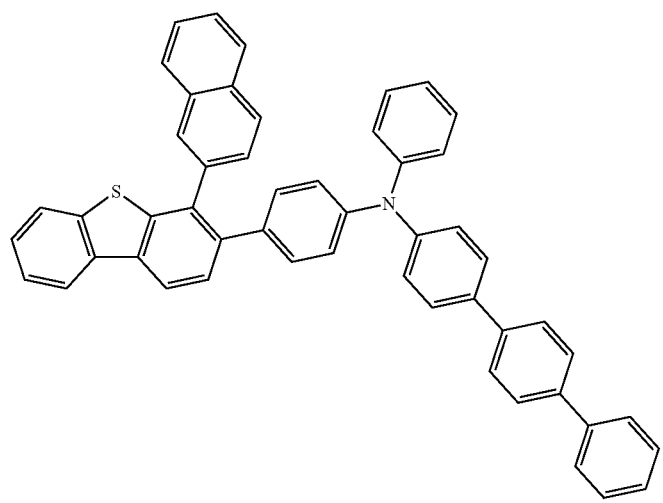
410
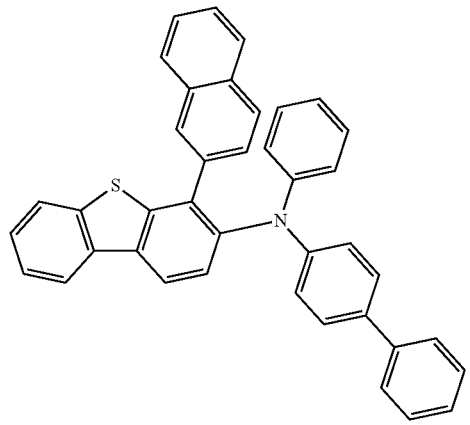
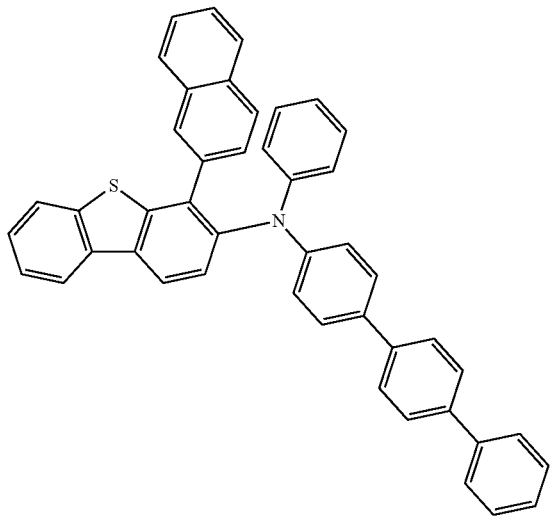
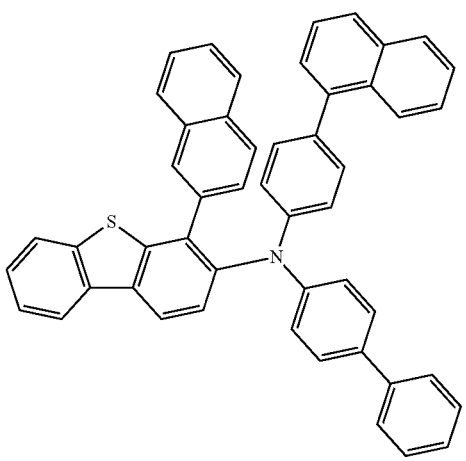

411
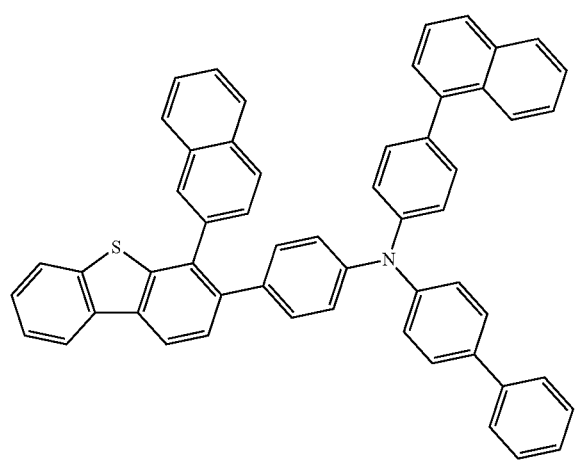
412
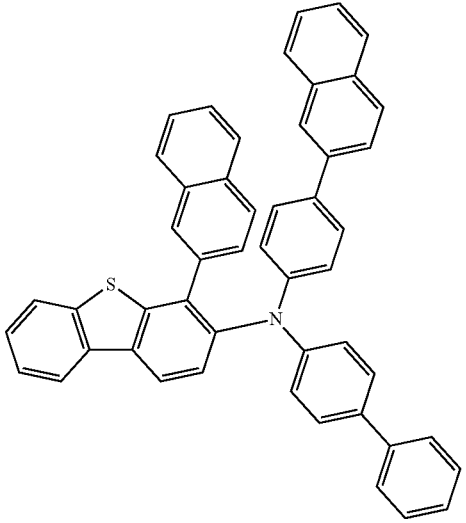
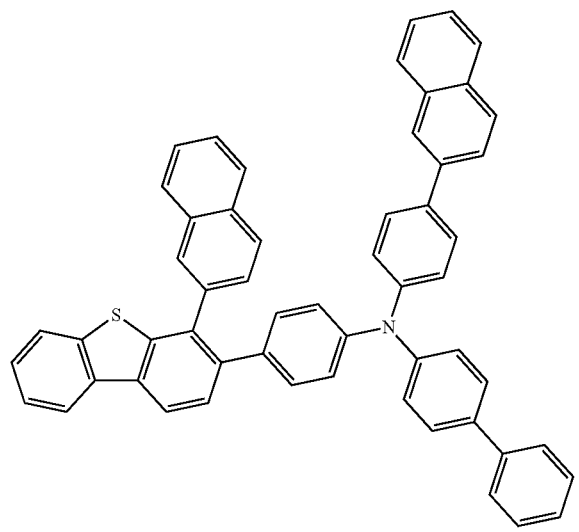
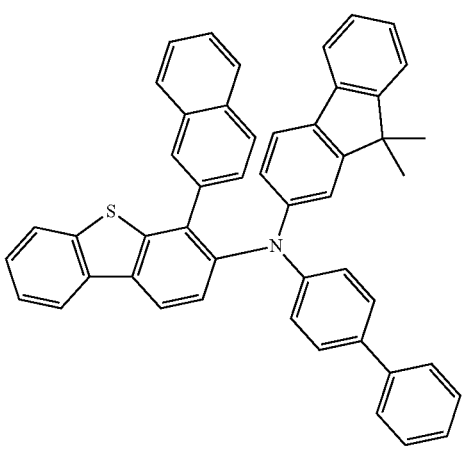
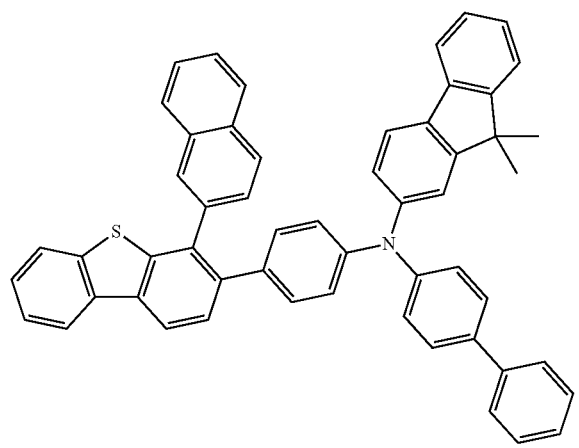
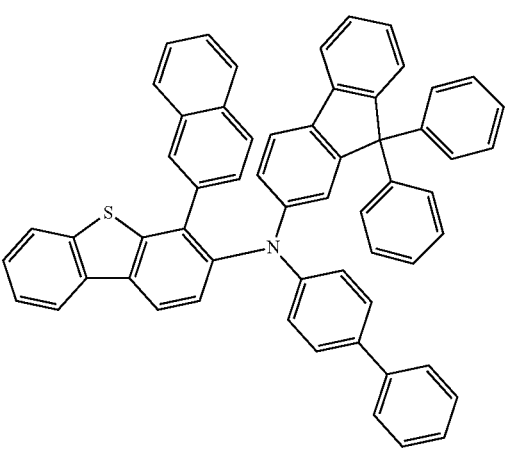

413 414
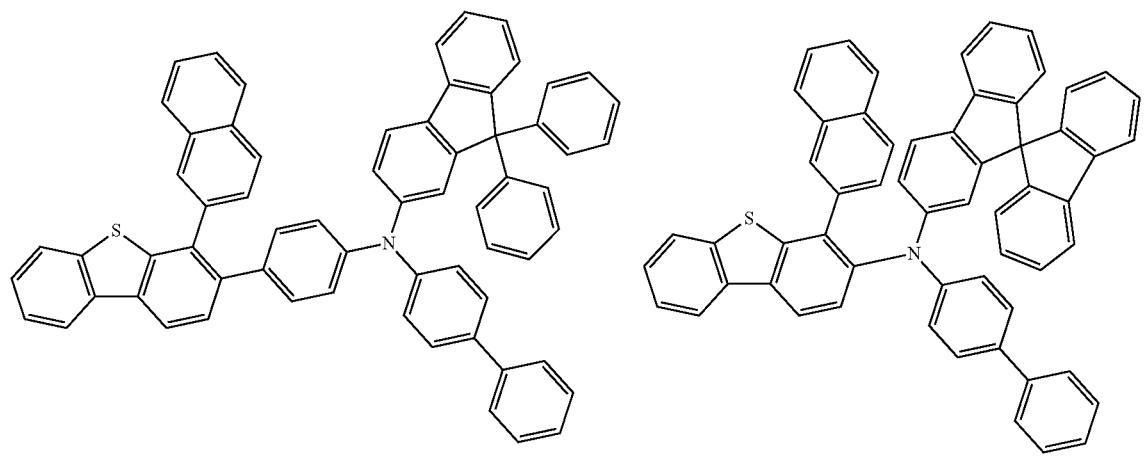
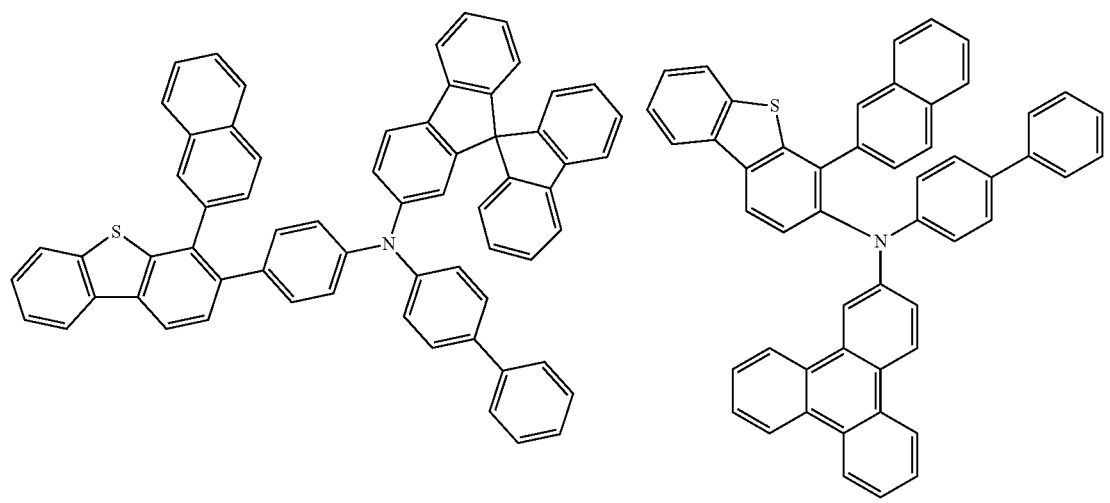
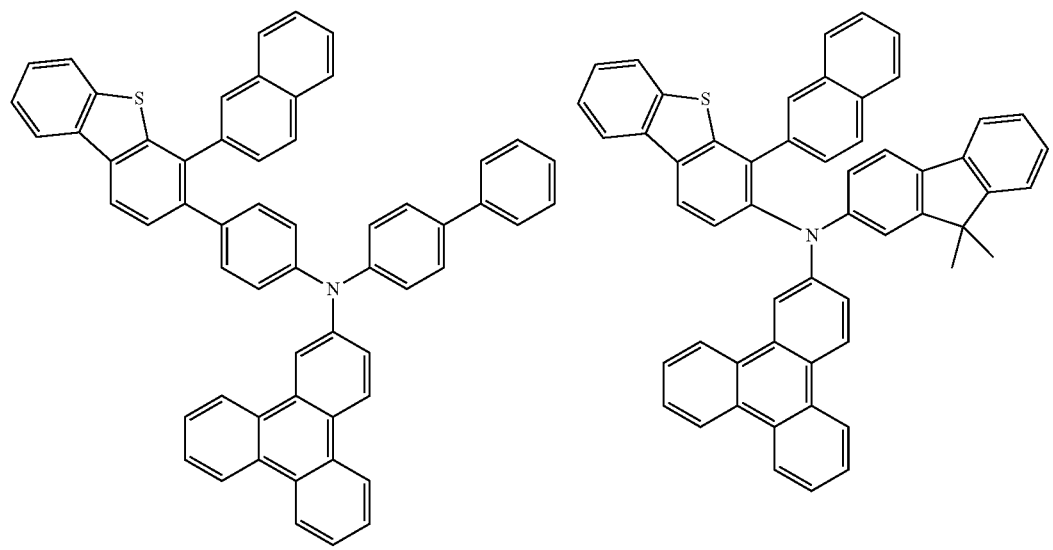

415 416
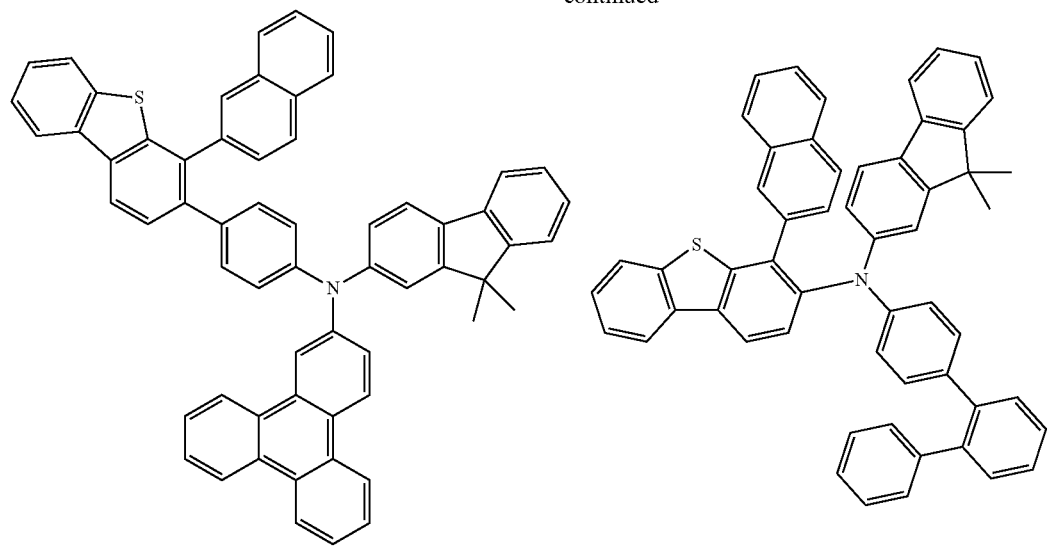
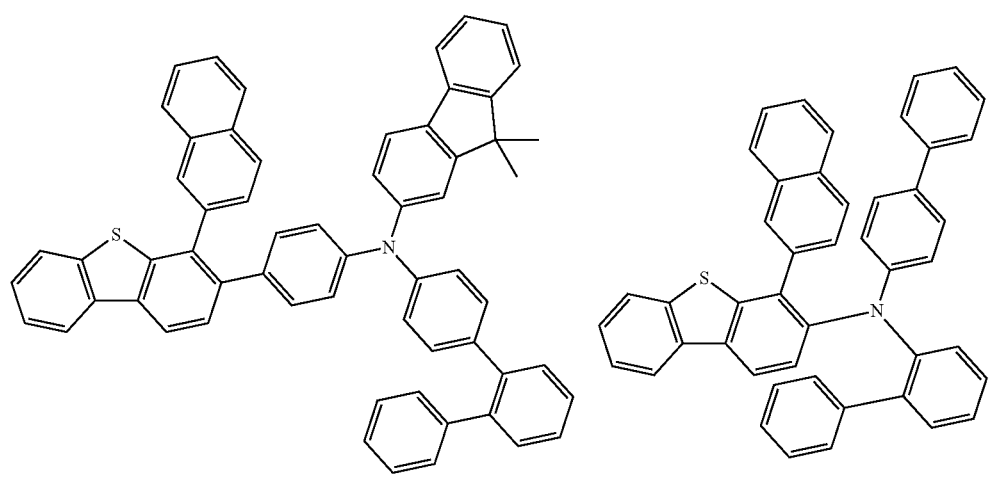
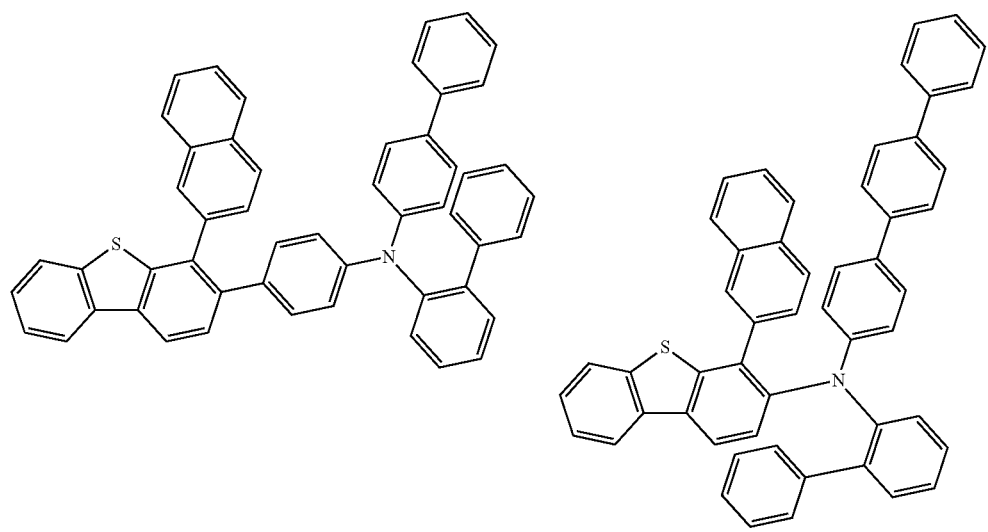

-continued
417 418
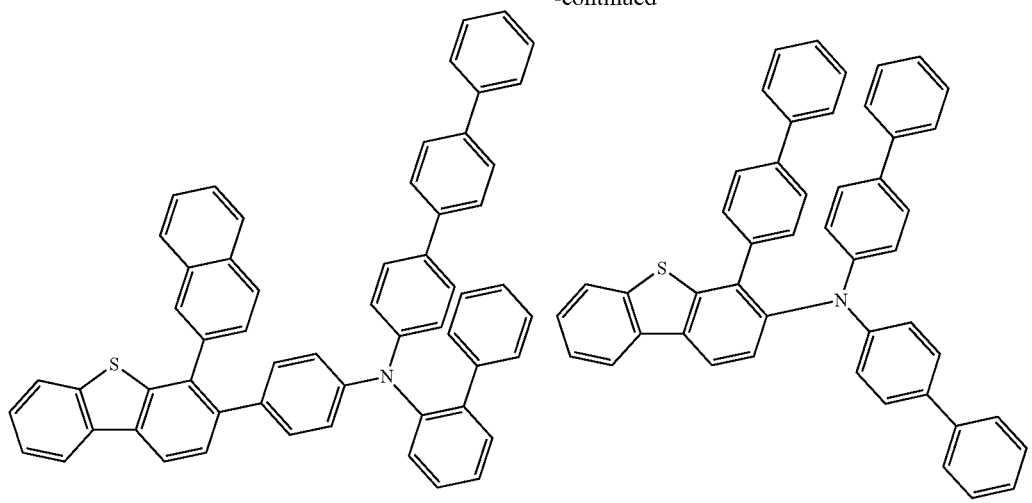
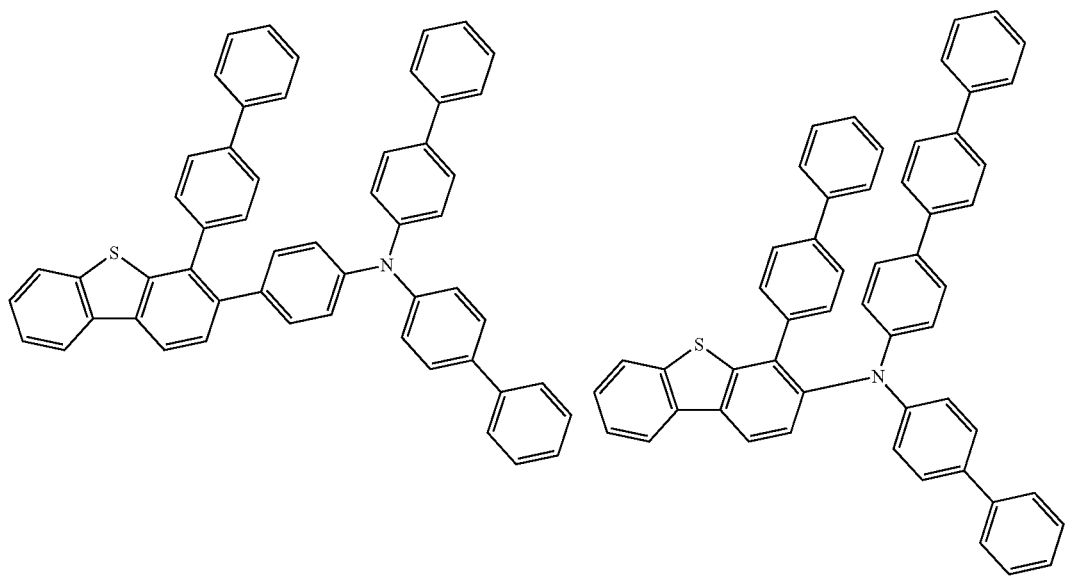
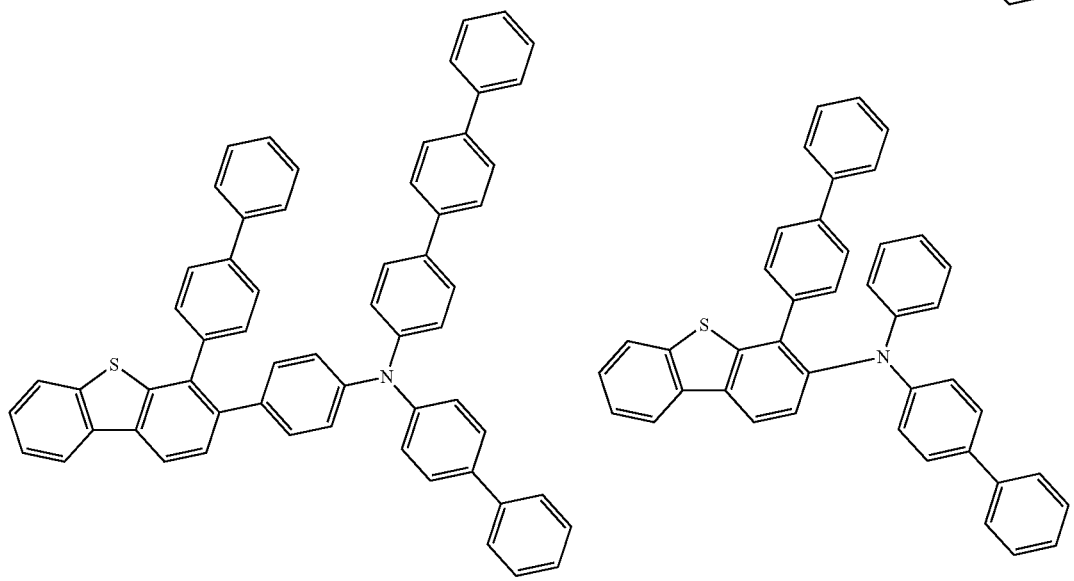

419 420
-continued
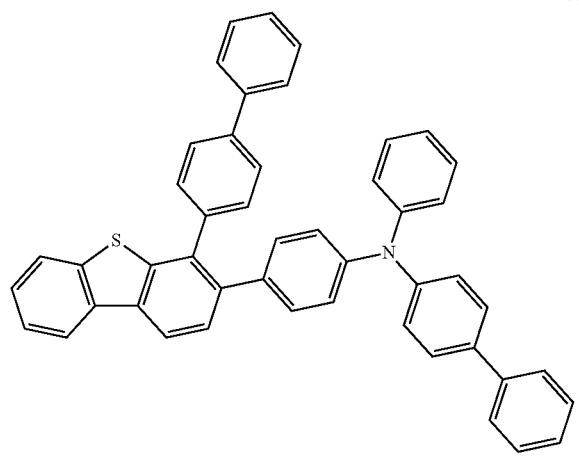

-continued
421
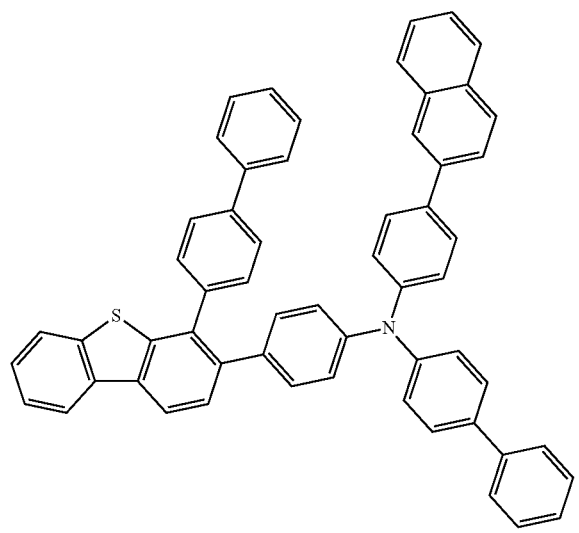
422
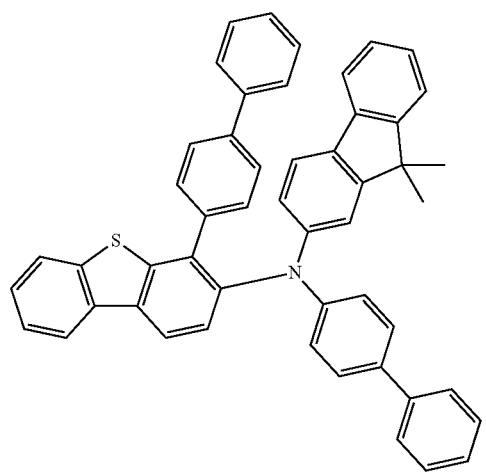
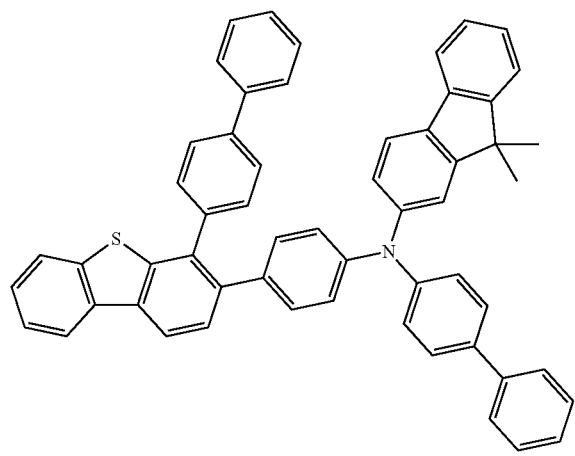
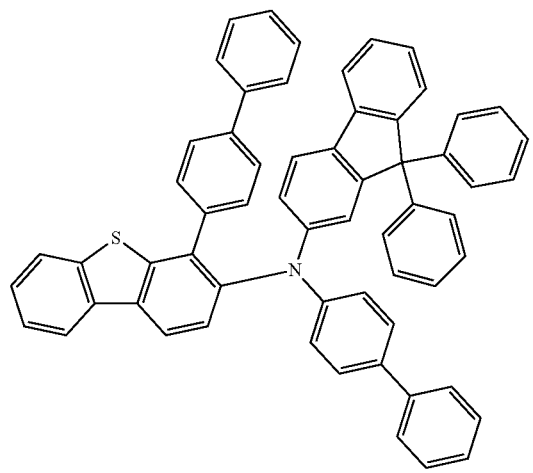
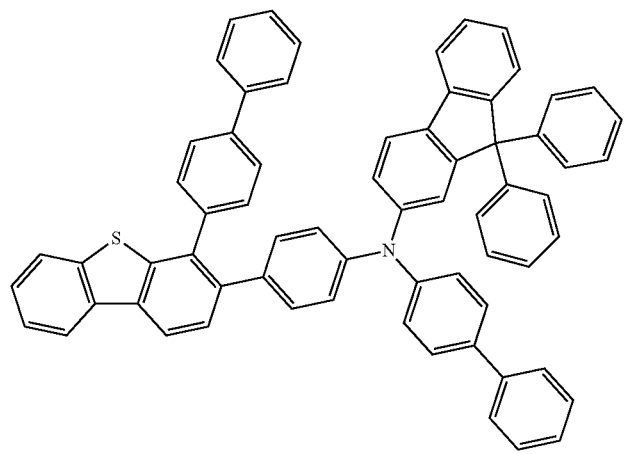
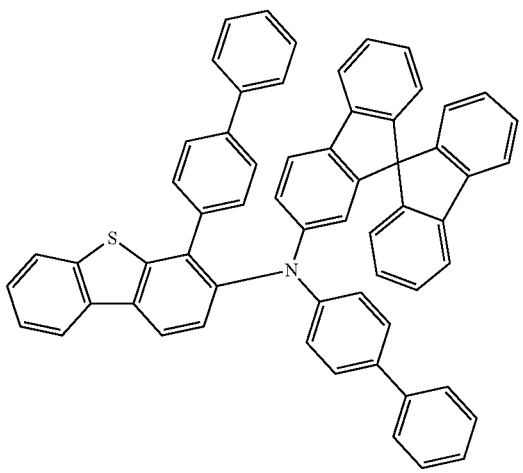

-continued
423
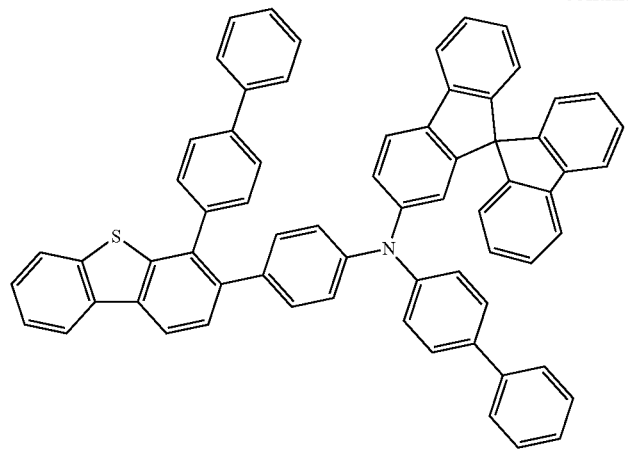
424
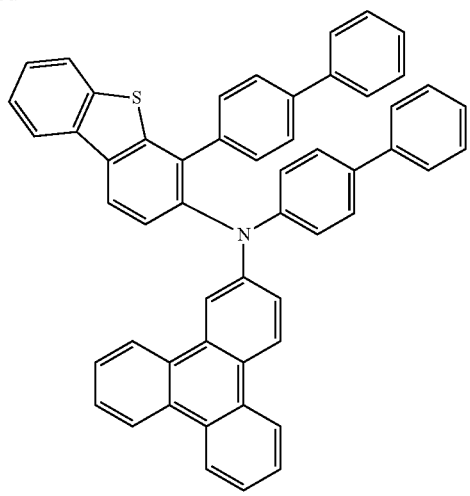
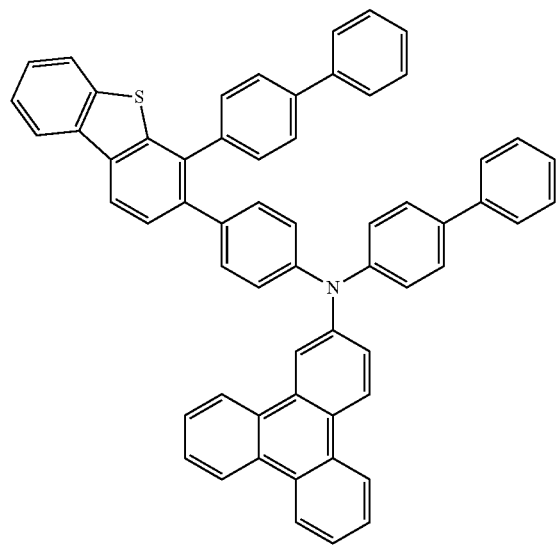
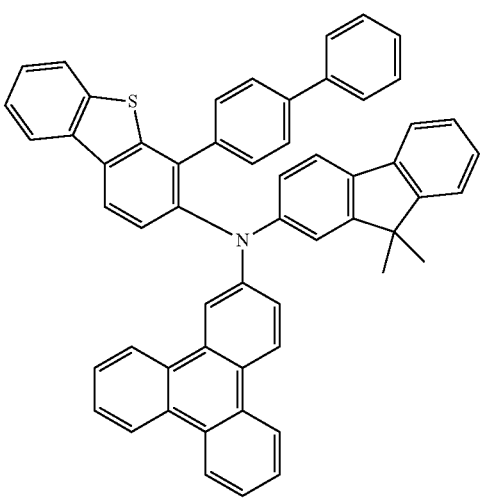
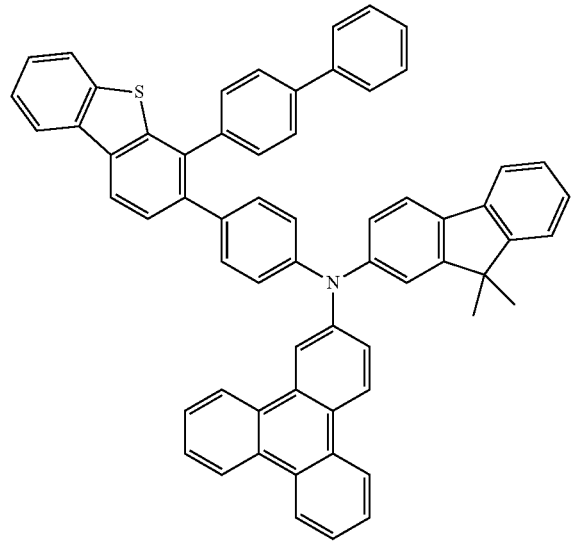
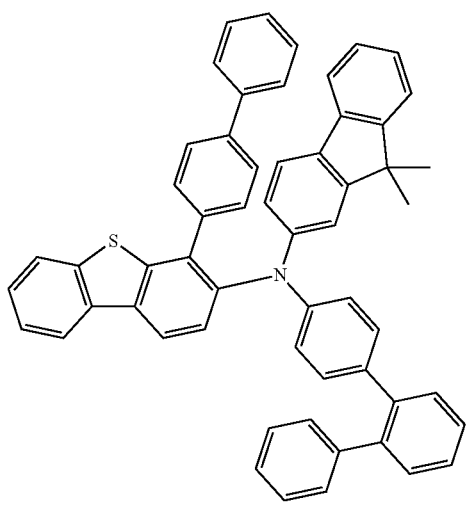

-continued
425
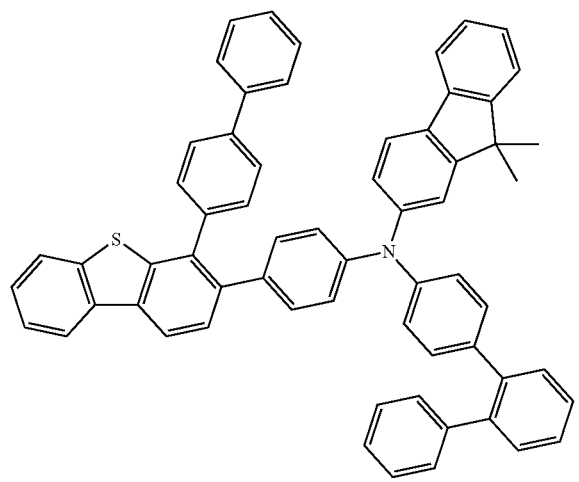
426
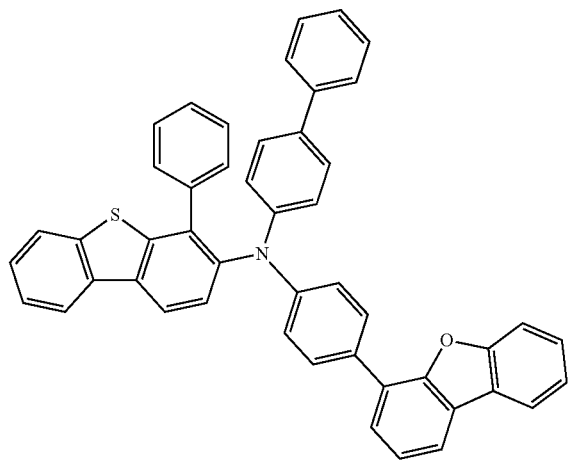
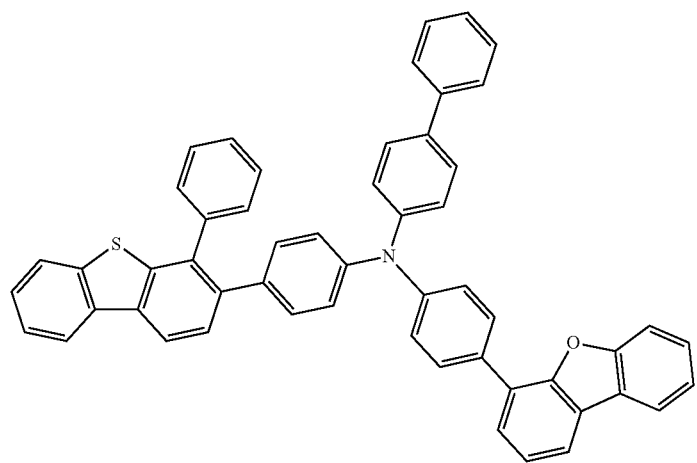
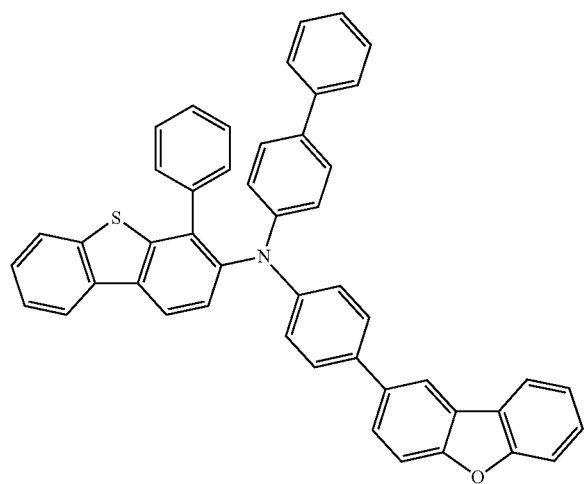

-continued
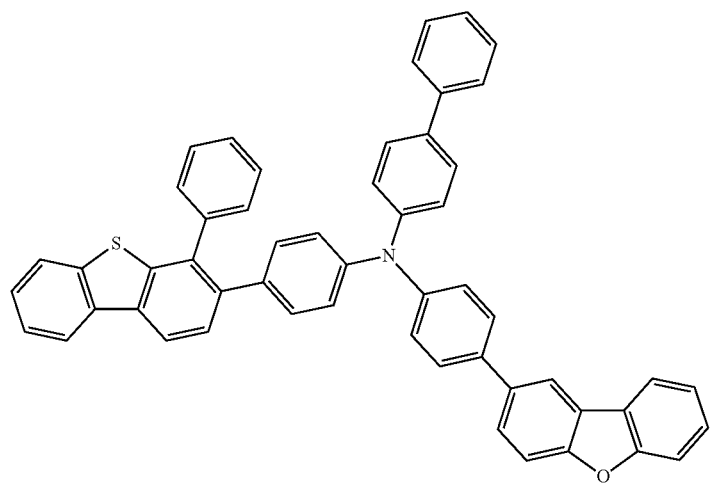
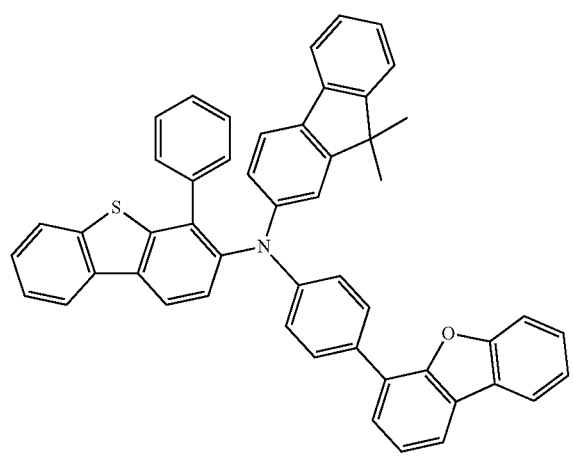
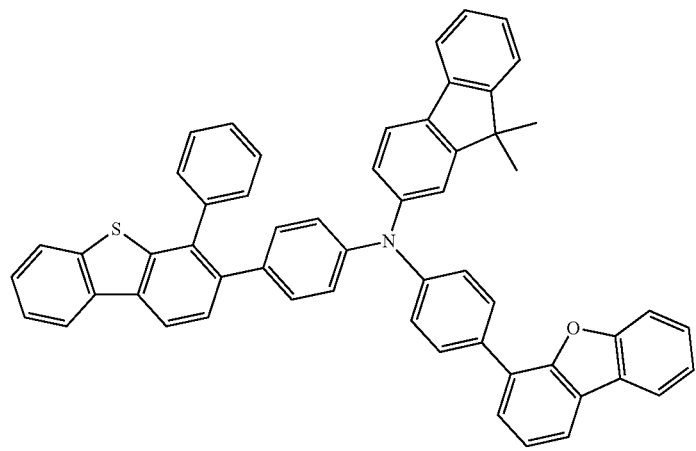

-continued
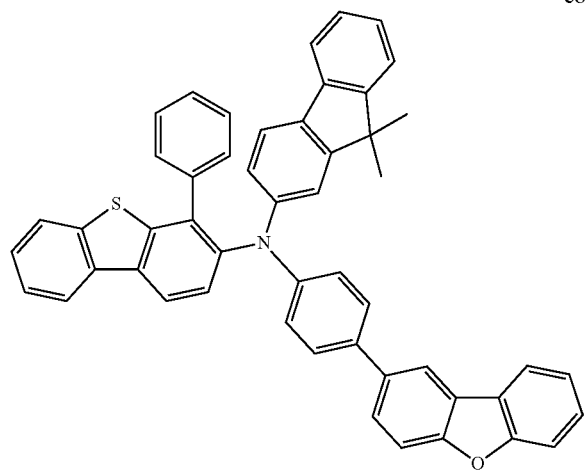
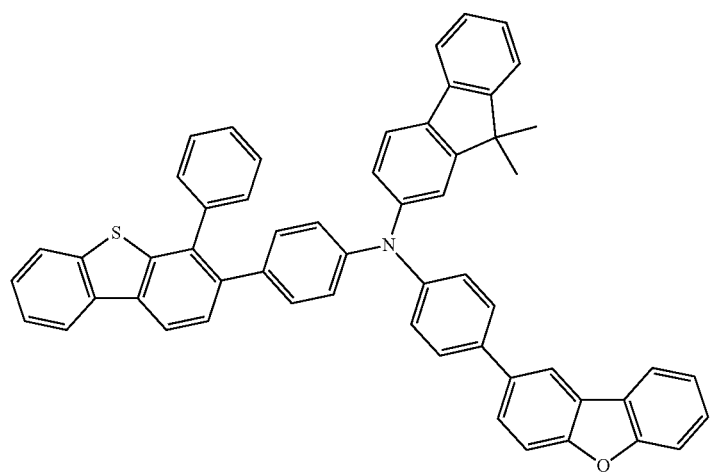
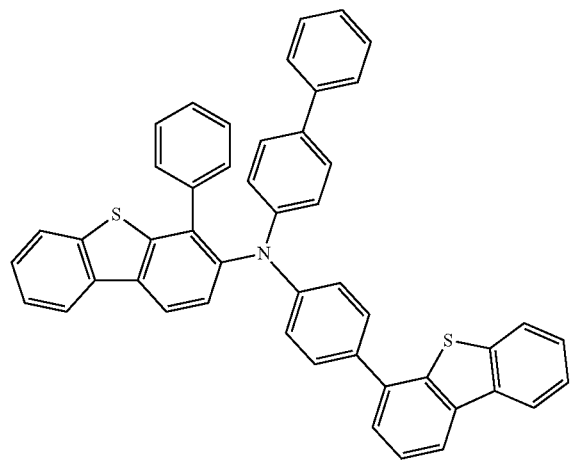

-continued
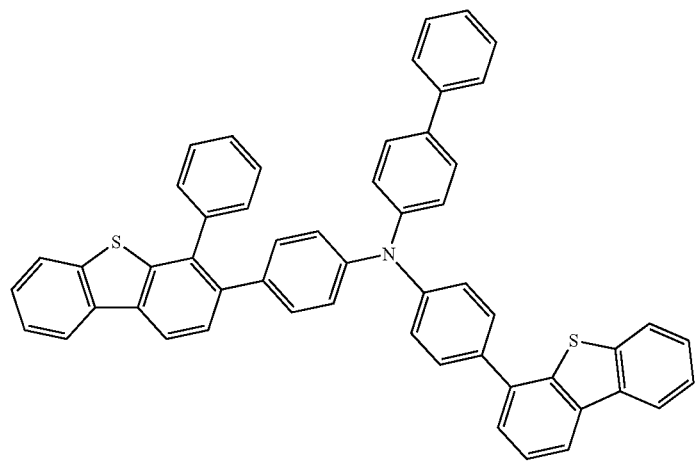
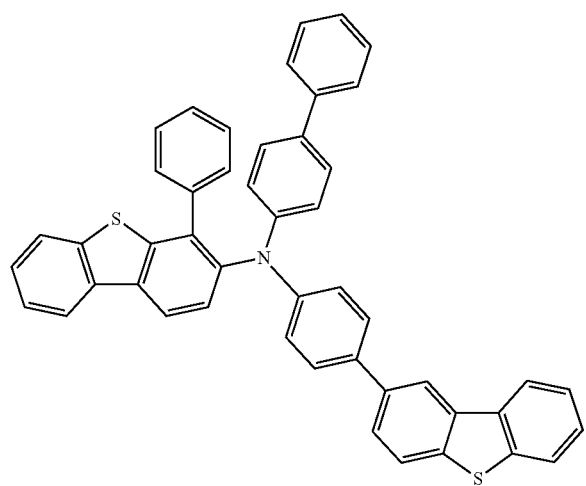
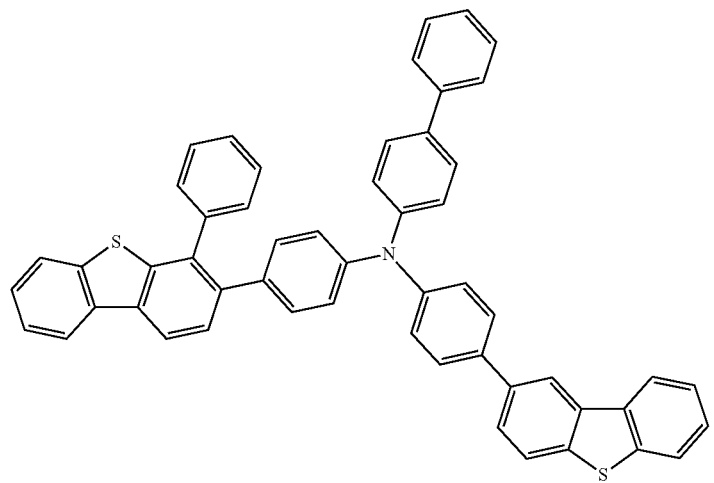

-continued
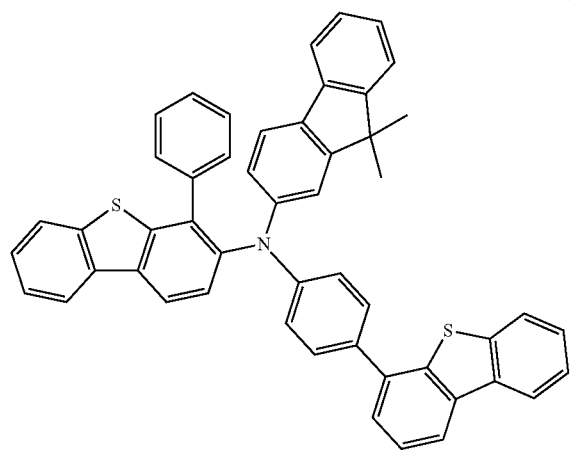
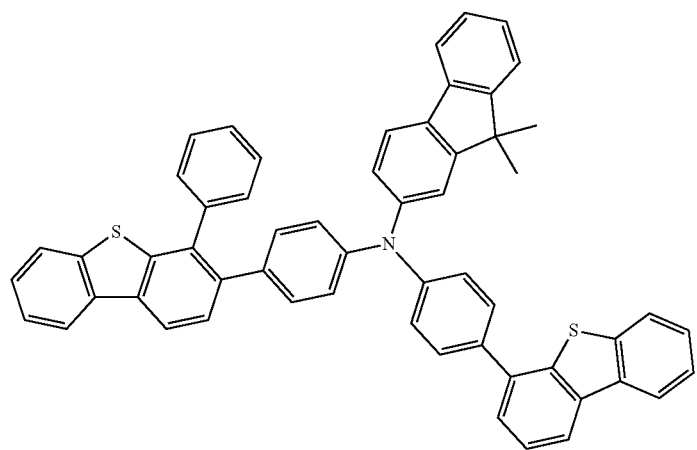
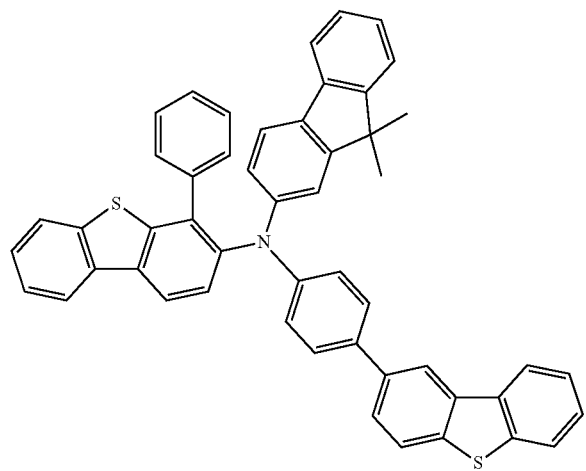

435 436
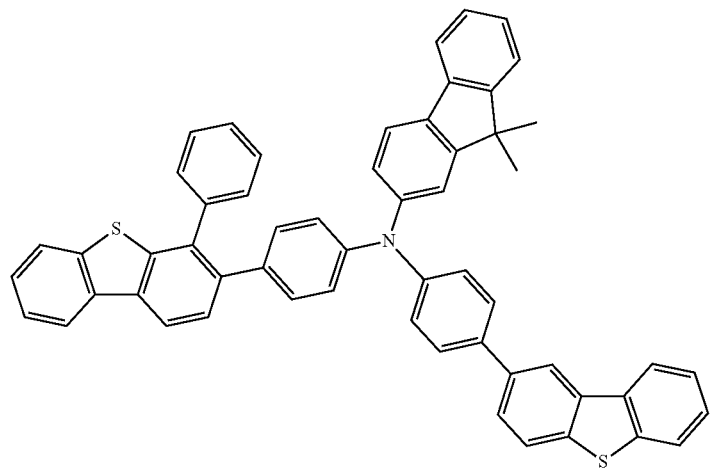
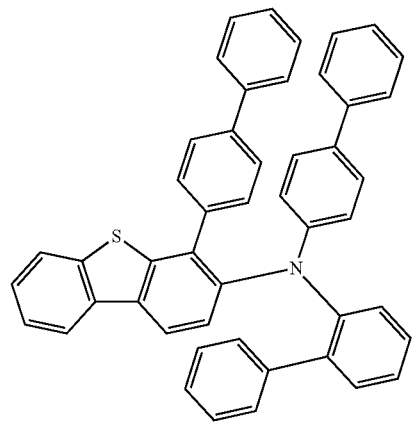
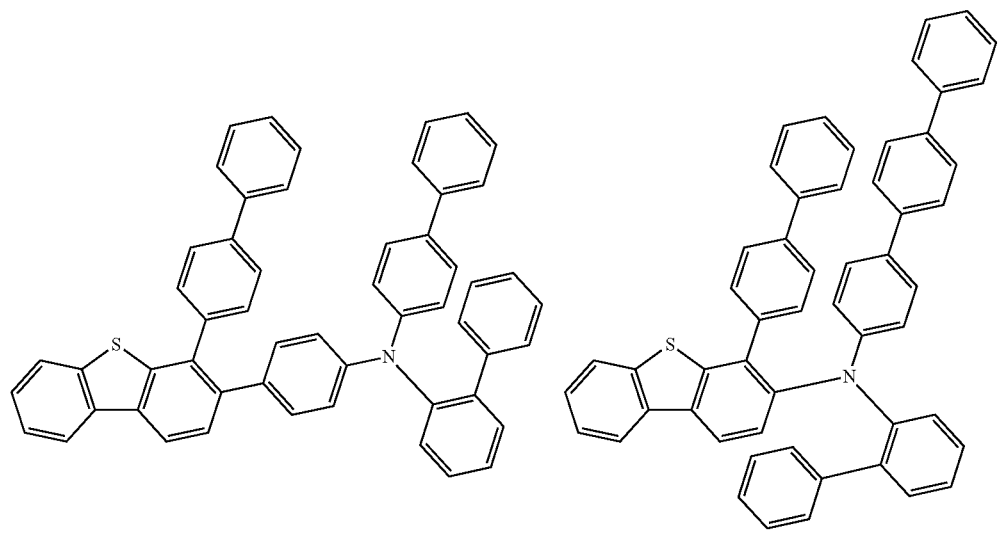
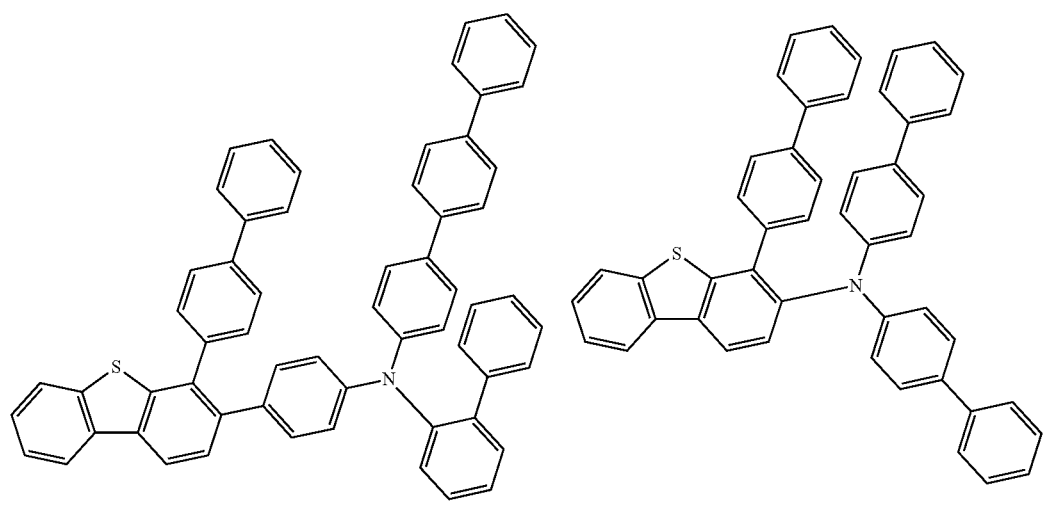

437

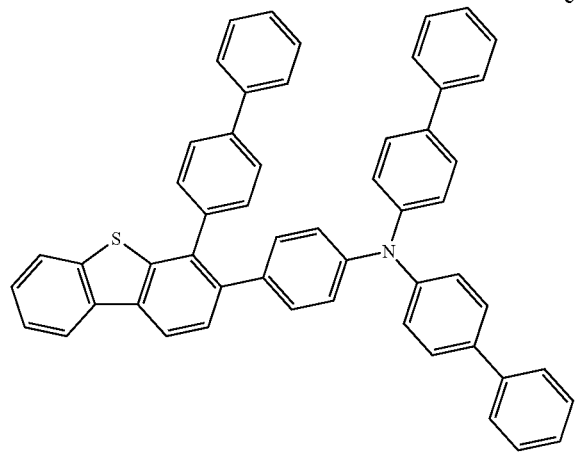

438

-continued

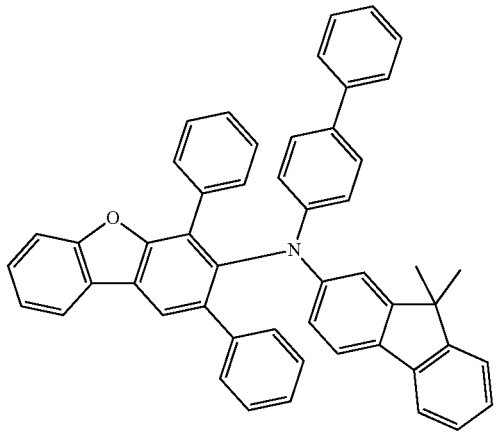

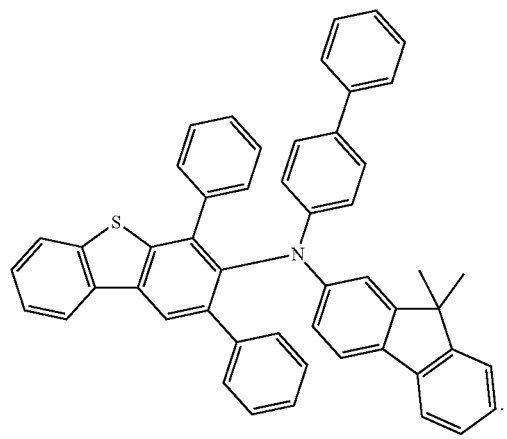

10. An organic light emitting device comprising: a first electrode;
 a second electrode provided to face the first electrode; and at least one layer of the organic material layers provided between the first electrode and the second electrode, wherein the at least one layer of the organic material layers includes the compound according to claim 1.

11. The organic light emitting device of claim 10, wherein the organic material layer including the compound is a hole injection layer, a hole transport layer, or a layer simultaneously performing hole injection and hole transport functions.

12. The organic light emitting device of claim 10, wherein the organic material layer including the compound is an electron blocking layer.

* * * * *